US012338203B2

(12) United States Patent
Kuroda et al.

(10) Patent No.: US 12,338,203 B2
(45) Date of Patent: Jun. 24, 2025

(54) UREA COMPOUND FOR ANTAGONIZING LPA1 RECEPTOR

(71) Applicant: TAISHO PHARMACEUTICAL CO., LTD., Tokyo (JP)

(72) Inventors: Shoichi Kuroda, Tokyo (JP); Yuki Kobayashi, Tokyo (JP); Kanako Hatanaka, Tokyo (JP); Yuji Ito, Tokyo (JP); Fumito Uneuchi, Tokyo (JP); Yuko Uehara, Tokyo (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 730 days.

(21) Appl. No.: 17/629,955

(22) PCT Filed: Jul. 29, 2020

(86) PCT No.: PCT/JP2020/029003
§ 371 (c)(1),
(2) Date: Jan. 25, 2022

(87) PCT Pub. No.: WO2021/020429
PCT Pub. Date: Feb. 4, 2021

(65) Prior Publication Data
US 2023/0097871 A1 Mar. 30, 2023

(30) Foreign Application Priority Data
Jul. 30, 2019 (JP) .................. 2019-140088

(51) Int. Cl.
| | | |
|---|---|---|
| *C07C 275/16* | (2006.01) | |
| *C07C 275/26* | (2006.01) | |
| *C07C 311/01* | (2006.01) | |
| *C07D 209/14* | (2006.01) | |
| *C07D 209/44* | (2006.01) | |
| *C07D 213/40* | (2006.01) | |
| *C07D 231/56* | (2006.01) | |
| *C07D 257/04* | (2006.01) | |
| *C07D 271/113* | (2006.01) | |
| *C07D 307/79* | (2006.01) | |
| *C07D 309/14* | (2006.01) | |
| *C07D 319/18* | (2006.01) | |
| *C07D 333/54* | (2006.01) | |
| *C07D 335/02* | (2006.01) | |
| *C07D 471/04* | (2006.01) | |
| *C07F 9/38* | (2006.01) | |

(52) U.S. Cl.
CPC .......... *C07C 275/16* (2013.01); *C07C 275/26* (2013.01); *C07C 311/01* (2013.01); *C07D 209/14* (2013.01); *C07D 209/44* (2013.01); *C07D 213/40* (2013.01); *C07D 231/56* (2013.01); *C07D 257/04* (2013.01); *C07D 271/113* (2013.01); *C07D 307/79* (2013.01); *C07D 309/14* (2013.01); *C07D 319/18* (2013.01); *C07D 333/54* (2013.01); *C07D 335/02* (2013.01); *C07D 471/04* (2013.01); *C07F 9/383* (2013.01)

(58) Field of Classification Search
CPC ... C07C 275/16; C07C 275/26; C07C 311/01; C07D 209/14; C07D 209/44; C07D 213/40; C07D 231/56; C07D 257/04; C07D 271/113; C07D 307/79; C07D 309/14; C07D 319/18; C07D 333/54; C07D 335/02; C07D 471/04; C07F 9/383
USPC ........................................................ 514/115
See application file for complete search history.

(56) References Cited

U.S. PATENT DOCUMENTS

| | | | |
|---|---|---|---|
| 7,285,680 B2 | 10/2007 | Habashita et al. | |
| 7,288,558 B2 | 10/2007 | Nakade et al. | |
| 7,820,682 B2 | 10/2010 | Terakado et al. | |
| 7,875,745 B2 | 1/2011 | Motoyuki et al. | |
| 10,071,078 B2 | 9/2018 | Cheng et al. | |
| 10,100,018 B2 | 10/2018 | Buffham et al. | |
| 2009/0099205 A1* | 4/2009 | Zhou .................. | C07D 401/12 544/335 |
| 2015/0376160 A1 | 12/2015 | Iwase et al. | |
| 2017/0158663 A1 | 6/2017 | Iwase et al. | |

FOREIGN PATENT DOCUMENTS

| | | |
|---|---|---|
| EA | 201101709 A1 | 6/2012 |
| WO | WO 2002/062389 A1 | 8/2002 |
| WO | WO 2003/099765 A1 | 12/2003 |
| WO | WO 2004/031118 A1 | 4/2004 |
| WO | WO 2005/032494 A2 | 4/2005 |
| WO | WO 2005/058790 A1 | 6/2005 |
| WO | WO 2010/141761 A2 | 12/2010 |
| WO | WO 2011/017350 A2 | 2/2011 |
| WO | WO 2011/041694 A2 | 4/2011 |

(Continued)

OTHER PUBLICATIONS

A. M. Tager, et al., "The lysophosphatidic acid receptor LPA$_1$ links pulmonary fibrosis to lung injury by mediating fibroblast recruitment and vascular leak," *Nat. Med.* 14(1), pp. 45-54 (2008).

(Continued)

*Primary Examiner* — Kristin A Vajda
(74) *Attorney, Agent, or Firm* — FINNEGAN, HENDERSON, FARABOW, GARRETT & DUNNER, LLP

(57) ABSTRACT

The present invention provides a compound represented by formula (I) or a pharmaceutically acceptable salt thereof which has the effect of antagonizing the LPA1 receptor.

15 Claims, No Drawings

(56) References Cited

FOREIGN PATENT DOCUMENTS

| WO | WO 2014/104372 A1 | 7/2014 |
|---|---|---|
| WO | WO 2015/025164 A1 | 2/2015 |
| WO | WO 2017/117004 A1 | 7/2017 |
| WO | WO 2017/223016 A1 | 12/2017 |
| WO | WO 2019/126090 A1 | 6/2019 |

OTHER PUBLICATIONS

A. Tokumura, et al., "Elevated Serum Levels of Arachidonoyl-lysophosphatidic Acid and Sphingosine 1-Phosphate in Systemic Sclerosis," *Int. J. Med. Sci.* 6(4) pp. 68-76 (2009).

T. Ohashi, et al., "Antifibrotic effect of lysophosphatidic acid receptors $LPA_1$ and $LPA_3$ antagonist on experimental murine scleroderma induced by bleomycin," *Exp Dermatol.*, 24, pp. 698-702 (2015).

J. S. Swaney, et al., "Pharmacokinetic and Pharmacodynamic Characterization of an Oral Lysophosphatidic Acid Type 1 Receptor-Selective Antagonist", *Pharmacol. Exp. Ther.*, 336, pp. 693-700 (2011).

J.-P. Pradére, et al., "$LPA_1$ Receptor Activation Promotes Renal Interstitial Fibrosis," *J. Am. Soc. Nephrol.* 18, pp. 3110-3118 (2007).

N. Watanabe, et al., "Both Plasma Lysophosphatidic Acid and Serum Autotaxin Levels are Increased in Chronic Hepatitis C," *Clin. Gastroenterol.* 41(6), pp. 616-623 (2007).

V.P. Rachakonda, et al., "Serum Autotaxin is Independently Associated with Hepatic Steatosis in Women with Severe Obesity," *Obesity*, 23, pp. 965-972 (2015).

G. Bain, et al., "Selective Inhibition of Autotaxin Is Efficacious in Mouse Models of Liver Fibrosis," *J. Pharmacol. Exp. Ther.* 360(1), pp. 1-13 (2017).

E. Kritikou, et al., "Inhibition of lysophosphatidic acid receptors 1 and 3 attenuates atherosclerosis development in LDL-receptor deficient mice", *Sci Rep.* 6:37585, pp. 1-10 (2016).

Yan Xu, et al., "Lysophosphatidic Acid as a Potential Biomarker for Ovarian and Other Gynecologic Cancers," *JAMA*, 280(8), pp. 719-723 (1998).

R. Guo, et al., "Expression and Function of Lysophosphatidic Acid $LPA_1$ Receptor in Prostate Cancer Cells," *Endocrinology*, 147(10), pp. 4883-4892 (2006).

A. Boucharaba, et al., "The type 1 lysophosphatidic acid receptor is a target for therapy in bone metastases," *Proc Natl Acad Sci USA.*, 103(25), pp. 9643-9648 (2006).

B. P. Kroop et al., "Characterization of Cultured Bladder Smooth Muscle Cells: Assessment of in Vitro Contractility," *J. Urol.*, 162, pp. 1779-1784 (1999).

C. Guo, et al., "Mitogenic Signaling in Androgen Sensitive and Insensitive Prostate Cancer Cell Lines," *J. Urol.* 163, pp. 1027-1032 (2000).

M. Inoue, et al., "Initiation of neuropathic pain requires lysophosphatidic acid receptor signaling", *Nat Med.* 10(7), pp. 712-718 (2004).

Translation of the International Search Report for PCT Application No. PCT/JP2020/029003, Oct. 6, 2020 (three pages).

Extended European Search Report for European Pat. App. No. EP20847275.3, dated Jul. 28, 2023 (seven pages).

Kümmerer, K. "Pharmaceuticals in the Environment," *Annu. Rev. Envrion. Resour.*, 2010, 35, pp. 57-75.

Russian Search Report for Russian Pat. App. No. 2022103571, dated Jun. 23, 2023 (three pages).

Office Action in Chinese Patent Application No. 202080054964.8, dated Sep. 11, 2024 (four pages).

STN Registry Number (RN) 1173062-11-7; STN entry date: Aug. 5, 2009.

STN Registry Number (RN) 684240-17-3; STN entry date: May 21, 2004.

STN Registry Number (RN) 337324-24-0; STN entry date: May 22, 2001.

STN Registry Number (RN) 334787-37-0; STN entry date: May 7, 2001.

STN Registry Number (RN) 337939-64-7; STN entry date: May 24, 2001.

STN Registry Number (RN) 337937-90-3; STN entry date: May 24, 2001.

STN Registry Number (RN) 334789-64-9; STN entry date: May 7, 2001.

STN Registry Number (RN) 294184-65-9; STN entry date: Oct. 10, 2000.

STN Registry Number (RN) 293317-11-0; STN entry date: Oct. 6, 2000.

STN Registry Number (RN) 294184-41-1; STN entry date: Oct. 10, 2000.

STN Registry Number (RN) 292049-27-5; STN entry date: Oct. 2, 2000.

STN Registry Number (RN) 291516-17-1; STN entry date: Sep. 28, 2000.

\* cited by examiner

UREA COMPOUND FOR ANTAGONIZING LPA1 RECEPTOR

This application is a national stage filing under 35 U.S.C. § 371 of International Application No. PCT/JP2020/029003, filed on Jul. 29, 2020, which claims priority to Japanese Patent Application No. JP 2019-140088, filed on Jul. 30, 2019. The contents of each of these applications are incorporated herein by reference in their entirety.

TECHNICAL FIELD

The present invention relates to a medicament comprising an LPA1 receptor antagonist as an active ingredient. More specifically, the present invention relates to a medicament comprising a urea compound that is an LPA1 receptor antagonist as an active ingredient.

BACKGROUND ART

Lysophosphatidic acids (these may also be referred to as "LPAs" herein) are physiologically active phospholipids in which a fatty acid is bonded to the first position or second position of the glycerol backbone and a phosphate group is bonded to the third position, and examples thereof include 1-acyl LPA, 1-alkyl LPA, and 2-acyl LPA. They also show diversity in terms of the type of bonded fatty acid, and there are many LPA subtypes that exhibit a variety of chemical and physiological properties depending on the carbon chain length and degree of unsaturation of the fatty acid.

LPAs are produced in vivo by various LPA-producing enzymes, and are known to bind to G protein-coupled receptors on the cell surface, thereby transmitting signals into the cell and exhibiting a variety of physiological actions. As for the LPA receptor, six subtypes are known, the LPA1 to LPA6 receptors. Three types of receptors, the LPA1 receptor, the LPA2 receptor, and the LPA3 receptor, belong to the EDG (Endothelial Differentiation Gene) family and are referred to as EDG2, EDG4, and EDG7, respectively. The LPA4 to LPA6 receptors are of the non-EDG family and have low homology to the EDG family mentioned above. The LPA receptor subtypes are distributed throughout the living body, but their localization differs depending on the subtype, and the subtypes are thought to contribute to the physiological function of the tissues where they exist.

LPAs have been shown to be involved in various fibrotic diseases, and as the receptor, the involvement of the EDG receptor family in particular has been suggested. With regard to pulmonary fibrosis, it has been reported that the LPA concentration increases in the alveolar lavage fluid of patients with idiopathic pulmonary fibrosis and bleomycin-induced pulmonary fibrosis model mice, and that, in the same model mice, the progression of fibrosis is markedly suppressed in Lpar1-deficient mice and mice to which an LPA1 receptor antagonistic drug is administered (see NPL 1). Similarly, the LPA concentration in serum increases in patients with systemic scleroderma as well, and it has been reported that LPA1 receptor antagonistic drugs and LPA1/3 receptor antagonistic drugs have an inhibitory action on fibrosis in bleomycin-induced skin fibrosis model mice (see NPLs 2 to 4). In renal fibrosis, LPA production is accelerated in model mice with unilateral ureteral ligation, and it has been reported that fibrosis formation is inhibited in Lpar1-deficient mice and by LPA1 receptor antagonistic drugs (see NPLs 4 and 5). In addition, in relation to liver fibrosis, it has been reported that the LPA concentration in blood increases in patients with chronic hepatitis C, and the extent thereof has been reported to correlate with the histological stage of fibrosis (see NPL 6). Also, it has been shown that expression of autotaxin, which is an LPA-producing enzyme, is accelerated in the blood of patients with non-alcoholic fatty liver disease (NAFLD), and that autotaxin inhibitors exhibit inhibitory effects in various mouse hepatic disorder models (see NPLs 7 and 8). Furthermore, it has been reported that LPA accumulation at a high concentration in atherosclerotic plaques results in acceleration of inflammation and an apoptosis-inducing action, but lesions in model mice are improved by administration of LPA1/3 receptor antagonistic drugs, suggesting the involvement of LPAs in circulatory system diseases as well (see NPL 9).

LPAs are also known to induce migration and proliferation of cancer cells, and an increase in the LPA concentration and accelerated expression of LPA1 receptors have been observed in the tissues of patients with a variety of cancers (see NPLs 10 to 12).

In addition, LPAs have been reported to contract bladder smooth muscle cells, to promote proliferation of prostate cells, and to be involved in the regulation of urethra internal pressure in vivo, suggesting their involvement in lower urinary tract diseases (see PTL 1 and NPLs 13 and 14).

In addition, LPAs have been reported to contract bladder smooth muscle cells, to promote proliferation of prostate cells, and to be involved in the regulation of urethra internal pressure in vivo, suggesting their involvement in lower urinary tract diseases (see PTL 1 and NPLs 13 and 14).

Furthermore, LPAs and LPA receptors are expressed in the nervous system, and LPAs have been shown to induce expression of neuropathic pain via the LPA1 receptor. It has been reported that Lpar1 knockout mice do not exhibit pain symptoms in a mouse nerve ligation pain model (see NPL 15).

As a substance that antagonizes the LPA1 receptor, alkanoic acid compounds having a ring (PTLs 2 to 4), cyclohexylcarboxylic acid compounds having a triazole ring (PTL 5), and carboxylic acid compounds having an amide structure (PTLs 6 to 7), for example, have been reported, but there is no disclosure of the urea compounds of the present invention.

CITATION LIST

Patent Literature

PTL 1: WO 02/062389
PTL 2: WO03/099765
PTL 3: WO2004/031118
PTL 4: WO2005/058790
PTL 5: WO2017/223016
PTL 6: WO2015/025164
PTL 7: WO2017/177004

Non Patent Literature

NPL 1: Nat Med. 2008 January; 14 (1): 45-54.
NPL 2: Int J Med Sci. 2009 Jun. 5; 6 (4): 168-76.
NPL 3: Exp Dermatol. 2015 September; 24 (9): 698-702.
NPL 4: Pharmacol Exp Ther. 2011 March; 336 (3): 693-700.
NPL 5: J Am Soc Nephrol. 2007 December; 18 (12): 3110-8.
NPL 6: J Clin Gastroenterol. 2007 July; 41 (6): 616-23.
NPL 7: Obesity (Silver Spring). 2015 May; 23 (5): 965-972.
NPL 8: J Pharmacol Exp Ther. 2017 January; 360 (1): 1-13.
NPL 9: Sci Rep. 2016 Nov. 24; 6:37585.
NPL 10: JAMA. 1998 Aug. 26; 280 (8): 719-23.
NPL 11: Endocrinology. 2006 October; 147 (10): 4883-92.

NPL 12: Proc Natl Acad Sci USA. 2006 Jun. 20; 103 (25): 9643-8.
NPL 13: J Urol. 1999 November; 162 (5): 1779-84.
NPL 14: J Urol. 2000 March; 163 (3): 1027-32.
NPL 15: Nat Med. 2004 July; 10 (7): 712-8.

SUMMARY OF INVENTION

Technical Problem

An object of the present invention is to provide a novel compound that antagonizes the LPA1 receptor.

Solution to Problem

As a result of diligent investigation to solve the problems described above, the present inventors have found that a compound represented by formula [I] below (hereinafter, this may also be referred to as compound [I]) has an LPA1 receptor-antagonizing action.

Hereinafter, the present invention will be described in detail.

That is, the aspects of the present invention are as follows.

(1) One aspect of the present invention is to provide a compound represented by formula [I]:

[Chemical Formula 1]

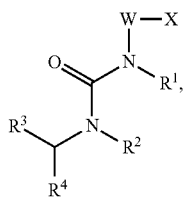

[I]

or a pharmaceutically acceptable salt thereof, or a hydrate thereof, wherein X represents carboxy, $C_{1-4}$ alkoxycarbonyl, carbamoyl, tetrazolyl, or a group selected from formula group [II]:

[Chemical Formula 2]
[II]

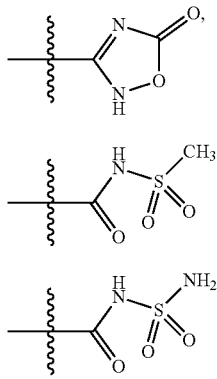

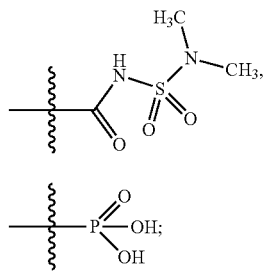

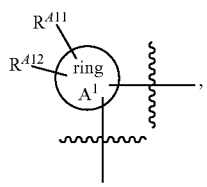

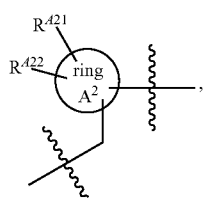

W represents linear $C_{1-3}$ alkanediyl or a structure selected from formula group [III]:

[Chemical Formula 3]
[III]

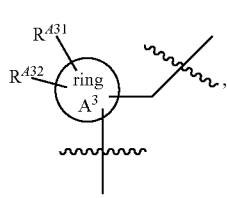

where
the linear $C_{1-3}$ alkanediyl is optionally substituted with one group selected from the group consisting of $C_{1-6}$ alkyl(the $C_{1-6}$ alkyl is optionally substituted with one group selected from the group consisting of hydroxy and carboxy), halo-$C_{1-6}$ alkyl, $C_{3-8}$ cycloalkyl, phenyl-$C_{1-3}$ alkyl, and pyridyl-$C_{1-3}$ alkyl, and
when the linear $C_{1-3}$ alkanediyl is substituted with one methyl, it is optionally further substituted with one methyl,
ring $A^1$, ring $A^2$, and ring $A^3$ each represent $C_{3-8}$ cycloalkane, a partially saturated 9- to 10-membered fused hydrocarbon aromatic ring, an oxygen atom-containing 4- to 8-membered saturated heterocycle, a sulfur atom-containing 4- to 8-membered saturated heterocycle, or a nitrogen atom-containing 4- to 8-membered saturated heterocycle,
where
the sulfur atom in the sulfur atom-containing 4- to 8-membered saturated heterocycle is optionally substituted with one to two oxo,
the nitrogen atom in the nitrogen atom-containing 4- to 8-membered saturated heterocycle is optionally substituted with one group selected from the group consisting of $C_{1-4}$ alkylcarbonyl and $C_{1-4}$ alkoxycarbonyl, and $R^{A11}$, $R^{A21}$, and $R^{A31}$ each independently represent a hydrogen atom, hydroxy, carboxy, a halogen atom, $C_{1-6}$ alkyl, $C_{1-6}$ alkoxy, $C_{1-6}$ alkylcarbonyl, or nitrogen atom-containing 4- to 6-membered saturated heterocyclyl(the nitrogen atom-containing 4- to 6-membered saturated heterocyclyl is optionally substituted with one $C_{1-3}$ alkyl), and $R^{A12}$, $R^{A22}$, and $R^{A32}$ each independently represent a hydrogen atom, a halogen atom, or methyl, or $R^{A11}$ and $R^{A12}$, $R^{A21}$ and $R^{A22}$, and $R^{A31}$ and $R^{A32}$ each optionally together form oxo, or $R^{A11}$ and $R^{A12}$, $R^{A21}$ and $R^{A22}$, and $R^{A31}$ and $R^{A32}$ each optionally form $C_{3-6}$ cycloalkane together with the carbon atom(s) in the adjacent ring;

$R^1$ represents a hydrogen atom or methyl;

$R^2$ represents $C_{6-10}$ alkyl, $C_{6-10}$ alkenyl, $C_{6-10}$ alkynyl, or a group represented by formula [IV-1] or [IV-2]:

[Chemical Formula 4]

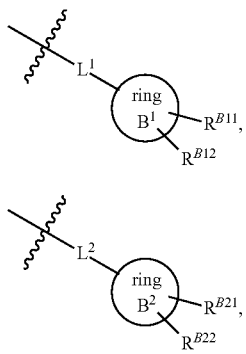

[IV-1]

[IV-2]

where ring $B^1$ represents $C_{3-8}$ cycloalkyl, nitrogen atom-containing 4- to 8-membered saturated heterocyclyl, phenyl, or nitrogen atom-containing 5- to 6-membered heteroaryl, $R^{B11}$ and $R^{B12}$ each independently represent a hydrogen atom, a halogen atom, $C_{1-6}$ alkyl, or $C_{1-6}$ alkoxy, $L^1$ represents $C_{3-8}$ alkanediyl(the $C_{3-8}$ alkanediyl is optionally substituted with 1 to 5 fluorine atoms), a structure represented by formula [V-6]: —$CH_2CH_2CH$=$C(CH_3)$—, or a structure represented by formula [V-1]:

[Chemical Formula 5]

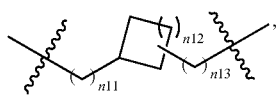

[V-1]

where n11 represents an integer of 0 to 3,
n12 represents an integer of 0 to 5,
n13 represents an integer of 0 to 3, and
one carbon atom in the $C_{3-8}$ alkanediyl, that is two or more atoms away from the nitrogen atom to which $R^2$ is bonded, is optionally replaced with formula —O—, formula —S—, or formula —N($R^{L11}$)—, and furthermore, two consecutive carbon atoms in the $C_{3-8}$ alkanediyl, that are one or more atoms away from the nitrogen atom to which $R^2$ is bonded, are optionally replaced with formula —C(=O)N($R^{L12}$)—, $R^{L11}$ represents a hydrogen atom or $C_{1-3}$ alkyl, and
$R^{L12}$ represents a hydrogen atom or $C_{1-3}$ alkyl, ring $B^2$ represents partially saturated 9- to 10-membered fused ring aryl or nitrogen atom-containing 9- to 10-membered fused ring heteroaryl, $R^{B21}$ and $R^{B22}$ each independently represent a hydrogen atom, a halogen atom, $C_{1-6}$ alkyl, or $C_{1-6}$ alkoxy, $L^2$ represents $C_{1-2}$ alkanediyl(the $C_{1-2}$ alkanediyl is optionally substituted with 1 to 4 fluorine atoms), $C_{3-6}$ alkanediyl(the $C_{3-6}$ alkanediyl is optionally substituted with 1 to 5 fluorine atoms), or a structure represented by formula [V-2]:

[Chemical Formula 6]

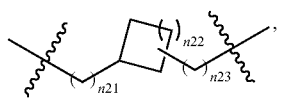

[V-2]

where n21 represents an integer of 0 to 3,
n22 represents an integer of 0 to 5,
n23 represents an integer of 0 to 3, and
one carbon atom in the $C_{3-6}$ alkanediyl, that is two or more atoms away from the nitrogen atom to which $R^2$ is bonded, is optionally replaced with formula —O—, formula —S—, or formula —N($R^{L21}$)—, and furthermore, two consecutive carbon atoms in the $C_{3-6}$ alkanediyl, that are one or more atoms away from the nitrogen atom to which $R^2$ is bonded, are optionally replaced with formula —C(=O)N($R^{L22}$)—, $R^{L21}$ represents a hydrogen atom or $C_{1-3}$ alkyl, and
$R^{L22}$ represents a hydrogen atom or $C_{1-3}$ alkyl;

$R^3$ represents a hydrogen atom or $C_{1-3}$ alkyl(the $C_{1-3}$ alkyl is optionally substituted with one group selected from the group consisting of hydroxy and methoxy); and $R^4$ represents a group represented by formula [VI]:

[Chemical Formula 7]

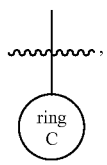

[VI]

where ring C represents phenyl, nitrogen atom-containing 6-membered heteroaryl, or 9- to 10-membered fused ring heteroaryl, the phenyl is substituted with one group selected from the group consisting of a halogen atom, $C_{1-6}$ alkyl, $C_{1-6}$ alkoxy, and $C_{1-6}$ alkylcarbonyl, and furthermore, the phenyl is optionally substituted with one to four groups that are the same or different, selected from the group consisting of hydroxy, carboxy, carbamoyl, cyano, a halogen atom, $C_{1-6}$ alkyl(the $C_{1-4}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one hydroxy), $C_{2-6}$ alkenyl, $C_{2-6}$ alkynyl, $C_{3-8}$ cycloalkyl(the $C_{3-8}$ cycloalkyl is optionally substituted with one hydroxy), $C_{1-6}$ alkoxy, halo-$C_{1-6}$ alkoxy, $C_3$-8 cycloalkoxy, $C_{1-6}$ alkylsulfanyl, $C_{1-6}$ alkylsulfinyl, $C_{1-6}$ alkylsulfonyl, mono-$C_{1-6}$ alkylamino, di-$C_{1-6}$ alkylamino, $C_{1-6}$ alkylcarbonyl, halo-$C_{1-6}$ alkylcarbonyl, $C_{1-6}$ alkoxycarbonyl, mono-$C_{1-6}$ alkylaminocarbonyl, and di-$C_{1-6}$ alkylaminocarbonyl, the nitrogen atom-containing 6-membered heteroaryl is substituted with one $C_{1-6}$ alkoxy, and furthermore, the nitrogen atom-containing 6-membered heteroaryl is optionally substituted with one to two groups that are the same or different, selected from the group consisting of cyano, $C_{1-6}$ alkyl, $C_{1-6}$ alkoxy, and oxo, and the 9- to 10-membered fused ring heteroaryl is optionally substituted with one to four groups that are the same or different, selected from the group consisting of $C_{1-6}$ alkyl, $C_{1-6}$ alkoxy, and oxo; or $R^3$ and $R^4$, together with their adjacent carbon atom, optionally form a partially saturated 9- to 10-membered fused hydrocarbon aromatic ring or a partially saturated oxygen atom-containing 9- to 10-membered fused heteroaromatic ring, where the partially saturated 9- to 10-membered fused hydrocarbon aromatic ring is optionally substituted with one to two halogen atoms, and the partially saturated oxygen atom-containing 9- to 10-membered fused heteroaromatic ring is optionally substituted with one to two halogen atoms.

(2) Another aspect of the present invention is to provide the compound according to (1), or a pharmaceutically acceptable salt thereof, or a hydrate thereof, wherein, in formula group [III] for W, $R^{A11}$, $R^{A21}$, and $R^{A31}$ each independently represent a hydrogen atom, hydroxy, carboxy, a halogen atom, $C_{1-6}$ alkyl, $C_{1-6}$ alkoxy, or nitrogen atom-containing 4- to 6-membered saturated heterocyclyl(the nitrogen atom-containing 4- to 6-membered saturated heterocyclyl is optionally substituted with one $C_{1-3}$ alkyl), and $R^{A12}$, $R^{A22}$, and $R^{A32}$ each independently represent a hydrogen atom, a halogen atom, or methyl, or $R^{A11}$ and $R^{A12}$, $R^{A21}$ and $R^{A22}$, and $R^{A31}$ and $R^{A32}$ each optionally together form oxo, or $R^{A11}$ and $R^{A12}$, $R^{A21}$ and $R^{A22}$, and $R^{A31}$ and $R^{A32}$ each optionally form $C_3$-6 cycloalkane together with the carbon atoms in the adjacent ring, and wherein, in formula [IV-1] for $R^2$, $L^1$ represents $C_{3-8}$ alkanediyl(the $C_{3-8}$ alkanediyl is optionally substituted with 1 to 5 fluorine atoms) or a structure represented by formula [V-1], where one carbon atom in the $C_{3-8}$ alkanediyl, that is two or more atoms away from the nitrogen atom to which $R^2$ is bonded, is optionally replaced with formula —O—, formula —S—, or formula —N($R^{L11}$)—, and furthermore, two consecutive carbon atoms in the $C_{3-8}$ alkanediyl, that are one or more atoms away from the nitrogen atom to which $R^2$ is bonded, are optionally replaced with formula —C(=O)N($R^{L12}$)—, $R^{L11}$ represents a hydrogen atom or $C_{1-3}$ alkyl, and $R^{L12}$ represents a hydrogen atom or $C_{1-3}$ alkyl.

(3) Another aspect of the present invention is to provide the compound according to (1) or (2), or a pharmaceutically acceptable salt thereof, or a hydrate thereof, wherein, in the above formula [I], W is linear $C_{1-3}$ alkanediyl or a structure selected from formula group [III]:

[Chemical Formula 8]

[III]

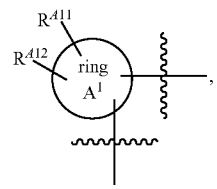

[III-1]

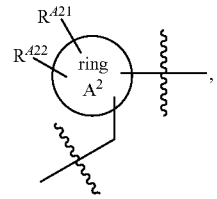

[III-2]

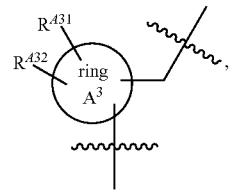

[III-3]

where the linear $C_{1-3}$ alkanediyl is optionally substituted with one group selected from the group consisting of $C_{1-6}$ alkyl(the $C_{1-6}$ alkyl is optionally substituted with one group selected from the group consisting of hydroxy and carboxy), halo-$C_{1-6}$ alkyl, $C_{3-8}$ cycloalkyl, phenyl-$C_{1-3}$ alkyl, and pyridyl-$C_{1-3}$ alkyl, and when the linear $C_{1-3}$ alkanediyl is substituted with one methyl, it is optionally further substituted with one methyl, ring $A^1$ is $C_{3-8}$ cycloalkane, dihydroindene, oxetane, tetrahydrofuran, tetrahydropyran, tetrahydrothiopyran, azetidine, pyrrolidine, or piperidine, ring $A^2$ is $C_{3-8}$ cycloalkane or tetrahydropyran, and ring $A^3$ is $C_{3-8}$ cycloalkane, dihydroindene, or tetrahydropyran, where the sulfur atom in the tetrahydrothiopyran is optionally substituted with one to two oxo, and the nitrogen atom in each of the azetidine, pyrrolidine, and piperidine is optionally substituted with one $C_{1-4}$ alkylcarbonyl, and $R^{A11}$ is a hydrogen atom, hydroxy, carboxy, a halogen atom, $C_{1-6}$ alkyl, $C_{1-6}$ alkoxy, $C_{1-6}$ alkylcarbonyl, or nitrogen atom-containing 4- to 6-membered saturated heterocyclyl(the nitrogen atom-containing 4- to 6-membered saturated heterocyclyl is optionally substituted with one $C_{1-3}$ alkyl), and
$R^{A12}$ represents a hydrogen atom, a halogen atom, or methyl, or
$R^{A11}$ and $R^{A12}$ optionally together form oxo,
$R^{A21}$ and $R^{A22}$ are both hydrogen atoms,
$R^{A31}$ and $R^{A32}$ are both hydrogen atoms, and furthermore,
$R^{A11}$ and $R^{A12}$ optionally form $C_{3-6}$ cycloalkane together with the carbon atom(s) in the adjacent ring;
$R^2$ is $C_{6-10}$ alkyl or a group represented by formula [IV-1] or [IV-2]:

[Chemical Formula 9]

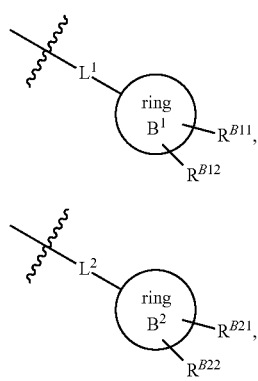

[IV-1]

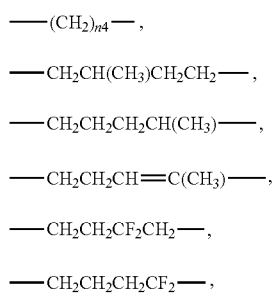

[IV-2]

where
ring $B^1$ is $C_{3-8}$ cycloalkyl, piperidinyl, phenyl, pyrazolyl, or pyridyl,
$R^{B11}$ and $R^{B12}$ are each independently a hydrogen atom, a halogen atom, $C_{1-6}$ alkyl, or $C_{1-6}$ alkoxy, and
$L^1$ is any of structures represented by formulas [V-3] to [V-12] and [V-14] to [V-19]:

[Chemical Formula 10]

——$(CH_2)_{n4}$——, [V-3]

——$CH_2CH(CH_3)CH_2CH_2$——, [V-4]

——$CH_2CH_2CH_2CH(CH_3)$——, [V-5]

——$CH_2CH_2CH═C(CH_3)$——, [V-6]

——$CH_2CH_2CF_2CH_2$——, [V-7]

——$CH_2CH_2CH_2CF_2$——, [V-8]

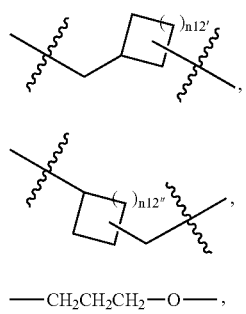

[V-9]

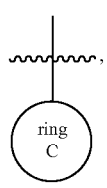

[V-10]

——$CH_2CH_2CH_2$—O——, [V-11]

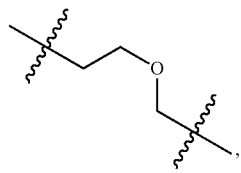

[V-12]

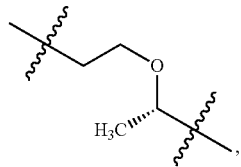

[V-14]

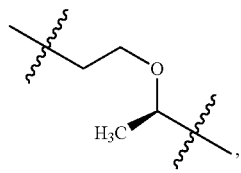

[V-15]

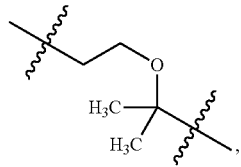

[V-16]

——$CH_2CH_2CH_2$—S——, [V-17]

——$CH_2CH_2CH_2$—$N(CH_3)$——, [V-18]

——$CH_2$—$C(═O)NH$—$CH_2$——, [V-19]

where
n4 represents an integer of 3 to 5,
n12' represents an integer of 0 to 3,
n12″ represents an integer of 0 to 3, and
ring $B^2$ is dihydroindenyl, indolyl, or isoindolinyl,
$R^{B21}$ and $R^{B22}$ are both hydrogen atoms, and
$L^2$ is a structure represented by formula [V-20]:
[Chemical Formula 11]

——$(CH_2)_{n5}$—— [V-20]

where
n5 represents an integer of 1 to 2; and
$R^4$ is a group represented by formula [VI]:

[Chemical Formula 12]

[VI]

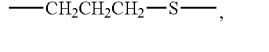

where
ring C is phenyl, pyridyl, pyrimidinyl, dihydropyridinyl, dihydrobenzofuranyl, benzodioxanyl, indolyl, indazolyl, benzimidazolyl, pyrazolopyridinyl, indolinyl, or dihydroquinazolinyl, the phenyl is substituted with one group selected from the group consisting of a halogen atom, $C_{1-6}$ alkyl, $C_{1-6}$ alkoxy, and $C_{1-6}$ alkylcarbonyl, and furthermore, the phenyl is optionally substituted with one to four groups that are the same or different, selected from the group consisting of hydroxy, carboxy, carbamoyl, cyano, a halogen atom, $C_{1-6}$ alkyl(the $C_{1-6}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one hydroxy), $C_{2-6}$ alkenyl, $C_{3-8}$ cycloalkyl(the $C_{3-8}$ cycloalkyl is optionally substituted with one hydroxy), $C_{1-6}$ alkoxy, halo-$C_{1-6}$ alkoxy, $C_{3-8}$ cycloalkoxy, $C_{1-6}$ alkylsulfinyl, $C_{1-6}$ alkylsulfonyl, mono-$C_{1-6}$ alkylamino, di-$C_{1-6}$ alkylamino, $C_{1-6}$ alkylcarbonyl, halo-$C_{1-6}$ alkylcarbonyl, $C_{1-6}$ alkoxycarbonyl, and mono-$C_{1-6}$ alkylaminocarbonyl, the pyridyl is substituted with one $C_{1-6}$ alkoxy, and furthermore, the pyridyl is optionally substituted with one group selected from the group consisting of cyano and $C_{1-6}$ alkoxy, the pyrimidinyl is substituted with one $C_{1-6}$ alkoxy, and furthermore, the pyrimidinyl is optionally substituted with one $C_{1-6}$ alkoxy, the dihydropyridinyl is substituted with one $C_{1-6}$ alkoxy, and furthermore, the dihydropyridinyl is optionally substituted with one to two groups that are the same or different, selected from the group consisting of $C_{1-6}$ alkyl and oxo, the dihydrobenzofuranyl and benzodioxanyl are optionally substituted with one $C_{1-6}$ alkoxy, the indolyl, indazolyl, benzimidazolyl, pyrazolopyridinyl, and indolinyl are optionally substituted with one to two groups that are the same or different, selected from the group consisting of $C_{1-6}$ alkyl and $C_{1-6}$ alkoxy, and the dihydroquinazolinyl is optionally substituted with one to four groups that are the same or different, selected from the group consisting of $C_{1-6}$ alkyl, $C_{1-6}$ alkoxy, and oxo; or the fused ring formed by $R^3$ and $R^4$ together with their adjacent carbon atom is dihydroindene or dihydrobenzofuran, and the dihydroindene and dihydrobenzofuran are optionally substituted with one to two halogen atoms.

(4) Another aspect of the present invention is to provide the compound according to (1) or (2), or a pharmaceutically acceptable salt thereof, or a hydrate thereof, wherein, in the above formula [I], X is carboxy, $C_{1-4}$ alkoxycarbonyl, or tetrazolyl;

$R^1$ is a hydrogen atom; and $R^2$ is a group represented by the above formula [IV-1] or [IV-2]:

[Chemical Formula 13]

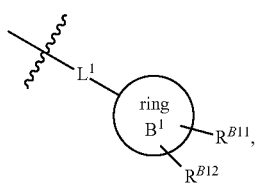

[IV-1]

-continued

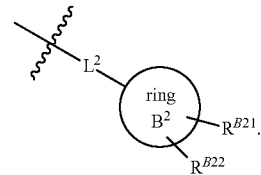

[IV-2]

(5) Another aspect of the present invention is to provide the compound according to any one of (1), (2), and (4), or a pharmaceutically acceptable salt thereof, or a hydrate thereof, wherein, in the above formula [I], W is methanediyl or a structure represented by formula [III-1]:

[Chemical Formula 14]

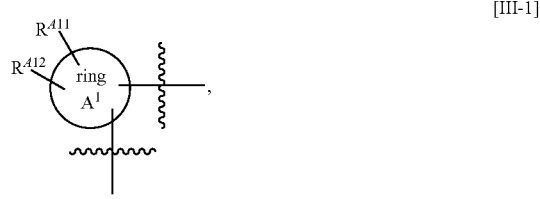

[III-1]

where the methanediyl is optionally substituted with one group selected from the group consisting of $C_{1-6}$ alkyl(the $C_{1-6}$ alkyl is optionally substituted with one group selected from the group consisting of hydroxy and carboxy), halo-$C_{1-6}$ alkyl, $C_{3-8}$ cycloalkyl, phenyl-$C_{1-3}$ alkyl, and pyridyl-$C_{1-3}$ alkyl, and when the methanediyl is substituted with one methyl, it is optionally further substituted with one methyl, and wherein, in the structure represented by formula [III-1], ring $A^1$ is $C_{3-8}$ cycloalkane, a partially saturated 9- to 10-membered fused hydrocarbon aromatic ring, an oxygen atom-containing 4- to 8-membered saturated heterocycle, a sulfur atom-containing 4- to 8-membered saturated heterocycle, or a nitrogen atom-containing 4- to 8-membered saturated heterocycle, where the sulfur atom in the sulfur atom-containing 4- to 8-membered saturated heterocycle is optionally substituted with one to two oxo, and the nitrogen atom in the nitrogen atom-containing 4- to 8-membered saturated heterocycle is optionally substituted with one group selected from the group consisting of $C_{1-4}$ alkylcarbonyl and $C_{1-4}$ alkoxycarbonyl, and $R^{A11}$ is a hydrogen atom, hydroxy, carboxy, a halogen atom, $C_{1-6}$ alkyl, $C_{1-6}$ alkoxy, or nitrogen atom-containing 4- to 6-membered saturated heterocyclyl(the nitrogen atom-containing 4- to 6-membered saturated heterocyclyl is optionally substituted with one $C_{1-3}$ alkyl), and $R^{A12}$ is a hydrogen atom, a halogen atom, or methyl, or $R^{A11}$ and $R^{A12}$ optionally together form oxo, and furthermore, $R^{A11}$ and $R^{A12}$ optionally form $C_{3-6}$ cycloalkane together with the carbon atom(s) in the adjacent ring.

(6) Another aspect of the present invention is to provide the compound according to any one of (1), (2), (4), and (5), or a pharmaceutically acceptable salt thereof, or a hydrate thereof, wherein, in the above formula [I],
$R^4$ is a group represented by formula [VI]:

[Chemical Formula 15]

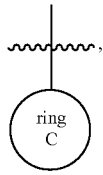

[VI]

where
ring C is phenyl,
the phenyl is substituted with one group selected from the group consisting of a halogen atom, $C_{1-6}$ alkyl, $C_{1-6}$ alkoxy, and $C_{1-6}$ alkylcarbonyl, and furthermore,
the phenyl is optionally substituted with one to four groups that are the same or different, selected from the group consisting of hydroxy, carboxy, carbamoyl, cyano, a halogen atom, $C_{1-6}$ alkyl(the $C_{1-6}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one hydroxy), $C_{2-6}$ alkenyl, $C_{2-6}$ alkynyl, $C_{3-8}$ cycloalkyl(the $C_{3-8}$ cycloalkyl is optionally substituted with one hydroxy), $C_{1-6}$ alkoxy, halo-$C_{1-6}$ alkoxy, $C_{3-8}$ cycloalkoxy, $C_{1-6}$ alkylsulfanyl, $C_{1-6}$ alkylsulfinyl, $C_{1-6}$ alkylsulfonyl, mono-$C_{1-6}$ alkylamino, di-$C_{1-6}$ alkylamino, $C_{1-6}$ alkylcarbonyl, halo-$C_{1-6}$ alkylcarbonyl, $C_{1-6}$ alkoxycarbonyl, mono-$C_{1-6}$ alkylaminocarbonyl, and di-$C_{1-6}$ alkylaminocarbonyl.

(7) Another aspect of the present invention is to provide the compound according to any one of (1), (2), and (4) to (6), or a pharmaceutically acceptable salt thereof, or a hydrate thereof,
wherein, in the above formula [I],
$R^2$ is a group represented by formula [IV-1] or [IV-2]:

[Chemical Formula 16]

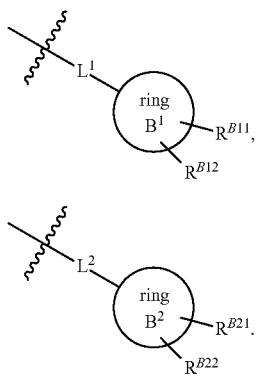

where
ring $B^1$ is phenyl,
$R^{B11}$ and $R^{B12}$ are each independently a hydrogen atom, a halogen atom, $C_{1-6}$ alkyl, or $C_{1-6}$ alkoxy, and
$L^1$ is any of structures represented by formulas [V-3] to [V-5], [V-7] to [V-8], [V-11] to [V-12], and [V-14] to [V-16]:

[Chemical Formula 17]

—(CH$_2$)$_{n4}$—,   [V-3]

—CH$_2$CH(CH$_3$)CH$_2$CH$_2$—,   [V-4]

—CH$_2$CH$_2$CH$_2$CH(CH$_3$)—,   [V-5]

—CH$_2$CH$_2$CF$_2$CH$_2$—,   [V-7]

—CH$_2$CH$_2$CH$_2$CF$_2$—,   [V-8]

—CH$_2$CH$_2$CH$_2$—O—,   [V-11]

[V-12]

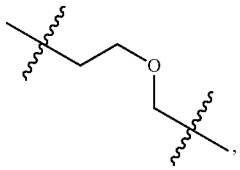

[V-14]

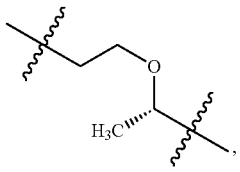

[V-15]

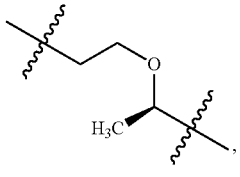

[V-16]

where
n4 represents an integer of 3 to 5, and
ring $B^2$ is dihydroindenyl, indolyl, or isoindolinyl,
$R^{B21}$ and $R^{B22}$ are both hydrogen atoms, and
$L^2$ is a structure represented by formula [V-20]:

[Chemical Formula 18]

—(CH$_2$)$_{n5}$—   [V-20]

where
n5 is an integer of 1 to 2.

(8) Another aspect of the present invention is to provide the compound according to any one of (4) to (7), or a pharmaceutically acceptable salt thereof, or a hydrate thereof, wherein, in the above formula [I],
X is carboxy;
W is any of structures represented by formulas [III-4] to [III-17]:
[Chemical Formula 19]
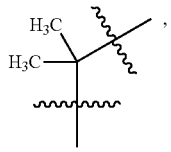  [III-4]
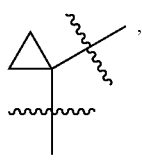  [III-5]
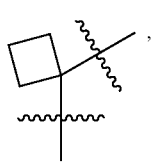  [III-6]
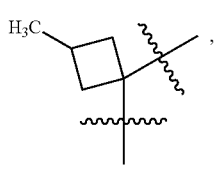  [III-7]
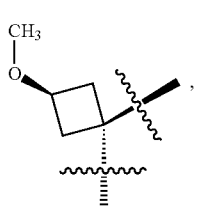  [III-8]
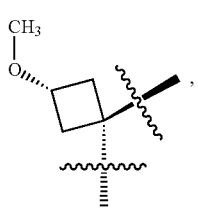  [III-9]
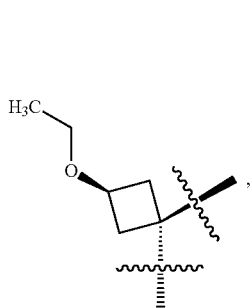  [III-10]
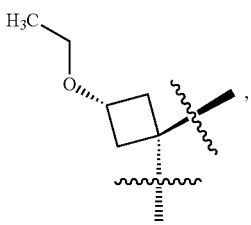  [III-11]
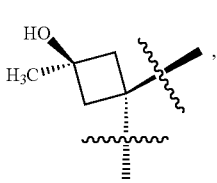  [III-12]
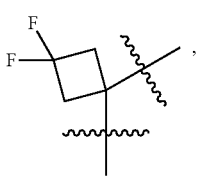  [III-13]
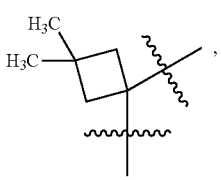  [III-14]
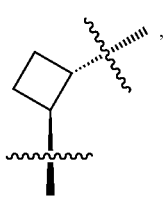  [III-15]
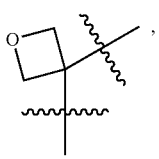  [III-16]
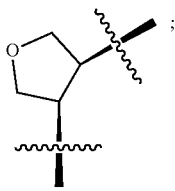  [III-17]

$R^2$ is a group represented by formula [IV-1] or [IV-2]:

[Chemical Formula 20]

[IV-1]

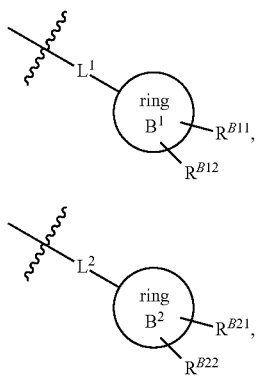

[IV-2]

where
ring $B^1$ is phenyl,
$R^{B11}$ and $R^{B12}$ are both hydrogen atoms, and
$L^1$ is a structure represented by formula [V-3], [V-8], [V-12], [V-14], or [V-15]:

[Chemical Formula 21]

[V-3]

[V-8]

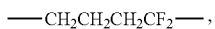

[V-12]

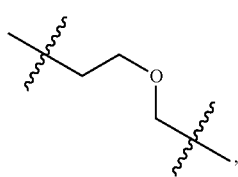

[V-14]

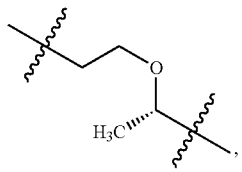

[V-15]

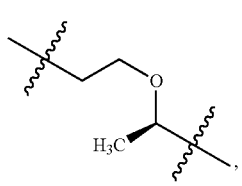

where
n4 is an integer of 3 to 4, and
ring $B^2$ is dihydroindenyl,
$R^{B21}$ and $R^{B22}$ are both hydrogen atoms, and
$L^2$ is a structure represented by formula [V-20]:

[Chemical Formula 22]

 [V-20], where
n5 is 2;
$R^3$ is methyl having a steric configuration represented by formula [VII]:

[Chemical Formula 23]

[VII]

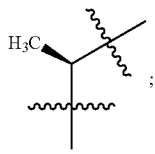

and
$R^4$ is a group represented by any of formulas [VI-1] to [VI-21]:

[Chemical Formula 24]

[VI-1]

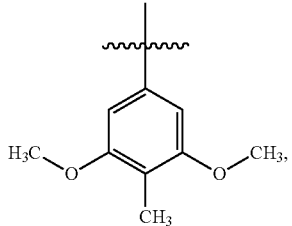

[VI-2]

[VI-3]

[VI-4]

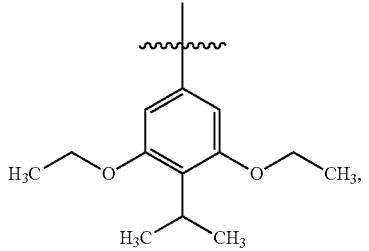

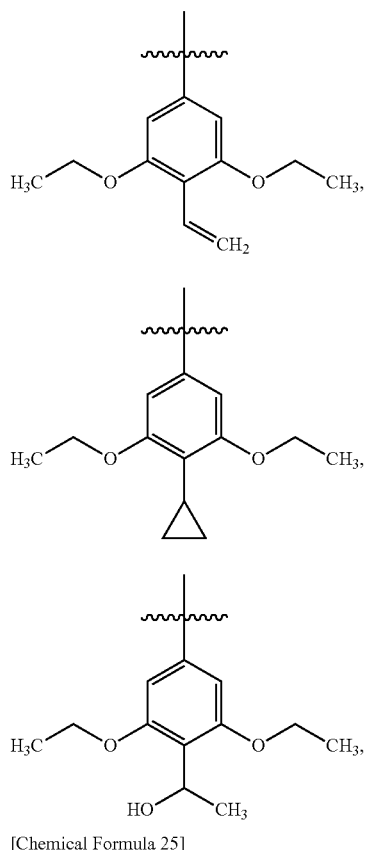
[Chemical Formula 25]
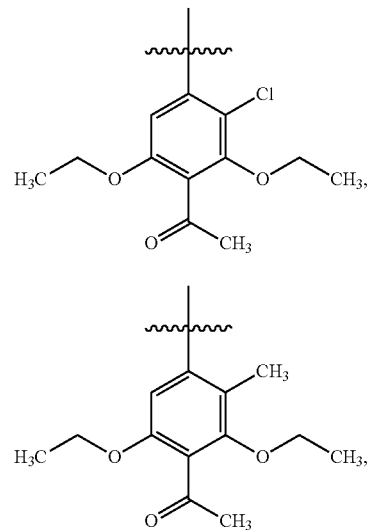
[Chemical Formula 26]
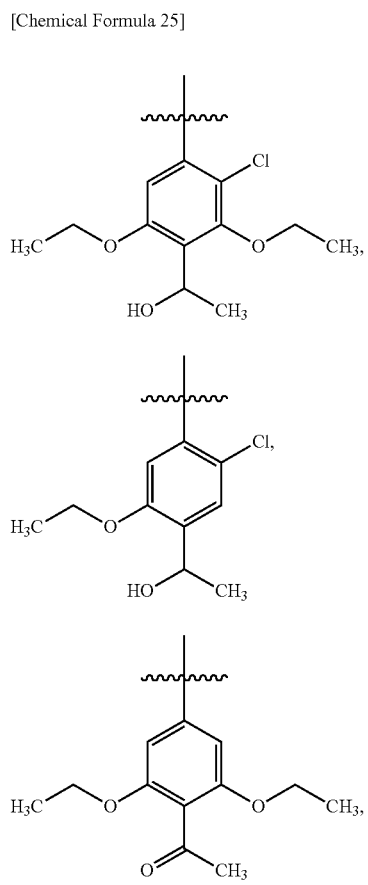

-continued
[VI-17]
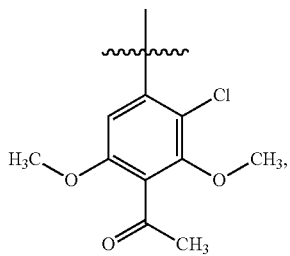
[VI-18]
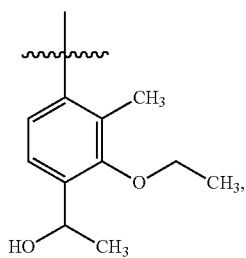
[VI-19]
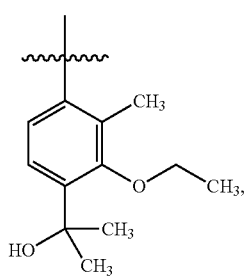
[VI-20]
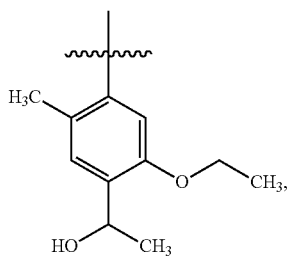
[VI-21]
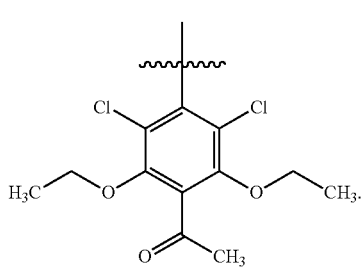
(9) Another aspect of the present invention is to provide the compound according to any one of (4) to (7), or a pharmaceutically acceptable salt thereof, or a hydrate thereof,
wherein, in the above formula [I],
X is carboxy;
W is a structure represented by any of formulas [III-4] to [III-11], [III-13] to [III-14], and [III-18] to [III-19]:
[Chemical Formula 27]
[III-4]
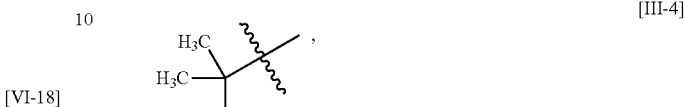
[III-5]
[III-6]
[III-7]
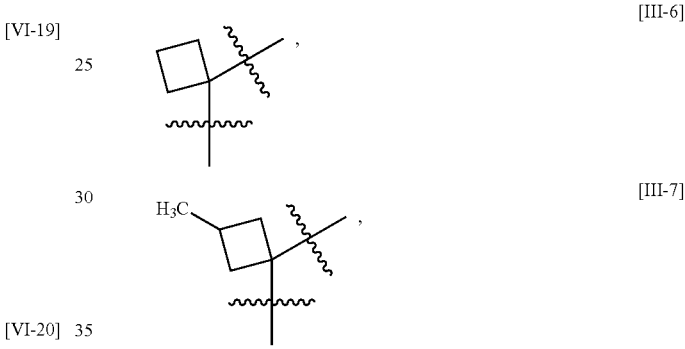
[III-8]
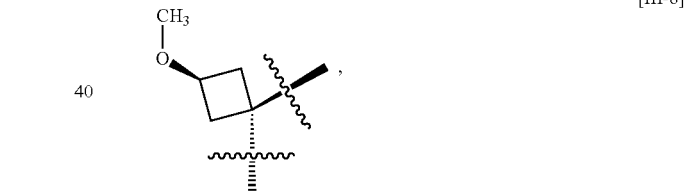
[III-9]
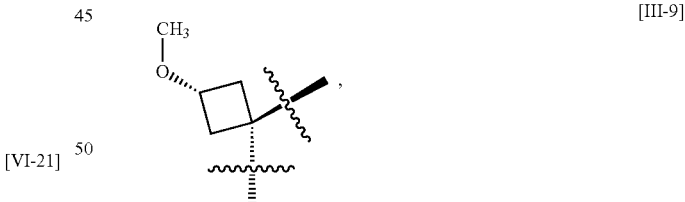
[III-10]
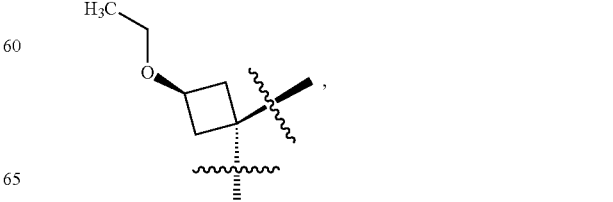

-continued

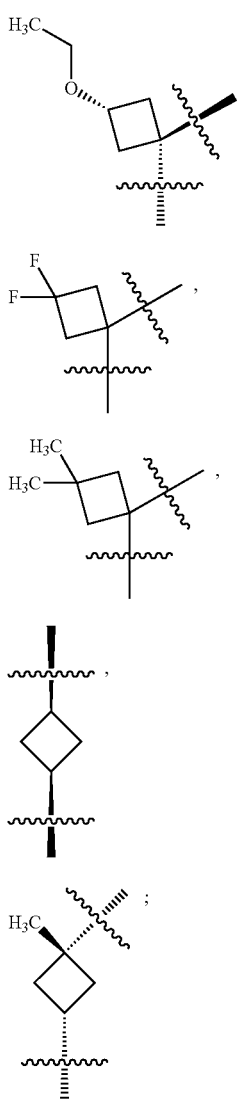

R² is a group represented by formula [IV-1] or [IV-2]:
[Chemical Formula 28]

[Chemical Formula 28]

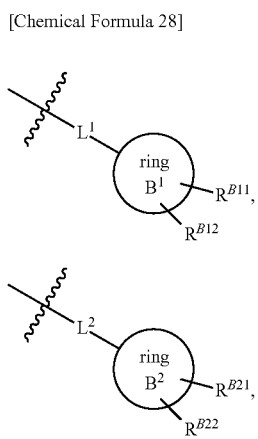

where ring B¹ is phenyl,
$R^{B11}$ and $R^{B12}$ are both hydrogen atoms, and
$L^1$ is a structure represented by formula [V-3], [V-8], or [V-14]:

[Chemical Formula 29]

$$—(CH_2)_{n4}—, \quad [V\text{-}3]$$

$$—CH_2CH_2CH_2CF_2—, \quad [V\text{-}8]$$

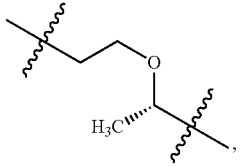

[V-14]

where
n4 is 4, and
ring B² is dihydroindenyl,
$R^{B21}$ and $R^{B22}$ are both hydrogen atoms, and
$L^2$ is a structure represented by formula [V-20]:
[Chemical Formula 30]

$$—(CH_2)_{n5}— \quad [V\text{-}20]$$

where
n5 is 2;
R³ is methyl having a steric configuration represented by formula [VII]:
[Chemical Formula 31]

[Chemical Formula 31]

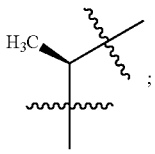

[VII]

and
R⁴ is a group represented by formula [VI-2], [VI-3], [VI-8], [VI-10] to [VI-12], [VI-16], [VI-19], or [VI-21]:

[Chemical Formula 32]

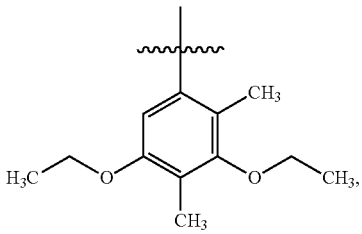

[VI-2]

[VI-3]
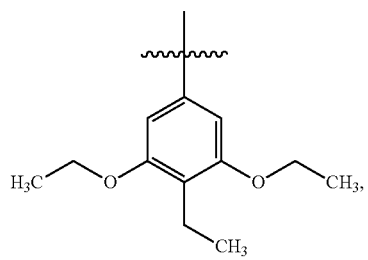
[VI-8]
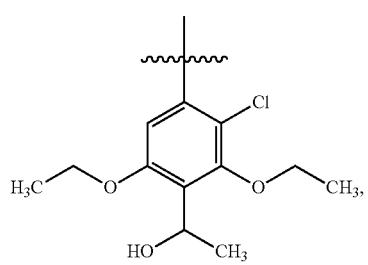
[VI-10]
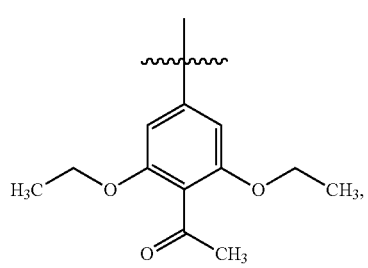
[VI-11]
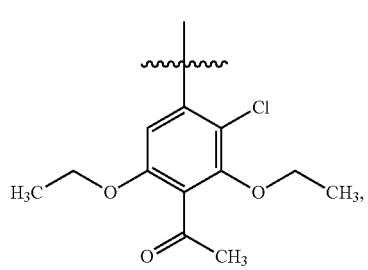
[Chemical Formula 33]
[VI-12]
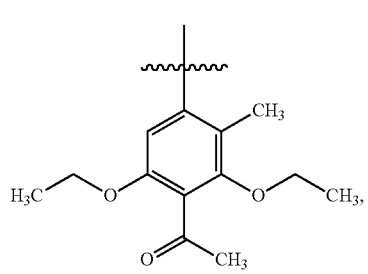
[VI-16]
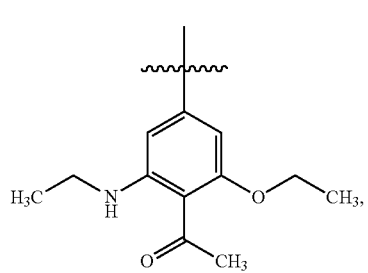
[VI-19]
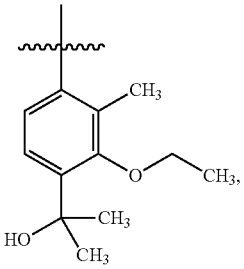
[VI-21]
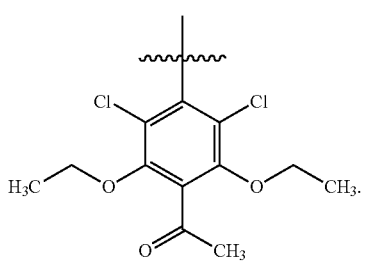
(10) Another aspect of the present invention is to provide the compound according to any one of (4) to (7), or a pharmaceutically acceptable salt thereof, or a hydrate thereof,
wherein, in the above formula [I],
X is carboxy or tetrazolyl;
W is a structure represented by formula [III-5], [III-8] to [III-11], or [III-13]:
[Chemical Formula 34]
[III-5]
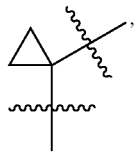
[III-8]
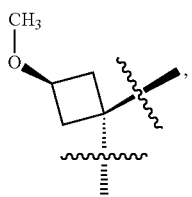
[III-9]
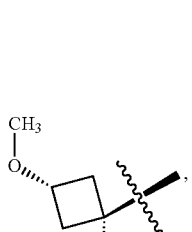

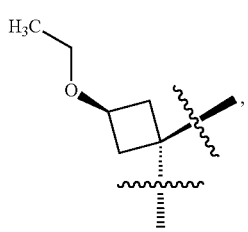  [III-10]

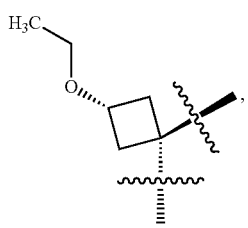  [III-11]

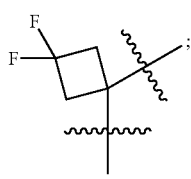  [III-13]

$R^2$ is a group represented by formula [IV-1] or [IV-2]:

[Chemical Formula 35]

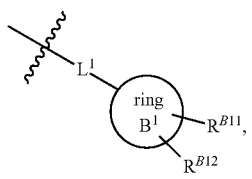  [IV-1]

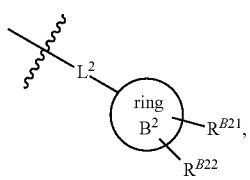  [IV-2]

where
ring $B^1$ is phenyl,
$R^{B11}$ and $R^{B12}$ are both hydrogen atoms, and
$L^1$ is a structure represented by formula [V-3], [V-12], or [V-14]:

[Chemical Formula 36]

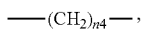  [V-3]

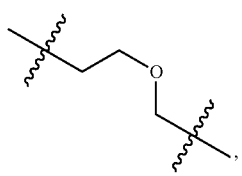  [V-12]

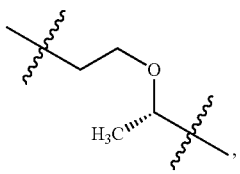  [V-14]

where
n4 is an integer of 4, and
ring $B^2$ is dihydroindenyl,
$R^{B21}$ and $R^{B22}$ are both hydrogen atoms, and
$L^2$ is a structure represented by formula [V-20]:

[Chemical Formula 37]

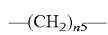  [V-20]

where
n5 is 2;
$R^3$ is methyl having a steric configuration represented by formula [VII]:

[Chemical Formula 38]

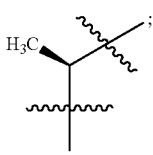  [VII]

and
$R^4$ is a group represented by formula [VI-2], [VI-7], [VI-8], [VI-10], [VI-11], or [VI-12]:

[Chemical Formula 39]

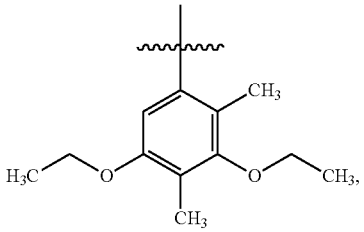  [VI-2]

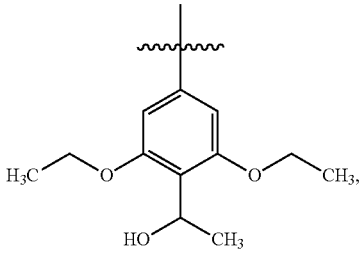  [VI-7]

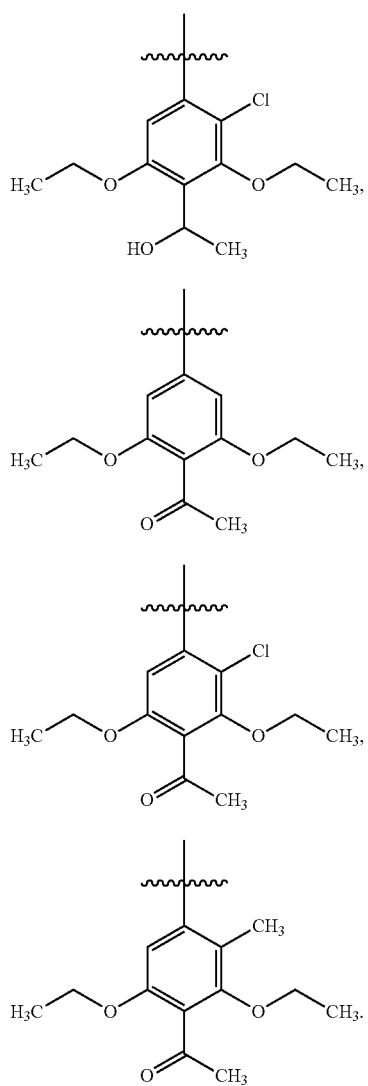
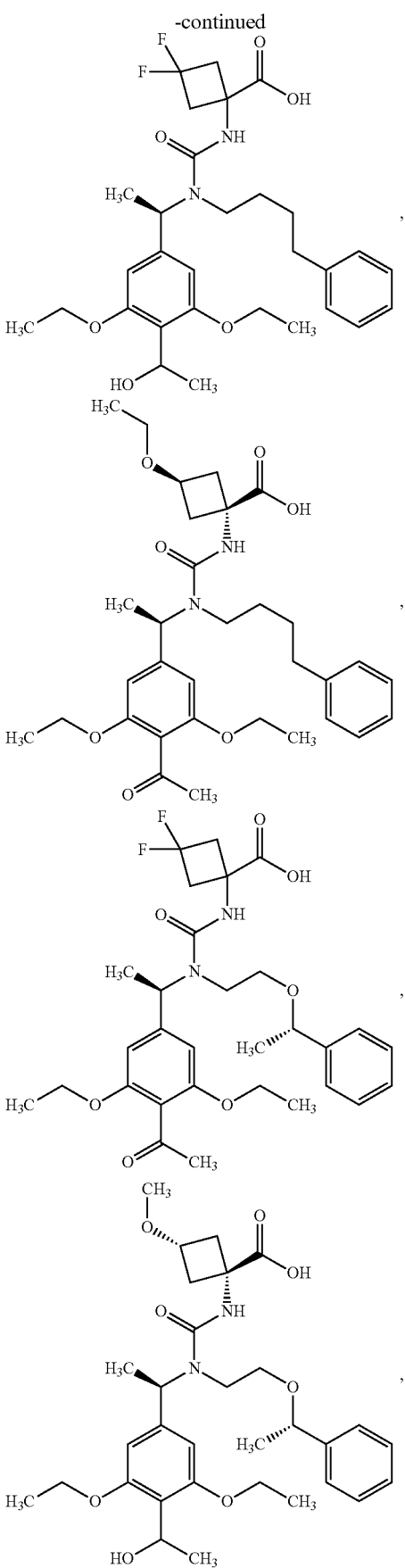
(11) Another aspect of the present invention is to provide the compound according to (1), which is any of the following:
[Chemical Formula 40]
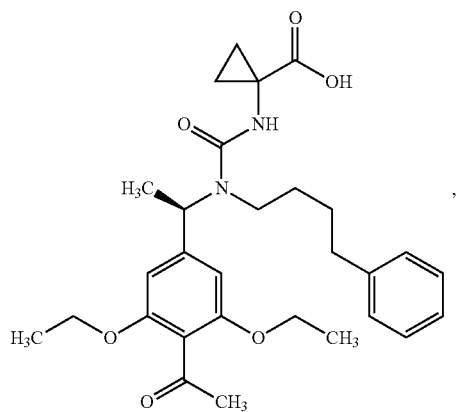

31
-continued
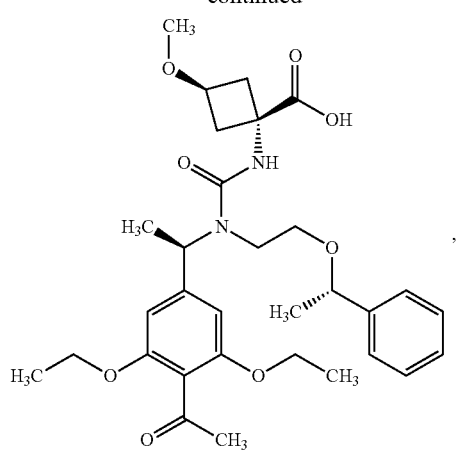
,
[Chemical Formula 14]
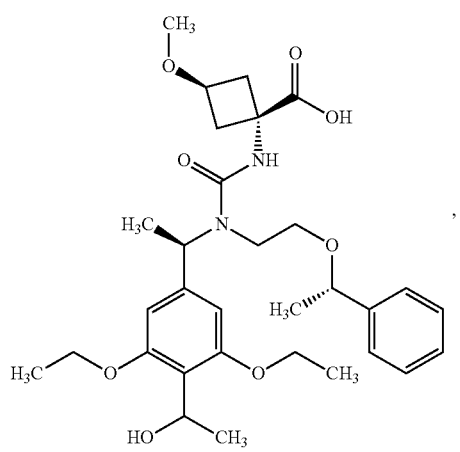
,
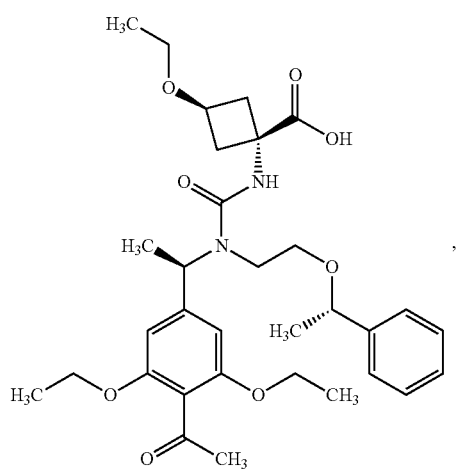
,
32
-continued
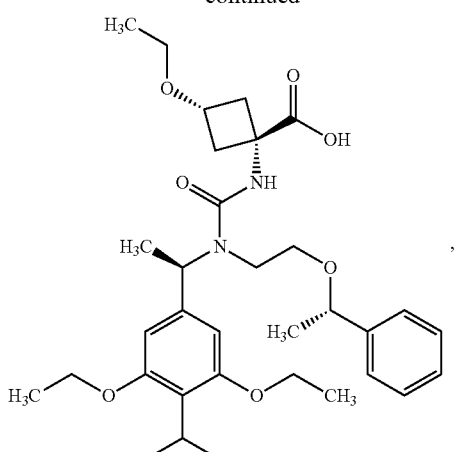
,
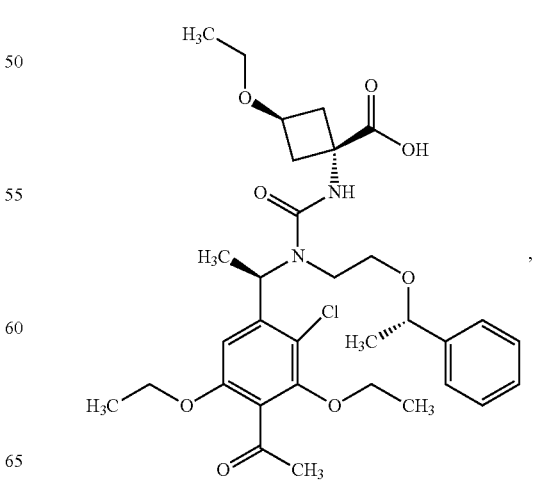
, 33
-continued
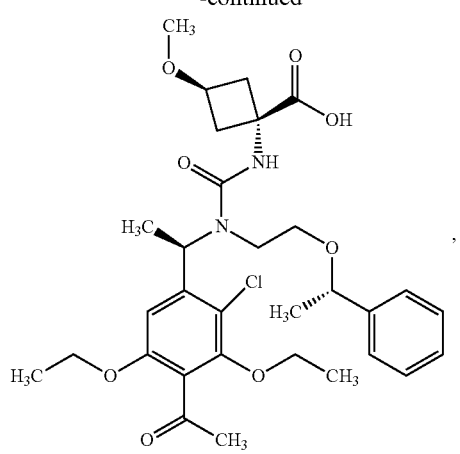
[Chemical Formula 42]
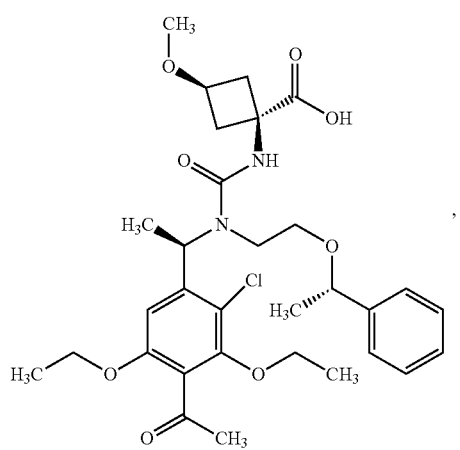
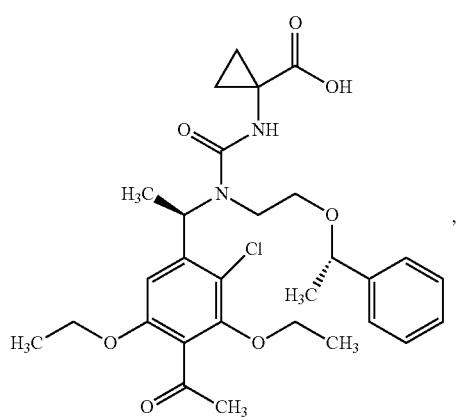
34
-continued
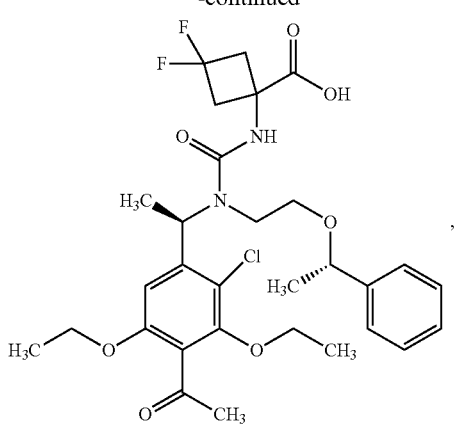
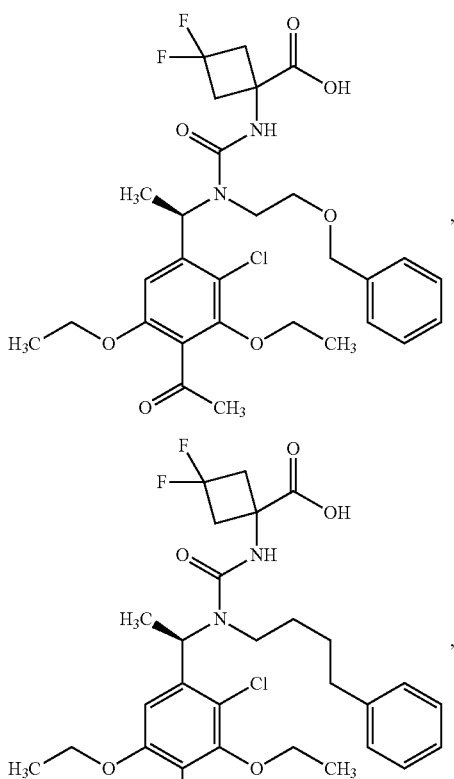
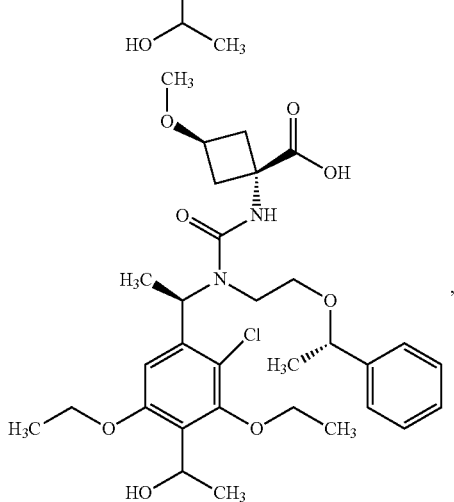

35
-continued
[Chemical Formula 43]
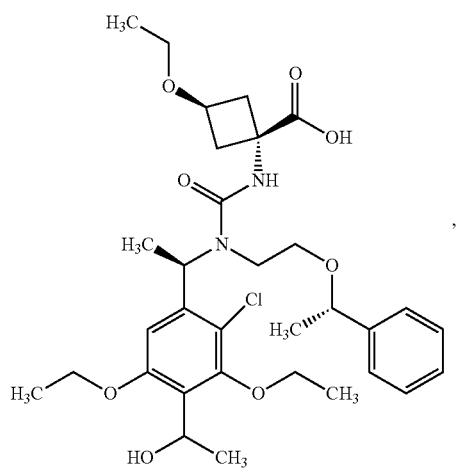
,
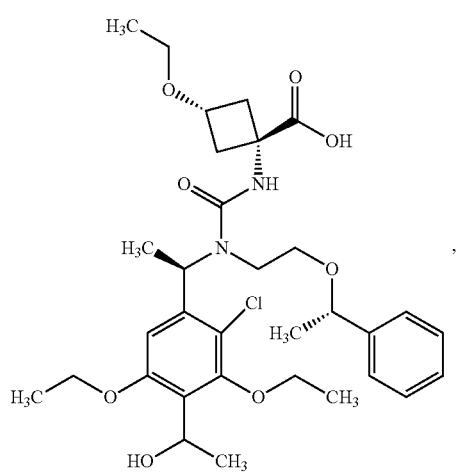
,
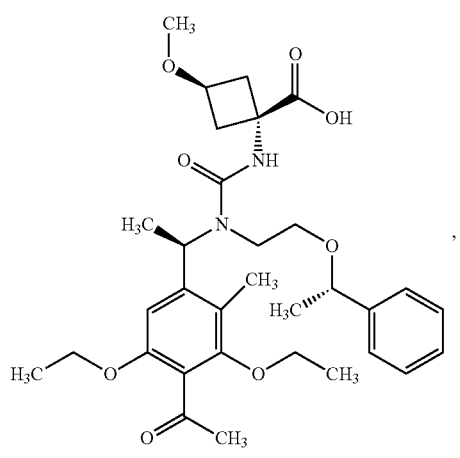
,
36
-continued
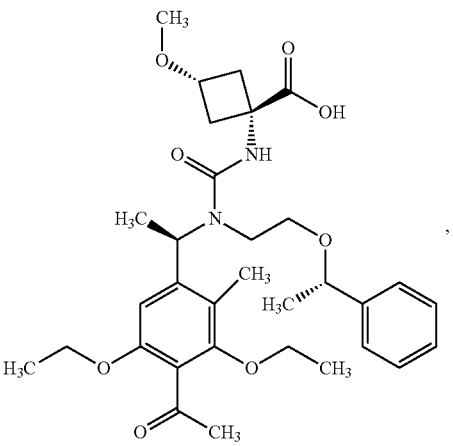
,
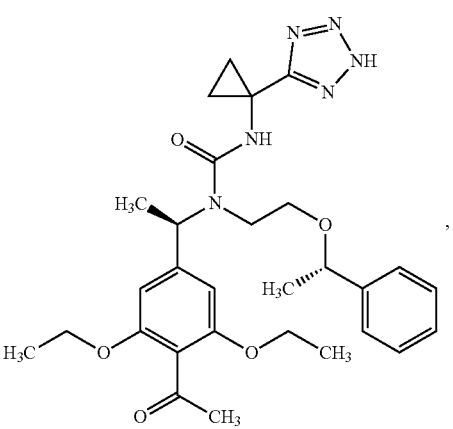
, -continued
[Chemical Formula 44]
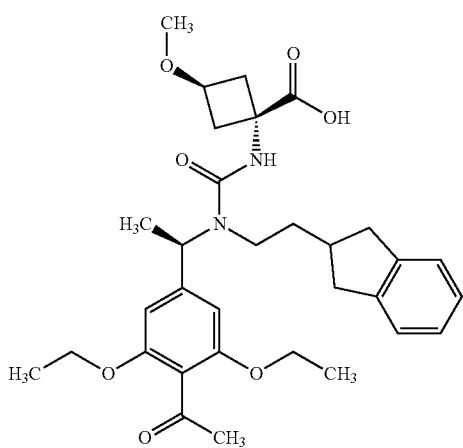
or a pharmaceutically acceptable salt thereof, or a hydrate thereof.
(12) Another aspect of the present invention is to provide the compound according to (1), which is any of the following:
[Chemical Formula 45]
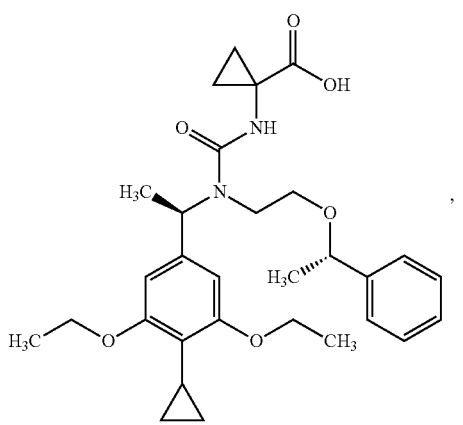
,
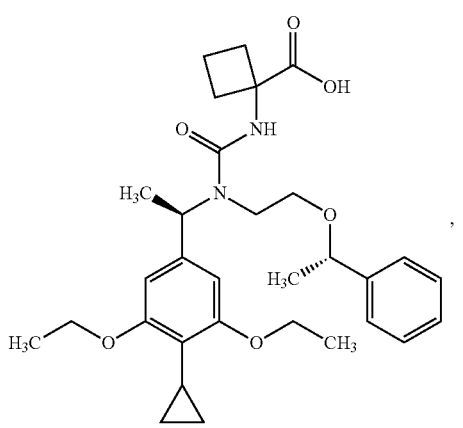
,
-continued
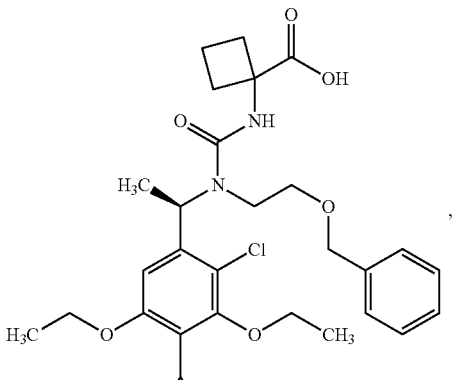
,
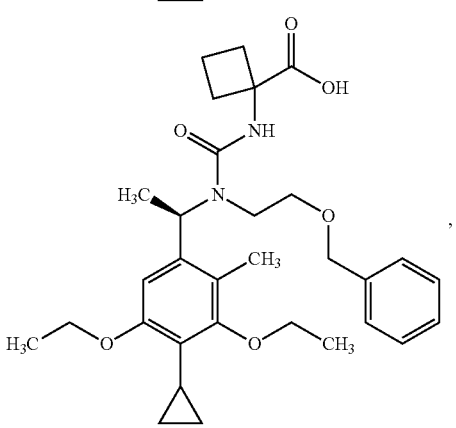
,
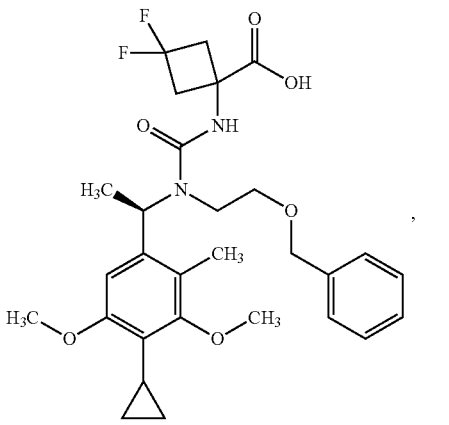
,
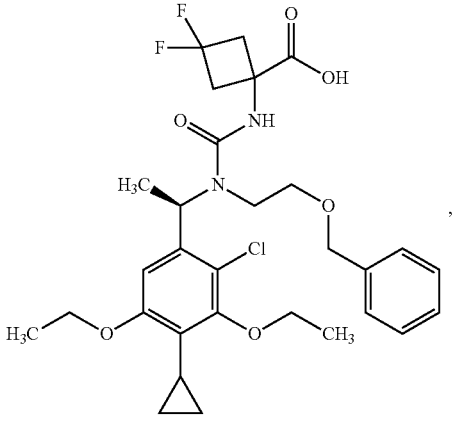
, 39
-continued
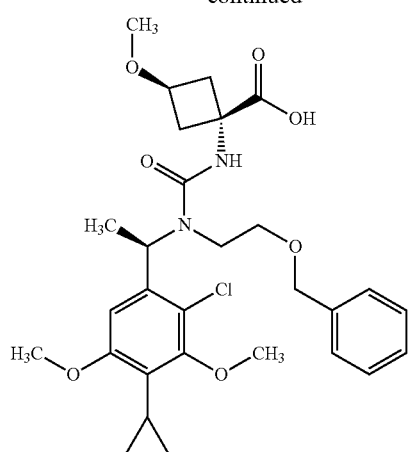
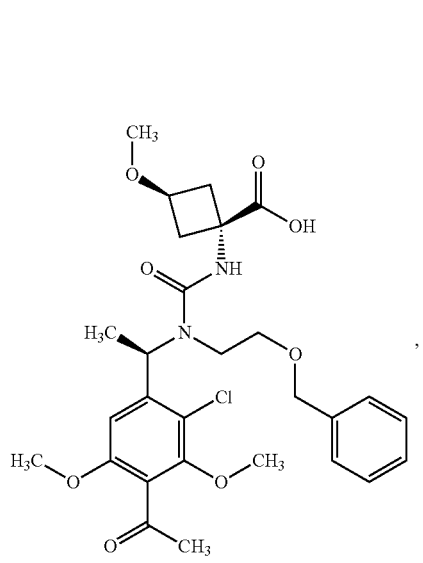
[Chemical Formula 46]
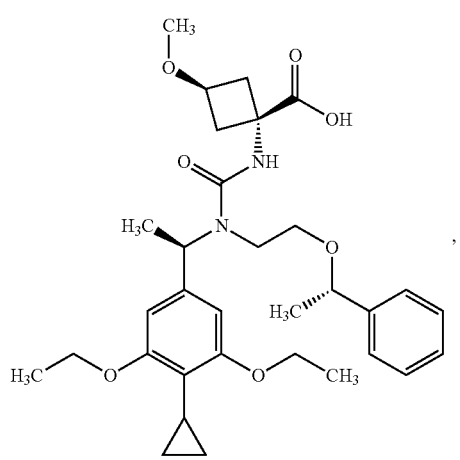
40
-continued
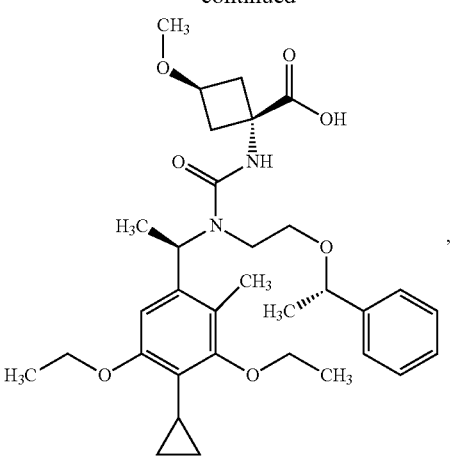
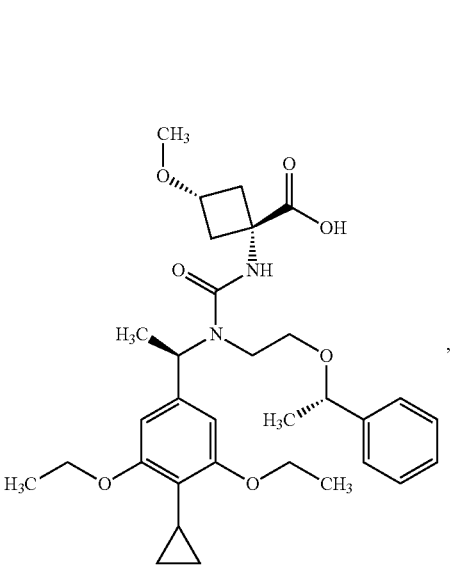
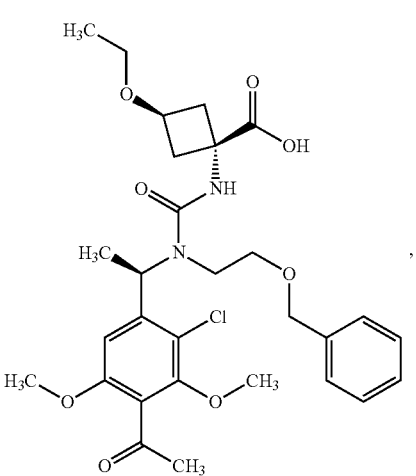

-continued

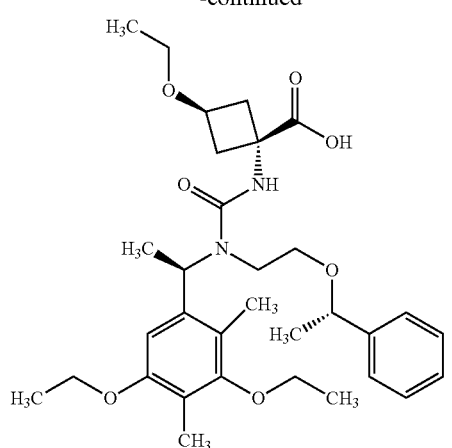,

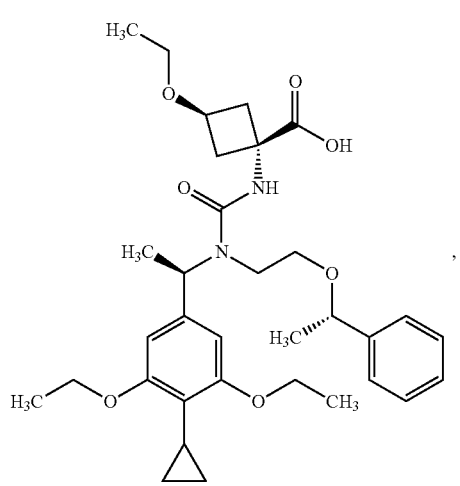,

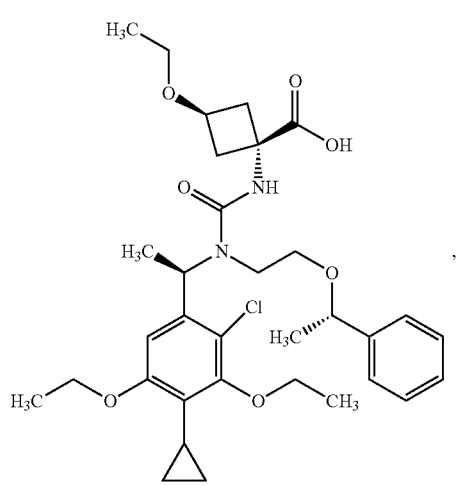,

-continued

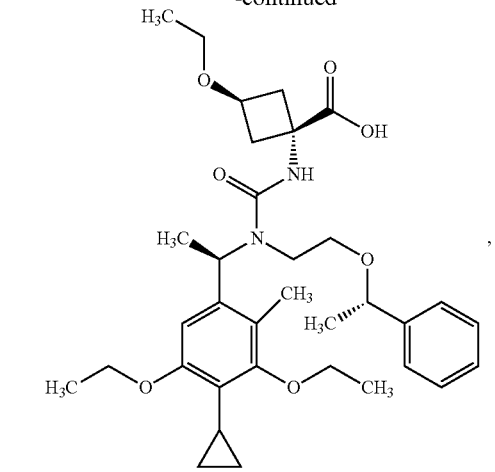,

[Chemical Formula 47]

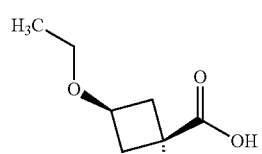

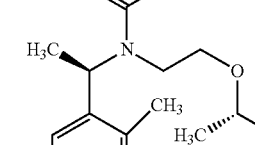

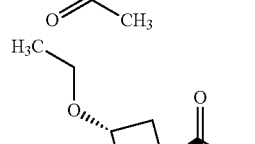

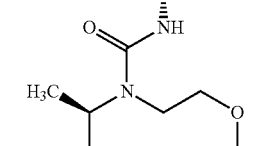

or a pharmaceutically acceptable salt thereof, or a hydrate thereof.

(13) Another aspect of the present invention is to provide a medicament comprising the compound according to any one of (1) to (12) or a pharmaceutically acceptable salt thereof, or a hydrate thereof, as an active ingredient.

(14) Another aspect of the present invention is to provide an LPA1 receptor antagonist comprising the compound according to any one of (1) to (12) or a pharmaceutically acceptable salt thereof, or a hydrate thereof, as an active ingredient.

(15) Another aspect of the present invention is to provide a drug for preventing or treating systemic scleroderma, comprising the compound according to any one of (1) to (12) or a pharmaceutically acceptable salt thereof, or a hydrate thereof, as an active ingredient.

(16) Another aspect of the present invention is to provide an LPA1 receptor antagonist comprising, as an active ingredient, a compound represented by formula [Ia]:

[Chemical Formula 48]

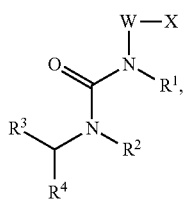

[Ia]

or a pharmaceutically acceptable salt thereof, or a hydrate thereof, wherein

X represents carboxy, $C_{1-4}$ alkoxycarbonyl, carbamoyl, tetrazolyl, or a structure selected from formula group [IIa]:

[Chemical Formula 49]
[IIa]

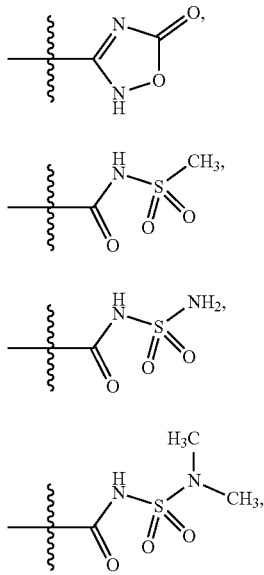

[II-1a]

[II-2a]

[II-3a]

[II-4a]

[II-5a]

W represents linear $C_{1-3}$ alkanediyl or a structure selected from formula group [IIIa]:

[Chemical Formula 50]
[IIIa]

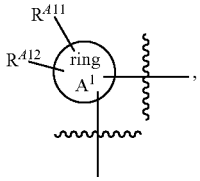

[III-1a]

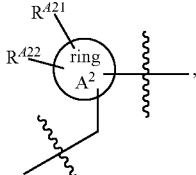

[III-2a]

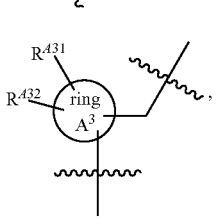

[III-3a]

where the linear $C_{1-3}$ alkanediyl is optionally substituted with one group selected from the group consisting of $C_{1-6}$ alkyl(the $C_{1-6}$ alkyl is optionally substituted with one group selected from the group consisting of hydroxy and carboxy), halo-$C_{1-6}$ alkyl, $C_{3-8}$ cycloalkyl, phenyl-$C_{1-3}$ alkyl, and pyridyl-$C_{1-3}$ alkyl, and when the linear $C_{1-3}$ alkanediyl is substituted with one methyl, it is optionally further substituted with one methyl, ring $A^1$, ring $A^2$, and ring $A^3$ each represent $C_{3-8}$ cycloalkane, a partially saturated 9- to 10-membered fused hydrocarbon aromatic ring, an oxygen atom-containing 4- to 8-membered saturated heterocycle, a partially saturated oxygen atom-containing 9- to 10-membered fused saturated heterocycle, a sulfur atom-containing 4- to 8-membered saturated heterocycle, a partially saturated nitrogen atom-containing 9- to 10-membered fused saturated heterocycle, a nitrogen atom-containing 4- to 8-membered saturated heterocycle, or a partially saturated sulfur atom-containing 9- to 10-membered fused saturated heterocycle, where the sulfur atom in each of the sulfur atom-containing 4- to 8-membered saturated heterocycle and partially saturated sulfur atom-containing 9- to 10-membered fused saturated heterocycle is optionally substituted with one to two oxo, and the nitrogen atom in each of the nitrogen atom-containing 4- to 8-membered saturated heterocycle and partially saturated nitrogen atom-containing 9- to 10-membered fused saturated heterocycle is optionally substituted with one group selected from the group consisting of $C_{1-4}$ alkylcarbonyl and $C_{1-4}$ alkoxycarbonyl, $R^{411}$, $R^{421}$, and $R^{431}$ each independently represent a hydrogen atom, hydroxy, carboxy, a halogen atom, $C_{1-6}$ alkyl, $C_{1-6}$ alkoxy, $C_{1-6}$ alkylcarbonyl, or nitrogen atom-containing 4- to 6-membered saturated heterocyclyl(the nitrogen atom-containing 4- to 6-membered saturated heterocyclyl is optionally substituted with one $C_{1-3}$ alkyl), and $R^{A12}$, $R^{A22}$, and $R^{A32}$ each independently represent a hydrogen atom, a halogen atom, or methyl, or $R^{A11}$ and $R^{A12}$, $R^{A21}$ and $R^{A22}$, and $R^{A31}$ and $R^{A32}$ each optionally together form oxo, or $R^{A11}$ and $R^{A12}$, $R^{A21}$ and $R^{A22}$, and $R^{A31}$ and $R^{A32}$ each optionally form $C_{3-6}$ cycloalkane together with the carbon atom(s) in the adjacent ring A;

$R^1$ represents a hydrogen atom or methyl;

$R^2$ represents $C_{1-10}$ alkyl, $C_{2-10}$ alkenyl, $C_{2-10}$ alkynyl, or a group represented by formula [IVa]:

[Chemical Formula 51]

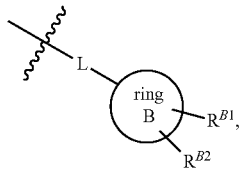

[IVa]

where ring B represents $C_{3-8}$ cycloalkyl, 4- to 8-membered saturated heterocyclyl, phenyl, 9- to 10-membered fused aryl, 5- to 6-membered heteroaryl, or 9- to 10-membered fused heteroaryl, $R^{B1}$ and $R^{B2}$ each independently represent a hydrogen atom, a halogen atom, $C_{1-6}$ alkyl, or $C_{1-6}$ alkoxy, and L represents $C_{1-2}$ alkanediyl(the $C_{1-2}$ alkanediyl is optionally substituted with 1 to 4 fluorine atoms), $C_{3-8}$ alkanediyl(the $C_{3-8}$ alkanediyl is optionally substituted with 1 to 5 fluorine atoms), a structure represented by formula [V-6]: —$CH_2CH_2CH$=$C(CH_3)$—, or a structure represented by formula [V-1a]:

[Chemical Formula 52]

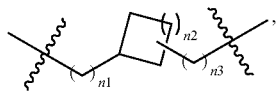

[V-1a]

where n1 represents an integer of 0 to 3, n2 represents an integer of 0 to 5, n3 represents an integer of 0 to 3, and one carbon atom in the $C_{3-8}$ alkanediyl, that is two or more atoms away from the nitrogen atom to which $R^2$ is bonded, is optionally replaced with formula —O—, formula —S—, or formula —N($R^{L1}$)—, and furthermore, two consecutive carbon atoms in the $C_{3-8}$ alkanediyl, that are one or more atoms away from the nitrogen atom to which $R^2$ is bonded, are optionally replaced with formula —C(=O)N($R^{L2}$)—, $R^{L1}$ represents a hydrogen atom or $C_{1-3}$ alkyl, and $R^{L2}$ represents a hydrogen atom or $C_{1-3}$ alkyl;

$R^3$ represents a hydrogen atom or $C_{1-3}$ alkyl(the $C_{1-3}$ alkyl is optionally substituted with one group selected from the group consisting of hydroxy and methoxy); and $R^4$ represents a group represented by formula [VIa]:

[Chemical Formula 53]

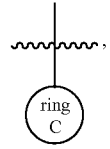

[VIa]

where ring C represents phenyl, 9- to 10-membered fused aryl, 5- to 6-membered heteroaryl, or 9- to 10-membered fused heteroaryl, the phenyl is optionally substituted with one to four groups that are the same or different, selected from the group consisting of hydroxy, carboxy, carbamoyl, cyano, a halogen atom, $C_{1-6}$ alkyl(the $C_{1-6}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one group selected from the group consisting of hydroxy and $C_{1-6}$ alkoxy), $C_{2-6}$ alkenyl, $C_{2-6}$ alkynyl, $C_{3-8}$ cycloalkyl(the $C_{3-8}$ cycloalkyl is optionally substituted with one group selected from the group consisting of hydroxy and $C_{1-6}$ alkoxy), $C_{1-6}$ alkoxy, halo-$C_{1-6}$ alkoxy (the $C_{1-6}$ alkoxy and halo-$C_{1-6}$ alkoxy are optionally substituted with one group selected from the group consisting of hydroxy and $C_{1-6}$ alkoxy), $C_{3-8}$ cycloalkoxy (the $C_{3-8}$ cycloalkoxy is optionally substituted with one group selected from the group consisting of hydroxy and $C_{1-6}$ alkoxy), $C_{1-6}$ alkylsulfanyl, $C_{1-6}$ alkylsulfinyl, $C_{1-6}$ alkylsulfonyl(the $C_{1-6}$ alkylsulfanyl, $C_{1-6}$ alkylsulfinyl, and $C_{1-6}$ alkylsulfonyl are optionally substituted with one group selected from the group consisting of hydroxy and $C_{1-6}$ alkoxy), mono-$C_{1-6}$ alkylamino, di-$C_{1-6}$ alkylamino (the mono-$C_{1-6}$ alkylamino and di-$C_{1-6}$ alkylamino are optionally substituted with one group selected from the group consisting of hydroxy and $C_{1-6}$ alkoxy), $C_{1-6}$ alkylcarbonyl, halo-$C_{1-6}$ alkylcarbonyl, $C_{1-6}$ alkoxycarbonyl, mono-$C_{1-6}$ alkylaminocarbonyl, and di-$C_{1-6}$ alkylaminocarbonyl (the $C_{1-6}$ alkylcarbonyl, halo-$C_{1-6}$ alkylcarbonyl, $C_{1-6}$ alkoxycarbonyl, mono-$C_{1-6}$ alkylaminocarbonyl, and di-$C_{1-6}$ alkylaminocarbonyl are optionally substituted with one group selected from the group consisting of hydroxy and $C_{1-6}$ alkoxy), the 9- to 10-membered fused aryl is optionally substituted with one to three groups that are the same or different, selected from the group consisting of a halogen atom, $C_{1-6}$ alkyl, and $C_{1-6}$ alkoxy, the 5- to 6-membered heteroaryl is optionally substituted with one to three groups that are the same or different, selected from the group consisting of a halogen atom, cyano, $C_{1-6}$ alkyl, $C_{1-6}$ alkoxy, and oxo, and the 9- to 10-membered fused heteroaryl is optionally substituted with one to four groups that are the same or different, selected from the group consisting of $C_{1-6}$ alkyl, $C_{1-6}$ alkoxy, and oxo; or $R^3$ and $R^4$, together with their adjacent carbon atom, optionally form a partially saturated 9- to 10-membered fused hydrocarbon aromatic ring or a partially saturated 9- to 10-membered fused heteroaromatic ring, where
the partially saturated 9- to 10-membered fused hydrocarbon aromatic ring is optionally substituted with one to two halogen atoms, and
the partially saturated 9- to 10-membered fused heteroaromatic ring is optionally substituted with one to two halogen atoms.

(17) Another aspect of the present invention is to provide the LPA1 receptor antagonist according to (16),
wherein, in formula group [IIIa] for W,
$R^{A11}$, $R^{A21}$, and $R^{A31}$ each independently represent a hydrogen atom, hydroxy, carboxy, a halogen atom, $C_{1-6}$ alkyl, $C_{1-6}$ alkoxy, or nitrogen atom-containing 4- to 6-membered saturated heterocyclyl(the nitrogen atom-containing 4- to 6-membered saturated heterocyclyl is optionally substituted with one $C_{1-3}$ alkyl), and
$R^{A12}$, $R^{A22}$, and $R^{A32}$ each independently represent a hydrogen atom, a halogen atom, or methyl, or
$R^{A11}$ and $R^{A12}$, $R^{A21}$ and $R^{A22}$, and $R^{A31}$ and $R^{A32}$ each optionally together form oxo, or
$R^{A11}$ and $R^{A12}$, $R^{A21}$ and $R^{A22}$, and $R^{A31}$ and $R^{A32}$ each optionally form $C_{3-6}$ cycloalkane together with the carbon atom(s) in the adjacent ring A, and
wherein, in formula [IVa] for $R^2$,
L represents $C_{1-2}$ alkanediyl(the $C_{1-2}$ alkanediyl is optionally substituted with 1 to 4 fluorine atoms), $C_{3-8}$ alkanediyl(the $C_{3-8}$ alkanediyl is optionally substituted with 1 to 5 fluorine atoms), or a structure represented by formula [V-1a], where
one carbon atom in the $C_{3-8}$ alkanediyl, that is two or more atoms away from the nitrogen atom to which $R^2$ is bonded, is optionally replaced with formula —O—, formula —S—, or formula —N($R^{L1}$)—, and furthermore,
two consecutive carbon atoms in the $C_{3-8}$ alkanediyl, that are one or more atoms away from the nitrogen atom to which $R^2$ is bonded, are optionally replaced with formula —C(=O)N($R^{12}$)—,
$R^{L1}$ represents a hydrogen atom or $C_{1-3}$ alkyl, and
$R^{12}$ represents a hydrogen atom or $C_{1-3}$ alkyl.

(18) Another aspect of the present invention is to provide a drug for preventing or treating systemic scleroderma, comprising the compound represented by formula [Ia] according to (16) or (17) or a pharmaceutically acceptable salt thereof, or a hydrate thereof, as an active ingredient.

(19) Another aspect of the present invention is to provide a method of preventing or treating systemic scleroderma, comprising administering to a patient in need thereof a therapeutically effective amount of the compound represented by formula [Ia] according to (16) or (17) or a pharmaceutically acceptable salt thereof, or a hydrate thereof.

(20) Another aspect of the present invention is to provide a medicament comprising the compound represented by formula [Ia] according to (16) or (17) or a pharmaceutically acceptable salt thereof, or a hydrate thereof, as an active ingredient.

Advantageous Effect of Invention

The compound of the present invention (hereinafter, this may also be referred to as a "present inventive compound") has an LPA1 receptor-antagonizing action.

DESCRIPTION OF EMBODIMENTS

The present invention provides a compound represented by the above formula [I] having an LPA1 receptor-antagonizing action, or a pharmaceutically acceptable salt thereof, or a hydrate thereof.

Hereinafter, the compound of the present invention will be described in further detail, but the present invention is not limited to those exemplified.

The term "halogen atom" refers to a fluorine atom, a chlorine atom, a bromine atom, or an iodine atom.

The term "$C_{1-3}$ alkyl" refers to linear or branched alkyl having 1 to 3 carbon atoms. Examples thereof include methyl, ethyl, n-propyl, and isopropyl.

The term "$C_{1-4}$ alkyl" refers to linear or branched alkyl having 1 to 4 carbon atoms. Examples thereof include methyl, ethyl, n-propyl, isopropyl, n-butyl, isobutyl, sec-butyl, and tert-butyl.

The term "$C_{1-6}$ alkyl" refers to linear or branched alkyl having 1 to 6 carbon atoms. Examples thereof include methyl, ethyl, n-propyl, isopropyl, n-butyl, isobutyl, sec-butyl, tert-butyl, n-pentyl, and n-hexyl.

The term "$C_{1-10}$ alkyl" refers to linear or branched alkyl having 1 to 10 carbon atoms. Examples thereof include methyl, ethyl, n-propyl, isopropyl, n-butyl, isobutyl, sec-butyl, tert-butyl, n-pentyl, n-hexyl, n-heptyl, n-octyl, n-nonyl, n-decyl, isoheptyl, and isooctyl.

The term "$C_{6-10}$ alkyl" refers to linear or branched alkyl having 6 to 10 carbon atoms. Examples thereof include n-hexyl, n-heptyl, n-octyl, n-nonyl, n-decyl, isoheptyl, and isooctyl.

The term "$C_{5-9}$ alkyl" refers to linear or branched alkyl having 5 to 9 carbon atoms. Examples thereof include n-pentyl, n-hexyl, n-heptyl, n-octyl, n-nonyl, isoheptyl, and isooctyl.

The term "halo-$C_{1-6}$ alkyl" refers to linear or branched alkyl having 1 to 6 carbon atoms, substituted with a halogen atom. The number of substitutions with halogen atoms is preferably 1 to 5, and a preferred halogen atom is a fluorine atom. Examples thereof include monofluoromethyl, difluoromethyl, trifluoromethyl, 1-fluoroethyl, 1,1-difluoroethyl, 2-fluoroethyl, 2,2,2-trifluoroethyl, 1,1,2,2,2-pentafluoroethyl, 3,3,3-trifluoropropyl, 4,4,4-trifluorobutyl, 5,5,5-trifluoropentyl, and 6,6,6-trifluorohexyl.

The term "hydroxy-$C_{1-6}$ alkyl" refers to linear or branched alkyl having 1 to 6 carbon atoms, substituted with a hydroxy group. The number of substitutions with hydroxy groups is preferably 1. Examples thereof include monohydroxymethyl, 1-hydroxyethyl, 2-hydroxyethyl, 3-hydroxypropyl, 4-hydroxybutyl, 5-hydroxypentyl, and 6-hydroxyhexyl.

The term "$C_{2-3}$ alkenyl" refers to linear or branched alkenyl having 2 to 3 carbon atoms. Examples thereof include ethenyl, (E)-prop-1-en-1-yl, (Z)-prop-1-en-1-yl, prop-1-en-2-yl, and prop-2-en-1-yl.

The term "$C_{2-6}$ alkenyl" refers to linear or branched alkenyl having 2 to 6 carbon atoms. Examples thereof include ethenyl, (E)-prop-1-en-1-yl, (Z)-prop-1-en-1-yl, prop-2-en-1-yl, but-3-en-1-yl, pent-4-en-1-yl, hex-5-en-1-yl, 1-methylethenyl.

The term "$C_{2-10}$ alkenyl" refers to linear or branched alkenyl having 2 to 10 carbon atoms. Examples thereof include ethenyl, n-propenyl, isopropenyl, n-butenyl, isobutenyl, sec-butenyl, tert-butenyl, n-pentenyl, n-hexenyl, n-heptenyl, n-octenyl, n-nonenyl, and n-decenyl.

The term "$C_{5-9}$ alkenyl" refers to linear or branched alkenyl having 5 to 9 carbon atoms. Examples thereof include n-pentenyl, n-hexenyl, n-heptenyl, n-octenyl, and n-nonenyl.

The term "$C_{6-10}$ alkenyl" refers to linear or branched alkenyl having 6 to 10 carbon atoms. Examples thereof include n-hexenyl, n-heptenyl, n-octenyl, n-nonenyl, and n-decenyl.

The term "$C_{2-6}$ alkynyl" refers to linear or branched alkynyl having 2 to 6 carbon atoms. Examples thereof include ethynyl, prop-1-yn-1-yl, prop-2-yn-1-yl, but-3-yn-1-yl, pent-4-yn-1-yl, and hex-5-yn-1-yl.

The term "$C_{2-10}$ alkynyl" refers to linear or branched alkynyl having 2 to 10 carbon atoms. Examples thereof include ethynyl, n-propynyl, n-butynyl, n-pentynyl, n-hexynyl, n-heptynyl, n-octynyl, n-nonynyl, and n-decynyl.

The term "$C_{5-9}$ alkynyl" refers to linear or branched alkynyl having 5 to 9 carbon atoms. Examples thereof include n-pentynyl, n-hexynyl, n-heptynyl, n-octynyl, and n-nonynyl.

The term "$C_{6-10}$ alkynyl" refers to linear or branched alkynyl having 6 to 10 carbon atoms. Examples thereof include n-hexynyl, n-heptynyl, n-octynyl, n-nonynyl, and n-decynyl.

The term "$C_{3-6}$ cycloalkane" refers to a hydrocarbon ring having 3 to 6 carbon atoms. Examples thereof include cyclopropane, cyclobutane, cyclopentane, and cyclohexane.

The term "$C_{3-8}$ cycloalkane" refers to a hydrocarbon ring having 3 to 8 carbon atoms. Examples thereof include cyclopropane, cyclobutane, cyclopentane, cyclohexane, cycloheptane, and cyclooctane.

The term "$C_{3-8}$ cycloalkyl" refers to cyclic alkyl having 3 to 8 carbon atoms. Examples thereof include cyclopropyl, cyclobutyl, cyclopentyl, cyclohexyl, cycloheptyl, and cyclooctyl.

The term "9- to 10-membered fused aryl" refers to a 9- to 10-membered fused polycyclic hydrocarbon aromatic ring group having 9 to 10 carbon atoms. Examples thereof include naphthyl.

Also, in the 9- to 10-membered fused aryl, partially saturated groups are also encompassed in the "9- to 10-membered fused aryl". Examples thereof include dihydroindenyl, dihydronaphthyl, and tetrahydronaphthyl.

The term "partially saturated 9- to 10-membered fused hydrocarbon aromatic ring" refers to a partially saturated 9- to 10-membered fused polycyclic hydrocarbon aromatic ring having 9 to 10 carbon atoms. Examples thereof include dihydroindene, dihydronaphthalene, and tetrahydronaphthalene.

The term "partially saturated 9- to 10-membered fused aryl" refers to a partially saturated 9- to 10-membered fused polycyclic hydrocarbon aromatic ring group having 9 to 10 carbon atoms. Examples thereof include dihydroindenyl, dihydronaphthyl, and tetrahydronaphthyl.

The term "4- to 8-membered saturated heterocyclyl" refers to a 4- to 8-membered monocyclic saturated heterocyclic group composed of 1 atom selected from the group consisting of an oxygen atom, a sulfur atom, and a nitrogen atom, and 3 to 7 carbon atoms, where it optionally further contains 1 atom selected from the group consisting of an oxygen atom, a sulfur atom, and a nitrogen atom, in addition to the above-mentioned oxygen atom, sulfur atom, or nitrogen atom. Examples thereof include oxetanyl, tetrahydrofuranyl, tetrahydropyranyl, tetrahydrothiopyranyl, azetidinyl, pyrrolidinyl, piperidinyl, oxazolidinyl, thiazolidinyl, imidazolidinyl, morpholinyl, thiomorpholinyl, and piperazinyl.

The term "oxygen atom-containing 4- to 8-membered saturated heterocycle" refers to a 4- to 8-membered monocyclic saturated heterocycle composed of 1 oxygen atom and 3 to 7 carbon atoms. Examples thereof include oxetane, tetrahydrofuran, and tetrahydropyran.

The term "sulfur atom-containing 4- to 8-membered saturated heterocycle" refers to a 4- to 8-membered monocyclic saturated heterocycle composed of 1 sulfur atom and 3 to 7 carbon atoms. Examples thereof include thietane, tetrahydrothiophene, and tetrahydrothiopyran.

The term "nitrogen atom-containing 4- to 8-membered saturated heterocycle" refers to a 4- to 8-membered monocyclic saturated heterocycle composed of 1 nitrogen atom and 3 to 7 carbon atoms, where it optionally further contains 1 atom selected from the group consisting of an oxygen atom, a sulfur atom, and a nitrogen atom, in addition to the above-mentioned nitrogen atom. Examples thereof include azetidine, pyrrolidine, piperidine, azepane, morpholine, thiomorpholine, and piperazine.

The term "nitrogen atom-containing 4- to 6-membered saturated heterocyclyl" refers to a 4- to 6-membered monocyclic saturated heterocyclic group composed of 1 nitrogen atom and 3 to 5 carbon atoms, where it optionally further contains 1 atom selected from the group consisting of an oxygen atom, a sulfur atom, and a nitrogen atom, in addition to the above-mentioned nitrogen atom. Examples thereof include azetidinyl, pyrrolidinyl, piperidinyl, morpholinyl, thiomorpholinyl, and piperazinyl.

The term "nitrogen atom-containing 4- to 8-membered saturated heterocyclyl" refers to a 4- to 8-membered monocyclic saturated heterocyclic group composed of 1 nitrogen atom and 3 to 7 carbon atoms, where it optionally further contains 1 atom selected from the group consisting of an oxygen atom, a sulfur atom, and a nitrogen atom, in addition to the above-mentioned nitrogen atom. Examples thereof include azetidinyl, pyrrolidinyl, piperidinyl, azepanyl, morpholinyl, thiomorpholinyl, and piperazinyl.

The term "5- to 6-membered heteroaryl" refers to a 5- to 6-membered monocyclic aromatic heterocyclic group composed of 1 or more atoms that are the same or different, selected from the group consisting of an oxygen atom, a sulfur atom, and a nitrogen atom, and 1 to 5 carbon atoms. Examples thereof include furanyl, thiophenyl, pyrrolyl, pyrazolyl, imidazolyl, oxazolyl, isoxazolyl, thiazolyl, isothiazolyl, triazolyl, tetrazolyl, pyridyl, pyridazinyl, pyrimidinyl, pyrazinyl, and triazinyl.

Also, in the 5- to 6-membered heteroaryl, partially saturated groups are also encompassed in the "5- to 6-membered heteroaryl". Examples thereof include dihydrothiazolyl, dihydropyridinyl, and tetrahydropyridinyl.

The term "nitrogen atom-containing 5- to 6-membered heteroaryl" refers to a 5- to 6-membered monocyclic aromatic heterocyclic group composed of 1 to 4 nitrogen atoms and 1 to 5 carbon atoms, where it optionally further contains 1 atom selected from the group consisting of an oxygen atom and a sulfur atom, in addition to the above-mentioned nitrogen atoms. Examples thereof include pyrrolyl, pyrazolyl, imidazolyl, oxazolyl, isoxazolyl, thiazolyl, isothiazolyl, triazolyl, tetrazolyl, pyridyl, pyridazinyl, pyrimidinyl, pyrazinyl, and triazinyl.

Also, in the nitrogen atom-containing 5- to 6-membered heteroaryl, partially saturated groups are also encompassed in the "nitrogen atom-containing 5- to 6-membered heteroaryl". Examples thereof include dihydrothiazolyl, dihydropyridinyl, and tetrahydropyridinyl.

The term "nitrogen atom-containing 6-membered heteroaryl" refers to a 6-membered monocyclic aromatic heterocyclic group composed of 1 to 3 nitrogen atoms and 3 to 5 carbon atoms. Examples thereof include pyridyl, pyridazinyl, pyrimidinyl, pyrazinyl, and triazinyl.

Also, in the nitrogen atom-containing 6-membered heteroaryl, partially saturated groups are also encompassed in the "nitrogen atom-containing 6-membered heteroaryl". Examples thereof include dihydropyridinyl and tetrahydropyridinyl.

The term "9- to 10-membered fused heteroaryl" refers to a 9- to 10-membered fused polycyclic aromatic heterocyclic group composed of 1 atom selected from the group consisting of an oxygen atom, a sulfur atom, and a nitrogen atom, and 5 to 9 carbon atoms, where it optionally further contains 1 to 3 atoms that are the same or different, selected from the group consisting of an oxygen atom, a sulfur atom, and a nitrogen atom, in addition to the above-mentioned oxygen atom, sulfur atom, or nitrogen atom. Examples thereof include benzofuranyl, benzothiophenyl, indolyl, indazolyl, benzimidazolyl, and pyrazolopyridinyl.

Also, in the 9- to 10-membered fused heteroaryl, partially saturated groups are also encompassed in the "9- to 10-membered fused heteroaryl". Examples thereof include dihydrobenzofuranyl, dihydrobenzothiophenyl, indolinyl, dihydrobenzodioxinyl, dihydroquinazolinyl, and isoindolinyl.

The term "partially saturated 9- to 10-membered fused heteroaromatic ring" refers to a partially saturated 9- to 10-membered fused polycyclic aromatic heterocycle composed of 1 atom selected from the group consisting of an oxygen atom, a sulfur atom, and a nitrogen atom, and 5 to 9 carbon atoms, where it optionally further contains 1 to 3 atoms that are the same or different, selected from the group consisting of an oxygen atom, a sulfur atom, and a nitrogen atom, in addition to the above-mentioned oxygen atom, sulfur atom, or nitrogen atom. Examples thereof include dihydrobenzofuran, dihydrobenzothiophene, indoline, dihydrobenzodioxine, and dihydroquinazoline.

The term "nitrogen atom-containing 9- to 10-membered fused heteroaryl" refers to a 9- to 10-membered fused polycyclic aromatic heterocyclic group composed of 1 nitrogen atom and 5 to 9 carbon atoms, where it optionally further contains 1 to 3 atoms that are the same or different, selected from the group consisting of an oxygen atom, a sulfur atom, and a nitrogen atom, in addition to the above-mentioned nitrogen atom. Examples thereof include indolyl, indazolyl, benzimidazolyl, and pyrazolopyridinyl.

Also, in the nitrogen atom-containing 9- to 10-membered fused heteroaryl, partially saturated groups are also encompassed in the "nitrogen atom-containing 9- to 10-membered fused heteroaryl". Examples thereof include indolinyl and dihydroquinazolinyl.

The term "partially saturated oxygen atom-containing 9- to 10-membered fused heterocycle" refers to a partially saturated 9- to 10-membered fused polycyclic aromatic heterocycle composed of 1 oxygen atom and 5 to 9 carbon atoms, where it optionally further contains 1 to 3 atoms that are the same or different, selected from the group consisting of an oxygen atom, a sulfur atom, and a nitrogen atom, in addition to the above-mentioned oxygen atom. Examples thereof include dihydrobenzofuran.

The term "partially saturated sulfur atom-containing 9- to 10-membered fused heterocycle" refers to a partially saturated 9- to 10-membered fused polycyclic aromatic heterocycle composed of 1 sulfur atom and 5 to 9 carbon atoms, where it optionally further contains 1 to 3 atoms that are the same or different, selected from the group consisting of an oxygen atom, a sulfur atom, and a nitrogen atom, in addition to the above-mentioned sulfur atom. Examples thereof include dihydrobenzothiophene.

The term "partially saturated nitrogen atom-containing 9- to 10-membered fused heterocycle" refers to a partially saturated 9- to 10-membered fused polycyclic aromatic heterocycle composed of 1 nitrogen atom and 5 to 9 carbon atoms, where it optionally further contains 1 to 3 atoms that are the same or different, selected from the group consisting of an oxygen atom, a sulfur atom, and a nitrogen atom, in addition to the above-mentioned nitrogen atom. Examples thereof include indoline.

The term "phenyl-$C_{1-3}$ alkyl" refers to the above-mentioned "$C_{1-3}$ alkyl" having one phenyl as a substituent. Examples thereof include benzyl, phenethyl, and 3-phenylpropyl.

The term "pyridyl-$C_{1-3}$ alkyl" refers to the above-mentioned "$C_{1-3}$ alkyl" having one pyridyl as a substituent. Examples thereof include (pyridin-2-yl)methyl, (pyridin-3-yl)methyl, (pyridin-4-yl)methyl, 2-(pyridin-2-yl)ethyl, and 3-(pyridin-2-yl) propyl. The term "$C_{1-4}$ alkoxy" refers to linear or branched alkoxy having 1 to 4 carbon atoms. Examples thereof include methoxy, ethoxy, n-propoxy, isopropoxy, n-butoxy, isobutoxy, sec-butoxy, and tert-butoxy.

The term "$C_{1-6}$ alkoxy" refers to linear or branched alkoxy having 1 to 6 carbon atoms. Examples thereof include methoxy, ethoxy, n-propoxy, isopropoxy, n-butoxy, isobutoxy, sec-butoxy, tert-butoxy, n-pentyloxy, and n-hexyloxy.

The term "halo-$C_{1-6}$ alkoxy" refers to linear or branched alkoxy having 1 to 6 carbon atoms, substituted with a halogen atom. The number of substitutions with halogen atoms is preferably 1 to 5, and a preferred halogen atom is a fluorine atom. Examples thereof include monofluoromethoxy, difluoromethoxy, trifluoromethoxy, 1-fluoroethoxy, 1,1-difluoroethoxy, 2-fluoroethoxy, 2,2,2-trifluoroethoxy, 1,1,2,2,2-pentafluoroethoxy, 3,3,3-trifluoropropoxy, 4,4,4-trifluorobutoxy, 5,5,5-trifluoropentyloxy, and 6,6,6-trifluorohexyloxy.

The term "$C_{3-8}$ cycloalkoxy" refers to cyclic alkoxy having 3 to 8 carbon atoms. Examples thereof include cyclopropoxy, cyclobutoxy, cyclopentyloxy, cyclohexyloxy, cycloheptyloxy, and cyclooctyloxy.

The term "$C_{1-6}$ alkylsulfanyl" refers to a group formed by bonding the above-mentioned "$C_{1-6}$ alkyl" and sulfanyl. Examples thereof include methylsulfanyl, ethylsulfanyl, n-propylsulfanyl, isopropylsulfanyl, n-butylsulfanyl, isobutylsulfanyl, sec-butylsulfanyl, tert-butylsulfanyl, n-pentylsulfanyl, and n-hexylsulfanyl.

The term "$C_{1-6}$ alkylsulfinyl" refers to a group formed by bonding the above-mentioned "$C_{1-6}$ alkyl" and sulfinyl. Examples thereof include methylsulfinyl, ethylsulfinyl, n-propylsulfinyl, isopropylsulfinyl, n-butylsulfinyl, isobutylsulfinyl, sec-butylsulfinyl, tert-butylsulfinyl, n-pentylsulfinyl, and n-hexylsulfinyl.

The term "$C_{1-6}$ alkylsulfonyl" refers to a group formed by bonding the above-mentioned "$C_{1-6}$ alkyl" and sulfonyl. Examples thereof include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, and n-hexylsulfonyl.

The term "$C_{1-4}$ alkylsulfonyloxy" refers to a group formed by bonding the above-mentioned "$C_{1-4}$ alkyl" and sulfonyloxy. Examples thereof include methylsulfonyloxy, ethylsulfonyloxy, n-propylsulfonyloxy, isopropylsulfonyloxy, n-butylsulfonyloxy, isobutylsulfonyloxy, sec-butylsulfonyloxy, and tert-butylsulfonyloxy.

The term "mono-$C_{1-6}$ alkylamino" refers to amino having one of the above-mentioned "$C_{1-6}$ alkyl" as a substituent. Examples thereof include methylamino, ethylamino, n-propylamino, isopropylamino, n-butylamino, isobutylamino, sec-butylamino, tert-butylamino, n-pentylamino, and n-hexylamino.

The term "di-$C_{1-6}$ alkylamino" refers to amino having two of the above-mentioned "$C_{1-6}$ alkyl" that are the same or different as substituents. Examples thereof include dimethylamino, diethylamino, di(n-propyl)amino, di(isopropyl) amino, ethylmethylamino, and methyl(n-propyl)amino.

The term "$C_{1-4}$ alkylcarbonyl" refers to a group formed by bonding the above-mentioned "$C_{1-4}$ alkyl" and carbonyl. Examples thereof include methylcarbonyl, ethylcarbonyl, n-propylcarbonyl, isopropylcarbonyl, n-butylcarbonyl, isobutylcarbonyl, sec-butylcarbonyl, and tert-butylcarbonyl.

The term "$C_{1-6}$ alkylcarbonyl" refers to a group formed by bonding the above-mentioned "$C_{1-6}$ alkyl" and carbonyl. Examples thereof include methylcarbonyl, ethylcarbonyl, n-propylcarbonyl, isopropylcarbonyl, n-butylcarbonyl, isobutylcarbonyl, sec-butylcarbonyl, tert-butylcarbonyl, n-pentylcarbonyl, and n-hexylcarbonyl.

The term "halo-$C_{1-6}$ alkylcarbonyl" refers to a group formed by bonding the above-mentioned "halo-$C_{1-6}$ alkyl" and carbonyl. The number of substitutions with halogen atoms is preferably 1 to 5, and a preferred halogen atom is a fluorine atom. Examples thereof include monofluoromethylcarbonyl, difluoromethylcarbonyl, trifluoromethylcarbonyl, 1-fluoroethylcarbonyl, 1,1-difluoroethylcarbonyl, 2-fluoroethylcarbonyl, 2,2,2-trifluoroethylcarbonyl, 1,1,2,2,2-pentafluoroethylcarbonyl, 3,3,3-trifluoropropylcarbonyl, 4,4,4-trifluorobutylcarbonyl, 5,5,5-trifluoropentylcarbonyl, and 6,6,6-trifluorohexylcarbonyl.

The term "$C_{1-4}$ alkoxycarbonyl" refers to a group formed by bonding the above-mentioned "$C_{1-4}$ alkoxy" and carbonyl. Examples thereof include methoxycarbonyl, ethoxycarbonyl, n-propoxycarbonyl, isopropoxycarbonyl, n-butoxycarbonyl, isobutoxycarbonyl, sec-butoxycarbonyl, and tert-butoxycarbonyl.

The term "$C_{1-6}$ alkoxycarbonyl" refers to a group formed by bonding the above-mentioned "$C_{1-6}$ alkoxy" and carbonyl. Examples thereof include methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, and n-hexyloxycarbonyl.

The term "mono-$C_{1-6}$ alkylaminocarbonyl" refers to a group formed by bonding the above-mentioned "mono-$C_{1-6}$ alkylamino" and carbonyl. Examples thereof include methylaminocarbonyl, ethylaminocarbonyl, n-propylaminocarbonyl, isopropylaminocarbonyl, n-butylaminocarbonyl, isobutylaminocarbonyl, sec-butylaminocarbonyl, tert-butylaminocarbonyl, n-pentylaminocarbonyl, and n-hexylaminocarbonyl.

The term "di-$C_{1-6}$ alkylaminocarbonyl" refers to a group formed by bonding the above-mentioned "di-$C_{1-6}$ alkylamino" and carbonyl. Examples thereof include dimethylaminocarbonyl, diethylaminocarbonyl, di(n-propyl)aminocarbonyl, di(isopropyl)aminocarbonyl, ethylmethylaminocarbonyl, and methyl(n-propyl)aminocarbonyl.

The term "oxo" refers to a substituent (=O) in which substitution with an oxygen atom occurs via a double bond. Accordingly, in the case where a carbon atom is substituted with oxo, it forms carbonyl together with that carbon atom, in the case where one sulfur atom is substituted with one oxo, it forms sulfinyl together with that sulfur atom, and in the case where one sulfur atom is substituted with two oxo, they form sulfonyl together with that sulfur atom.

Examples of the saturated heterocyclyl substituted with oxo include, for example, 2-oxopyrrolidinyl, 2-oxopiperidinyl, 2-oxopiperazinyl, 1,1-dioxidotetrahydrothiophenyl, 1-oxidotetrahydro-2H-thiopyranyl, 1,1-dioxidotetrahydro-2H-thiopyranyl, 1,1-dioxidoisothiazolidinyl, 2-oxo-1,3-oxazolidinyl, and 2-oxo-1,3-oxazinanyl.

Also, examples of the partially saturated heteroaryl substituted with oxo include, for example, 6-oxo-1,6-dihydropyridinyl, 6-oxo-1,1-dihydropyridazinyl, 2-oxo-1,2-dihydroquinolyl, 2-oxo-1,2-dihydroquinazolyl, and 1-oxo-1,2,3,4-tetrahydroisoquinolyl.

The term "linear $C_{1-3}$ alkanediyl" refers to a divalent linear hydrocarbon group formed by removing one hydrogen atom from alkyl having 1 to 3 carbon atoms. Examples thereof include methanediyl, ethane-1,2-diyl, and propane-1,3-diyl.

The term "$C_{1-2}$ alkanediyl" refers to a divalent linear hydrocarbon group formed by removing one hydrogen atom from alkyl having 1 to 2 carbon atoms. Examples thereof include methanediyl, ethane-1,1-diyl, and ethane-1,2-diyl.

The term "$C_{1-8}$ alkanediyl" refers to a divalent hydrocarbon group formed by removing one hydrogen atom from alkyl having 1 to 8 carbon atoms. Examples thereof include methanediyl, ethane-1,1-diyl, ethane-1,2-diyl, propane-1,1-diyl, propane-1,3-diyl, propane-2,2-diyl, butane-1,4-diyl, pentane-1,4-diyl, pentane-1,5-diyl, pentane-2,5-diyl, hexane-1,6-diyl, heptane-1,7-diyl, octane-1,8-diyl, 2-methylbutane-1,4-diyl, 2-methylpentane-2,5-diyl, and 4-methylpentane-1,4-diyl.

The term "$C_{2-7}$ alkanediyl" refers to a divalent hydrocarbon group formed by removing one hydrogen atom from alkyl having 2 to 7 carbon atoms. Examples thereof include ethane-1,1-diyl, ethane-1,2-diyl, propane-1,1-diyl, propane-1,3-diyl, propane-2,2-diyl, butane-1,4-diyl, pentane-1,4-diyl, pentane-1,5-diyl, pentane-2,5-diyl, hexane-1,6-diyl, heptane-1,7-diyl, 2-methylbutane-1,4-diyl, 2-methylpentane-2,5-diyl, and 4-methylpentane-1,4-diyl. The term "$C_{3-6}$ alkanediyl" refers to a divalent hydrocarbon group formed by removing one hydrogen atom from alkyl having 3 to 6 carbon atoms. Examples thereof include propane-1,1-diyl, propane-1,3-diyl, propane-2,2-diyl, butane-1,4-diyl, pentane-1,4-diyl, pentane-1,5-diyl, pentane-2,5-diyl, hexane-1,6-diyl, 2-methylbutane-1,4-diyl, 2-methylpentane-2,5-diyl, and 4-methylpentane-1,4-diyl.

The term "$C_{3-8}$ alkanediyl" refers to a divalent hydrocarbon group formed by removing one hydrogen atom from alkyl having 3 to 8 carbon atoms. Examples thereof include propane-1,1-diyl, propane-1,3-diyl, propane-2,2-diyl, butane-1,4-diyl, pentane-1,4-diyl, pentane-1,5-diyl, pentane-2,5-diyl, hexane-1,6-diyl, heptane-1,7-diyl, octane-1,8-diyl, 2-methylbutane-1,4-diyl, 2-methylpentane-2,5-diyl, and 4-methylpentane-1,4-diyl.

The term "$C_4$ alkanediyl" refers to a divalent hydrocarbon group formed by removing one hydrogen atom from alkyl having 4 carbon atoms. Examples thereof include butane-1,4-diyl.

One preferred aspect of the compound of the present invention is aspect (A) below.

Aspect (A):

In the compound represented by the above formula [I]:

[Chemical Formula 54]

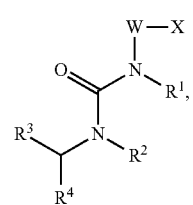

[I]

or a pharmaceutically acceptable salt thereof;

X is carboxy, $C_{1-4}$ alkoxycarbonyl, tetrazolyl, or a group represented by formula [II-2] to [II-5]:

[Chemical Formula 55]

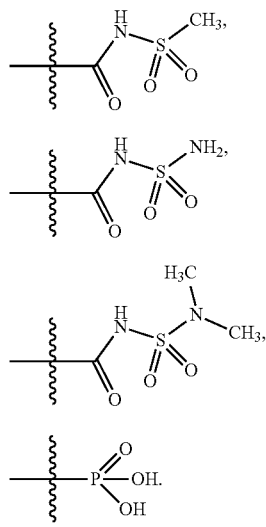

[II-2]

[II-3]

[II-4]

[II-5]

In the present aspect, W is linear $C_{1-3}$ alkanediyl or a structure selected from formula group [III]:

[Chemical Formula 56]
[III]

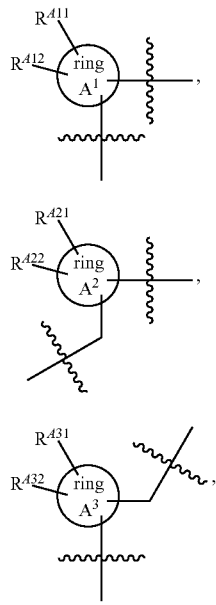

[III-1]

[III-2]

[III-3]

where the linear $C_{1-3}$ alkanediyl is optionally substituted with one group selected from the group consisting of $C_{1-6}$ alkyl, halo-$C_{1-6}$ alkyl, phenyl-$C_{1-3}$ alkyl, and pyridyl-$C_{1-3}$ alkyl, and when the linear $C_{1-3}$ alkanediyl is substituted with one methyl, it is optionally further substituted with one methyl, ring $A^1$, ring $A^2$, and ring $A^3$ are each $C_{3-8}$ cycloalkane, a partially saturated 9- to 10-membered fused hydrocarbon aromatic ring, an oxygen atom-containing 4- to 8-membered saturated heterocycle, a sulfur atom-containing 4- to 8-membered saturated heterocycle, or a nitrogen atom-containing 4- to 8-membered saturated heterocycle, where the sulfur atom in the sulfur atom-containing 4- to 8-membered saturated heterocycle is optionally substituted with one to two oxo, the nitrogen atom in the nitrogen atom-containing 4- to 8-membered saturated heterocycle is optionally substituted with one $C_{1-4}$ alkylcarbonyl, and $R^{A11}$, $R^{A21}$, and $R^{A31}$ are each independently a hydrogen atom, hydroxy, a halogen atom, $C_{1-6}$ alkyl, $C_{1-6}$ alkoxy, or nitrogen atom-containing 4- to 6-membered saturated heterocyclyl, and $R^{A12}$, $R^{A22}$, and $R^{A32}$ are each independently a hydrogen atom, a halogen atom, or methyl, or $R^{A11}$ and $R^{A12}$, $R^{A21}$ and $R^{A22}$, and $R^{A31}$ and $R^{A32}$ each optionally together form oxo, or $R^{A11}$ and $R^{A12}$, $R^{A21}$ and $R^{A22}$, and $R^{A31}$ and $R^{A32}$ each optionally form $C_3$-6 cycloalkane together with the carbon atom(s) in the adjacent ring.

More preferred W is linear $C_{1-3}$ alkanediyl or a structure selected from formula group [III]:

[Chemical Formula 57]
[III]

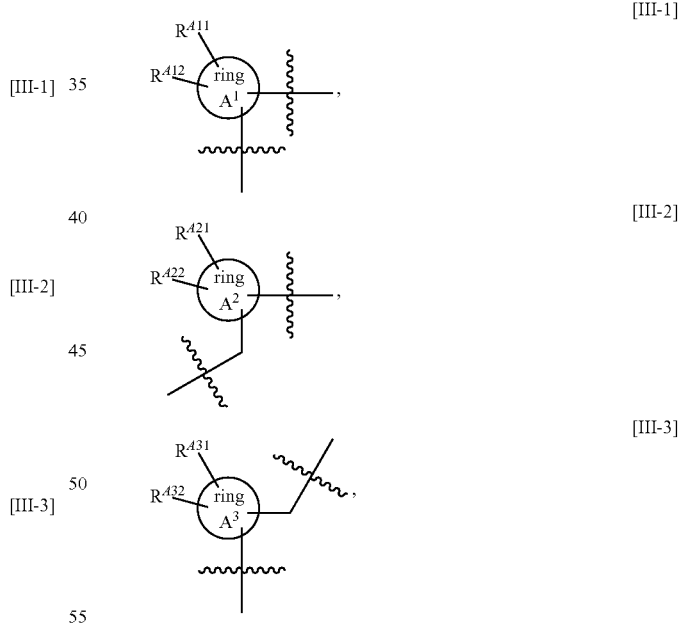

[III-1]

[III-2]

[III-3]

where the linear $C_{1-3}$ alkanediyl is optionally substituted with one group selected from the group consisting of $C_{1-4}$ alkyl, halo-$C_2$ alkyl, phenyl-$C_{1-2}$ alkyl, and pyridyl-$C_1$ alkyl, and when the linear $C_{1-3}$ alkanediyl is substituted with one methyl, it is optionally further substituted with one methyl, ring $A^1$ is $C_{3-7}$ cycloalkane, a partially saturated 9-membered fused hydrocarbon aromatic ring, an oxygen atom-containing 4- to 6-membered saturated heterocycle, a sulfur atom-containing 6-membered saturated heterocycle, or a nitrogen atom-containing 4- to 6-membered saturated heterocycle,
where
the sulfur atom in the sulfur atom-containing 6-membered saturated heterocycle is optionally substituted with one to two oxo, and
the nitrogen atom in the nitrogen atom-containing 4- to 6-membered saturated heterocycle is optionally substituted with one $C_1$ alkylcarbonyl, and
$R^{A11}$ is a hydrogen atom, hydroxy, a halogen atom, $C_1$ alkyl, $C_{1-3}$ alkoxy, or nitrogen atom-containing 6-membered saturated heterocyclyl, and
$R^{A12}$ is a hydrogen atom, a halogen atom, or methyl, or
$R^{A11}$ and $R^{A12}$ optionally together form oxo, or
$R^{A11}$ and $R^{A12}$ optionally form $C_4$ cycloalkane together with the carbon atom(s) in the adjacent ring,
ring $A^2$ is $C_3$ cycloalkane or an oxygen atom-containing 6-membered saturated heterocycle,
where
$R^{A21}$ is a hydrogen atom, and
$R^{A22}$ is a hydrogen atom, and
ring $A^3$ is $C_{3-5}$ cycloalkane, a partially saturated 9-membered fused hydrocarbon aromatic ring, or an oxygen atom-containing 6-membered saturated heterocycle,
where
$R^{A31}$ is a hydrogen atom, and
$R^{A32}$ is a hydrogen atom.
Further preferred W is methanediyl, propane-1,3-diyl, or a structure represented by formula [III-1] to [III-3]:

[Chemical Formula 58]

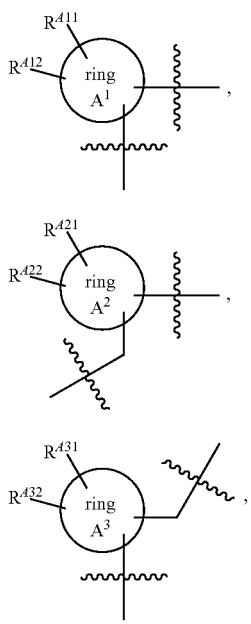

[III-1]

[III-2]

[III-3]

where
the methanediyl is optionally substituted with one group selected from the group consisting of methyl, n-butyl, haloethyl, benzyl, phenethyl, and pyridylmethyl, and when the methanediyl is substituted with one methyl, it is optionally further substituted with one methyl,
ring $A^1$ is cyclopropane, cyclobutane, cyclopentane, cyclohexane, cycloheptane, dihydroindene, oxetane, tetrahydrofuran, tetrahydropyran, tetrahydrothiopyran, azetidine, pyrrolidine, or piperidine,
where
the sulfur atom in the tetrahydrothiopyran is optionally substituted with two oxo, and
the nitrogen atom in the azetidine, pyrrolidine, and piperidine is optionally substituted with one methylcarbonyl, and
$R^{A11}$ is a hydrogen atom, hydroxy, a fluorine atom, methyl, methoxy, ethoxy, isopropoxy, or morpholinyl, and
$R^{A12}$ is a hydrogen atom, a fluorine atom, or methyl, or
$R^{A11}$ and $R^{A12}$ optionally together form oxo, or
$R^{A11}$ and $R^{A12}$ optionally form cyclobutane together with the carbon atom in the adjacent ring,
ring $A^2$ is cyclopropane or tetrahydropyran,
where
$R^{A21}$ is a hydrogen atom, and
$R^{A22}$ is a hydrogen atom, and
ring $A^3$ is cyclopropane, cyclobutane, cyclopentane, dihydroindene, or tetrahydropyran,
where
$R^{A31}$ is a hydrogen atom, and
$R^{A32}$ is a hydrogen atom.
$R^1$ is a hydrogen atom.
$R^2$ is $C_{6-10}$ alkyl or a group represented by formula [IV-1] or [IV-2]:

[Chemical Formula 59]

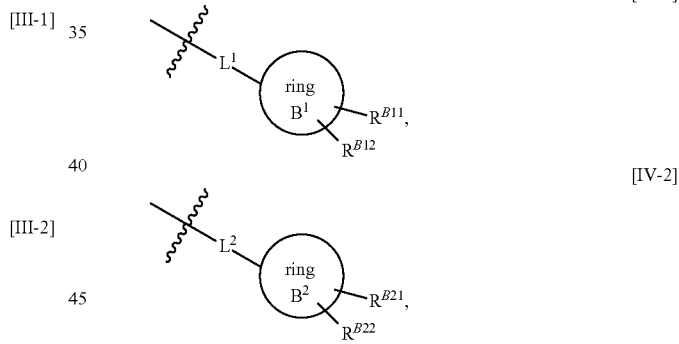

[IV-1]

[IV-2]

where
ring $B^1$ is $C_{3-8}$ cycloalkyl, phenyl, or nitrogen atom-containing 5- to 6-membered heteroaryl,
$R^{B11}$ and $R^{B12}$ are each independently a hydrogen atom, a halogen atom, $C_{1-6}$ alkyl, or $C_{1-6}$ alkoxy, and
$L^1$ is $C_{3-8}$ alkanediyl(the $C_{3-8}$ alkanediyl is optionally substituted with 1 to 5 fluorine atoms), a structure represented by formula [V-6]: —$CH_2CH_2CH=C(CH_3)$—, or a structure represented by formula [V-1]:

[Chemical Formula 60]

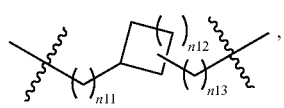

[V-1]

where
n11 is an integer of 0 to 3,
n12 is an integer of 0 to 5,
n13 is an integer of 0 to 3, and
one carbon atom in the $C_{3-8}$ alkanediyl, that is two or more atoms away from the nitrogen atom to which $R^2$ is bonded, is optionally replaced with formula —O—, formula —S—, or formula —N($R^{L11}$)—, and
$R^{L1}$ is $C_{1-3}$ alkyl, and
ring $B^2$ is partially saturated 9- to 10-membered fused aryl, or partially saturated nitrogen atom-containing 9- to 10-membered fused heteroaryl,
$R^{B1}$ and $R^{B2}$ are each independently a hydrogen atom, a halogen atom, $C_{1-6}$ alkyl, or $C_{1-6}$ alkoxy, and
$L^2$ is $C_{1-2}$ alkanediyl(the $C_{1-2}$ alkanediyl is optionally substituted with 1 to 4 fluorine atoms).

More preferred $R^2$ is $C_{7-8}$ alkyl or a group represented by formula [IV-1] or [IV-2]:

[Chemical Formula 61]

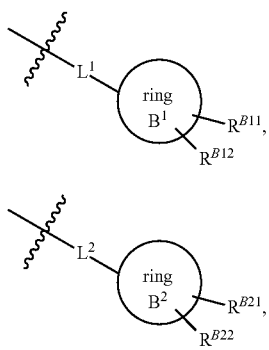

[IV-1]

[IV-2]

where
ring $B^1$ is $C_6$ cycloalkyl, phenyl, or nitrogen atom-containing 6-membered heteroaryl,
$R^{B11}$ and $R^{B12}$ are each independently a hydrogen atom, a halogen atom, Ct alkyl, or $C_1$ alkoxy, and
$L^1$ is $C_{3-5}$ alkanediyl(the $C_{3-5}$ alkanediyl is optionally substituted with 1 to 2 fluorine atoms), a structure represented by formula [V-6]: —CH$_2$CH$_2$CH═C(CH$_3$)—, or a structure represented by formula [V-1]:

[Chemical Formula 62]

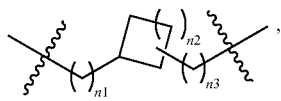

[V-1]

where
n1 is an integer of 0 to 1,
n2 is 1,
n3 is an integer of 0 to 1, and
one carbon atom in the $C_{3-5}$ alkanediyl, that is two or more atoms away from the nitrogen atom to which $R^2$ is bonded, is optionally replaced with formula —O—, formula —S—, or formula —N($R^{L1}$)—, and
$R^{L1}$ is $C_1$ alkyl, and
ring $B^2$ is partially saturated 9-membered fused aryl or partially saturated nitrogen atom-containing 9-membered fused heteroaryl, $R^{B1}$ and $R^{B2}$ are both hydrogen atoms, and
$L^2$ is $C_2$ alkanediyl.

Further preferred $R^2$ is isoheptyl, isooctyl, or a group represented by formula [IV-1] or [IV-2]:

[Chemical Formula 63]

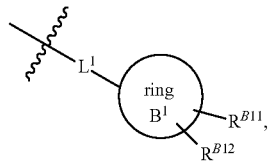

[IV-1]

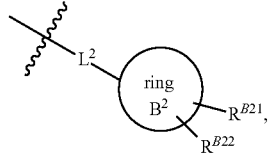

[IV-2]

where
ring $B^1$ is cyclohexyl, phenyl, or pyridyl,
$R^{B11}$ and $R^{B12}$ are each independently a hydrogen atom, a fluorine atom, methyl, or methoxy, and $L^1$ is any of structures represented by formulas [V-3] to [V-12] and [V-14] to [V-19]:

[Chemical Formula 64]

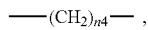

—(CH$_2$)$_{n4}$—,   [V-3]

—CH$_2$CH(CH$_3$)CH$_2$CH$_2$—,   [V-4]

—CH$_2$CH$_2$CH$_2$CH(CH$_3$)—,   [V-5]

—CH$_2$CH$_2$CH═C(CH$_3$)—,   [V-6]

—CH$_2$CH$_2$CF$_2$CH$_2$—,   [V-7]

—CH$_2$CH$_2$CH$_2$CF$_2$—,   [V-8]

[Chemical Formula 65]

[V-9]

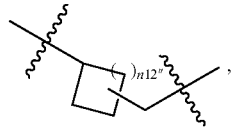

[V-10]

—CH$_2$CH$_2$CH$_2$—O—,   [V-11]

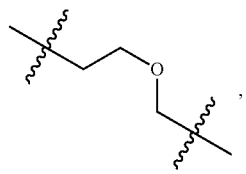

[V-12]

-continued

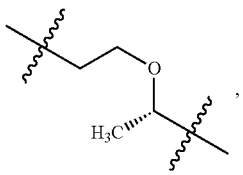 [V-14]

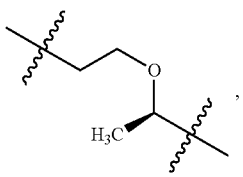 [V-15]

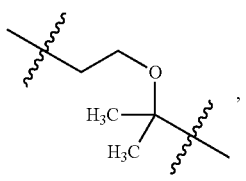 [V-16]

—CH$_2$CH$_2$CH$_2$—S— , [V-17]

—CH$_2$CH$_2$CH$_2$—N(CH$_3$)— , [V-18]

—CH$_2$—C(=O)NH—CH$_2$— , [V-19]

where
n4 is an integer of 3 to 5,
n12' is 1, and
n12" is 1, and
ring B$^2$ is dihydroindenyl or isoindolinyl,
R$^{B1}$ and R$^{B2}$ are both hydrogen atoms, and
L$^2$ is a structure represented by formula [V-20]:
[Chemical Formula 66]

—(CH$_2$)$_{n5}$— [V-20]

where
n5 is 2.
R$^3$ is a hydrogen atom or C$_{1-3}$ alkyl(the C$_{1-3}$ alkyl is optionally substituted with one group selected from the group consisting of hydroxy and methoxy),
more preferred R$^3$ is a hydrogen atom or C$_{1-2}$ alkyl(the C$_{1-2}$ alkyl is optionally substituted with one group selected from the group consisting of hydroxy and methoxy), and
further preferred R$^3$ is a hydrogen atom, methyl(the methyl is optionally substituted with one group selected from the group consisting of hydroxy and methoxy), or ethyl.
R$^4$ is a group represented by formula [VI]:

[Chemical Formula 67]

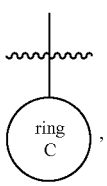 [VI]

where
ring C is phenyl, nitrogen atom-containing 6-membered heteroaryl, or 9- to 10-membered fused heteroaryl,
the phenyl is substituted with one group selected from the group consisting of a halogen atom, C$_{1-6}$ alkyl, C$_{1-6}$ alkoxy, and C$_{1-6}$ alkylcarbonyl, and furthermore,
the phenyl is optionally substituted with one to four groups that are the same or different, selected from the group consisting of hydroxy, carbamoyl, cyano, a halogen atom, C$_{1-6}$ alkyl(the C$_{1-6}$ alkyl is optionally substituted with one group selected from the group consisting of hydroxy and C$_{1-6}$ alkoxy), halo-C$_{1-6}$ alkyl(the halo-C$_{1-6}$ alkyl is optionally substituted with one hydroxy), C$_{2-6}$ alkenyl, C$_{3-8}$ cycloalkyl(the C$_{3-8}$ cycloalkyl is optionally substituted with one hydroxy), C$_{1-6}$ alkoxy, halo-C$_{1-6}$ alkoxy, C$_{3-8}$ cycloalkoxy, C$_{1-6}$ alkylsulfinyl, C$_{1-6}$ alkylsulfonyl, mono-C$_{1-6}$ alkylamino, di-C$_{1-6}$ alkylamino, C$_{1-6}$ alkylcarbonyl, halo-C$_{1-6}$ alkylcarbonyl, C$_{1-6}$ alkoxycarbonyl, and mono-C$_{1-6}$ alkylaminocarbonyl,
the nitrogen atom-containing 6-membered heteroaryl is substituted with one C$_{1-6}$ alkoxy, and furthermore,
the nitrogen atom-containing 6-membered heteroaryl is optionally substituted with one group selected from the group consisting of cyano and C$_{1-6}$ alkoxy, and
the 9- to 10-membered fused heteroaryl is optionally substituted with one to two groups that are the same or different, selected from the group consisting of C$_{1-6}$ alkyl or C$_{1-6}$ alkoxy.
More preferred R$^4$ is a group represented by formula [VI]:

[Chemical Formula 68]

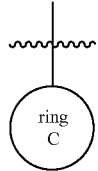 [VI]

where
ring C is phenyl, nitrogen atom-containing 6-membered heteroaryl, or 9- to 10-membered fused heteroaryl,
the phenyl is substituted with one group selected from the group consisting of a halogen atom, C$_{1-3}$ alkyl, C$_{1-3}$ alkoxy, and C$_{1-2}$ alkylcarbonyl, and furthermore,
the phenyl is optionally substituted with one to three groups that are the same or different, selected from the group consisting of hydroxy, carbamoyl, cyano, a halogen atom, C$_{1-3}$ alkyl(the C$_{1-3}$ alkyl is optionally substituted with one group selected from the group consisting of hydroxy and C$_1$ alkoxy), halo-C$_2$ alkyl(the halo-C$_2$ alkyl is optionally substituted with one hydroxy), C$_{2-3}$ alkenyl, C$_3$ cycloalkyl(the C$_3$ cycloalkyl is optionally substituted with one hydroxy), C$_{1-3}$ alkoxy, halo-C$_2$ alkoxy, C$_3$ cycloalkoxy, C$_1$ alkylsulfinyl, C$_1$ alkylsulfonyl, mono-C$_2$ alkylamino, di-C$_{1-2}$ alkylamino, C$_{1-2}$ alkylcarbonyl, halo-C$_1$ alkylcarbonyl, C$_1$ alkoxycarbonyl, and mono-C$_1$ alkylaminocarbonyl,
the nitrogen atom-containing 6-membered heteroaryl is substituted with one C$_{1-2}$ alkoxy, and furthermore,
the nitrogen atom-containing 6-membered heteroaryl is optionally substituted with one group selected from the group consisting of cyano and C$_{1-2}$ alkoxy, and the 9- to 10-membered fused heteroaryl is optionally substituted with one to two groups that are the same or different, selected from the group consisting of $C_{2-3}$ alkyl or $C_2$ alkoxy.

Further preferred $R^4$ is a group represented by formula [VI]:

[Chemical Formula 69]

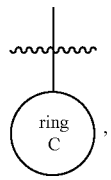

[VI]

where ring C is phenyl, pyridyl, pyrimidinyl, indolyl, indazolyl, benzimidazolyl, pyrazolopyridyl, dihydrobenzofuranyl, or dihydroindolyl, the phenyl is substituted with one group selected from the group consisting of a fluorine atom, a chlorine atom, a bromine atom, methyl, ethyl, n-propyl, isopropyl, methoxy, ethoxy, n-propoxy, isopropoxy, methylcarbonyl, and ethylcarbonyl, and furthermore, the phenyl is optionally substituted with one to four groups that are the same or different, selected from the group consisting of hydroxy, carbamoyl, cyano, a fluorine atom, a chlorine atom, a bromine atom, methyl, ethyl, n-propyl, isopropyl, (the methyl, ethyl, n-propyl, and isopropyl are optionally substituted with one group selected from the group consisting of hydroxy and methoxy), haloethyl(the haloethyl is optionally substituted with one hydroxy), ethenyl, isopropenyl, cyclopropyl(the cyclopropyl is optionally substituted with one hydroxy), methoxy, ethoxy, n-propoxy, isopropoxy, haloethoxy, cyclopropoxy, methylsulfinyl, methylsulfonyl, ethylamino, ethylmethylamino, diethylamino, methylcarbonyl, ethylcarbonyl, halomethylcarbonyl, methoxycarbonyl, and methylaminocarbonyl, the pyridyl and pyrimidinyl are substituted with one methoxy or ethoxy, and furthermore, they are optionally substituted with one group selected from the group consisting of cyano and ethoxy, the pyrimidinyl is substituted with one methoxy, and furthermore, it is optionally substituted with one methoxy, and the indolyl, indazolyl, benzimidazolyl, pyrazolopyridyl, dihydrobenzofuranyl, or dihydroindolyl is optionally substituted with one to two groups that are the same or different, selected from the group consisting of ethyl, n-propyl, or ethoxy.

Alternatively, when $R^3$ and $R^4$, together with their adjacent carbon atom, form a fused ring, a preferred fused ring is a partially saturated 9- to 10-membered fused hydrocarbon aromatic ring (the partially saturated 9- to 10-membered fused hydrocarbon aromatic ring is optionally substituted with one to two halogen atoms) or a partially saturated 9- to 10-membered fused oxygen atom-containing 9- to 10-membered fused heteroaromatic ring (the partially saturated oxygen atom-containing 9- to 10-membered fused heteroaromatic ring is optionally substituted with one to two halogen atoms), a more preferred fused ring is a partially saturated 9-membered fused hydrocarbon aromatic ring (the partially saturated 9-membered fused hydrocarbon aromatic ring is optionally substituted with one to two halogen atoms) or a partially saturated oxygen atom-containing 9-membered fused heteroaromatic ring (the partially saturated oxygen atom-containing 9-membered fused heteroaromatic ring is optionally substituted with one to two halogen atoms), and a further preferred fused ring is dihydroindene (the dihydroindene is optionally substituted with one to two halogen atoms) or dihydrobenzofuran (the dihydrobenzofuran is optionally substituted with one to two halogen atoms).

Another preferred aspect of the compound of the present invention is aspect (B) below.

Aspect (B):

In the compound represented by the above formula [I], or a pharmaceutically acceptable salt thereof, or a hydrate thereof, the compound represented by formula [I] is a compound represented by formula [I-1]:

[Chemical Formula 70]

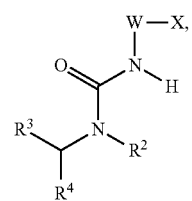

[I-1]

where $R^2$ is a group represented by formula [IV-1] or [IV-2]:

[Chemical Formula 71]

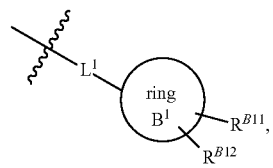

[IV-1]

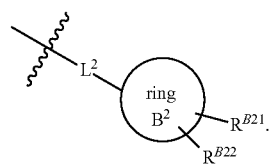

[IV-2]

In this aspect,

X is carboxy, $C_{1-4}$ alkoxycarbonyl, or tetrazolyl, one more preferred X is carboxy or tetrazolyl, in this case, one further preferred X is carboxy, and in this case, another further preferred X is tetrazolyl, and another more preferred X is $C_{1-4}$ alkoxycarbonyl, in this case, one further preferred X is $C_1$ alkoxycarbonyl, in this case, another further preferred X is $C_2$ alkoxycarbonyl, and in this case, another further preferred X is $C_4$ alkoxycarbonyl.

W is methanediyl or a structure represented by formula [III-1]:

[Chemical Formula 72]

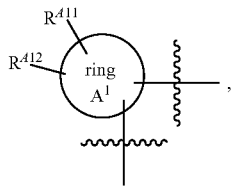

[III-1]

where
the methanediyl is optionally substituted with one group selected from the group consisting of $C_{1-6}$ alkyl(the $C_{1-6}$ alkyl is optionally substituted with one group selected from the group consisting of hydroxy and carboxy), halo-$C_{1-6}$ alkyl, $C_{3-8}$ cycloalkyl, phenyl-$C_{1-3}$ alkyl, and pyridyl-$C_{1-3}$ alkyl, and
when the methanediyl is substituted with one methyl, it is optionally further substituted with one methyl, and
in the structure represented by formula [III-1],
preferred ring $A^1$ is $C_{3-8}$ cycloalkane, a partially saturated 9- to 10-membered fused hydrocarbon aromatic ring, an oxygen atom-containing 4- to 8-membered saturated heterocycle, a sulfur atom-containing 4- to 8-membered saturated heterocycle, or a nitrogen atom-containing 4- to 8-membered saturated heterocycle,
where
the sulfur atom in the sulfur atom-containing 4- to 8-membered saturated heterocycle is optionally substituted with one to two oxo, and
the nitrogen atom in the nitrogen atom-containing 4- to 8-membered saturated heterocycle is optionally substituted with one group selected from the group consisting of $C_{1-4}$ alkylcarbonyl and $C_{1-4}$ alkoxycarbonyl,
preferred $R^{A11}$ is a hydrogen atom, hydroxy, carboxy, a halogen atom, $C_{1-6}$ alkyl, $C_{1-6}$ alkoxy, or nitrogen atom-containing 4- to 6-membered saturated heterocyclyl(the nitrogen atom-containing 4- to 6-membered saturated heterocyclyl is optionally substituted with one $C_{1-3}$ alkyl), and
preferred $R^{A12}$ is a hydrogen atom, a halogen atom, or methyl, or
$R^{A11}$ and $R^{A12}$ optionally together form oxo, or
$R^{A11}$ and $R^{A12}$ optionally form $C_{3-6}$ cycloalkane together with the carbon atom(s) in the adjacent ring.

More preferred W is methanediyl or a structure represented by formula [III-1]:

[Chemical Formula 73]

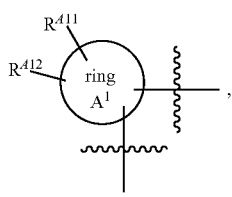

[III-1]

where
the methanediyl is optionally substituted with one group selected from the group consisting of $C_{1-4}$ alkyl(the $C_{1-4}$ alkyl is optionally substituted with one group selected from the group consisting of hydroxy and carboxy), halo-$C_2$ alkyl, phenyl-$C_{1-2}$ alkyl, and pyridyl-$C_1$ alkyl, and
when the methanediyl is substituted with one methyl, it is optionally further substituted with one methyl, and
in the structure represented by formula [III-1],
preferred ring $A^1$ is $C_{3-7}$ cycloalkane, a partially saturated 9-membered fused hydrocarbon aromatic ring, an oxygen atom-containing 4- to 6-membered saturated heterocycle, a sulfur atom-containing 6-membered saturated heterocycle, or a nitrogen atom-containing 4- to 6-membered saturated heterocycle,
where
the sulfur atom in the sulfur atom-containing 6-membered saturated heterocycle is optionally substituted with one to two oxo, and
the nitrogen atom in the nitrogen atom-containing 4- to 6-membered saturated heterocycle is optionally substituted with one group selected from the group consisting of $C_1$ alkylcarbonyl,
preferred $R^{A11}$ is
a hydrogen atom, hydroxy, carboxy, a halogen atom, $C_1$ alkyl, $C_{1-3}$ alkoxy, or nitrogen atom-containing 5- to 6-membered saturated heterocyclyl(the nitrogen atom-containing 5- to 6-membered saturated heterocyclyl is optionally substituted with one $C_1$ alkyl), and
preferred $R^{A12}$ is a hydrogen atom, a halogen atom, or methyl, or
$R^{A11}$ and $R^{A12}$ optionally together form oxo, or
$R^{A11}$ and $R^{A12}$ optionally form $C_4$ cycloalkane together with the carbon atom(s) in the adjacent ring.

Further preferred W is methanediyl or a structure represented by formula [III-1]:

[Chemical Formula 74]

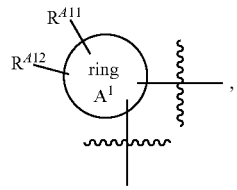

[III-1]

where
the methanediyl is optionally substituted with one group selected from the group consisting of methyl(the methyl is optionally substituted with one group selected from the group consisting of hydroxy and carboxy), ethyl, n-butyl, isobutyl, haloethyl, benzyl, phenethyl, and pyridylmethyl, and
when the methanediyl is substituted with one methyl, it is optionally further substituted with one methyl, and
in the structure represented by formula [III-1],
preferred ring $A^1$ is cyclopropane, cyclobutane, cyclopentane, cyclohexane, cycloheptane, dihydroindene, oxetane, tetrahydrofuran, tetrahydropyran, tetrahydrothiopyran, azetidine, pyrrolidine, or piperidine,
where
the sulfur atom in the tetrahydrothiopyran is optionally substituted with two oxo, and the nitrogen atom in the azetidine, pyrrolidine, and piperidine is optionally substituted with one methylcarbonyl, preferred $R^{A11}$ is a hydrogen atom, hydroxy, carboxy, a fluorine atom, methyl, methoxy, ethoxy, isopropoxy, pyrrolidinyl, morpholinyl, or piperazinyl(the piperazinyl is optionally substituted with one methyl), and preferred $R^{A12}$ is a hydrogen atom, a fluorine atom, or methyl, or $R^{A11}$ and $R^{A12}$ optionally together form oxo, or $R^{A11}$ and $R^{A12}$ optionally form cyclobutane together with the carbon atom in the adjacent ring.

Ring $B^1$ is phenyl, $R^{B11}$ and $R^{B12}$ are each independently a hydrogen atom, a halogen atom, $C_{1-6}$ alkyl, or $C_{1-6}$ alkoxy, $L^1$ is $C_{3-8}$ alkanediyl(the $C_{3-8}$ alkanediyl is optionally substituted with one to five fluorine atoms), and one carbon atom in the $C_{3-8}$ alkanediyl, that is two or more atoms away from the nitrogen atom to which $R^2$ is bonded, is optionally replaced with formula —O—.

Ring $B^2$ is partially saturated 9- to 10-membered fused aryl or nitrogen atom-containing 9- to 10-membered fused heteroaryl, $R^{B21}$ and $R^{B22}$ are both hydrogen atoms, and $L^2$ is $C_{1-2}$ alkanediyl(the $C_{1-2}$ alkanediyl is optionally substituted with 1 to 4 fluorine atoms).

More preferred ring $B^1$ is phenyl, $R^{B11}$ and $R^{B12}$ are each independently a hydrogen atom, a halogen atom, $C_1$ alkyl, or $C_1$ alkoxy, $L^1$ is $C_{3-6}$ alkanediyl(the $C_{3-6}$ alkanediyl is optionally substituted with one to two fluorine atoms), and one carbon atom in the $C_{3-6}$ alkanediyl, that is two or more atoms away from the nitrogen atom to which $R^2$ is bonded, is optionally replaced with formula —O—.

More preferred ring $B^2$ is partially saturated 9-membered fused aryl or nitrogen atom-containing 9-membered fused heteroaryl, $R^{B21}$ and $R^{B22}$ are both hydrogen atoms, and $L^2$ is $C_{1-2}$ alkanediyl.

Further preferred ring $B^1$ is phenyl, $R^{B11}$ and $R^{B12}$ are each independently a hydrogen atom, a fluorine atom, methyl, or methoxy, and $L^1$ is any of structures represented by formulas [V-3] to [V-5], [V-7] to [V-8], [V-11] to [V-12], and [V-14] to [V-16]:

[Chemical Formula 75]

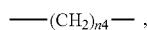 [V-3]

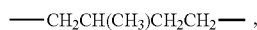 [V-4]

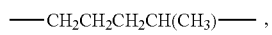 [V-5]

 [V-7]

 [V-8]

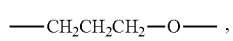 [V-11]

-continued

[Chemical Formula 76]

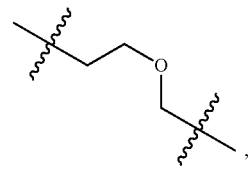 [V-12]

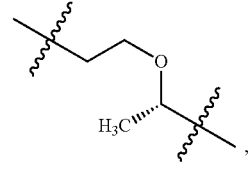 [V-14]

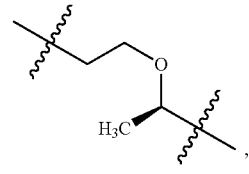 [V-15]

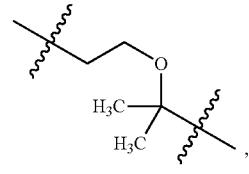 [V-16]

where n4 is an integer of 3 to 5.

Further preferred ring $B^2$ is dihydroindenyl, indolyl, or isoindolinyl, $R^{B21}$ and $R^{B22}$ are both hydrogen atoms, and $L^2$ is a structure represented by formula [V-20]:

[Chemical Formula 77]

 [V-20]

where n5 is an integer of 1 to 2.

$R^3$ is $C_{1-3}$ alkyl(the $C_{1-3}$ alkyl is optionally substituted with one group selected from the group consisting of hydroxy and methoxy), more preferred $R^3$ is methyl(the methyl is optionally substituted with one group selected from the group consisting of hydroxy and methoxy) or ethyl, further preferred $R^3$ is methyl, and particularly preferred $R^3$ is methyl having a steric configuration represented by formula [VII]:

[Chemical Formula 78]

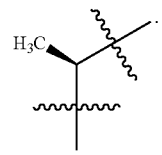 [VII]

$R^4$ is a group represented by formula [VI]:

[Chemical Formula 79]

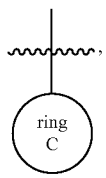
[VI]

where
ring C is phenyl,
where
the phenyl is substituted with one group selected from the group consisting of a halogen atom, $C_{1-6}$ alkyl, $C_{1-6}$ alkoxy, and $C_{1-6}$ alkylcarbonyl, and furthermore,
the phenyl is optionally substituted with one to four groups that are the same or different, selected from the group consisting of hydroxy, carboxy, carbamoyl, cyano, a halogen atom, $C_{1-6}$ alkyl(the $C_{1-6}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one hydroxy), $C_{2-6}$ alkenyl, $C_{2-6}$ alkynyl, $C_{3-8}$ cycloalkyl(the $C_3$-8 cycloalkyl is optionally substituted with one hydroxy), $C_{1-6}$ alkoxy, halo-$C_{1-6}$ alkoxy, $C_3$-8 cycloalkoxy, $C_{1-6}$ alkylsulfanyl, $C_{1-6}$ alkylsulfinyl, $C_{1-6}$ alkylsulfonyl, mono-$C_{1-6}$ alkylamino, di-$C_{1-6}$ alkylamino, $C_{1-6}$ alkylcarbonyl, halo-$C_{1-6}$ alkylcarbonyl, $C_{1-6}$ alkoxycarbonyl, mono-$C_{1-6}$ alkylaminocarbonyl, and di-$C_{1-6}$ alkylaminocarbonyl.

More preferred $R^4$ is a group represented by formula [VI]:

[Chemical Formula 80]

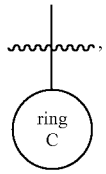
[VI]

where
ring C is phenyl,
where
the phenyl is substituted with one group selected from the group consisting of a halogen atom, $C_{1-3}$ alkyl, $C_{1-3}$ alkoxy, and $C_{1-2}$ alkylcarbonyl, and furthermore,
the phenyl is optionally substituted with one to four groups that are the same or different, selected from the group consisting of hydroxy, carboxy, carbamoyl, cyano, a halogen atom, $C_{1-3}$ alkyl(the $C_{1-3}$ alkyl is optionally substituted with one group selected from the group consisting of hydroxy and $C_1$ alkoxy), halo-$C_{1-2}$ alkyl(the halo-$C_{1-2}$ alkyl is optionally substituted with one hydroxy), $C_{2-3}$ alkenyl, $C_3$ cycloalkyl(the $C_3$ cycloalkyl is optionally substituted with one hydroxy), $C_{1-3}$ alkoxy, halo-$C_2$ alkoxy, $C_3$ cycloalkoxy, $C_1$ alkylsulfinyl, $C_1$ alkylsulfonyl, mono-$C_2$ alkylamino, di-$C_2$ alkylamino, $C_{1-2}$ alkylcarbonyl, halo-$C_1$ alkylcarbonyl, $C_1$ alkoxycarbonyl, and mono-$C_1$ alkylaminocarbonyl.

Further preferred $R^4$ is a group represented by formula [VI]:

[Chemical Formula 81]

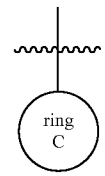
[VI]

where
ring C is phenyl,
where
the phenyl is substituted with one group selected from the group consisting of a fluorine atom, a chlorine atom, a bromine atom, methyl, ethyl, n-propyl, isopropyl, methoxy, ethoxy, n-propoxy, isopropoxy, methylcarbonyl, and ethylcarbonyl, and furthermore,
the phenyl is optionally substituted with one to four groups that are the same or different, selected from the group consisting of hydroxy, carboxy, carbamoyl, cyano, a fluorine atom, a chlorine atom, a bromine atom, methyl(the methyl is optionally substituted with one group selected from the group consisting of hydroxy and methoxy), ethyl, n-propyl, isopropyl, (the ethyl, n-propyl, and isopropyl are optionally substituted with one hydroxy), halomethyl, haloethyl(the haloethyl is optionally substituted with one hydroxy), ethenyl, isopropenyl, cyclopropyl(the cyclopropyl is optionally substituted with one hydroxy), methoxy, ethoxy, n-propoxy, isopropoxy, haloethoxy, cyclopropoxy, methylsulfinyl, methylsulfonyl, monoethylamino, diethylamino, methylcarbonyl, ethylcarbonyl, halomethylcarbonyl, methoxycarbonyl, and methylaminocarbonyl.

Another preferred aspect of the compound of the present invention is aspect (C) below.

Aspect (C):

In the present aspect (C), a preferred aspect is as follows.

In the compound represented by the above formula [I-1], or a pharmaceutically acceptable salt thereof, or a hydrate thereof,
the compound represented by formula [I-1] is a compound represented by formula [I-2]:

[Chemical Formula 82]

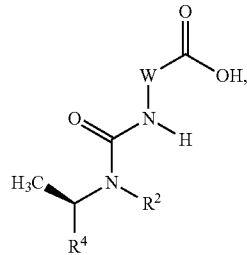
[I-2]

where $R^2$ is a group represented by formula [IV-1] or [IV-2]:

[Chemical Formula 83]

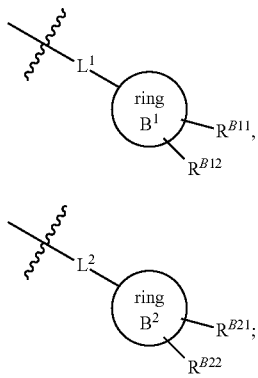

[IV-1]

[IV-2]

where

W, ring $B^1$, $R^{B11}$, $R^{B12}$, $L^1$, ring $B^2$, $R^{B21}$, $R^{B22}$, $L^2$, and $R^4$ are as mentioned above.

In the present aspect (C), a more preferred aspect is as follows.

In the above formula [I-2],

W is methanediyl or a structure represented by formula [III-1]:

[Chemical Formula 84]

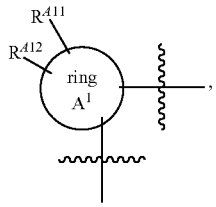

[III-1]

where the methanediyl is optionally substituted with one methyl, and the methanediyl is optionally further substituted with one methyl, and in the structure represented by formula [III-1], ring $A^1$ is $C_{3-4}$ cycloalkane or an oxygen atom-containing 4- to 5-membered saturated heterocycle, $R^{A11}$ is a hydrogen atom, hydroxy, a halogen atom, $C_1$ alkyl, or $C_{1-2}$ alkoxy, $R^{A12}$ is a hydrogen atom, a halogen atom, or methyl;

ring $B^1$ is phenyl, $R^{B11}$ and $R^{B12}$ are both hydrogen atoms, $L^1$ is $C_{3-5}$ alkanediyl (the $C_{3-5}$ alkanediyl is optionally substituted with one to two fluorine atoms), where one carbon atom in the $C_{3-5}$ alkanediyl, that is two or more atoms away from the nitrogen atom to which $R^2$ is bonded, is optionally replaced with formula —O—, ring $B^2$ is partially saturated 9-membered fused aryl, $R^{B21}$ and $R^{B22}$ are both hydrogen atoms;

$L^2$ is $C_2$ alkanediyl; and $R^4$ is a group represented by formula [VI]:

[Chemical Formula 85]

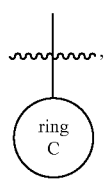

[VI]

where ring C is phenyl, the phenyl is substituted with one group selected from the group consisting of a halogen atom, $C_{1-3}$ alkyl, $C_{1-2}$ alkoxy, and $C_1$ alkylcarbonyl, and furthermore, the phenyl is optionally substituted with one to four groups that are the same or different, selected from the group consisting of cyano, a halogen atom, $C_{1-3}$ alkyl (the $C_{1-3}$ alkyl is optionally substituted with one hydroxy), $C_2$ alkenyl, $C_3$ cycloalkyl, $C_{1-2}$ alkoxy, mono-$C_2$ alkylamino, and $C_1$ alkylcarbonyl.

In the present aspect (C), a further preferred aspect is as follows.

In the above formula [I-2],

W is any of structures represented by formulas [III-4] to [III-17]:

[Chemical Formula 86]

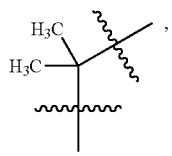

[III-4]

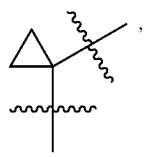

[III-5]

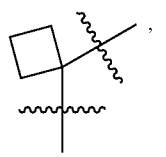

[III-6]

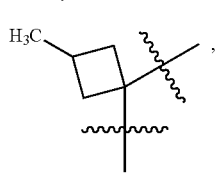

[III-7]

[III-8] 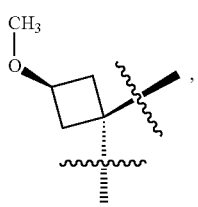

[III-9] 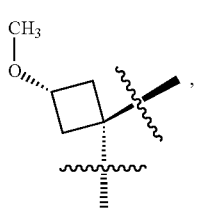

[III-10] 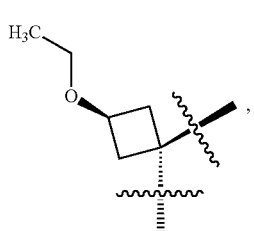

[III-11] 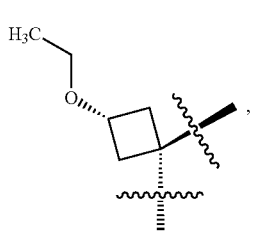

[III-12] 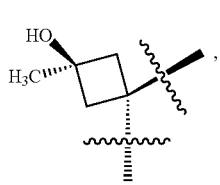

[III-13] 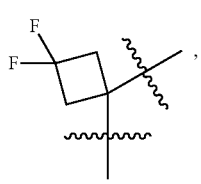

[III-14] 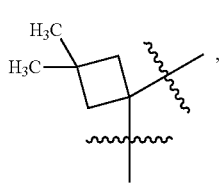

[III-15] 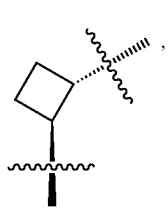

[III-16] 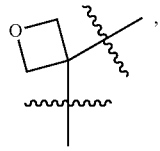

[III-17] 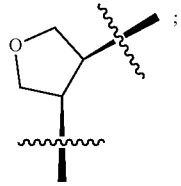

ring $B^1$ is phenyl,
$R^{B11}$ and $R^{B12}$ are both hydrogen atoms, and
$L^1$ is a structure represented by formula [V-3], [V-8], [V-12], [V-14], or [V-15]:

[Chemical Formula 87]

$$-(CH_2)_{n4}-\quad\quad [V-3]$$

$$-CH_2CH_2CH_2CF_2-\quad\quad [V-8]$$

[V-12] 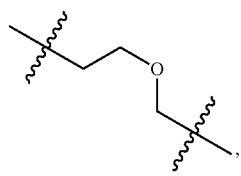

[V-14] 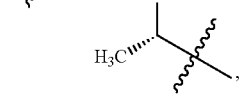

[V-15] 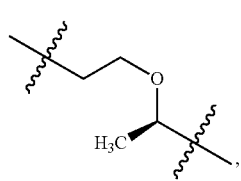

where
n4 is an integer of 3 to 4, and
ring $B^2$ is dihydroindenyl,
$R^{B21}$ and $R^{B22}$ are both hydrogen atoms, and
$L^2$ is a structure represented by formula [V-20]:

[Chemical Formula 88]

$$-(CH_2)_{n5}-\quad\quad [V-20]$$

where
n5 is 2; and
$R^4$ is any of groups represented by formula [VI-1] to [VI-21]:
[Chemical Formula 89]
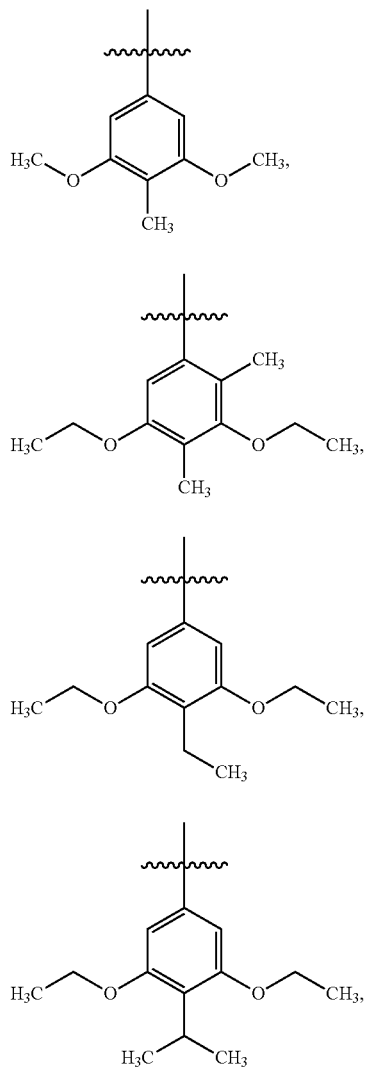
[VI-1]
[VI-2]
[VI-3]
[VI-4]
[VI-5]
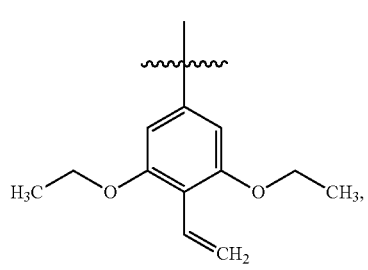
-continued
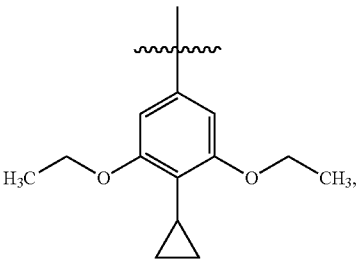
[VI-6]
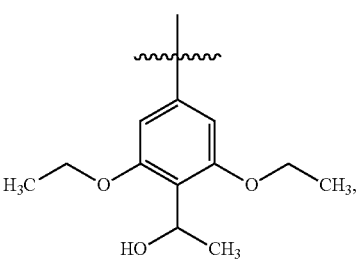
[VI-7]
[Chemical Formula 90]
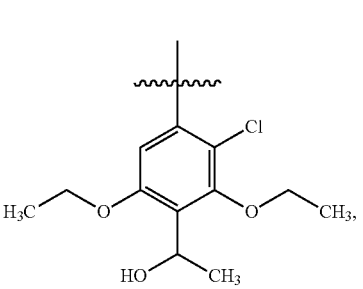
[VI-8]
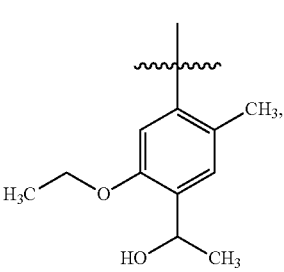
[VI-9]
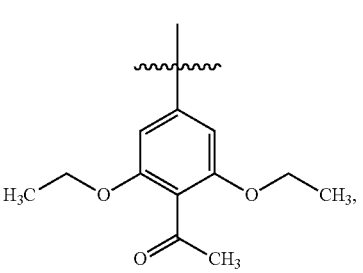
[VI-10]
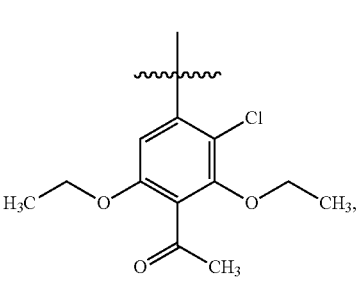
[VI-11]

[VI-12]
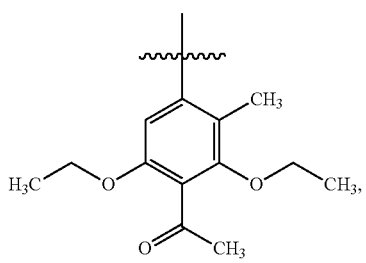
[VI-13]
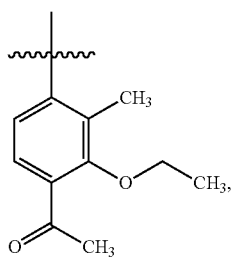
[Chemical Formula 91]
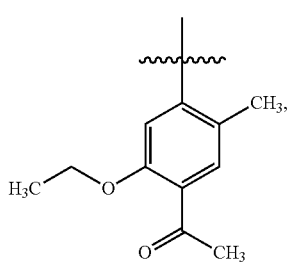
[VI-14]
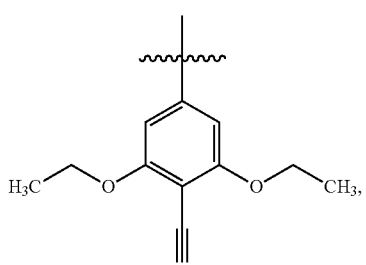
[VI-15]
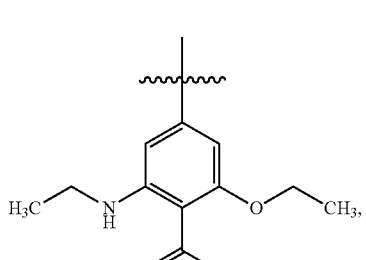
[VI-16]
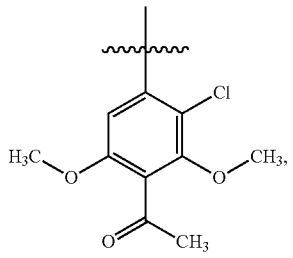
[VI-17]
[VI-18]
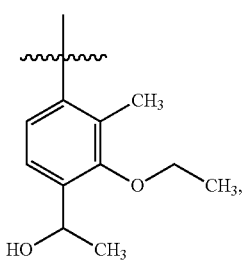
[VI-19]
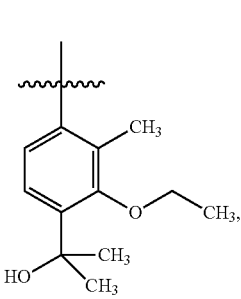
[VI-20]
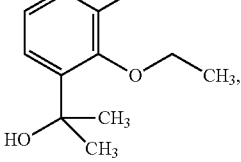
[VI-21]
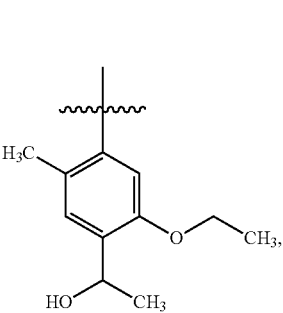
Another preferred aspect of the compound of the present invention is aspect (D) below.
Aspect (D):
In the present aspect (D), a preferred aspect is as follows.
In the compound represented by the above formula [I-1], or a pharmaceutically acceptable salt thereof, or a hydrate thereof, the compound represented by formula [I-1] is a compound represented by formula [I-3]:

[Chemical Formula 92]

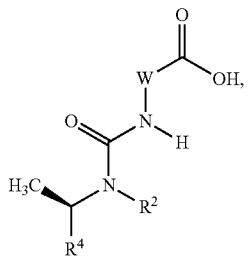

[I-3]

where
$R^2$ is a group represented by formula [IV-1] or [IV-2]:

[Chemical Formula 93]

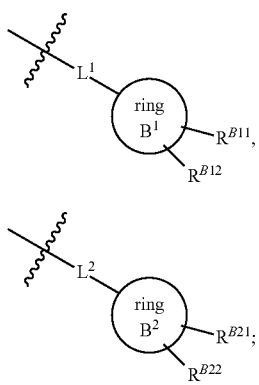

[IV-1]

[IV-2]

where
W, ring $B^1$, $R^{B11}$, $R^{B12}$, $L^1$, ring $B^2$, $R^{B21}$, $R^{B22}$, $L^2$, and $R^4$ are as mentioned above.

In the present aspect (D), a more preferred aspect is as follows.
In the above formula [I-3],
W is methanediyl or a structure represented by formula [III-1]:

[Chemical Formula 94]

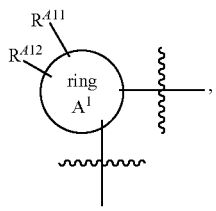

[III-1]

where
the methanediyl is optionally substituted with one methyl, and
the methanediyl is optionally further substituted with one methyl, and
in the structure represented by formula [III-1], ring $A^1$ is $C_{3-4}$ cycloalkane,
$R^{A11}$ is a hydrogen atom, a halogen atom, $C_1$ alkyl, or $C_{1-2}$ alkoxy, and
$R^{A12}$ is a hydrogen atom, a halogen atom, or methyl;
ring $B^1$ is phenyl,
$R^{B11}$ and $R^{B12}$ are both hydrogen atoms,
$L^1$ is $C_{4-5}$ alkanediyl(the $C_{4-5}$ alkanediyl is optionally substituted with two fluorine atoms), and
one carbon atom in the $C_{4-5}$ alkanediyl, that is two or more atoms away from the nitrogen atom to which $R^2$ is bonded, is optionally replaced with formula —O—,
ring $B^2$ is partially saturated 9-membered fused aryl,
$R^{B21}$ and $R^{B22}$ are both hydrogen atoms, and
$L^2$ is $C_2$ alkanediyl; and
$R^4$ is a group represented by formula [VI]:

[Chemical Formula 95]

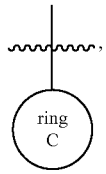

[VI]

where
ring C is phenyl,
the phenyl is substituted with one group selected from the group consisting of a halogen atom, $C_{1-3}$ alkyl, $C_{1-2}$ alkoxy, and $C_1$ alkylcarbonyl, and furthermore,
the phenyl is optionally substituted with one to four groups that are the same or different, selected from the group consisting of a halogen atom, $C_{1-3}$ alkyl(the $C_{1-3}$ alkyl is optionally substituted with one hydroxy), $C_{1-2}$ alkoxy, mono-$C_2$ alkylamino, and $C_1$ alkylcarbonyl.

In the present aspect (D), a further preferred aspect is as follows.
In the above formula [I-3],
W is a structure represented by any of formulas [III-4] to [III-11], [III-13] to [III-14] and [III-18] to [III-19]:

[Chemical Formula 96]

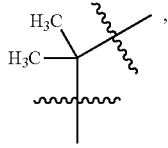

[III-4]

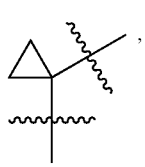

[III-5]

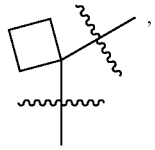

[III-6]

-continued

[III-7]
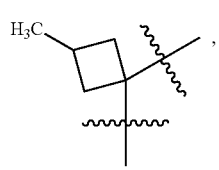

[III-8]
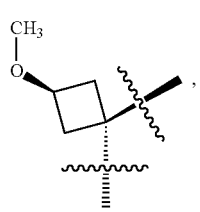

[III-9]
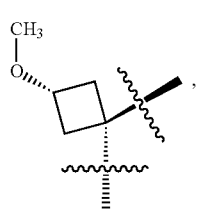

[III-10]
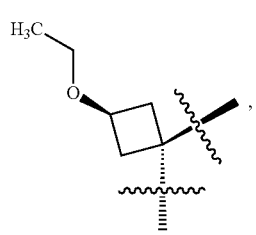

[III-11]
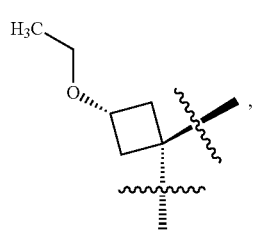

[III-13]
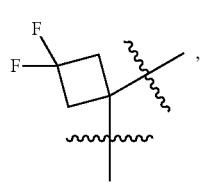

[III-14]
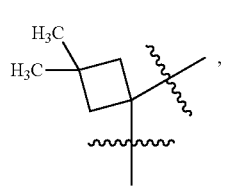

[III-18]
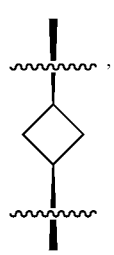

-continued

[III-19]
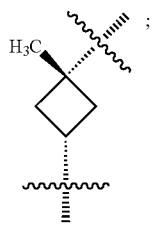

ring $B^1$ is phenyl, $R^{B11}$ and $R^{B12}$ are both hydrogen atoms, and $L^1$ is a structure represented by formula [V-3], [V-8], or [V-14]:

[Chemical Formula 97]

$$—(CH_2)_{n4}—, \quad [V\text{-}3]$$

$$—CH_2CH_2CH_2CF_2—, \quad [V\text{-}8]$$

[V-14]
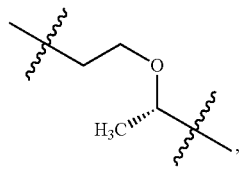

where n4 is 4, and ring $B^2$ is dihydroindenyl, $R^{B21}$ and $R^{B22}$ are both hydrogen atoms, and $L^2$ is a structure represented by formula [V-20]:

[Chemical Formula 98]

$$—(CH_2)_{n5}— \quad [V\text{-}20],$$

where n5 is 2; and $R^4$ is any of groups represented by formula [VI-2], [VI-3], [VI-8], [VI-10] to [VI-12], [VI-16], [VI-19], and [VI-21]:

[Chemical Formula 99]

[VI-2]
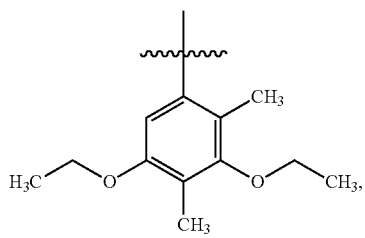

[VI-3]
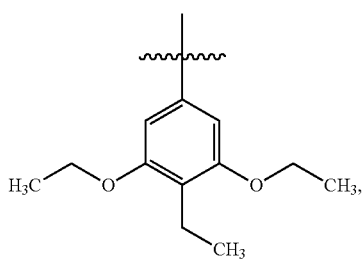

[VI-8]
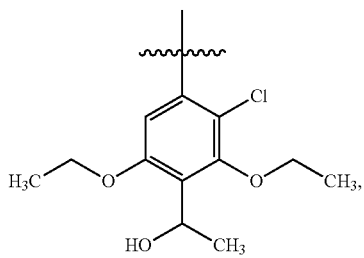

[VI-10]
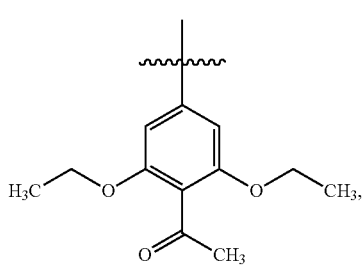

[VI-11]
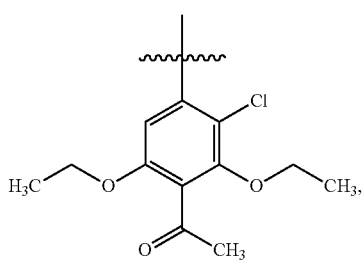

[Chemical Formula 100]

[VI-12]
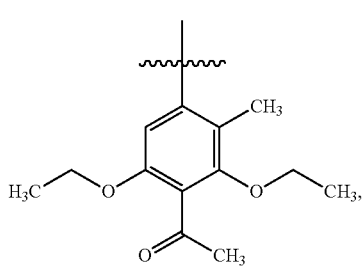

[VI-16]
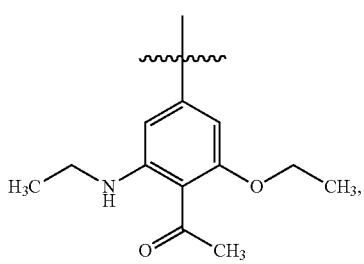

[VI-19]
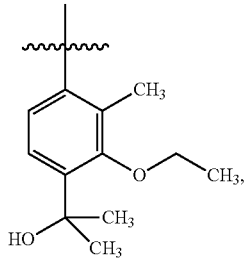

[VI-21]
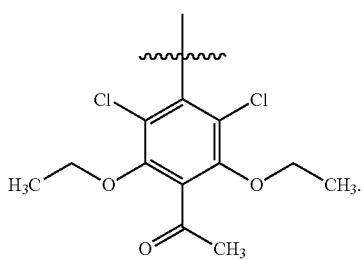

Another preferred aspect of the compound of the present invention is aspect (E) below.

Aspect (E):

In the present aspect (E), a preferred aspect is as follows.

In the compound represented by the above formula [I-1], or a pharmaceutically acceptable salt thereof, or a hydrate thereof, the compound represented by formula [I-1] is a compound represented by formula [I-4]:

[Chemical Formula 101]

[I-4]
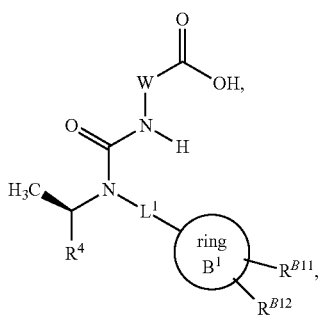

where
R⁴ is a group represented by formula [VI-22]:

[Chemical Formula 102]

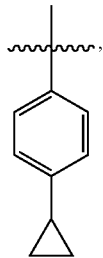

[VI-22]

the group represented by formula [VI-22] is substituted with one to two $C_{1-6}$ alkoxy; and
preferred W, ring $B^1$, $R^{B11}$, $R^{B12}$, and $L^1$ are as mentioned above.

In the present aspect (E), a more preferred aspect is as follows.
In the above formula [I-4],
W is a structure represented by formula [III-1]:

[Chemical Formula 103]

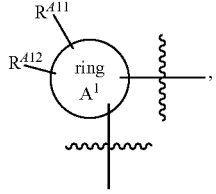

[III-1]

where,
in the structure represented by formula [III-1],
ring $A^1$ is $C_4$ cycloalkane,
$R^{A11}$ is $C_{1-2}$ alkoxy, and
$R^{A12}$ is a hydrogen atom;
ring $B^1$ is phenyl,
$R^{B11}$ and $R^{B12}$ are both hydrogen atoms,
$L^1$ is $C_5$ alkanediyl, and
one carbon atom in the $C_5$ alkanediyl, that is two or more atoms away from the nitrogen atom to which $R^2$ is bonded, is optionally replaced with formula —O—; and
$R^4$ is a group represented by the above formula [VI-22]:

[Chemical Formula 104]

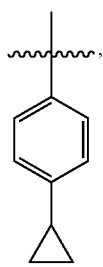

[VI-22]

where
the group represented by formula [VI-22] is substituted with two $C_2$ alkoxy.

In the present aspect (E), a further preferred aspect is as follows.
In the above formula [I-4],
W is any of structures represented by formulas [III-8] to [III-11]:

[Chemical Formula 105]

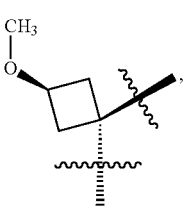

[III-8]

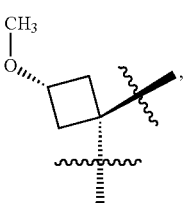

[III-9]

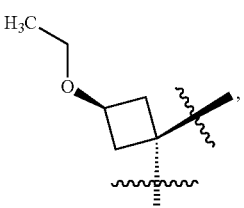

[III-10]

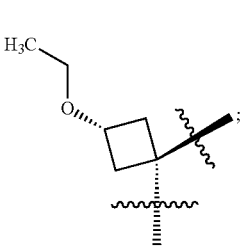

[III-11]

ring $B^1$ is phenyl,
$R^{B11}$ and $R^{B12}$ are both hydrogen atoms, and
$L^1$ is a structure represented by formula [V-14]:

[Chemical Formula 106]

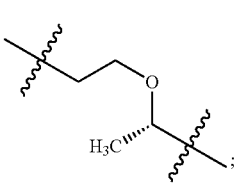

[V-14]

$R^4$ is a group represented by formula [VI-6]:

[Chemical Formula 107]

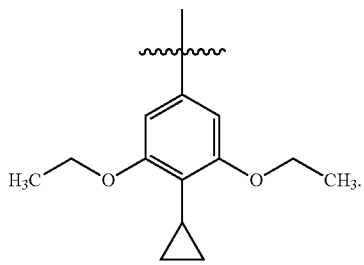

[VI-6]

Then, in the present aspect (E), one particularly preferred aspect is as follows.

It is the case where the compound represented by the above formula [I-4] is any of the following:

[Chemical Formula 108]

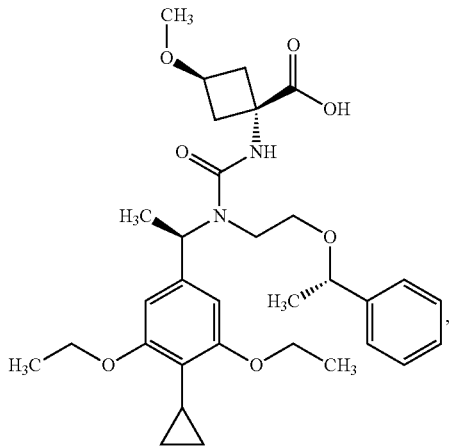

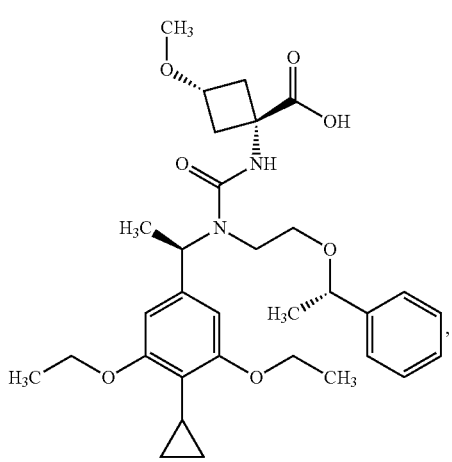

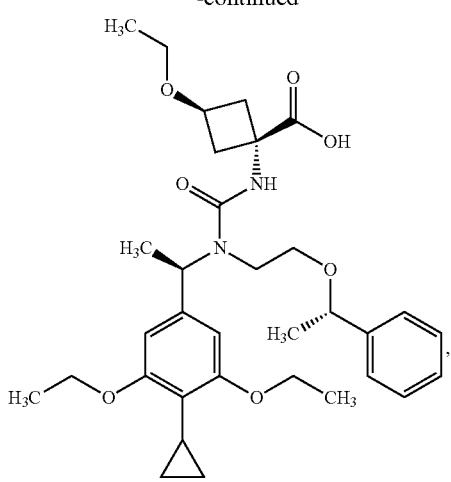

Also, in the present aspect (E), another particularly preferred aspect is as follows.

It is the case where the compound represented by the above formula [I-4] is the

[Chemical Formula 109]

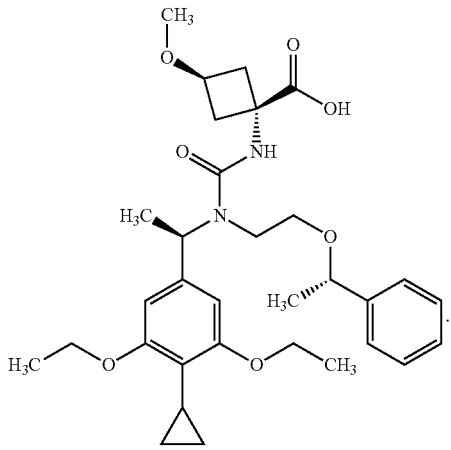

Also, in the present aspect (E), another particularly preferred aspect is as follows.

It is the case where the compound represented by the above formula [I-4] is the following:

[Chemical Formula 110]

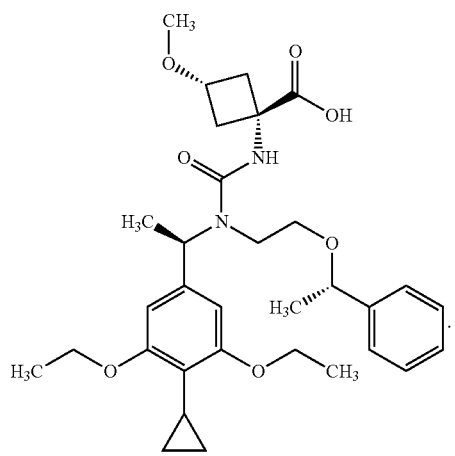

Also, in the present aspect (E), another particularly preferred aspect is as follows.

It is the case where the compound represented by the above formula [I-4] is the

[Chemical Formula 111]

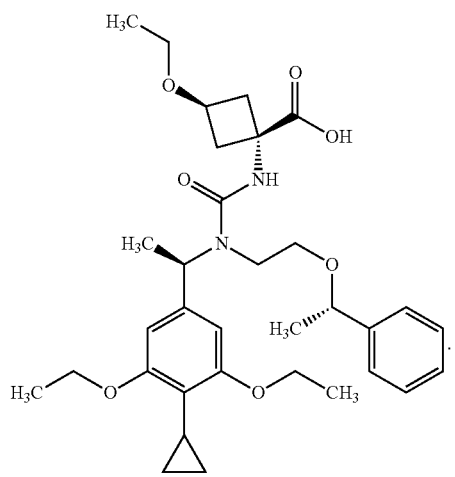

Also, in the present aspect (E), another particularly preferred aspect is as follows.

It is the case where the compound represented by the above formula [I-4] is the following:

[Chemical Formula 112]

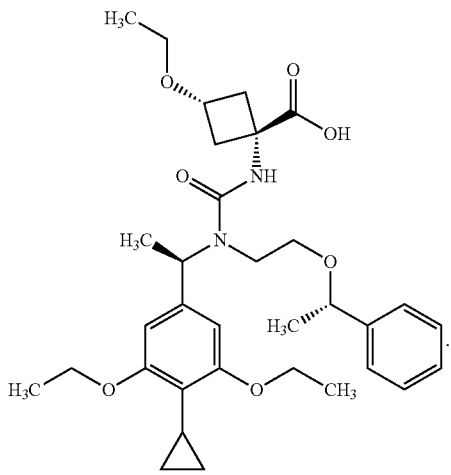

Another preferred aspect of the compound of the present invention is aspect (F) below.

Aspect (F):

In the present aspect (F), a preferred aspect is as follows.

In the compound represented by the above formula [I-1], or a pharmaceutically acceptable salt thereof, or a hydrate thereof, the compound represented by formula [I-1] is a compound represented by formula [I-5]:

[Chemical Formula 113]

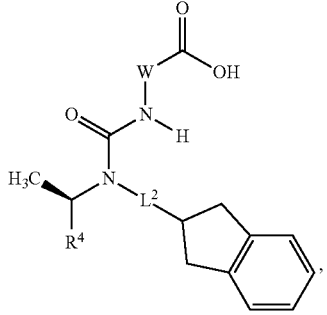

where

W, $L^2$, and $R^4$ are as mentioned above.

In the present aspect (F), a more preferred aspect is as follows.
In the above formula [I-5],
W is a structure represented by formula [III-1]:

[Chemical Formula 114]

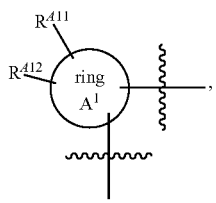

[III-1]

where,
in the structure represented by formula [III-1],
ring $A^1$ is $C_4$ cycloalkane,
$R^{411}$ is $C_1$ alkoxy, and
$R^{412}$ is a hydrogen atom;
$L^2$ is $C_2$ alkanediyl; and
$R^4$ is a group represented by formula [VI]:

[Chemical Formula 115]

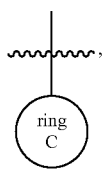

[VI]

where
ring C is phenyl,
the phenyl is substituted with three groups that are the same or different, selected from the group consisting of $C_2$ alkoxy and $C_1$ alkylcarbonyl, and furthermore,
the phenyl is optionally substituted with one $C_1$ alkyl.

In the present aspect (F), a further preferred aspect is as follows.
In the above formula [I-5],
W is a structure represented by formula [III-8] or [III-9]:

[Chemical Formula 116]

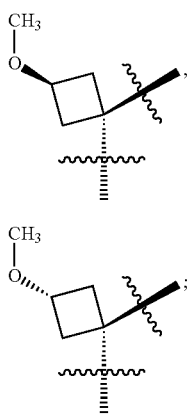

[III-8]

[III-9]

$L^2$ is a structure represented by formula [V-20]:
[Chemical Formula 117]

$$—(CH_2)_{n5}— \quad [V-20],$$

where
n5 is 2; and
$R^4$ is a group represented by formula [VI-10] or [VI-12]:

[Chemical Formula 118]

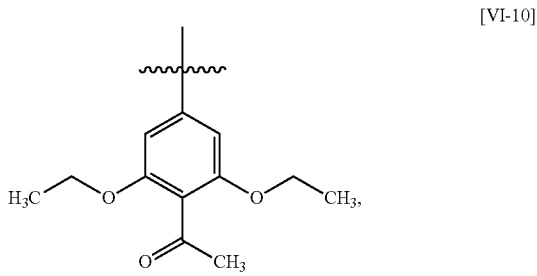

[VI-10]

[VI-12]

Then, in the present aspect (F), one particularly preferred aspect is as follows. 1
It is the case where the compound represented by the above formula [I-5] is any of the following:

[Chemical Formula 119]

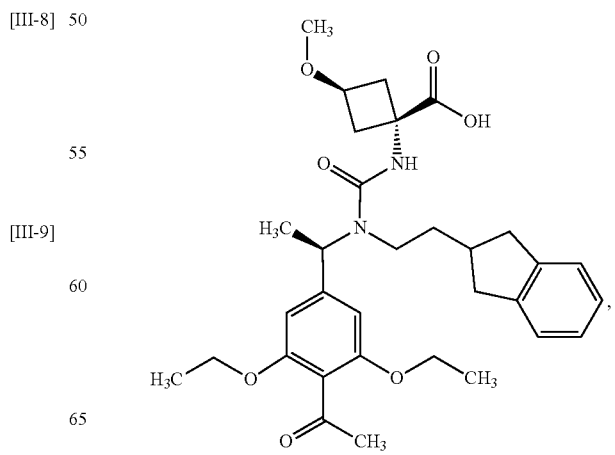

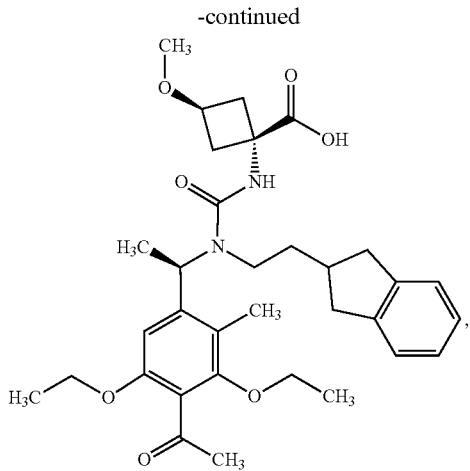
,

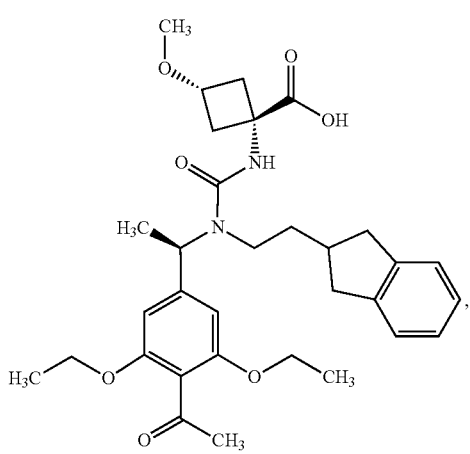
,

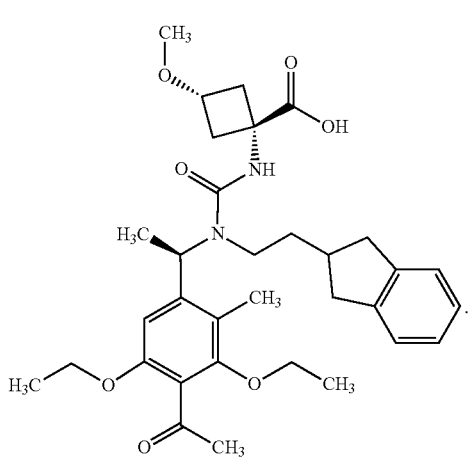
,

Also, in the present aspect (F), another particularly preferred aspect is as follows.

It is the case where the compound represented by the above formula [I-5] is the following:

[Chemical Formula 120]

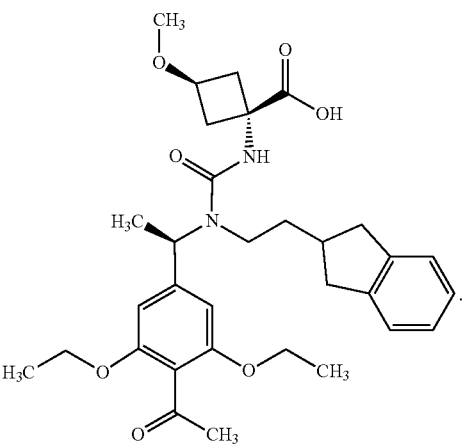

Also, in the present aspect (F), another particularly preferred aspect is as follows.

It is the case where the compound represented by the above formula [I-5] is the following:

[Chemical Formula 121]

.

Also, in the present aspect (F), another particularly preferred aspect is as follows.

It is the case where the compound represented by the above formula [I-5] is the following:

[Chemical Formula 122]

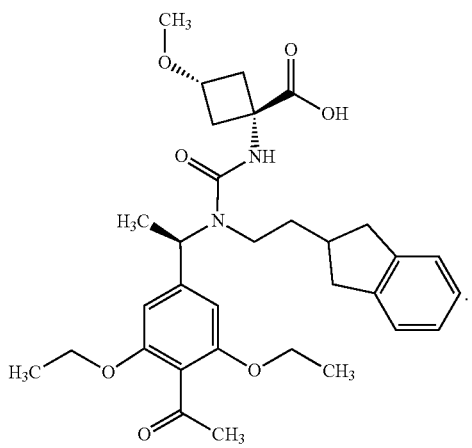

Also, in the present aspect (F), another particularly preferred aspect is as follows.

It is the case where the compound represented by the above formula [I-5] is the following:

[Chemical Formula 123]

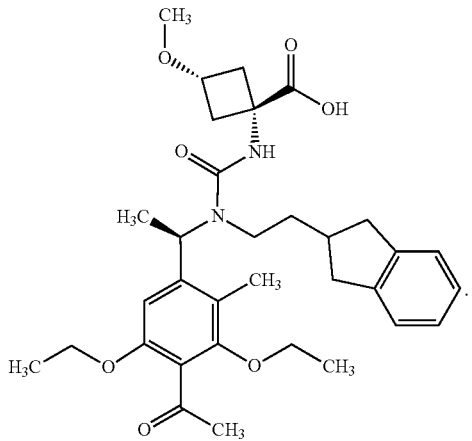

Another preferred aspect of the compound of the present invention is aspect (F-2) below.

Aspect (F-2):

In the present aspect (F-2), a preferred aspect is as follows.

In the compound represented by the above formula [I-1], or a pharmaceutically acceptable salt thereof, or a hydrate thereof, the compound represented by formula [I-1] is a compound represented by formula [I-5-2]:

[Chemical Formula 124]

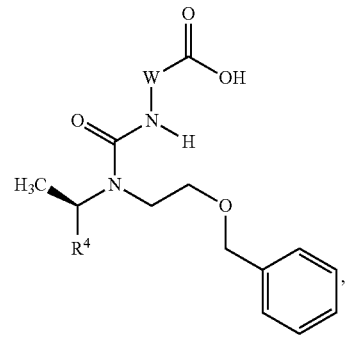

[I-5-2]

where
$R^4$ is a group represented by formula [VI-26]:

[Chemical Formula 125]

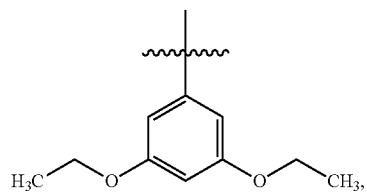

[VI-26]

the group represented by formula [VI-26] is substituted with one group selected from the group consisting of $C_{1-6}$ alkyl, $C_{3-8}$ cycloalkyl, and $C_{1-6}$ alkylcarbonyl, and furthermore, it is optionally substituted with one group selected from the group consisting of a halogen atom and $C_{1-6}$ alkyl; and W is as mentioned above.

In the present aspect (F-2), a more preferred aspect is as follows.

In the above formula [I-5-2],

W is a structure represented by formula [III-1]:

[Chemical Formula 126]

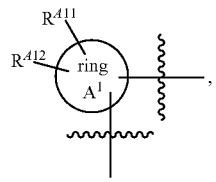

[III-1]

where,
in the structure represented by formula [III-1],
ring $A^1$ is $C_4$ cycloalkane,
$R^{411}$ is $C_{1-2}$ alkoxy, and
$R^{412}$ is a hydrogen atom;

$R^4$ is a group represented by the above formula [VI-26]:

[Chemical Formula 127]

[VI-26]

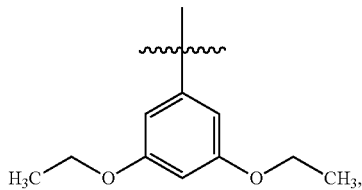

where the group represented by formula [VI-26] is substituted with one group selected from the group consisting of $C_1$ alkyl, $C_3$ cycloalkyl, and $C_1$ alkylcarbonyl, and furthermore, it is optionally substituted with one group selected from the group consisting of a halogen atom and $C_1$ alkyl.

In the present aspect (F-2), a further preferred aspect is as follows.

In the above formula [I-5-2],

W is a structure represented by formula [III-8] or [III-10]:

[Chemical Formula 128]

[III-8]

[III-10]

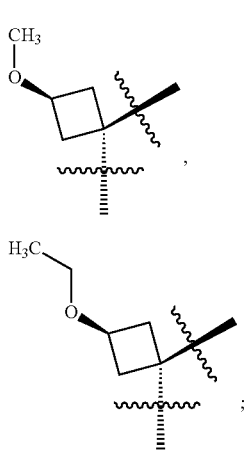

and $R^4$ is a group represented by formula [VI-2], [VI-6], [VI-10] to [VI-12], [VI-27], or [VI-28]:

[Chemical Formula 129]

[VI-2]

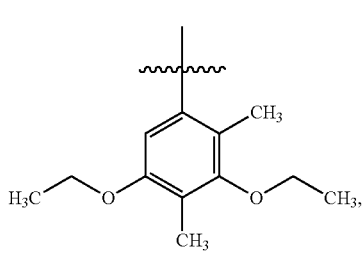

-continued

[VI-6]

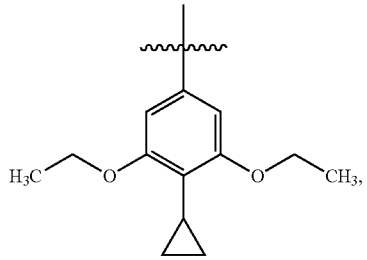

[VI-10]

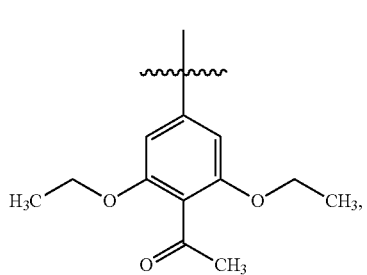

[VI-11]

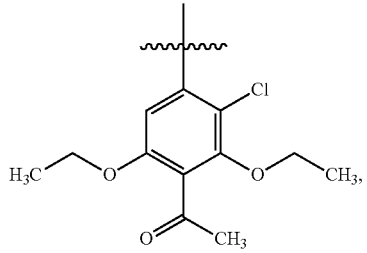

[VI-12]

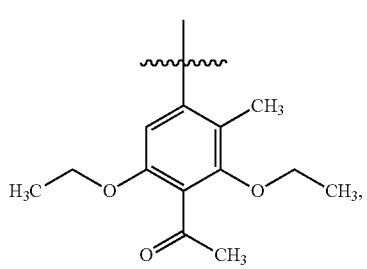

[VI-27]

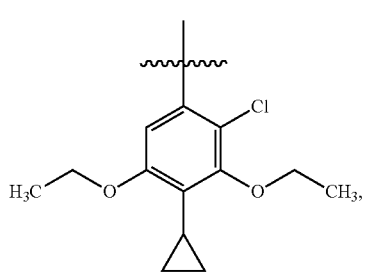

[VI-28]

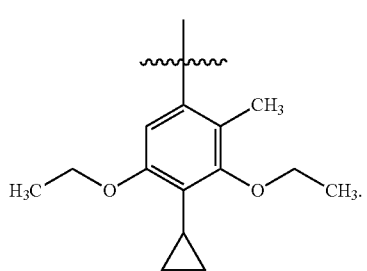

Then, in the present aspect (F-2), a particularly preferred aspect is as follows.

It is the case where the compound represented by the above formula [I-5-2] is the following:

[Chemical Formula 130]

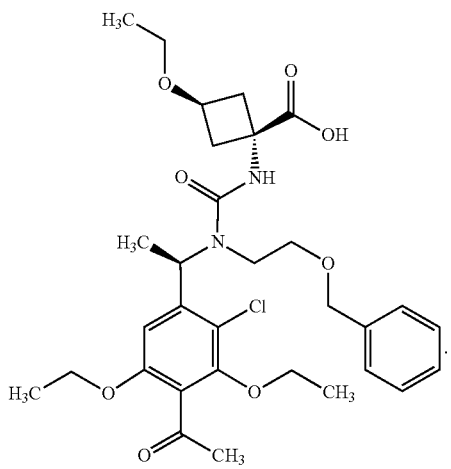

Another preferred aspect of the compound of the present invention is aspect (G) below.

Aspect (G):

In the present aspect (G), a preferred aspect is as follows.

In the compound represented by the above formula [I-1], or a pharmaceutically acceptable salt thereof, or a hydrate thereof, the compound represented by formula [I-1] is a compound represented by formula [I-6]:

[Chemical Formula 131]

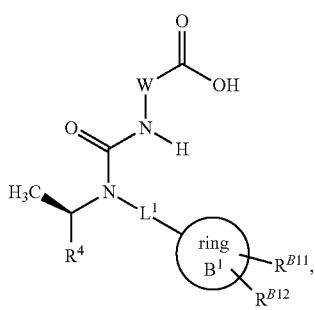

[I-6]

where
R$^4$ is a group represented by formula [VI-23]:

[Chemical Formula 132]

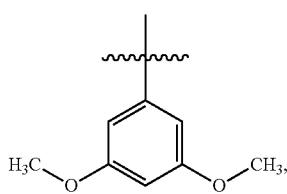

[VI-23]

the group represented by formula [VI-23] is substituted with one $C_{1-6}$ alkylcarbonyl, and furthermore, it is optionally substituted with one halogen atom; and W, ring B$^1$, R$^{B11}$, R$^{B12}$, and L$^1$ are as mentioned above.

In the present aspect (G), a more preferred aspect is as follows.

In the above formula [I-6],

W is a structure represented by formula [III-1]:

[Chemical Formula 133]

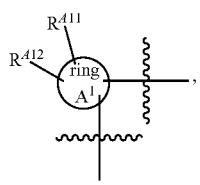

[III-1]

where,
in the structure represented by formula [III-1],
ring A$^1$ is $C_4$ cycloalkane,
R$^{A11}$ is $C_{1-2}$ alkoxy, and
R$^{A12}$ is a hydrogen atom;
ring B$^1$ is phenyl,
R$^{B11}$ and R$^{B12}$ are both hydrogen atoms,
L$^1$ is $C_{4-5}$ alkanediyl, and
one carbon atom in the $C_{4-5}$ alkanediyl, that is two or more atoms away from the nitrogen atom to which R$^2$ is bonded, is optionally replaced with formula —O—; and
R$^4$ is a group represented by the above formula [VI-23]:

[Chemical Formula 134]

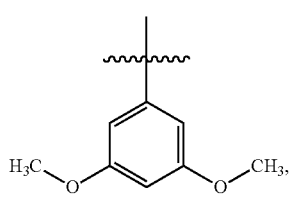

[VI-23]

where
the group represented by formula [VI-23] is substituted with one $C_1$ alkylcarbonyl, and furthermore,
it is optionally substituted with one halogen atom.

In the present aspect (G), a further preferred aspect is as follows.

In the above formula [I-6],

W is a structure represented by formula [III-8] or [III-10]:

[Chemical Formula 135]

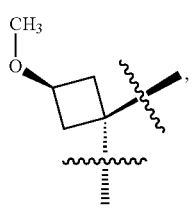

[III-8]

-continued

[III-10]

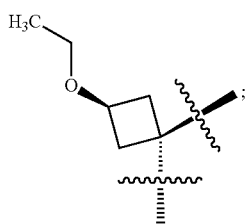

ring B¹ is phenyl,
$R^{B11}$ and $R^{B12}$ are both hydrogen atoms, and
L¹ is a structure represented by formula [V-12] or [V-14]:

[Chemical Formula 136]

[V-12]

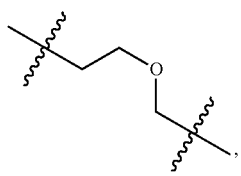

[V-14]

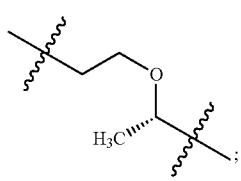

and
R⁴ is a group represented by formula [VI-24] or [VI-25]:

[Chemical Formula 137]

[VI-24]

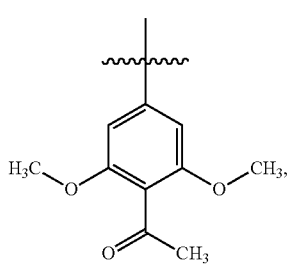

[VI-25]

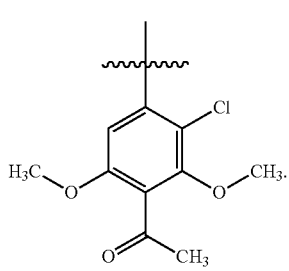

Then, in the present aspect (G), one particularly preferred aspect is as follows.

It is the case where the compound represented by the above formula [I-6] is any of the following:

[Chemical Formula 138]

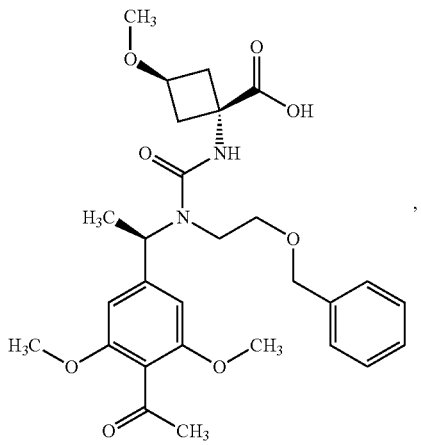

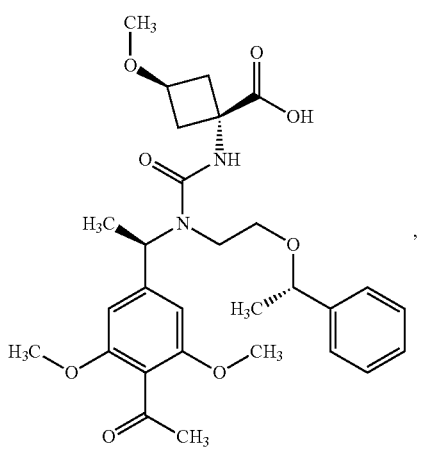

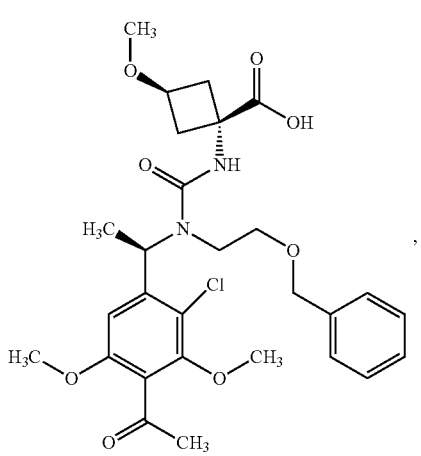

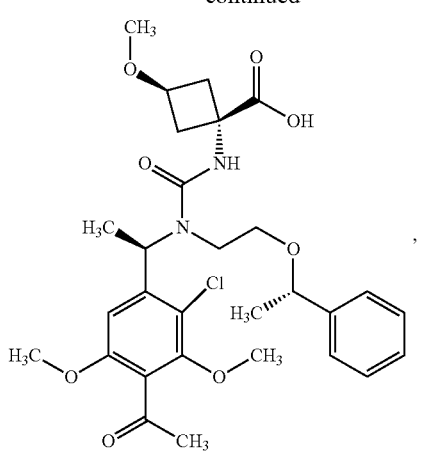
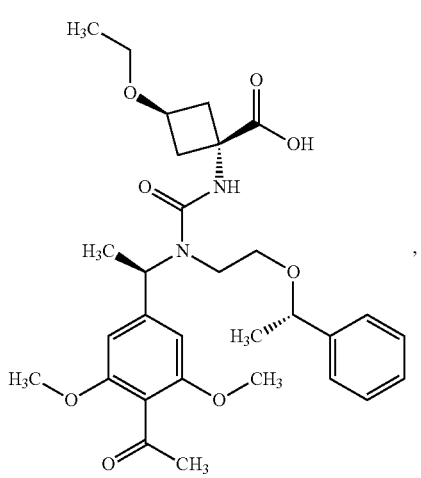
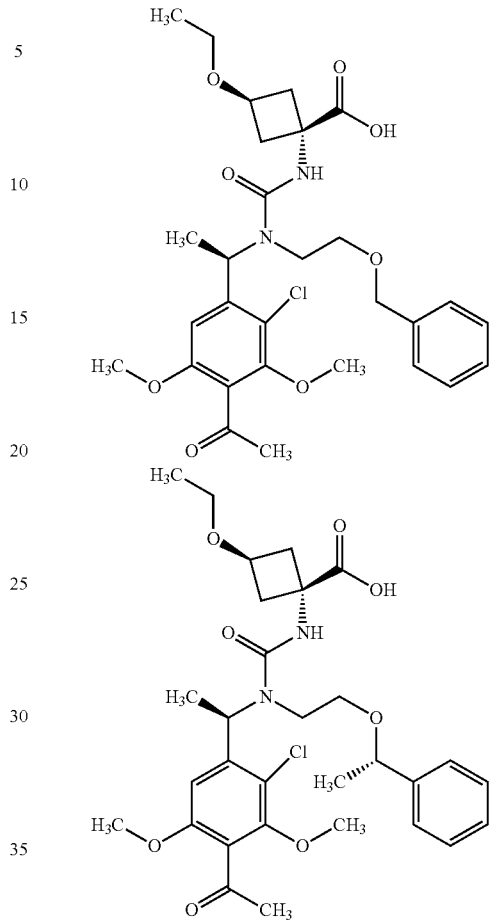
[Chemical Formula 139]
Also, in the present aspect (G), another particularly preferred aspect is as follows.
It is the case where the compound represented by the above formula [I-6] is the following:
[Chemical Formula 140]
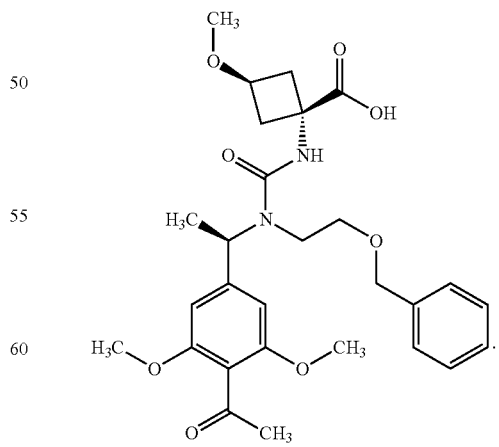
Also, in the present aspect (G), another particularly preferred aspect is as follows.

It is the case where the compound represented by the above formula [I-6] is the following:

[Chemical Formula 141]

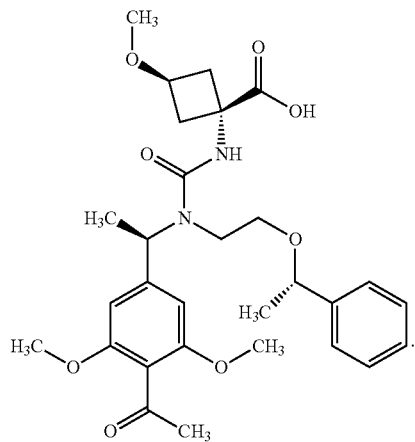

Also, in the present aspect (G), another particularly preferred aspect is as follows.

It is the case where the compound represented by the above formula [I-6] is the following:

[Chemical Formula 142]

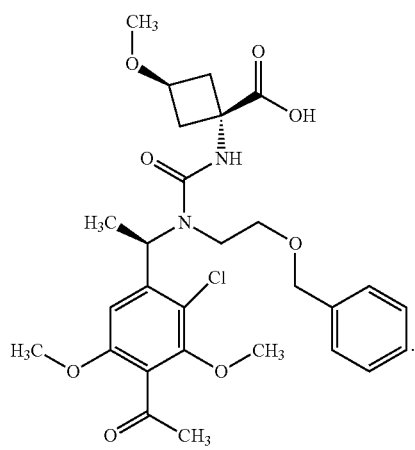

Also, in the present aspect (G), another particularly preferred aspect is as follows.

It is the case where the compound represented by the above formula [I-6] is the following:

[Chemical Formula 143]

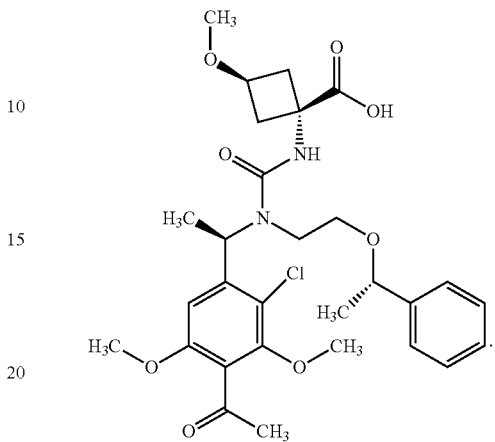

Also, in the present aspect (G), another particularly preferred aspect is as follows.

It is the case where the compound represented by the above formula [I-6] is the following:

[Chemical Formula 144]

Also, in the present aspect (G), another particularly preferred aspect is as follows.

It is the case where the compound represented by the above formula [I-6] is the following:

[Chemical Formula 145]

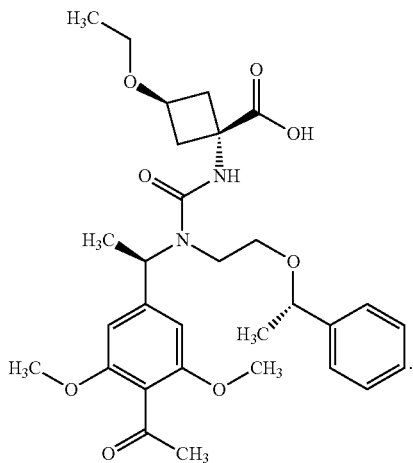

Also, in the present aspect (G), another particularly preferred aspect is as follows.

It is the case where the compound represented by the above formula [I-6] is the following:

[Chemical Formula 146]

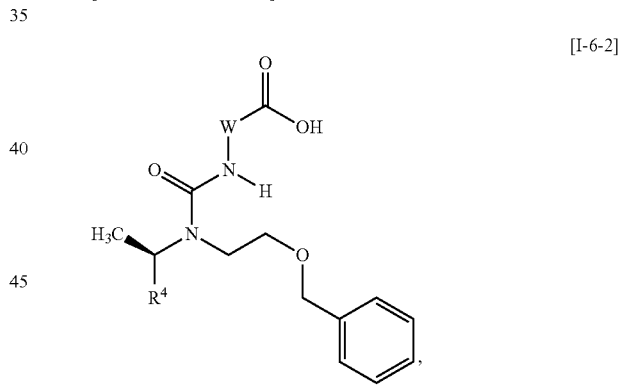

Also, in the present aspect (G), another particularly preferred aspect is as follows.

It is the case where the compound represented by the above formula [I-6] is the following:

[Chemical Formula 147]

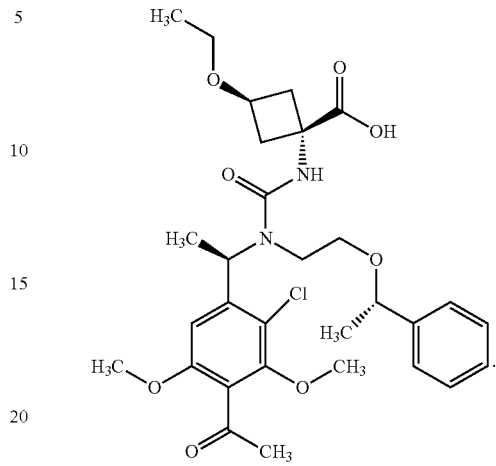

Another preferred aspect of the compound of the present invention is aspect (G-2) below.

Aspect (G-2):

In the present aspect (G-2), a preferred aspect is as follows.

In the compound represented by the above formula [I-1], or a pharmaceutically acceptable salt thereof, or a hydrate thereof, the compound represented by formula [I-1] is a compound represented by formula [I-6-2]:

[Chemical Formula 148]

[I-6-2]

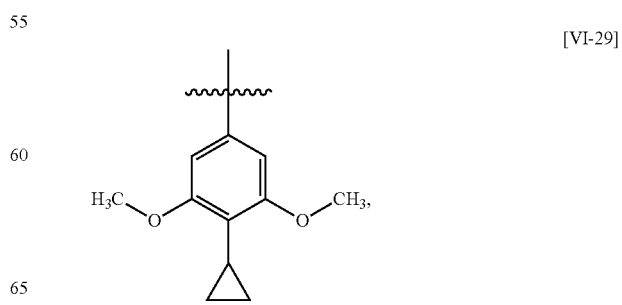

where
$R^4$ is a group represented by formula [VI-29]:

[Chemical Formula 149]

[VI-29]

and
the group represented by formula [VI-29] is substituted with one group selected from the group consisting of a halogen atom and $C_{1-6}$ alkyl; and W is as mentioned above.

In the present aspect (G-2), a more preferred aspect is as follows.

In the above formula [I-6-2],
W is a structure represented by formula [III-1]:

[Chemical Formula 150]

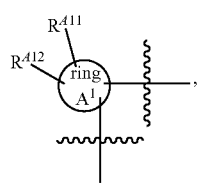
[III-1]

where,
in the structure represented by formula [III-1],
ring $A^1$ is $C_4$ cycloalkane,
$R^{411}$ is a hydrogen atom, a halogen atom, or $C_{1-2}$ alkoxy, and
$R^{412}$ is a hydrogen atom or a halogen atom; and
$R^4$ is a group represented by the above formula [VI-29]:

[Chemical Formula 151]

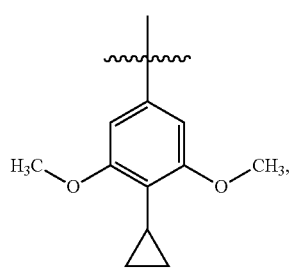
[VI-29]

where
the group represented by formula [VI-29] is substituted with one group selected from the group consisting of a halogen atom and $C_1$ alkyl.

In the present aspect (G-2), a further preferred aspect is as follows.

In the above formula [I-6-2],
W is a structure represented by formula [III-6], [III-8] to [III-11], or [III-13]:

[Chemical Formula 152]

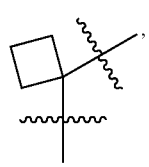
[III-6]

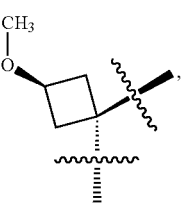
[III-8]

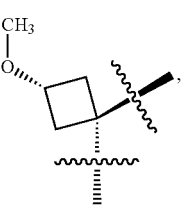
[III-9]

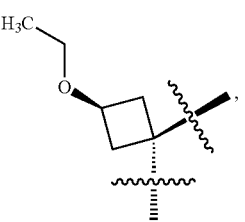
[III-10]

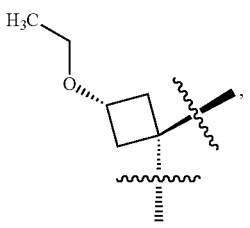
[III-11]

[III-13]

and
$R^4$ is a group represented by formula [VI-30] or [VI-31]:

[Chemical Formula 153]

[VI-30]

[VI-31]
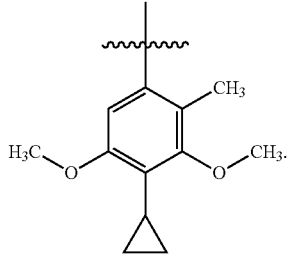
Then, in the present aspect (G-2), one particularly preferred aspect is as follows.
It is the case where the compound represented by the above formula [I-6-2] is any of the following:
[Chemical Formula 154]
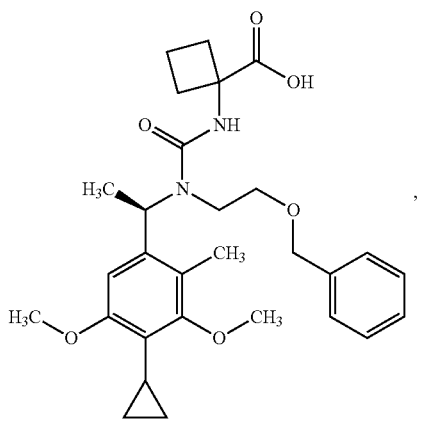
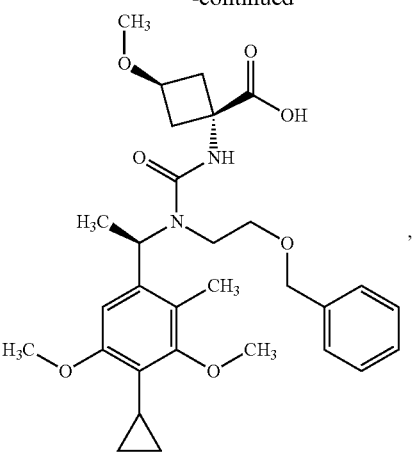
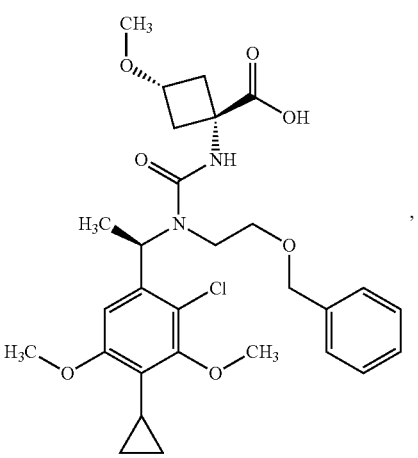
[Chemical Formula 155]
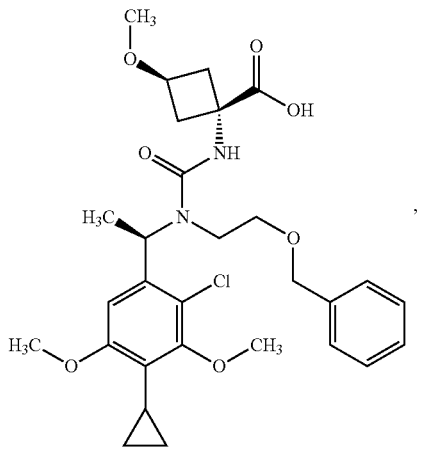
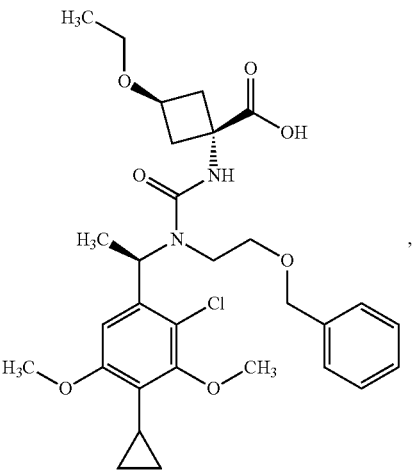

-continued

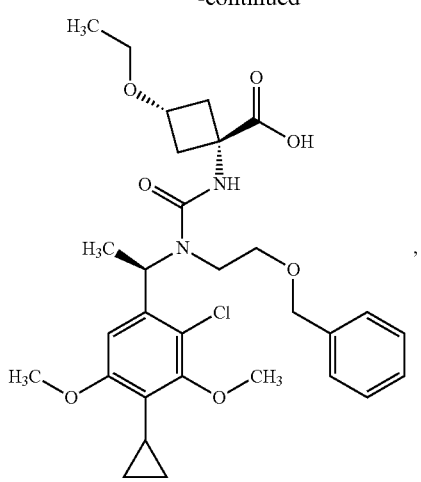

,

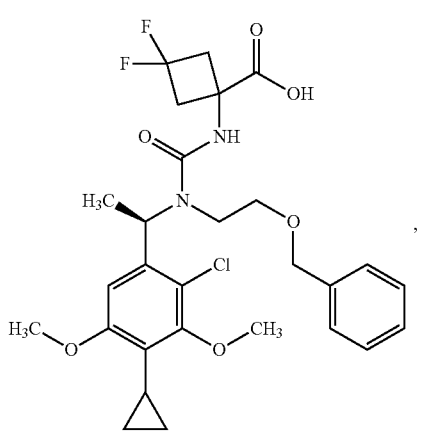

,

Also, in the present aspect (G-2), another particularly preferred aspect is as follows.

It is the case where the compound represented by the above formula [I-6-2] is the following:

[Chemical Formula 156]

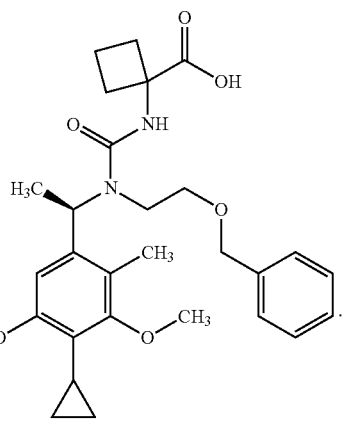

Also, in the present aspect (G-2), another particularly preferred aspect is as follows.

It is the case where the compound represented by the above formula [I-6-2] is the following:

[Chemical Formula 157]

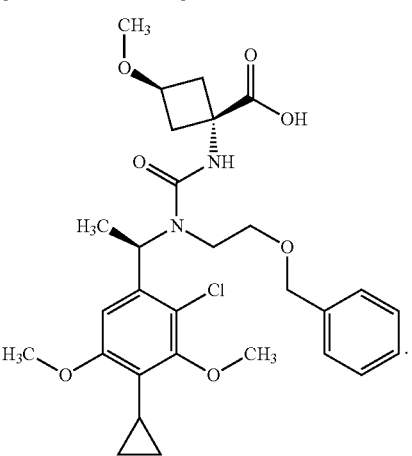

.

Also, in the present aspect (G-2), another particularly preferred aspect is as follows.

It is the case where the compound represented by the above formula [I-6-2] is the following:

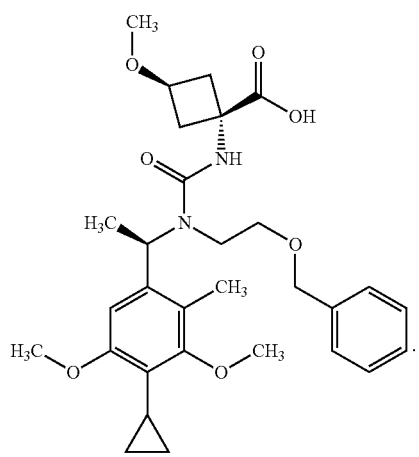

Also, in the present aspect (G-2), another particularly preferred aspect is as follows.

It is the case where the compound represented by the above formula [I-6-2] is the following:

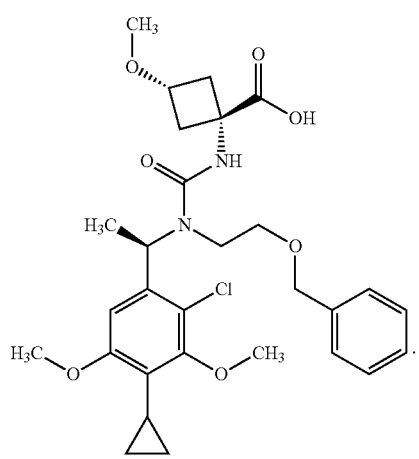

Also, in the present aspect (G-2), another particularly preferred aspect is as follows.

It is the case where the compound represented by the above formula [I-6-2] is the following:

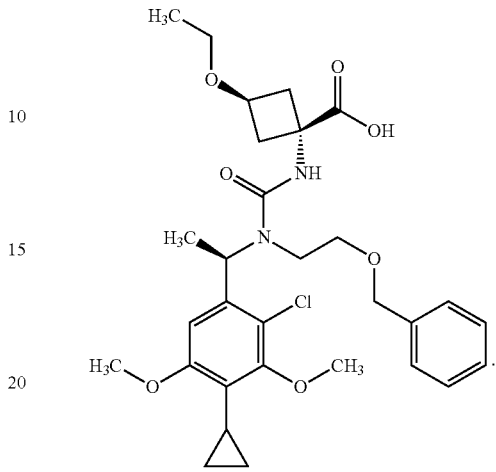

Also, in the present aspect (G-2), another particularly preferred aspect is as follows.

It is the case where the compound represented by the above formula [I-6-2] is the following:

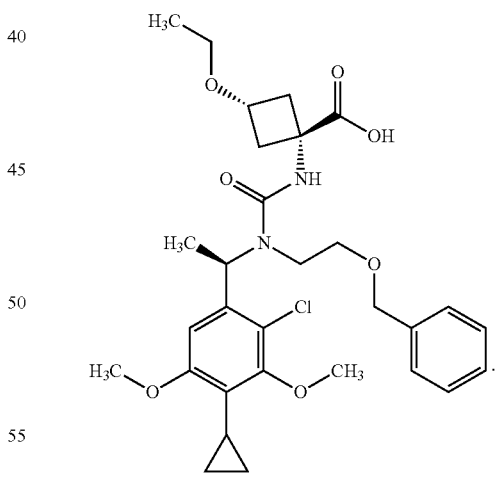

Also, in the present aspect (G-2), another particularly preferred aspect is as follows.

It is the case where the compound represented by the above formula [I-6-2] is the following:

[Chemical Formula 162]

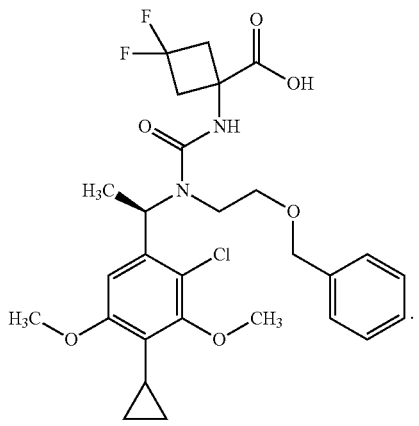

Also, in the present aspect (G-2), another particularly preferred aspect is as follows.

It is the case where the compound represented by the above formula [I-6-2] is the following:

[Chemical Formula 163]

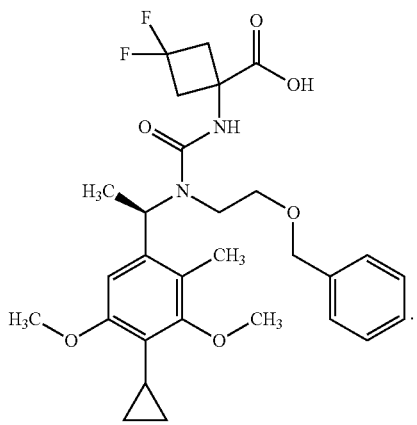

Another preferred aspect of the compound of the present invention is aspect (H) below.

Aspect (H):

In the present aspect (H), a preferred aspect is as follows.

In the compound represented by the above formula [I-1], or a pharmaceutically acceptable salt thereof, or a hydrate thereof, the compound represented by formula [I-1] is a compound represented by formula [I-7]:

[Chemical Formula 164]

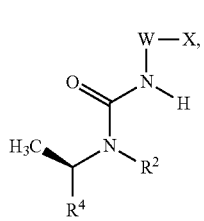

[I-7]

where
$R^2$ is a group represented by formula [IV-1] or [IV-2]:

[Chemical Formula 165]

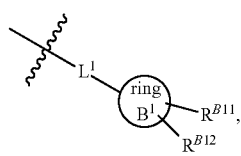

[IV-1]

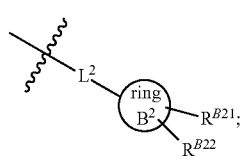

[IV-2]

and
X, W, ring $B^1$, $R^{B11}$, $R^{B12}$, $L^1$, ring $B^2$, $R^{B21}$, $R^{B22}$, $L^2$, and $R^4$ are as mentioned above.

In the present aspect (H), a more preferred aspect is as follows.

In the above formula [I-7],
X is carboxy or tetrazolyl;
W is a structure represented by formula [III-1]:

[Chemical Formula 166]

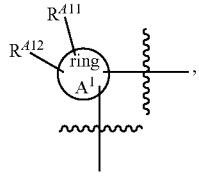

[III-1]

where,
in the structure represented by formula [III-1], ring $A^1$ is $C_{3-4}$ cycloalkane,
$R^{A11}$ is
a hydrogen atom, a halogen atom, or $C_{1-2}$ alkoxy, and
$R^{A12}$ is
a hydrogen atom or a halogen atom;
ring $B^1$ is phenyl,
$R^{B11}$ and $R^{B12}$ are both hydrogen atoms,
$L^1$ is $C_{4-5}$ alkanediyl(the $C_{4-5}$ alkanediyl is optionally substituted with two fluorine atoms), and one carbon atom in the $C_{4-5}$ alkanediyl, that is two or more atoms away from the nitrogen atom to which $R^2$ is bonded, is optionally replaced with formula —O—, ring $B^2$ is partially saturated 9-membered fused aryl, $R^{B21}$ and $R^{B22}$ are both hydrogen atoms, and $L^2$ is $C_2$ alkanediyl; and $R^4$ is a group represented by formula [VI]:

[Chemical Formula 167]

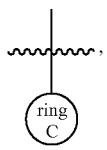

[VI]

where ring C is phenyl, the phenyl is substituted with one group selected from the group consisting of a halogen atom, $C_{1-3}$ alkyl, $C_{1-2}$ alkoxy, and $C_1$ alkylcarbonyl, and furthermore, the phenyl is optionally substituted with one to three groups that are the same or different, selected from the group consisting of a halogen atom, $C_{1-3}$ alkyl(the $C_{1-3}$ alkyl is optionally substituted with one hydroxy), $C_{1-2}$ alkoxy, and $C_1$ alkylcarbonyl.

In the present aspect (H), a further preferred aspect is as follows.

In the above formula [I-7],

X is carboxy or tetrazolyl;

W is a structure represented by formula [III-5], [III-8] to [III-11], or [III-13]:

[Chemical Formula 168]

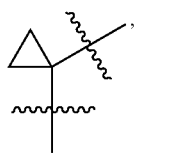

[III-5]

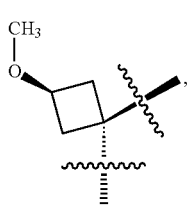

[III-8]

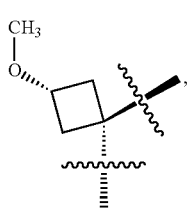

[III-9]

-continued

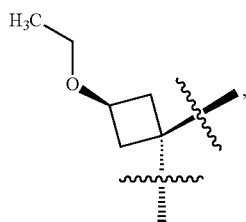

[III-10]

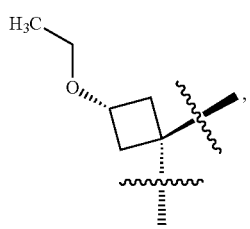

[III-11]

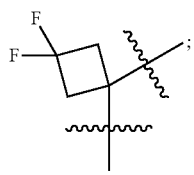

[III-13]

ring $B^1$ is phenyl, $R^{B11}$ and $R^{B12}$ are both hydrogen atoms, and $L^1$ is a structure represented by formula [V-3], [V-12], or [V-14]:

[Chemical Formula 169]

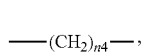

[V-3]

$—(CH_2)_{n4}—$,

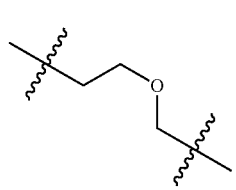

[V-12]

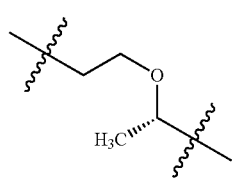

[V-14]

where n4 is an integer of 4, and ring $B^2$ is dihydroindenyl, $R^{B21}$ and $R^{B22}$ are both hydrogen atoms, and $L^2$ is a structure represented by formula [V-20]:

[Chemical Formula 170]

$—(CH_2)_{n5}—$

[V-20]

where
n5 is 2; and
$R^4$ is a group represented by formula [VI-2], [VI-7], [VI-8], [VI-10], [VI-11], or [VI-12]:
[Chemical Formula 171]
[VI-2]
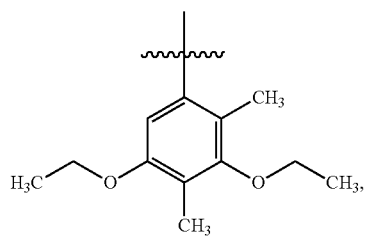
[VI-7]
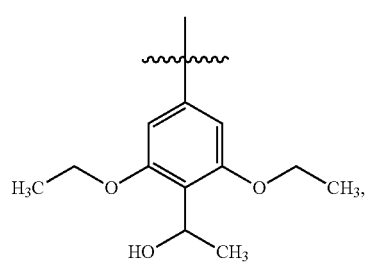
[VI-8]
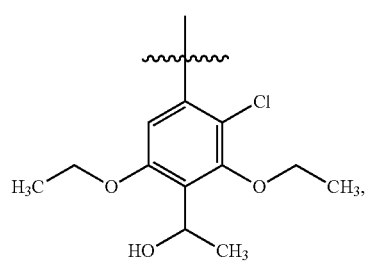
[VI-10]
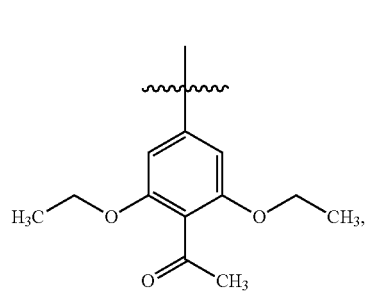
[VI-11]
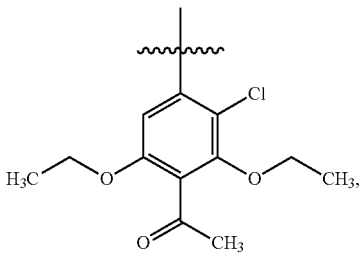
[VI-12]
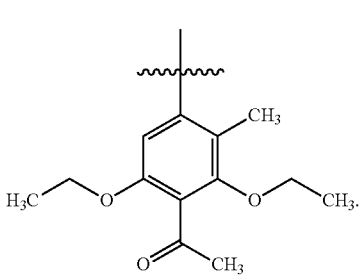
Then, in the present aspect (H),
one particularly preferred aspect is the case where the compound represented by the above formula [I-7] is any of the following:
[Chemical Formula 172]
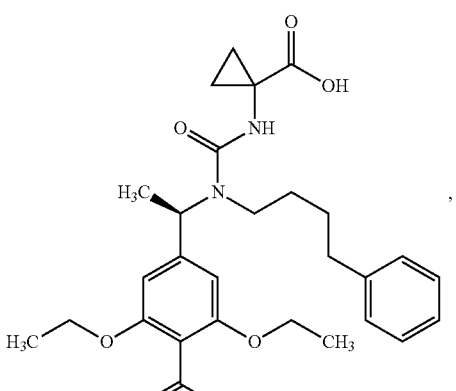
,
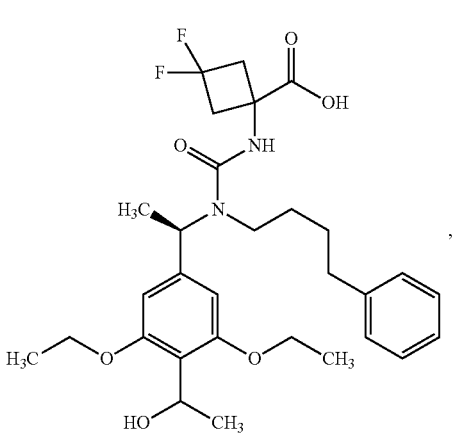
, 123
-continued
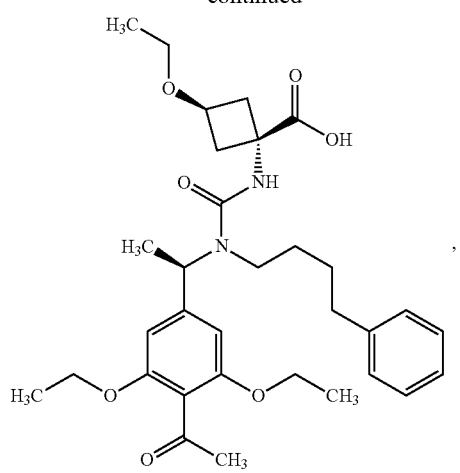
,
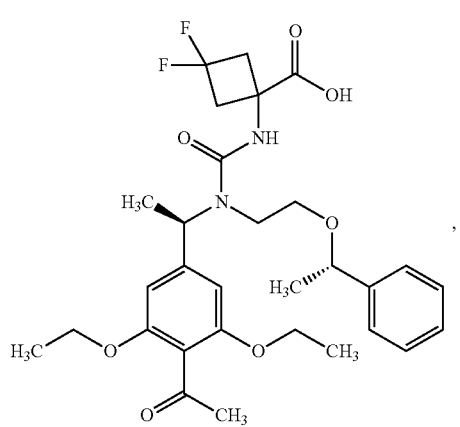
,
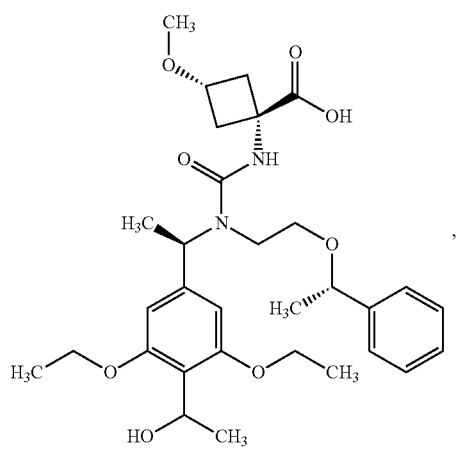
,
124
-continued
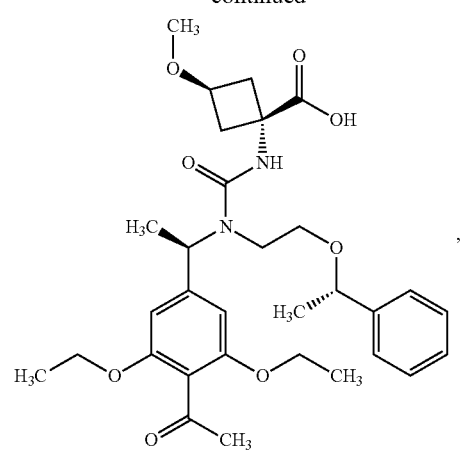
,
[Chemical Formula 173]
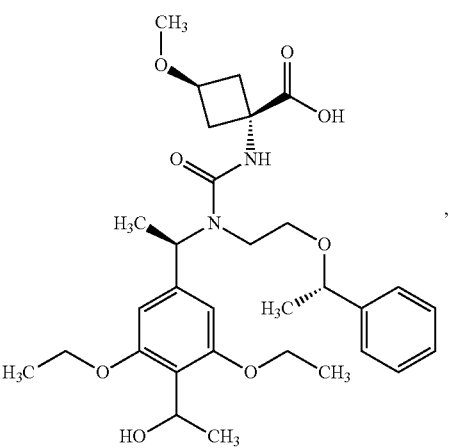
,
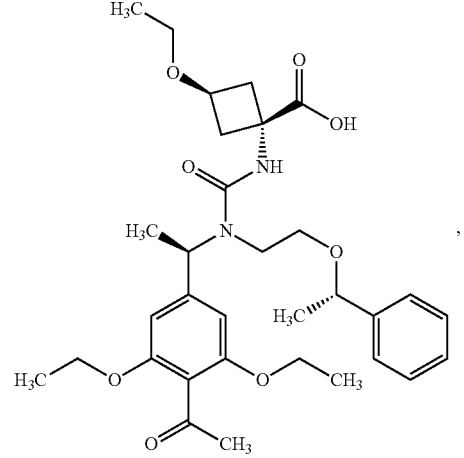
, 125
-continued
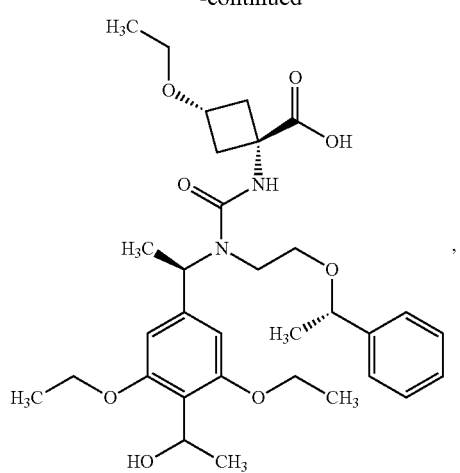
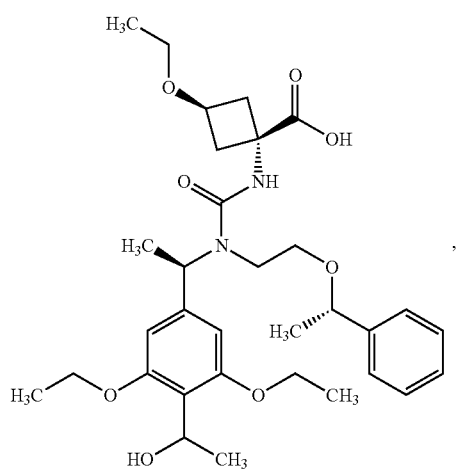
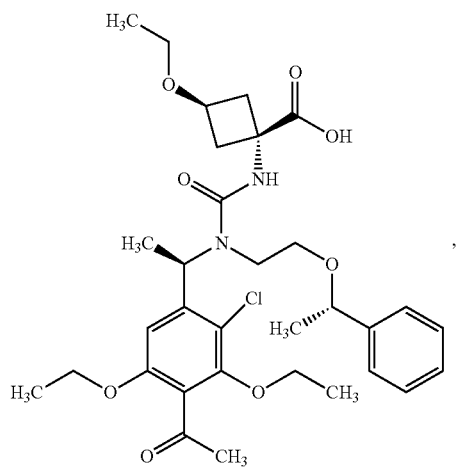
126
-continued
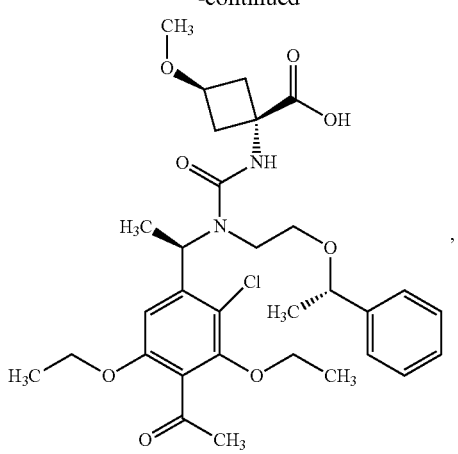
[Chemical Formula 174]
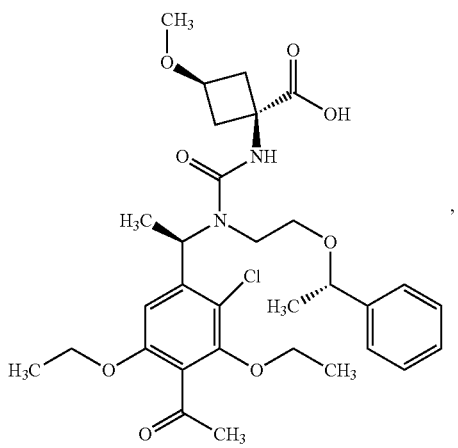
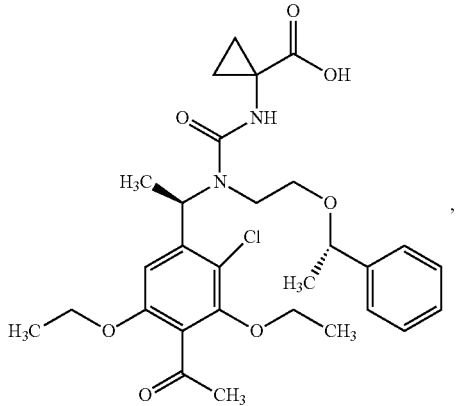

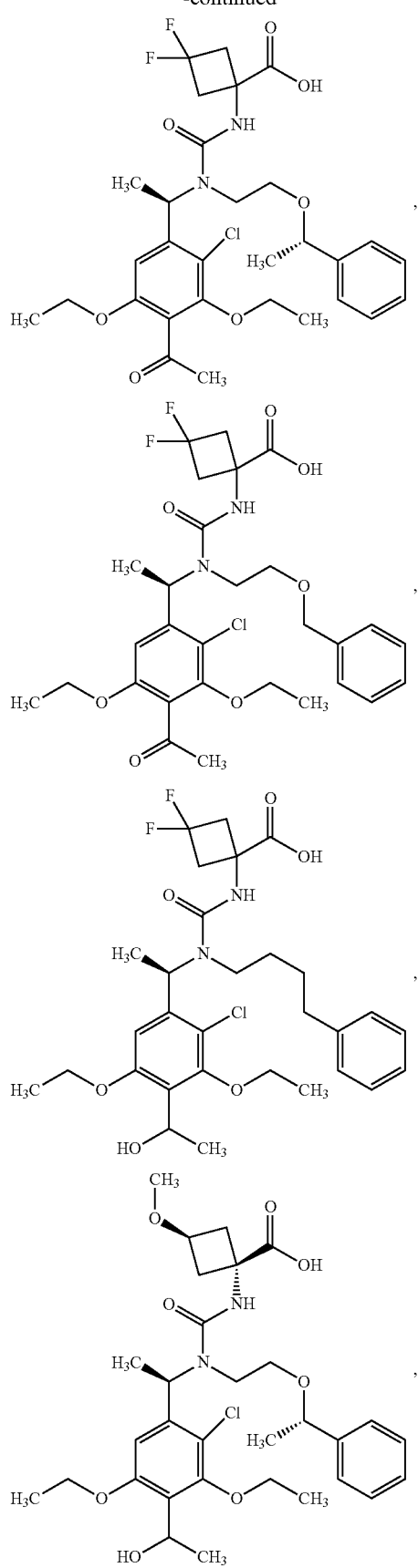
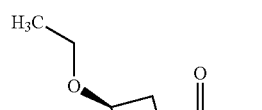
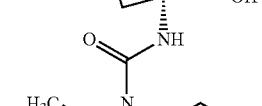
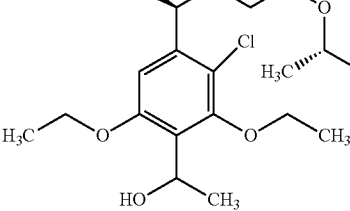
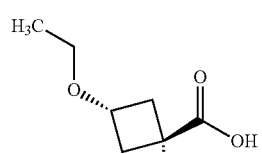
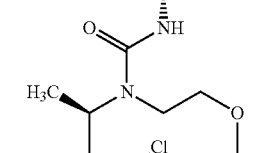
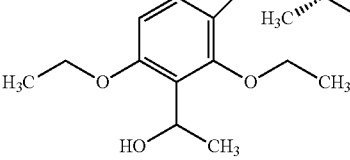
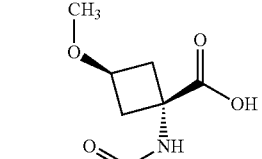
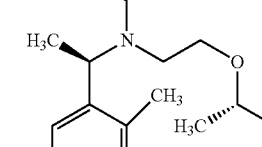
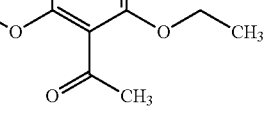

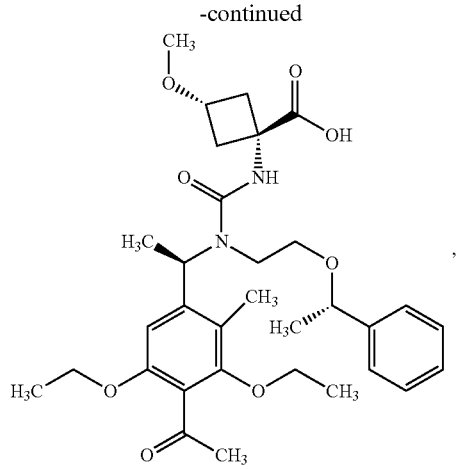
,
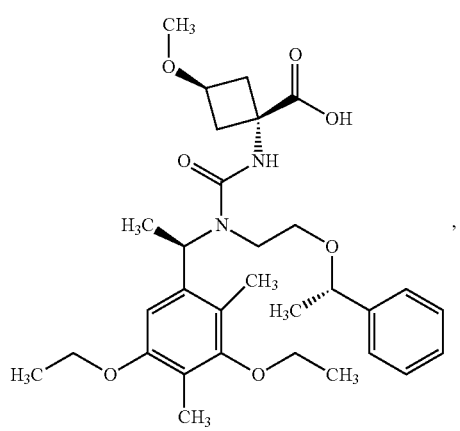
,
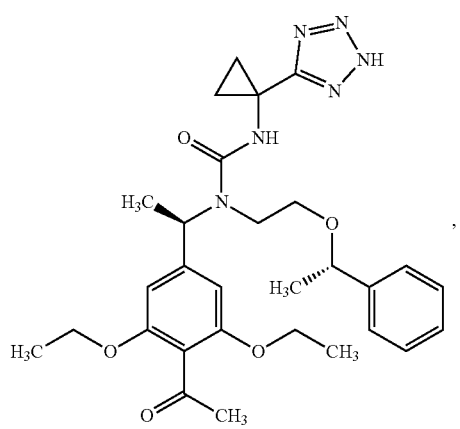
,
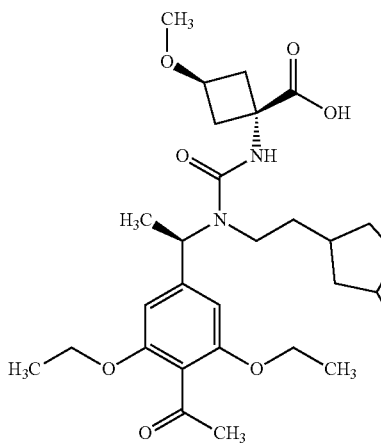
Also, in the present aspect (H), another particularly preferred aspect is as follows.
It is the case where the compound represented by the above formula [I-7] is the following:
[Chemical Formula 177]
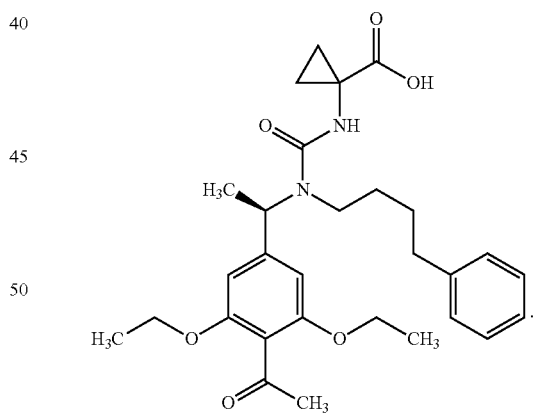
.
Also, in the present aspect (H), another particularly preferred aspect is as follows.

It is the case where the compound represented by the above formula [I-7] is the following:

[Chemical Formula 178]

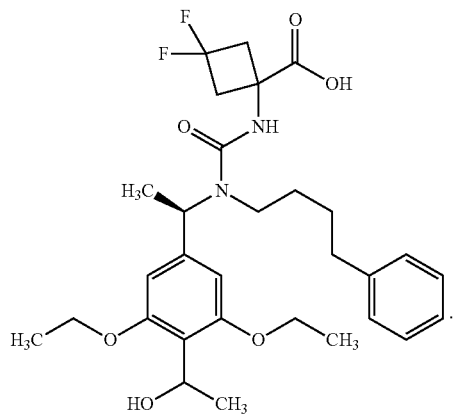

Also, in the present aspect (H), another particularly preferred aspect is as follows.

It is the case where the compound represented by the above formula [I-7] is the following:

[Chemical Formula 179]

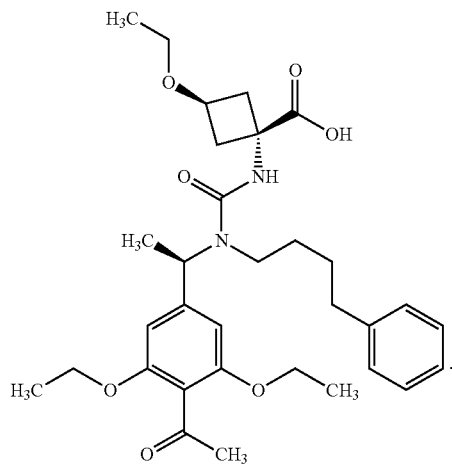

Also, in the present aspect (H), another particularly preferred aspect is as follows.

It is the case where the compound represented by the above formula [I-7] is the following:

[Chemical Formula 180]

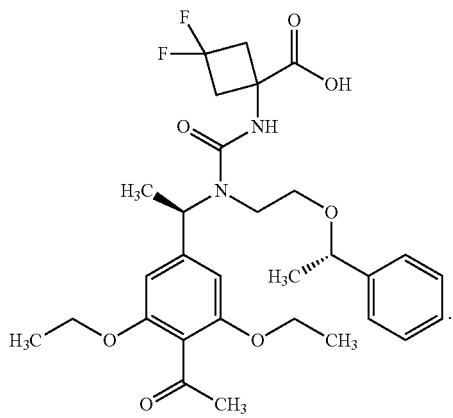

Also, in the present aspect (H), another particularly preferred aspect is as follows.

It is the case where the compound represented by the above formula [I-7] is the following:

[Chemical Formula 181]

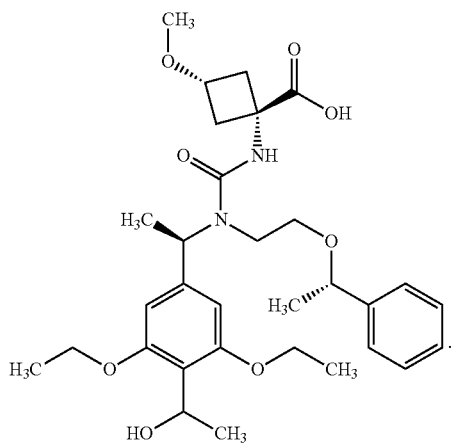

Also, in the present aspect (H), another particularly preferred aspect is as follows.

It is the case where the compound represented by the above formula [I-7] is the following:

[Chemical Formula 182]

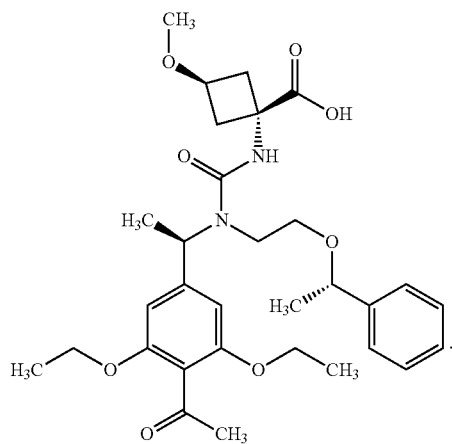

Also, in the present aspect (H), another particularly preferred aspect is as follows.

It is the case where the compound represented by the above formula [I-7] is the following:

[Chemical Formula 183]

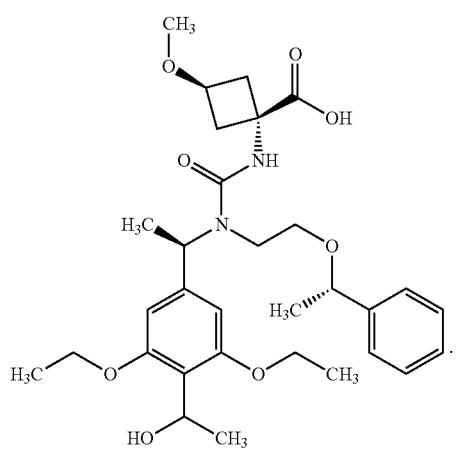

Also, in the present aspect (H), another particularly preferred aspect is as follows.

It is the case where the compound represented by the above formula [I-7] is the following:

[Chemical Formula 184]

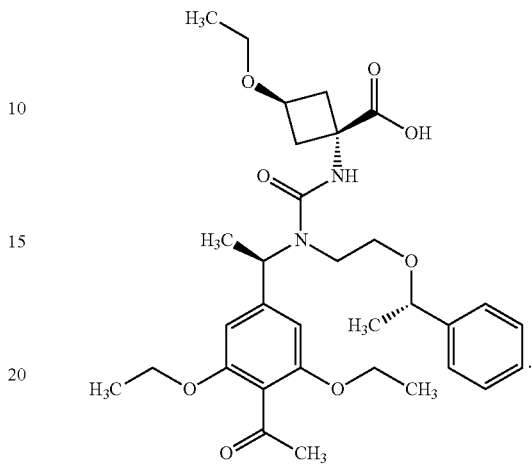

Also, in the present aspect (H), another particularly preferred aspect is as follows.

It is the case where the compound represented by the above formula [I-7] is the following:

[Chemical Formula 185]

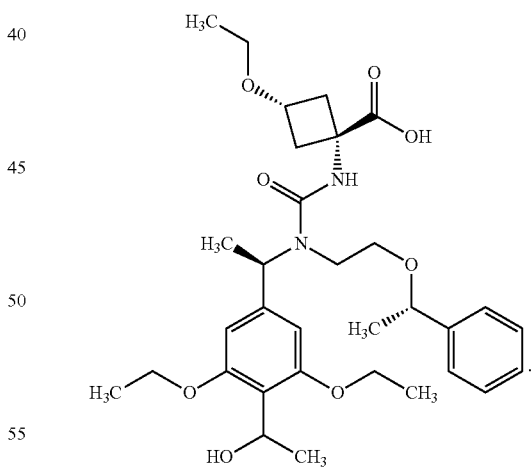

Also, in the present aspect (H), another particularly preferred aspect is as follows.

It is the case where the compound represented by the above formula [I-7] is the following:

[Chemical Formula 186]

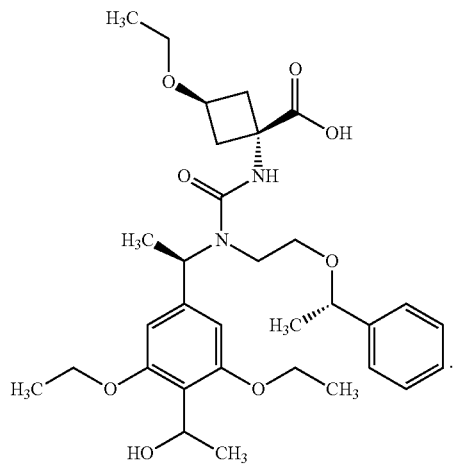

Also, in the present aspect (H), another particularly preferred aspect is as follows.

It is the case where the compound represented by the above formula [I-7] is the following:

[Chemical Formula 187]

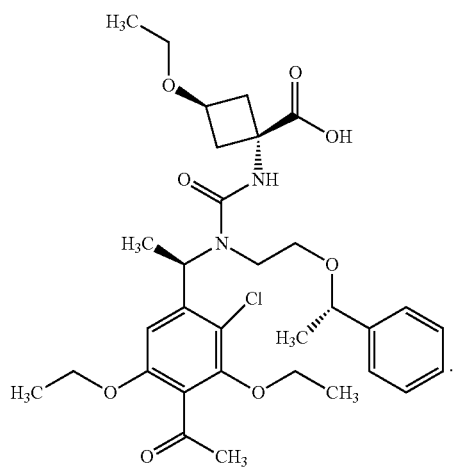

Also, in the present aspect (H), another particularly preferred aspect is as follows.

It is the case where the compound represented by the above formula [I-7] is the following:

[Chemical Formula 188]

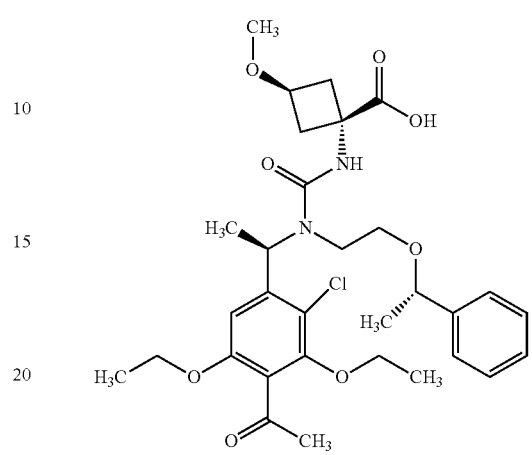

Also, in the present aspect (H), another particularly preferred aspect is as follows.

It is the case where the compound represented by the above formula [I-7] is the following:

[Chemical Formula 189]

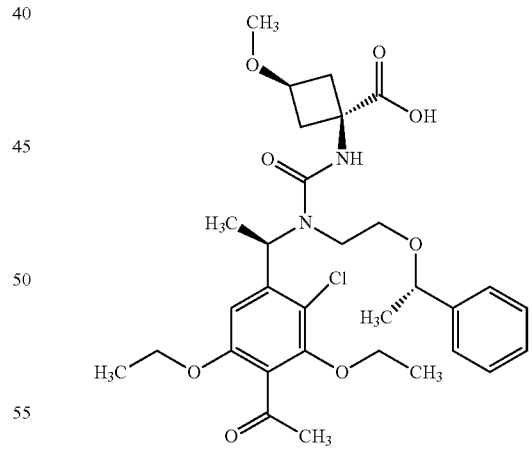

Also, in the present aspect (H), another particularly preferred aspect is as follows.

It is the case where the compound represented by the above formula [I-7] is the following:

[Chemical Formula 190]

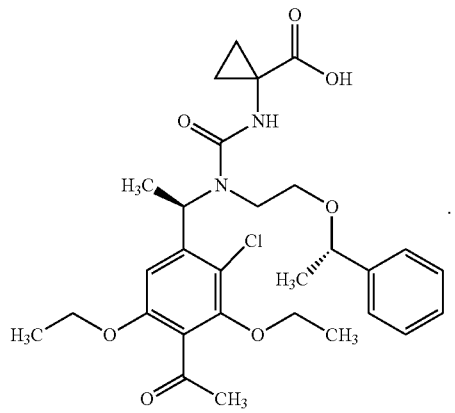

Also, in the present aspect (H), another particularly preferred aspect is as follows.

It is the case where the compound represented by the above formula [I-7] is the following:

[Chemical Formula 191]

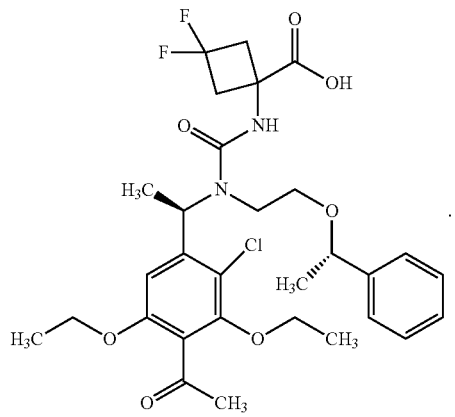

Also, in the present aspect (H), another particularly preferred aspect is as follows.

It is the case where the compound represented by the above formula [I-7] is the following:

[Chemical Formula 192]

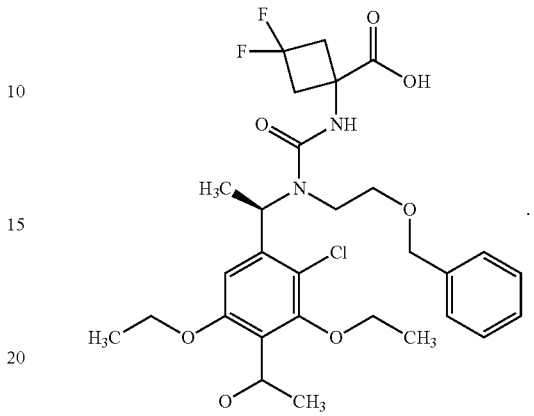

Also, in the present aspect (H), another particularly preferred aspect is as follows.

It is the case where the compound represented by the above formula [I-7] is the following:

[Chemical Formula 193]

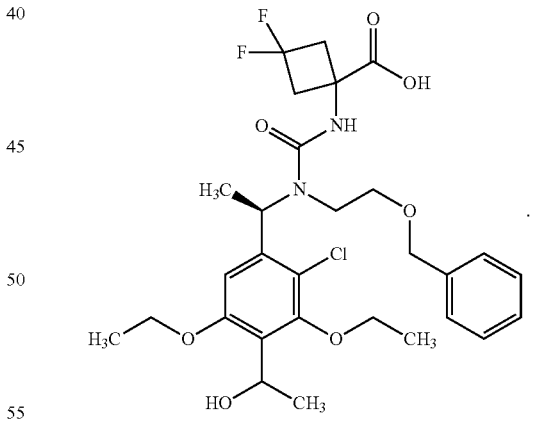

Also, in the present aspect (H), another particularly preferred aspect is as follows.

It is the case where the compound represented by the above formula [I-7] is the following:

[Chemical Formula 194]

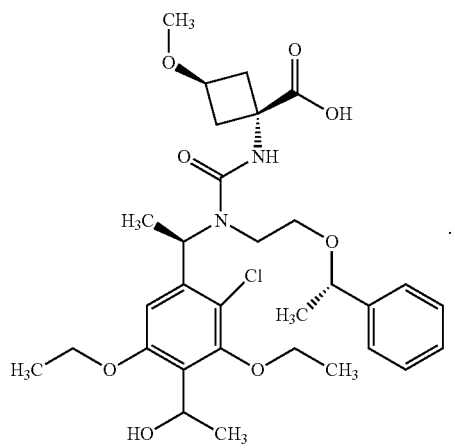

Also, in the present aspect (H), another particularly preferred aspect is as follows.

It is the case where the compound represented by the above formula [I-7] is the following:

[Chemical Formula 195]

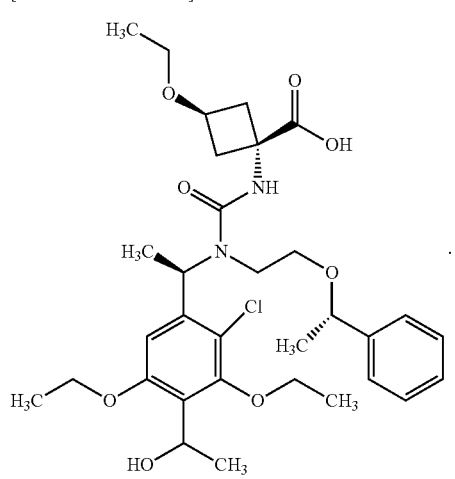

Also, in the present aspect (H), another particularly preferred aspect is as follows.

It is the case where the compound represented by the above formula [I-7] is the following:

[Chemical Formula 196]

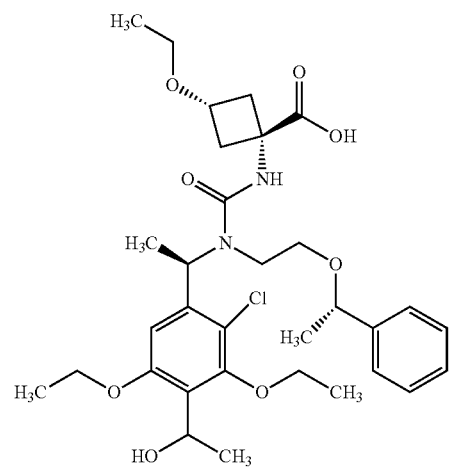

Also, in the present aspect (H), another particularly preferred aspect is as follows.

It is the case where the compound represented by the above formula [I-7] is the following:

[Chemical Formula 197]

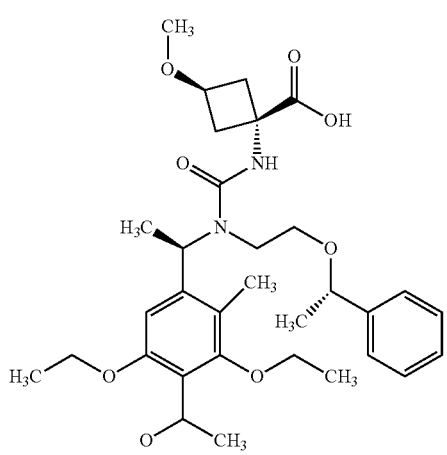

Also, in the present aspect (H), another particularly preferred aspect is as follows.

It is the case where the compound represented by the above formula [I-7] is the following:

[Chemical Formula 198]

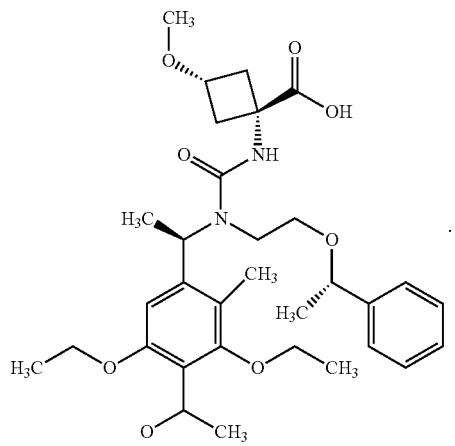

Also, in the present aspect (H), another particularly preferred aspect is as follows.

It is the case where the compound represented by the above formula [I-7] is the following:

[Chemical Formula 199]

Also, in the present aspect (H), another particularly preferred aspect is as follows.

It is the case where the compound represented by the above formula [I-7] is the following:

[Chemical Formula 200]

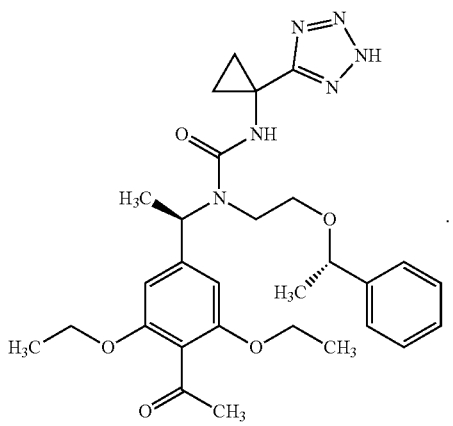

Also, in the present aspect (H), another particularly preferred aspect is as follows.

It is the case where the compound represented by the above formula [I-7] is the following:

[Chemical Formula 201]

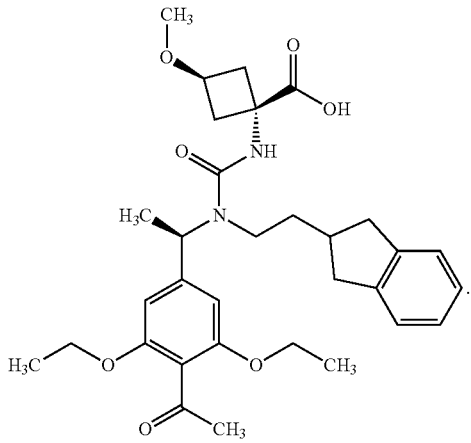

Another preferred aspect of the compound of the present invention is aspect (H-2) below.

Aspect (H-2):

In the present aspect (H-2), a preferred aspect is as follows.

In the compound represented by the above formula [I-1], or a pharmaceutically acceptable salt thereof, or a hydrate thereof, the compound represented by formula [I-1] is a compound represented by formula [I-7]:

[Chemical Formula 202]

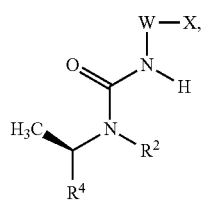

[I-7]

where
$R^2$ is a group represented by formula [IV-1]:
[Chemical Formula 203]

[Chemical Formula 203]

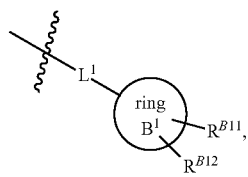

[IV-1]

and
X, W, ring $B^1$, $R^{B11}$, $R^{B12}$, $L^1$, and $R^4$ are as mentioned above.

In the present aspect (H-2), a more preferred aspect is as follows.
In the above formula [I-7],
X is carboxy;
W is a structure represented by formula [III-1]:

[Chemical Formula 204]

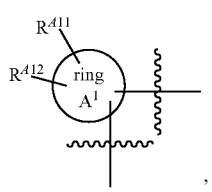

[III-1]

where,
in the structure represented by formula [III-1],
ring $A^1$ is
$C_{3-4}$ cycloalkane,
$R^{A11}$ is
a hydrogen atom, a halogen atom, or $C_{1-2}$ alkoxy, and
$R^{A12}$ is
a hydrogen atom or a halogen atom;
ring $B^1$ is phenyl,
$R^{B11}$ and $R^{B12}$ are both hydrogen atoms,
$L^1$ is $C_{4-5}$ alkanediyl, and
one carbon atom in the $C_{4-5}$ alkanediyl, that is two or more atoms away from the nitrogen atom to which $R^2$ is bonded, is optionally replaced with formula —O—, and $R^4$ is a group represented by formula [VI]:

[Chemical Formula 205]

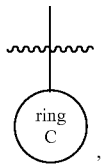

[VI]

where
ring C is phenyl,
the phenyl is substituted with one group selected from the group consisting of a halogen atom, $C_1$ alkyl, $C_{1-2}$ alkoxy, and $C_1$ alkylcarbonyl, and furthermore,
the phenyl is optionally substituted with one to three groups that are the same or different, selected from the group consisting of a halogen atom, $C_1$ alkyl, $C_3$ cycloalkyl, $C_{1-2}$ alkoxy, and $C_1$ alkylcarbonyl.

In the present aspect (H-2), a further preferred aspect is as follows.
In the above formula [I-7],
X is carboxy;
W is a structure represented by formula [III-5], [III-6], [III-8] to [III-11], or [III-13]:

[Chemical Formula 206]

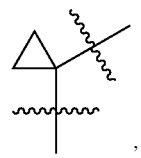

[III-5]

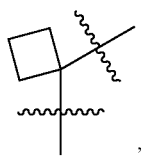

[III-6]

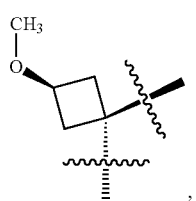

[III-8]

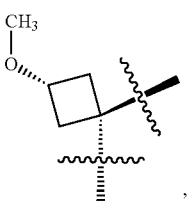

[III-9]

-continued
[III-10]
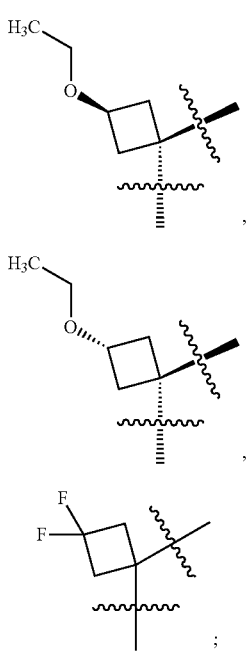
,
[III-11]
,
[III-13]
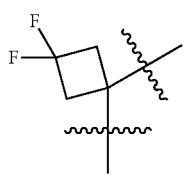
;
ring B¹ is phenyl,
$R^{B11}$ and $R^{B12}$ are both hydrogen atoms, and
L¹ is a structure represented by formula [V-12] or [V-14]:
[Chemical Formula 207]
[V-12]
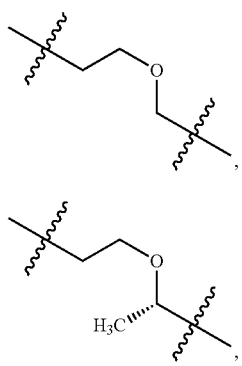
,
[V-14]
,
and
R⁴ is a group represented by formula [VI-2], [VI-6], [VI-12], [VI-25], [VI-27], [VI-28], [VI-30], or [VI-31]:
[Chemical Formula 208]
[VI-2]
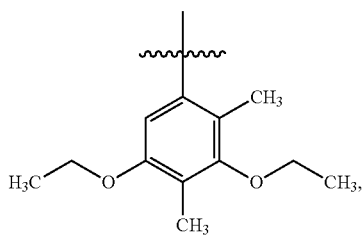
,
-continued
[VI-6]
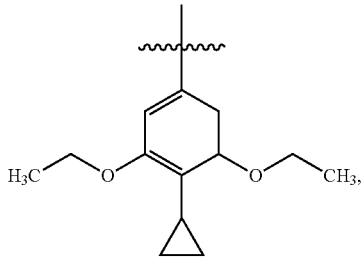
,
[VI-12]
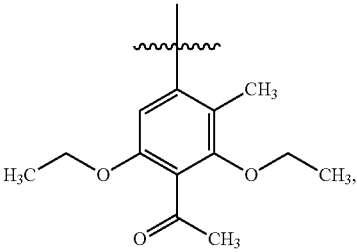
,
[VI-25]
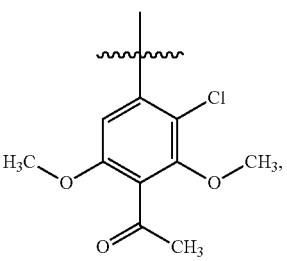
,
[VI-27]
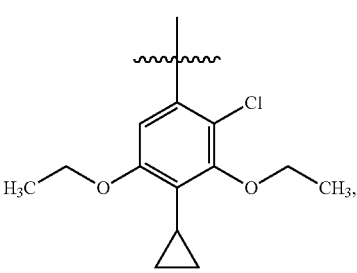
,
[VI-28]
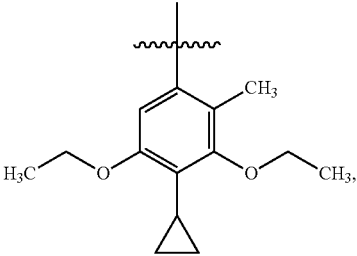
,
[VI 30]
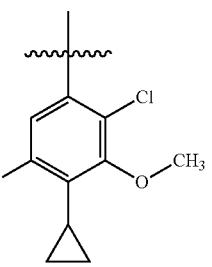

-continued
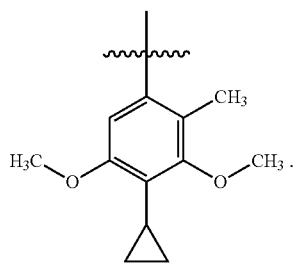
[VI-31]
Then, in the present aspect (H-2),
one particularly preferred aspect is the case where the compound represented by the above formula [I-7] is any of the following:
[Chemical Formula 209]
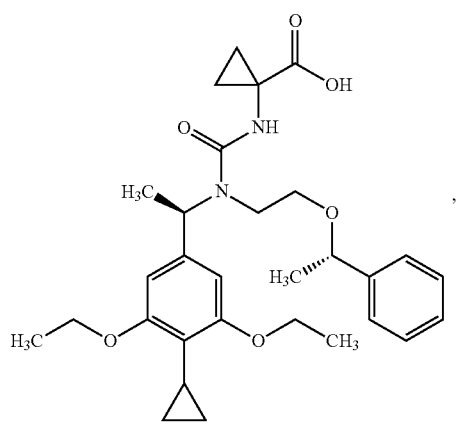
,
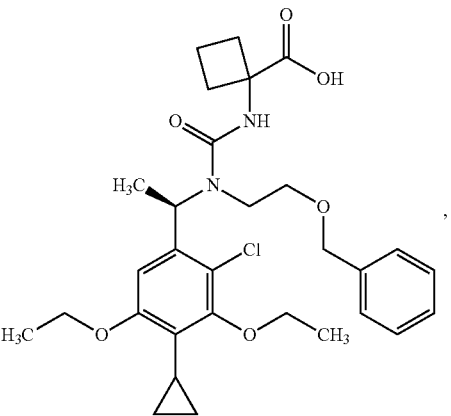
,
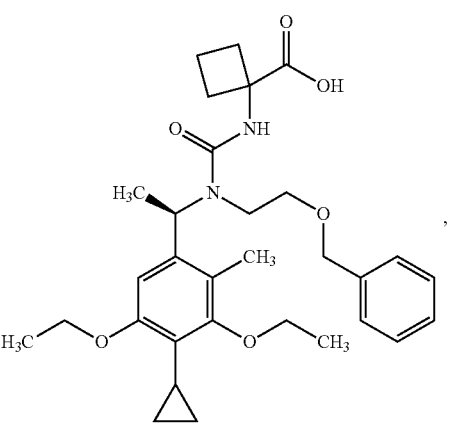
,
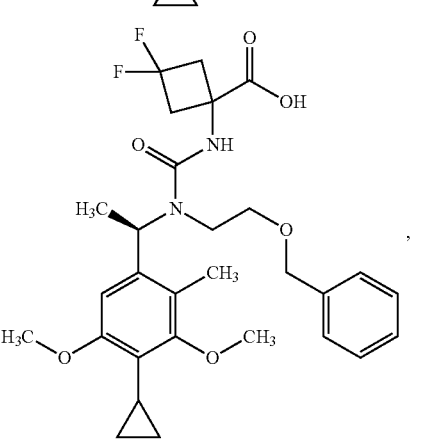
,
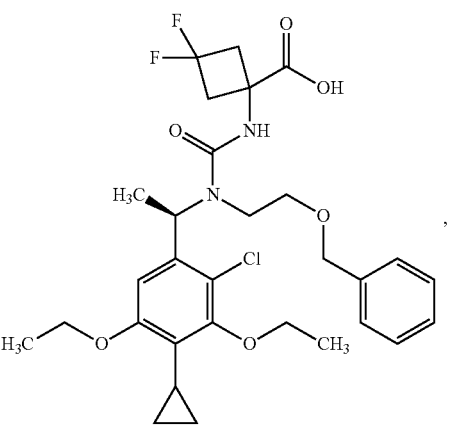
, 149
-continued
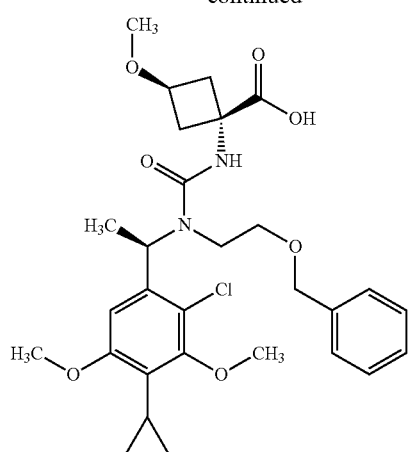
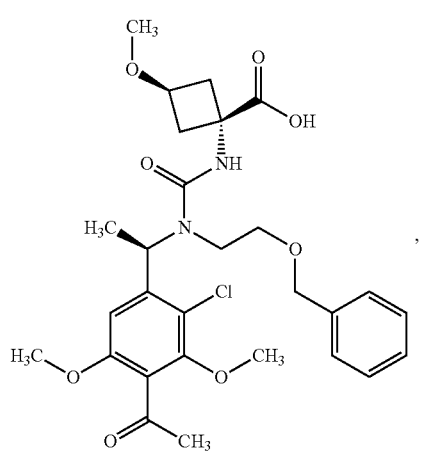
[Chemical Formula 210]
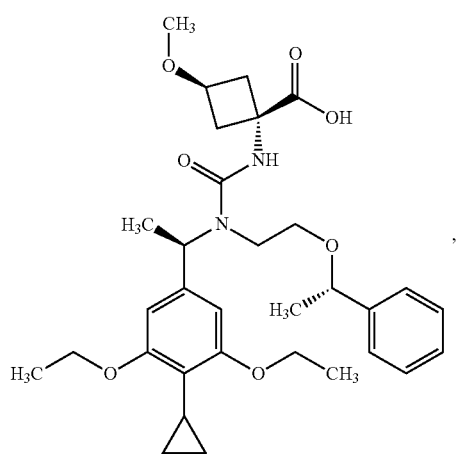
150
-continued
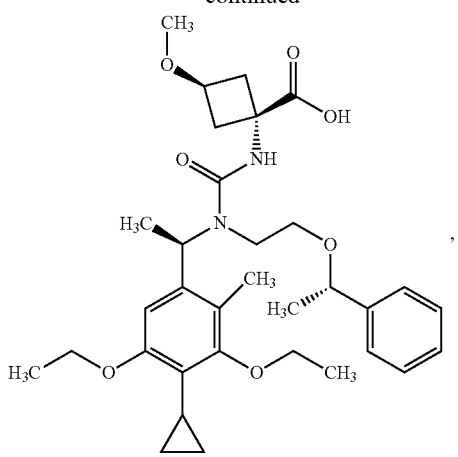
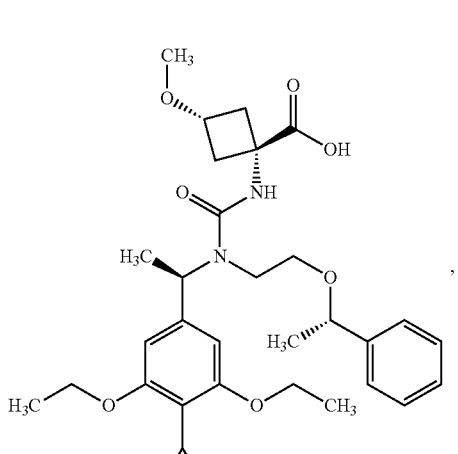
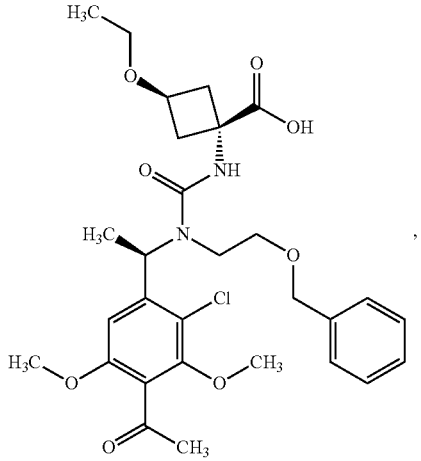

-continued
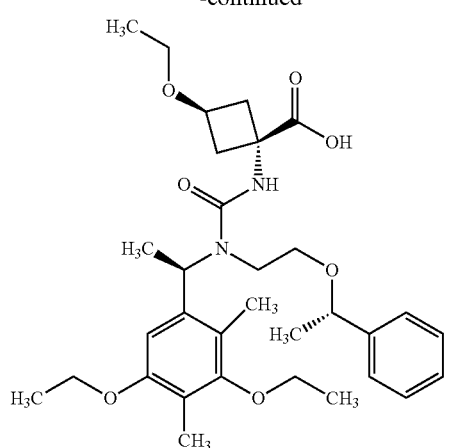
,
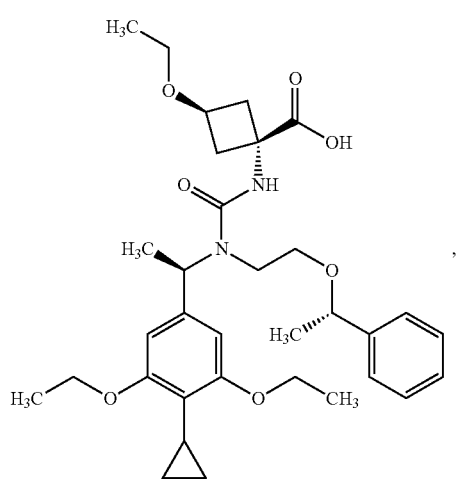
,
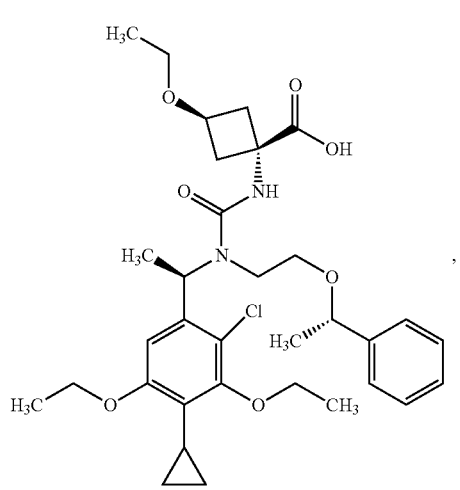
,
-continued
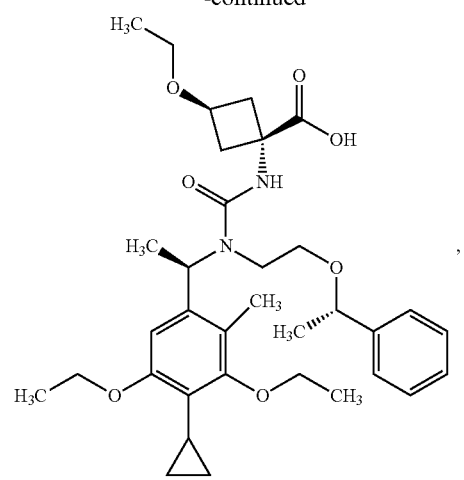
,
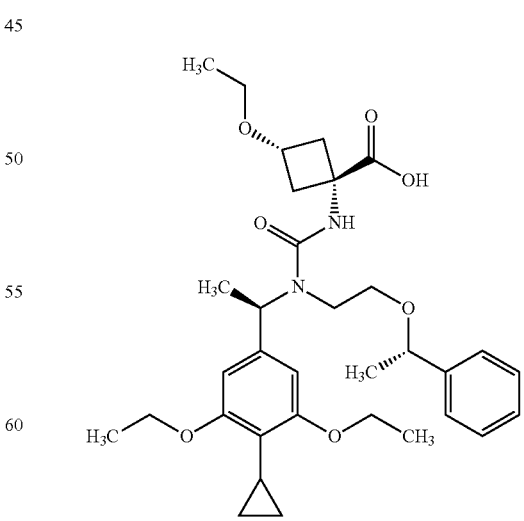
Also, in the present aspect (H-2), another particularly preferred aspect is as follows.

It is the case where the compound represented by the above formula [I-7] is the following:

[Chemical Formula 211]

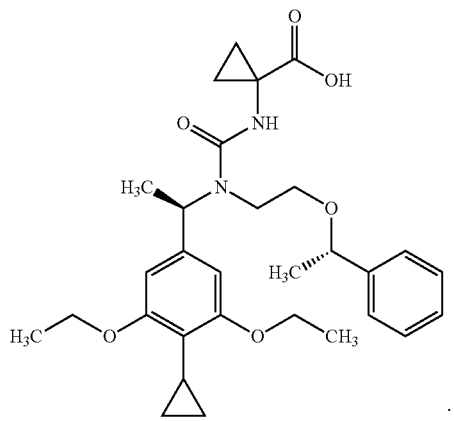

It is the case where the compound represented by the above formula [I-7] is the following:

[Chemical Formula 213]

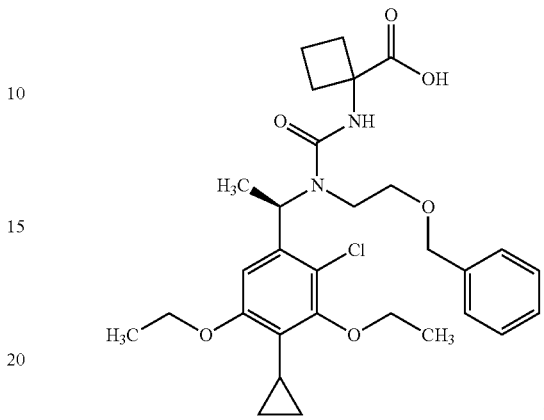

Also, in the present aspect (H-2), another particularly preferred aspect is as follows.

It is the case where the compound represented by the above formula [I-7] is the following:

Also, in the present aspect (H-2), another particularly preferred aspect is as follows.

It is the case where the compound represented by the above formula [I-7] is the following:

[Chemical Formula 212]

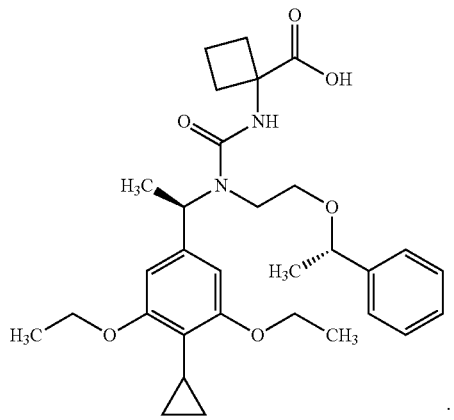

[Chemical Formula 214]

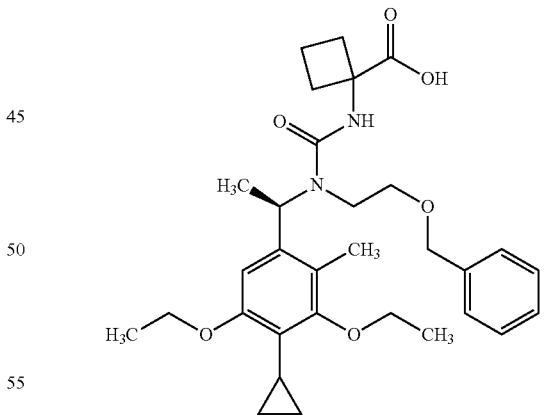

Also, in the present aspect (H-2), another particularly preferred aspect is as follows.

Also, in the present aspect (H-2), another particularly preferred aspect is as follows.

It is the case where the compound represented by the above formula [I-7] is the following:

[Chemical Formula 215]

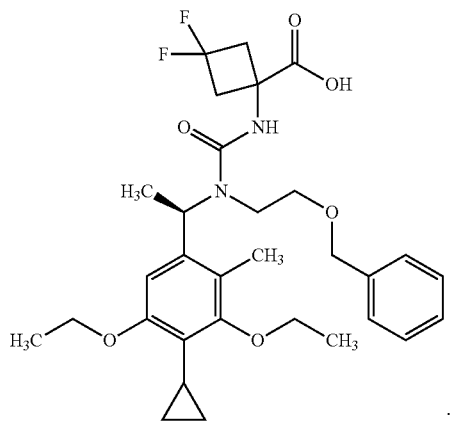

Also, in the present aspect (H-2), another particularly preferred aspect is as follows.

It is the case where the compound represented by the above formula [I-7] is the following:

[Chemical Formula 216]

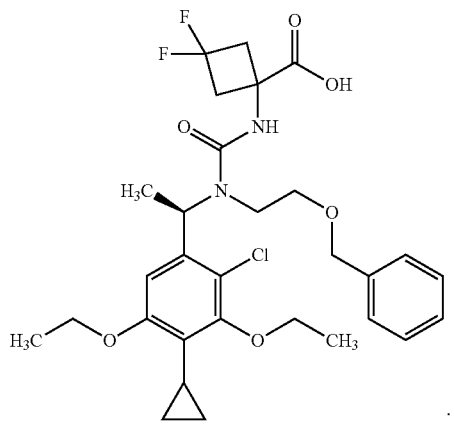

Also, in the present aspect (H-2), another particularly preferred aspect is as follows.

It is the case where the compound represented by the above formula [I-7] is the following:

[Chemical Formula 217]

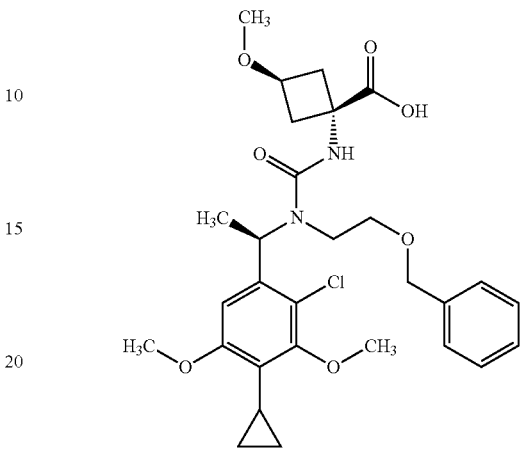

Also, in the present aspect (H-2), another particularly preferred aspect is as follows.

It is the case where the compound represented by the above formula [I-7] is the following:

[Chemical Formula 218]

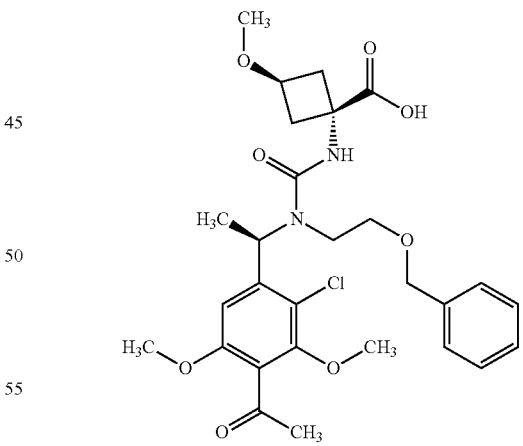

Also, in the present aspect (H-2), another particularly preferred aspect is as follows.

It is the case where the compound represented by the above formula [I-7] is the following:

[Chemical Formula 219]

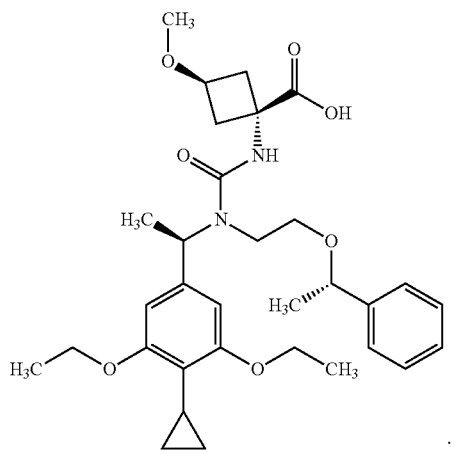

Also, in the present aspect (H-2), another particularly preferred aspect is as follows.

It is the case where the compound represented by the above formula [I-7] is the following:

[Chemical Formula 220]

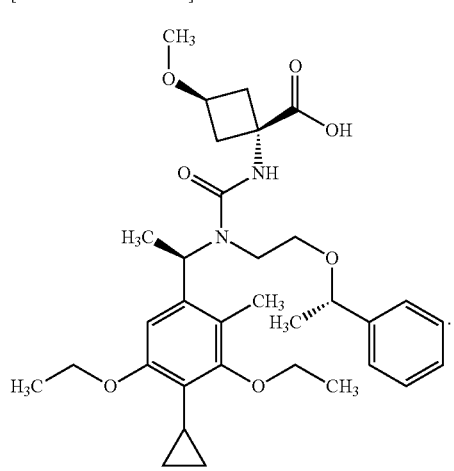

Also, in the present aspect (H-2), another particularly preferred aspect is as follows.

It is the case where the compound represented by the above formula [I-7] is the following:

[Chemical Formula 221]

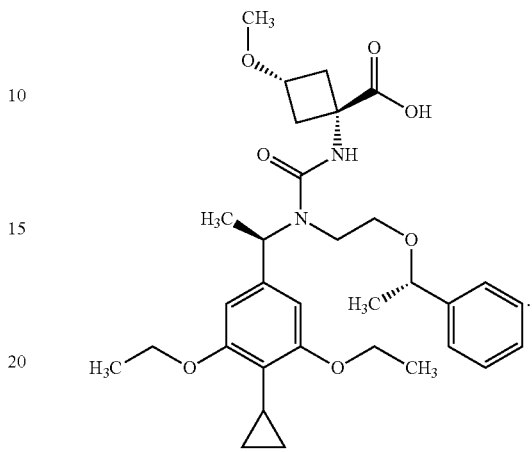

Also, in the present aspect (H-2), another particularly preferred aspect is as follows.

It is the case where the compound represented by the above formula [I-7] is the following:

[Chemical Formula 222]

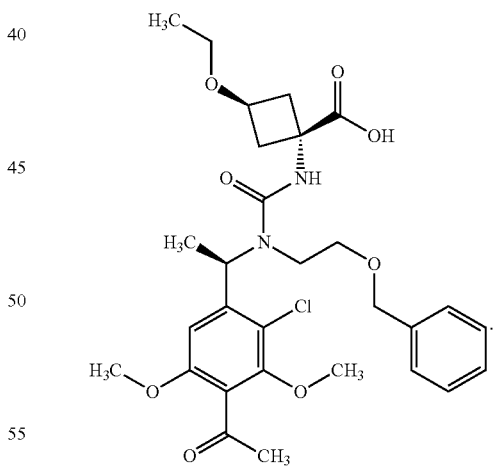

Also, in the present aspect (H-2), another particularly preferred aspect is as follows.

It is the case where the compound represented by the above formula [I-7] is the following:

[Chemical Formula 223]

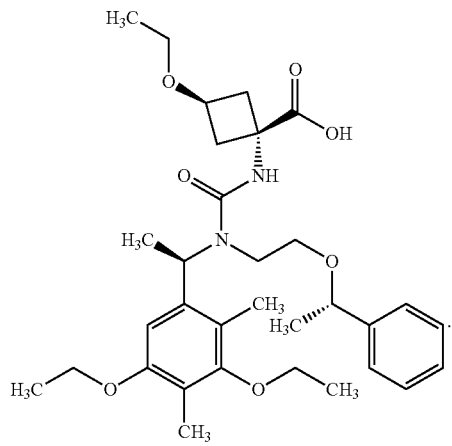

Also, in the present aspect (H-2), another particularly preferred aspect is as follows.

It is the case where the compound represented by the above formula [I-7] is the following:

[Chemical Formula 224]

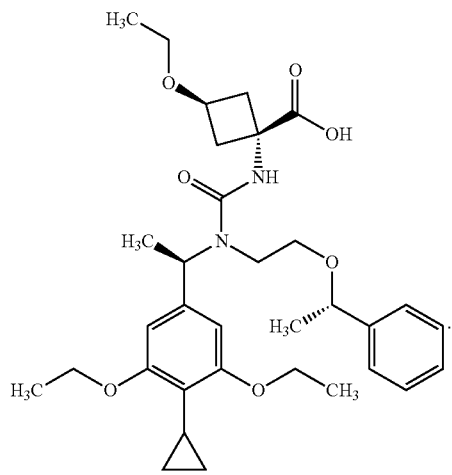

Also, in the present aspect (H-2), another particularly preferred aspect is as follows.

It is the case where the compound represented by the above formula [I-7] is the following:

[Chemical Formula 225]

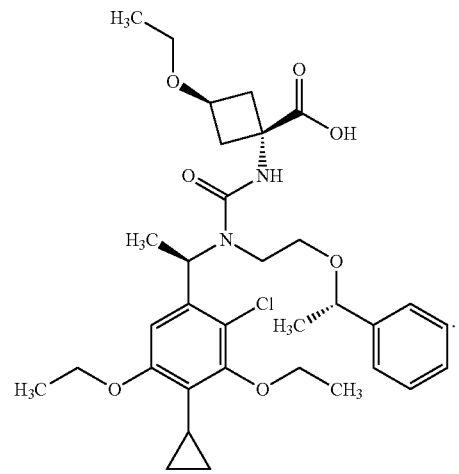

Also, in the present aspect (H-2), another particularly preferred aspect is as follows. It is the case where the compound represented by the above formula [I-7] is the following:

[Chemical Formula 226]

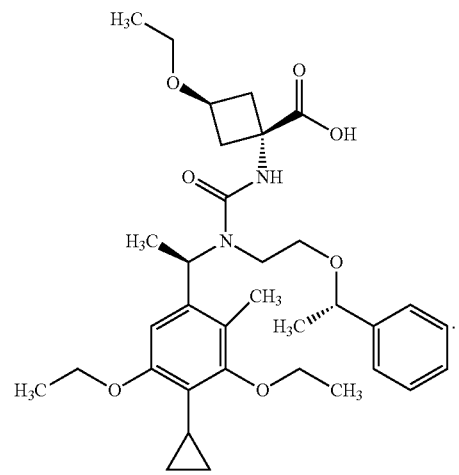

Also, in the present aspect (H-2), another particularly preferred aspect is as follows.

It is the case where the compound represented by the above formula [I-7] is the following:

[Chemical Formula 227]

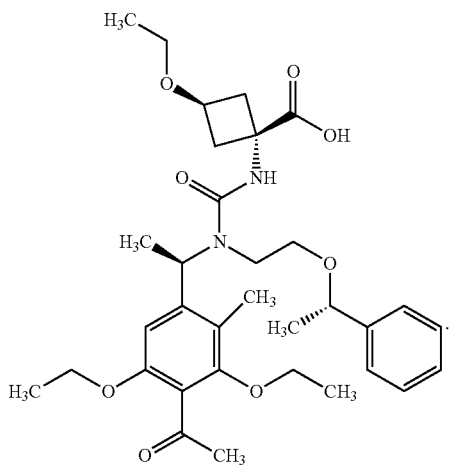

Also, in the present aspect (H-2), another particularly preferred aspect is as follows.

It is the case where the compound represented by the above formula [I-7] is the following:

[Chemical Formula 228]

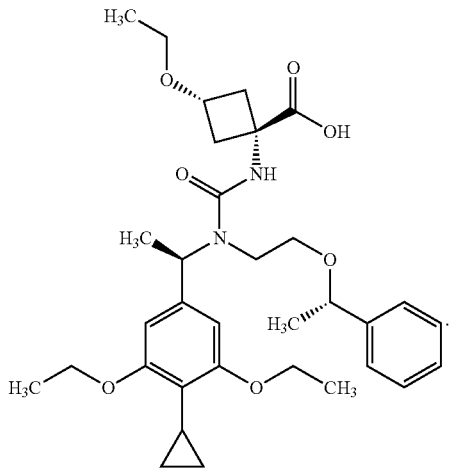 [SMILES: CCOc1cc([C@@H](C)N(CCO[C@@H](C)c2ccccc2)C(=O)N[C@]2(C(=O)O)C[C@H](OCC)C2)cc(OCC)c1C1CC1]

Another preferred aspect of the compound of the present invention is aspect (H-3) below.

Aspect (H-3):

In the present aspect (H-3), a preferred aspect is as follows.

In the compound represented by the above formula [I-1], or a pharmaceutically acceptable salt thereof, or a hydrate thereof, the compound represented by formula [I-1] is a compound represented by formula [I-7]:

[Chemical Formula 229]

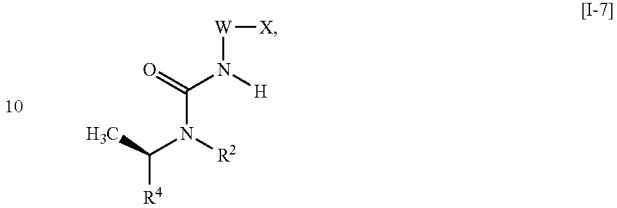

where
$R^2$ is a group represented by formula [IV-1] or [IV-2]:

[Chemical Formula 230]

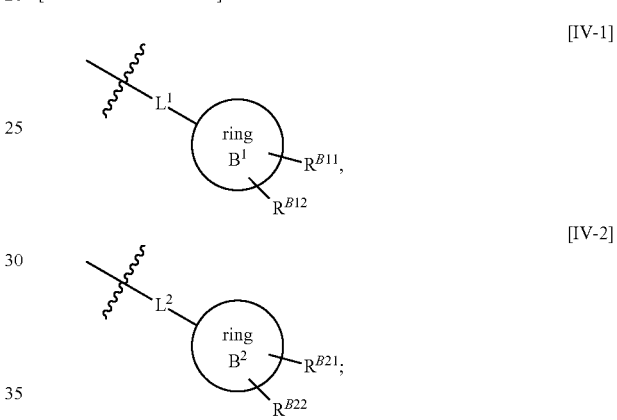

and
X, W, ring $B^1$, $R^{B11}$, $R^{B12}$, $L^1$, ring $B^2$, $R^{B21}$, $R^{B22}$, $L^2$, and $R^4$ are as mentioned above.

In the present aspect (H-3), a more preferred aspect is as follows.

In the above formula [I-7],
X is carboxy or tetrazolyl;
W is a structure represented by formula [III-1]:

[Chemical Formula 231]

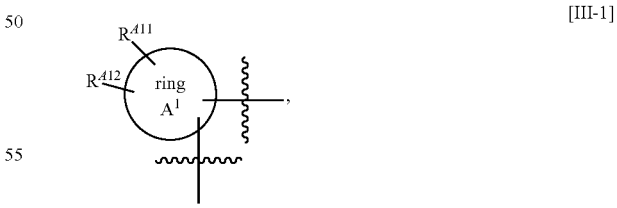

where,
in the structure represented by formula [III-1],
ring $A^1$ is
$C_{3-4}$ cycloalkane,
$R^{411}$ is
a hydrogen atom, a halogen atom, or $C_{1-2}$ alkoxy, and
$R^{412}$ is
a hydrogen atom or a halogen atom;
ring $B^1$ is phenyl, $R^{B11}$ and $R^{B12}$ are both hydrogen atoms, $L^1$ is $C_{4-5}$ alkanediyl(the $C_{4-5}$ alkanediyl is optionally substituted with two fluorine atoms), and one carbon atom in the $C_{4-5}$ alkanediyl, that is two or more atoms away from the nitrogen atom to which $R^2$ is bonded, is optionally replaced with formula —O—, ring $B^2$ is partially saturated 9-membered fused aryl, $R^{B21}$ and $R^{B22}$ are both hydrogen atoms, and $L^2$ is $C_2$ alkanediyl; and $R^4$ is a group represented by formula [VI]:

[Chemical Formula 232]

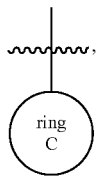

[VI]

where ring C is phenyl, the phenyl is substituted with one group selected from the group consisting of a halogen atom, $C_{1-3}$ alkyl, $C_{1-2}$ alkoxy, and $C_1$ alkylcarbonyl, and furthermore, the phenyl is optionally substituted with one to three groups that are the same or different, selected from the group consisting of a halogen atom, $C_{1-3}$ alkyl(the $C_{1-3}$ alkyl is optionally substituted with one hydroxy), $C_{1-2}$ alkoxy, and $C_1$ alkylcarbonyl.

In the present aspect (H-3), a further preferred aspect is as follows.

In the above formula [I-7], further preferred X is carboxy or tetrazolyl;

W is a structure represented by formula [III-5], [III-6], [III-8] to [III-11], or [III-13]:

[Chemical Formula 233]

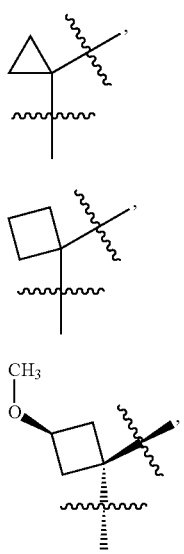

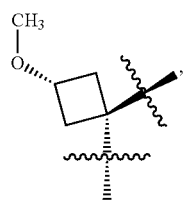

[III-9]

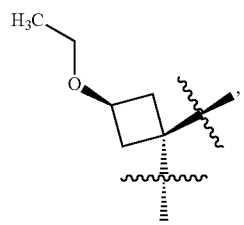

[III-10]

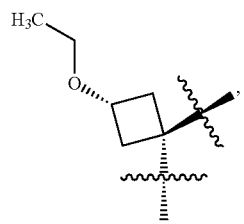

[III-11]

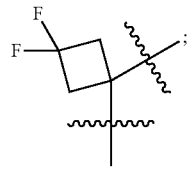

[III-13]

ring $B^1$ is phenyl, $R^{B11}$ and $R^{B12}$ are both hydrogen atoms, and $L^1$ is a structure represented by formula [V-3], [V-12], or [V-14]:

[Chemical Formula 234]

[V-3]

—$(CH_2)_{n4}$—,

[V-12]

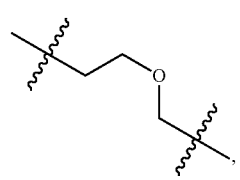

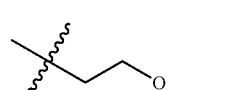

[V-14]

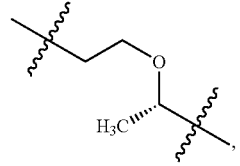

where n4 is an integer of 4, and ring $B^2$ is dihydroindenyl, $R^{B21}$ and $R^{B22}$ are both hydrogen atoms, and $L^2$ is a structure represented by formula [V-20]:

[Chemical Formula 235]

—$(CH_2)_{n5}$—

[V-20]

where
n5 is 2; and
R⁴ is a group represented by formula [VI-2], [VI-6], [VI-7], [VI-8], [VI-10], [VI-11], [VI-12], [VI-25], [VI-27], [VI-28], [VI-30], or [VI-31]:
[Chemical Formula 236]
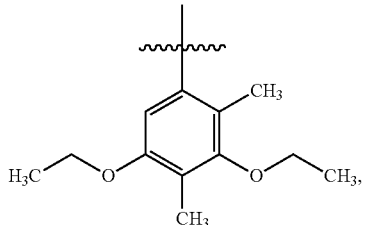
[VI-2]
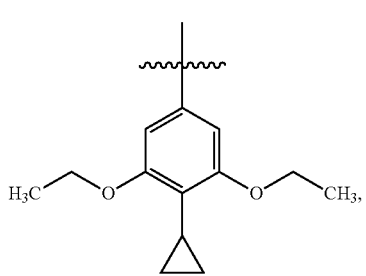
[VI-6]
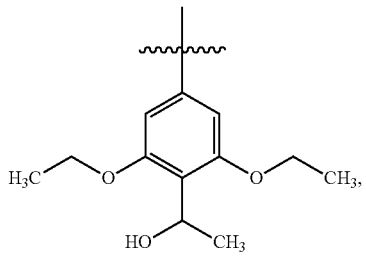
[VI-7]
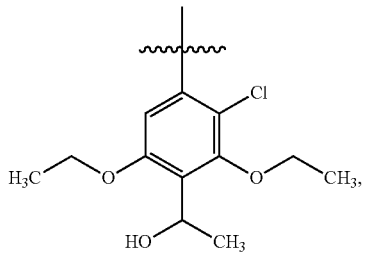
[VI-8]
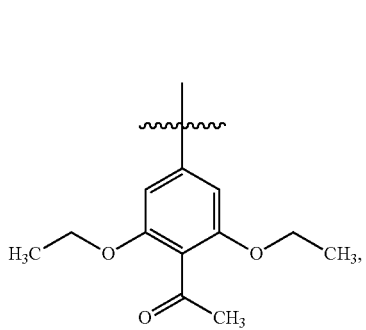
[VI-10]
-continued
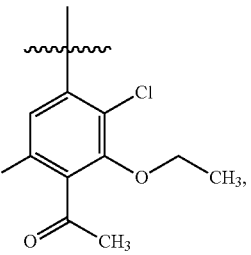
[VI-11]
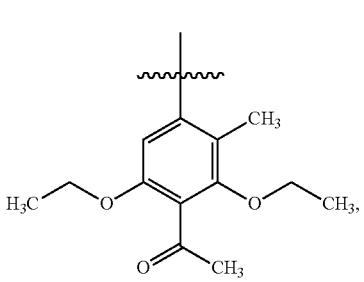
[VI-12]
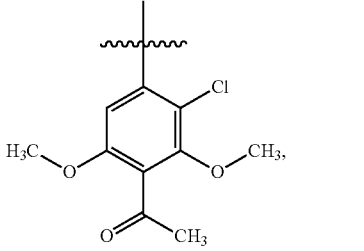
[VI-25]
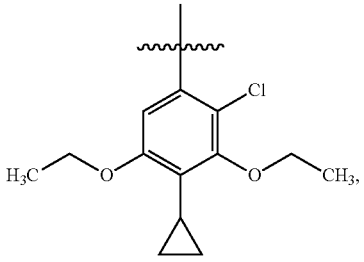
[VI-27]
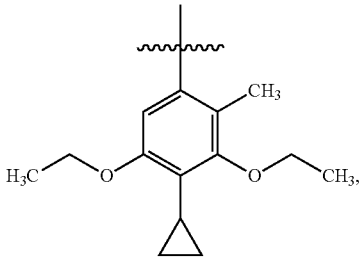
[VI-28]
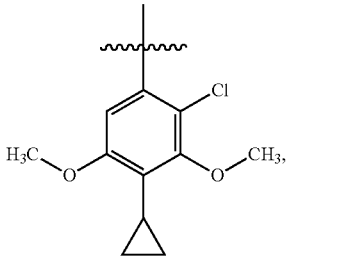
[VI-30]

167
-continued
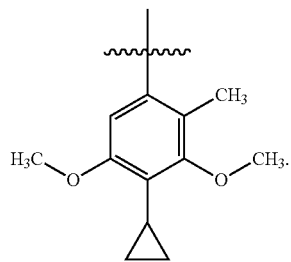
[VI-31]
Then, in the present aspect (H-3),
one particularly preferred aspect is the case where the compound represented by the above formula [I-7] is any of the following:
[Chemical Formula 237]
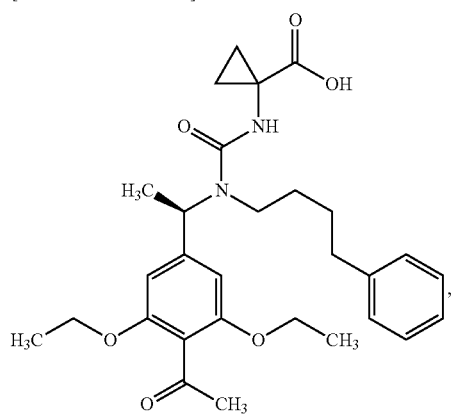
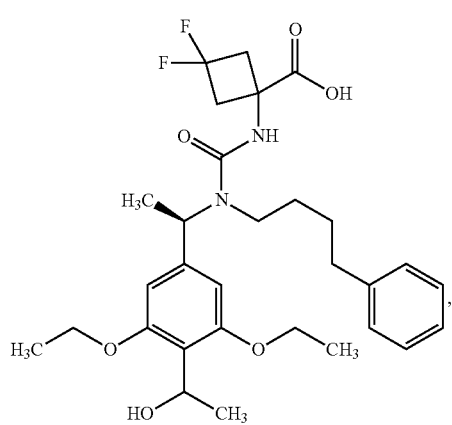
168
-continued
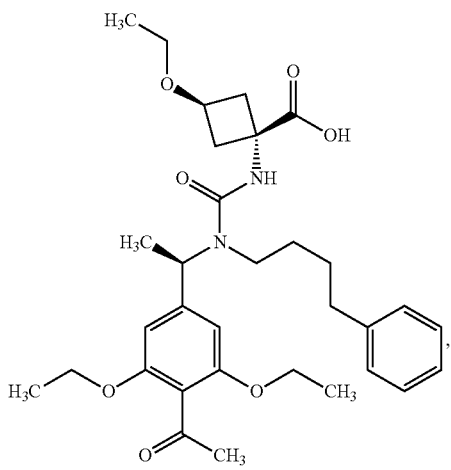
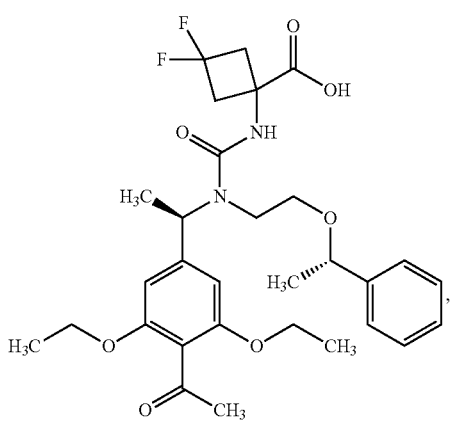
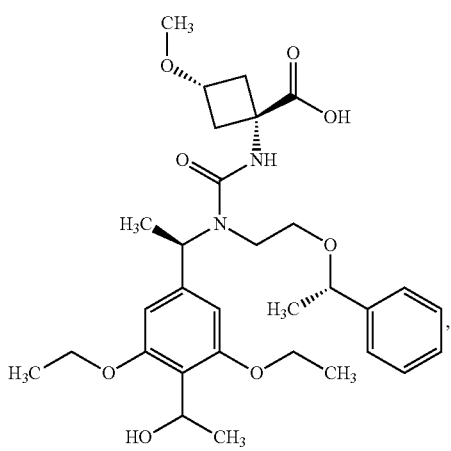

169
-continued
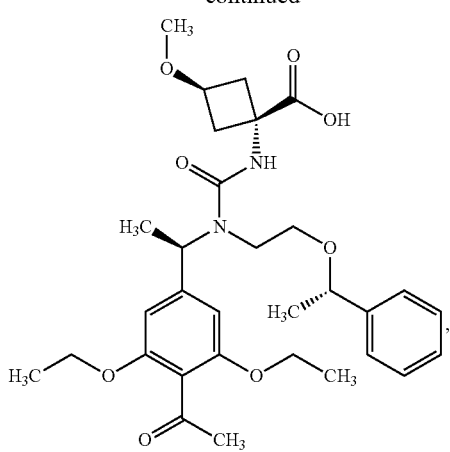
[Chemical Formula 238]
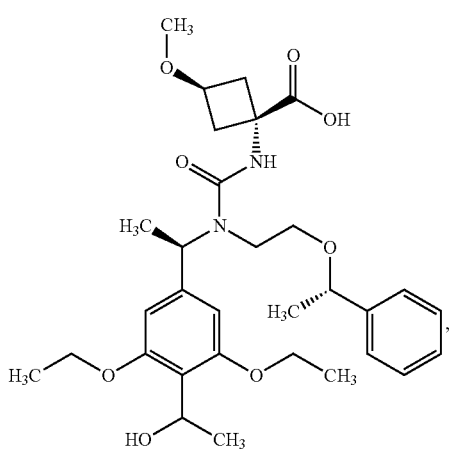
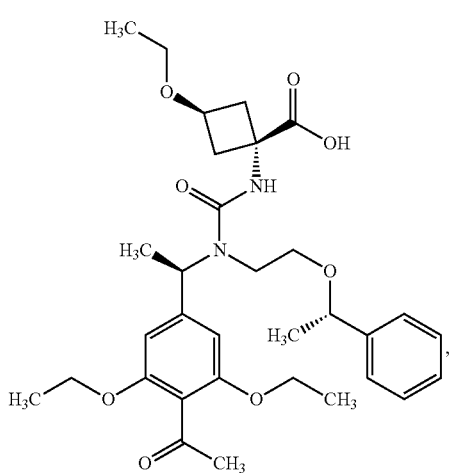
170
-continued
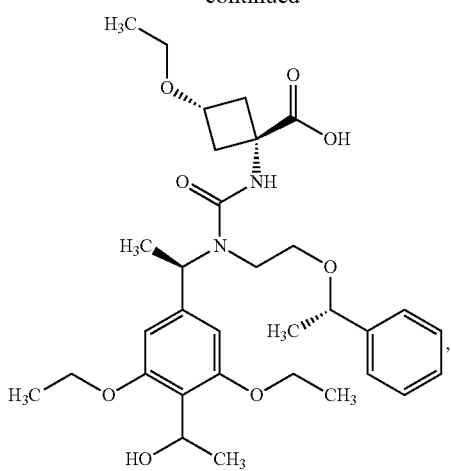
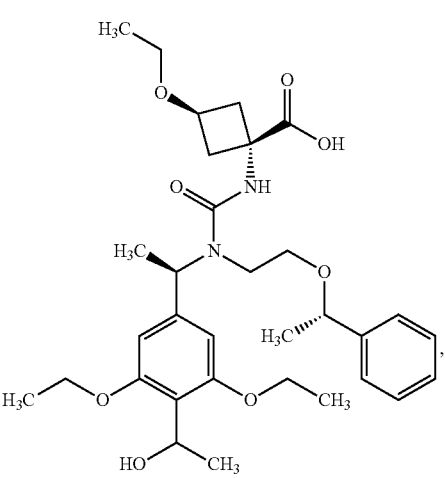
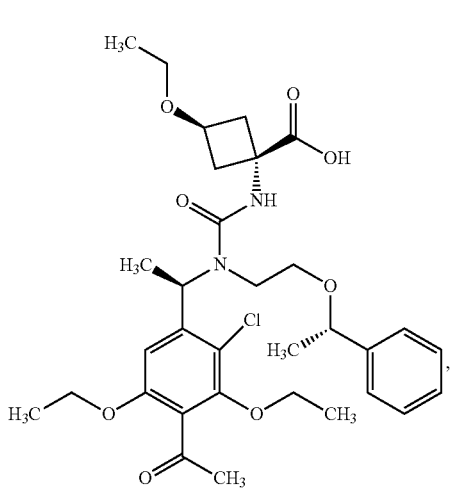

-continued
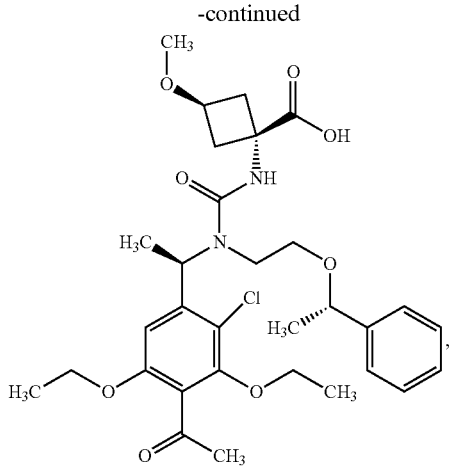
[Chemical Formula 239]
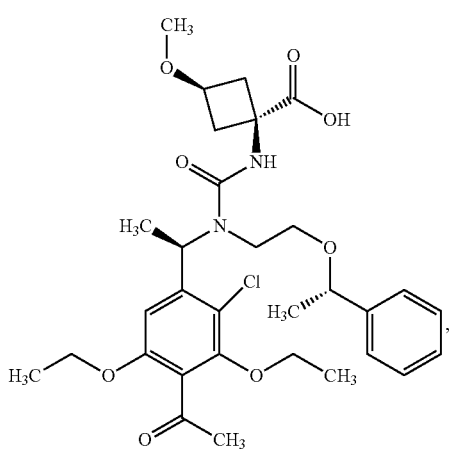
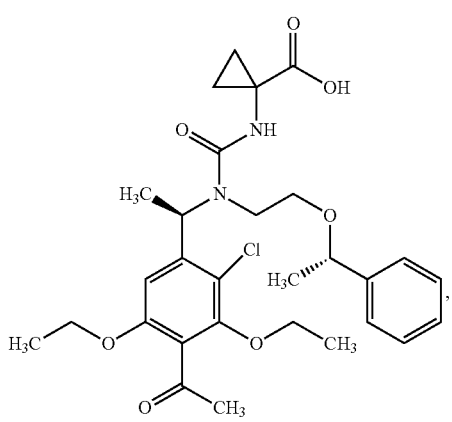
-continued
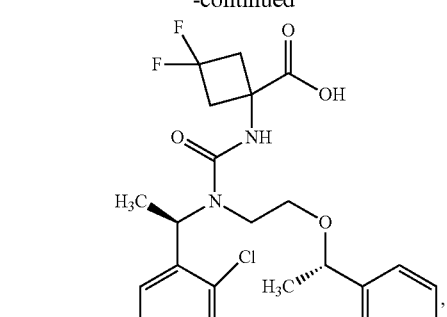
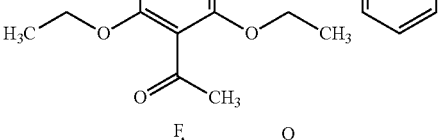
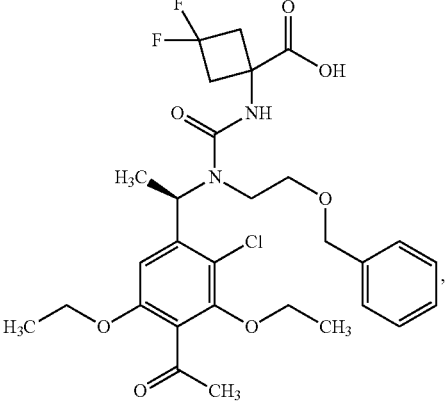
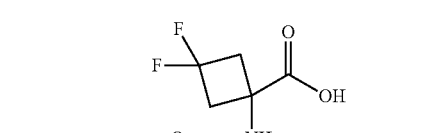
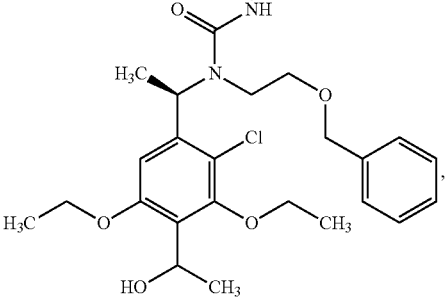
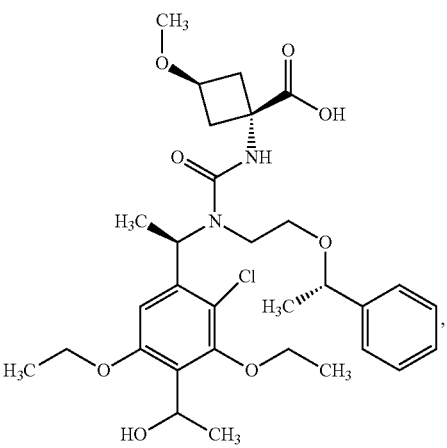

173
-continued
[Chemical Formula 240]
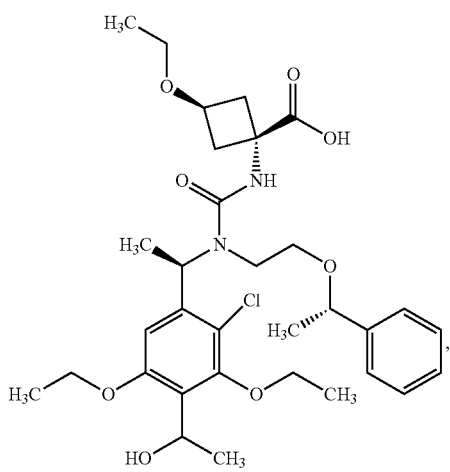
,
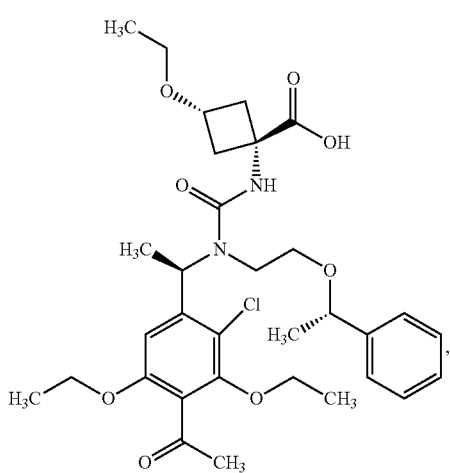
,
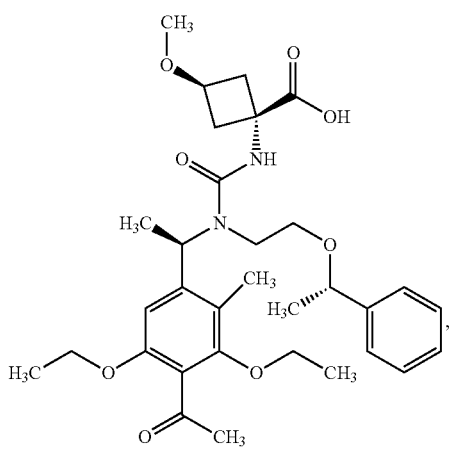
,
174
-continued
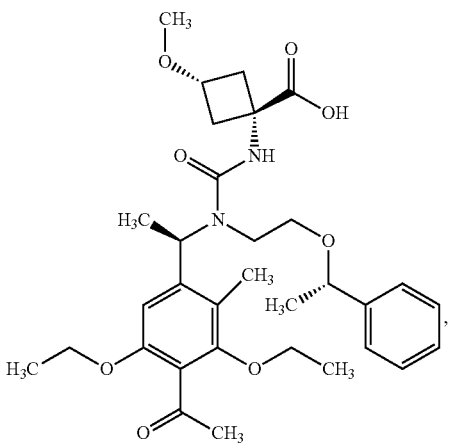
,
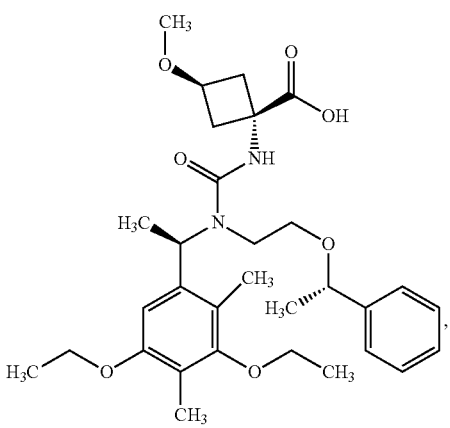
,
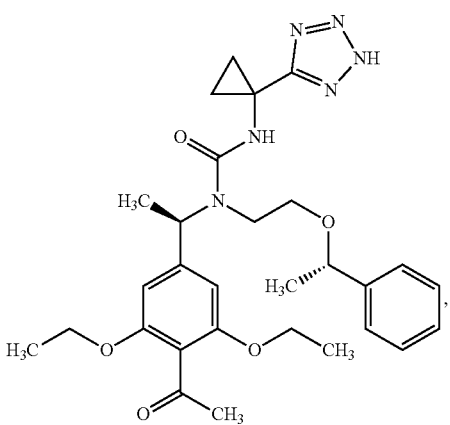
,

[Chemical Formula 241]
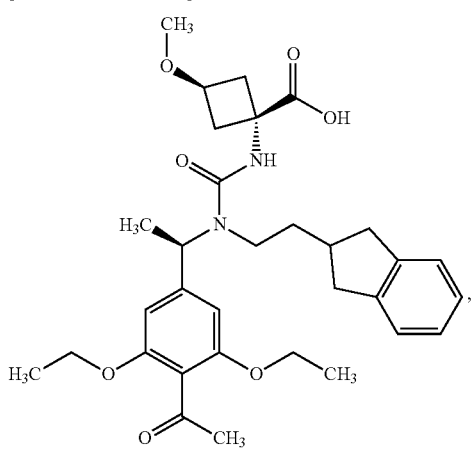
[Chemical Formula 242]
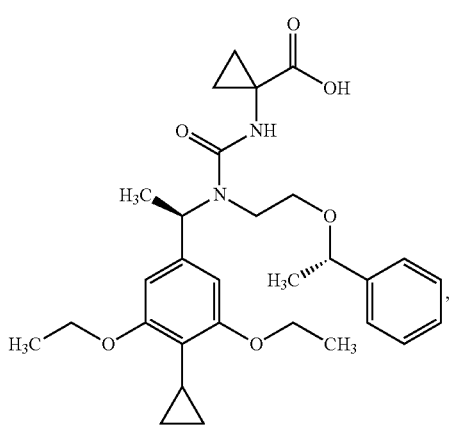
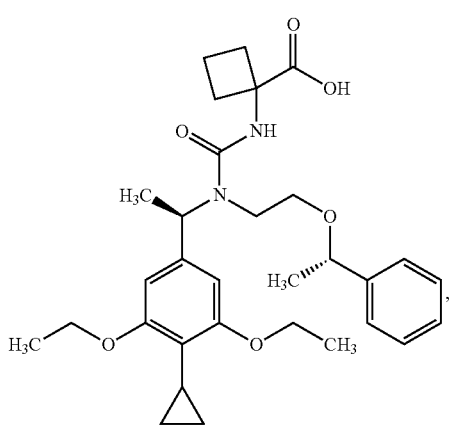
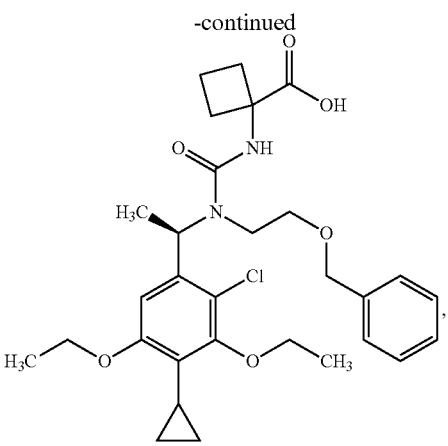
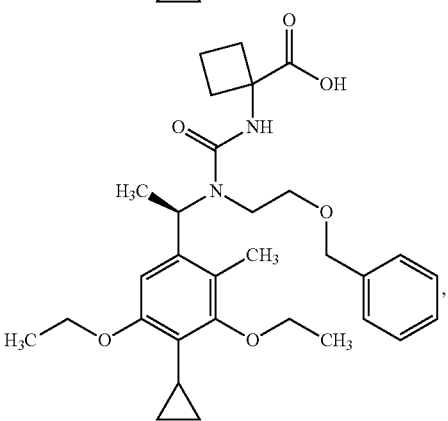
[Chemical Formula 243]
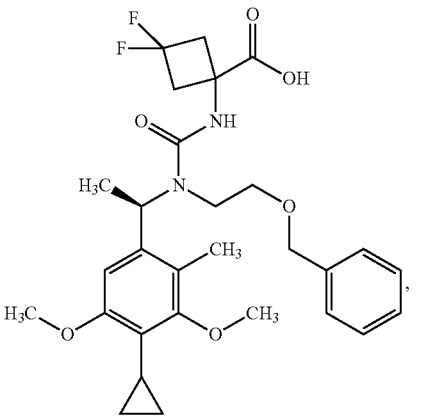
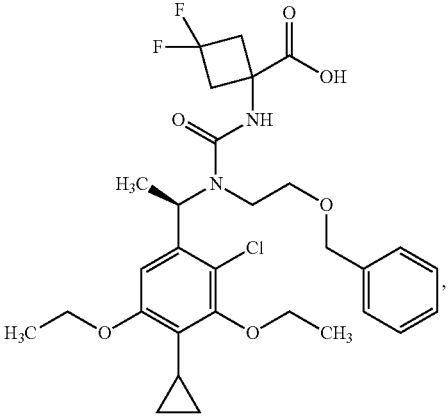

177
-continued
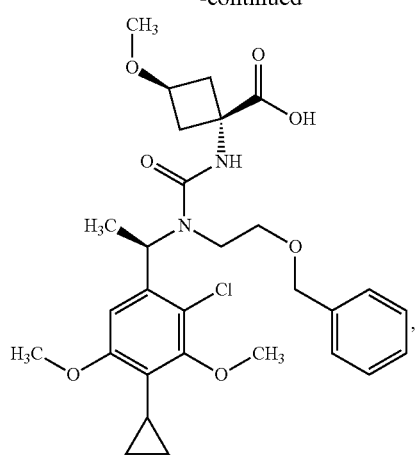
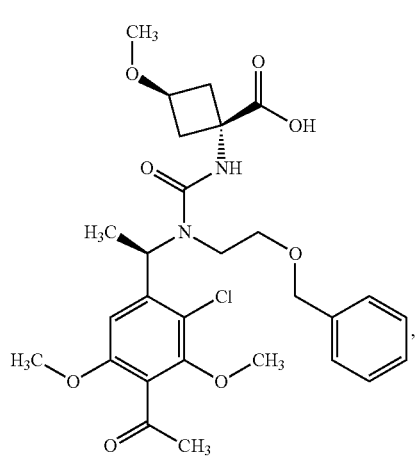
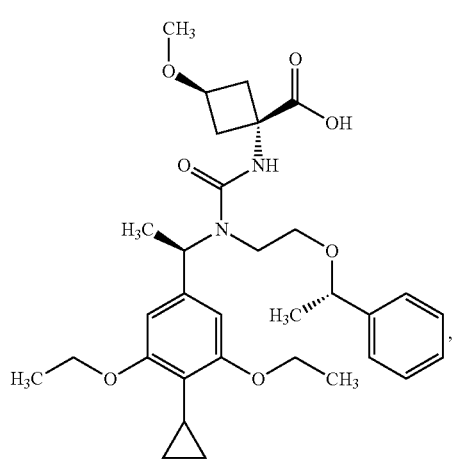
178
-continued
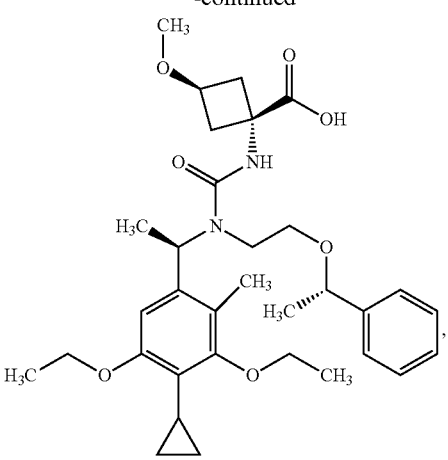
[Chemical Formula 244]
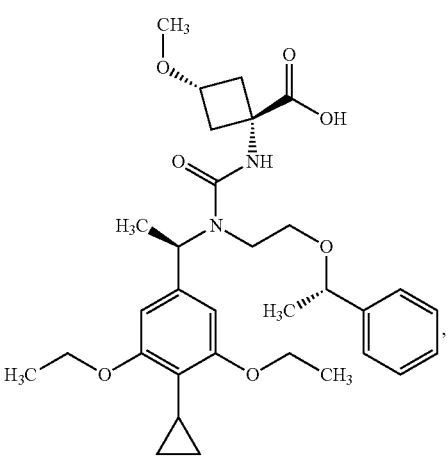
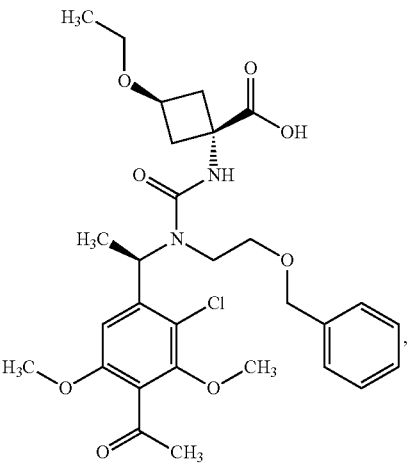

179
-continued
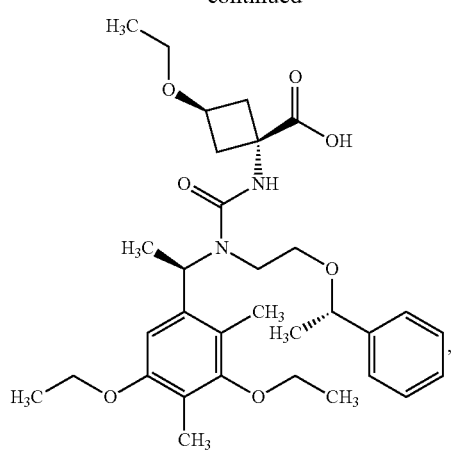
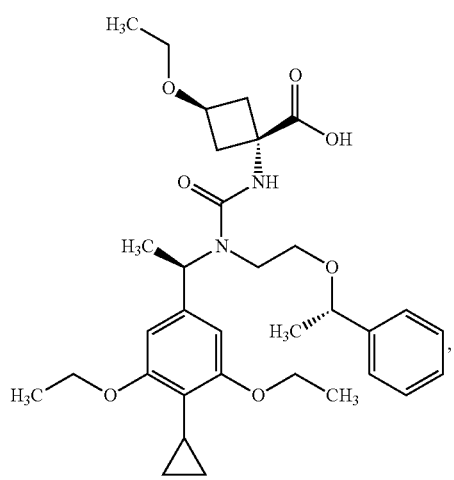
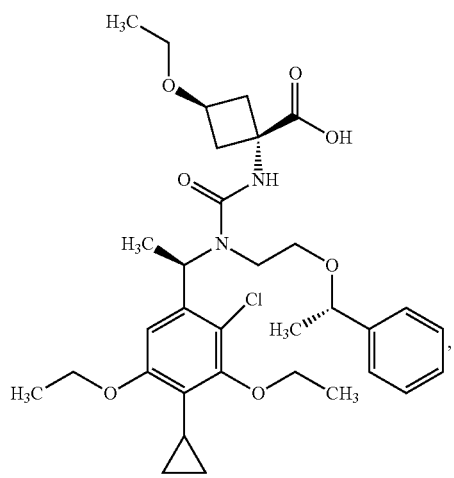
180
-continued
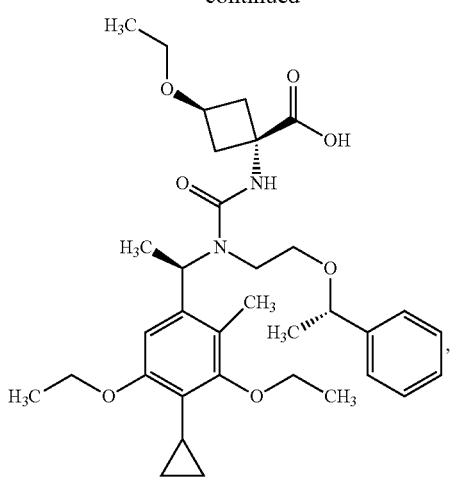
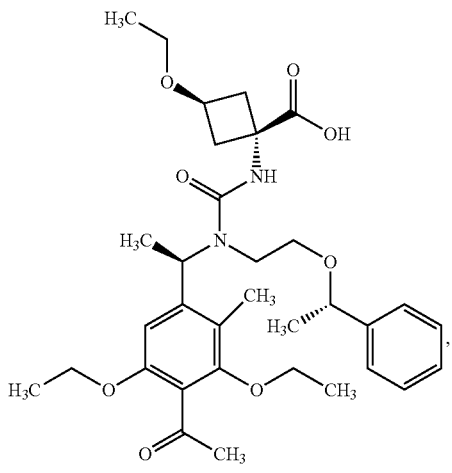
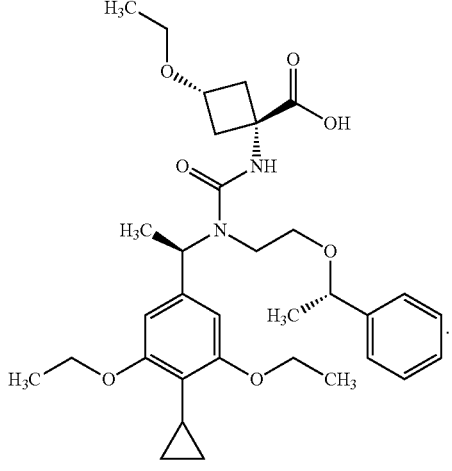

Also, in the present aspect (H-3), another particularly preferred aspect is as follows.

It is the case where the compound represented by the above formula [I-7] is the following:

[Chemical Formula 245]

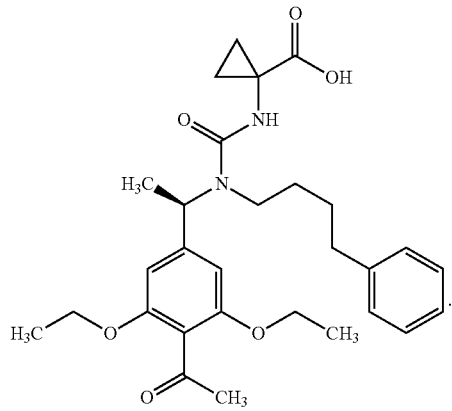

Also, in the present aspect (H-3), another particularly preferred aspect is as follows.

It is the case where the compound represented by the above formula [I-7] is the following:

[Chemical Formula 246]

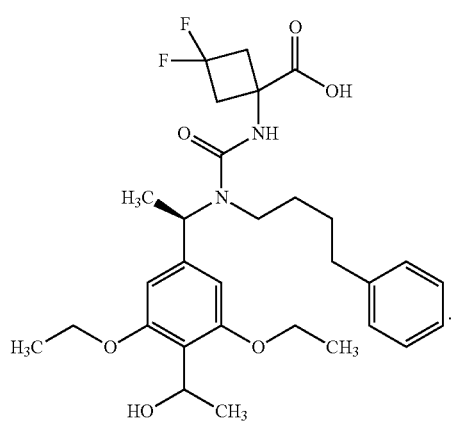

It is the case where the compound represented by the above formula [I-7] is the following:

[Chemical Formula 247]

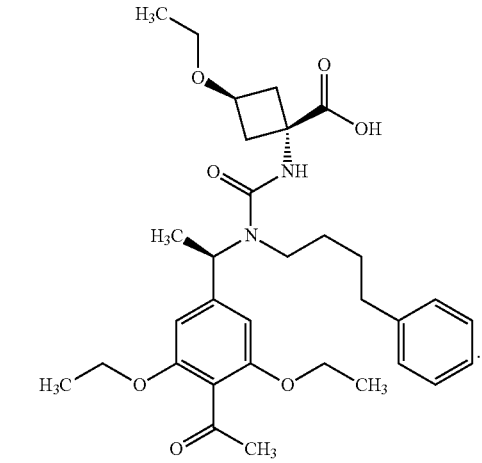

Also, in the present aspect (H-3), another particularly preferred aspect is as follows.

It is the case where the compound represented by the above formula [I-7] is the following:

[Chemical Formula 248]

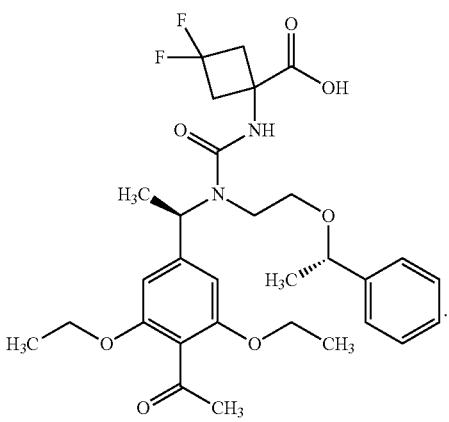

Also, in the present aspect (H-3), another particularly preferred aspect is as follows.

It is the case where the compound represented by the above formula [I-7] is the following:

[Chemical Formula 249]

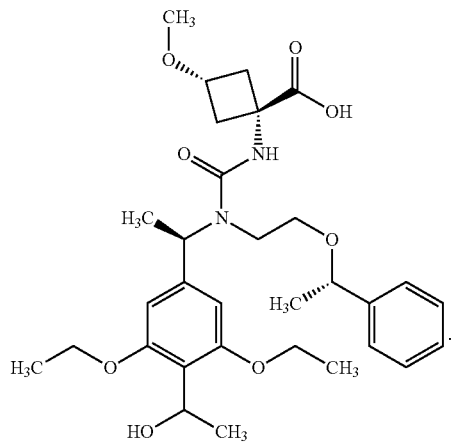

Also, in the present aspect (H-3), another particularly preferred aspect is as follows.

It is the case where the compound represented by the above formula [I-7] is the following:

[Chemical Formula 250]

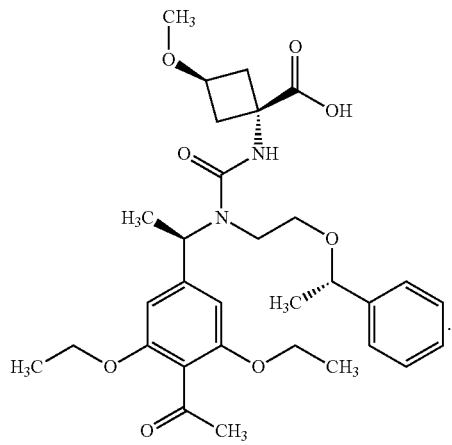

Also, in the present aspect (H-3), another particularly preferred aspect is as follows.

It is the case where the compound represented by the above formula [I-7] is the following:

[Chemical Formula 251]

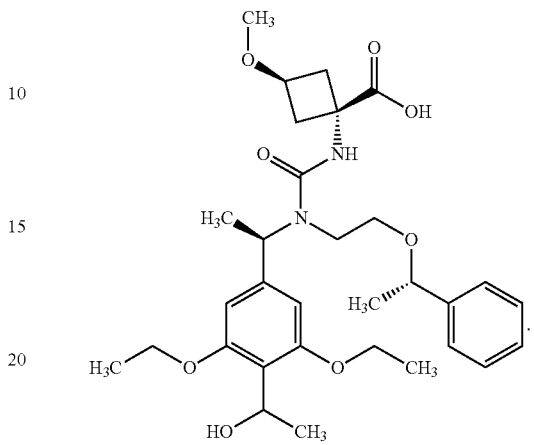

Also, in the present aspect (H-3), another particularly preferred aspect is as follows.

It is the case where the compound represented by the above formula [I-7] is the following:

[Chemical Formula 252]

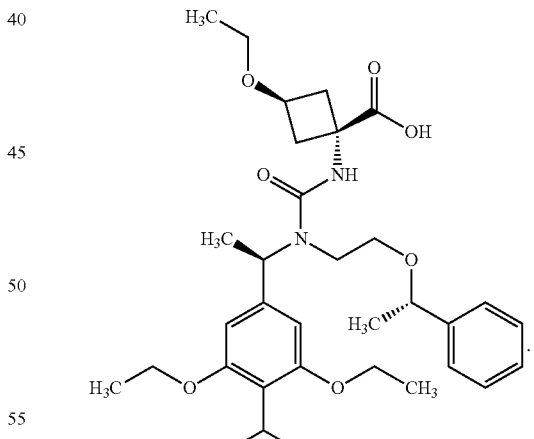

Also, in the present aspect (H-3), another particularly preferred aspect is as follows.

It is the case where the compound represented by the above formula [I-7] is the following:

[Chemical Formula 253]

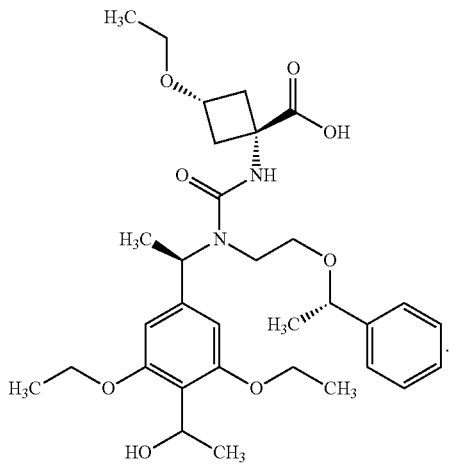

Also, in the present aspect (H-3), another particularly preferred aspect is as follows.

It is the case where the compound represented by the above formula [I-7] is the following:

[Chemical Formula 254]

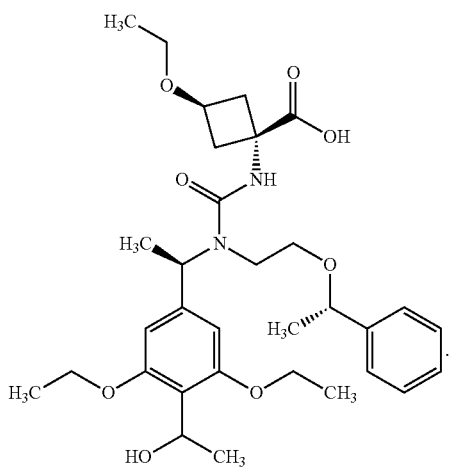

Also, in the present aspect (H-3), another particularly preferred aspect is as follows.

It is the case where the compound represented by the above formula [I-7] is the following:

[Chemical Formula 255]

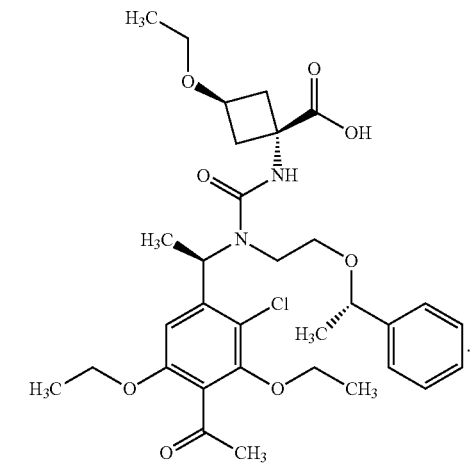

Also, in the present aspect (H-3), another particularly preferred aspect is as follows.

It is the case where the compound represented by the above formula [I-7] is the following:

[Chemical Formula 256]

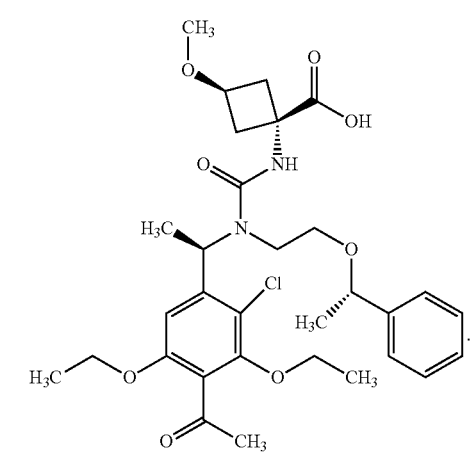

Also, in the present aspect (H-3), another particularly preferred aspect is as follows.

It is the case where the compound represented by the above formula [I-7] is the following:

[Chemical Formula 257]

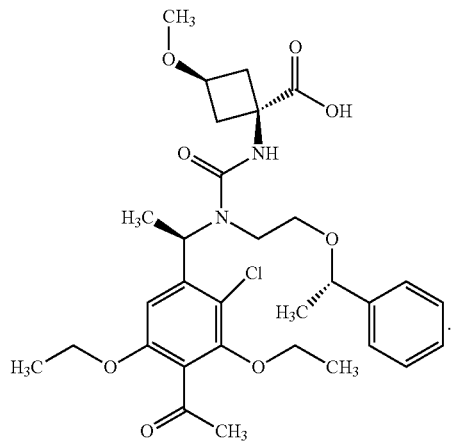

Also, in the present aspect (H-3), another particularly preferred aspect is as follows.

It is the case where the compound represented by the above formula [I-7] is the following:

[Chemical Formula 258]

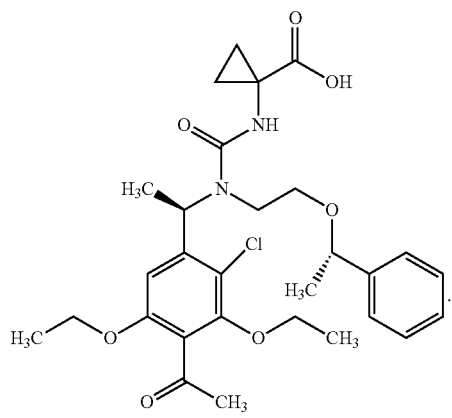

Also, in the present aspect (H-3), another particularly preferred aspect is as follows.

It is the case where the compound represented by the above formula [I-7] is the following:

[Chemical Formula 259]

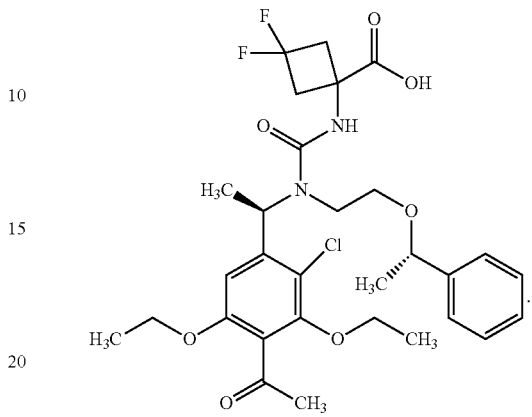

Also, in the present aspect (H-3), another particularly preferred aspect is as follows.

It is the case where the compound represented by the above formula [I-7] is the following:

[Chemical Formula 260]

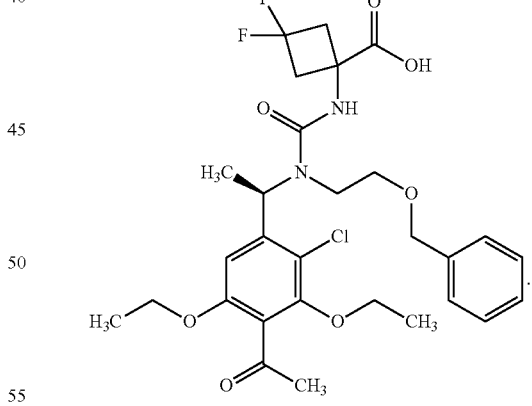

Also, in the present aspect (H-3), another particularly preferred aspect is as follows.

It is the case where the compound represented by the above formula [I-7] is the following:

[Chemical Formula 261]

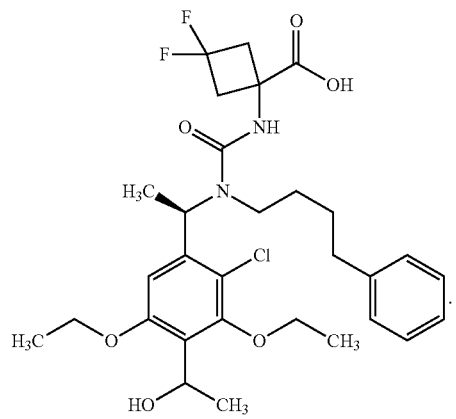

Also, in the present aspect (H-3), another particularly preferred aspect is as follows.

It is the case where the compound represented by the above formula [I-7] is the following:

[Chemical Formula 262]

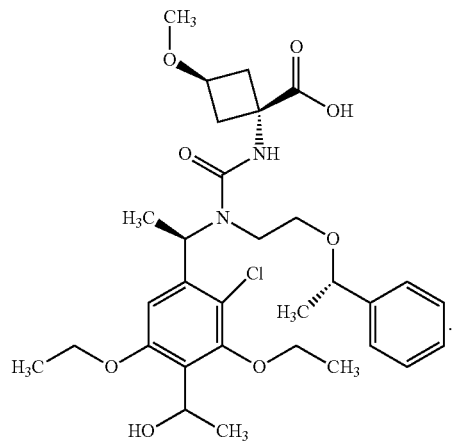

Also, in the present aspect (H-3), another particularly preferred aspect is as follows.

It is the case where the compound represented by the above formula [I-7] is the following:

[Chemical Formula 263]

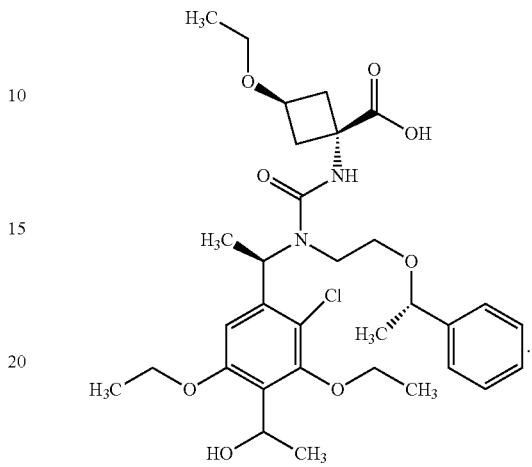

Also, in the present aspect (H-3), another particularly preferred aspect is as follows.

It is the case where the compound represented by the above formula [I-7] is the following:

[Chemical Formula 264]

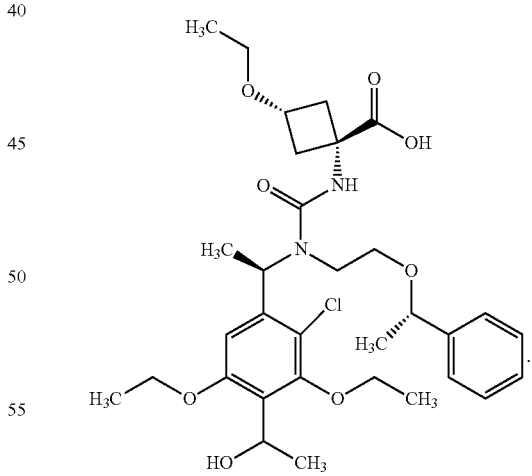

Also, in the present aspect (H-3), another particularly preferred aspect is as follows.

It is the case where the compound represented by the above formula [I-7] is the following:

[Chemical Formula 265]

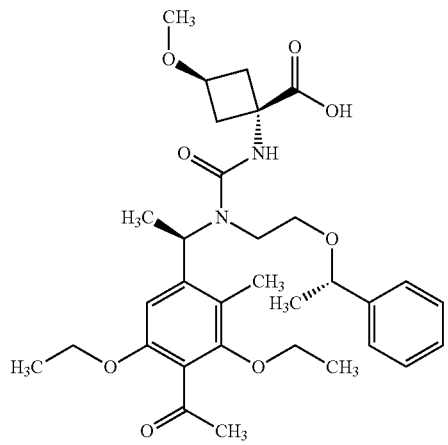

Also, in the present aspect (H-3), another particularly preferred aspect is as follows.

It is the case where the compound represented by the above formula [I-7] is the following:

[Chemical Formula 266]

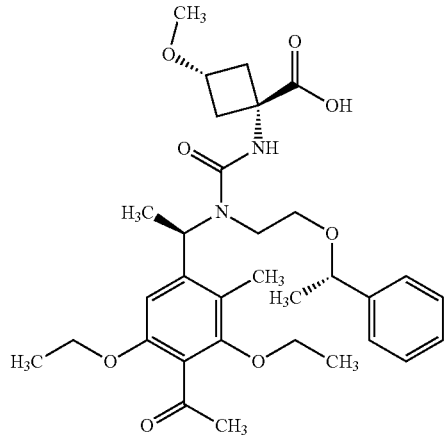

Also, in the present aspect (H-3), another particularly preferred aspect is as follows.

It is the case where the compound represented by the above formula [I-7] is the following:

[Chemical Formula 267]

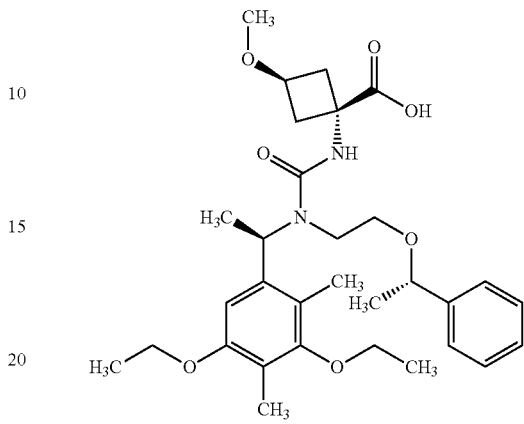

Also, in the present aspect (H-3), another particularly preferred aspect is as follows.

It is the case where the compound represented by the above formula [I-7] is the following:

[Chemical Formula 268]

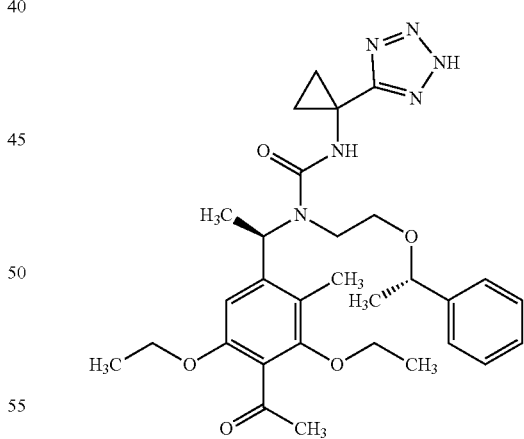

Also, in the present aspect (H-3), another particularly preferred aspect is as follows.

It is the case where the compound represented by the above formula [I-7] is the following:

[Chemical Formula 269]

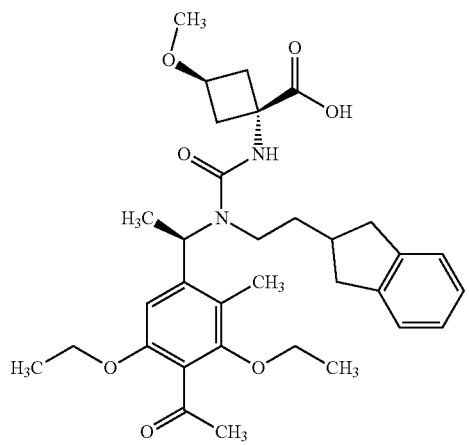

Also, in the present aspect (H-3), another particularly preferred aspect is as follows.

It is the case where the compound represented by the above formula [I-7] is the following:

[Chemical Formula 270]

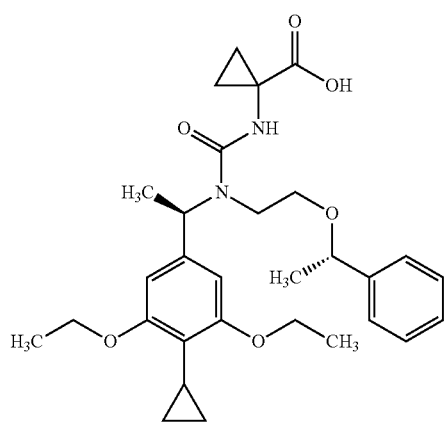

Also, in the present aspect (H-3), another particularly preferred aspect is as follows.

It is the case where the compound represented by the above formula [I-7] is the following:

[Chemical Formula 271]

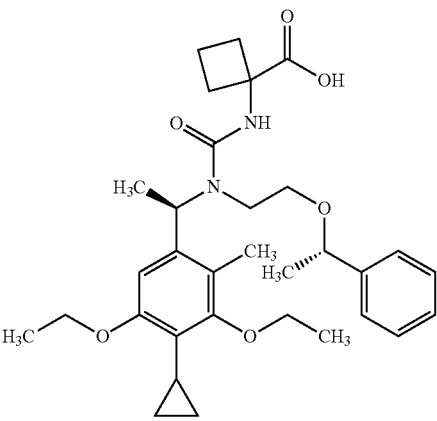

Also, in the present aspect (H-3), another particularly preferred aspect is as follows.

It is the case where the compound represented by the above formula [I-7] is the following:

[Chemical Formula 272]

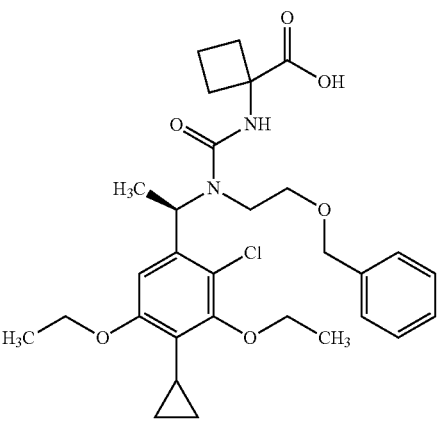

Also, in the present aspect (H-3), another particularly preferred aspect is as follows.

It is the case where the compound represented by the above formula [I-7] is the following:

[Chemical Formula 273]

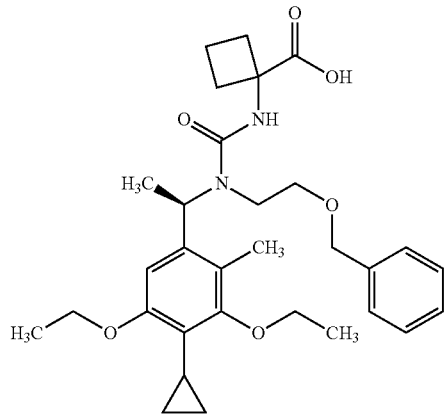

Also, in the present aspect (H-3), another particularly preferred aspect is as follows.

It is the case where the compound represented by the above formula [I-7] is the following:

[Chemical Formula 274]

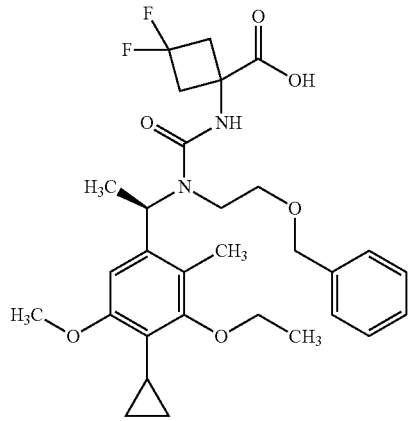

Also, in the present aspect (H-3), another particularly preferred aspect is as follows.

It is the case where the compound represented by the above formula [I-7] is the following:

[Chemical Formula 275]

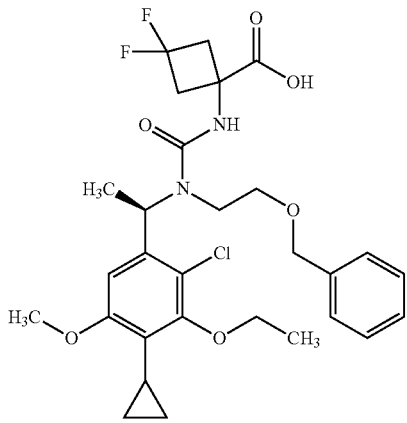

Also, in the present aspect (H-3), another particularly preferred aspect is as follows.

It is the case where the compound represented by the above formula [I-7] is the following:

[Chemical Formula 276]

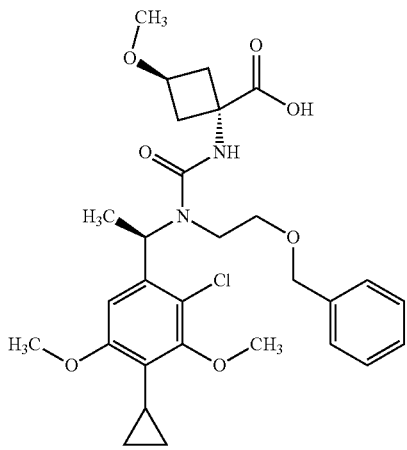

Also, in the present aspect (H-3), another particularly preferred aspect is as follows.

It is the case where the compound represented by the above formula [I-7] is the following:

[Chemical Formula 277]

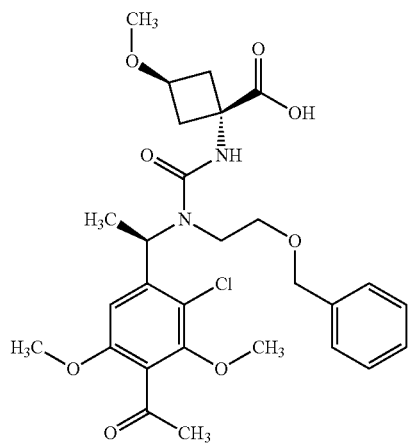

Also, in the present aspect (H-3), another particularly preferred aspect is as follows.

It is the case where the compound represented by the above formula [I-7] is the following:

[Chemical Formula 278]

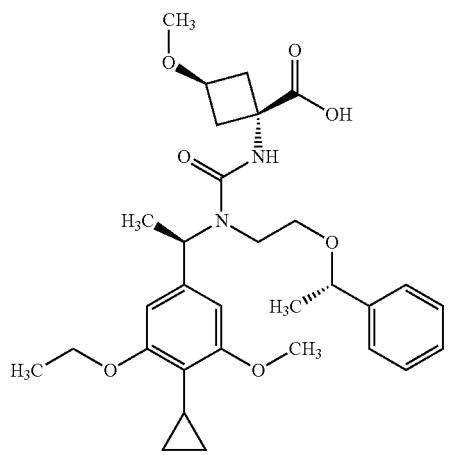

Also, in the present aspect (H-3), another particularly preferred aspect is as follows.

It is the case where the compound represented by the above formula [I-7] is the following:

[Chemical Formula 279]

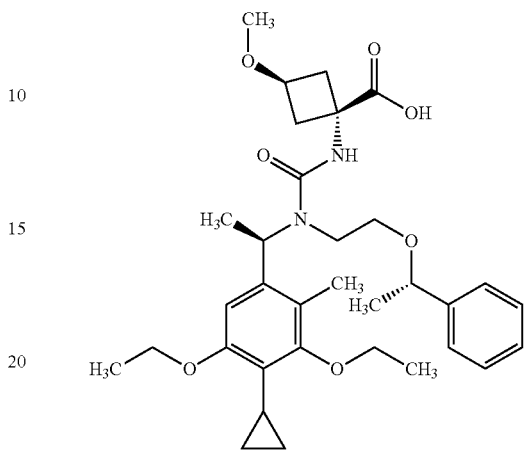

Also, in the present aspect (H-3), another particularly preferred aspect is as follows.

It is the case where the compound represented by the above formula [I-7] is the following:

[Chemical Formula 280]

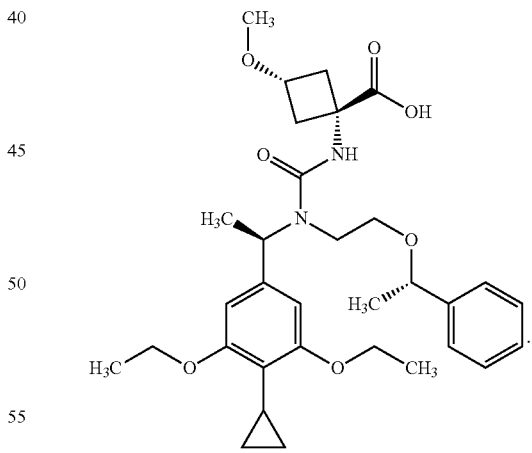

Also, in the present aspect (H-3), another particularly preferred aspect is as follows.

It is the case where the compound represented by the above formula [I-7] is the following:

[Chemical Formula 281]

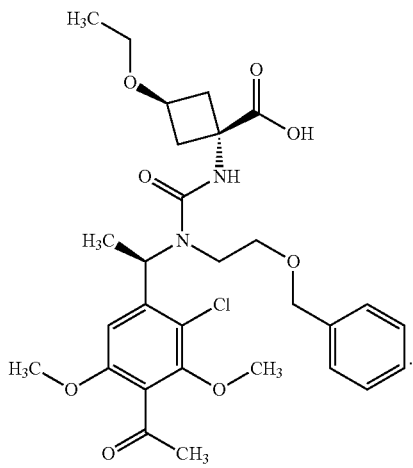

Also, in the present aspect (H-3), another particularly preferred aspect is as follows.

It is the case where the compound represented by the above formula [I-7] is the following:

[Chemical Formula 282]

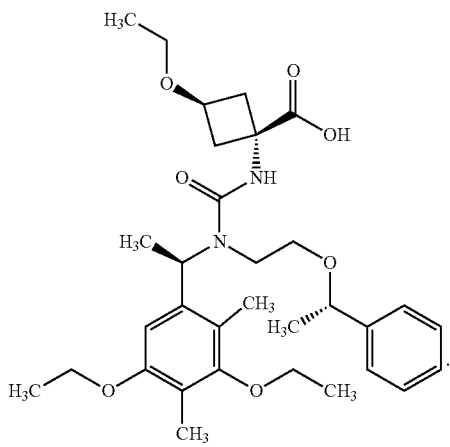

Also, in the present aspect (H-3), another particularly preferred aspect is as follows.

It is the case where the compound represented by the above formula [I-7] is the following:

[Chemical Formula 283]

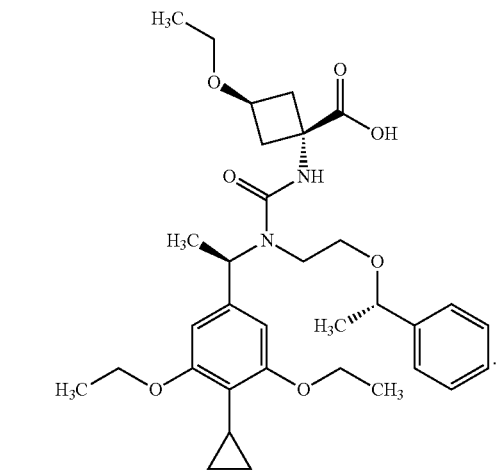

Also, in the present aspect (H-3), another particularly preferred aspect is as follows.

It is the case where the compound represented by the above formula [I-7] is the following:

[Chemical Formula 284]

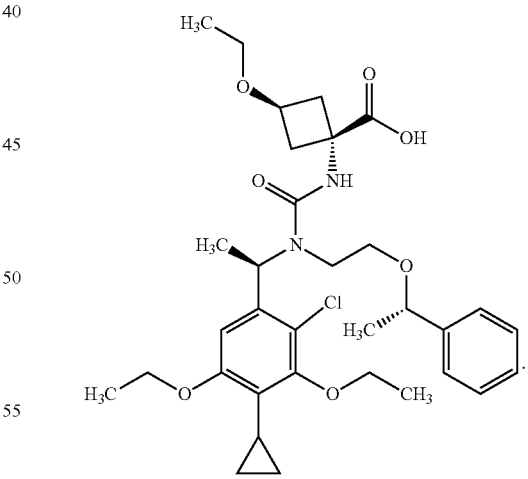

Also, in the present aspect (H-3), another particularly preferred aspect is as follows.

It is the case where the compound represented by the above formula [I-7] is the following:

[Chemical Formula 285]

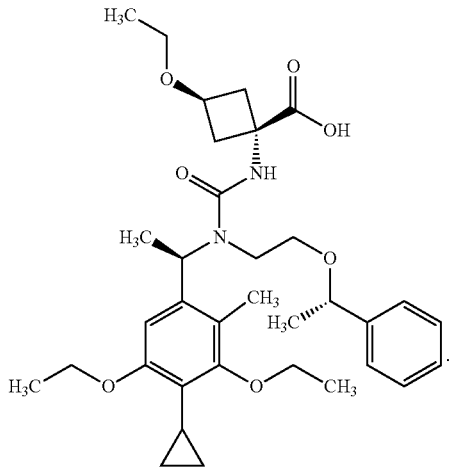

Also, in the present aspect (H-3), another particularly preferred aspect is as follows.

It is the case where the compound represented by the above formula [I-7] is the following:

[Chemical Formula 286]

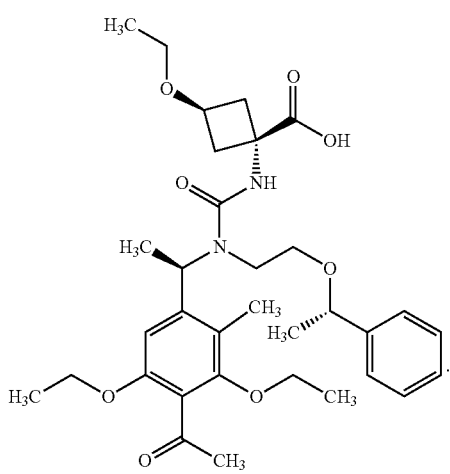

Also, in the present aspect (H-3), another particularly preferred aspect is as follows.

It is the case where the compound represented by the above formula [I-7] is the following:

[Chemical Formula 287]

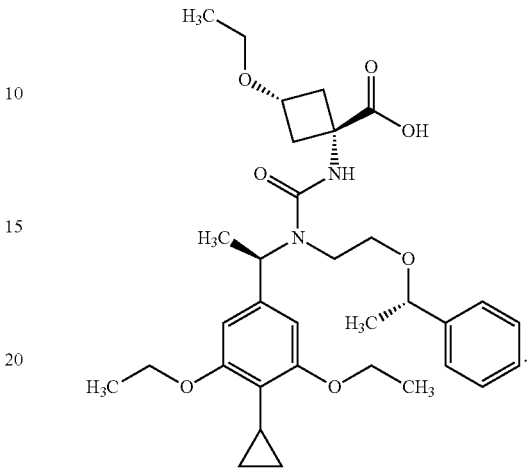

Another preferred aspect of the compound of the present invention is aspect (J) below.

Aspect (J):

In the present aspect (J), a preferred aspect is as follows.

In the compound represented by the above formula [I], or a pharmaceutically acceptable salt thereof, or a hydrate thereof, the compound represented by formula [I] is a compound represented by formula [I-8]:

[Chemical Formula 288]

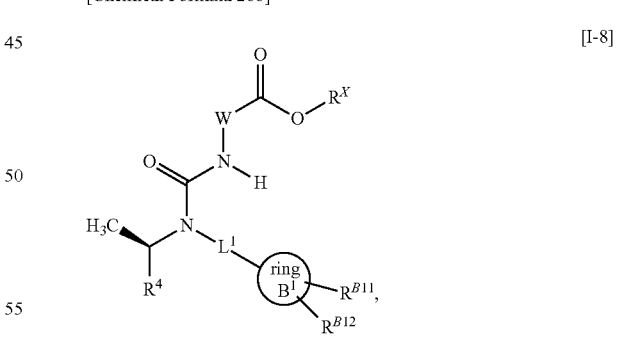

[I-8]

where $R^X$ is $C_{1-4}$ alkyl; and

W, ring $B^1$, $R^{B11}$, $R^{B12}$, $L^1$, and $R^4$ are as mentioned above.

In the present aspect (J), a more preferred aspect is as follows.
In the above formula [I-8],
$R^X$ is $C_1$ alkyl, $C_2$ alkyl, or $C_4$ alkyl;
W is a structure represented by formula [III-1]:

[Chemical Formula 289]

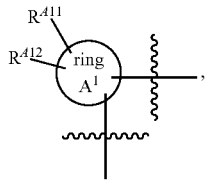

[III-1]

where,
in the structure represented by formula [III-1],
ring $A^1$ is $C_{3-4}$ cycloalkane,
$R^{A11}$ is a hydrogen atom, a halogen atom, or $C_2$ alkoxy, and
$R^{A12}$ is a hydrogen atom or a halogen atom;
ring $B^1$ is phenyl,
$R^{B11}$ and $R^{B12}$ are both hydrogen atoms,
$L^1$ is $C_5$ alkanediyl, and
one carbon atom in the $C_5$ alkanediyl, that is two or more atoms away from the nitrogen atom to which $R^2$ is bonded, is optionally replaced with formula —O—; and
$R^4$ is a group represented by formula [VI]:

[Chemical Formula 290]

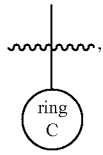

[VI]

where
ring C is phenyl,
the phenyl is substituted with three groups that are the same or different, selected from the group consisting of $C_2$ alkoxy and $C_1$ alkylcarbonyl, and furthermore,
the phenyl is optionally substituted with one halogen atom.

In the present aspect (J), a further preferred aspect is as follows.
In the above formula [I-8],
$R^X$ is methyl, ethyl, or tert-butyl;
W is a structure represented by formula [III-5], [III-10], or [III-13]:

[Chemical Formula 291]

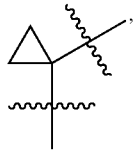

[III-5]

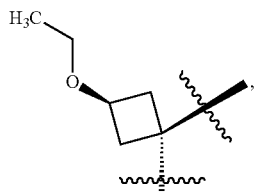

[III-10]

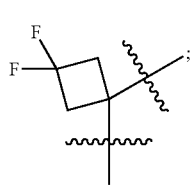

[III-13]

ring $B^1$ is phenyl,
$R^{B11}$ and $R^{B12}$ are both hydrogen atoms, and
$L^1$ is a structure represented by formula [V-14]:
[Chemical Formula 292]

[Chemical Formula 292]

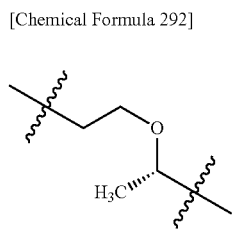

[V-14]

and
$R^4$ is a group represented by formula [VI-10] or [VI-11]:

[Chemical Formula 293]

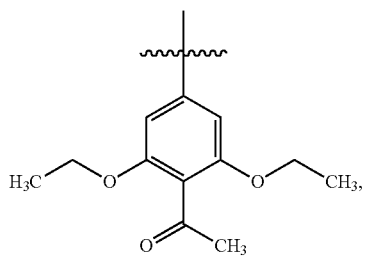

[VI-10]

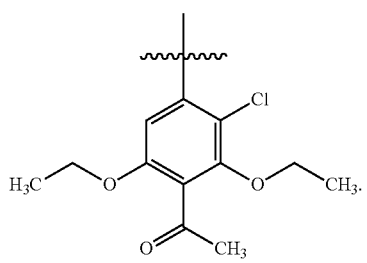

[VI-11]

Then, in the present aspect (J), one particularly preferred aspect is as follows.

It is the case where the compound represented by the above formula [I-8] is any of the following:
[Chemical Formula 294]
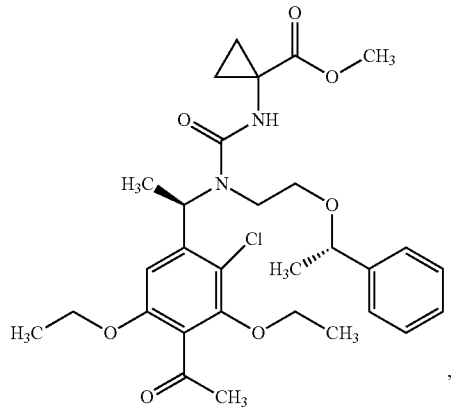
,
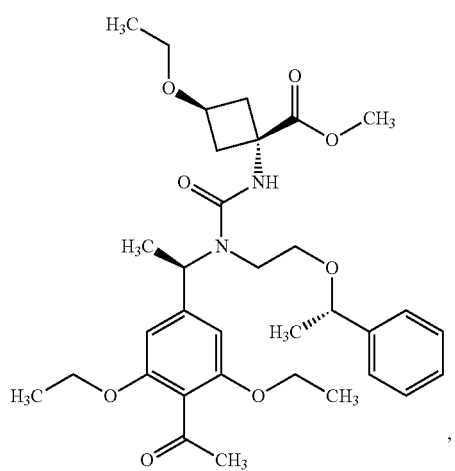
,
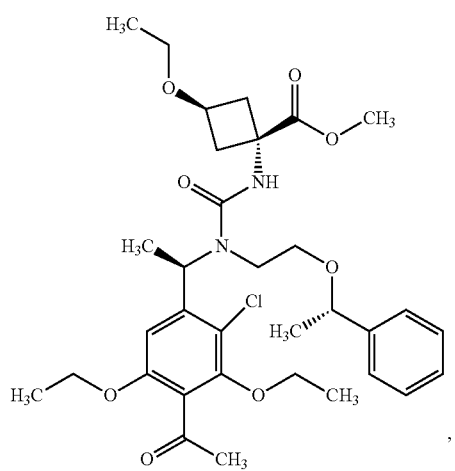
,
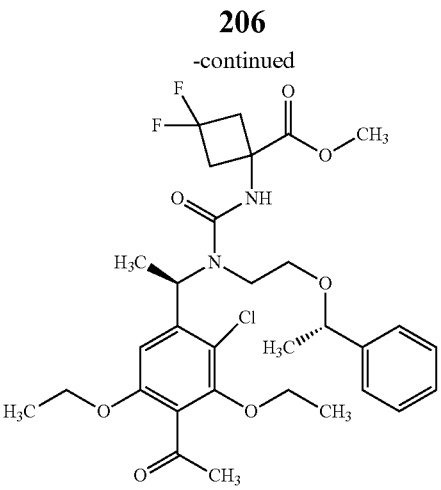
,
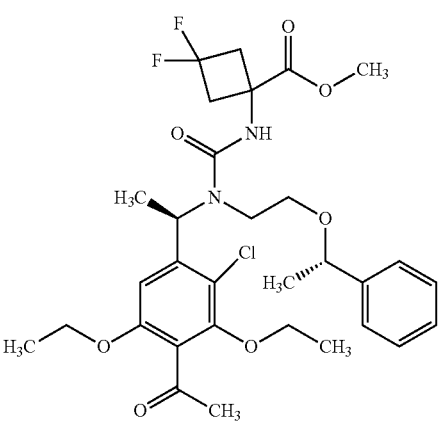
,
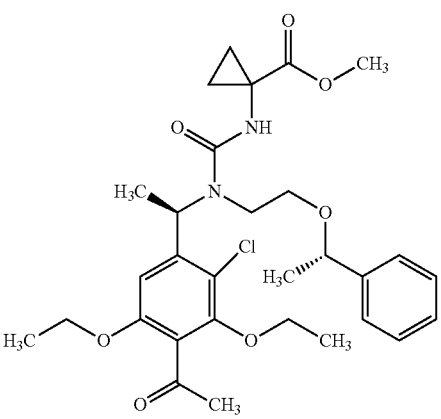
,

[Chemical Formula 295]
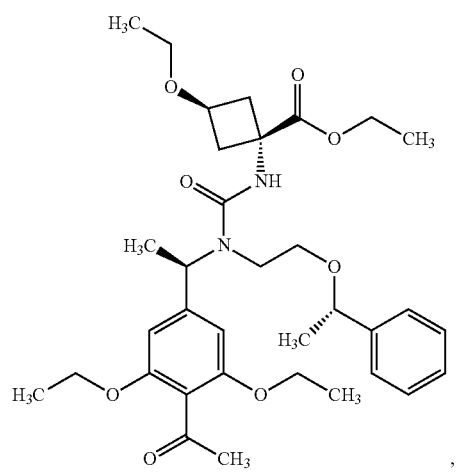
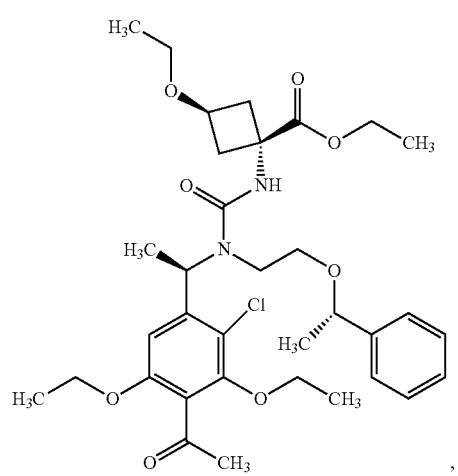
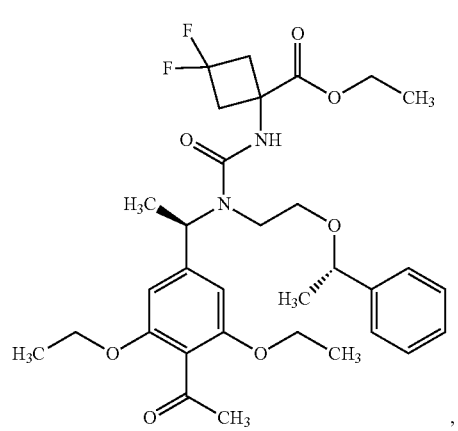
-continued
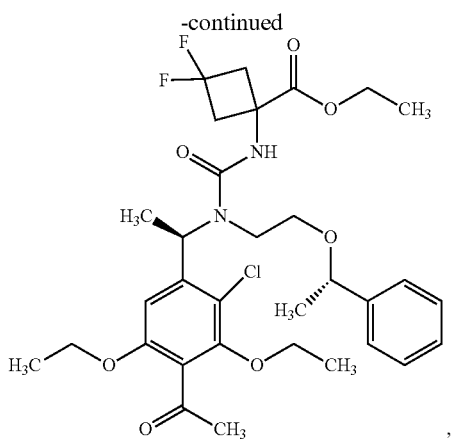
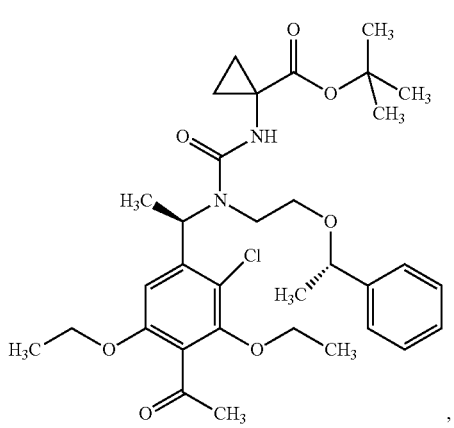
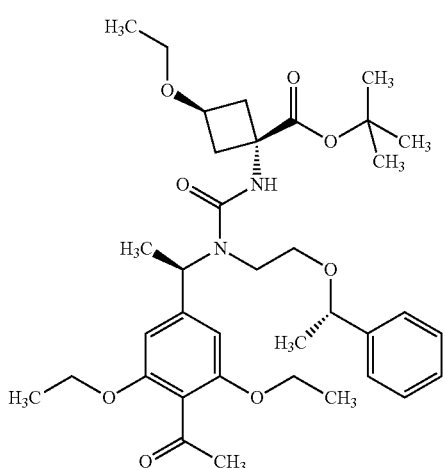

[Chemical Formula 296]

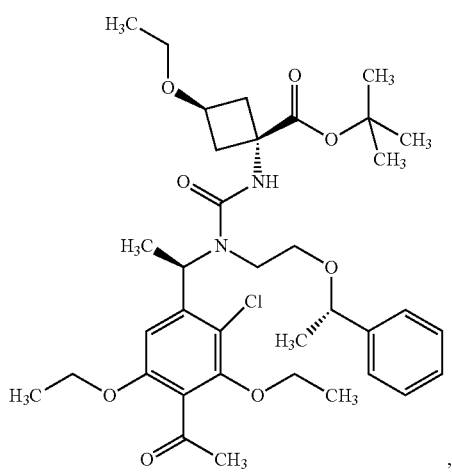

,

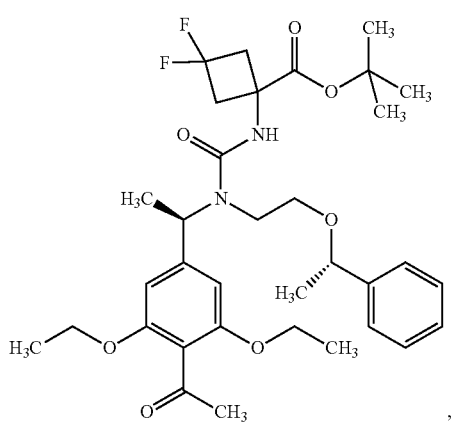

,

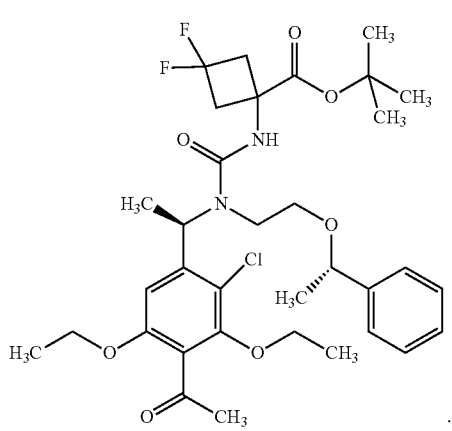

.

Also, in the present aspect (J), another particularly preferred aspect is as follows.

It is the case where the compound represented by the above formula [I-8] is the following:

[Chemical Formula 297]

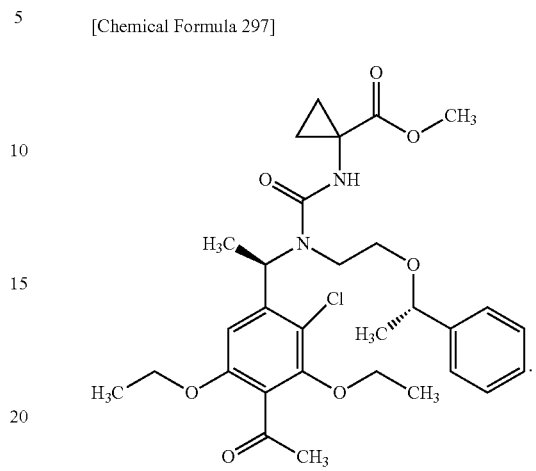

.

Also, in the present aspect (J), another particularly preferred aspect is as follows.

It is the case where the compound represented by the above formula [I-8] is the following:

[Chemical Formula 298]

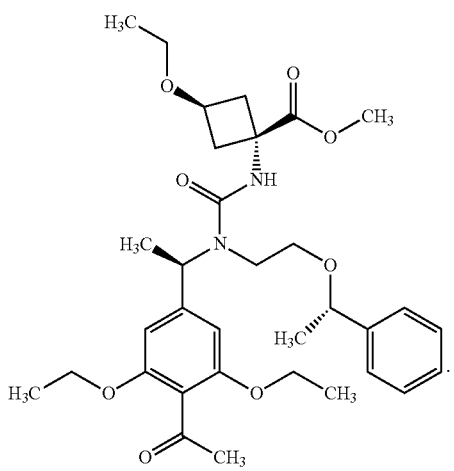

.

Also, in the present aspect (J), another particularly preferred aspect is as follows.

It is the case where the compound represented by the above formula [I-8] is the following:

[Chemical Formula 299]

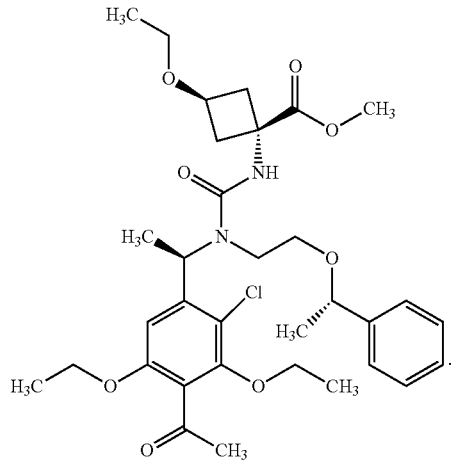

Also, in the present aspect (J), another particularly preferred aspect is as follows.

It is the case where the compound represented by the above formula [I-8] is the following:

[Chemical Formula 300]

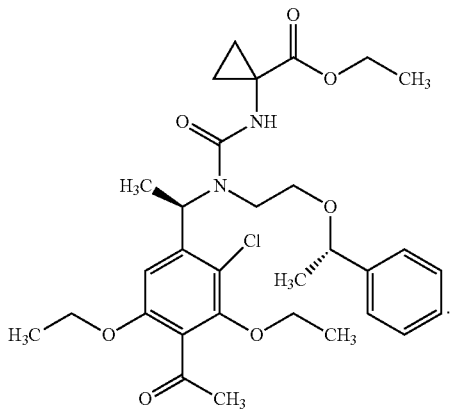

Also, in the present aspect (J), another particularly preferred aspect is as follows.

It is the case where the compound represented by the above formula [I-8] is the following:

[Chemical Formula 301]

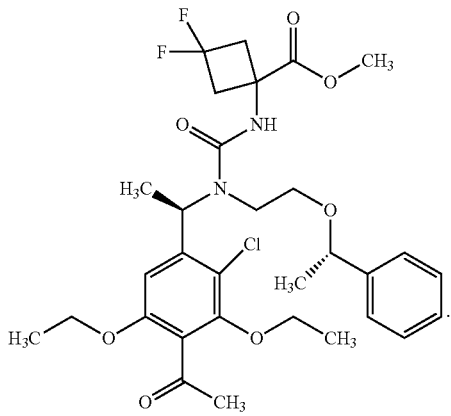

Also, in the present aspect (J), another particularly preferred aspect is as follows.

It is the case where the compound represented by the above formula [I-8] is the following:

[Chemical Formula 302]

Also, in the present aspect (J), another particularly preferred aspect is as follows.

It is the case where the compound represented by the above formula [I-8] is the following:

[Chemical Formula 303]

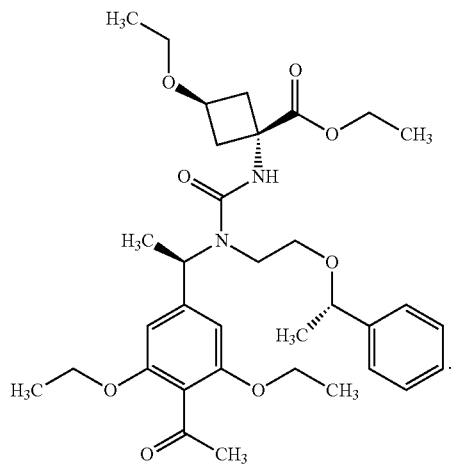

Also, in the present aspect (J), another particularly preferred aspect is as follows.

It is the case where the compound represented by the above formula [I-8] is the following:

[Chemical Formula 304]

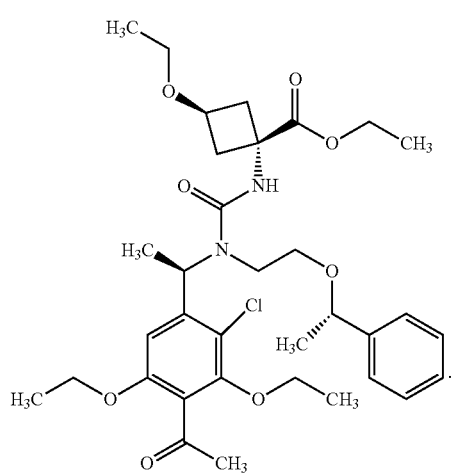

Also, in the present aspect (J), another particularly preferred aspect is as follows.

It is the case where the compound represented by the above formula [I-8] is the following:

[Chemical Formula 305]

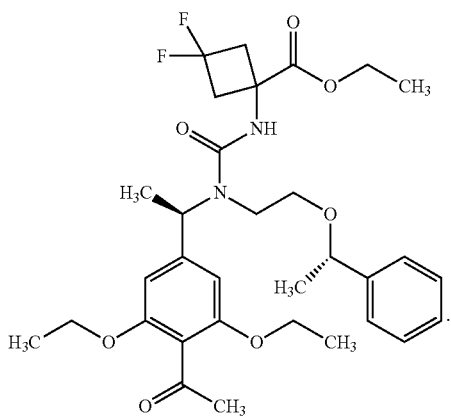

Also, in the present aspect (J), another particularly preferred aspect is as follows.

It is the case where the compound represented by the above formula [I-8] is the following:

[Chemical Formula 306]

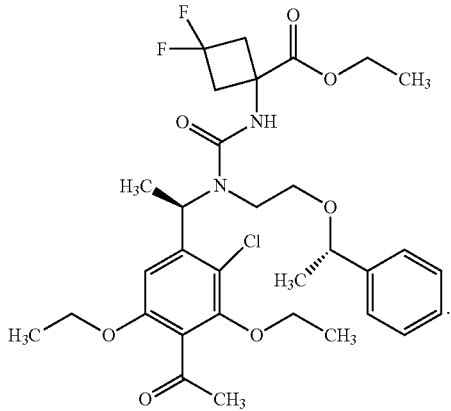

Also, in the present aspect (J), another particularly preferred aspect is as follows.

It is the case where the compound represented by the above formula [I-8] is the following:

[Chemical Formula 307]

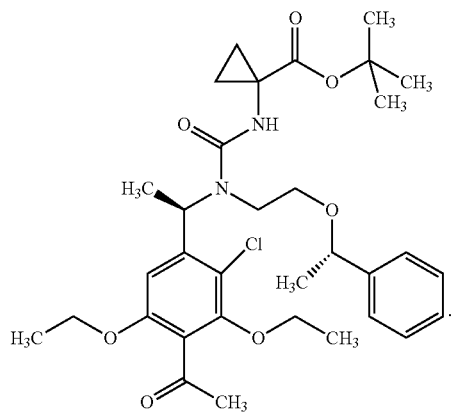

Also, in the present aspect (J), another particularly preferred aspect is as follows.

It is the case where the compound represented by the above formula [I-8] is the following:

[Chemical Formula 308]

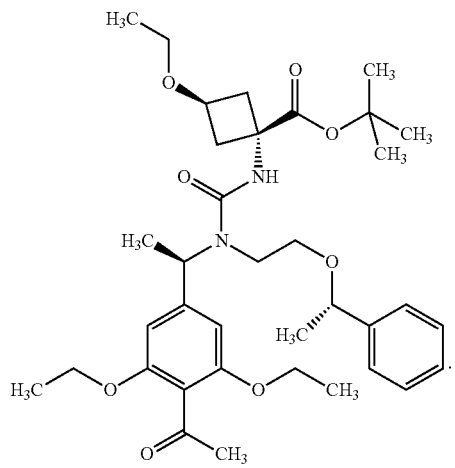

Also, in the present aspect (J), another particularly preferred aspect is as follows.

It is the case where the compound represented by the above formula [I-8] is the following:

[Chemical Formula 309]

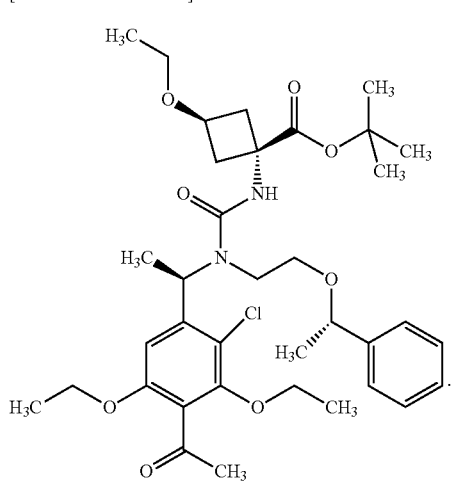

Also, in the present aspect (J), another particularly preferred aspect is as follows.

It is the case where the compound represented by the above formula [I-8] is the following:

[Chemical Formula 310]

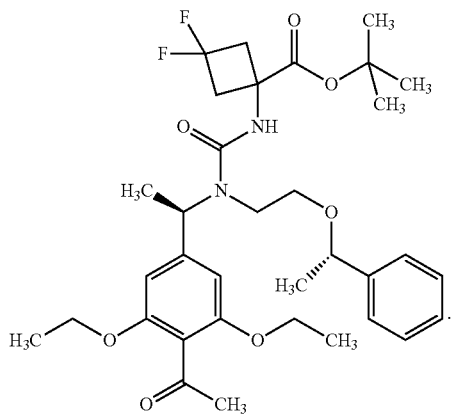

Also, in the present aspect (J), another particularly preferred aspect is as follows.

It is the case where the compound represented by the above formula [I-8] is the following:

[Chemical Formula 311]

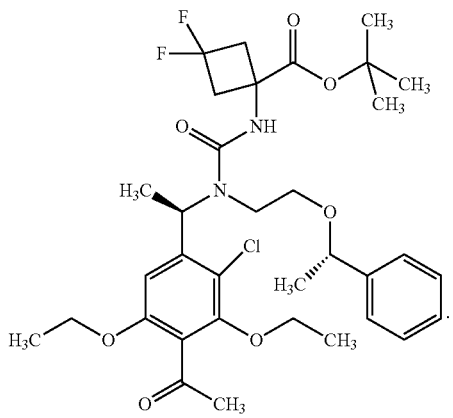

The compound of the present invention is a compound having a urea structure as its basic skeleton, and may be a pharmaceutically acceptable salt thereof, or a hydrate thereof.

Examples of the pharmaceutically acceptable salt include, for example, acid addition salts including mineral acid salts such as hydrochloride, hydrobromide, hydriodide, phosphate, sulfate, and nitrate, sulfonates such as methanesulfonate, ethanesulfonate, benzenesulfonate, p-toluenesulfonate, and trifluoromethanesulfonate, and organic acid salts such as oxalate, tartarate, citrate, maleate, succinate, acetate, trifluoroacetate, benzoate, mandelate, ascorbate, lactate, gluconate, and malate, amino acid salts such as glycine salt, lysine salt, arginine salt, ornithine salt, glutamate, and aspartate, inorganic salts such as lithium salt, sodium salt, potassium salt, calcium salt, and magnesium salt, and salts with organic bases such as ammonium salt, triethylamine salt, diisopropylamine salt, cyclohexylamine salt, and N-methyl-D-glucamine salt. Note that the salt includes a hydrated salt.

The compound of the present invention may have an asymmetric center, in which case a variety of optical isomers are present. Thus, the compound of the present invention can be present as a separate optically active form of (R) or(S), or as a racemate or (RS) mixture. In addition, in the case of a compound having two or more asymmetric centers, there are also diastereomers due to each optical isomerism. The compound of the present invention also encompasses a mixture containing all of these forms in an arbitrary proportion. For example, diastereomers can be separated by methods well known to those skilled in the art, such as fractional crystallization method, and optically active forms can be obtained by organic chemical methods well known for this purpose. Also, geometric isomers such as cis form and trans form may be present in the compound of the present invention. Furthermore, the compound of the present invention is tautomeric, and a variety of tautomers are present. The compound of the present invention encompasses these isomers and a mixture containing these isomers in an arbitrary proportion.

Furthermore, when the compound of the present invention or a salt thereof forms a hydrate or solvate, they are also encompassed within the scope of the present invention.

As mentioned above, the LPA1 receptor, the LPA3 receptor, and the like have a wide variety of functions in the living body.

Examples of the disease caused by LPA receptors include, for example, diseases associated with fibrosis (idiopathic pulmonary fibrosis, systemic scleroderma, chronic kidney disease, chronic hepatitis, chronic rejection after organ transplantation, and the like), inflammatory diseases (rheumatoid arthritis, osteoarthritis of the knee, and the like), circulatory system diseases (atherosclerosis, and the like), cancer-related diseases (prostate cancer, breast cancer, ovarian cancer, and the like), urological diseases (prostatic hyperplasia, overactive bladder, and the like), and neurological diseases (neuropathic pain, diabetic neuropathy, and the like).

Agents that inhibit the physiological activity of LPA receptors, in particular, antagonists against the EDG family such as the LPA1 receptor and the LPA3 receptor, are thought to be useful as drugs for preventing or treating diseases associated with organ fibrosis such as idiopathic pulmonary fibrosis, systemic scleroderma, chronic kidney disease, and chronic hepatitis, circulatory system diseases such as atherosclerosis, proliferative diseases including various cancers, urological diseases such as prostatic hyperplasia, and central or peripheral neurological diseases.

Note that evaluation of the compound of the present invention for its LPA receptor-antagonizing action can be carried out according to publicly known methods, such as the methods described in Test Examples herein, which will be mentioned later.

With respect to the medicament according to the present invention, a compound that antagonizes the LPA1 receptor contained therein, which is the compound of the present invention, or a pharmaceutically acceptable salt thereof, or a hydrate thereof, may be administered alone or together with a pharmacologically or pharmaceutically acceptable additive agent.

As the additive agent, a commonly used excipient or diluent can be used, as well as a generally used binder, disintegrant, lubricant, coating agent, sugar coating agent, pH adjuster, solubilizing agent, or aqueous or non-aqueous solvent, if necessary. Specific examples thereof may include water, lactose, dextrose, fructose, sucrose, sorbitol, mannitol, polyethylene glycol, propylene glycol, starch, corn starch, gum, gelatin, alginate, calcium silicate, calcium phosphate, cellulose, water syrup, methylcellulose, polyvinylpyrrolidone, alkyl parahydroxybenzoate, talc, stearic acid, magnesium stearate, agar, pectin, gum arabic, glycerin, sesame oil, olive oil, soybean oil, cocoa butter, ethylene glycol, low viscosity hydroxypropyl cellulose (HPC-L), microcrystalline cellulose, carboxymethyl cellulose (CMC), sodium carboxymethyl cellulose (CMC-Na), and other commonly used materials.

The medicament according to the present invention may be in any form of solid composition, liquid composition, and other compositions, and the optimal form is selected depending on the need.

The medicament according to the present invention can be prepared into a tablet, a pill, a capsule, a granule, a powder, a pulvis, a liquid, an emulsion, a suspension, an injection, or the like by adding the above-mentioned additive agent to the compound of the present invention and using commonly used formulation technologies.

Also, the medicament according to the present invention can be formulated by forming a clathrate compound with the compound of the present invention and α-, β-, or γ-cyclodextrin, methylated cyclodextrin, or the like.

With respect to compounds that can be used in combination with the compound of the present invention, the medicament according to the present invention can be made into a single formulation (combined drug) or into two or more formulations (concomitant drugs) obtained by separate formulation.

When these compounds are separately formulated into two or more formulations, the individual formulations can be administered simultaneously or after a certain time interval. In this case, any of them can be administered first. The two or more formulations may also be administered independently at different times in a day. In addition, the two or more formulations can also be administered by different routes.

When these compounds are separately formulated into two formulations, they may be administered simultaneously or with a very short interval, and it is preferable to state that they are to be used in combination, for example, in the package inserts, sales brochures, and other documents of commercially available medicaments.

It is also preferable that these active ingredients should be separately formulated into the form of a kit consisting of two formulations.

When the compound of the present invention is used as an LPA1 receptor antagonist or the like, the compound of the present invention may be administered orally as it is. Alternatively, the compound of the present invention may be administered orally as an agent containing it as an active ingredient.

When the compound of the present invention is used as a drug for preventing or treating systemic scleroderma or the like, the compound of the present invention may be administered orally as it is. Alternatively, the compound of the present invention may be administered orally as an agent containing it as an active ingredient.

The dosage of the compound of the present invention varies depending on the target of administration, route of administration, target disease, symptoms, and the like, but for example, when administered orally to an adult patient, the single dose is normally 0.1 mg to 1000 mg, preferably 1 mg to 200 mg. It is desirable to administer this dose once to three times a day, or once every two to three days.

Hereinafter, methods for producing compounds [I] according to the present invention will be described in detail, but the production method is not particularly limited to those exemplified.

Note that, in the production of compounds [I] of the present invention, the order of the respective steps in each production method can be rearranged as appropriate.

In addition, the solvents used in the reactions are not particularly limited to those described below, as long as they do not interfere with each reaction.

Also, in each production method below, the raw material compound may be used as a salt. In addition, the desired compound may be produced as a salt.

Here, examples of the salt that can be used include, for example, the "pharmaceutically acceptable salt" mentioned above.

Note that compound [Ia] according to the present invention can be produced by the method for producing compound [I] or a method equivalent thereto.

Compound [I] of the present invention can be produced by methods known per se, for example, production methods 1 to 6 shown below, or methods equivalent thereto.

Specifically, among compounds [I] of the present invention, the method for producing a compound wherein X is carboxy or $C_{1-4}$ alkoxycarbonyl is shown in production method 1, and the methods for producing its production intermediates are shown in production methods 2 to 8.

In addition, the methods for producing a compound wherein X is tetrazolyl, a compound wherein X is a group represented by formula [II-1] below (hereinafter, this may also be referred to as compound [II-1]), a compound wherein X is carbamoyl, a compound wherein X is a group represented by formula [II-2], [II-3], or [II-4] below (hereinafter, they may also be referred to as compound [II-2], compound [II-3], and compound [II-4], respectively), and a compound wherein X is a group represented by formula [II-5] below (hereinafter, this may also be referred to as compound [II-5]) are shown in production method 9.

[Chemical Formula 312]

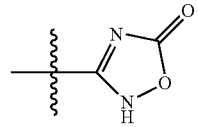

[II-1]

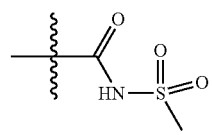

[II-2]

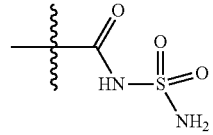

[II-3]

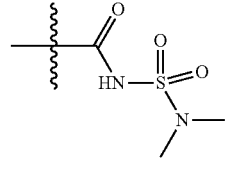

[II-4]

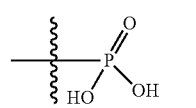

[II-5]

Here, in the present general production methods, a "reductive amination reaction" means, for example, a reaction in which an amine compound is produced by forming the corresponding imine compound from an aldehyde compound or ketone compound and an amine compound in the presence or absence of an acid such as formic acid or acetic acid in an inert solvent or under solvent-free condition at ice-cooled temperature to reflux temperature and then allowing a reducing agent to act on it, such as sodium triacetoxyborohydride, sodium cyanoborohydride, sodium borohydride, 2-picoline borane, or an iridium catalyst including chloro(pentamethylcyclopentadienyl) (8-quinolinolate) iridium (III) (described in, for example, Advanced Synthesis and Catalysis, vol. 360, p. 322, 2018).

Also, in the present general production methods, a "condensation reaction" means, for example, a reaction in which an amide compound is produced by allowing a carboxylic acid compound and an amine compound to react with each other using a condensing agent in the presence or absence of a base and an additive agent in an inert solvent at room temperature to reflux temperature.

Examples of the condensing agent used in the "condensation reaction" include, for example, O-(7-azabenzotriazol-1-yl)-N,N,N',N'-tetramethyluronium hexafluorophosphate (HATU), O-benzotriazol-1-yl-N,N,N',N'-tetramethyluronium hexafluorophosphate (HBTU), 1-(3-dimethylaminopropyl)-3-ethylcarbodiimide hydrochloride (EDC), 1,1'-carbonyldiimidazole (CDI), (1H-benzotriazol-1-yloxy)(tripyrrolidin-1-yl)phosphonium hexafluorophosphate (PyBOP), propylphosphonic anhydride (T3P), and 4-(4,6-dimethoxy-1,3,5-triazin-2-yl)-4-methylmorpholinium chloride (DMT-MM).

Examples of the additive agent used in the "condensation reaction" include, for example, N-hydroxybenzotriazole monohydrate (HOBt) and N-hydroxysuccinimide.

Examples of the base used in the "condensation reaction" include tertiary aliphatic amines such as N,N-diisopropylethylamine and triethylamine, and pyridine.

Furthermore, in the present general production methods, a "hydrolysis reaction" means, for example, a reaction in which a carboxylic acid compound and an alcohol compound are produced from an ester compound using a base such as lithium hydroxide, sodium hydroxide, or potassium hydroxide in an inert solvent at ice-cooled temperature to reflux temperature.

Among compounds [I] of the present invention, compound [1-d] wherein X is carboxy and $R^1$ is a hydrogen atom and compound [1-f] wherein $R^1$ is methyl can be produced by, for example, production method 1 below or a method equivalent thereto.

Production Method 1:

Scheme 1 (Method for producing compounds [1-d] and [1-f] from compound [1-a]):

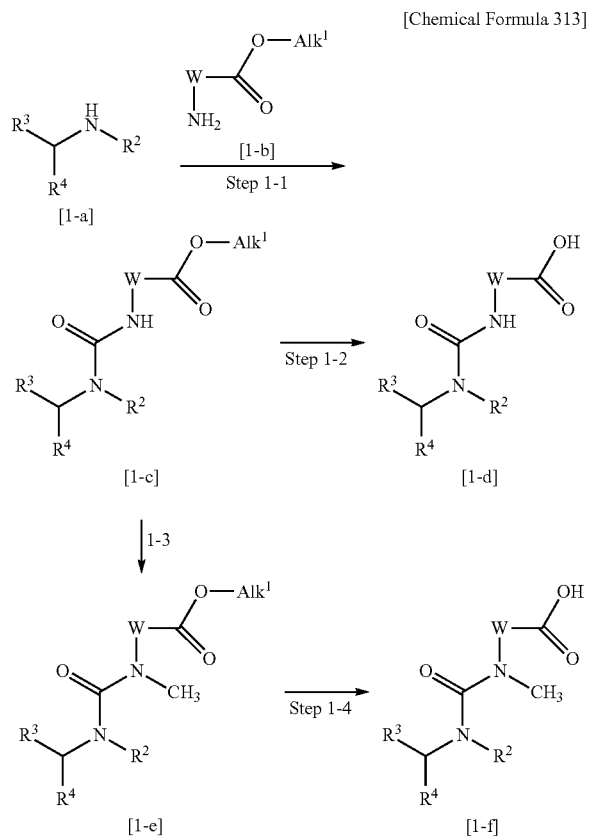

[Chemical Formula 313]

[In the scheme,
$R^2$, $R^3$, $R^4$, and W are as defined above, and
$Alk^1$ represents $C_{1-4}$ alkyl.]

Step 1-1:

Method for producing compound [1-c]: Compound [1-a] is used as the starting substance, and by allowing it to react with compound [1-b] in the presence of a base such as triethylamine, pyridine, 4-dimethylaminopyridine, or N,N-diisopropylethylamine, and an agent that generates a urea derivative, such as 4-nitrophenyl chloroformate, CDI, or triphosgene in an inert solvent at ice-cooled temperature to reflux temperature, compound [1-c] can be produced.

Step 1-2:

Method for producing compound [1-d]: Compound [1-c] is used as the starting substance, and by carrying out a "hydrolysis reaction", compound [1-d] can be produced.

Step 1-3:

Method for producing compound [1-e]: Compound [1-c] is used as the starting substance, and by allowing it to react with a methylating agent such as methyl iodide in the presence of a base such as sodium hydride in an inert solvent at ice-cooled temperature to reflux temperature, compound [1-e] can be produced.

Step 1-4:

Method for producing compound [1-f]: Compound [1-e] is used as the starting substance, and by carrying out a "hydrolysis reaction" by the method described in the above-mentioned step 1-2 or a method equivalent thereto, compound [1-f] can be produced.

Compounds [1-d] and [1-f] thus obtained can be isolated and purified by publicly known separation and purification means such as concentration, concentration under reduced pressure, reprecipitation, solvent extraction, crystallization, and chromatography.

Note that, among compounds [I] of the present invention, a compound wherein X is $C_{1-4}$ alkoxycarbonyl can be produced as compound [1-c] or [1-e] by, for example, the present production method 1 or a method equivalent thereto.

Among the production intermediates for compound [I] of the present invention, compounds [1-a] and [1-b] shown in scheme 1 can be acquired by production according to methods known per se or by purchase of commercially available products.

Alternatively, compound [1-a] can also be produced by, for example, production method 2, which will be mentioned later, or a method equivalent thereto.

Similarly, compound [1-b] can also be produced by, for example, production method 8, which will be mentioned later, or a method equivalent thereto.

A production example for compound [1-a], which is a production intermediate for compound [I] of the present invention, is shown in scheme 2-1 of production method 2 below.

Production Method 2:
Scheme 2-1 (Method for producing compound [1-a] from compound [2-a]):

where
ring $B^1$, ring $B^2$, $R^{B11}$, $R^{B12}$, $R^{B21}$, and $R^{B22}$ are as defined above, and

[Chemical Formula 314]

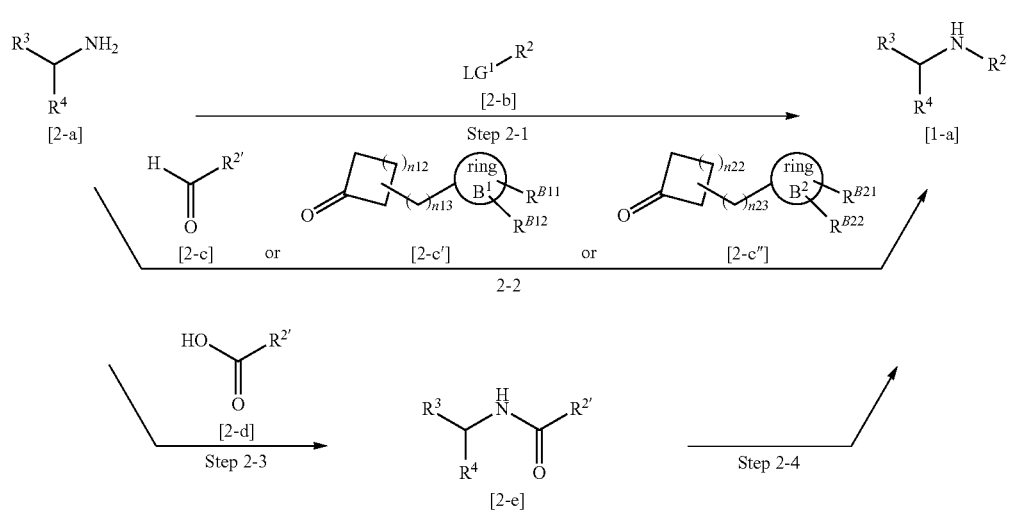

[In the scheme,
$R^2$, $R^3$, $R^4$, n12, n13, n22, n23, ring $B^1$, $R^{B11}$, $R^{B12}$, ring $B^2$, $R^{B21}$, and $R^{B22}$ are as defined above;
ring $B^1$ represents, as mentioned above, $C_{3-8}$ cycloalkyl, nitrogen atom-containing 4- to 8-membered saturated heterocyclyl, phenyl, or nitrogen atom-containing 5- to 6-membered heteroaryl,
ring $B^2$ also represents, as mentioned above, partially saturated 9- to 10-membered fused aryl or nitrogen atom-containing 9- to 10-membered fused heteroaryl, and
$LG^1$ represents a leaving group,
where
the "leaving group" represented by $LG^1$ represents, for example, a halogen atom such as a chlorine atom or a bromine atom; $C_{1-4}$ alkylsulfonyloxy such as methanesulfonyloxy; or arylsulfonyloxy such as p-toluenesulfonyloxy;
$R^{2'}$ represents $C_{5-9}$ alkyl, $C_{5-9}$ alkenyl, $C_{5-9}$ alkynyl, or a group represented by formula [IV-1'] or [IV-2']:

[Chemical Formula 315]

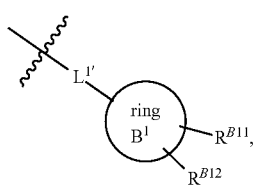

[IV-1']

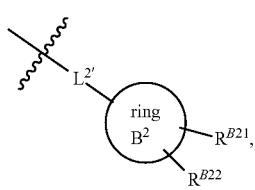

[IV-2']

$L^{1'}$ represents $C_{2-7}$ alkanediyl(the $C_{2-7}$ alkanediyl is optionally substituted with 1 to 5 fluorine atoms) or a structure represented by formula [V-1']:

[Chemical Formula 316]

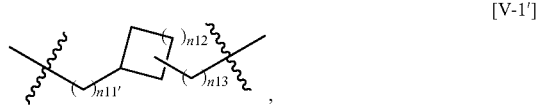

[V-1']

where
n12 and n13 are as defined above,
n11' represents an integer of 1 to 2, and
when $L^{1'}$ is $C_{2-7}$ alkanediyl(the $C_{2-7}$ alkanediyl is optionally substituted with 1 to 5 fluorine atoms), one carbon atom in the $C_{2-7}$ alkanediyl, that is one or more atoms away from the carboxy or formyl to which $R^{2'}$ is bonded, is optionally replaced with formula —O—, formula —S—, or formula —N($R^{L11}$)—,
where
$R^{L11}$ is as defined above, and
when $L^{1'}$ is $C_{2-7}$ alkanediyl(the $C_{2-7}$ alkanediyl is optionally substituted with 1 to 5 fluorine atoms), two consecutive carbon atoms in the $C_{2-7}$ alkanediyl are optionally replaced with formula —C(=O)N($R^{L12}$)—, where $R^{L12}$ is as defined above, and
$L^{2'}$ represents $C_{2-7}$ alkanediyl(the $C_{2-7}$ alkanediyl is optionally substituted with 1 to 5 fluorine atoms) or a structure represented by formula [V-2']:

[Chemical Formula 317]

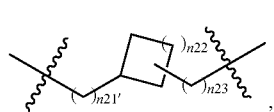

[V-2']

where n22 and n23 are as defined above, n21' represents an integer of 1 to 2, and when $L^{2'}$ is $C_{2-7}$ alkanediyl(the $C_{2-7}$ alkanediyl is optionally substituted with 1 to 5 fluorine atoms), one carbon atom in the $C_{2-7}$ alkanediyl, that is one or more atoms away from the carboxy or formyl to which $R^{2'}$ is bonded, is optionally replaced with formula —O—, formula —S—, or formula —N($R^{L21}$)—, where $R^{L21}$ represents, as mentioned above, a hydrogen atom or $C_{1-3}$ alkyl, and two consecutive carbon atoms in the $C_{2-7}$ alkanediyl are optionally replaced with formula —C(=O)N($R^{L22}$)—, where $R^{L22}$ represents, as mentioned above, a hydrogen atom or a $C_{1-3}$ alkyl group.]

Step 2-1:

Method for producing compound [1-a]: Compound [2-a] is used as the starting substance, and by allowing it to react with compound [2-b] in the presence of a base in an inert solvent at room temperature to reflux temperature, compound [1-a] can be produced.

Examples of the base used in the present reaction include, for example, amine compounds such as triethylamine, N,N-diisopropylethylamine, and 1,8-diazabicyclo[4,3,0] undec-7-ene, alkali metal hydrides such as sodium hydride, alkali metal hydroxides such as potassium hydroxide, alkali metal carbonates such as cesium carbonate, potassium carbonate, and sodium carbonate, and alkoxyalkali metals such as potassium tert-butoxide.

Step 2-2:

Another method for producing compound [1-a]: By carrying out a "reductive amination reaction" between compound [2-a] and compound [2-c], [2-c'], or [2-c''], compound [1-a] can also be produced.

Step 2-3:

Method for producing compound [2-e]: By carrying out a "condensation reaction" between compound [2-a] and compound [2-d], compound [2-e] can also be produced.

Step 2-4:

Another method for producing compound [1-a]: Compound [2-e] is used as the starting substance, and by allowing a reducing agent such as borane-tetrahydrofuran complex or borane-dimethyl sulfide complex to act on it in an inert solvent at ice-cooled temperature to reflux temperature, compound [1-a] can be produced.

Alternatively, compound [1-a] can also be produced by, for example, the production method shown in scheme 2-2 below or a method equivalent thereto.

Scheme 2-2 (Method for producing compound [1-a] from compound [2-f]):

[Chemical Formula 318]

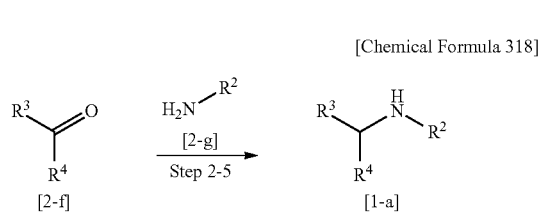

[In the scheme, $R^2$, $R^3$, and $R^4$ are as defined above.]

Step 2-5:

Another method for producing compound [1-a]: By carrying out a "reductive amination reaction" between compound [2-f] and compound [2-g], compound [1-a] can be produced.

Furthermore, compound [1-a'], which is compound [1-a] wherein $R^3$ is $C_{1-3}$ alkyl, can also be produced by, for example, the production method shown in scheme 2-3 below or a method equivalent thereto.

Scheme 2-3 (Method for producing compound [1-a'] from compound [2-h]):

[Chemical Formula 319]

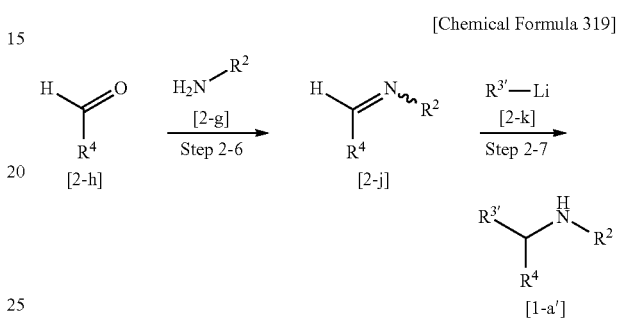

[In the scheme, $R^2$ and $R^4$ are as defined above, and $R^{31}$ represents $C_{1-3}$ alkyl.]

Step 2-6:

Method for producing compound [2-j]: Compound [2-h] is used as the starting substance, and by allowing it to react with compound [2-g] in the presence or absence of an acid such as formic acid or acetic acid in an inert solvent or under solvent-free condition at ice-cooled temperature to reflux temperature, compound [2-j] can be produced.

Step 2-7:

Method for producing compound [1-a']: Compound [2-j] is used as the starting substance, and by allowing compound [2-k] to act on it in an inert solvent at ice-cooled temperature to room temperature, compound [1-a'] can be produced.

In addition, step 2-6 and step 2-7 can also be performed consecutively without taking out compound [2-j], which is the imine produced in step 2-6 (without post treatment for the reaction of step 2-6).

Compounds [1-a] and [1-a'] thus obtained can be isolated and purified by publicly known separation and purification means such as concentration, concentration under reduced pressure, reprecipitation, solvent extraction, crystallization, and chromatography.

Note that, by allowing a reducing agent used in the "reductive amination reaction" to act on compound [2-j] obtained in step 2-6, it is also possible to produce compound [1-a] wherein $R^3$ is a hydrogen atom.

Among the production intermediates for compound [I] of the present invention, compounds [2-a], [2-b], [2-c], [2-c'], [2-c''], and [2-d] shown in scheme 2-1, compounds [2-f] and [2-g] shown in scheme 2-2, and compounds [2-g], [2-h], and [2-k] shown in scheme 2-3 can be acquired by production according to methods known per se or by purchase of commercially available products.

Also, among these compounds, a compound [2-a] whose structure is represented by [2-a'], which will be mentioned later (hereinafter, this may also be referred to as compound [2-a']) can also be produced by, for example, production method 3, which will be mentioned later, or a method equivalent thereto. A compound [2-f] whose structure is represented by [2-f], which will be mentioned later (hereinafter, this may also be referred to as compound [2-f]) and compound [2-h] can also be produced by, for example, production method 6, which will be mentioned later, or a method equivalent thereto.

[Chemical Formula 320]

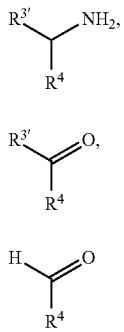

Similarly, compounds [2-b] and [2-c], a compound [2-d] whose structure is represented by [5-e], which will be mentioned later (hereinafter, this may also be referred to as compound [5-e]), compound [2-d] whose structure is represented by [5-e'], which will be mentioned later (hereinafter, this may also be referred to as compound [5-e']), and compound [2-g] can also be produced by, for example, production method 4, 5, or 7, which will be mentioned later, or a method equivalent thereto.

[Chemical Formula 321]

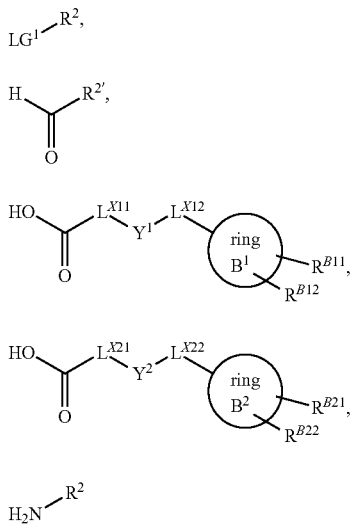

A production example for compound [2-a'], which is a production intermediate for compound [I] of the present invention, is shown in scheme 3-1 of production method 3 below.

Production Method 3:

Scheme 3-1 (Method for producing compound [2-a'] from compound [2-h]):

[Chemical Formula 322]

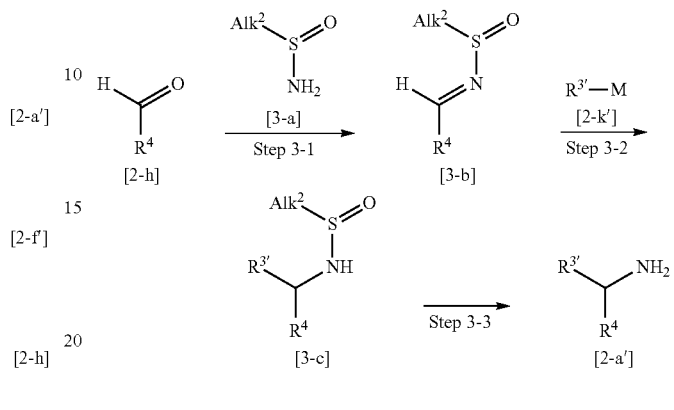

[In the scheme, $R^{31}$ and $R^4$ are as defined above,

M represents a lithium atom or formula $-MgX^M$, $X^M$ represents a chlorine atom, a bromine atom, or an iodine atom, compound [2-k'] ($R^{3'}$-M) represents an alkyl metal reagent, and $Alk^2$ represents tert-butyl or the like.]

Step 3-1:

Method for producing compound [3-b]: Compound [2-h] is used as the starting substance, and by allowing it to react with compound [3-a] in the presence of a Lewis acid such as tetraethyl orthotitanate in an inert solvent from room temperature to 160° C., compound [3-b] can be produced.

Step 3-2:

Method for producing compound [3-c]: Compound [3-b] is used as the starting substance, and by allowing it to react with compound [2-k'] in an inert solvent from −20° C. to room temperature, compound [3-c] can be produced.

Step 3-3:

Method for producing compound [2-a']: Compound [3-c] is used as the starting substance, and by allowing an acid such as hydrochloric acid to act on it in an inert solvent at ice-cooled temperature to room temperature, compound [2-a'] can be produced.

Also, steps 3-1, 3-2, and 3-3 can be performed with reference to the methods described in, for example, Journal of Combinatorial Chemistry, vol. 5, p. 590, 2003; and Organic Letters, vol. 3, p. 3707, 2001.

In addition, in the present scheme 3-1, by allowing optically active compound [3-a] to react in step 3-1, compound [2-a'] can be produced in a stereoselective manner.

Compound [3-e] which is compound [2-a] in which $R^4$ is substituted phenyl and the para position of the phenyl is substituted with $C_{1-6}$ alkylcarbonyl, and compound [3-f] which is compound [2-a] in which $R^4$ is substituted phenyl and the para position of the phenyl is substituted with $C_{1-6}$ alkyl substituted with hydroxy, can each also be produced by, for example, the method shown in scheme 3-2 below or a method equivalent thereto.

Scheme 3-2 (Method for producing compounds [3-e] and [3-f] from compound [3-c']):

[Chemical Formula 323]

[3-c']

[3-d]

[3-e]

[3-f]

[In the scheme,
R³ and Alk² are as defined above,
Alk³ and Alk⁴ each independently represent $C_{1-6}$ alkyl, halo-$C_{1-6}$ alkyl, or $C_{3-8}$ cycloalkyl,
$R^{α1}$ represents $C_{1-6}$ alkyl(the $C_{1-6}$ alkyl is optionally substituted with one hydroxy), halo-$C_{1-6}$ alkyl, $C_{3-8}$ cycloalkyl, $C_{1-6}$ alkylcarbonyl, or halo-$C_{1-6}$ alkylcarbonyl,
Alk⁵ represents $C_{1-6}$ alkyl or $C_{1-6}$ alkyl substituted with hydroxy, and
LG² represents a leaving group.
Here, the "leaving group" represented by LG² represents, for example, a halogen atom such as a chlorine atom, a bromine atom, or an iodine atom.]

Step 3-4:

Method for producing compound [3-d]: Compound [3-c'] is used as the starting substance, and by allowing it to react with vinyl ether such as ethylene glycol monovinyl ether or butyl vinyl ether in the presence of a palladium catalyst such as palladium (II) acetate, a phosphine ligand such as 1,3-bis(diphenylphosphino) propane or 2,2'-bis(diphenylphosphino)-1,1'-binaphthyl, and a base such as potassium carbonate or triethylamine in an inert solvent at ice-cooled temperature to reflux temperature, compound [3-d] can be produced.

The present step can be performed with reference to the methods described in, for example, The Journal of Organic Chemistry, vol. 66, p. 4340, 2001; and The Journal of Organic Chemistry, vol. 72, p. 6390, 2007.

Step 3-5:

Method for producing compound [3-e]: Compound [3-d] is used as the starting substance, and by allowing an acid such as hydrochloric acid to act on it in an inert solvent at ice-cooled temperature to room temperature, compound [3-e] can be produced.

Note that step 3-4 and step 3-5 can also be performed consecutively as a one pot reaction. Also, the present step may be performed in a later step.

Step 3-6:

Method for producing compound [3-f]: Compound [3-e] is used as the starting substance, and by allowing a reducing agent such as lithium aluminum hydride ($LiAlH_4$) or lithium borohydride ($LiBH_4$) to act on it in an inert solvent from −78° C. to room temperature, compound [3-f] can be produced.

Compounds [2-a'], [3-e], and [3-f] thus obtained can be isolated and purified by publicly known separation and purification means such as concentration, concentration under reduced pressure, reprecipitation, solvent extraction, crystallization, and chromatography.

Among the production intermediates for compound [I] of the present invention, compounds [2-h] and [3-a] shown in scheme 3-1 and compound [3-c'] shown in scheme 3-2 can be acquired by production according to methods known per se or by purchase of commercially available products.

Alternatively, among these compounds, compound [3-c'] can also be produced by, for example, the method described in the above-mentioned step 3-2 or a method equivalent thereto.

Among the production intermediates for compound [I] of the present invention, compound [2-b] below described in production method 2 can also be produced by, for example, production method 4 below or a method equivalent thereto.

[Chemical Formula 324]

[2-b]

A production example for compound [2-b], which is a production intermediate for compound [I] of the present invention, is shown in the following scheme 4-1.

Production Method 4:

Scheme 4-1: Method for producing compound [2-b] from compound [4-a]

[Chemical Formula 325]

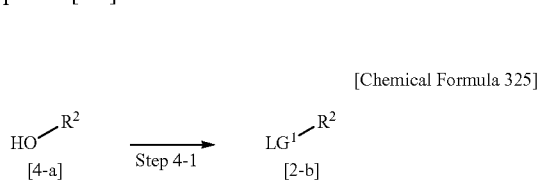

[In the scheme, $R^2$ and $LG^1$ are as defined above.]

Step 4-1:

Method for producing compound [2-b]: Compound [4-a] is used as the starting substance, and (i) by allowing it to react with arylsulfonyl chloride such as p-toluenesulfonyl chloride or $C_{1-4}$ alkylsulfonyl chloride such as methanesulfonyl chloride in the presence of a base such as triethylamine and in the presence or absence of an additive agent such as trimethylamine hydrochloride in an inert solvent at ice-cooled temperature to room temperature, or (ii) by allowing it to react with a brominating agent such as lithium bromide in an inert solvent at room temperature to reflux temperature, compound [2-b] can be produced.

The present step can be performed with reference to the method described in, for example, Tetrahedron, vol. 55, p. 2183, 1999.

Note that compound [4-a], which is used as the raw material compound in the above step 4-1, can be acquired by production according to methods known per se or by purchase of commercially available products.

Alternatively, among compounds [4-a], those whose structure is represented by formula [5-b] which will be mentioned later (hereinafter, this may also be referred to as compound [5-b]) can be produced by, for example, the method shown in scheme 5-1 of production method 5, which will be mentioned later, or a method equivalent thereto.

[Chemical Formula 326]

[5-b]

In addition, compound [4-m], which is compound [2-b] wherein $R^2$ is a group represented by the above formula [IV-1] and $L^1$ is $C_4$ alkanediyl substituted with one fluorine atom, and compound [4-h], which is compound [2-b] wherein $R^2$ is a group represented by the above formula [IV-1] and $L^1$ is $C_4$ alkanediyl substituted with two fluorine atoms, can also be produced by, for example, the production method shown in scheme 4-5 below or a method equivalent thereto.

[Chemical Formula 327]

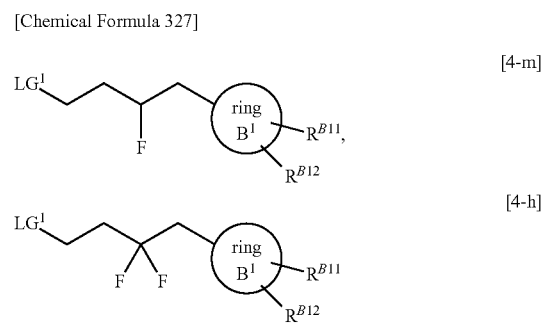

Production examples for the above-mentioned compounds [4-m] and [4-h] are shown in scheme 4-2.

Here, compound [4-m], which is substituted with one fluorine atom, can be produced by using compound [4-b] as the starting substance and fluorinating the corresponding hydroxy compound [4-d] leading to compound [4-j], while compound [4-h], which is substituted with two fluorine atoms, can be produced by fluorinating the corresponding ketone compound [4-e] leading to compound [4-f].

Note that, in the functional group conversion, protection and deprotection of hydroxy and the like can be carried out as appropriate.

Scheme 4-2 (Method for producing compound [4-h] or compound [4-m] from compound [4-b]):

[Chemical Formula 328]

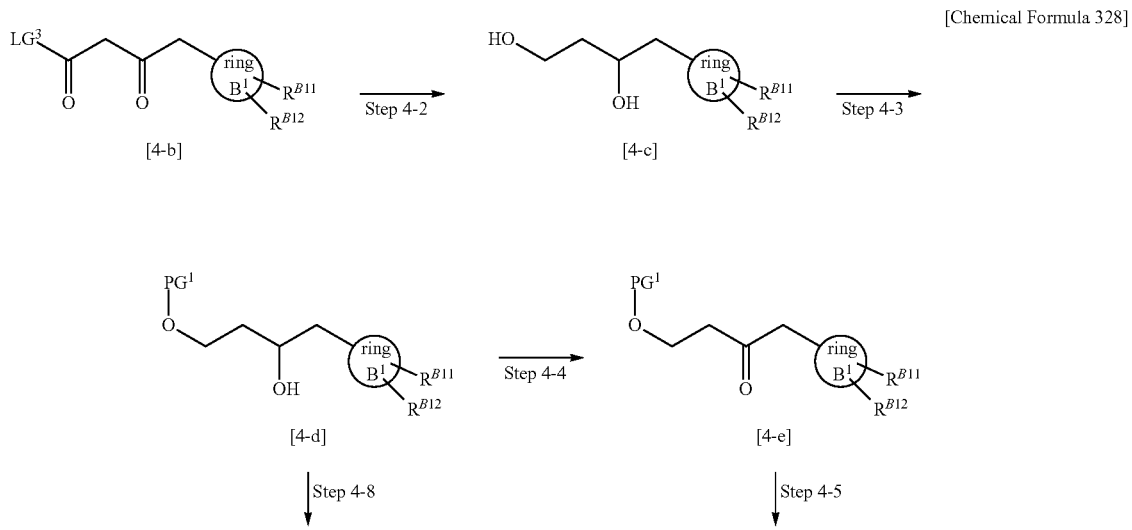

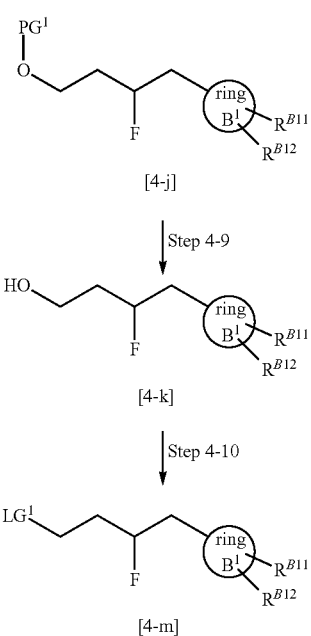

[4-j]

↓ Step 4-9

[4-k]

↓ Step 4-10

[4-m]

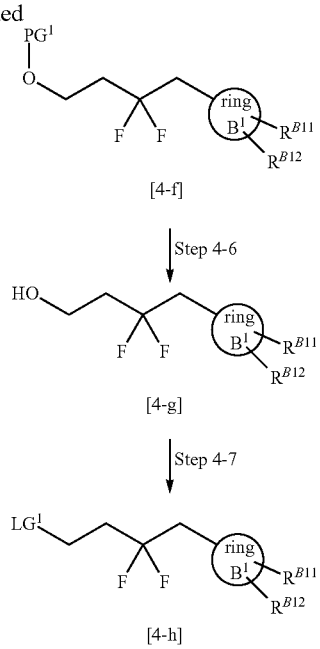

[4-f]

↓ Step 4-6

[4-g]

↓ Step 4-7

[4-h]

[In the scheme, ring $B^1$, $LG^1$, $R^{B11}$, and $R^{B12}$ are as defined above, $PG^1$ represents a protecting group for hydroxy such as acetyl, and $LG^3$ represents a leaving group.

Here, the "leaving group" represented by $LG^3$ represents, for example, $C_{1-6}$ alkoxy.]

Step 4-2:

Method for producing compound [4-c]: Compound [4-b] is used as the starting substance, and by allowing a reducing agent to act on it in an inert solvent at ice-cooled temperature to room temperature, compound [4-c] can be produced.

As the reducing agent, when $LG^3$ is $C_{1-6}$ alkoxy, lithium aluminum hydride or lithium borohydride can be used, for example.

Step 4-3:

Method for producing compound [4-d]: Compound [4-c] is used as the starting substance, and by allowing it to react with acetic anhydride or the like in the presence of a base such as N,N-diisopropylethylamine in an inert solvent at ice-cooled temperature to room temperature, thereby selectively protecting the primary hydroxy, compound [4-d] can be produced.

Step 4-4:

Method for producing compound [4-e]: Compound [4-d] is used as the starting substance, and by allowing an oxidizing agent such as manganese dioxide or Dess-Martin periodinane to act on it in an inert solvent at ice-cooled temperature to room temperature, compound [4-e] can be produced.

Step 4-5:

Method for producing compound [4-f]: Compound [4-e] is used as the starting substance, and by allowing a fluorinating agent such as bis(2-methoxyethyl)aminosulfur trifluoride or (diethylamino) sulfur trifluoride to act on it in an inert solvent or under solvent-free condition from ice-cooled temperature to 50° C., compound [4-f] can be produced.

Step 4-6:

Method for producing compound [4-g]: Compound [4-f] is used as the starting substance, and by allowing a basic aqueous solution such as aqueous sodium hydroxide solution to act on it in an inert solvent at ice-cooled temperature to room temperature, thereby deprotecting the protecting group for hydroxy, compound [4-g] can be produced.

Step 4-7:

Method for producing compound [4-h]: Compound [4-g] is used as the starting substance, and by the method described in the above-mentioned step 4-1 or a method equivalent thereto, compound [4-h] can be produced.

Step 4-8:

Method for producing compound [4-j]: Compound [4-d] is used as the starting substance, and by the method described in the above-mentioned step 4-5 or a method equivalent thereto, compound [4-j] can be produced.

Step 4-9:

Method for producing compound [4-k]: Compound [4-j] is used as the starting substance, and by the method described in the above-mentioned step 4-6 or a method equivalent thereto, compound [4-k] can be produced.

Step 4-10:

Method for producing compound [4-m]: Compound [4-k] is used as the starting substance, and by the method described in the above-mentioned step 4-7 or a method equivalent thereto, compound [4-m] can be produced.

In scheme 4-2, by using compound [4-b'] as the starting raw material instead of compound [4-b], compound [4-m'], wherein $R^2$ is a group represented by the above formula [IV-2] and $L^2$ is $C_4$ alkanediyl substituted with one fluorine atom, and compound [4-h'], wherein $L^2$ is $C_4$ alkanediyl substituted with two fluorine atoms, can be produced by methods that are similar to the above-mentioned production methods for compounds [4-m] and [4-h], respectively. Note that compound [4-b'] can be acquired by production according to methods known per se or by purchase of commercially available products.

[Chemical Formula 329]

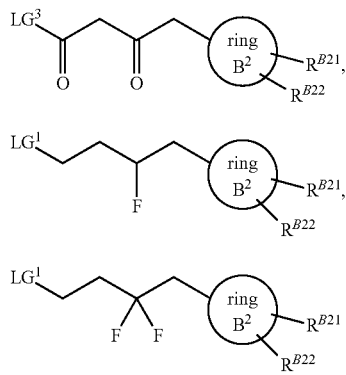

[In the formulas,
ring $B^2$, $R^{B21}$, $R^{B22}$, $LG^1$, and $LG^3$ are as defined above.]

In addition, compound [4-x], which is compound [2-b] wherein $R^2$ is a group represented by the above formula [IV-1] and $L^1$ is $C_4$ alkanediyl substituted with one fluorine atom, and compound [4-u], which is compound [2-b] wherein $R^2$ is a group represented by the above formula [IV-1] and $L^1$ is $C_4$ alkanediyl substituted with two fluorine atoms, can also be produced by, for example, the production method shown in scheme 4-3 below or a method equivalent thereto.

[Chemical Formula 330]

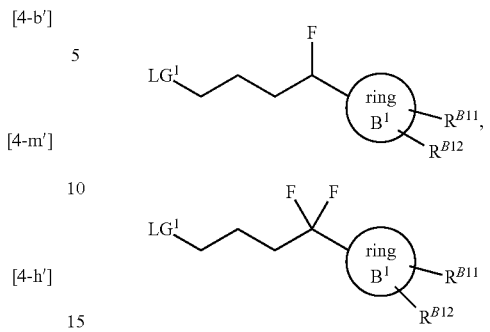

Production examples for the above-mentioned compounds [4-x] and [4-u] are shown in scheme 4-3.

Here, compound [4-x], which is substituted with one fluorine atom, can be produced by using compound [4-n] as the starting substance and fluorinating the corresponding hydroxy compound [4-q] leading to compound [4-v], while compound [4-u], which is substituted with two fluorine atoms, can be produced by fluorinating the corresponding ketone compound [4-r] leading to compound [4-s].

Note that, in the functional group conversion, protection and deprotection of hydroxy and the like can be carried out as appropriate.

Scheme 4-3 (Method for producing compound [4-u] or compound [4-x] from compound [4-n]):

[Chemical Formula 331]

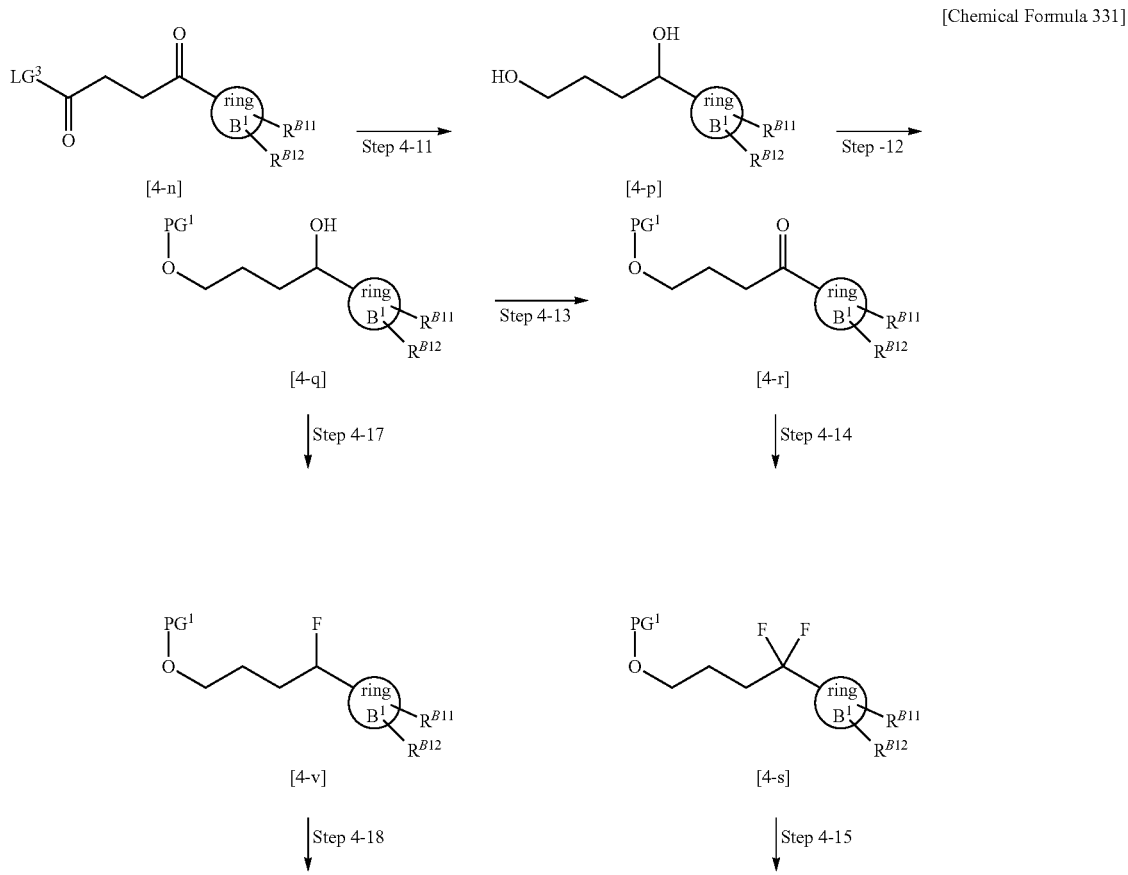

-continued

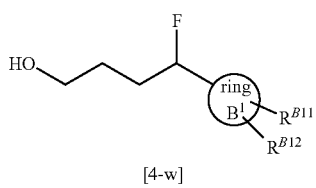

[4-w]

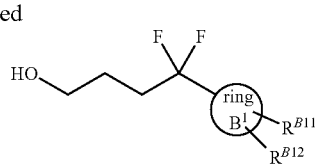

[4-t]

Step 4-19

Step 4-16

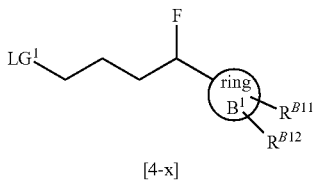

[4-x]

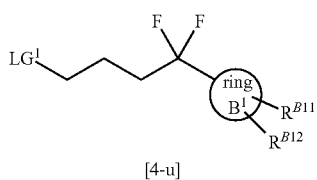

[4-u]

[In the scheme,
ring $B^1$, $R^{B11}$, $R^{B12}$, $PG^1$, $LG^1$, and $LG^3$ are as defined above.]

Step 4-11:
Method for producing compound [4-p]: Compound [4-n] is used as the starting substance, and by the method described in the above-mentioned step 4-2 or a method equivalent thereto, compound [4-p] can be produced.

Step 4-12:
Method for producing compound [4-q]: Compound [4-p] is used as the starting substance, and by the method described in the above-mentioned step 4-3 or a method equivalent thereto, compound [4-q] can be produced.

Step 4-13:
Method for producing compound [4-r]: Compound [4-q] is used as the starting substance, and by the method described in the above-mentioned step 4-4 or a method equivalent thereto, compound [4-r] can be produced.

Step 4-14:
Method for producing compound [4-s]: Compound [4-r] is used as the starting substance, and by the method described in the above-mentioned step 4-5 or a method equivalent thereto, compound [4-s] can be produced.

Step 4-15:
Method for producing compound [4-t]: Compound [4-s] is used as the starting substance, and by the method described in the above-mentioned step 4-6 or a method equivalent thereto, compound [4-t] can be produced.

Step 4-16:
Method for producing compound [4-u]: Compound [4-t] is used as the starting substance, and by the method described in the above-mentioned step 4-7 or a method equivalent thereto, compound [4-u] can be produced.

Step 4-17:
Method for producing compound [4-v]: Compound [4-q] is used as the starting substance, and by the method described in the above-mentioned step 4-8 or a method equivalent thereto, compound [4-v] can be produced.

Step 4-18:
Method for producing compound [4-w]: Compound [4-v] is used as the starting substance, and by the method described in the above-mentioned step 4-9 or a method equivalent thereto, compound [4-w] can be produced.

Step 4-19:
Method for producing compound [4-x]: Compound [4-w] is used as the starting substance, and by the method described in the above-mentioned step 4-10 or a method equivalent thereto, compound [4-x] can be produced.

In scheme 4-3, by using compound [4-n'] as the starting raw material instead of compound [4-n], compound [4-x'], wherein $R^2$ is a group represented by the above formula [IV-2] and $L^2$ is $C_4$ alkanediyl substituted with one fluorine atom, and compound [4-u'], wherein $L^2$ is $C_4$ alkanediyl substituted with two fluorine atoms, can be produced by methods that are similar to the above-mentioned production methods for compounds [4-x] and [4-u], respectively. Note that compound [4-n'] can be acquired by production according to methods known per se or by purchase of commercially available products.

[Chemical Formula 332]

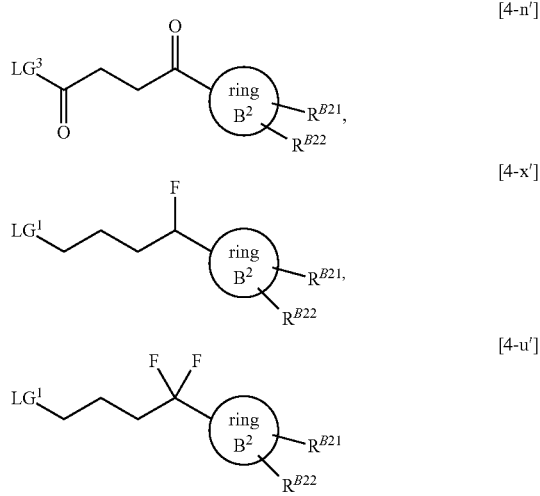

[In the formulas,
ring $B^2$, $R^{B21}$, $R^{B22}$, $LG^1$, and $LG^3$ are as defined above.]

Compounds [2-b], [4-h], [4-h'], [4-m], [4-m'], [4-u], [4-u'], [4-x], and [4-x'] thus obtained can be isolated and purified by publicly known separation and purification means such as concentration, concentration under reduced pressure, reprecipitation, solvent extraction, crystallization, and chromatography.

Among the production intermediates for compound [I] of the present invention, compound [4-a] shown in scheme 4-1, compound [4-b] shown in scheme 4-2, and compound [4-n] shown in scheme 4-3 can be acquired by production according to methods known per se or by purchase of commercially available products.

Among the production intermediates for compound [I] of the present invention, compounds [2-c] and [5-e] below described in production method 2 can also be produced by, for example, production method 5 below or a method equivalent thereto.

[Chemical Formula 333]

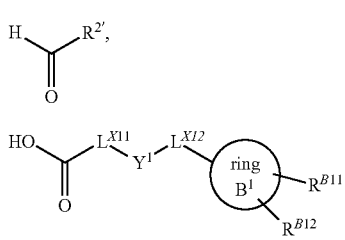

Production Method 5:

A production example for compound [2-c], which is a production intermediate for compound [I] of the present invention, is shown in the following scheme 5-1.

Scheme 5-1 (Method for producing compound [2-c] from compound [2-d]):

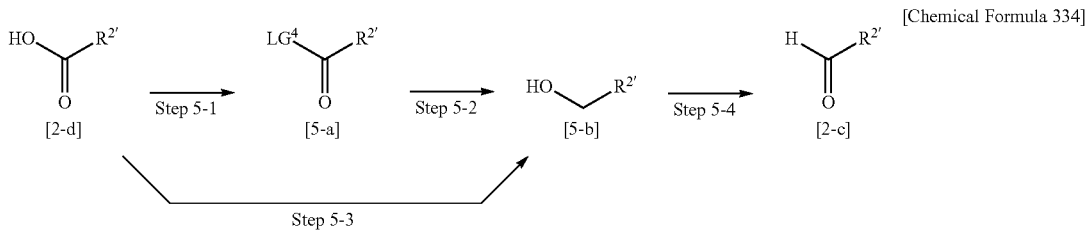

[Chemical Formula 334]

[In the scheme,
$R^{2'}$ is as defined above, and
$LG^4$ represents a leaving group.
Here, the "leaving group" represented by $LG^4$ represents, for example, $C_{1-6}$ alkoxy.]

Step 5-1:
Method for producing compound [5-a]: Compound [2-d] is used as the starting substance, and by allowing an acid such as sulfuric acid to act on it in an alcohol solvent such as methanol or ethanol at ice-cooled temperature to reflux temperature, compound [5-a] can be produced.

Step 5-2:
Method for producing compound [5-b]: Compound [5-a] is used as the starting substance, and by the method described in the above-mentioned step 4-2 or a method equivalent thereto, compound [5-b] can be produced.

Step 5-3:
Another method for producing compound [5-b]: Compound [2-d] is used as the starting substance, and by allowing a reducing agent such as borane-tetrahydrofuran complex to act on it in an inert solvent at ice-cooled temperature to room temperature, compound [5-b] can be produced.

Step 5-4:
Method for producing compound [2-c]: Compound [5-b] is used as the starting substance, and by the method described in the above-mentioned step 4-4 or a method equivalent thereto, compound [2-c] can be produced.

Note that compound [2-d], which is used as the raw material compound in the above steps 5-1 and 5-3, can be acquired by production according to methods known per se or by purchase of commercially available products.

A production example for compound [5-e] is shown in the following scheme 5-2.

Scheme 5-2 (Method for producing compound [5-e] from compound [5-c]):

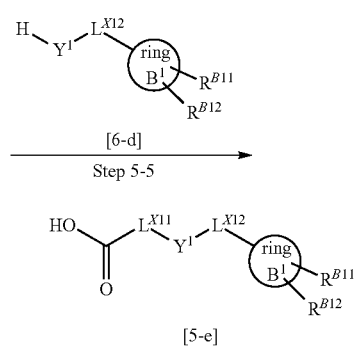

[Chemical Formula 335]

[In the scheme,
ring $B^1$, $R^{B11}$, and $R^{B12}$ are as defined above,
$LG^5$ represents a leaving group,
where the "leaving group" represented by $LG^5$ represents, for example, a halogen atom such as a chlorine atom or a bromine atom; $C_{1-4}$ alkylsulfonyloxy such as methanesulfonyloxy; or arylsulfonyloxy such as p-toluenesulfonyloxy,
$Y^1$ represents formula —O—, formula —S—, or formula —N($R^{L11}$)—,
where $R^{L11}$ is as defined above,
$L^{X11}$ represents $C_{1-5}$ alkanediyl, and
$L^{X12}$ represents a single bond or $C_{1-5}$ alkanediyl substituted with 1 to 5 fluorine atoms.]

Step 5-5:
Method for producing compound [5-e]: Compound [5-c] is used as the starting substance, and by allowing it to react with compound [5-d] in the presence of a base such as sodium hydride in an inert solvent such as tetrahydrofuran or N-methylpyrrolidone at ice-cooled temperature to reflux temperature, compound [5-e] can be produced.

In scheme 5-2, by using compound [5-c'] as the starting raw material instead of compound [5-c] and using compound [5-d'] instead of compound [5-d], compound [5-e'] can be produced by a method that is similar to the above-mentioned production method for compound [5-e]. Note that compounds [5-c'] and [5-d'] can be acquired by production according to methods known per se or by purchase of commercially available products.

[Chemical Formula 336]

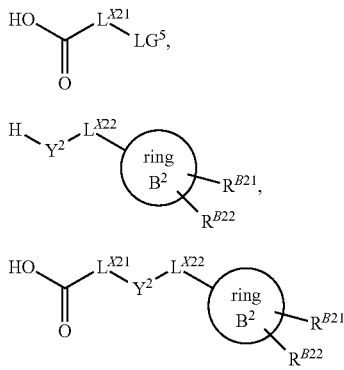

[In the formulas, ring $B^2$, $R^{B21}$, $R^{B22}$, and $LG^5$ are as defined above, $Y^2$ represents formula —O—, formula —S—, or formula —N($R^{L21}$)—, where $R^{121}$ is as defined above, $L^{X21}$ represents $C_{1-5}$ alkanediyl, and $L^{X22}$ represents a single bond or $C_{1-5}$ alkanediyl substituted with 1 to 5 fluorine atoms.]

Compounds [2-c], [5-e], and [5-e'] thus obtained can be isolated and purified by publicly known separation and purification means such as concentration, concentration under reduced pressure, reprecipitation, solvent extraction, crystallization, and chromatography.

Among the production intermediates for compound [I] of the present invention, compound [2-d] shown in scheme 5-1 and compounds [5-c] and [5-d] shown in scheme 5-2 can be acquired by production according to methods known per se or by purchase of commercially available products.

Among the production intermediates for compound [I] of the present invention, compound [2-f'] below described in production method 2 can also be produced by, for example, production method 6 below or a method equivalent thereto.

[Chemical Formula 337]

[2-f']

Production Method 6:

A production example for compound [2-f'], which is a production intermediate for compound [I] of the present invention, is shown in the following scheme 6-1.

Scheme 6-1 (Method for producing compound [2-f] from compound [6-a]):

[Chemical Formula 338]

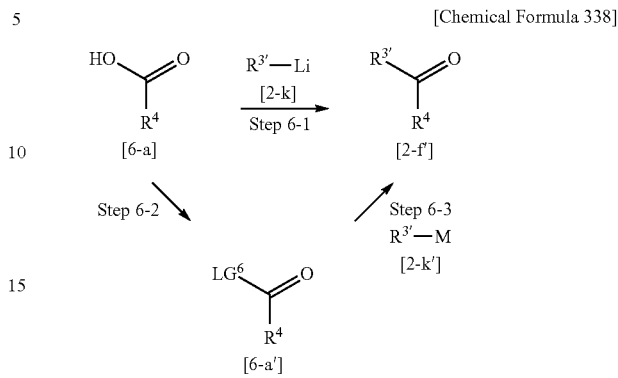

[In the scheme, $R^{3'}$, $R^4$, and M are as defined above, and $LG^6$ represents a leaving group.

Here, the "leaving group" represented by $LG^6$ represents, for example, a group represented by formula —N(CH$_3$)OCH$_3$.]

Step 6-1:

Method for producing compound [2-f]: Compound [6-a] is used as the starting substance, and by allowing it to react with alkyllithium [2-k] in an inert solvent from −78° C. to room temperature, compound [2-f'] can be produced.

The present step can be performed with reference to the method described in, for example, Synlett, vol. 26, p. 1395, 2015.

Step 6-2:

Method for producing compound [6-a']: By carrying out a "condensation reaction" between compound [6-a] and an amine compound such as N,O-dimethylhydroxylamine hydrochloride, compound [6-a'] can be produced.

Step 6-3:

Another method for producing compound [2-f]: Compound [6-a'] is used as the starting substance, and by allowing it to react with compound [2-k'] in an inert solvent at ice-cooled temperature to room temperature, compound [2-f] can be produced.

Scheme 6-2 (Method for producing compound [2-h] from compound [6-b]):

[Chemical Formula 339]

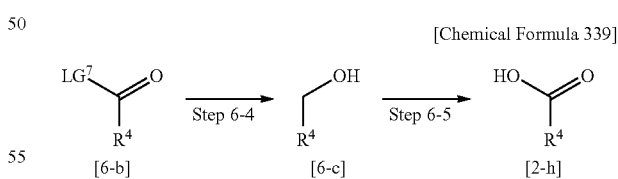

[In the scheme, $R^4$ is as defined above, and $LG^7$ represents a leaving group.

Here, the "leaving group" represented by $LG^7$ represents, for example, hydroxy or $C_{1-6}$ alkoxy.]

Step 6-4:

Method for producing compound [6-c]: Compound [6-b] is used as the starting substance, and by allowing a reducing agent to act on it in an inert solvent at ice-cooled temperature to room temperature, compound [6-c] can be produced.

As the reducing agent, (i) when LG⁷ is hydroxy, borane-tetrahydrofuran complex can be used in the same manner as in the above-mentioned step 5-3, for example, and (ii) when LG⁷ is $C_{1-6}$ alkoxy, lithium aluminum hydride or lithium borohydride can be used in the same manner as in the above-mentioned step 4-2, for example.

Step 6-5:

Method for producing compound [2-h]: Compound [6-c] is used as the starting substance, and by the method described in the above-mentioned step 4-4 or a method equivalent thereto, compound [2-h] can be produced.

Compound [6-g], which is compound [2-h] in which R⁴ is substituted phenyl and an ortho position of the phenyl is substituted with a chlorine atom, can also be produced by, for example, the method shown in scheme 6-3 below or a method equivalent thereto.

Scheme 6-3 (Method for producing compound [6-g] from compound [6-d]):

[Chemical Formula 340]

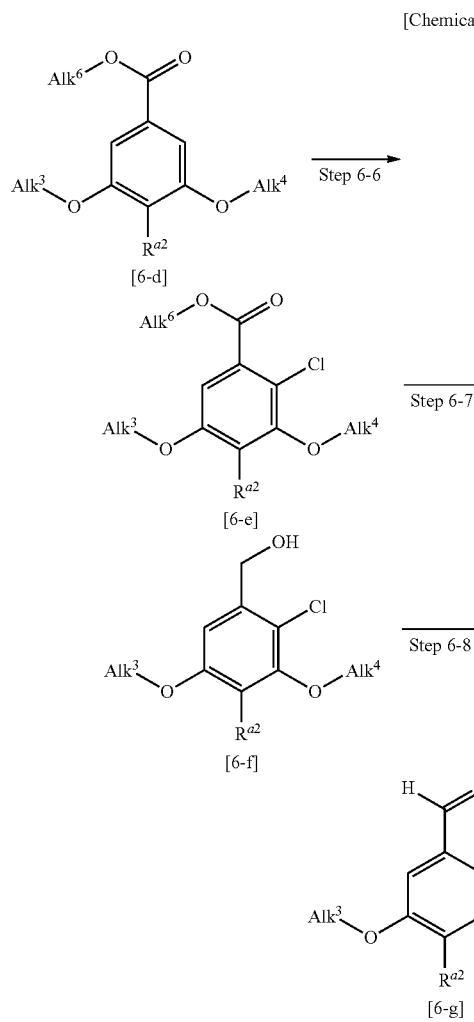

Step 6-6:

Method for producing compound [6-e]: Compound [6-d] is used as the starting substance, and by allowing a chlorinating agent such as sulfuryl chloride or N-chlorosuccinimide (NCS) to act on it in an inert solvent from −60° C. to 100° C., compound [6-e] can be produced.

Note that the present chlorination reaction can also be performed in another step.

Also, in the present step, by using 2 equivalents of the chlorinating agent with respect to compound [6-d], compound [6-e'] below, in which both ortho positions are substituted with chlorine atoms, can be produced.

[Chemical Formula 341]

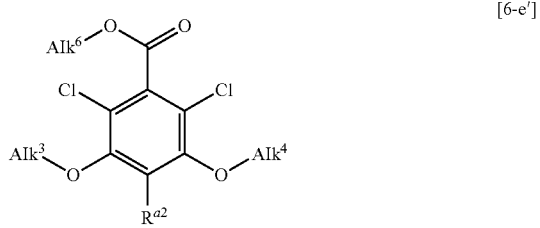

Step 6-7:

Method for producing compound [6-f]: Compound [6-e] is used as the starting substance, and by the method described in the above-mentioned step 4-2 or a method equivalent thereto, compound [6-f] can be produced.

Step 6-8:

Method for producing compound [6-g]: Compound [6-f] is used as the starting substance, and by the method described in the above-mentioned step 4-4 or a method equivalent thereto, compound [6-g] can be produced.

In addition, compound [6-m], which is compound [2-h] wherein R⁴ is substituted phenyl and an ortho position of the phenyl is substituted with methyl, can also be produced by, for example, the method shown in scheme 6-4 below or a method equivalent thereto.

Scheme 6-4 (Method for producing compound [6-m] from compound [6-d]):

[Chemical Formula 342]

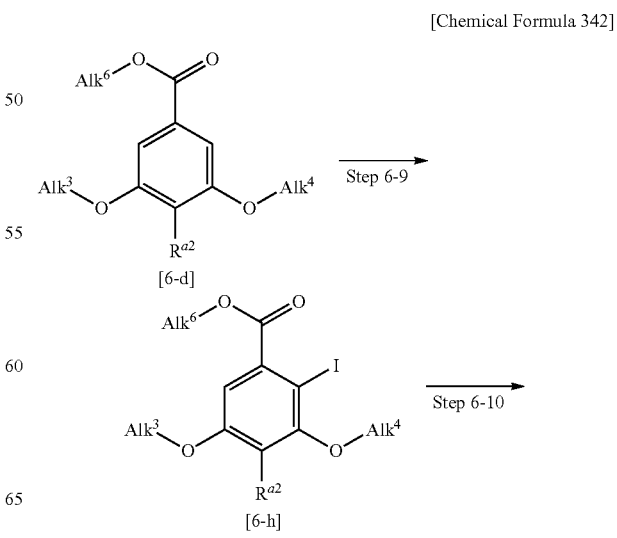

[In the scheme,
Alk³ and Alk⁴ are as defined above,
Alk⁶ represents $C_{1-6}$ alkyl, and
$R^{a2}$ represents $C_{1-6}$ alkyl(the $C_{1-6}$ alkyl is optionally substituted with one hydroxy), halo-$C_{1-6}$ alkyl, $C_{3-8}$ cycloalkyl, $C_{1-6}$ alkylcarbonyl, or halo-$C_{1-6}$ alkylcarbonyl.]

245

-continued

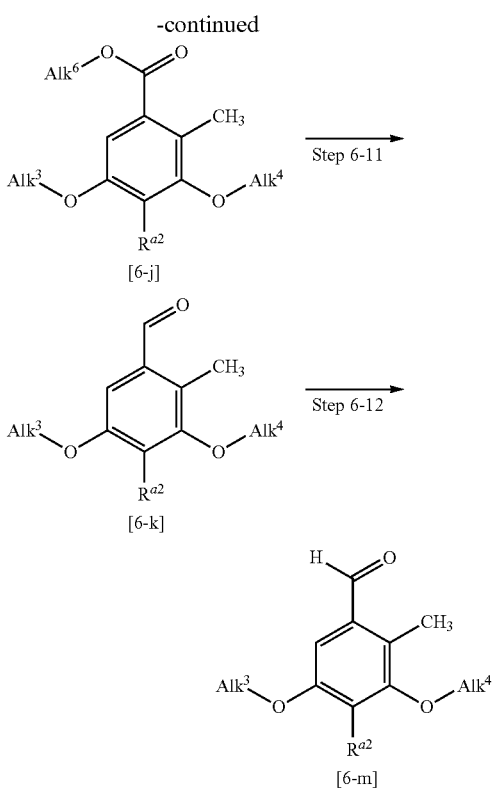

[In the scheme,

Alk$^3$, Alk$^4$, Alk$^6$, and R$^{a2}$ are as defined above.]

Step 6-9:

Method for producing compound [6-h]: Compound [6-d] is used as the starting substance, and by allowing an iodinating agent such as iodine to act on it in the presence of a silver compound such as silver trifluoroacetate in an inert solvent at ice-cooled temperature to room temperature, compound [6-h] can be produced.

Note that the present iodination reaction can also be performed in another step.

Step 6-10:

Method for producing compound [6-j]: Compound [6-h] is used as the starting substance, and by allowing it to react with a methylating agent such as methylboronic acid in the presence of a palladium catalyst such as tetrakis(triphenylphosphine) palladium (0) and a base such as tripotassium phosphate in an inert solvent from room temperature to 160° C., compound [6-j] can be produced. Note that the present methylation reaction can also be performed in another step.

Step 6-11:

Method for producing compound [6-k]: Compound [6-j] is used as the starting substance, and by the method described in the above-mentioned step 6-7 or a method equivalent thereto, compound [6-k] can be produced.

Step 6-12:

Method for producing compound [6-m]: Compound [6-k] is used as the starting substance, and by the method described in the above-mentioned step 6-8 or a method equivalent thereto, compound [6-m] can be produced.

246

Scheme 6-5 (Another method for producing compound [6-j] from compound [6-d]):

[Chemical Formula 343]

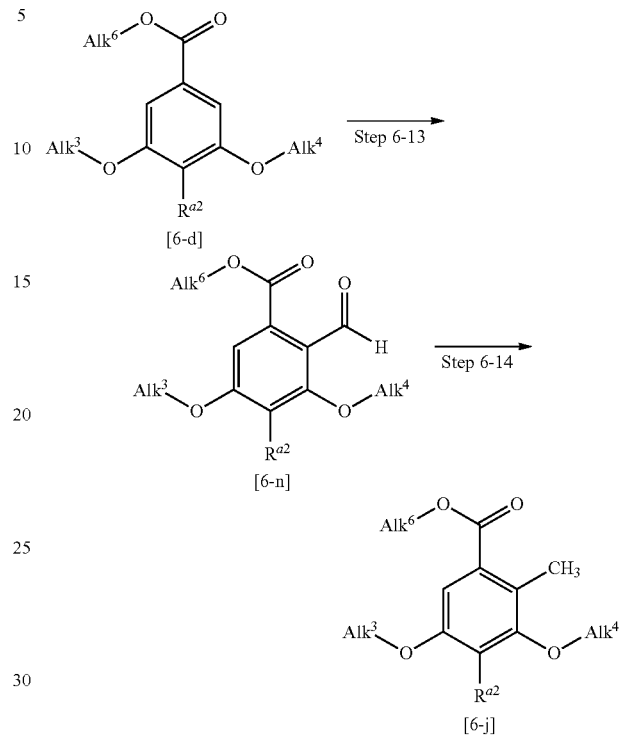

[In the scheme,

Alk$^3$, Alk$^4$, Alk$^6$, and R$^{a2}$ are as defined above.]

Step 6-13:

Method for producing compound [6-n]: Compound [6-d] is used as the starting substance, and by allowing dichloromethyl methyl ether to act on it in the presence of a Lewis acid such as titanium (IV) chloride in an inert solvent at ice-cooled temperature to room temperature, compound [6-n] can be produced.

Note that the present formylation reaction can also be performed in another step.

Step 6-14:

Another method for producing compound [6-j]: Compound [6-n] is used as the starting substance, and by allowing a reducing agent such as triethylsilane to act on it in the presence of an acid such as trifluoroacetic acid at ice-cooled temperature to room temperature, compound [6-j] can be produced. Note that the present methylation reaction can also be performed in another step.

Among the production intermediates for compound [I] of the present invention, compound [2-g] below described in production method 2 can be acquired by production according to methods known per se or by purchase of commercially available products, but it can also be produced by, for example, production method 7 below or a method equivalent thereto.

[Chemical Formula 344]

[2-g]

Production Method 7:

A production example for compound [2-g], which is a production intermediate for compound [I] of the present invention, is shown in the following scheme 7.

Scheme 7 (Method for producing compound [2-g] from compound [2-b]):

[Chemical Formula 345]

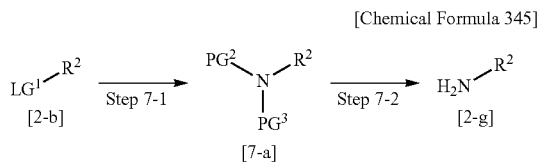

[In the scheme,

R² and LG¹ are as defined above,

PG² represents a protecting group for amino such as tert-butoxycarbonyl, and

PG³ represents a hydrogen atom or a protecting group for amino such as tert-butoxycarbonyl, or PG² and PG³ can also form phthalimide or the like, together with the adjacent nitrogen atom, to protect amino.]

Step 7-1:

Method for producing compound [7-a]: Compound [2-b] is used as the starting substance, and by allowing potassium phthalimide, di-tert-butyl iminodicarboxylate, or the like to act on it in the presence or absence of a base such as potassium carbonate in an inert solvent from room temperature to 120° C., compound [7-a] can be produced.

Step 7-2:

Method for producing compound [2-g]: Compound [7-a] is used as the starting substance, and under any of the following reaction conditions (i) to (ii), compound [2-g] can be produced:
  (i) condition under which an acid such as hydrochloric acid is allowed to react in an inert solvent from ice-cooled temperature to 100° C., or
  (ii) condition under which hydrazine monohydrate or the like is allowed to react in an inert solvent at room temperature to reflux temperature.

Compound [2-b], which is used as the raw material compound in the above step 7-1, can be acquired by production according to methods known per se, by production according to the method shown in the above-mentioned scheme 4-1, or by purchase of commercially available products.

Compound [2-g] thus obtained can be isolated and purified by publicly known separation and purification means such as concentration, concentration under reduced pressure, reprecipitation, solvent extraction, crystallization, and chromatography.

Among the production intermediates for compound [I] of the present invention, compound [2-b] shown in scheme 7 can be acquired by production according to methods known per se or by purchase of commercially available products.

Among the production intermediates for compound [I] of the present invention, a compound whose structure is represented by formula [1-b] (hereinafter, this may also be referred to as compound [1-b]) can also be produced by, for example, production method 8 below or a method equivalent thereto.

[Chemical Formula 346]

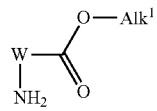

Production Method 8:

Compound [1-b], which is a production intermediate for compound [I] of the present invention, can be acquired by production according to methods known per se or by purchase of commercially available products, but it can also be produced by, for example, the method shown in scheme 8-1 below or a method equivalent thereto.

Scheme 8-1 (Method for producing compound [1-b] from compound [8-a])

[Chemical Formula 347]

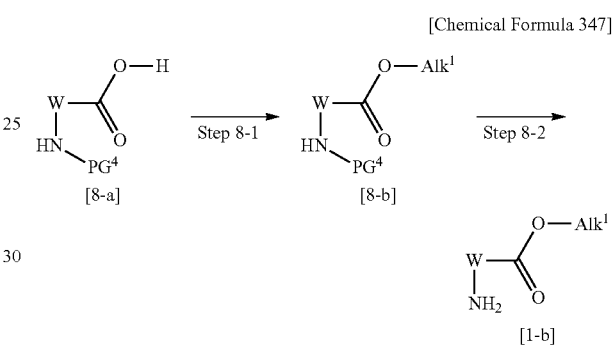

[In the scheme,

W and Alk¹ are as defined above, and

PG⁴ represents a protecting group for amino such as benzyloxycarbonyl, tert-butoxycarbonyl, or allyloxycarbonyl.]

Step 8-1:

Method for producing compound [8-b]: Compound [8-a] is used as the starting substance, and under any of the following reaction conditions (i) to (iii), compound [8-b] can be produced:
  (i) condition under which an alkylating agent such as methyl iodide is allowed to react in the presence or absence of a base such as potassium carbonate in an inert solvent at room temperature to reflux temperature,
  (ii) condition under which an alcohol such as methanol or ethanol is allowed to react in the presence of p-toluenesulfonic acid, thionyl chloride, and the like, in the presence or absence of an inert solvent at room temperature to reflux temperature, or
  (iii) condition under which an alkylating agent such as methyl iodide is allowed to react in the presence of a silver compound such as silver oxide in an inert solvent at room temperature to reflux temperature.

Step 8-2:

Method for producing compound [1-b]: Compound [8-b] is used as the starting substance, and through the following deprotection reactions (i) to (iii) in an inert solvent, compound [1-b] can be produced:
  (i) deprotection reaction in which an acid such as hydrochloric acid, hydrobromic acid, or trifluoroacetic acid is used from ice-cooled temperature to 80° C., (ii) deprotection reaction in which palladium carbon or the like is used in the presence or absence of an acid in a pressurized or non-pressurized hydrogen atmosphere at ice-cooled temperature to room temperature, or (iii) deprotection reaction in which a palladium catalyst such as tetrakis(triphenylphosphine) palladium (0) is used in the presence of an allyl scavenger such as 1,3-dimethylbarbituric acid from ice-cooled temperature to 80° C.

Compound [8-f], which is compound [1-b] wherein W is a structure represented by the above formula [III-1], can be acquired by production according to methods known per se or by purchase of commercially available products.

Alternatively, this compound can also be produced by, for example, the method shown in scheme 8-2 below or a method equivalent thereto.

[Chemical Formula 348]

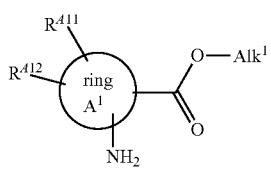

[8-f]

Scheme 8-2 (Method for producing compound [8-f] from compound [8-c]):

[Chemical Formula 349]

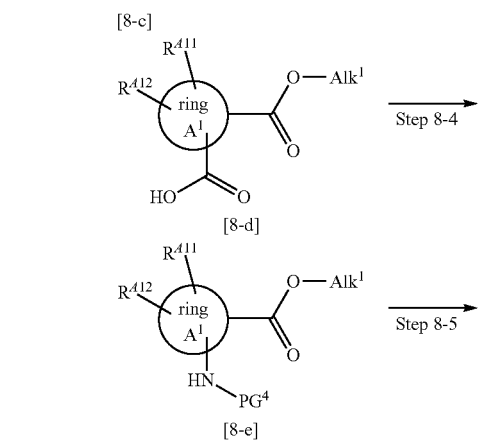

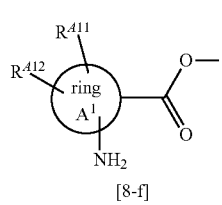

[In the scheme,
ring $A^1$, $R^{411}$, $R^{412}$, $Alk^1$, and $PG^4$ are as defined above.]

Step 8-3:

Method for producing compound [8-d]: Compound [8-c] is used as the starting substance, and by allowing tetramethylammonium hydroxide, tetraethylammonium hydroxide, or the like to act on it in an inert solvent at ice-cooled temperature to room temperature, thereby selectively hydrolyzing only one of the two esters in compound [8-c], compound [8-d] can be produced.

The present step can be performed with reference to the method described in, for example, The Journal of Organic Chemistry, vol. 82, p. 12863, 2017.

Step 8-4:

Method for producing compound [8-e]: Compound [8-d] is used as the starting substance, and by allowing an azidating agent such as diphenylphosphoryl azide to act on it in the presence of a base such as triethylamine in an inert solvent from ice-cooled temperature to 100° C., thereby forming the corresponding isocyanate, and then allowing an alcohol such as benzyl alcohol, tert-butyl alcohol, or allyl alcohol to act on it, compound [8-e] can be produced.

Step 8-5:

Method for producing compound [8-f]: Compound [8-e] is used as the starting substance, and by the method described in the above-mentioned step 8-2 or a method equivalent thereto, compound [8-f] can be produced.

Also, compound [8-f'] or [8-f'], which is compound [1-b] wherein W is a structure represented by the above formula [III-2] or [III-3], can be acquired by production according to methods known per se or by purchase of commercially available products.

Alternatively, these compounds can also be produced by, for example, the method described in the above scheme 8-2 or a method equivalent thereto.

[Chemical Formula 350]

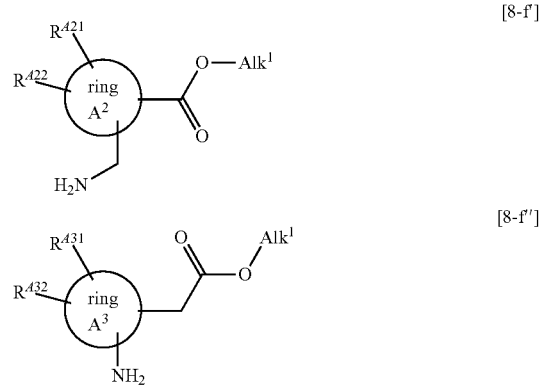

[In the formulas,
ring $A^2$, ring $A^3$, $R^{421}$, $R^{422}$, $R^{431}$, $R^{432}$, and $Alk^1$ are as defined above.]

Compound [8-p], which is compound [1-b] wherein W is a structure represented by the above formula [III-1], and in that structure, ring $A^1$ is $C_{3-8}$ cycloalkane substituted with one group selected from the group consisting of "hydroxy, $C_{1-6}$ alkoxy, and nitrogen atom-containing 4- to 6-membered saturated heterocyclyl", can be acquired by production according to methods known per se or by purchase of commercially available products.

Alternatively, this compound can also be produced by, for example, the method shown in scheme 8-3 below or a method equivalent thereto, using compound [8-g], which is a $C_{3-8}$ cycloalkane compound substituted with oxo, as the starting substance.

[Chemical Formula 351]

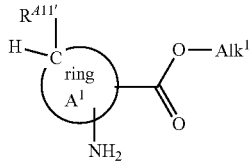

[8-p]

Scheme 8-3 (Method for producing compound [8-p] from compound [8-g]):

[Chemical Formula 352]

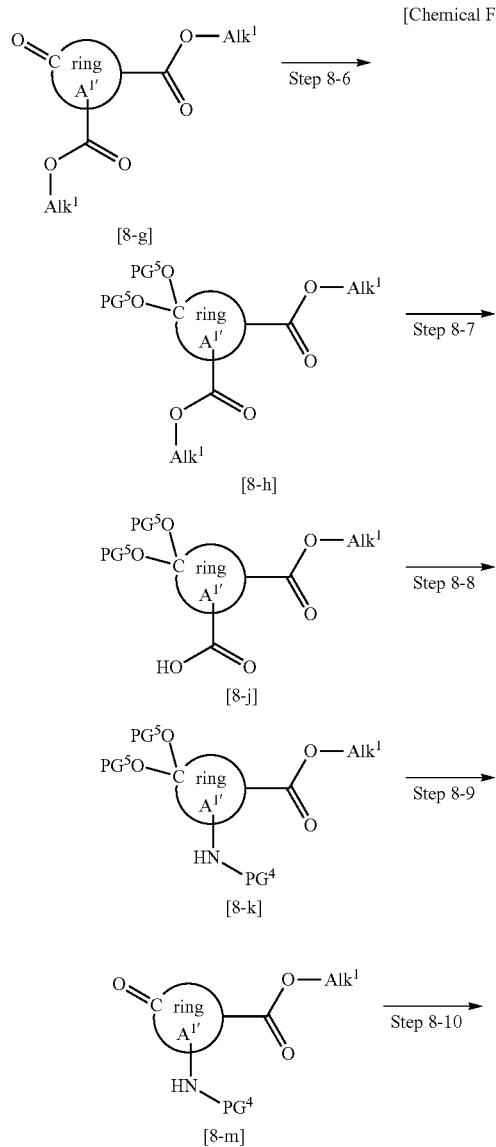

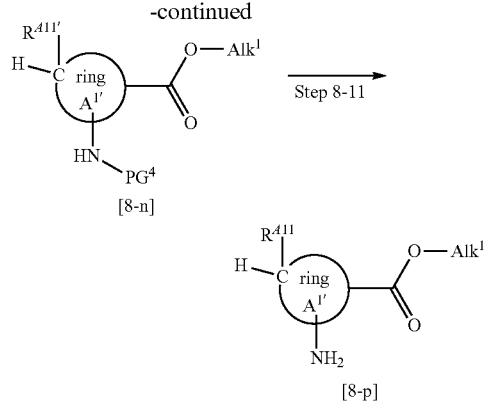

[In the scheme,
Alk$^1$ and PG$^4$ are as defined above,
ring A$^{1\prime}$ is $C_{3-8}$ cycloalkane,
PG$^5$ represents $C_{1-3}$ alkyl,
where
two PG$^5$ may form a 5- to 6-membered ring (the 5- to 6-membered ring may be substituted with one to two groups selected from the group consisting of methyl and phenyl) together with the bonded oxygen atoms and carbon atom to protect carbonyl, and
R$^{411\prime\prime}$ represents hydroxy, $C_{1-6}$ alkoxy, or nitrogen atom-containing 4- to 6-membered saturated heterocyclyl (the nitrogen atom-containing 4- to 6-membered saturated heterocyclyl may be substituted with one $C_{1-3}$ alkyl).]

Step 8-6:
Method for producing compound [8-h]: Compound [8-g] is used as the starting substance, and by allowing it to react with an alcohol such as methanol, ethylene glycol, or hydrobenzoin, or orthoester such as triethyl orthoformate in the presence of an acid such as p-toluenesulfonic acid in an inert solvent at room temperature to reflux temperature, compound [8-h] can be produced.

Step 8-7:
Method for producing compound [8-j]: Compound [8-h] is used as the starting substance, and by the method described in the above-mentioned step 8-3 or a method equivalent thereto, compound [8-j] can be produced.

Step 8-8:
Method for producing compound [8-k]: Compound [8-j] is used as the starting substance, and by the method described in the above-mentioned step 8-4 or a method equivalent thereto, compound [8-k] can be produced.

Step 8-9:
Method for producing compound [8-m]: Compound [8-k] is used as the starting substance, and through a deprotection reaction using an acid such as hydrochloric acid or trifluoroacetic acid in an inert solvent at room temperature to reflux temperature, compound [8-m] can be produced.

Step 8-10:
Method for producing compound [8-n]: Compound [8-m] is used as the starting substance, and by carrying out any of the following reactions (i) to (iv), compound [8-n] can be produced:
(i) reduction reaction in which a reducing agent such as sodium borohydride, lithium borohydride, diisobutylaluminum hydride, lithium triethylborohydride, lithium tri-sec-butylborohydride, or borane-tetrahydrofuran is used in the presence or absence of an additive agent such as zinc chloride in an inert solvent from −80° C. to reflux temperature;

(ii) "hydrolysis reaction" after carrying out the operation of step 8-10 (i) and then allowing a reaction with 4-nitrobenzoic acid or the like in the presence of a phosphorus compound such as triphenylphosphine and an azodicarboxylic acid diester such as bis(2-methoxyethyl) azodicarboxylate in an inert solvent at ice-cooled temperature to reflux temperature;

(iii) reaction of, after carrying out the operation of step 8-10 (i) or 8-10 (ii), using an alkyl halide such as methyl iodide or ethyl iodide in the presence of a silver compound such as silver oxide in an inert solvent at room temperature to reflux temperature; or (iv) "reductive amination reaction" with an amine corresponding to $R^{411'}$.

The above step 8-10 (i) can be performed with reference to, for example, the method described in Bioorganic & Medicinal Chemistry, vol. 17, p. 1982, 2009.

In addition, in the present step 8-10 (i), by selecting an appropriate reducing agent, compound [8-n] can be produced in a stereoselective manner.

Step 8-11:

Method for producing compound [8-p]: Compound [8-n] is used as the starting substance, and by the method described in the above-mentioned step 8-2 or a method equivalent thereto, compound [8-p] can be produced.

Alternatively, the present compound [8-p] can also be produced by, for example, the method shown in scheme 8-4 below or a method equivalent thereto, using compound [8-m] obtained in scheme 8-3, which is a $C_{3-8}$ cycloalkane compound substituted with oxo, as the starting substance.

Scheme 8-4 (Method for producing compound [8-p] from compound [8-m]):

[Chemical Formula 353]

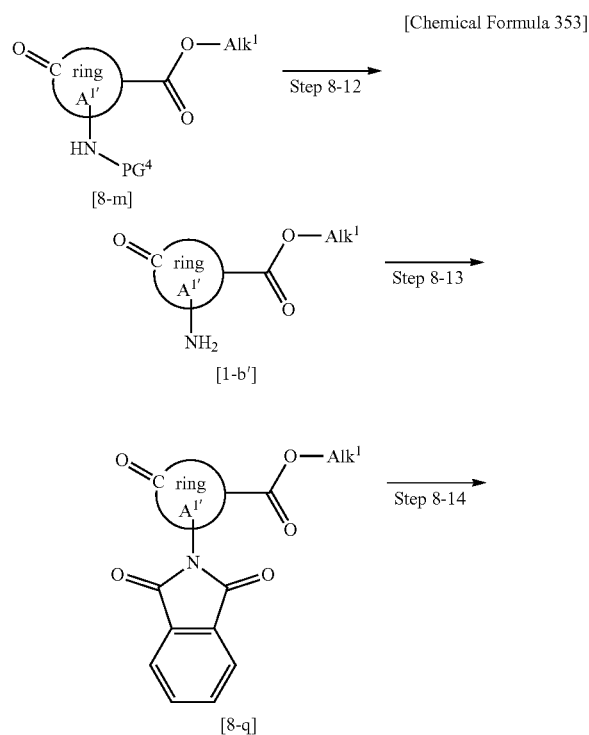

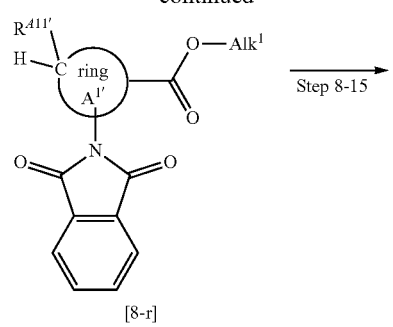

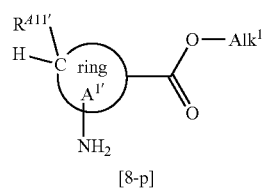

[In the scheme, $Alk^1$, $PG^4$, ring $A^{1'}$, and $R^{411'}$ are as defined above.]

Step 8-12:

Method for producing compound [1-b']: Compound [8-m] is used as the starting substance, and by the method described in the above-mentioned step 8-2 or a method equivalent thereto, compound [1-b'] can be produced.

Step 8-13:

Method for producing compound [8-q]: Compound [1-b'] is used as the starting substance, and by allowing it to react with phthalic anhydride or the like in the presence of a base such as triethylamine in an inert solvent at room temperature to reflux temperature, compound [8-q] can be produced.

Step 8-14:

Method for producing compound [8-r]: Compound [8-q] is used as the starting substance, and by the method described in the above-mentioned step 8-10 or a method equivalent thereto, compound [8-r] can be produced.

Step 8-15:

Method for producing compound [8-p]: Compound [8-r] is used as the starting substance, and by allowing an acid such as hydrochloric acid, hydrazine, or the like to act on it in an inert solvent at ice-cooled temperature to reflux temperature, compound [8-p] can also be produced.

In addition, compound [8-p'] or [8-p"], which is compound [1-b] wherein W is a structure represented by the above formula [III-2] or [III-3], and in that structure, ring $A^2$ and ring $A^3$ are each $C_{3-8}$ cycloalkane substituted with one group selected from the group consisting of "hydroxy, $C_{1-6}$ alkoxy, and nitrogen atom-containing 4- to 6-membered saturated heterocyclyl", can be acquired by production according to methods known per se or by purchase of commercially available products.

Alternatively, these compounds can also be produced by, for example, the method described in the above scheme 8-3 or 8-4, or a method equivalent thereto.

[Chemical Formula 354]

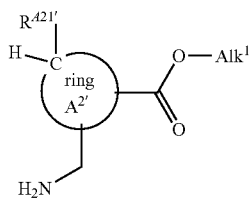

[8-p′]

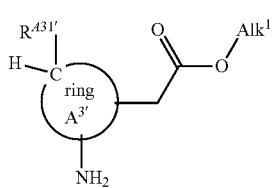

[8-p″]

[In the formulas,

Alk$^1$ is as defined above, ring A$^{2'}$ and ring A$^{3'}$ are as defined as ring A$^{1'}$, and are each C$_{3-8}$ cycloalkane, and R$^{421'}$ and R$^{431'}$ are as defined as R$^{411'}$, and are each hydroxy, C$_{1-6}$ alkoxy, or nitrogen atom-containing 4- to 6-membered saturated heterocyclyl(the nitrogen atom-containing 4- to 6-membered saturated heterocyclyl may be substituted with one C$_{1-3}$ alkyl).]

Compound [8-w], which is compound [1-b] wherein W is a structure represented by the above formula [III-1], and in that structure, ring A$^1$ is C$_{3-8}$ cycloalkane substituted with one hydroxy, and compound [8-z], which is compound [1-b] wherein W is a structure represented by the above formula [III-1] and ring A$^1$ is C$_{3-8}$ cycloalkane substituted with one C$_{1-6}$ alkoxy, can be acquired by production according to methods known per se or by purchase of commercially available products.

Alternatively, these compounds can also be produced by, for example, the method shown in scheme 8-5 below or a method equivalent thereto, using compound [8-g], which is a C$_{3-8}$ cycloalkane compound substituted with oxo, as the starting substance.

Note that, when corresponding enantiomers or diastereomers are present in compounds [8-w] and [8-z], the enantiomers or diastereomers can likewise be acquired by production according to methods known per se, by production according to the method shown in scheme 8-5, or by purchase of commercially available products.

[Chemical Formula 355]

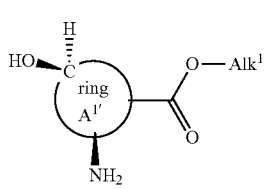

[8-w]

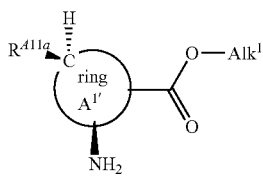

[8-z]

Scheme 8-5 (Method for producing compounds [8-w] and [8-z] from compound [8-g]):

[Chemical Formula 356]

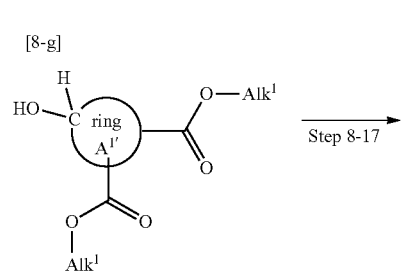

[8-g]

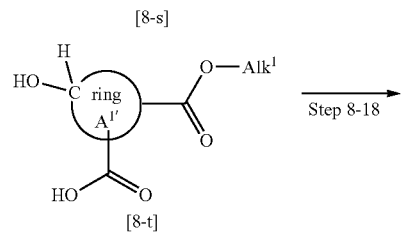

[8-s]

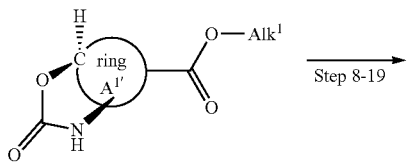

[8-t]

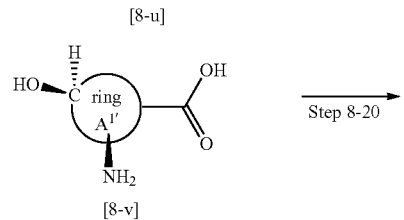

[8-u]

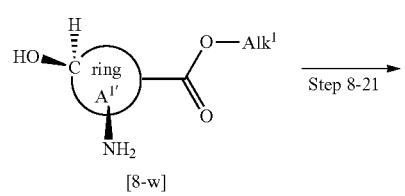

[8-v]

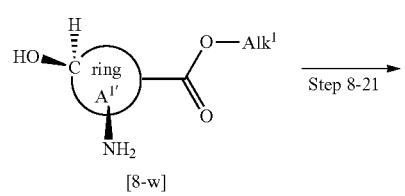

[8-w]

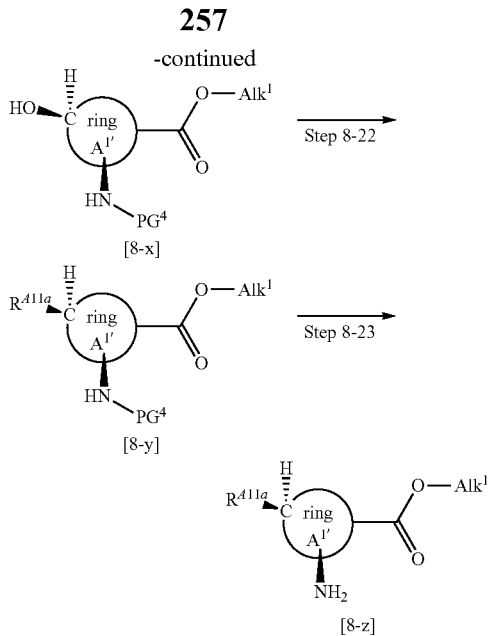

[In the scheme,
Alk$^1$, ring A$^{1\prime}$, and PG$^4$ are as defined above, and
R$^{A11a}$ represents C$_{1-6}$ alkoxy.]

Step 8-16:
Method for producing compound [8-s]: Compound [8-g] is used as the starting substance, and by the method described in the above-mentioned step 8-10 (i) or a method equivalent thereto, compound [8-s] can be produced.

Step 8-17:
Method for producing compound [8-t]: Compound [8-s] is used as the starting substance, and by the method described in the above-mentioned step 8-3 or a method equivalent thereto, compound [8-t] can be produced.

Step 8-18:
Method for producing compound [8-u]: Compound [8-t] is used as the starting substance, and by allowing an azide such as diphenylphosphoryl azide to act on it in the presence of a base such as triethylamine in an inert solvent at ice-cooled temperature to reflux temperature, compound [8-u] can be produced.

The above step 8-18 can be performed with reference to the method described in, for example, Journal of the Organic Chemistry, vol. 82, p. 12863, 2017.

Step 8-19:
Method for producing compound [8-v]: Compound [8-u] is used as the starting substance, and by allowing a base such as potassium hydroxide and water to act on it in an inert solvent at ice-cooled temperature to reflux temperature, compound [8-v] can be produced.

Step 8-20:
Method for producing compound [8-w]: Compound [8-v] is used as the starting substance, and by the method described in the above-mentioned step 8-1 (ii) or a method equivalent thereto, compound [8-w] can also be produced.

Step 8-21:
Method for producing compound [8-x]: Compound [8-w] is used as the starting substance, and by allowing di-tert-butyl dicarbonate, allyl chloroformate, benzyl chloroformate, or the like to act on it in the presence of a base such as triethylamine, sodium hydroxide, or sodium carbonate in an inert solvent at ice-cooled temperature to reflux temperature, compound [8-x] can be produced.

Step 8-22:
Method for producing compound [8-y]: Compound [8-x] is used as the starting substance, and by allowing it to react with an alkyl halide such as methyl iodide or ethyl iodide in the presence of a silver compound such as silver oxide in an inert solvent at room temperature to reflux temperature, compound [8-y] can be produced.

Step 8-23:
Method for producing compound [8-z]: Compound [8-y] is used as the starting substance, and by the method described in the above-mentioned step 8-2 or a method equivalent thereto, compound [8-z] can also be produced.

Compound [8-ac], which is compound [1-b] wherein W is a structure represented by the above formula [III-1], and in that structure, ring A$^1$ is a nitrogen atom-containing 4- to 8-membered saturated heterocycle substituted with one group selected from the group consisting of "C$_{1-4}$ alkylcarbonyl and C$_{1-4}$ alkoxycarbonyl", can be acquired by production according to methods known per se or by purchase of commercially available products.

Alternatively, this compound can also be produced by, for example, the method shown in scheme 8-6 below or a method equivalent thereto, using compound [8-aa], which is a nitrogen atom-containing 4- to 8-membered saturated heterocycle compound, as the starting substance.

[Chemical Formula 357]

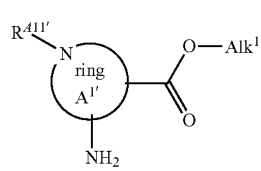

Scheme 8-6 (Method for producing compound [8-ac] from compound [8-aa]):

[Chemical Formula 358]

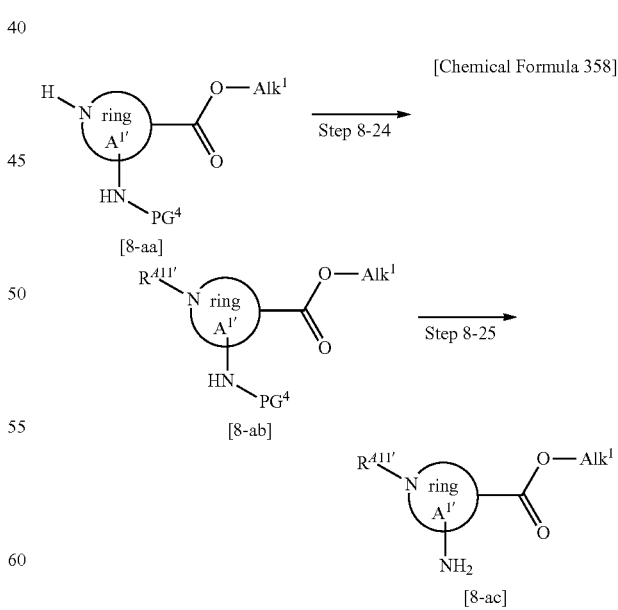

[In the scheme,
Alk$^1$ and PG$^4$ are as defined above,
ring A$^{1\prime\prime\prime}$ is a nitrogen atom-containing 4- to 8-membered saturated heterocycle, and $R^{411'''}$ represents $C_{1-4}$ alkylcarbonyl or $C_{1-4}$ alkoxycarbonyl.]

Step 8-24:

Method for producing compound [8-ac]: Compound [8-aa] is used as the starting substance, and by carrying out the following reaction (i) or (ii), compound [8-ab] can be produced:

(i) reaction in which an acyl chloride corresponding to $R^{411'''}$, such as acetyl chloride, or an acid anhydride corresponding to $R^{411'''}$, such as acetic anhydride, is used in the presence of a base in an inert solvent from ice-cooled temperature to 50° C., or (ii) reaction in which a chloroformate ester corresponding to $R^{411'''}$, such as ethyl chloroformate, is used in the presence or absence of a base in an inert solvent from ice-cooled temperature to 50° C.

Step 8-25:

Method for producing compound [8-ac]: Compound [8-ab] is used as the starting substance, and by the method described in the above-mentioned step 8-2 or a method equivalent thereto, compound [8-ac] can be produced.

Also, compound [8-ac'] or [8-ac"], which is compound [1-b] wherein W is a structure represented by the above formula [III-2] or [III-3], and in that structure, ring $A^2$ and ring $A^3$ are each a nitrogen atom-containing 4- to 8-membered saturated heterocycle substituted with one group selected from the group consisting of "$C_{1-4}$ alkylcarbonyl and $C_{1-4}$ alkoxycarbonyl", can be acquired by production according to methods known per se or by purchase of commercially available products.

Alternatively, these compounds can also be produced by, for example, the method described in the above scheme 8-6 or a method equivalent thereto.

[Chemical Formula 359]

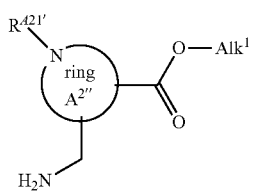

[8-ac']

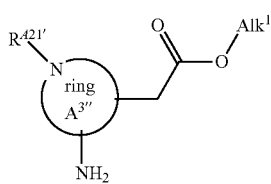

[8-ac"]

[In the formulas,

Alk$^1$ is as defined above, ring $A^{2'''}$ and ring $A^{3'''}$ are as defined as ring $A^{1'''}$, and are each a nitrogen atom-containing 4- to 8-membered saturated heterocycle, and $R^{421'''}$ and $R^{431'''}$ are as defined as $R^{411'''}$, and are each $C_{1-4}$ alkylcarbonyl or $C_{1-4}$ alkoxycarbonyl.]

Compounds [1-b], [8-f], [8-f'], [8-f"], [8-p], [8-p'], [8-p"], [8-w], [8-z], [8-ac], [8-ac'], and [8-ac"] thus obtained can be isolated and purified by publicly known separation and purification means such as concentration, concentration under reduced pressure, reprecipitation, solvent extraction, crystallization, and chromatography.

Among the production intermediates for compound [I] of the present invention, compound [8-a] shown in scheme 8-1, compound [8-c] shown in scheme 8-2, compound [8-g] shown in schemes 8-3 and 8-5, and compound [8-aa] shown in scheme 8-6 can be acquired by production according to methods known per se or by purchase of commercially available products.

Among compounds [I] of the present invention, a compound wherein X is carbamoyl, a compound wherein X is a group represented by formula [II-2], [II-3], [II-4], [II-5], or [II-1] below, and a compound wherein X is tetrazolyl can be produced by, for example, production method 9 below or a method equivalent thereto.

[Chemical Formula 360]

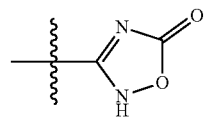

[II-1]

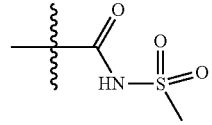

[II-2]

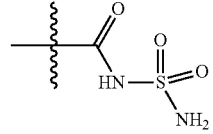

[II-3]

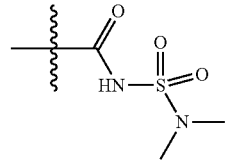

[II-4]

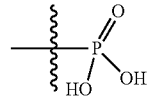

[II-5]

Among compounds [I] of the present invention, a production example for compound [9-a] wherein X is carbamoyl, or a group represented by formula [II-2], [II-3], or [II-4], is shown in the following scheme 9-1.

Production Method 9:

Scheme 9-1 (Method for producing compound [9-a] from compound [1-d]):

[Chemical Formula 361]

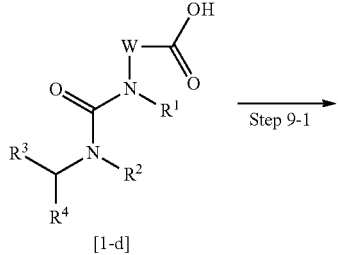

[1-d] Step 9-1

-continued

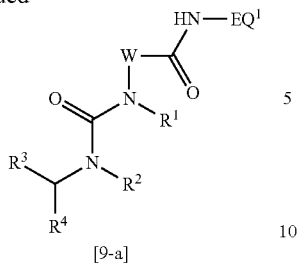

[9-a]

[In the scheme,
$R^1$, $R^2$, $R^3$, $R^4$, and W are as defined above, and
$EQ^1$ represents a hydrogen atom or a group selected from formula group [II']:
[Chemical Formula 362]

[Chemical Formula 362]

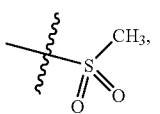   [II-2']

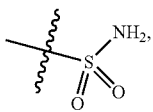   [II-3']

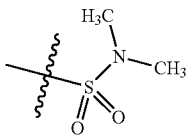   [II-4']

.]   [II']

Step 9-1:
Method for producing [9-a]: Compound [1-d] is used as the starting substance, and by allowing it to react with an amine compound such as methanesulfonamide, sulfamide, N,N-dimethylsulfamide, or ammonium chloride in the presence or absence of a base such as N,N-diisopropylethylamine, in the presence or absence of an additive agent such as 4-dimethylaminopyridine or HOBt, and in the presence of a condensing agent such as EDC or CDI, in an inert solvent at ice-cooled temperature to reflux temperature, compound [9-a] can be produced.

Among compounds [I] of the present invention, a production example for compound [9-h] wherein X is a group represented by formula [II-5] is shown in the following scheme 9-2.

Scheme 9-2 (Method for producing compound [9-h] from compound [9-b]):

[Chemical Formula 363]

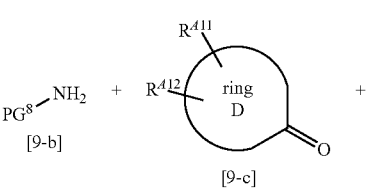

-continued

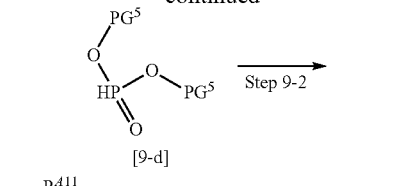

[9-d]   Step 9-2

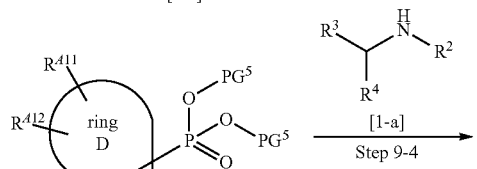

[9-e]   Step 9-3

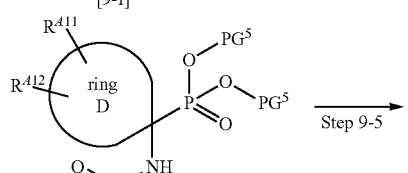

[9-f]   [1-a] Step 9-4

[9-g]   Step 9-5

[9-h]

[In the scheme,
$R^2$, $R^3$, $R^4$, $R^{411}$, and $R^{412}$ are as defined above,
ring D represents $C_{3-8}$ cycloalkane, a partially saturated 9- to 10-membered fused hydrocarbon aromatic ring, an oxygen atom-containing 4- to 8-membered saturated heterocycle, a sulfur atom-containing 4- to 8-membered saturated heterocycle, or a nitrogen atom-containing 4- to 8-membered saturated heterocycle,
where
the sulfur atom in the sulfur atom-containing 4- to 8-membered saturated heterocycle is optionally substituted with one to two oxo, and
the nitrogen atom in the nitrogen atom-containing 4- to 8-membered saturated heterocycle is optionally substituted with one group selected from the group consisting of $C_{1-4}$ alkylcarbonyl and $C_{1-4}$ alkoxycarbonyl, PG[5] represents a protecting group for the phosphate group such as benzyl, and
PG[6] represents a protecting group for the amino such as diphenylmethyl.]

Step 9-2:
Method for producing compound [9-e]: Compounds [9-b], [9-c], and [9-d] are used as the starting substances, and by allowing a Lewis acid such as bismuth (III) chloride to act on them in an inert solvent from room temperature to 120° C., compound [9-e] can be produced.

The present step can be performed with reference to the method described in, for example, Organic Letters, vol. 1, p. 1395, 1999.

In addition, the present reaction can also be carried out under microwave irradiation.

Step 9-3:
Method for producing compound [9-f]: Compound [9-e] is used as the starting substance, and by allowing an oxidizing agent such as 2,3-dichloro-5,6-dicyano-1,4-benzoquinone to act on it in an inert solvent from room temperature to 100° C., thereby forming the corresponding imine, and then allowing an acidic aqueous solution such as hydrochloric acid to act on it in an inert solvent from room temperature to 60° C., compound [9-f] can be produced.

The present step can be performed with reference to the method described in, for example, Organic Letters, vol. 1, p. 1395, 1999.

Step 9-4:
Method for producing compound [9-g]: Compound [9-f] is used as the starting substance, and by allowing it to react with compound [1-a] in the presence of a base such as triethylamine, pyridine, 4-dimethylaminopyridine, or N,N-diisopropylethylamine, and an agent that generates a urea derivative, such as 4-nitrophenyl chloroformate, CDI, or triphosgene in an inert solvent at ice-cooled temperature to reflux temperature, compound [9-g] can be produced.

Step 9-5:
Method for producing compound [9-h]: Compound [9-g] is used as the starting substance, and through a deprotection reaction in which palladium carbon or the like is used in the presence or absence of an acid in an inert solvent in a pressurized or non-pressurized hydrogen atmosphere at ice-cooled temperature to room temperature, compound [9-h] can be produced.

Among compounds [I] of the present invention, a production example for compound [9-r] wherein X is a group represented by formula [II-1] is shown in the following scheme 9-3.

Scheme 9-3 (Method for producing compound [9-q] from compound [8-a]):

[Chemical Formula 364]

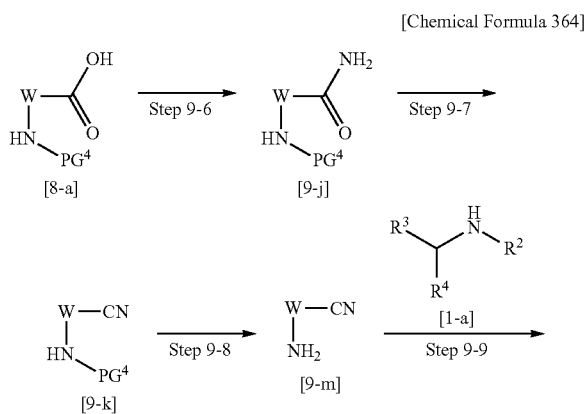

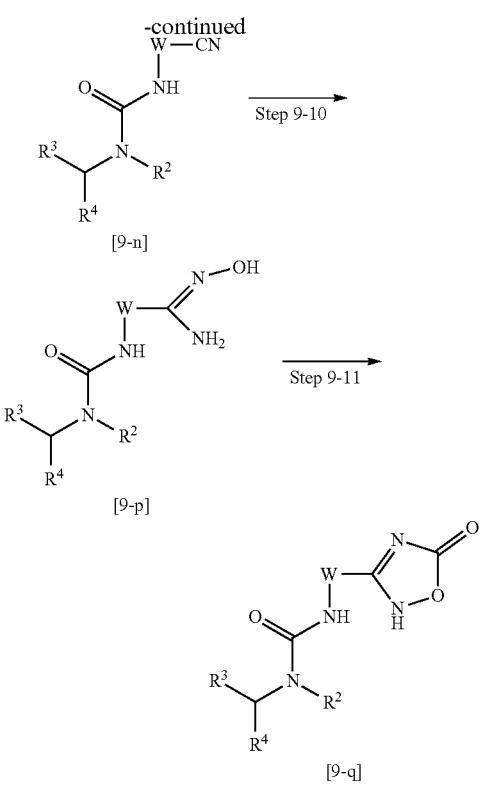

[In the scheme,
PG[4], R[2], R[3], R[4], and W are as defined above.]

Step 9-6:
Method for producing compound [9-j]: By carrying out a "condensation reaction" between compound [8-a] and an amine compound such as ammonium chloride, compound [9-j] can be produced.

Step 9-7:
Method for producing compound [9-k]: Compound [9-j] is used as the starting substance, and by allowing arylsulfonyl chloride such as p-toluenesulfonyl chloride or $C_{1-4}$ alkylsulfonyl chloride such as methanesulfonyl chloride to act on it in the presence of a base such as pyridine in an inert solvent from ice-cooled temperature to 50° C., compound [9-k] can be produced.

Step 9-8:
Method for producing compound [9-m]: Compound [9-k] is used as the starting substance, and by the method described in the above-mentioned step 8-2 or a method equivalent thereto, compound [9-m] can be produced.

Step 9-9:
Method for producing compound [9-n]: Compound [9-m] is used as the starting substance, and by the method described in the above-mentioned step 9-4 or a method equivalent thereto, compound [9-n] can be produced.

Step 9-10:
Method for producing compound [9-p]: Compound [9-n] is used as the starting substance, and by allowing it to react with hydroxylamine hydrochloride in the presence or absence of a base such as sodium carbonate or N,N-diisopropylethylamine in an inert solvent from ice-cooled temperature to 90° C., compound [9-p] can be produced.

Step 9-11:
Method for producing compound [9-q]: Compound [9-p] is used as the starting substance, and by allowing it to react with CDI or the like in the presence of a base such as 1,8-diazabicyclo[5.4.0]-7-undecene in an inert solvent at ice-cooled temperature to room temperature, compound [9-q] can be produced.

Among compounds [I] of the present invention, a production example for compound [9-v] wherein X is tetrazolyl is shown in the following scheme 9-4.

Scheme 9-4 (Method for producing compound [9-v] from compound [9-k]):

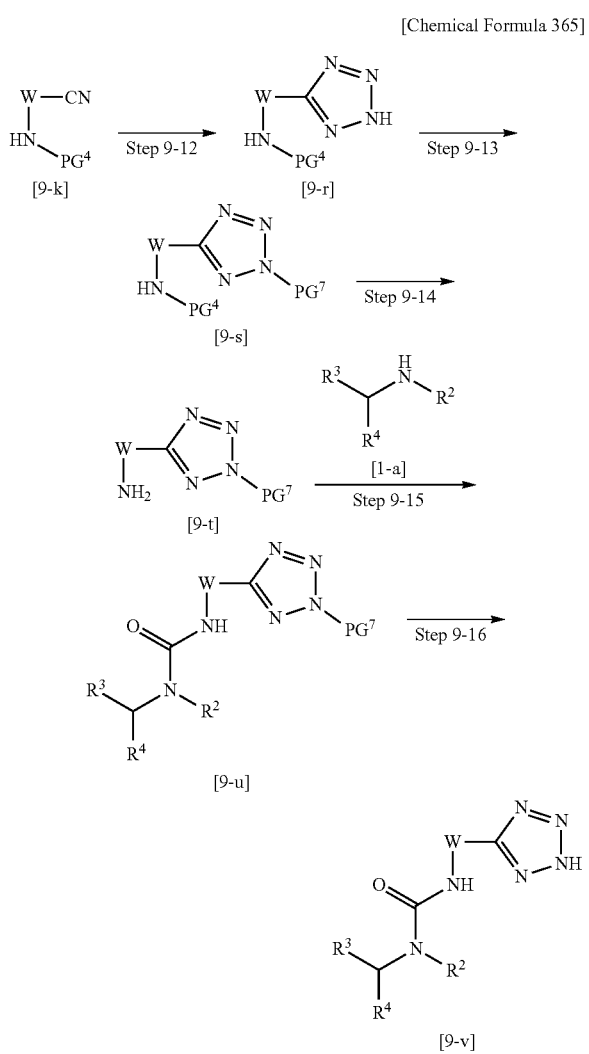

[Chemical Formula 365]

[In the scheme,
PG⁴, R², R³, R⁴, and W are as defined above, and
PG⁷ represents a protecting group for the tetrazolyl such as triphenylmethyl or benzyl.]

Step 9-12:

Method for producing compound [9-r]: Compound [9-k] is used as the starting substance, and by allowing it to react with an azide such as sodium azide in the presence of an inorganic acid salt of an amine compound such as ammonium chloride or trimethylamine hydrochloride, and in the presence or absence of a copper catalyst, in an inert solvent from room temperature to 150° C., compound [9-r] can be produced. In addition, the present reaction can also be carried out under microwave irradiation.

Step 9-13:

Method for producing compound [9-s]: Compound [9-r] is used as the starting substance, and by allowing trityl chloride, benzyl bromide, or the like to act on it in the presence of a base such as triethylamine or potassium carbonate in an inert solvent at ice-cooled temperature to room temperature, compound [9-s] can be produced.

Step 9-14:

Method for producing compound [9-t]: Compound [9-s] is used as the starting substance, and by the method described in the above-mentioned step 8-2 or a method equivalent thereto, compound [9-t] can be produced.

Step 9-15:

Method for producing compound [9-u]: Compound [9-t] is used as the starting substance, and by the method described in the above-mentioned step 9-4 or a method equivalent thereto, compound [9-u] can be produced.

Step 9-16:

Method for producing compound [9-v]: Compound [9-u] is used as the starting substance, and in an inert solvent at ice-cooled temperature to room temperature, (i) by allowing an acid such as hydrochloric acid to act on it, or (ii) by a deprotection reaction in which palladium carbon or the like is used in the presence or absence of an acid in a pressurized or non-pressurized hydrogen atmosphere, compound [9-v] can be produced.

Compounds [9-a], [9-h], [9-q], and [9-v] thus obtained can be isolated and purified by separation and purification means such as concentration, concentration under reduced pressure, reprecipitation, solvent extraction, crystallization, and chromatography.

Among the production intermediates for compound [I] of the present invention, compounds [9-b], [9-c], and [9-d] shown in scheme 9-2, and compound [8-a] shown in scheme 9-3 can be acquired by production according to methods known per se or by purchase of commercially available products.

The present invention will be further described in detail with reference to the following Reference Examples, Examples, and Test Examples. However, they do not limit the present invention, and may be varied in the range without departing the scope of the present invention.

Also, in the following Reference Examples and Examples, there are some cases where the yield exceeds the theoretical amount due to the influence of residual solvent or the like.

In the following Reference Examples and Examples, a packed column (Reveleris (registered trademark) Flash Cartridges Silica manufactured by W. R. Grace & Co., or Biotage (registered trademark) SNAP Cartridge HP-Sphere manufactured by Biotage AB) was used for silica gel column chromatography. For NH silica gel column chromatography, a packed column (Reveleris (registered trademark) Flash Cartridges Amino manufactured by W. R. Grace & Co., or Biotage (registered trademark) SNAP Cartridge KP-NH manufactured by Biotage AB) was used. For preparative thin layer chromatography, the PLC plate 20×20 cm silica gel 60 F254, 2 mm manufactured by Merck KGaA was used. The ratio of eluting solvents indicates the volume ratio unless otherwise noted. The phase separator used was the ISO-LUTE (registered trademark) Phase Separator manufactured by Biotage AB.

Abbreviations as used herein have the following meanings:

s: singlet
d: doublet
t: triplet
q: quartet
quin: quintet
sxt: sextet spt: septet
dd: double doublet
dt: double triplet
td: triple doublet
tt: triple triplet
qd: quarter doublet
m: multiplet
br: broad
J: coupling constant
Hz: Hertz
CHLOROFORM-d: deuterated chloroform
DMSO-$d_6$: deuterated dimethyl sulfoxide
METHANOL-$d_4$: deuterated methanol
ACETONE-$d_6$: deuterated acetone
$D_2O$: deuterated water
HATU: O-(7-azabenzotriazol-1-yl)-N,N,N',N'-tetramethyluronium hexafluorophosphate
EDC: 1-(3-dimethylaminopropyl)-3-ethylcarbodiimide hydrochloride
CDI: 1,1'-carbonyldiimidazole
DMT-MM: 4-(4,6-dimethoxy-1,3,5-triazin-2-yl)-4-methylmorpholinium chloride
HOBt: N-hydroxybenzotriazole monohydrate
DBU: 1,8-diazabicyclo[5.4.0]-7-undecene
Rf: retardation factor
posi: positive (mode)
nega: negative (mode)
$^1$H-NMR (proton nuclear magnetic resonance spectrum) was measured by the Fourier transform NMR described below using tetramethylsilane as the internal standard, and all δ values are shown in ppm.
  200 MHz: Gemini2000 (Agilent Technologies)
  300 MHz: Inova300 (Agilent Technologies)
  400 MHz: AVANCE III HD400 (Bruker)
  500 MHz: JNM-ECA500 (JEOL)
  600 MHz: JNM-ECA600 (JEOL)

For the analysis, the ACD/Spectrus Processor 2015 ACD/Labs 2015 Release (File Version S30S41, Build 76327, 28 Feb. 2015) (trade name) and the like were used. Very gentle peaks of protons such as those for hydroxy, amino, amide, pyrazole, urea, and carboxy may not be described.

Note that, in the analysis of compounds, there may be protons that have not been identified due to overlap with the peak of water or solvent.

The MS (mass spectrum) was measured using the following apparatus.
  PlatformLC (Waters)
  LCMS-2010EV (Shimadzu)
  LCMS-IT-TOF (Shimadzu)
  Agilent6130 (Agilent)
  Agilent6150 (Agilent)

As for the ionization method, the ESI (Electrospray Ionization) method, the EI (Electron Ionization) method, or a dual ionization method combining the ESI and APCI (Atmospheric Pressure Chemical Ionization) methods were used. For the data, measured values (found) are described. Normally, molecular ion peaks are observed, but in the case of a compound having tert-butoxycarbonyl(-Boc), the peak for which tert-butoxycarbonyl or tert-butyl has been eliminated may appear as a fragment ion. Also, in the case of a compound having tetrahydropyranyl (THP), the peak for which tetrahydropyranyl has been eliminated may appear as a fragment ion. In addition, in the case of a compound having hydroxy (—OH), the peak for which $H_2O$ or an OH radical has been eliminated may appear as a fragment peak. In the case of a salt, the molecular ion peak of the free form or a fragment ion peak is normally observed.

When the measurement conditions for the analytical data were the following conditions, it is described as mode M.
  Apparatus: LCMS-IT-TOF (Shimadzu)
  Ionization method: ESI/APCI multimode The LC-MS in Examples and Reference Examples was measured under the following conditions.
  HPLC: Agilent 1290 Infinity
  MS: Agilent 6130 or 6150
  [HPLC Conditions]
  Column: Acquity UPLC CSH C18, 1.7 µm, 2.1×50 mm (WATERS)
  Solvent: solution A, water containing 0.1% formic acid and solution B, acetonitrile containing 0.1% formic acid (method A, Normal mode)
  Gradient: 0.00 min (solution A/solution B=80/20), 1.20 min (solution A/solution B=1/99), 1.40 min (solution A/solution B=1/99), 1.41 min (solution A/solution B=80/20), 1.50 min (solution A/solution B=80/20)

(method B, HP mode)
  Gradient: 0.00 min (solution A/solution B=95/5), 0.80 min (solution A/solution B=60/40), 1.08 min (solution A/solution B=1/99), 1.38 min (solution A/solution B=1/99), 1.41 min (solution A/solution B=95/5), 1.50 min (solution A/solution B=80/20)

(method C, LP mode)
  Gradient: 0.00 min (solution A/solution B=70/30), 0.80 min (solution A/solution B=1/99), 1.40 min (solution A/solution B=1/99), 1.42 min (solution A/solution B=70/30), 1.50 min (solution A/solution B=70/30)

Injection volume: 0.5 µL, Flow rate: 0.8 mL/min
Detection method: UV 210 nm, 254 nm
Agilent 385-ELSD when equipped with an evaporative light scattering detector (ELSD)
MS Conditions
Ionization method: ESI or ESI/APCI multimode
The measurement conditions for the analytical data are described as follows.

TABLE 1-1

| Ionization method | mode | | |
|---|---|---|---|
| | LP | normal | HP |
| ESI | A | B | C |
| ESI/APCI multimode | D | E | F |

Purification by preparative HPLC in Examples and Reference Examples was carried out under the following conditions.
  Instrument: GILSON high throughput purification system
  Column: Triart C18, 5 µm, 30×50 mm (YMC) or X-Bridge Prep C18 5 µm OBD, 30× 50 (Waters)
  Solvent: solution A, water containing 0.1% formic acid and solution B, acetonitrile containing 0.1% formic acid; or solution A, water containing 0.1% trifluoroacetic acid and solution B, acetonitrile containing 0.1% trifluoroacetic acid (method A)
  Gradient: 0.00 min (solution A/solution B=90/10), 2.00 min (solution A/solution B=90/10), 11.0 min (solution A/solution B=20/80), 12.0 min (solution A/solution B=5/95), 13.52 min (solution A/solution B=5/95), 15.0 min (solution A/solution B=90/10)

(method B)
  Gradient: 0.00 min (solution A/solution B=95/5), 3.00 min (solution A/solution B=95/5), 8.53 min (solution A/solution B=80/20), 10.0 min (solution A/solution B=80/20), 11.0 min (solution A/solution B=50/50), 12.02 min (solution A/solution B=5/95), 13.5 min (solution A/solution B=5/95), 13.65 min (solution A/solution B=95/5), 15.0 min (solution A/solution B=95/5)

(method C)
  Gradient: 0.00 min (solution A/solution B=80/20), 2.00 min (solution A/solution B=80/20), 10.0 min (solution A/solution B=5/95), 11.0 min (solution A/solution B=1/99), 13.5 min (solution A/solution B=1/99), 13.55 min (solution A/solution B=80/20), 15.0 min (solution A/solution B=80/20)
  Flow rate: 40 mL/min
  Detection method: UV 210 nm, UV 254 nm
  SofTA MODEL 300S ELSD when equipped with ELSD
  Diastereomer separation was carried out by preparative HPLC in Examples below.

[HPLC Conditions]

TABLE 2-1

| | Conditions |
|---|---|
| Example 5-52<br>Example 5-53 | Column: YMC Triart C18 5 μm, 30 × 50 mm<br>Solvent: solution A, 0.1% formic acid-water and solution B, 0.1% formic acid-acetonitrile<br>Elution condition: solution A/solution B = 80/20 → 1/99<br>Flow rate: 40 mL/min, Temperature: room temperature |
| Example 5-65<br>Example 5-66 | Column: YMC Triart C18 5 μm, 30 × 50 mm<br>Solvent: solution A, 0.1% formic acid-water and solution B, 0.1% formic acid-acetonitrile<br>Elution condition: solution A/solution B = 80/20 → 1/99<br>Flow rate: 40 mL/min, Temperature: room temperature |
| Example 5-67<br>Example 5-68 | Column: YMC Triart C18 5 μm, 30 × 50 mm<br>Solvent: solution A, 0.1% formic acid-water and solution B, 0.1% formic acid-acetonitrile<br>Elution condition: solution A/solution B = 80/20 → 1/99<br>Flow rate: 40 mL/min, Temperature: room temperature |
| Example 5-69<br>Example 5-70 | Column: YMC Triart C18 5 μm, 30 × 50 mm<br>Solvent: solution A, 0.1% formic acid-water and solution B, 0.1% formic acid-acetonitrile<br>Elution condition: solution A/solution B = 80/20 → 1/99<br>Flow rate: 40 mL/min, Temperature: room temperature |
| Example 10-10<br>Example 10-11 | Column: YMC Triart C18 5 μm, 30 × 50 mm<br>Solvent: solution A, 0.1% formic acid-water and solution B, 0.1% formic acid-acetonitrile<br>Elution condition: solution A/solution B = 80/20 → 1/99<br>Flow rate: 40 mL/min, Temperature: room temperature |

Detection method: UV 210 nm, 254 nm
Preparative isolation by chiral HPLC in Examples was performed under the following conditions.
  HPLC: GILSON high throughput purification system or Waters preparative LC system

[HPLC Conditions]

TABLE 3-1

| | Conditions |
|---|---|
| Example 1-21 (2) | Column: CHIRALPAK IF, 5 μm, 20 × 250 mm<br>Solvent: solution A, 2-propanol and solution B, n-hexane<br>Elution condition: solution A/solution B = 15/85<br>Flow rate: 10 mL/min, Temperature: room temperature |
| Example 1-30 (2) | Column: CHIRALPAK ID3, 5 μm, 20 × 250 mm<br>Solvent: solution A, ethanol and solution B, n-hexane<br>Elution condition: solution A/solution B = 10/90<br>Flow rate: 10 mL/min, Temperature: room temperature |
| Example 1-35<br>Example 1-36 | Column: CHIRALPAK IF3, 5 μm, 20 × 250 mm<br>Solvent: solution A, 2-propanol and solution B, n-hexane<br>Elution condition: solution A/solution B = 10/90<br>Flow rate: 10 mL/min, Temperature: room temperature |
| Example 1-44<br>Example 1-45 | Column: CHIRALPAK ID3, 5 μm, 20 × 250 mm<br>Solvent: solution A, 2-propanol and solution B, n-hexane<br>Elution condition: solution A/solution B = 8/92<br>Flow rate: 10 mL/min, Temperature: room temperature |
| Example 1-78<br>Example 1-79 | Column: CHIRALPAK IE, 5 μm, 20 × 250 mm<br>Solvent: solution A, ethanol and solution B, n-hexane<br>Elution condition: solution A/solution B = 20/80<br>Flow rate: 10 mL/min, Temperature: room temperature |
| Example 1-86 (1) | Column: CHIRALPAK AD-H, 5 μm, 20 × 250 mm<br>Solvent: solution A, ethanol and solution B, n-hexane<br>Elution condition: solution A/solution B = 10/90<br>Flow rate: 10 mL/min, Temperature: room temperature |
| Example 1-88<br>Example 1-89 | Column: CHIRALPAK IF, 5 μm, 20 × 250 mm<br>Solvent: solution A, 2-propanol and solution B, n-hexane<br>Elution condition: solution A/solution B = 15/85<br>Flow rate: 10 mL/min, Temperature: room temperature |
| Example 1-98<br>Example 1-99 | Column: CHIRALPAK IF, 5 μm, 20 × 250 mm<br>Solvent: solution A, 2-propanol and solution B, n-hexane<br>Elution condition: solution A/solution B = 15/85<br>Flow rate: 10 mL/min, Temperature: room temperature |
| Example 1-117 | Column: CHIRALPAK ID, 5 μm, 20 × 250 mm<br>Solvent: solution A, 2-propanol and solution B, n-hexane<br>Elution condition: solution A/solution B = 10/90<br>Flow rate: 10 mL/min, Temperature: room temperature |
| Example 1-123<br>Example 1-124 | Column: CHIRALPAK ID, 5 μm, 20 × 250 mm<br>Solvent: solution A, 2-propanol and solution B, n-hexane<br>Elution condition: solution A/solution B = 5/95<br>Flow rate: 20 mL/min, Temperature: room temperature |
| Example 4-47<br>Example 4-48 | Column: CHIRALPAK ID, 5 μm, 20 × 250 mm<br>Solvent: solution A, 2-propanol and solution B, n-hexane<br>Elution condition: solution A/solution B = 20/80<br>Flow rate: 10 mL/min, Temperature: room temperature |
| Example 4-52<br>Example 4-53 | Column: CHIRALPAK ID, 5 μm, 20 × 250 mm<br>Solvent: solution A, 2-propanol and solution B, n-hexane<br>Elution condition: solution A/solution B = 20/80<br>Flow rate: 10 mL/min, Temperature: room temperature |

TABLE 3-2

| | Conditions |
|---|---|
| Example 4-61<br>Example 4-62 | Column: CHIRALPAK IF, 5 μm, 20 × 250 mm<br>Solvent: solution A, 2-propanol and solution B, n-hexane<br>Elution condition: solution A/solution B = 15/85<br>Flow rate: 10 mL/min, Temperature: room temperature |
| Example 4-76<br>Example 4-77 | Column: CHIRALPAK ID, 5 μm, 20 × 250 mm<br>Solvent: solution A, 2-propanol and solution B, n-hexane<br>Elution condition: solution A/solution B = 30/70<br>Flow rate: 10 mL/min, Temperature: room temperature |
| Example 4-85<br>Example 4-86 | Column: CHIRALPAK ID, 5 μm, 20 × 250 mm<br>Solvent: solution A, 2-propanol and solution B, n-hexane<br>Elution condition: solution A/solution B = 10/90<br>Flow rate: 10 mL/min, Temperature: room temperature |

TABLE 3-2-continued

| | Conditions |
|---|---|
| Example 4-103 | Column: CHIRALPAK ID, 5 μm, 20 × 250 mm |
| Example 4-104 | Solvent: solution A, 2-propanol and solution B, n-hexane |
| | Elution condition: solution A/solution B = 30/70 |
| | Flow rate: 10 mL/min, Temperature: room temperature |
| Example 4-123 | Column: CHIRALPAK IF, 5 μm, 20 × 250 mm |
| Example 4-124 | Solvent: solution A, 2-propanol and solution B, n-hexane |
| | Elution condition: solution A/solution B = 20/80 |
| | Flow rate: 10 mL/min, Temperature: room temperature |
| Example 4-125 | Column: CHIRALPAK IF, 5 μm, 20 × 250 mm |
| Example 4-126 | Solvent: solution A, 2-propanol and solution B, n-hexane |
| | Elution condition: solution A/solution B = 20/80 |
| | Flow rate: 10 mL/min, Temperature: room temperature |
| Example 4-133 | Column: CHIRALPAK ID, 5 μm, 20 × 250 mm |
| Example 4-134 | Solvent: solution A, 2-propanol and solution B, n-hexane |
| | Elution condition: solution A/solution B = 30/70 |
| | Flow rate: 10 mL/min, Temperature: room temperature |
| Example 4-135 | Column: CHIRALPAK ID, 5 μm, 20 × 250 mm |
| Example 4-136 | Solvent: solution A, 2-propanol and solution B, n-hexane |
| | Elution condition: solution A/solution B = 30/70 |
| | Flow rate: 10 mL/min, Temperature: room temperature |
| Example 4-143 | Column: CHIRALPAK IF, 5 μm, 20 × 250 mm |
| Example 4-144 | Solvent: solution A, 2-propanol and solution B, n-hexane |
| | Elutiou condition: solution A/solution B = 20/80 |
| | Flow rate: 10 mL/min, Temperature: room temperature |
| Example 5-59 | Column: CHIRALPAK IF, 5 μm, 20 × 250 mm |
| Example 5-60 | Solvent: solution A, 2-propanol and solution B, n-hexane |
| | Elution condition: solution A/solution B = 82/18 |
| | Flow rate: 10 mL/min, Temperature: room temperature |
| Example 5-61 | Column: CHIRALPAK IF3, 5 μm, 20 × 250 mm |
| Example 5-62 | Solvent: solution A, 2-propanol and solution B, n-hexane |
| | Elution condition: solution A/solution B = 20/80 |
| | Flow rate: 10 mL/min, Temperature: room temperature |
| Example 5-63 | Column: CHIRALPAK IF, 5 μm, 20 × 250 mm |
| Example 5-64 | Solvent: solution A, 2-propanol and solution B, n-hexane |
| | Elution condition: solution A/solution B = 82/18 |
| | Flow rate: 10 mL/min, Temperature: room temperature |

TABLE 3-3

| | Conditions |
|---|---|
| Example 5-108 | Column: CHIRALPAK ID3, 5 μm, 20 × 250 mm |
| Example 5-109 | Solvent: solution A, ethanol and solution B, n-hexane |
| | Elution condition: solution A/solution B = 5/95 |
| | Flow rate: 11 mL/min, Temperature: room temperature |
| Example 5-110 | Column: CHIRALPAK ID3, 5 μm, 20 × 250 mm |
| Example 5-111 | Solvent: solution A, ethanol and solution B, n-hexane |
| | Elution condition: solution A/solution B = 20/80 |
| | Flow rate: 11 mL/min, Temperature: room temperature |
| Example 5-115 | Column: CHIRALPAK ID3, 5 μm, 20 × 250 mm |
| | Solvent: solution A, ethanol and solution B, n-hexane |
| | Elution condition: solution A/solution B = 10/90 |
| | Flow rate: 10 mL/min, Temperature: room temperature |

TABLE 3-3-continued

| | Conditions |
|---|---|
| Example 5-57 | Column: CHIRALPAK IF3, 5 μm, 20 × 250 mm |
| Example 5-58 | Solvent: solution A, ethanol and solution B, n-hexane |
| | Elution condition: solution A/solution B = 15/85 |
| | Flow rate: 10 mL/min, Temperature: room temperature |

Detection method: UV 210 nm, 254 nm

Preparative isolation by chiral supercritical fluid chromatography (SFC) in Examples was performed under the following conditions.

SFC: SFC30 manufactured by Waters Corporation

[SFC Conditions]

TABLE 4-1

| | Conditions |
|---|---|
| Example 5-55 | Column: CHIRALCEL IC, 20 × 250 mm |
| Example 5-56 | Solvent: solution A, ethanol and solution B, carbon dioxide |
| | Elution condition: solution A/solution B = 12/88 |
| | Flow rate: 30 mL/min, Temperature: 40° C. |

Detection method: UV 210 nm, 254 nm

Autopol V (Rudolph Research Analytical Corporation) was used as the optical rotation measuring apparatus, and the sodium D line (589 nm) was used as the light source.

For the X-ray crystal structure analysis, the R-AXIS RAPID II apparatus (manufacturer: Rigaku Corporation) was used.

Biotage Initiator or Anton-Paar MONOWAVE 300 was used as the microwave reaction apparatus.

Thermogravimetry-differential thermal analysis (TG/DTA) was performed by Thermo Plus Evo TG8120 (Rigaku).

Compound names were assigned by ACD/Name (ACD/Name 2017.1.3 and ACD/Name 2019.1.2, Advanced Chemistry Development, Inc.) and a component of Pipeline Pilot 9.1, LexiChem (version 0.95) manufactured by OpenEye Scientific Software, Inc.

As for the asymmetric carbons in the compounds of Reference Examples and Examples, the steric structure shown herein indicates the absolute configuration. Note that the relative configuration is shown for meso forms.

Compounds for which the absolute configuration of the asymmetric carbon is indicated are optically active forms.

Also, in compounds where an asterisk (*) is indicated at the asymmetric carbon in the structural formula, the asterisk means that the ratio of one absolute configuration is greater than that of the other with respect to stereoisomerism at the asymmetric carbon indicated. Note that it is preferable for such compounds to have a substantially single absolute configuration. Alternatively, the absolute configuration of the asymmetric carbon may be unknown.

As used herein, the term "room temperature" refers to 20 to 30° C. unless otherwise noted. The term "ice-cooled temperature" refers to 0 to 5° C. unless otherwise noted.

The present invention will be further described in detail with reference to the following Reference Examples, Examples, and Test Examples. However, they do not limit the present invention, and may be varied in the range without departing the scope of the present invention.

Reference Example 1-1-1

Methyl 3-Methoxy-5-(Methoxymethyl)Benzoate

[Chemical Formula 366]

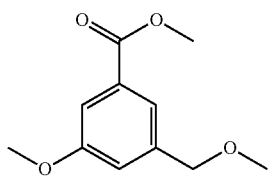

To a mixed solution of methyl 3-(bromomethyl)-5-methoxybenzoate (150 mg) in methanol-tetrahydrofuran (2.9 mL-2.9 mL), potassium carbonate (168 mg) was added, and the reaction solution was stirred at 55° C. for 3 hours and at room temperature overnight. The reaction solution was filtered through Celite (registered trademark), and the filtrate was concentrated to afford a mixture (327 mg) containing the title compound as a colorless solid.

MS ESI posi: 211 [M+H]$^+$.
Retention time: 0.912 min (method B)

Reference Example 1-1-2

Ethyl 6-Ethoxy-1-Ethyl-2,3-Dihydro-1H-Indole-4-Carboxylate

[Chemical Formula 367]

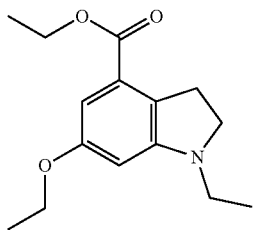

(1) A solution of ethyl 6-ethoxy-1H-indole-4-carboxylate (0.488 g) in N,N-dimethylformamide (4.2 mL) was ice-cooled, sodium hydride (60% mineral oil dispersion, 92.0 mg) was added thereto, and the reaction solution was stirred at the same temperature for 30 minutes. A solution of iodoethane (0.254 mL) in N,N-dimethylformamide (3 mL) was added dropwise thereto, and the reaction solution was stirred for 30 minutes while bringing it back to room temperature. The reaction solution was ice-cooled, a saturated aqueous ammonium chloride solution was added thereto, and extraction with ethyl acetate was carried out. The organic layer was washed with a brine and dried over anhydrous magnesium sulfate. After filtering off the desiccating agent, the filtrate was concentrated. The obtained residue was purified by silica gel column chromatography (n-hexane only to ethyl acetate only) to afford ethyl 6-ethoxy-1-ethyl-1H-indole-4-carboxylate (0.402 g) as a colorless powder.

(2) To a solution of the compound (0.2 g) obtained in (1) above in acetic acid (1 mL), sodium cyanoborohydride (0.144 g) was slowly added, and the reaction solution was stirred at room temperature for 1 hour. A saturated aqueous sodium bicarbonate solution was added to the reaction solution, which was then extracted with ethyl acetate. The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=80:20) to afford the title compound (0.142 g) as a light yellow oily substance.

MS ESI posi: 264 [M+H]$^+$.
Retention time: 1.264 min (method B)

Reference Example 1-2-1

Methyl 3,5-Diethoxy-2,4-Dimethylbenzoate

[Chemical Formula 368]

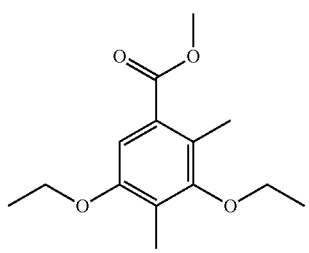

(1) To a solution of methyl 3,5-dihydroxy-4-methylbenzoate (5 g) in N,N-dimethylformamide (55 mL), potassium carbonate (3.79 g) and iodoethane (2.66 mL) were added, and the reaction solution was stirred at room temperature for 18 hours. Water was added to the reaction solution, which was then extracted with a mixed solvent of n-hexane-ethyl acetate (2:1). The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=70:30) to afford methyl 3,5-diethoxy-4-methylbenzoate (2.16 g) and methyl 3-ethoxy-5-hydroxy-4-methylbenzoate (2.02 g) each as a colorless powder.

(2) Under a nitrogen atmosphere, a solution of methyl 3,5-diethoxy-4-methylbenzoate (0.5 g) obtained in (1) above in chloroform (0.8 mL) was ice-cooled, and titanium (IV) chloride (0.506 mL) was added dropwise. The reaction solution was stirred at the same temperature for 30 minutes, and dichloromethyl methyl ether (0.187 mL) was added dropwise thereto. Chloroform (0.8 mL) was further added to the reaction solution, which was then stirred for 30 minutes while bringing it back to room temperature. A saturated aqueous ammonium chloride solution was added to the reaction solution, which was then stirred for 1 hour. Water was further added thereto, and extraction with chloroform was carried out. The organic layer was washed with 0.1 mol/L hydrochloric acid, a saturated aqueous sodium bicarbonate solution, and a brine sequentially, and dried over anhydrous magnesium sulfate. After filtering off the desiccating agent, the filtrate was concentrated. The obtained residue was purified by silica gel column chromatography (n-hexane only to n-hexane:ethyl acetate=85:15) to afford methyl 3,5-diethoxy-2-formyl-4-methylbenzoate (0.527 g) as a yellow oily substance.

(3) To a solution of the compound (0.1 g) obtained in (2) above in trifluoroacetic acid (0.3 mL), triethylsilane (0.72 mL) was added, and the reaction solution was stirred at room temperature for 1 hour. Water was added to the reaction solution, which was then extracted with chloroform. The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=80:20) to afford the title compound (0.062 g) as a colorless oily substance.

MS ESI posi: 253 [M+H]$^+$.
Retention time: 1.057 min (method A)

Reference Example 1-2-2

Methyl 3,5-Diethoxy-2-Fluoro-4-Methylbenzoate

[Chemical Formula 369]

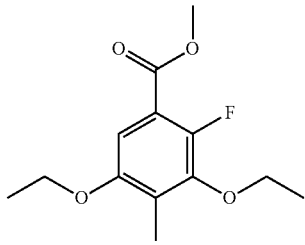

Under a nitrogen atmosphere, a solution of methyl 3,5-diethoxy-4-methylbenzoate (0.5 g) obtained in Reference Example 1-2-1 (1) in acetonitrile (1.0 mL) was ice-cooled, a solution of N-fluoro-N'-(chloromethyl)triethylenediamine bis(tetrafluoroborate) (1.12 g) in acetonitrile (21 mL) was added thereto, and the reaction solution was stirred at room temperature for 23 hours. A saturated aqueous sodium bicarbonate solution was added to the reaction solution, which was then extracted with ethyl acetate. The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=90:10) to afford the title compound (0.32 g) as a yellow oily substance.

MS ESI posi: 257 [M+H]$^+$, 279 [M+Na]$^+$.
Retention time: 0.953 min (method A)

Reference Example 1-2-3

Ethyl 2-Chloro-3,5-Diethoxy-4-Methylbenzoate

[Chemical Formula 370]

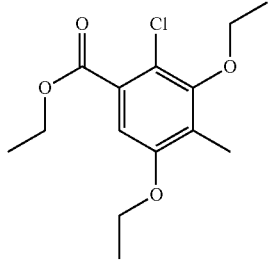

(1) To a solution of 3,5-dihydroxy-4-methylbenzoic acid (2 g) in methanol (30 mL), N-chlorosuccinimide (1.75 g) was added, and the reaction solution was stirred at 60° C. for 4 hours and at room temperature for 15 hours. Water was added to the reaction solution, which was then extracted with ethyl acetate. The organic layer was washed with a brine and dried over anhydrous magnesium sulfate. After filtering off the desiccating agent, the filtrate was concentrated to afford 2-chloro-3,5-dihydroxy-4-methylbenzoic acid (2.55 g) as a light yellow powder.

(2) To a solution of the compound (2.41 g) obtained in (1) above and potassium carbonate (8.22 g) in N,N-dimethylformamide (24 mL), iodoethane (4.81 mL) was added, and the reaction solution was stirred at room temperature for 18 hours. Water was added to the reaction solution, which was then extracted with a mixed solvent of n-hexane-ethyl acetate (2:1). The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=90:10) to afford the title compound (2.99 g) as a colorless oily substance.

MS ESI posi: 287 [M+H]$^+$, 309 [M+Na]$^+$.
Retention time: 1.023 min (method A)

Reference Example 1-3-1

3-Ethoxy-5-(Methoxymethyl)-4-Methylbenzoic Acid

[Chemical Formula 371]

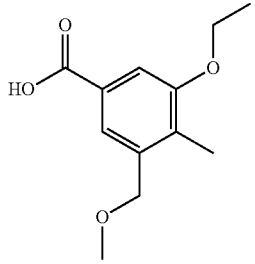

(1) Under a nitrogen atmosphere, to a solution of methyl 3-ethoxy-5-hydroxy-4-methylbenzoate (300 mg) obtained in Reference Example 1-2-1 (1) in chloroform (5.7 mL), pyridine (0.23 mL) and trifluoromethanesulfonic anhydride (0.288 mL) were added, and the reaction solution was stirred at room temperature for 3 hours. After distilling off the solvent under reduced pressure, the obtained residue was purified by silica gel column chromatography (n-hexane:ethyl acetate=95:5 to 20:80) to afford methyl 3-ethoxy-4-methyl-5-[(trifluoromethanesulfonyl)oxy]benzoate (450 mg) as a colorless oily substance.

(2) The present reaction was carried out with reference to the method described in the literature (Organic Letters, vol. 14, p. 1278, 2012). Under a nitrogen atmosphere, to a mixed solution of the compound (400 mg) obtained in (1) above in 1,4-dioxane-water (2 mL-0.2 mL), sodium carbonate (0.186 g), potassium (acetoxymethyl)trifluoroborate (0.316 g), and (2-dicyclohexylphosphino-2',6'-diisopropoxy-1,1'-biphenyl) [2-(2'-amino-1,1'-biphenyl)]palladium (II) methanesulfonate (RuPhosPdG3, Sigma-Aldrich, 97.7 mg) were added, and the reaction solution was stirred at 100° C. for 5 hours. After distilling off the solvent under reduced pressure, the obtained residue was purified by silica gel column chromatography (n-hexane:ethyl acetate=95:5 to 20:80) to afford methyl 3-ethoxy-5-(hydroxymethyl)-4-methylbenzoate (250 mg) as a colorless oily substance.

(3) To a solution of the compound (250 mg) obtained in (2) above in tetrahydrofuran (11 mL), sodium hydride (60% mineral oil dispersion, 67 mg) was added, and the reaction solution was stirred under ice cooling for 1 hour. Iodomethane (0.1 mL) was added thereto, and the reaction solution was stirred at room temperature overnight. Water was added to the reaction solution, which was then extracted with ethyl acetate. The organic layer was washed with water and a brine sequentially, and anhydrous magnesium sulfate was added thereto. The desiccating agent was filtered off, followed by concentration. The residue was purified by silica gel column chromatography (n-hexane only to ethyl acetate only) to afford methyl 3-ethoxy-5-(methoxymethyl)-4-methylbenzoate (84 mg) as a brown oily substance.

(4) To a solution of the compound (84 mg) obtained in (3) above in tetrahydrofuran (3.5 mL), a 1 mol/L aqueous sodium hydroxide solution (3.5 mL) and methanol (1.8 mL) were added, and the reaction solution was stirred at 60° C. for 30 minutes. The reaction solution was concentrated, 1 mol/L hydrochloric acid was added thereto to make the solution acidic, and extraction with chloroform was carried out. The organic layer was filtered through Phase Separator and concentrated to afford the title compound (85 mg) as a colorless powder.

MS ESI posi: 225 [M+H]$^+$.

MS ESI nega: 223 [M−H]$^−$.

Retention time: 1.128 min (method B)

Reference Example 1-4-1

4-Bromo-3,5-Dimethoxybenzaldehyde

[Chemical Formula 372]

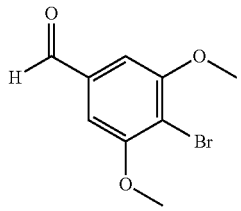

(1) A solution of 4-bromo-3,5-dimethoxybenzoic acid (3.0 g) in tetrahydrofuran (7.7 mL) was ice-cooled, and borane-tetrahydrofuran complex (0.9 mol/L tetrahydrofuran solution, 20 mL) was slowly added thereto. The reaction solution was stirred at the same temperature for 30 minutes and stirred at room temperature for 2 hours. The reaction solution was ice-cooled, a saturated aqueous sodium bicarbonate solution was added thereto, and extraction with ethyl acetate was carried out. The organic layer was filtered through Phase Separator and concentrated to afford (4-bromo-3,5-dimethoxyphenyl) methanol (2.8 g) as a colorless powder.

(2) To a solution of the compound (2.3 g) obtained in (1) above in toluene (62 mL), manganese dioxide (8.1 g) was added, and the reaction solution was stirred at room temperature for 16 hours. The reaction solution was filtered through Celite (registered trademark), and the filtrate was concentrated to afford the title compound (2.18 g) as a light yellow powder.

MS ESI posi: 254 [M+H]$^+$.

Retention time: 0.996 min (method B)

Reference Example 1-4-2

3,5-Diethoxy-4-Methylbenzaldehyde

[Chemical Formula 373]

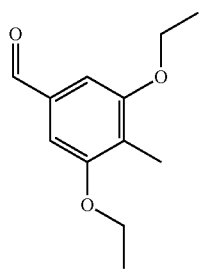

(1) A solution of methyl 3,5-diethoxy-4-methylbenzoate (1.1 g) obtained in Reference Example 1-2-1 (1) in tetrahydrofuran (18 mL) was ice-cooled, lithium aluminum hydride (0.26 g) was added thereto, and the reaction solution was stirred at room temperature for 1 hour. Sodium sulfate decahydrate (3 g) was added thereto, and the reaction solution was stirred for 2 hours. The reaction solution was filtered through Celite (registered trademark), and the filtrate was concentrated to afford (3,5-diethoxy-4-methylphenyl) methanol (0.98 g) as a light yellow solid.

(2) Using the compound (0.98 g) obtained in (1) above, the reaction and post treatment were carried out in accordance with the method described in Reference Example 1-4-1 (2), and the obtained residue was purified by silica gel column chromatography (n-hexane:ethyl acetate=95:5 to 60:40) to afford the title compound (205 mg) as a yellow solid.

MS ESI posi: 209 [M+H]$^+$.

Retention time: 1.196 min (method B)

The following Reference Examples 1-4-3 to 1-4-6 were synthesized by the method described in Reference Example 1-4-1 or Reference Example 1-4-2 or by a method equivalent thereto, using commercially available compounds or compounds obtained by synthesis according to methods described in literatures or methods equivalent thereto. The structures and LCMS data of the compounds are shown in Table 5-1.

TABLE 5-1

| Reference Example No. | Structural Formula | MS posi m/z MS nega m/z | Retention time (min) | method |
|---|---|---|---|---|
| 1-4-3 | (3,5-dimethoxy-4-methylbenzaldehyde) | 181 [M + H]+ | 1.031 | B |
| 1-4-4 | (4,6-diethoxypyridine-2-carbaldehyde) | 196 [M + H]+ | 0.976 | E |
| 1-4-5 | (2,6-diethoxypyridine-4-carbaldehyde) | 196 [M + H]+ | 1.036 | E |
| 1-4-6 | (4-ethoxy-2,3-dihydrobenzofuran-6-carbaldehyde) | 193 [M + H]+ | 0.939 | B |

Reference Example 1-5-1

1-(4-Bromo-3,5-Diethoxyphenyl) Ethan-1-One

[Chemical Formula 374]

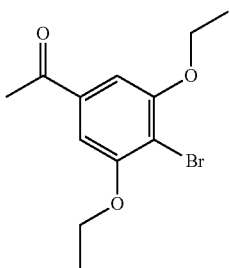

(1) Using 4-bromo-3,5-dihydroxybenzoic acid (4 g), the reaction and post treatment were carried out in accordance with the method described in Reference Example 1-2-3 (2). A mixed solution of n-hexane-ethyl acetate (4:3, 7 mL) was added to the obtained residue, which was then dissolved therein, and n-hexane (12 mL) was further added thereto. The precipitated solid was filtered off and the filtrate was concentrated. Ethyl acetate (3 mL) was added to the obtained residue, which was then dissolved therein, n-hexane (16 mL) was further added thereto, and the precipitated solid was filtered off. The obtained solids were combined to afford ethyl 4-bromo-3,5-diethoxybenzoate (5.11 g) as a colorless solid.

(2) Using the compound (5.11 g) obtained in (1) above, the reaction was carried out in accordance with the method described in Reference Example 1-3-1 (4), and 4-bromo-3,5-diethoxybenzoic acid (4.68 g) was obtained as a colorless solid.

(3) To a solution of the compound (4.68 g) obtained in (2) above in N,N-dimethylformamide (26 mL), N,O-dimethylhydroxylamine hydrochloride (1.65 g), HATU (9.19 g), and N,N-diisopropylethylamine (11.2 mL) were added, and the reaction solution was stirred at room temperature for 3 hours. A saturated aqueous sodium bicarbonate solution (150 mL) was added to the reaction solution, which was then extracted with a mixed solvent of n-hexane-ethyl acetate (2:1, 100 mL) twice. The organic layer was washed with a brine, filtered through Phase Separator, and concentrated. The obtained residue was purified by NH silica gel column chromatography (n-hexane only to n-hexane:ethyl acetate=60:40) to afford 4-bromo-3,5-diethoxy-N-methoxy-N-methylbenzamide (6.2 g) as a light yellow oily substance.

(4) Under a nitrogen atmosphere, a solution of the compound (5.36 g) obtained in (3) above in tetrahydrofuran (54 mL) was ice-cooled, methylmagnesium bromide (3 mol/L diethyl ether solution, 16.1 mL) was added thereto, and the reaction solution was stirred at the same temperature for 30 minutes and at room temperature for 4.5 hours. The reaction solution was ice-cooled, a saturated aqueous ammonium chloride solution was added thereto, and extraction with ethyl acetate was carried out. The organic layer was washed with a brine, filtered through Phase Separator, and concentrated. To the obtained residue, a mixed solvent of n-hexane-ethyl acetate (2:1, 60 mL) was added, and the precipitated solid was filtered off to afford the title compound (3.18 g) as a colorless solid.

MS ESI posi: 287, 289 [M+H]⁺.
Retention time: 1.149 min (method B)

Reference Example 1-5-2

1-(3,5-Diethoxy-4-Methylphenyl) Ethan-1-One

[Chemical Formula 375]

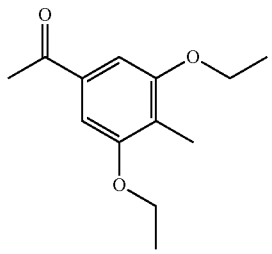

(1) Using 3,5-dihydroxy-4-methylbenzoic acid (3 g), the reaction was carried out in accordance with the method described in Reference Example 1-2-3 (2), and ethyl 3,5-diethoxy-4-methylbenzoate (4.45 g) was obtained as a light brown solid.

(2) Using the compound (4.2 g) obtained in (1) above, the reaction was carried out in accordance with the method described in Reference Example 1-3-1 (4), and 3,5-diethoxy-4-methylbenzoic acid (3.74 g) was obtained as a colorless powder.

(3) The present reaction was carried out with reference to the method described in the literature (Synlett, vol. 26, p. 1395, 2015). Under a nitrogen atmosphere, a solution of the compound (3.7 g) obtained in (2) above in diethyl ether (130 mL) was ice-cooled, methyllithium (1 mol/L diethyl ether solution, 50 mL) was added thereto, and the reaction solution was stirred at the same temperature for 10 minutes and at room temperature overnight. The reaction solution was ice-cooled, water was slowly added thereto, and the reaction solution was made acidic with 2 mol/L hydrochloric acid. The reaction solution was stirred for 30 minutes and extracted with diethyl ether three times. The organic layer was washed with a saturated aqueous sodium bicarbonate solution (60 mL) and a brine (60 mL) sequentially, filtered through Phase Separator, and concentrated. The obtained residue was purified by silica gel column chromatography (n-hexane:ethyl acetate=88:12 to ethyl acetate only) to afford the title compound (2.0 g) as a colorless powder.

MS ESI posi: 223 [M+H]⁺.
Retention time: 0.931 min (method A)

The following Reference Examples 1-5-3 to 1-5-30 were synthesized by the method described in Reference Example 1-5-1 or Reference Example 1-5-2 or by a method equivalent thereto, using the compounds obtained in Reference Examples 1-1-1 to 1-1-2, Reference Examples 1-2-1 to 1-2-3, and Reference Example 1-3-1, commercially available compounds, or compounds obtained by synthesis according to methods described in literatures or methods equivalent thereto. The structures and LCMS data of the compounds are shown in Table 6-1 to Table 6-6.

TABLE 6-1

| Reference Example No. | | MS posi m/z MS nega m/z | Retention time (min) | method |
|---|---|---|---|---|
| 1-5-3 | | 237 [M + H]+ | 1.189 | E |
| 1-5-4 | | 209 [M + H]+ | 1.008 | E |

TABLE 6-1-continued

| Reference Example No. | Structure | MS posi m/z MS nega m/z | Retention time (min) | method |
|---|---|---|---|---|
| 1-5-5 | | 223 [M + H]+ | 1.159 | B |
| 1-5-6 | | 190 [M + H]+ | 1.003 | B |
| 1-5-7 | | 195 [M + H]+ | 0.851 | B |

TABLE 6-2

| Reference Example No. | Structure | MS posi m/z MS nega m/z | Retention time (min) | method |
|---|---|---|---|---|
| 1-5-8 | | 243 [M + H]+ | 1.171 | B |
| 1-5-9 | | 207 [M + H]− | 0.695 | E |
| 1-5-10 | | 243 [M + H]+ | 1.014 | B |

TABLE 6-2-continued

| Reference Example No. | | MS posi m/z MS nega m/z | Retention time (min) | method |
|---|---|---|---|---|
| 1-5-11 | | 277 [M + H]+ | 0.893 | A |
| 1-5-12 | | 237 [M + H]+ | 1.285 | B |

TABLE 6-3

| Reference Example No. | Structural Formula | MS posi m/z MS nega m/z | Retention time (min) | method |
|---|---|---|---|---|
| 1-5-13 | | 251 [M + H]+ | 1.029 | A |
| 1-5-14 | | 223 [M + H]+ | 1.235 | B |

TABLE 6-3-continued

| Reference Example No. | Structural Formula | MS posi m/z MS nega m/z | Retention time (min) | method |
|---|---|---|---|---|
| 1-5-15 | | 237 [M + H]+ | 0.988 | A |
| 1-5-16 | | 215 [M + H]+ | 0.711 | A |
| 1-5-17 | | 195 [M + H]+ | 0.743 | D |

TABLE 6-4

| Reference Example No. | Structural Formula | MS posi m/z MS nega m/z | Retention time (min) | method |
|---|---|---|---|---|
| 1-5-18 | | 253 [M + H]+ | 0.997 | B |
| 1-5-19 | | 237 [M + H]+ | 1.020 | A |

TABLE 6-4-continued

| Reference Example No. | Structural Formula | MS posi m/z MS nega m/z | Retention time (min) | method |
|---|---|---|---|---|
| 1-5-20 | | 241 [M + H]+ | 0.947 | A |
| 1-5-21 | | 257 [M + H]+ 279 [M + H]+ | 0.908 | A |
| 1-5-22 | | 183 [M + H]+ | 0.687 | B |

TABLE 6-5

| Reference Example No. | Structural Formula | MS posi m/z MS nega m/z | Retention time (min) | method |
|---|---|---|---|---|
| 1-5-23 | | 183 [M + H]+ | 0.791 | B |
| 1-5-24 | | 166 [M + H]+ | 0.587 | B |

TABLE 6-5-continued
| Reference Example No. | Structural Formula | MS posi m/z MS nega m/z | Retention time (min) | method |
|---|---|---|---|---|
| 1-5-25 | 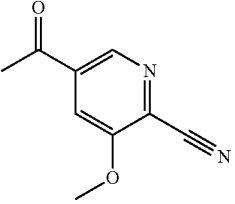 | 177 [M + H]+ | 0.660 | B |
| 1-5-26 | 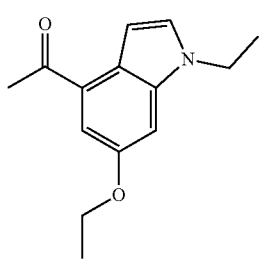 [SMILES: CCOc1cc(C(C)=O)c2ccn(CC)c2c1] | 232 [M + H]+<br>254 [M + Na]+ | 1.052 | B |
| 1-5-27 | 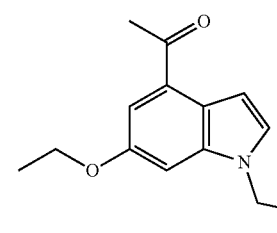 | 246 [M + H]+ | 0.985 | A |
TABLE 6-6
| Reference Example No. | Structural Formula | MS posi m/z MS nega m/z | Retention time (min) | method |
|---|---|---|---|---|
| 1-5-28 | 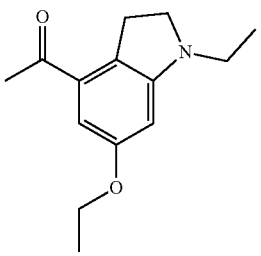 [SMILES: CCOc1cc(C(C)=O)c2c(c1)N(CC)CC2] | 234 [M + H]+ | 1.100 | B |
| 1-5-29 | 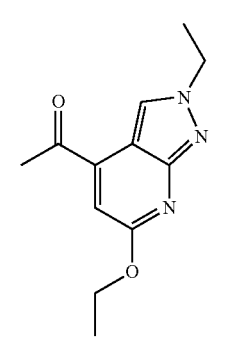 [SMILES: CCOc1cc(C(C)=O)c2cn(CC)nc2n1] | 234 [M + H]+ | 0.715 | A |

TABLE 6-6-continued

| Reference Example No. | Structural Formula | MS posi m/z MS nega m/z | Retention time (min) | method |
|---|---|---|---|---|
| 1-5-30 | | 209 [M + H]+ | 1.096 | B |

Reference Example 1-6-1

1-(4-Bromo-3,5-Dimethoxyphenyl) Ethan-1-One

[Chemical Formula 376]

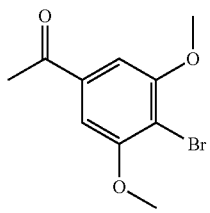

(1) A solution of the compound (506 mg) obtained in Reference Example 1-4-1 in tetrahydrofuran (4.1 mL) was ice-cooled, methylmagnesium bromide (3 mol/L diethyl ether solution, 688 μL) was added thereto, and the reaction solution was stirred at room temperature for 2.5 hours. The reaction solution was ice-cooled, a saturated aqueous ammonium chloride solution (5 mL) was added thereto, and the reaction solution was extracted with chloroform, filtered through Phase Separator, and concentrated. The obtained residue was purified by silica gel column chromatography (n-hexane:ethyl acetate=95:5 to 35:65) to afford 1-(4-bromo-3,5-dimethoxyphenyl) ethan-1-ol (443 mg) as a colorless solid.

(2) Using the compound (443 mg) obtained in (1) above, the reaction was carried out in accordance with the method described in Reference Example 1-4-1 (2), and the title compound (394 mg) was obtained as a colorless powder.

MS ESI posi: 259 [M+H]⁺.

Retention time: 1.012 min (method B)

The following Reference Example 1-6-2 was synthesized by the method described in Reference Example 1-6-1 or by a method equivalent thereto, using the compound obtained in Reference Example 1-4-3, a commercially available compound, or a compound obtained by synthesis according to methods described in literatures or methods equivalent thereto. The structure and LCMS data of the compound are shown in Table 7-1.

TABLE 7-1

| Reference Example No. | Structural Formula | MS posi m/z MS nega m/z | Retention time (min) | method |
|---|---|---|---|---|
| 1-6-2 | | 209 [M + H]+ | 1.090 | E |

Reference Example 1-7-1

1-(3-Ethoxy-5-Propylphenyl) Ethan-1-One

[Chemical Formula 377]

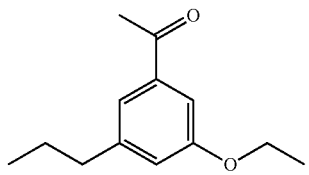

The present reaction was carried out with reference to the method described in the literature (The Journal of Organic Chemistry, vol. 74, p. 3626, 2009). Toluene (2.1 mL) and water (0.206 mL) were added to the compound (0.05 g) obtained in Reference Example 1-5-8, ethylboronic acid (22.8 mg), potassium carbonate (85.3 mg), palladium (II) acetate (9.23 mg), 2-dicyclohexylphosphino-2',6'-diisopropoxybiphenyl(RuPhos, 38.4 mg), and the reaction solution was stirred at 120° C. for 70 minutes under microwave irradiation. Insolubles in the reaction solution were filtered off and the filtrate was concentrated. The obtained residue was purified by NH silica gel column chromatography (n-hexane only to n-hexane:ethyl acetate=80:20) to afford the title compound (32.3 mg) as a colorless oily substance.

MS ESI posi: 207 [M+H]$^+$.

Retention time: 1.265 min (method B)

Reference Example 1-7-2

3-Acetyl-5-Ethoxybenzamide

[Chemical Formula 378]

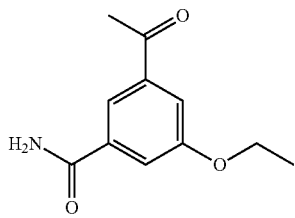

To a solution of the compound (53.6 mg) obtained in Reference Example 1-5-6 in dimethyl sulfoxide (1 mL), a 1 mol/L aqueous sodium hydroxide solution (2.83 mL), hydrogen peroxide (30% aqueous solution, 86.8 L), and ethanol (1 mL) were added, and the reaction solution was stirred at room temperature for 4 hours. A mixed solution of saturated aqueous sodium thiosulfate solution-water (1:1) was added to the reaction solution, which was then extracted with ethyl acetate. The organic layer was washed with a brine, filtered through Phase Separator, and concentrated. The obtained residue was purified by silica gel column chromatography (n-hexane:ethyl acetate=70:30 to ethyl acetate only) to afford the title compound (66.1 mg) as a colorless solid.

MS ESI posi: 208 [M+H]$^+$.

Retention time: 0.741 min (method B)

Reference Example 1-7-3

3-Acetyl-5-Ethoxy-N-Methylbenzamide

[Chemical Formula 379]

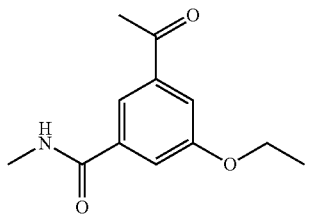

A solution of the compound (1.5 g) obtained in Reference Example 1-5-9 in tetrahydrofuran (23 mL) was ice-cooled, methylamine (2 mol/L tetrahydrofuran solution, 25 mL), EDC (2.8 g), and HOBt (2.2 g) were added thereto, and the reaction solution was stirred at room temperature for 17 hours. The reaction solution was ice-cooled, a saturated aqueous sodium bicarbonate solution and water were added thereto, and extraction with ethyl acetate was carried out three times. The organic layer was washed with a brine, filtered through Phase Separator, and concentrated. The obtained residue was purified by preparative HPLC to afford the title compound (35 mg) as a light yellow oily substance.

MS ESI/APCI Multi posi: 222 [M+H]$^+$.

Retention time: 0.965 min (method F)

Reference Example 1-7-4

1,1'-(2-Ethoxy-6-Fluoro-1,4-Phenylene)Di(Ethan-1-One)

[Chemical Formula 380]

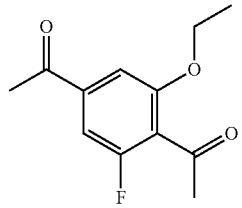

(1) The present reaction was carried out with reference to the method described in the literature (WO 2014/191535). To a solution of 4-bromo-2,6-difluorobenzaldehyde (3 g) in N,N-dimethylformamide (14 mL), potassium carbonate (3.38 g) and water (1.2 mL) were added, and the reaction solution was stirred at 90° C. for 11 hours and at room temperature overnight. Potassium carbonate (1.78 g) and iodoethane (3.91 mL) were further added to the reaction solution, which was then stirred at 65° C. for 7 hours. The reaction solution was filtered through Celite (registered trademark), and water was added to the filtrate, which was then extracted with ethyl acetate twice. The organic layer was washed with 0.5 mol/L hydrochloric acid three times and with a brine once, filtered through Phase Separator, and concentrated. The obtained residue was purified by silica gel column chromatography (n-hexane only to n-hexane:ethyl acetate=80:20) to afford 4-bromo-2-ethoxy-6-fluorobenzaldehyde (0.752 g) as a colorless solid.

(2) Using the compound (0.2 g) obtained in (1) above, the reaction was carried out in accordance with the method described in Reference Example 1-6-1 (1), and 1-(4-bromo-2-ethoxy-6-fluorophenyl) ethan-1-ol (218 mg) was obtained as a light pink oily substance.

(3) To a solution of the compound (218 mg) obtained in (2) above in n-hexane (10 mL), manganese dioxide (0.8 g) was added, and the reaction solution was stirred at room temperature overnight. The reaction solution was filtered through Celite (registered trademark), and the filtrate was concentrated. The obtained residue was purified by silica gel column chromatography (n-hexane only to n-hexane:ethyl acetate=70:30) to afford 1-(4-bromo-2-ethoxy-6-fluorophenyl) ethan-1-one (81.3 mg) as a colorless oily substance.

(4) To a mixed solution of the compound (81.3 mg) obtained in (3) above in N,N-dimethylformamide-water (1.56 mL-0.156 mL), butyl vinyl ether (200 μL), palladium (II) acetate (2.10 mg), 1,3-bis(diphenylphosphino) propane (7.70 mg), and potassium carbonate (0.129 g) were added, and the reaction solution was stirred at 120° C. for 1 hour under microwave irradiation. Butyl vinyl ether (200 μL), palladium (II) acetate (6.99 mg), and 1,3-bis(diphenylphosphino) propane (25.7 mg) were further added thereto, and the reaction solution was stirred at 120° C. for 1 hour under microwave irradiation. 1 mol/L hydrochloric acid (3 mL) and ethyl acetate were added to the reaction solution, which was then stirred at room temperature for 1.5 hours. The reaction solution was added to a 10% aqueous potassium carbonate solution, and extracted with ethyl acetate. The organic layer was washed with a brine, filtered through Phase Separator, and concentrated. The obtained residue was purified by silica gel column chromatography (n-hexane only to n-hexane:ethyl acetate=70:30) to afford the title compound (18.3 mg) as a light yellow oily substance.

MS ESI posi: 225 [M+H]$^+$.

Retention time: 0.879 min (method B)

Reference Example 1-7-5

1-[3-Ethoxy-5-Fluoro-4-(1-Hydroxyethyl)Phenyl]Ethan-1-One

[Chemical Formula 381]

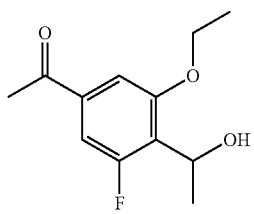

Using the compound (95.3 mg) obtained in Reference Example 1-7-4 (2), the reaction was carried out in accordance with the method described in Reference Example 1-7-4 (4), and the title compound (22.4 mg) was obtained as a colorless solid.

MS ESI posi: 209 [M−OH]$^+$.

Retention time: 0.773 min (method B)

Reference Example 1-7-6

4-Ethoxy-1-Ethyl-1H-Indazole-6-Carbaldehyde

[Chemical Formula 382]

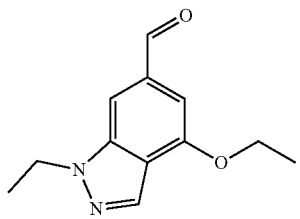

(1) To a solution of the compound (5.8 g) obtained in Reference Example 1-7-4 (1) in N-methylpyrrolidone (8.7 mL), ethylhydrazine oxalate (3.9 g) was added, and the reaction solution was stirred at room temperature for 24 hours. N-Methylpyrrolidone (78 mL) was added to the reaction solution, which was then stirred at 200° C. for 2.5 hours. By adding n-hexane, ethyl acetate, water, and a brine to the reaction solution, it was partitioned into two layers. The aqueous layer was extracted with a mixed solvent of n-hexane-ethyl acetate. The organic layers were combined, washed with water and a brine sequentially, and dried over anhydrous magnesium sulfate. After filtering off the desiccating agent, the filtrate was concentrated. The obtained residue was purified by silica gel column chromatography (n-hexane:ethyl acetate=95:5 to 60:40). To the residue, n-hexane was added, and insolubles were filtered off, followed by concentration. The obtained residue was purified by NH silica gel column chromatography (n-hexane:ethyl acetate=98:2 to 60:40) to afford 6-bromo-4-ethoxy-1-ethylindazole (2.48 g) as a light green oily substance.

(2) Under a nitrogen atmosphere, a solution of the compound (2.48 g) obtained in (1) above and copper (I) cyanide (1.57 g) in N,N-dimethylacetamide (31 mL) was stirred at 150° C. for 30 hours. After cooling to room temperature, 10% aqueous ammonia, a brine, and water were added to the reaction solution, which was then extracted with ethyl acetate and concentrated. The obtained residue was purified by NH silica gel column chromatography (n-hexane:ethyl acetate=95:5 to ethyl acetate only). To the obtained residue, a mixed solution of n-hexane-ethyl acetate was added. The organic layer was washed with water and a brine sequentially, and dried over anhydrous magnesium sulfate. After filtering off the desiccating agent, the filtrate was concentrated to afford 4-ethoxy-1-ethylindazole-6-carbonitrile (800 mg) as a light yellow powder.

(3) Under a nitrogen atmosphere, a solution of the compound (1.54 g) obtained in (2) above in toluene (36 mL) was cooled to −40° C., diisobutylaluminum hydride (1.0 mol/L toluene solution, 8.6 mL) was added thereto, and the reaction solution was stirred at the same temperature for 1 hour. Diisobutylaluminum hydride (1.0 mol/L toluene solution, 3.0 mL) was further added thereto, and the reaction solution was stirred at the same temperature for 10 minutes. To the reaction solution, isopropyl alcohol (6 mL) was added dropwise, silica gel was added thereto, and the reaction solution was stirred for 5 minutes. After bringing the reaction solution back to room temperature, it was filtered through Celite (registered trademark), and the filtrate was concentrated to afford the title compound (1.37 g) as a light yellow oily substance.

MS ESI/APCI Multi posi: 219 [M+H]$^+$.

Retention time: 0.980 min (method E)

Reference Example 1-7-7

1-[3,5-Bis(Cyclopropyloxy)-4-Methylphenyl]Ethan-1-One

[Chemical Formula 383]

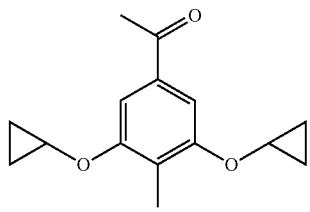

(1) N-Methylpyrrolidone (15 mL) was added to methyl 3,5-dihydroxy-4-methylbenzoate (700 mg), cesium carbonate (3.76 g), potassium iodide (32 mg), and cyclopropyl bromide (1.86 g), and the reaction solution was stirred at 200° C. for 2 hours under microwave irradiation. Water was added to the reaction solution, which was then extracted with a mixed solvent of n-hexane-ethyl acetate and concentrated. The obtained residue was purified by silica gel column chromatography (n-hexane:ethyl acetate=98:2 to 80:20) to afford a mixture (540 mg) containing methyl 3,5-bis(cyclopropoxy)-4-methylbenzoate as a colorless solid.

(2) To a solution of the mixture (540 mg) obtained in (1) above in tetrahydrofuran (21 mL), a 1 mol/L aqueous sodium hydroxide solution (21 mL) and methanol (10 mL) were added, and the reaction solution was stirred at room temperature for 5 days. The reaction solution was concentrated, and the aqueous layer was washed with n-hexane. To the aqueous layer, 3 mol/L hydrochloric acid was added dropwise to set the pH to 5 to 6, and insolubles were filtered off. The obtained residue was purified by preparative HPLC to afford 3,5-bis(cyclopropoxy)-4-methylbenzoic acid (75 mg) as a colorless powder.

(3) A solution of the compound (72 mg) obtained in (2) above in tetrahydrofuran (1.5 mL) was ice-cooled, methyllithium (1 mol/L diethyl ether solution, 0.87 mL) was added dropwise thereto, and the reaction solution was stirred at room temperature for 5 hours. The reaction solution was ice-cooled, isopropyl alcohol was added dropwise thereto, 1 mol/L hydrochloric acid was added thereto to make the solution acidic, and extraction with ethyl acetate was carried out. The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=70:30) to afford the title compound (92 mg) as a colorless oily substance.

MS ESI posi: 247 [M+H]$^+$.
Retention time: 0.942 min (method A)

Reference Example 1-7-8

5-Acetyl-3-Ethoxy-1-Ethylpyridin-2 (1H)-One

[Chemical Formula 384]

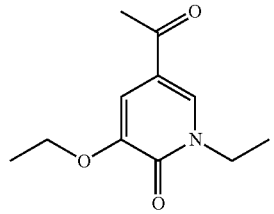

(1) Under a nitrogen atmosphere, a solution of 5-bromopyridine-2,3-diol (2 g) in N,N-dimethylformamide (35 mL) was ice-cooled, sodium hydride (60% mineral oil dispersion, 1.0 g) was added thereto, and the reaction solution was stirred at the same temperature for 45 minutes. Iodomethane (2.0 mL) was added dropwise thereto, and the reaction solution was stirred at room temperature for 3 days. Water was added to the reaction solution, which was then extracted with ethyl acetate. The organic layer was washed with a brine and dried over anhydrous magnesium sulfate. After filtering off the desiccating agent, the filtrate was concentrated. The obtained residue was purified by silica gel column chromatography (n-hexane:ethyl acetate=92:8 to 34:66) to afford 5-bromo-3-ethoxy-1-ethylpyridin-2-one (2.31 g) as a light yellow oily substance.

(2) Using the compound (0.512 g) obtained in (1) above, the reaction was carried out in accordance with the method described in Reference Example 1-7-6 (2). However, N-methylpyrrolidone was used instead of N,N-dimethylacetamide, and the reaction was performed at a temperature of 180° C. 5-Ethoxy-1-ethyl-6-oxopyridine-3-carbonitrile (0.3 g) was obtained as a colorless oily substance.

(3) The present reaction was carried out with reference to the method described in the literature (Journal of Medicinal Chemistry, vol. 59, p. 1556, 2016). Under a nitrogen atmosphere, a solution of the compound (0.439 g) obtained in (2) above in diethyl ether (23 mL) was ice-cooled, and methylmagnesium bromide (3 mol/L diethyl ether solution, 1.5 mL) was added dropwise thereto. The reaction solution was stirred at the same temperature for 3 hours, and stirred for 12 hours while gradually bringing it back to room temperature. Toluene (10 mL) was added to the reaction solution, which was then stirred at 65° C. for 2 hours. The reaction solution was ice-cooled, methylmagnesium bromide (3 mol/L diethyl ether solution, 0.53 mL) was further added thereto, and the reaction solution was stirred at room temperature for 40 minutes and at 60° C. for 50 minutes. The reaction solution was ice-cooled, methylmagnesium bromide (3 mol/L diethyl ether solution, 0.53 mL) was further added thereto, the reaction solution was stirred at room temperature for 10 minutes and at 60° C. for 80 minutes, and it was brought back to room temperature. Water was added to the reaction solution, which was then extracted with ethyl acetate. To the aqueous layer, 2 mol/L hydrochloric acid and a 1 mol/L aqueous sodium hydroxide solution were added to adjust the pH to 6 to 7, and extraction with ethyl acetate was carried out. The organic layers were combined, washed with a brine, and dried over anhydrous magnesium sulfate. After filtering off the desiccating agent, the filtrate was concentrated. The obtained residue was purified by silica gel column chromatography (n-hexane:ethyl acetate=85:15 to ethyl acetate only) to afford the title compound (0.069 g) as a colorless powder.

MS ESI/APCI Multi posi: 210 [M+H]$^+$.
Retention time: 1.156 min (method F)

Reference Example 1-7-9

1-(4-Ethoxy-1-Ethyl-1H-Benzimidazol-6-Yl) Ethan-1-One

[Chemical Formula 385]

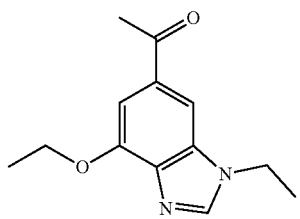

(1) To a solution of 5-bromo-1,3-difluoro-2-nitrobenzene (1.5 g) in ethanol (20 mL), potassium hydroxide (0.38 g)

was added, and the reaction solution was stirred at room temperature for 2.5 days and at 90° C. for 45 minutes. The reaction solution was concentrated, and ethyl acetate was added thereto. The reaction solution was washed with water and a brine sequentially, and dried over anhydrous magnesium sulfate. After filtering off the desiccating agent, the filtrate was concentrated to afford 5-bromo-1-ethoxy-3-fluoro-2-nitrobenzene (1.63 g) as an orange oily substance.

(2) A solution of the compound (1.63 g) obtained in (1) above in tetrahydrofuran (12 mL) was ice-cooled, a 12 mol/L aqueous ethylamine solution (2.1 mL) was added thereto, and the reaction solution was stirred at room temperature for 23 hours. The reaction solution was concentrated, and diethyl ether was added thereto. The reaction solution was washed with water and a brine sequentially, and dried over anhydrous magnesium sulfate. After filtering off the desiccating agent, the filtrate was concentrated to afford 5-bromo-3-ethoxy-N-ethyl-2-nitroaniline (1.79 g) as an orange powder.

(3) Using the compound (1.62 g) obtained in (2) above, the reaction was carried out in accordance with the method described in Reference Example 1-7-8 (2), and 3-ethoxy-5-(ethylamino)-4-nitrobenzonitrile (1.0 g) was obtained as a red powder.

(4) A mixture of the compound (0.5 g) obtained in (3) above, iron powder (0.593 g), a saturated aqueous ammonium chloride solution (5 mL), and ethanol (16 mL) was stirred at room temperature for 11 hours and at 65° C. for 80 minutes. To the reaction solution, a 1 mol/L aqueous sodium hydroxide solution was added to adjust the pH to 9 to 10, the reaction solution was filtered through Celite (registered trademark), and the filtrate was concentrated. By adding water and ethyl acetate to the residue, the reaction solution was partitioned into two layers. To the aqueous layer, a 1 mol/L aqueous sodium hydroxide solution was added to adjust the pH to 9 to 10, and extraction with ethyl acetate was carried out. The organic layers were combined, washed with a brine, and dried over anhydrous magnesium sulfate. After filtering off the desiccating agent, the filtrate was concentrated. The obtained residue was purified by silica gel column chromatography (n-hexane only to n-hexane:ethyl acetate=50:50) to afford 4-amino-3-ethoxy-5-(ethoxyamino)benzonitrile (222 mg) as a beige powder.

(5) To a solution of the compound (0.1 g) obtained in (4) above in triethyl orthoformate (2.4 mL), p-toluenesulfonic acid monohydrate (9 mg) was added, and the reaction solution was stirred at room temperature for 17 hours. The reaction solution was diluted by adding ethyl acetate, and washed by adding a saturated aqueous sodium bicarbonate solution. The aqueous layer was extracted with ethyl acetate and concentrated. The obtained residue was purified by preparative HPLC to afford 7-ethoxy-3-ethylbenzimidazole-5-carbonitrile (82 mg) was obtained as a colorless gum-like substance.

(6) A solution of the compound (82 mg) obtained in (5) above in diethyl ether (3.8 mL) was ice-cooled, methylmagnesium bromide (3 mol/L diethyl ether solution, 0.254 mL) was added dropwise thereto, and the reaction solution was stirred at the same temperature for 25 minutes and at room temperature for 20 hours. Tetrahydrofuran (3.8 mL) was added to the reaction solution, which was then ice-cooled. Methylmagnesium bromide (3 mol/L diethyl ether solution, 0.254 mL) was further added thereto, and the reaction solution was stirred at the same temperature for 30 minutes and at room temperature for 90 minutes. The reaction solution was ice-cooled, methylmagnesium bromide (3 mol/L diethyl ether solution, 1 mL) was further added thereto, and an operation of stirring the reaction solution at room temperature for 1 hour was repeated twice. Water was added to the reaction solution, which was then concentrated. The obtained residue was purified by preparative HPLC to afford the title compound (35 mg) as a colorless solid.

MS ESI posi: 233 [M+H]$^+$.
Retention time: 0.752 min (method C)

Reference Example 1-8-1

4-Acetyl-2,6-Diethoxybenzonitrile

[Chemical Formula 386]

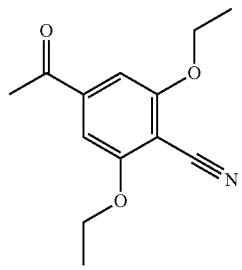

To a solution of the compound (232 mg) obtained in Reference Example 1-5-1 in N,N-dimethylacetamide (3.2 mL), copper (1) cyanide (217 mg) was added, and the reaction solution was stirred at 150° C. for 1 hour under microwave irradiation. After adding ethyl acetate to the reaction solution, this was added to a 10% aqueous ammonium solution, and extraction with ethyl acetate was carried out. The organic layer was washed with a brine, filtered through Phase Separator, and concentrated. The obtained residue was purified by silica gel column chromatography (n-hexane only to n-hexane:ethyl acetate=50:50) to afford the title compound (31.7 mg) as a colorless solid.

MS ESI posi: 234 [M+H]$^+$.
Retention time: 1.004 min (method B)

Reference Example 1-8-2

1-(4-Cyclopropyl-3,5-Diethoxyphenyl) Ethan-1-One

[Chemical Formula 387]

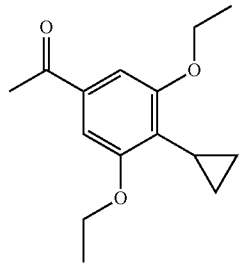

Using the compound (50 mg) obtained in Reference Example 1-5-1 and cyclopropylboronic acid (22.4 mg), the reaction was carried out in accordance with the method described in Reference Example 1-7-1, and the title compound (34 mg) was obtained as a colorless solid.

MS ESI posi: 249 [M+H]$^+$.

Retention time: 1.199 min (method B)

The following Reference Examples 1-8-3 to 1-8-4 were synthesized by the method described in Reference Example 1-8-2 or by a method equivalent thereto, using the compound obtained in Reference Example 1-5-1, a commercially available compound, or a compound obtained by synthesis according to methods described in literatures or methods equivalent thereto. The structures and LCMS data of the compounds are shown in Table 8-1.

TABLE 8-1

| Reference Example No. | Structural Formula | MS posi m/z MS nega m/z | Retention time (min) | method |
|---|---|---|---|---|
| 1-8-3 | | 249 [M + H]+ | 1.203 | B |
| 1-8-4 | | 237 [M + H]+ | 0.976 | A |

Reference Example 1-8-5

1,1'-(2,6-Diethoxy-1,4-Phenylene)Di(Ethan-1-One)

[Chemical Formula 388]

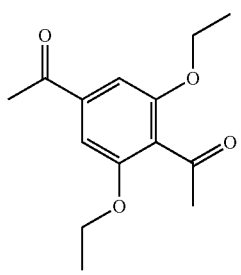

The present reaction was carried out with reference to the method described in the literature (The Journal of Organic Chemistry, vol. 66, p. 4340, 2001). Under a nitrogen atmosphere, to a solution of the compound (0.5 g) obtained in Reference Example 1-5-1 in N,N-dimethylformamide (8.7 mL), butyl vinyl ether (1.12 mL), palladium (II) acetate (11.7 mg), 1,3-bis(diphenylphosphino) propane (43.1 mg), potassium carbonate (722 mg), and water (0.87 mL) were added, and the reaction solution was stirred at 120° C. for 1 hour under microwave irradiation. 1 mol/L hydrochloric acid (10 mL) was added to the reaction solution, which was then stirred at room temperature for 3 hours. A 10% aqueous potassium carbonate solution (50 mL) was added thereto, and extraction with ethyl acetate was carried out. The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=60:40) to afford the title compound (407 mg) as a colorless solid.

MS ESI posi: 251 [M+H]+.

Retention time: 0.994 min (method B)

Reference Example 1-8-6

1-[3,5-Diethoxy-4-(Propan-2-Yl)Phenyl]Ethan-1-One

[Chemical Formula 389]

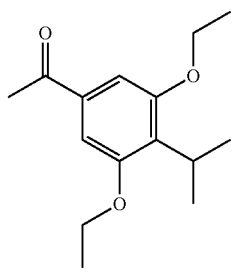 [SMILES: C=C(C)c1c(OCC)cc(C(C)=O)cc1OCC]

To a solution of the compound (37 mg) obtained in Reference Example 1-8-3 in methanol (3 mL), palladium carbon (19 mg) was added, and the reaction solution was stirred at room temperature for 3 hours under a hydrogen atmosphere. Insolubles were filtered off and the filtrate was concentrated. The obtained residue was purified by silica gel column chromatography (n-hexane only to n-hexane:ethyl acetate=75:25) to afford the title compound (29 mg) as a colorless solid.

MS ESI posi: 251 [M+H]$^+$.

Retention time: 1.338 min (method B)

The following Reference Example 1-8-7 was synthesized by the method described in Reference Example 1-8-2 or by a method equivalent thereto, using the compound obtained in Reference Example 1-14-6 and cyclopropylboronic acid. The structure and LCMS data of the compound are shown in Table 8-2.

TABLE 8-2

| Reference Example No. | Structural Formula | MS posi m/z MS nega m/z | Retention time (min) | method |
|---|---|---|---|---|
| 1-8-7 | | 235 [M + H]+ | 0.938 | A |

Reference Example 1-9-1

1-[3,5-Diethoxy-4-(1-Hydroxycyclopropyl)Phenyl]Ethan-1-One

[Chemical Formula 390]

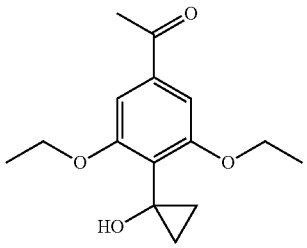

(1) To a solution of the compound (0.604 g) obtained in Reference Example 1-5-1 in toluene (21 mL), ethylene glycol (8.42 mL) and p-toluenesulfonic acid monohydrate (40.0 mg) were added, and the reaction solution was stirred with heating under reflux for 3 hours. The reaction solution was ice-cooled, a saturated aqueous sodium bicarbonate solution was added thereto, and extraction with ethyl acetate was carried out. The organic layer was washed with a brine, filtered through Phase Separator, and concentrated. The obtained residue was purified by silica gel column chromatography (n-hexane:ethyl acetate=95:5 to 90:10) to afford 2-(4-bromo-3,5-diethoxyphenyl)-2-methyl-1,3-dioxolane (0.633 g) as a colorless solid.

(2) The present reaction was carried out with reference to the method described in the literature (WO 2015/159233). Under a nitrogen atmosphere, to a suspension of magnesium (66 mg) and iodine (14 mg) in diethyl ether (3.6 mL), a mixed solution of the compound (900 mg) obtained in (1) above in diethyl ether-tetrahydrofuran (1:1, 1.8 mL) and tetrahydrofuran (3.6 mL) were added. The temperature was gradually raised, and the reaction solution was stirred with heating under reflux for 5 hours. The reaction solution was ice-cooled, a solution of 1,3-dichloroacetone (345 mg) in tetrahydrofuran (3.6 mL) was added thereto, and the reaction solution was stirred at room temperature for 80 minutes. The reaction solution was ice-cooled, a solution of iron (III) chloride (9 mg) in tetrahydrofuran (1.8 mL) and ethylmagnesium bromide (3 mol/L diethyl ether solution, 4.5 mL) were added thereto over 5 minutes, and the reaction solution was stirred at room temperature for 12 hours. The reaction solution was ice-cooled, a saturated aqueous ammonium chloride solution (18 mL) was added thereto, 1 mol/L hydrochloric acid was added to adjust the solution to be acidic, and the reaction solution was partitioned into two layers by adding ethyl acetate. The aqueous layer was extracted with ethyl acetate, and the organic layers were combined, washed with a brine, and dried over anhydrous magnesium sulfate. After filtering off the desiccating agent, the filtrate was concentrated. The obtained residue was purified by silica gel column chromatography (n-hexane:ethyl acetate=94:6 to 60:40) to afford 1-[2,6-diethoxy-4-(2-methyl-1,3-dioxolan-2-yl)phenyl]cyclopropan-1-ol (220 mg) as a light yellow solid.

(3) A solution of the compound (0.11 g) obtained in (2) above in tetrahydrofuran (2.5 mL) was ice-cooled, 1 mol/L hydrochloric acid (2.5 mL) was added thereto, and the reaction solution was stirred at room temperature for 30 minutes. Water was added to the reaction solution, which was then extracted with ethyl acetate, filtered through Phase Separator, and concentrated to afford the title compound (0.088 g) as a light yellow oily substance.

MS ESI posi: 247 [M−OH]$^+$.

Retention time: 0.742 min (method A)

Reference Example 1-9-2

1-[3,5-Diethoxy-4-(Methanesulfinyl)Phenyl]Ethan-1-One

[Chemical Formula 391]

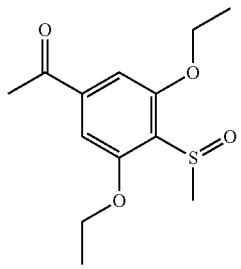

(1) The present reaction was carried out with reference to the method described in the literature (Journal of Medicinal Chemistry, vol. 59, p. 6772, 2016). Under a nitrogen atmosphere, a mixed solution of the compound (0.1 g) obtained in Reference Example 1-9-1 (1) in diethyl ether-tetrahydrofuran (2 mL-1 mL) was cooled to −78° C., and n-butyllithium (1.60 mol/L n-hexane solution, 0.38 mL) was added thereto. The reaction solution was stirred for 30 minutes under ice cooling and cooled to −78° C. Dimethyl disulfide (68.0 μL) was added thereto, and the reaction solution was stirred at the same temperature for 1 hour. The reaction solution was ice-cooled, a saturated aqueous ammonium chloride solution was added thereto, and extraction with diethyl ether was carried out. The organic layer was washed with a brine, filtered through Phase Separator, and concentrated. The obtained residue was purified by silica gel column chromatography (n-hexane only to n-hexane:ethyl acetate=80:20) to afford 2-[3,5-diethoxy-4-(methylsulfanyl)phenyl]-2-methyl-1,3-dioxolane (75.8 mg) as a colorless solid.

(2) Under a nitrogen atmosphere, a solution of the compound (40.8 mg) obtained in (1) above in methanol (1.4 mL) was ice-cooled, and a solution of sodium periodate (29.2 mg) in water (1.4 mL) was added thereto. The reaction solution was stirred at the same temperature for 1 hour and stirred at room temperature for 7 hours. A brine was added to the reaction solution, which was then extracted with chloroform, filtered through Phase Separator, and concentrated. The obtained residue was purified by NH silica gel column chromatography (n-hexane:ethyl acetate=70:30 to ethyl acetate only) to afford 2-[3,5-diethoxy-4-(methanesulfinyl)phenyl]-2-methyl-1,3-dioxolane (33.8 mg) as a colorless solid.

(3) Using the compound (33.8 mg) obtained in (2) above, the reaction was carried out in accordance with the method described in Reference Example 1-9-1 (3), and the title compound (34.0 mg) was obtained as a colorless solid.

MS ESI posi: 271 [M+H]$^+$.

Retention time: 0.636 min (method B)

Reference Example 1-9-3

1-[3,5-Diethoxy-4-(Methanesulfonyl)Phenyl]Ethan-1-One

[Chemical Formula 392]

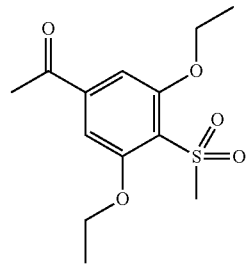

(1) A solution of the compound (35 mg) obtained in Reference Example 1-9-2 (1) in chloroform (1.2 mL) was ice-cooled, meta-chloroperoxybenzoic acid (64.8 mg) was added thereto, and the reaction solution was stirred at the same temperature for 10 minutes and at room temperature for 20 minutes. The reaction solution was ice-cooled, a saturated aqueous sodium bicarbonate solution was added thereto, and extraction with chloroform was carried out three times. The organic layer was washed with a saturated aqueous sodium thiosulfate solution, filtered through Phase Separator, and concentrated. The obtained residue was purified by silica gel column chromatography (n-hexane only to ethyl acetate only) to afford 2-[3,5-diethoxy-4-(methanesulfonyl)phenyl]-2-methyl-1,3-dioxolane (37.6 mg) as a colorless solid.

(2) Using the compound (37.6 mg) obtained in (1) above, the reaction was carried out in accordance with the method described in Reference Example 1-9-1 (3), and the title compound (35.6 mg) was obtained as a colorless solid.

MS ESI posi: 287 [M+H]$^+$.

Retention time: 0.696 min (method B)

Reference Example 1-10-1

1-[2,6-Diethoxy-4-(2-Methyl-1,3-Dioxolan-2-Yl)Phenyl]Ethan-1-Ol

[Chemical Formula 393]

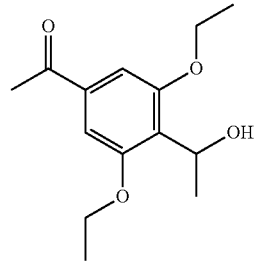

(1) Under a nitrogen atmosphere, a mixed solution of the compound (1 g) obtained in Reference Example 1-9-1 (1) in diethyl ether-tetrahydrofuran (20 mL-10 mL) was cooled to −78° C., n-butyllithium (1.60 mol/L n-hexane solution, 2.5 mL) was added thereto, and the reaction solution was stirred for 30 minutes under ice cooling. After cooling the reaction solution to −78° C., N,N-dimethylformamide (0.35 mL) was added thereto, and the reaction solution was stirred at the same temperature for 1 hour. The reaction solution was brought back to ice-cold, a saturated aqueous ammonium chloride solution (30 mL) was added thereto, and extraction with ethyl acetate was carried out. The organic layer was washed with a brine, filtered through Phase Separator, and concentrated. The obtained residue was purified by silica gel column chromatography (n-hexane only to n-hexane:ethyl acetate=75:25) to afford 2,6-diethoxy-4-(2-methyl-1,3-dioxolan-2-yl)benzaldehyde (0.602 g) as a colorless solid.

(2) Using the compound (0.1 g) obtained in (1) above, the reaction was carried out in accordance with the method described in Reference Example 1-6-1 (1), and 1-[2,6-diethoxy-4-(2-methyl-1,3-dioxolan-2-yl)phenyl]ethan-1-ol (83.3 mg) was obtained as a colorless solid.

(3) Using the compound (83.3 mg) obtained in (2) above, the reaction was carried out in accordance with the method described in Reference Example 1-9-1 (3), and the title compound (68.0 mg) was obtained as a colorless solid.
MS ESI posi: 235 [M−OH]+.
Retention time: 0.965 min (method B)

Reference Example 1-10-2

1-[4-(Difluoromethyl)-3,5-Diethoxyphenyl]Ethan-1-One

[Chemical Formula 394]

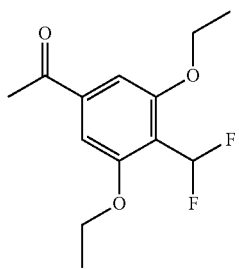

(1) To a solution of the compound (0.07 g) obtained in Reference Example 1-10-1 (1) in chloroform (1.7 mL), bis(2-methoxyethyl)aminosulfur trifluoride (138 μL) was added, and the reaction solution was stirred at room temperature for 1 hour. Bis(2-methoxyethyl)aminosulfur trifluoride (138 μL) was further added thereto, and the reaction solution was stirred at 60° C. for 10 hours and at room temperature overnight. A saturated aqueous sodium bicarbonate solution was added to the reaction solution, which was then extracted with chloroform, filtered through Phase Separator, and concentrated. The obtained residue was purified by silica gel column chromatography (n-hexane only to n-hexane:ethyl acetate=50:50) to afford 2-[4-(difluoromethyl)-3,5-diethoxyphenyl]-2-methyl-1,3-dioxolane (31.3 mg) as a light yellow solid.

(2) Using the compound (31.3 mg) obtained in (1) above, the reaction was carried out in accordance with the method described in Reference Example 1-9-1 (3), and the title compound (60.6 mg) was obtained as a colorless solid.
MS ESI posi: 259 [M+H]+.
Retention time: 1.115 min (method B)

Reference Example 1-10-3

(4-Acetyl-2,6-Diethoxyphenyl)Methyl Acetate

[Chemical Formula 395]

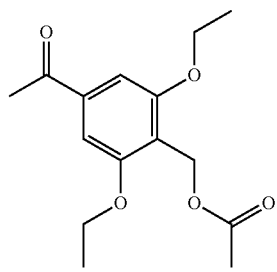

(1) A solution of the compound (50.0 mg) obtained in Reference Example 1-10-1 (1) in methanol (2 mL) was ice-cooled, and sodium borohydride (10.1 mg) was added thereto. The reaction solution was stirred at the same temperature for 40 minutes. The reaction solution was ice-cooled, a saturated aqueous ammonium chloride solution was added thereto, and extraction with ethyl acetate was carried out. The organic layer was washed with a brine, filtered through Phase Separator, and concentrated. The obtained residue was purified by silica gel column chromatography (n-hexane only to n-hexane:ethyl acetate=60:40) to afford[2,6-diethoxy-4-(2-methyl-1,3-dioxolan-2-yl)phenyl]methanol (43.4 mg) as a colorless solid.

(2) To a solution of the compound (43.4 mg) obtained in (1) above in chloroform (1.5 mL), triethylamine (64.3 μL) and acetyl chloride (66.0 μL) were added, and the reaction solution was stirred at room temperature for 4 hours. The reaction solution was ice-cooled, and a saturated aqueous sodium bicarbonate solution was added thereto. The reaction solution was extracted with chloroform, filtered through Phase Separator, and concentrated to afford[2,6-diethoxy-4-(2-methyl-1,3-dioxolan-2-yl)phenyl]methyl acetate (59.7 mg) as a light yellow oily substance.

(3) Using the compound (59.7 mg) obtained in (2) above, the reaction was carried out in accordance with the method described in Reference Example 1-9-1 (3), and the title compound (30.7 mg) was obtained as a colorless solid.
MS ESI posi: 303 [M+Na]+.
Retention time: 0.975 min (method B)

Reference Example 1-10-4

1-[3,5-Diethoxy-4-(2,2,2-Trifluoro-1-Hydroxyethyl)Phenyl]Ethan-1-One

[Chemical Formula 396]

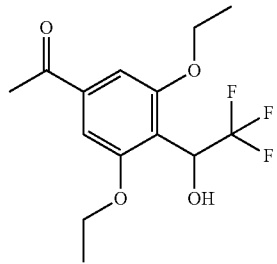

(1) The present reaction was carried out with reference to the method described in the literature (Journal of the American Chemical Society, vol. 111, p. 393, 1989). Under a nitrogen atmosphere, a solution of the compound (70 mg) obtained in Reference Example 1-10-1 (1) in tetrahydrofuran (2.5 mL) was ice-cooled, (trifluoromethyl)trimethylsilane (55.4 µL) and tetrabutylammonium fluoride (1 mol/L tetrahydrofuran solution, 25.0 µL) were added thereto, and the reaction solution was stirred at room temperature for 1.5 hours. 1 mol/L hydrochloric acid (1 mL) was further added thereto, and the reaction solution was stirred at room temperature for 3 hours. Water was added to the reaction solution, which was then extracted with ethyl acetate. The organic layer was washed with a brine, filtered through Phase Separator, and concentrated. The obtained residue was purified by silica gel column chromatography (n-hexane only to n-hexane:ethyl acetate=50:50) to afford 1-[2,6-diethoxy-4-(2-methyl-1,3-dioxolan-2-yl)phenyl]-2,2,2-trifluoroethan-1-ol (42 mg) as a colorless oily substance.

(2) Using the compound (90 mg) obtained in (1) above, the reaction was carried out in accordance with the method described in Reference Example 1-9-1 (3), and the title compound (61 mg) was obtained as a colorless solid.

MS ESI posi: 307 [M+H]$^+$.

Retention time: 1.053 min (method B)

Reference Example 1-10-5

1-(4-Acetyl-2,6-Diethoxyphenyl)-2,2,2-Trifluoroethan-1-One

[Chemical Formula 397]

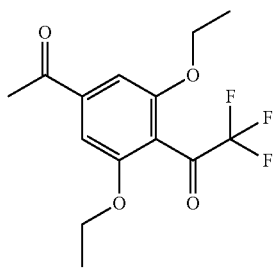

(1) To a solution of the compound (42 mg) obtained in Reference Example 1-10-4 (1) in n-hexane (3 mL), manganese dioxide (0.8 g) was added, and the reaction solution was stirred at room temperature for 3.5 hours and at 60 degrees for 2 hours. The reaction solution was filtered through Celite (registered trademark), and the filtrate was concentrated. The obtained residue was purified by silica gel column chromatography (n-hexane only to n-hexane:ethyl acetate=50:50) to afford 1-[2,6-diethoxy-4-(2-methyl-1,3-dioxolan-2-yl)phenyl]-2,2,2-trifluoroethan-1-one (31 mg) as a colorless solid.

(2) Using the compound (31 mg) obtained in (1) above, the reaction was carried out in accordance with the method described in Reference Example 1-9-1 (3), and the title compound (34 mg) was obtained as a colorless solid.

MS ESI posi: 305 [M+H]$^+$.

Retention time: 1.145 min (method B)

Reference Example 1-10-6

Methyl 4-Acetyl-2,6-Diethoxybenzoate

[Chemical Formula 398]

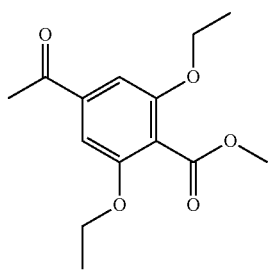

(1) To a solution of the compound (266 mg) obtained in Reference Example 1-10-1 (1) in 2-methyl-2-butene (0.81 mL), sodium dihydrogen phosphate (456 mg), tert-butyl alcohol (3.8 mL), water (1.3 mL), and tetrahydrofuran (3.8 mL) were added, and the reaction solution was ice-cooled. Sodium chlorite (344 mg) was slowly added thereto, and the reaction solution was stirred at room temperature for 1.5 hours. The reaction solution was ice-cooled, water (50 mL) and citric acid (1 g) were added thereto to make the solution acidic (the pH was 1 to 2), and extraction with ethyl acetate was carried out twice. The organic layer was extracted with a saturated aqueous sodium bicarbonate solution (30 mL) twice. Citric acid (4 g) was added to the aqueous layer to make it acidic (the pH was 5), and extraction with ethyl acetate was carried out twice. The organic layer was washed with a brine, filtered through Phase Separator, and concentrated to afford 2,6-diethoxy-4-(2-methyl-1,3-dioxolan-2-yl)benzoic acid (205 mg) as a colorless solid.

(2) Under a nitrogen atmosphere, a mixed solution of the compound (32 mg) obtained in (1) above in chloroform-methanol (2 mL-1 mL) was ice-cooled, trimethylsilyldiazomethane (2 mol/L diethyl ether solution, 162 µmL) was added thereto, and the reaction solution was stirred at room temperature for 2 hours. The reaction solution was ice-cooled, water was added thereto, and the reaction solution was extracted with chloroform, filtered through Phase Separator, and concentrated. The obtained residue was purified by silica gel column chromatography (n-hexane only to n-hexane:ethyl acetate=50:50) to afford methyl 2,6-diethoxy-4-(2-methyl-1,3-dioxolan-2-yl)benzoate (28.6 mg) as a colorless solid.

(3) To a mixed solution of the compound (28.6 mg) obtained in (2) above in acetone-water (920 µL-920 µL), p-toluenesulfonic acid monohydrate (17.5 mg) was added, and the reaction solution was stirred for 2.5 hours. p-Toluenesulfonic acid monohydrate (17.5 mg) was further added thereto, and the reaction solution was stirred at room temperature overnight. A saturated aqueous sodium bicarbonate solution was added to the reaction solution, which was then extracted with ethyl acetate. The organic layer was washed with a brine, filtered through Phase Separator, and concentrated. The obtained residue was purified by silica gel column chromatography (n-hexane only to n-hexane:ethyl acetate=50:50) to afford the title compound (24.2 mg) as a colorless solid.

MS ESI posi: 267 [M+H]$^+$, 289 [M+Na]$^+$.

Retention time: 0.995 min (method B)

Reference Example 1-11-1

1-[3,5-Diethoxy-4-(2-Hydroxypropan-2-Yl)Phenyl]Ethan-1-One

[Chemical Formula 399]

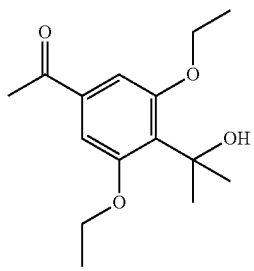

(1) Using the compound (111 mg) obtained in Reference Example 1-8-5, the reaction was carried out in accordance with the method described in Reference Example 1-9-1 (1), and 1-[2,6-diethoxy-4-(2-methyl-1,3-dioxolan-2-yl)phenyl]ethan-1-one (110 mg) was obtained as a colorless solid.

(2) Using the compound (45.5 mg) obtained in (1) above, the reaction was carried out in accordance with the method described in Reference Example 1-6-1 (1), and 2-[2,6-diethoxy-4-(2-methyl-1,3-dioxolan-2-yl)phenyl]propan-2-ol (41.9 mg) was obtained as a colorless oily substance.

(3) Using the compound (41.9 mg) obtained in (2) above, the reaction was carried out in accordance with the method described in Reference Example 1-9-1 (3), and the title compound (19.7 mg) was obtained as a colorless solid.

MS ESI posi: 249 [M−OH]+.

Retention time: 1.037 min (method B)

Reference Example 1-11-2

1-[3,5-Diethoxy-4-(1-Hydroxypropyl)Phenyl]Ethan-1-One

[Chemical Formula 400]

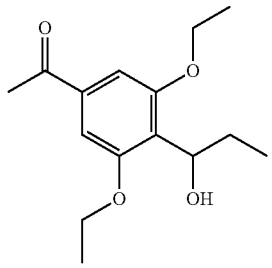

(1) Using the compound (80 mg) obtained in Reference Example 1-10-1 (1) and ethylmagnesium bromide (3 mol/L diethyl ether solution, 143 μL), the reaction was carried out in accordance with the method described in Reference Example 1-6-1 (1), and 1-[2,6-diethoxy-4-(2-methyl-1,3-dioxolan-2-yl)phenyl]propan-1-ol (85.0 mg) was obtained as a colorless oily substance.

(2) Using the compound (85.0 mg) obtained in (1) above, the reaction was carried out in accordance with the method described in Reference Example 1-10-6 (3), and the title compound (71.4 mg) was obtained as a colorless oily substance.

MS ESI posi: 249 [M−OH]+.

Retention time: 0.994 min (method B)

Reference Example 1-11-3

1-(4-Acetyl-2,6-Diethoxyphenyl) Propan-1-One

[Chemical Formula 401]

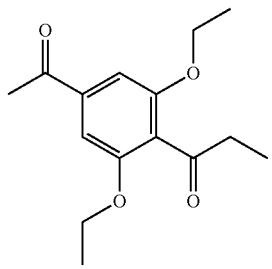

Using the compound (34.6 mg) obtained in Reference Example 1-11-2, the reaction was carried out in accordance with the method described in Reference Example 1-10-5 (1), and the title compound (19.2 mg) was obtained as a colorless solid.

MS ESI posi: 265 [M+H]+.

Retention time: 1.018 min (method B)

Reference Example 1-12-1

4-Acetyl-2,6-Diethoxybenzamide

[Chemical Formula 402]

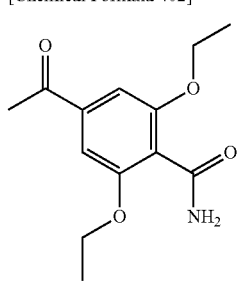

(1) To a mixed solution of the compound (50.0 mg) obtained in Reference Example 1-10-6 (1) in tetrahydrofuran-methanol (1.1 mL-0.22 mL), ammonium chloride (13.5 mg), triethylamine (70.6 μL), and DMT-MM (93.4 mg) were added, and the reaction solution was stirred at room temperature for 6 hours, at 40° C. for 3 hours, and at room temperature overnight. Ammonium chloride (13.5 mg), triethylamine (70.6 μL), and DMT-MM (93.4 mg) were further added thereto, and the reaction solution was stirred at 40° C. for 4 hours. 0.5 mol/L hydrochloric acid was added to the reaction solution, which was then extracted with chloroform, filtered through Phase Separator, and concentrated. The obtained residue was purified by silica gel column chromatography (n-hexane:ethyl acetate=50:50 to ethyl acetate only, and then chloroform only to chloroform: methanol=80:20) to afford 2,6-diethoxy-4-(2-methyl-1,3-dioxolan-2-yl)benzamide (64.0 mg) as a colorless solid.

(2) Using the compound (64.0 mg) obtained in (1) above, the reaction was carried out in accordance with the method described in Reference Example 1-9-1 (3), and the title compound (34.8 mg) was obtained as a colorless solid.

$^1$H NMR (400 MHZ, CHLOROFORM-d) δ ppm 1.38-1.48 (m, 6H) 2.59 (s, 3H) 4.11-4.20 (m, 4H) 7.12 (s, 2H).

MS ESI/APCI Multi posi: 252 [M+H]$^+$.

Reference Example 1-12-2

4-Acetyl-2,6-Diethoxy-N-Methylbenzamide

[Chemical Formula 403]

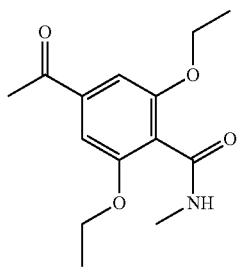

(1) Using the compound (47.7 mg) obtained in Reference Example 1-10-6 (1), the reaction and post treatment were carried out in accordance with the method described in Reference Example 1-7-3. The obtained residue was purified by NH silica gel column chromatography (n-hexane:ethyl acetate=70:30 to 10:90) to afford 2,6-diethoxy-N-methyl-4-(2-methyl-1,3-dioxolan-2-yl)benzamide (47.4 mg) as a colorless solid.

(2) Using the compound (47.4 mg) obtained in (1) above, the reaction was carried out in accordance with the method described in Reference Example 1-9-1 (3), and the title compound (40.7 mg) was obtained as a colorless solid.

$^1$H NMR (400 MHZ, CHLOROFORM-d) δ ppm 1.36-1.46 (m, 6H) 2.58 (s, 3H) 2.97-3.05 (m, 3H) 4.07-4.18 (m, 4H) 5.61-5.73 (m, 1H) 7.10 (s, 2H).

MS ESI/APCI Multi posi: 266 [M+H]$^+$.

Reference Example 1-13-1

1-(4-Acetyl-3,5-Diethoxyphenyl)-2-{[Tert-Butyl (Dimethyl) Silyl]Oxy}Ethan-1-One

[Chemical Formula 404]

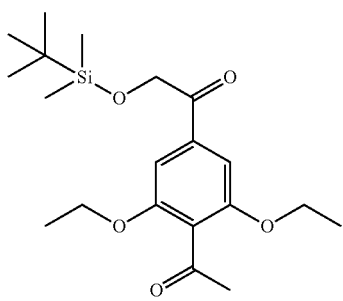

(1) To a solution of the compound (1.6 g) obtained in Reference Example 1-8-5 in methanol (32 mL), potassium hydroxide (1.6 g) was added, and the reaction solution was stirred for 5 minutes. The reaction solution was ice-cooled, iodobenzene diacetate (3.1 g) was added thereto, and the reaction solution was stirred at the same temperature for 1 hour. A saturated aqueous sodium bicarbonate solution (10 mL) was added to the reaction solution, which was then extracted with chloroform, filtered through Phase Separator, and concentrated to afford a mixture containing 1-[2,6-diethoxy-4-(2-hydroxy-1,1-dimethoxyethyl)phenyl]ethan-1-one.

(2) To a solution of the mixture obtained in (1) above in tetrahydrofuran (21 mL), water (7.1 mL) and p-toluenesulfonic acid monohydrate (2.4 g) were added, and the reaction solution was stirred at room temperature for 2 days. A saturated aqueous sodium bicarbonate solution was added to the reaction solution, which was then extracted with ethyl acetate three times. The organic layer was washed with a brine, filtered through Phase Separator, and concentrated. The obtained residue was purified by silica gel column chromatography (n-hexane:ethyl acetate=90:10 to 30:70) to afford 1-(4-acetyl-3,5-diethoxyphenyl)-2-hydroxyethan-1-one (1.15 g) as a light yellow solid.

(3) A solution of the compound (1.15 g) obtained in (2) above in N,N-dimethylformamide (17 mL) was ice-cooled, imidazole (0.882 g) and tert-butyldimethylchlorosilane (1.95 g) were added thereto, and the reaction solution was stirred at room temperature for 1.5 hours. Water was added to the reaction solution, which was then extracted with ethyl acetate three times. The organic layer was washed with water and a brine, filtered through Phase Separator, and concentrated. The obtained residue was purified by silica gel column chromatography (n-hexane:ethyl acetate=95:5 to 60:40) to afford the title compound (1.85 g) as a light yellow oily substance.

MS ESI posi: 381 [M+H]$^+$.

Retention time: 1.021 min (method A)

The following Reference Examples 1-13-2 to 1-13-3 were synthesized by the method described in Reference Example 1-13-1 or by a method equivalent thereto, using the compounds obtained in Reference Example 1-5-2 and Reference Example 1-5-17, commercially available compounds, or compounds obtained by synthesis according to methods described in literatures or methods equivalent thereto. The structures and LCMS data of the compounds are shown in Table 9-1.

TABLE 9-1

| Reference Example No. | Structural Formula | MS posi m/z MS nega m/z | Retention time (min) | method |
| --- | --- | --- | --- | --- |
| 1-13-2 | (structure) | 353 [M + H]+<br>375 [M + Na]+ | 1.135 | A |
| 1-13-3 | (structure) | 325 [M + H]+<br>347 [M + Na]+ | 1.114 | A |

Reference Example 1-13-4

1-(3,5-Diethoxy-4-Methylphenyl)-2-Methoxyethan-1-One

[Chemical Formula 405]

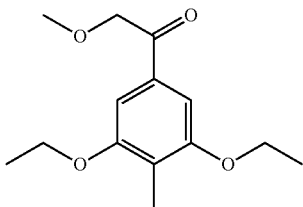

To a solution of the compound (100 mg) obtained in Reference Example 1-13-1 (2) in acetonitrile (2.1 mL), iodomethane (157 μL) and silver (I) oxide (0.486 g) were added, and the reaction solution was stirred at room temperature overnight. The reaction solution was filtered through Celite (registered trademark), and the filtrate was concentrated. The obtained residue was purified by silica gel column chromatography (n-hexane:ethyl acetate=95:5 to 60:40) to afford the title compound (77 mg) as a colorless solid.

MS ESI posi: 253 [M+H]$^+$, 275 [M+Na]$^+$.

Retention time: 0.820 min (method A)

Reference Example 1-14-1

4-Bromo-2-Chloro-3,5-Diethoxybenzaldehyde

[Chemical Formula 406]

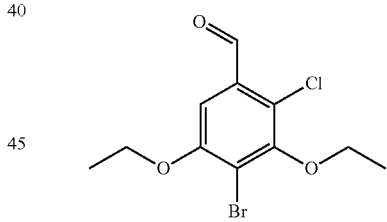

(1) Under a nitrogen atmosphere, a solution of the compound (10 g) obtained in Reference Example 1-5-1 (1) in acetonitrile (105 mL) was cooled with a mixture of sodium chloride-ice, sulfuryl chloride (2.55 mL) was added thereto (internal temperature: −18° C. to −16° C.), and the reaction solution was stirred for 1 hour (internal temperature: −17° C. to −12° C.). At the same temperature, a saturated aqueous sodium bicarbonate solution (75 mL) was added thereto (internal temperature: −17° C. to −10° C., the pH was 7), and extraction with ethyl acetate (50 mL) was carried out. The organic layer was washed with a brine (50 mL) and dried over anhydrous magnesium sulfate. After filtering off the desiccating agent, the filtrate was concentrated to afford ethyl 4-bromo-2-chloro-3,5-diethoxybenzoate (10.4 g) as a colorless oily substance.

(2) A solution of the compound (12.5 g) obtained in (1) above in tetrahydrofuran (59 mL) was ice-cooled, lithium borohydride (1.93 g) and ethanol (3.0 mL) were slowly added thereto, and the reaction solution was stirred at the same temperature for 1.5 hours. At the same temperature, a saturated aqueous ammonium chloride solution was added thereto, and the reaction solution was extracted with chloroform, filtered through Phase Separator, and concentrated to afford (4-bromo-2-chloro-3,5-diethoxyphenyl) methanol (10.5 g) as a colorless oily substance.

(3) To a solution of the compound (9 g) obtained in (2) above in toluene (97 mL), manganese dioxide (50.5 g) was added, and the reaction solution was stirred at room temperature for 1 hour. The reaction solution was filtered through Celite (registered trademark), and the filtrate was concentrated to afford the title compound (8.1 g) as a yellow powder.

MS ESI posi: 307 [M+H]+.
Retention time: 0.974 min (method A)

Reference Example 1-14-2

4-Bromo-3,5-Diethoxy-2-Methylbenzaldehyde

[Chemical Formula 407]

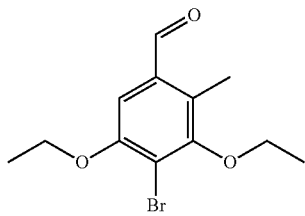

(1) A solution of the compound (25 g) obtained in Reference Example 1-5-1 (1) in chloroform (197 mL) was ice-cooled, silver trifluoroacetate (22.6 g) and iodine (24.0 g) were added thereto, and the reaction solution was stirred at the same temperature for 1 hour. At the same temperature, a mixed solution of 10% aqueous sodium thiosulfate solution-saturated aqueous sodium bicarbonate solution (1:1, 260 mL) was added thereto, the reaction solution was filtered through Celite (registered trademark), and the filtrate was extracted with chloroform. The organic layer was washed with a brine and dried over anhydrous magnesium sulfate. After filtering off the desiccating agent, the filtrate was concentrated to afford ethyl 4-bromo-3,5-diethoxy-2-iodobenzoate (35.6 g) as a pale yellow oily substance.

(2) To a solution of the compound (32.2 g) obtained in (1) above in 1,4-dioxane (121 mL), methylboronic acid (4.57 g) and tripotassium phosphate (46.3 g) were added, and the reaction solution was degassed under reduced pressure. Tetrakis(triphenylphosphine) palladium (0) (4.20 g) was added thereto, and the reaction solution was degassed under reduced pressure and then subjected to heating reflux for 2.5 hours. At the same temperature, water (2 mL) was added dropwise thereto over 30 minutes, and the reaction solution was subjected to heating reflux for 1.5 hours. At the same temperature, water (2 mL) was added dropwise thereto over 30 minutes, and the reaction solution was subjected to heating reflux for 5 hours. The reaction solution was allowed to be cooled and filtered through Celite (registered trademark), and water was added to the filtrate, which was then extracted with ethyl acetate twice. The organic layer was washed with a brine and dried over anhydrous magnesium sulfate. After filtering off the desiccating agent, the filtrate was concentrated. The obtained residue was purified by silica gel column chromatography (n-hexane only to n-hexane:ethyl acetate=93:7) to afford ethyl 4-bromo-3,5-diethoxy-2-methylbenzoate (19.2 g) as a colorless oily substance.

(3) Using the compound (21.4 g) obtained in (2) above, the reaction was carried out in accordance with the method described in Reference Example 1-14-1 (2), and a mixture (19.0 g) containing (4-bromo-3,5-diethoxy-2-methylphenyl) methanol was obtained as a colorless oily substance.

(4) Using the mixture (19.0 g) obtained in (3) above, the reaction was carried out in accordance with the method described in Reference Example 1-14-1 (3), and the title compound (15.6 g) was obtained as a pale yellow oily substance.

MS ESI posi: 287, 289 [M+H]+, 309 [M+Na]+.
Retention time: 0.926 min (method A)

Reference Example 1-14-3

4-Bromo-2-Chloro-3-Ethoxybenzaldehyde

[Chemical Formula 408]

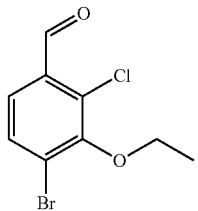

(1) To a solution of 2-chloro-3-hydroxybenzaldehyde (10.0 g) in methanol (106 mL), trimethyl orthoformate (11.2 mL) and tetrabutylammonium tribromide (1.54 g) were added, and the reaction solution was stirred at room temperature for 17 hours. By adding ethyl acetate (500 ml) and a 0.01 mol/L aqueous sodium bicarbonate solution (500 ml) to the reaction solution, it was partitioned into two layers. The organic layer was dried over anhydrous sodium sulfate. After filtering off the desiccating agent, the filtrate was concentrated. The obtained residue was purified by silica gel column chromatography (n-hexane:ethyl acetate=92:8 to 70:30) to afford 2-chloro-3-(dimethoxymethyl) phenol (14.8 g) as a colorless oily substance.

(2) The present reaction was carried out with reference to the method described in the literature (WO 2010/016230). A solution of the compound (12.9 g) obtained in (1) above in chloroform (80 mL) was ice-cooled, a solution of bromine (2.78 mL) in chloroform (11 mL) was added thereto over 1 hour, and the reaction solution was stirred at room temperature for 17 hours. The reaction solution was ice-cooled, a 5% aqueous sodium bisulfite solution (110 mL) was added thereto, and extraction with chloroform was carried out (the pH of the aqueous layer was 1). The organic layer was washed with a brine and dried over anhydrous magnesium sulfate. After filtering off the desiccating agent, the filtrate was concentrated to afford 4-bromo-2-chloro-3-hydroxybenzaldehyde (14.9 g) as a light yellow solid.

(3) To the compound (14.9 g) obtained in (2) above and potassium carbonate (17.5 g), N,N-dimethylformamide (63 mL) and iodoethane (7.67 mL) were added, and the reaction solution was stirred at room temperature for 2 hours. The reaction solution was ice-cooled, water (140 mL) was added thereto, and extraction with a mixed solvent of n-hexane-ethyl acetate (3:1) was carried out. The organic layer was washed with a brine and dried over anhydrous magnesium sulfate. After filtering off the desiccating agent, the filtrate was concentrated to afford the title compound (17.4 g) as a light yellow oily substance.

$^1$H NMR (600 MHz, CHLOROFORM-d) δ ppm 1.51-1.54 (m, 3H) 4.12-4.16 (m, 2H) 7.55-7.57 (m, 1H) 7.59-7.61 (m, 1H) 10.43 (s, 1H).

The following Reference Examples 1-14-4 to 1-14-6 were synthesized by the method described in Reference Example 1-14-1 (2) to (3) or Reference Example 1-14-2, or by a method equivalent thereto, using the compounds obtained in Reference Example 1-2-1 and Reference Example 1-5-1 (1), commercially available compounds, or compounds obtained by synthesis according to methods described in literatures or methods equivalent thereto. The structures and LCMS data of the compounds are shown in Table 10-1.

Reference Example 1-14-7

3,5-Diethoxy-4-(1-Hydroxycyclopropyl)Benzaldehyde

[Chemical Formula 409]

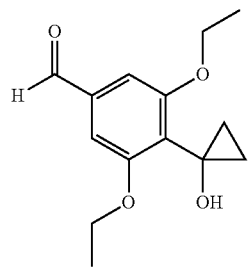

(1) Using the compound (8.0 g) obtained in Reference Example 1-14-6, the reaction was carried out in accordance with the method described in Reference Example 1-9-1 (1), and 2-(4-bromo-3,5-diethoxyphenyl)-1,3-dioxolane (9.1 g) was obtained as a light purple oily substance.

(2) Using the compound (3.5 g) obtained in (1) above, the reaction was carried out in accordance with the method described in Reference Example 1-9-1 (2), and 1-[4-(1,3-

TABLE 10-1

| Reference Example No. | Structural Formula | MS posi m/z MS nega m/z | Retention time (min) | method |
|---|---|---|---|---|
| 1-14-4 | 2,6-dimethyl-3,5-diethoxybenzaldehyde | 223 [M + H]+ | 0.926 | A |
| 1-14-5 | 3,5-diethoxybenzaldehyde | 195 [M + H]+ | 1.208 | B |
| 1-14-6 | 4-bromo-3,5-diethoxybenzaldehyde | 273 [M + H]+ | 1.126 | B | dioxolan-2-yl)-2,6-diethoxyphenyl]cyclopropan-1-ol (460 mg) was obtained as a light yellow solid.

(3) Using the compound (460 mg) obtained in (2) above, the reaction was carried out in accordance with the method described in Reference Example 1-9-1 (3), and the title compound (400 mg) was obtained as a light yellow oily substance.

MS ESI posi: 233 [M−OH]+, 273 [M+Na]+.

Retention time: 0.733 min (method A)

Reference Example 1-14-8

4-Bromo-5-Ethoxy-2-Methylbenzaldehyde

[Chemical Formula 410]

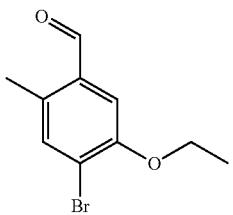

(1) A solution of 5-hydroxy-2-methylbenzoic acid (1 g) and acetic acid (4 mL) in chloroform (32 mL) was ice-cooled, bromine (1 mL) was added, and the reaction solution was stirred at the same temperature for 1 hour and at room temperature for 20 hours. The reaction solution was ice-cooled, a saturated aqueous sodium sulfite solution was added thereto, and extraction with ethyl acetate and chloroform was carried out sequentially. The organic layer was washed with a brine, filtered through Phase Separator, and concentrated to afford a mixture (2.4 g) containing 4-bromo-5-hydroxy-2-methylbenzoic acid as a light yellow powder.

(2) To a solution of the mixture (2.4 g) obtained in (1) above in N,N-dimethylformamide (6.6 mL), potassium carbonate (2.7 g) was added, and the reaction solution was stirred at room temperature for 5 minutes. Iodoethane (1.6 mL) was added thereto, and the reaction solution was stirred at 60° C. for 4 hours. Water was added to the reaction solution, which was then extracted with a mixed solvent of n-hexane-ethyl acetate (1:1), filtered through Phase Separator, and concentrated. Diethyl ether was added to the residue, the precipitated solid was filtered off, and the filtrate was concentrated. The residue was purified by silica gel column chromatography (n-hexane:ethyl acetate=98:2 to 75:25) to afford a mixture (2.0 g) containing ethyl 4-bromo-5-ethoxy-2-methylbenzoate as a light yellow oily substance.

(3) A solution of the mixture (2.0 g) obtained in (2) above in tetrahydrofuran (26 mL) was ice-cooled, lithium borohydride (0.429 g) was added thereto, and the reaction solution was stirred at room temperature for 12 hours and at 50° C. for 3 hours. The reaction solution was ice-cooled, a saturated aqueous ammonium chloride solution (20 mL) was slowly added thereto, and the reaction solution was stirred at room temperature for 0.5 hours. The reaction solution was extracted with chloroform, filtered through Phase Separator, and concentrated. The residue was purified by silica gel column chromatography (n-hexane:ethyl acetate=98:2 to 60:40) to afford (4-bromo-5-ethoxy-2-methylphenyl) methanol (0.75 g) as a colorless oily substance.

(4) To a solution of the compound (0.75 g) obtained in (3) above in toluene (12 mL), manganese dioxide (3.2 g) was added, and the reaction solution was stirred at room temperature for 16 hours. Insolubles were filtered off with Celite (registered trademark), and the filtrate was concentrated to afford the title compound (0.75 g) as a colorless oily substance.

MS ESI posi: 243, 245 [M+H]+.

Retention time: 1.138 min (method B)

The following Reference Example 1-14-9 was synthesized by the method described in Reference Example 1-14-8 (2) to (4) or by a method equivalent thereto, using methyl 4-bromo-3-hydroxy-2-methylbenzoate. The structure and LCMS data of the compound are shown in Table 10-2.

TABLE 10-2

| Reference Example No. | Structural Formula | MS posi m/z MS nega m/z | Retention time (min) | method |
|---|---|---|---|---|
| 1-14-9 | 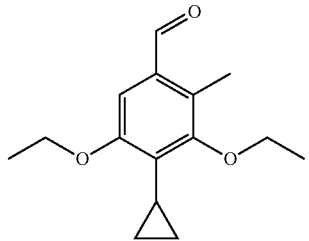 | 243, 245 [M + H]+ | 0.878 | A |

Reference Example 1-14-10

4-Cyclopropyl-3,5-Diethoxy-2-Methylbenzaldehyde

[Chemical Formula 411]

(1) A solution of the compound (2.27 g) obtained in Reference Example 1-8-7 in chloroform (24 mL) was ice-cooled, silver trifluoroacetate (2.78 g) and iodine (2.95 g) were added thereto, and the reaction solution was stirred at the same temperature for 50 minutes. A saturated aqueous sodium thiosulfate solution and a saturated aqueous sodium bicarbonate solution were added dropwise to the reaction solution, which was then filtered through Celite (registered trademark), and the filtrate was partitioned into two layers. The organic layer was filtered through Phase Separator and concentrated. The obtained residue was purified by silica gel column chromatography (n-hexane:ethyl acetate=98:2 to 80:20) to afford 4-cyclopropyl-3,5-diethoxy-2-iodobenzaldehyde (751 mg) as an orange oily substance.

(2) Under a nitrogen atmosphere, to a solution of the compound (1.5 g) obtained in (1) above in 1,4-dioxane (21 mL), methylboronic acid (0.37 g), [1,1'-bis(diphenylphosphino) ferrocene]palladium (II) dichloride dichloromethane adduct (0.34 g), tripotassium phosphate (2.7 g), and water (2.1 mL) were added, and the reaction solution was stirred at 100° C. for 7 hours and at room temperature for 15 hours.

Ethyl acetate and water were added to the reaction solution, which was then filtered through Celite (registered trademark), and the filtrate was partitioned into two layers. The organic layer was concentrated, and the obtained residue was purified by silica gel column chromatography (n-hexane:ethyl acetate=95:5 to 60:40) to afford the title compound (617 mg) as a colorless oily substance.

MS ESI posi: 249 [M+H]$^+$.

Retention time: 0.968 min (method A)

The following Reference Examples 1-14-11 to 1-14-12 were synthesized by the method described in Reference Example 1-14-10 or by a method equivalent thereto, using the compounds obtained in Reference Example 1-4-1 and Reference Example 1-4-3. The structures, NMR data, and LCMS data of the compounds are shown in Table 10-3 to Table 10-4.

TABLE 10-3

| Reference Example No. | Structural Formula | Analytical data |
|---|---|---|
| 1-14-11 | (structure: benzaldehyde with 3,5-dimethoxy, 4-Br, 2-methyl) | 1H NMR (600 MHz, CHLOROFORM-d) δ ppm 2.60 (m, 3H) 3.83 (m, 3H) 2.96 (s, 3H) 7.18 (s 1H) 10.32 (m, 1H). |

TABLE 10-4

| Reference Example No. | Structural Formula | MS posi m/z MS nega m/z | Retention time (min) | method |
|---|---|---|---|---|
| 1-14-12 | (structure: benzaldehyde with 3,5-dimethoxy, 4-methyl, 2-methyl) | 156 [M + H]+ | 0.748 | A |

Reference Example 1-15-1

(1R)-1-(3,5-Diethoxy-4-Methylphenyl) Ethan-1-Amine

[Chemical Formula 412]

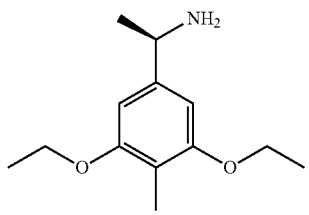 [SMILES: CCOc1cc([C@@H](C)N)c(C)c(OCC)c1C]

(1) The present reaction was carried out with reference to the methods described in the literatures (Journal of Combinatorial Chemistry, vol. 5, p. 590, 2003; and Organic Letters, vol. 3, p. 3707, 2001). To a solution of (S)-(−)-tert-butylsulfinamide (1 g) and the compound (1.80 g) obtained in Reference Example 1-4-2 in chloroform (21 mL), tetraethyl orthotitanate (containing 35% or less of tetraisopropyl orthotitanate) (3.74 mL) was added, and the reaction solution was stirred at 110° C. for 15 minutes under microwave irradiation. The reaction solution was filtered through a mixed pad of Celite (registered trademark)-sodium sulfate decahydrate (2:1, 20 g), and the filtrate was concentrated. The obtained residue was purified by silica gel column chromatography (n-hexane only to n-hexane:ethyl acetate=70:30) to afford (SS)-N-[(E)-(3,5-diethoxy-4-methylphenyl)methylidene]-2-methylpropane-2-sulfinamide (2.52 g) as a light yellow solid.

(2) The present reaction was carried out with reference to the method described in the literature (Chemical Reviews, vol. 110, p. 3600, 2010). Under a nitrogen atmosphere, a solution of the compound (3.40 g) obtained in (1) above in 1,2-dichloroethane (55 mL) was ice-cooled, methylmagnesium bromide (3 mol/L diethyl ether solution, 18.2 mL) was slowly added thereto, and the reaction solution was stirred at room temperature for 15 hours. The reaction solution was ice-cooled, a saturated aqueous ammonium chloride solution was added thereto, and extraction with ethyl acetate was carried out twice. The organic layer was washed with a brine and dried over anhydrous magnesium sulfate. After filtering off the desiccating agent, the filtrate was concentrated. The obtained residue was purified by silica gel column chromatography (n-hexane:ethyl acetate=95:5 to 50:50) to afford (SS)-N-[(1R)-1-(3,5-diethoxy-4-methylphenyl)ethyl]-2-methylpropane-2-sulfinamide (2.81 g) as a colorless solid.

$^1$H NMR (400 MHZ, CHLOROFORM-d) δ ppm 1.21 (s, 9H) 1.37-1.44 (m, 6H) 1.49-1.57 (m, 3H) 2.08 (s, 3H) 3.24-3.29 (m, 1H) 3.95-4.06 (m, 4H) 4.46-4.53 (m, 1H) 6.49 (s, 2H).

The obtained colorless solid was recrystallized from ethyl acetate to acquire a single crystal, which was confirmed to have the target structure below by X-ray structure analysis.

[Chemical Formula 413]

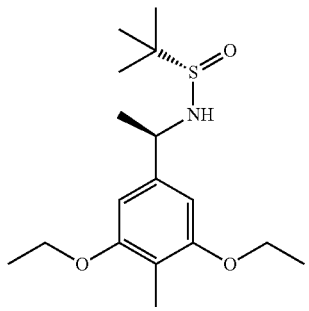

(3) A solution of the compound (2.81 g) obtained in (2) above in methanol (43 mL) was ice-cooled, a 4 mol/L hydrogen chloride-1,4-dioxane solution (6.4 mL) was added thereto, and the reaction solution was stirred at room temperature for 1.5 hours. The reaction solution was concentrated, a saturated aqueous sodium bicarbonate solution was added thereto, and extraction with a mixed solvent of chloroform-methanol (9:1) was carried out. The organic layer was dried over anhydrous magnesium sulfate. After filtering off the desiccating agent, the filtrate was concentrated to afford the title compound (2.10 g) as a light yellow oily substance.

$^1$H NMR (400 MHZ, CHLOROFORM-d) δ ppm 1.35-1.44 (m, 9H) 2.08 (s, 3H) 4.01-4.08 (m, 5H) 6.51 (s, 2H).

Reference Example 1-15-2

(1R)-1-(4-Bromo-2-Chloro-3,5-Diethoxyphenyl) Ethan-1-Amine Hydrochloride

[Chemical Formula 414]

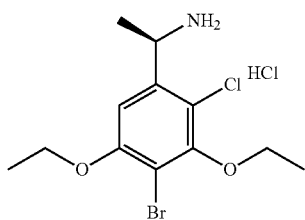

(1) To a solution of the compound (6.00 g) obtained in Reference Example 1-14-1 in toluene (39 mL), (S)-(−)-tert-butylsulfinamide (2.48 g) and tetraethyl orthotitanate (containing 35% or less of tetraisopropyl orthotitanate) (6.43 mL) were added, and the reaction solution was stirred at 100° C. for 3 hours and left standing at room temperature overnight. A 10% aqueous disodium citrate 1.5-hydrate solution was added to the reaction solution, which was then stirred for 30 minutes and subsequently filtered through Celite (registered trademark), and the filtrate was extracted with ethyl acetate. The organic layer was washed with a 10% aqueous disodium citrate 1.5-hydrate solution and a brine sequentially, and dried over anhydrous magnesium sulfate. After filtering off the desiccating agent, the filtrate was concentrated. The obtained residue was purified by silica gel column chromatography (n-hexane only to n-hexane:ethyl acetate=90:10) to afford (SS)-N-[(E)-(4-bromo-2-chloro-3,5-diethoxyphenyl)methylidene]-2-methylpropane-2-sulfinamide (7.06 g) as a colorless powder.

(2) Using the compound (7.06 g) obtained in (1) above, the reaction was carried out in accordance with the method described in Reference Example 1-15-1 (2), and (SS)-N-[(1R)-1-(4-bromo-2-chloro-3,5-diethoxyphenyl)ethyl]-2-methylpropane-2-sulfinamide (5.93 g) was obtained as a colorless amorphous.

(3) To a solution of the compound (2 g) obtained in (2) above in methanol (16 mL), a 4 mol/L hydrogen chloride-1,4-dioxane solution (3.5 mL) was added, and the reaction solution was stirred at room temperature for 30 minutes. The reaction solution was concentrated to afford the title compound (1.36 g) as a colorless powder.

$^1$H NMR (400 MHZ, METHANOL-d$_4$) δ ppm 1.41-1.52 (m, 6H) 1.56-1.66 (m, 3H) 4.03-4.21 (m, 4H) 4.88-4.97 (m, 1H) 6.99 (s, 1H).

MS ESI posi: 322, 324 [M+H]$^+$.

Retention time: 0.953 min (method C)

The following Reference Examples 1-15-3 to 1-15-13 were synthesized by the method described in Reference Example 1-15-1 to 1-15-2 or Reference Example 1-16-1, or by a method equivalent thereto, using the compounds obtained in Reference Example 1-4-1, Reference Example 1-4-3, and Reference Examples 1-14-4 to 1-14-12, commercially available compounds, or compounds obtained by synthesis according to methods described in literatures or methods equivalent thereto. The structures and NMR data of the compounds are shown in Table 11-1 to Table 11-3.

TABLE 11-1

| Reference Example No. | Structural Formula | Analytical data |
|---|---|---|
| 1-15-3 | ![structure with NH2, HCl, OMe groups] | $^1$H NMR (400 MHz, DMSO-d$_6$) δ ppm 1.47-1.54 (m, 3H) 1.98 (s, 3H) 3.79 (s, 6H) 4.28-4.38 (m, 1H) 6.82 (s, 2H) 8.39 (br s, 3H). |

TABLE 11-1-continued

| Reference Example No. | Structural Formula | Analytical data |
|---|---|---|
| 1-15-4 | [(1-(3,5-diethoxyphenyl)ethyl)amine · HCl] | $^1$H NMR (600 MHz, CHLOROFORM-d) δ ppm 1.21-1.90 (m, 9H) 3.84-4.13 (m, 5H) 6.38 (br s, 1H) 6.62 (br s, 2H) 8.52-9.01 (m, 3H). |
| 1-15-5 | [(1-(3,5-diethoxy-2,6-dimethylphenyl)ethyl)amine] | $^1$H NMR (400 MHz, METHANOL-d$_6$) δ ppm 1.36-1.46 (m, 6H) 1.51-1.62 (m, 3H) 2.12 (s, 3H) 2.24 (s, 3H) 3.72-3.85 (m, 2H) 3.99-4.14 (m, 2H) 4.64-4.74 (m, 1H) 6.79 (s, 1H). |
| 1-15-6 | [(1-(4-bromo-3,5-diethoxyphenyl)ethyl)amine · HCl] | $^1$H NMR (600 MHz, DMSO-d$_6$) δ ppm 1.34-1.39 (m, 6H) 1.48-1.52 (m, 3H) 4.08-4.15 (m, 4H) 4.30-4.42 (m, 1H) 6.88-6.97 (m, 2H) 8.37-8.55 (m, 3H). |
| 1-15-7 | [(1-(4-(1-hydroxycyclopropyl)-3,5-diethoxyphenyl)ethyl)amine · formate] | $^1$H NMR (400 MHz, CHLOROFORM-d) δ ppm 0.81-0.95 (m, 2H) 1.05-1.20 (m, 2H) 1.37-1.47 (m, 6H) 1.47-1.60 (m, 3H) 3.93-4.09 (m, 4H) 4.09-4.24 (m, 1H) 6.15 (br s, 3H) 6.58 (s, 2H) 8.24 (br s, 1H). |

TABLE 11-2

| Reference Example No. | Structural Formula | Analytical data |
|---|---|---|
| 1-15-8 | [(1-(4-acetyl-5-ethoxy-2-methylphenyl)ethyl)amine] | $^1$H NMR (400 MHz, CHLOROFORM-d) δ ppm 1.23-1.39 (m, 3H) 1.40-1.50 (m, 3H) 2.27 (s, 3H) 2.62 (s 3H) 4.07-4.23 (m, 2H) 4.31-4.43 (m, 1H) 7.13-7.76 (m, 4H). |
| 1-15-9 | [(1-(4-bromo-3,5-dimethoxyphenyl)ethyl)amine · HCl] | 1H NMR (600 MHz, DMSO-d) δ ppm 1.40-1.64 (m, 3H) 3.86 (m, 6H) 4.26-4.53 (m, 1H) 6.79-7.14 (m, 2H) 8.18-8.70 (m, 3H) |

TABLE 11-3

| Reference Example No. | Structural Formula | Analytical data |
|---|---|---|
| 1-15-10 | (dimethyl dimethoxyphenyl aminoethyl) · HCl | 1H NMR (400 MHz, CHLOROFORM-d) δ ppm 1.53-1.62 (m, 3H) 2.13 (m, 3H) 2.20 (s, 3H) 3.59 (s, 3H) 2.67 (s, 3H) 4.59-4.74 (m, 1H) 6.95 (s, 1H) 8.69 (br s, 3H). |
| 1-15-11 | (bromo dimethoxy methyl phenyl aminoethyl) · HCl | 1H NMR (600 MHz, CHLOROFORM-d) δ ppm 1.57-1.60 (m, 3H) 2.26 (m, 3H) 2.72-2.80 (s, 3H) 4.59-4.65 (m, 1H) 7.96 (s, 1H) 8.78 (br s, 3H) |
| 1-15-12 | (cyclopropyl diethoxy methyl phenyl aminoethyl) · HCl | 1H NMR (400 MHz, METHANOL-d) δ ppm 0.80-0.89 (m, 3H) 0.90-1.00 (m, 2H) 1.34-1.50 (m, 6H) 1.52-1.57 (s, 3H) 1.78-1.88 (m, 1H) 2.22 (s, 3H) 3.81-3.90 (m, 2H) 3.95-4.07 (m, 2H) 4.62-4.70 (s, 1H) 6.74 (s, 1H). |
| 1-15-13 | (bromo ethoxy methyl phenyl aminoethyl) · HCl | 1H NMR (400 MHz, CHLOROFORM-d) δ ppm 1.40-1.51 (m, 3H) 1.30-1.74 (m, 3H) 2.32 (s, 2H) 3.35-4.62 (m, 2H) 4.60-4.69 (m, 1H) 7.20-7.38 (s, 1H) 7.39-7.48 (m, 1H) 8.71 (br s, 3H). |

Reference Example 1-16-1

1-{4-[(1R)-1-Aminoethyl]-3-Chloro-2,6-Diethoxyphenyl}Ethan-1-One

[Chemical Formula 415]

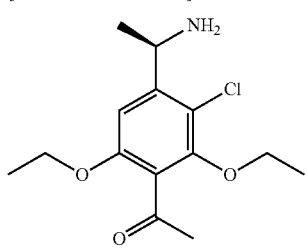

(1) Using the compound (500 mg) obtained in Reference Example 1-15-2 (2), the reaction was carried out in accordance with the method described in Reference Example 1-8-5. However, instead of the 10% aqueous potassium carbonate solution, a saturated aqueous sodium bicarbonate solution was used for the post treatment. By the above method, (SS)-N-[(1R)-1-(4-acetyl-2-chloro-3,5-diethoxyphenyl)ethyl]-2-methylpropane-2-sulfinamide (457 mg) was obtained as a brown oily substance.

(2) To a solution of the compound (457 mg) obtained in (1) above in methanol (3.9 mL), a 4 mol/L hydrogen chloride-1,4-dioxane solution (0.88 mL) was added, and the reaction solution was stirred at room temperature for 45 minutes. The reaction solution was concentrated, and the obtained residue was purified by silica gel column chromatography (chloroform only to chloroform:methanol=95:5) to afford the title compound (320 mg) as a brown amorphous.

$^1$H NMR (400 MHZ, CHLOROFORM-d) δ ppm 1.23-1.41 (m, 6H) 1.63-1.72 (m, 3H) 2.48 (s, 3H) 3.89-4.10 (m, 4H) 4.92-5.01 (m, 1H) 7.20 (s, 1H) 8.99 (br s, 2H).

MS ESI posi: 286, 288 [M+H]$^+$.

Retention time: 0.813 min (method C)

Reference Example 1-16-2

1-{4-[(1R)-1-Aminoethyl]-2,6-Diethoxy-3-Methylphenyl}Ethan-1-One Hydrochloride

[Chemical Formula 416]

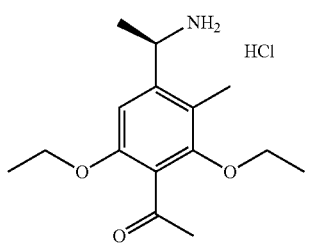

(1) Using the compound (15.4 g) obtained in Reference Example 1-14-2, the reaction was carried out in accordance with the method described in Reference Example 1-15-2 (1), and (SS)-N-[(E)-(4-bromo-3,5-diethoxy-2-methylphenyl)methylidene]-2-methylpropane-2-sulfinamide (19.5 g) was obtained as a yellow oily substance.

(2) Using the compound (19.5 g) obtained in (1) above, the reaction and post treatment were carried out in accordance with the method described in Reference Example 1-15-1 (2). To the obtained residue, ethyl acetate (5 mL) and hexane (30 mL) were added, and they were dissolved by heating and stirring. To this, ethyl acetate (5 mL) and hexane (160 mL) were further added, and the reaction solution was stirred at room temperature for 2 hours and for 1 hour under ice cooling. The precipitated solid was filtered off. To the obtained solid, ethyl acetate (6 mL) and hexane (14 mL) were added, and they were dissolved by heating and stirring. To this, hexane (150 mL) was added, and the reaction solution was stirred for 30 minutes under ice cooling. The precipitated solid was filtered off, and (SS)-N-[(1R)-1-(4-bromo-3,5-diethoxy-2-methylphenyl)ethyl]-2-methylpropane-2-sulfinamide (10.8 g) was obtained as a colorless powder.

(3) A solution of the compound (2.00 g) obtained in (2) above in methanol (16 mL) was ice-cooled, a 4 mol/L hydrogen chloride-1,4-dioxane solution (3.69 mL) was added thereto, and the reaction solution was stirred at the same temperature for 1 hour. The reaction solution was concentrated, and (1R)-1-(4-bromo-3,5-diethoxy-2-methylphenyl) ethan-1-amine hydrochloride (1.60 g) was obtained as a colorless powder.

(4) A solution of the compound (1.60 g) obtained in (3) above in chloroform (12 mL) was ice-cooled, N,N-diisopropylethylamine (1.71 mL) and a solution of di-tert-butyl dicarbonate (1.29 g) in chloroform (4 mL) were added thereto, and the reaction solution was stirred at room temperature for 1 hour. Water was added to the reaction solution, which was then extracted with chloroform. The organic layer was filtered through Phase Separator and concentrated. The obtained residue was purified by silica gel column chromatography (n-hexane:ethyl acetate: chloroform=93:2:5 to 71:24:5) to afford tert-butyl[(1R)-1-(4-bromo-3,5-diethoxy-2-methylphenyl)ethyl]carbamate (1.63 g) as a colorless solid.

(5) To a solution of the compound (1.63 g) obtained in (4) above and butyl vinyl ether (4.05 g) in N,N-dimethylformamide (13 mL), water (1.3 mL), palladium (II) acetate (90.8 mg), 1,3-bis(diphenylphosphino) propane (350 mg), and potassium carbonate (1.68 g) were added, and the reaction solution was stirred at 120° C. for 3 hours under microwave irradiation. Water was added to the reaction solution, which was then filtered through Celite (registered trademark), and water was added to the filtrate, which was then extracted with diethyl ether. The organic layer was washed with a mixed solution of saturated aqueous sodium bicarbonate solution-water (1:1) and a brine, and dried over anhydrous magnesium sulfate. After filtering off the desiccating agent, the filtrate was concentrated to afford a mixture (2.1 g) containing tert-butyl {(1R)-1-[4-(1-butoxyethenyl)-3,5-diethoxy-2-methylphenyl]ethyl}carbamate.

(6) A solution of the mixture (2.1 g) obtained in (5) above in tetrahydrofuran (10 mL) was ice-cooled, 1 mol/L hydrochloric acid (2 mL) was added thereto, and the reaction solution was stirred at the same temperature for 1 hour. 1 mol/L hydrochloric acid (4 mL) was further added to the reaction solution, which was then stirred at the same temperature for 30 minutes. The reaction solution was extracted with diethyl ether. The organic layer was washed with a brine, dried over anhydrous magnesium sulfate, filtered through Phase Separator, and concentrated. The obtained residue was purified by silica gel column chromatography (n-hexane only to n-hexane:ethyl acetate=75:25) to afford tert-butyl[(1R)-1-(4-acetyl-3,5-diethoxy-2-methylphenyl)ethyl]carbamate (1.21 g) as a colorless solid.

(7) A solution of the compound (1.21 g) obtained in (6) above in 1,4-dioxane (4 mL) was ice-cooled, a 4 mol/L hydrogen chloride-1,4-dioxane solution (3.3 mL) was added thereto, and the reaction solution was stirred at room temperature for 2 hours. The reaction solution was concentrated to afford the title compound (1.01 g) as a pale brown powder. $^1$H NMR (400 MHZ, DMSO-$d_6$) δ ppm 1.18-1.38 (m, 6H) 1.41-1.51 (m, 3H) 2.15 (s, 3H) 2.39 (s, 3H) 3.69-3.82 (m, 2H) 4.03-4.15 (m, 2H) 4.50-4.59 (m, 1H) 7.18 (s, 1H) 8.43 (br s, 2H).

The following Reference Example 1-16-3 was synthesized by the method described in Reference Example 1-16-2 or by a method equivalent thereto, using the compound obtained in Reference Example 1-15-6, a commercially available compound, or a compound obtained by synthesis according to methods described in literatures or methods equivalent thereto. The structure and NMR data of the compound are shown in Table 12-1.

TABLE 12-1

| Reference Example No. | Structural Formula | Analytical data |
|---|---|---|
| 1-16-3 | ![structure with NH2, HCl, two ethoxy groups, and acetyl] | $^1$H NMR (400 MHz, CHLOROFORM-d) δ ppm 1.26-1.40) (m, 6H) 1.60-1.67 (m, 3H) 2.45 (s, 3H) 3.97-4.12 (m, 4H) 4.17-4.36 (m, 1H) 6.72 (s, 2H) 8.70 (br s, 2H). |

Reference Example 1-17-1

(1R)-1-(4-Cyclopropyl-3,5-Diethoxyphenyl) Ethan-1-Amine Hydrochloride

[Chemical Formula 417]

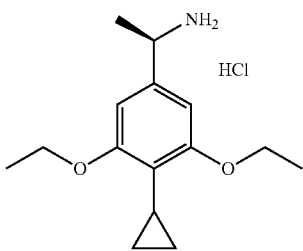

(1) To a solution of the compound (500 mg) obtained in Reference Example 1-15-6 in chloroform (4 mL), N,N-diisopropylethylamine (537 μL) was added, the reaction solution was ice-cooled, a solution of di-tert-butyl dicarbonate (403 μg) in chloroform (2 mL) was added thereto, and the reaction solution was stirred at room temperature for 1 hour. Water was added to the reaction solution, and the organic layer was separated, filtered through Phase Separator, and concentrated. The obtained residue was purified by silica gel column chromatography (n-hexane only to n-hexane:ethyl acetate=75:25) to afford tert-butyl[(1R)-1-(4-bromo-3,5-diethoxyphenyl)ethyl]carbamate (584 mg) as a colorless solid.

(2) Using the compound (598 mg) obtained in (1) above and cyclopropylboronic acid (198 mg), the reaction was carried out in accordance with the method described in Reference Example 1-7-1, and tert-butyl[(1R)-1-(4-cyclopropyl-3,5-diethoxyphenyl)ethyl]carbamate (644 mg) was obtained as a yellow solid.

(3) A solution of the compound (644 mg) obtained in (2) above in chloroform (2.5 mL) was ice-cooled, a 4 mol/L hydrogen chloride-1,4-dioxane solution (1.2 mL) was added thereto, and the reaction solution was stirred at room temperature for 1 hour. Chloroform (3 mL), methanol (2 mL), and a 4 mol/L hydrogen chloride-1,4-dioxane solution (0.77 mL) was further added thereto, and the reaction solution was stirred at the same temperature for 6 hours. The reaction solution was concentrated, chloroform was added thereto, and the reaction solution was stirred at room temperature for 10 minutes. The precipitated solid was filtered off to afford the title compound (380 mg) as a colorless solid.

$^1$H NMR (400 MHz, DMSO-d$_6$) δ ppm 0.65-0.81 (m, 2H) 0.91-1.12 (m, 2H) 1.33 (t, J=6.90 Hz, 6H) 1.41-1.54 (m, 3H) 1.83-1.94 (m, 1H) 4.00 (q, J=6.90 Hz, 4H) 4.19-4.36 (m, 1H) 6.73 (s, 2H) 8.32 (br s, 2H).

The following Reference Examples 1-17-2 to 1-17-3 were synthesized by the method described in Reference Example 1-17-1 or by a method equivalent thereto, using the compounds obtained in Reference Example 1-15-9 and Reference Example 1-15-13. The structures and NMR data of the compounds are shown in Table 12-2.

TABLE 12-2

| Reference Example No. | Structural Formula | Analytical data |
|---|---|---|
| 1-17-2 | ![structure with NH2, two methoxy groups, and cyclopropyl] | 1H NMR (400 MHz, CHLOROFORM-d) δ ppm 0.77-0.84 (m, 2H) 0.89-0.96 (m, 2H) 1.36-1.41 (s, 3H) 1.76-1.85 (m, 1H) 3.82 (m, 1H) 4.03-4.10 (m, 1H) 6.53 (s, 2H). |

TABLE 12-2-continued

| Reference Example No. | Structural Formula | Analytical data |
|---|---|---|
| 1-17-3 | (structure: chiral NH₂ on benzene with methyl, ethoxy, cyclopropyl substituents; HCl salt) | 1H NMR (400 MHz, METHANOL-d4) δ ppm 0.59-0.73 (m, 2H) 0.91-1.05 (m, 2H) 1.37-1.48 (m, 3H) 1.50-1.63 (m, 3H) 2.14-2.24 (m, 1H) 2.29-2.37 (m, 3H) 3.86-3.99 (m, 2H) 4.62-4.72 (m, 1H) 6.73-6.83 (m, 1H) 7.05-7.16 (m, 1H). |

Reference Example 1-17-4

(1R)-1-(2-Chloro-4-Cyclopropyl-3-Ethoxyphenyl)Ethan-1-Amine Hydrochloride

[Chemical Formula 418]

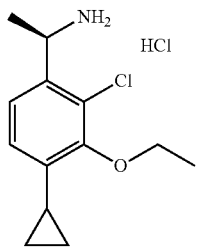

(1) To a solution of the compound (4.00 g) obtained in Reference Example 1-14-3 in toluene (30 mL), (S)-(–)-tert-butylsulfinamide (1.93 g) and tetraethyl orthotitanate (containing 35% or less of tetraisopropyl orthotitanate) (5.00 mL) were added, and the reaction solution was stirred at 100° C. for 1 hour. After bringing the reaction solution back to room temperature, a brine (4 mL) was added thereto. The reaction solution was filtered through a mixed pad of Celite (registered trademark)-diatomaceous earth (1:1, 150 mL), and the filtrate was concentrated to afford (SS)-N-[(E)-(4-bromo-2-chloro-3-ethoxyphenyl)methylidene]-2-methyl-propane-2-sulfinamide (5.90 g) was obtained as a light yellow oily substance.

(2) Using the compound (5.57 g) obtained in (1) above, the reaction was carried out in accordance with the method described in Reference Example 1-15-1 (2), and (SS)-N-[(1R)-1-(4-bromo-2-chloro-3-ethoxyphenyl)ethyl]-2-methylpropane-2-sulfinamide (2.58 g) was obtained as a colorless solid.

(3) Under a nitrogen atmosphere, to a mixed solution of the compound (2.57 g) obtained in (2) above in toluene-water (67 mL-6.7 mL), cesium carbonate (6.56 g), cyclopropylboronic acid (865 mg), and tetrakis(triphenylphosphine) palladium (0) (776 mg) were added, and the reaction solution was stirred at 100° C. for 14 hours, at 120° C. for 20 minutes, and at 130° C. for 1 hour. After bringing the reaction solution back to room temperature, cyclopropylboronic acid (404 mg) and tetrakis(triphenylphosphine) palladium (0) (388 mg) were further added thereto, and the reaction solution was stirred at 130° C. for 2 hours. The reaction solution was concentrated, and the obtained residue was purified by silica gel column chromatography (n-hexane:ethyl acetate=80:20 to ethyl acetate only) to afford (SS)-N-[(1R)-1-(2-chloro-4-cyclopropyl-3-ethoxyphenyl)ethyl]-2-methylpropane-2-sulfinamide (1.89 g) as a light yellow solid.

(3) To a solution of the compound (1.89 g) obtained in (2) above in methanol (3 mL), 2 mol/L hydrogen chloride-methanol (5.50 mL) was added, and the reaction solution was stirred at room temperature for 80 minutes. The reaction solution was concentrated, the obtained residue was suspended by adding isopropyl ether, and the solid was filtered off to afford the title compound (1.29 g) as a light yellow powder.

MS ESI posi: 240 [M+H]⁺.

Retention time: 0.876 min (method C)

Reference Example 1-18-1

1-{4-[(1R)-1-Aminoethyl]-2-Ethoxy-3-Methylphenyl}Ethan-1-One

[Chemical Formula 419]

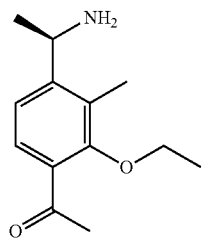

(1) To a solution of 1-(4-benzyloxy-2-hydroxy-3-methylphenyl) ethanone (14.9 g) in N,N-dimethylformamide (58 mL), potassium carbonate (12.0 g) and iodoethane (9.3 mL) were added, and the reaction solution was stirred at 60° C. for 10 hours and at room temperature overnight. Potassium carbonate (8.0 g) and iodoethane (4.6 mL) were further added thereto, and the reaction solution was stirred at 60° C. for 20 hours. Water was added to the reaction solution, which was then extracted with a mixed solvent of n-hexane-ethyl acetate. The organic layer was washed with water and a brine sequentially, and dried over anhydrous magnesium sulfate. After filtering off the desiccating agent, the filtrate was concentrated to afford a mixture (18.0 g) containing 1-[4-(benzyloxy)-2-ethoxy-3-methylphenyl]ethan-1-one as a brown oily substance.

(2) To a solution of the mixture (18.0 g) obtained in (1) above in ethanol (58 mL), palladium carbon (3.3 g) was added, and the reaction solution was stirred at room temperature for 20 hours under a hydrogen atmosphere. The reaction solution was filtered through Celite (registered trademark), and the filtrate was concentrated to afford a mixture (12.8 g) containing 1-(2-ethoxy-4-hydroxy-3-methylphenyl) ethan-1-one as a light brown oily substance.

(3) Under a nitrogen atmosphere, to a solution of the mixture (11.3 g) obtained in (2) above in chloroform (232 mL), pyridine (10 mL) was added, and the reaction solution was ice-cooled. Trifluoromethanesulfonic anhydride (11.7 mL) was added thereto, and the reaction solution was stirred for 2 hours while gradually bringing it back to room temperature. Pyridine (1 mL) was added thereto at room temperature, and the reaction solution was stirred at the same temperature for 80 minutes. The reaction solution was ice-cooled, pyridine (2 mL) and trifluoromethanesulfonic anhydride (2.3 mL) were added thereto, and the reaction solution was stirred at room temperature for 80 minutes. The reaction solution was concentrated, ethyl acetate was added thereto, and the reaction solution was ice-cooled. A saturated aqueous sodium bicarbonate solution was added dropwise thereto, and the reaction solution was stirred at room temperature until it stopped foaming. The organic layer was washed with a saturated aqueous sodium bicarbonate solution, water, and a brine sequentially, and dried over anhydrous magnesium sulfate. After filtering off the desiccating agent, the filtrate was concentrated. The obtained residue was purified by silica gel column chromatography (n-hexane:ethyl acetate=97:3 to 65:35) to afford 4-acetyl-3-ethoxy-2-methylphenyl trifluoromethanesulfonate (15.9 g) as a light yellow oily substance.

(4) To a solution of the compound (15.9 g) obtained in (3) above in toluene (325 mL), ethylene glycol (122 mL) and p-toluenesulfonic acid monohydrate (0.9 g) were added, and the reaction solution was stirred at 125° C. for 4.5 hours and at room temperature overnight. The reaction solution was ice-cooled, a saturated aqueous sodium bicarbonate solution was added thereto, and extraction with ethyl acetate was carried out. The organic layer was washed with water and a brine sequentially, filtered through Phase Separator, and concentrated. The obtained residue was purified by silica gel column chromatography (n-hexane:ethyl acetate=97:3 to 78:22) to afford 3-ethoxy-2-methyl-4-(2-methyl-1,3-dioxolan-2-yl)phenyl trifluoromethanesulfonate (17.3 g) as a colorless oily substance.

(5) Under a nitrogen atmosphere, to a mixed solution of the compound (17.3 g) obtained in (4) above in 1,4-dioxane-water (93 mL-9.3 mL), sodium carbonate (7.43 g), potassium (acetoxymethyl)trifluoroborate (12.6 g), and (2-dicyclohexylphosphino-2',6'-diisopropoxy-1,1'-biphenyl) [2-(2'-amino-1,1'-biphenyl)]palladium (II) methanesulfonate (RuPhosPdG3, Sigma-Aldrich, 1.95 g) were added, and the reaction solution was stirred at 100° C. for 20 hours. The reaction solution was concentrated, and the obtained residue was purified by silica gel column chromatography (n-hexane:ethyl acetate=98:2 to 60:40) to afford[3-ethoxy-2-methyl-4-(2-methyl-1,3-dioxolan-2-yl)phenyl]methanol (8.3 g) and 1-[2-ethoxy-4-(hydroxymethyl)-3-methylphenyl]ethan-1-one (1.59 g) each as a light yellow oily substance.

(6) To a solution of [3-ethoxy-2-methyl-4-(2-methyl-1,3-dioxolan-2-yl)phenyl]methanol (8.3 g) obtained in (5) above in toluene (82 mL), manganese (IV) oxide (29 g) was added, and the reaction solution was stirred at room temperature for 16 hours. Manganese (IV) oxide (29 g) and toluene (50 mL) were further added thereto, and the reaction solution was stirred at room temperature for 4 hours. The reaction solution was filtered through Celite (registered trademark), and the filtrate was concentrated to afford a mixture (7.89 g) containing 3-ethoxy-2-methyl-4-(2-methyl-1,3-dioxolan-2-yl)benzaldehyde as a light yellow oily substance.

(7) To a solution of the mixture (7.89 g) obtained in (6) above and(S)-(−)-tert-butylsulfinamide (3.82 g) in toluene (63 mL), tetraethyl orthotitanate (containing 35% or less of tetraisopropyl orthotitanate) (10.4 mL) were added, and the reaction solution was stirred at room temperature for 45 minutes. Tetraethyl orthotitanate (containing 35% or less of tetraisopropyl orthotitanate) (3.9 mL) were further added thereto, and the reaction solution was stirred at room temperature for 14 hours. The reaction solution was filtered through a mixture of Celite (registered trademark) and sodium sulfate decahydrate, and the filtrate was concentrated. The obtained residue was purified by silica gel column chromatography (n-hexane:ethyl acetate=94:6 to 50:50) to afford (SS)-N-{(E)-[3-ethoxy-2-methyl-4-(2-methyl-1,3-dioxolan-2-yl)phenyl]methylidene}-2-methylpropane-2-sulfinamide (9.56 g) as a light yellow oily substance.

(8) A solution of the compound (9.56 g) obtained in (7) above in 1,2-dichloroethane (90 mL) was ice-cooled, methylmagnesium bromide (3 mol/L diethyl ether solution, 27.0 mL) was added dropwise thereto, and the reaction solution was stirred at the same temperature for 1 hour and at room temperature for 3 hours. The reaction solution was ice-cooled, methylmagnesium bromide (3 mol/L diethyl ether solution, 4.5 mL) was added dropwise thereto, and the reaction solution was stirred at the same temperature for 10 minutes, brought back to room temperature, and stirred for 50 minutes. The reaction solution was ice-cooled, a saturated aqueous ammonium chloride solution was added thereto, and the reaction solution was stirred overnight while gradually bringing it back to room temperature. Water was added to the reaction solution, which was then separated into the organic layer and the aqueous layer. The aqueous layer was extracted with chloroform, and the organic layers were combined, washed with a brine, filtered through Phase Separator, and concentrated. The obtained residue was purified by silica gel column chromatography (n-hexane:ethyl acetate: methanol=84:16:0 to 0:100:0 to 0:90:10) to afford (SS)-N-{(1R)-1-[3-ethoxy-2-methyl-4-(2-methyl-1,3-dioxolan-2-yl)phenyl]ethyl}-2-methylpropane-2-sulfinamide (7.52 g) as a colorless gum-like substance.

(9) A solution of the compound (7.5 g) obtained in (8) above in methanol (100 mL) was ice-cooled, 2 mol/L hydrochloric acid (100 mL) was added thereto, and the reaction solution was stirred for 2.5 days while gradually raising the temperature to room temperature. A saturated aqueous sodium bicarbonate solution was added to the reaction solution to adjust the pH to 8 to 9, and extraction with ethyl acetate was carried out. The organic layer was washed with a brine, filtered through Phase Separator, and concentrated. The obtained residue was dissolved in methanol, insolubles were filtered off, and the filtrate was then concentrated to afford the title compound (5.1 g) as a light yellow oily substance. $^1$H NMR (400 MHZ, CHLOROFORM-d) δ ppm 1.16-1.48 (m, 8H) 2.30 (s, 3H) 2.62 (s, 3H) 3.77-3.86 (m, 2H) 4.38-4.46 (m, 1H) 7.34 (d, J=8.07 Hz, 1H) 7.46 (d, J=8.07 Hz, 1H).

Reference Example 1-18-2

(1R)-1-[3-Ethoxy-4-(2-Hydroxypropan-2-Yl)-2-Methylphenyl]Ethan-1-Amine Formate

[Chemical Formula 420]

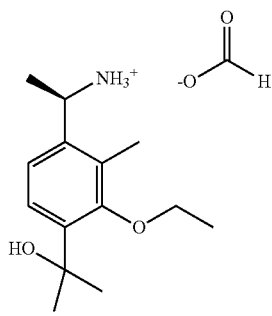

(1) To a solution of 1-[2-ethoxy-4-(hydroxymethyl)-3-methylphenyl]ethan-1-one (50 mg) obtained in Reference Example 1-18-1 (5) in toluene (1.2 mL), manganese dioxide (209 mg) was added, and the reaction solution was stirred at room temperature for 18 hours and at 40° C. for 2 hours. Manganese dioxide (104 mg) was further added thereto, and the reaction solution was stirred at 40° C. for 4 hours. The reaction solution was filtered through Celite (registered trademark), and the filtrate was concentrated. The concentrate was purified by silica gel column chromatography (n-hexane only to n-hexane:ethyl acetate=80:20) to afford 4-acetyl-3-ethoxy-2-methylbenzaldehyde (30.5 mg) as a yellow oily substance.

(2) To a solution of the compound (0.70 g) obtained in (1) above in toluene (6.8 mL), (S)-(-)-tert-butylsulfinamide (0.41 g) and tetraethyl orthotitanate (containing 35% or less of tetraisopropyl orthotitanate) (1.1 mL) were added, and the reaction solution was stirred at room temperature for 18 hours. The reaction solution was filtered through a mixed pad of Celite (registered trademark)-sodium sulfate decahydrate (2:1, 15 g), and the filtrate was concentrated. The residue was purified by silica gel column chromatography (n-hexane:ethyl acetate=94:6 to 60:40) to afford (SS)-N-[(E)-(4-acetyl-3-ethoxy-2-methylphenyl)methylidene]-2-methylpropane-2-sulfinamide (0.279 g) as a yellow oily substance.

(3) Under a nitrogen atmosphere, a solution of the compound (0.279 g) obtained in (2) above in 1,2-dichloroethane (3.0 mL) was ice-cooled, and methylmagnesium bromide (0.9 mL) was slowly added dropwise thereto. 1,2-Dichloroethane (3.0 mL) was further added thereto, and the reaction solution was stirred at 0° C. for 1 hour. Tetrahydrofuran (3.0 mL) was added thereto, methylmagnesium bromide (0.9 mL) was added dropwise thereto, and the reaction solution was stirred at the same temperature for 1 hour. A saturated aqueous ammonium chloride solution was slowly added thereto, and extraction with chloroform was carried out. The organic layers were collected, filtered through Phase Separator, and concentrated. The concentrate was purified by silica gel column chromatography (n-hexane:ethyl acetate=90:10 to ethyl acetate only) to afford (SS)-N-{(1R)-1-[3-ethoxy-4-(2-hydroxypropan-2-yl)-2-methylphenyl]ethyl}-2-methylpropane-2-sulfinamide (0.176 g) as a colorless gum-like substance.

(4) A solution of the compound (174 mg) obtained in (3) above in methanol (2.5 mL) was ice-cooled, 2 mol/L hydrochloric acid (2.5 mL) was added thereto, and the reaction solution was stirred at the same temperature for 20 minutes and at room temperature for 22 hours. A saturated aqueous sodium bicarbonate solution was added to the reaction solution to adjust the pH to 8 to 9, sodium chloride was added thereto, and extraction with ethyl acetate was carried out. The organic layer was washed with a brine, filtered through Phase Separator, and concentrated. The concentrate was purified by preparative HPLC to afford the title compound (53 mg) as a colorless oily substance.

$^1$H NMR (400 MHZ, METHANOL-$d_4$) δ ppm 1.34-1.69 (m, 12H) 2.32 (s, 3H) 3.78-3.97 (m, 2H) 4.60-4.80 (m, 1H) 7.19 (d, J=8.0 Hz, 1H) 7.54 (d, J=8.0 Hz, 1H) 8.53 (br s, 1H).

Reference Example 2-1-1

4-Phenylbutyl 4-Methylbenzene-1-Sulfonate

[Chemical Formula 421]

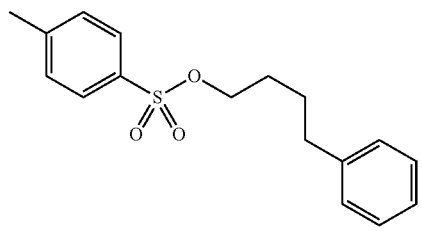

A solution of 4-phenyl-1-butanol (3 g) in chloroform (80 mL) was ice-cooled, trimethylamine hydrochloride (0.477 g), triethylamine (4.18 mL), and p-toluenesulfonyl chloride (4.38 g) were added thereto, and the reaction solution was stirred at room temperature for 45 minutes. The reaction solution was ice-cooled, and a mixed solution of water-saturated aqueous ammonium chloride solution (50 mL-50 mL) was added thereto. The reaction solution was extracted with chloroform, filtered through Phase Separator, and concentrated. The obtained residue was purified by silica gel column chromatography (n-hexane only to n-hexane:ethyl acetate=65:35) to afford the title compound (6.24 g) as a colorless oily substance.

$^1$H NMR (400 MHZ, CHLOROFORM-d) δ ppm 1.60-1.70 (m, 4H) 2.44 (s, 3H) 2.53-2.59 (m, 2H) 4.01-4.06 (m, 2H) 7.07-7.13 (m, 2H) 7.14-7.21 (m, 1H) 7.22-7.29 (m, 2H) 7.30-7.35 (m, 2H) 7.76-7.80 (m, 2H).

The following Reference Examples 2-1-2 to 2-1-6 were synthesized by the method described in Reference Example 2-1-1 or by a method equivalent thereto, using commercially available compounds or compounds obtained by synthesis according to methods described in literatures or methods equivalent thereto. The structures and LCMS data of the compounds are shown in Table 13-1.

TABLE 13-1
| Reference Example No. | Structural Formula | MS posi m/z MS nega m/z | Retention time (min) | method |
|---|---|---|---|---|
| 2-1-2 | 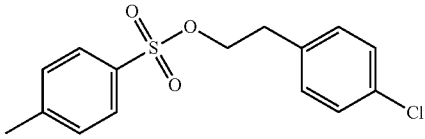 [SMILES: Cc1ccc(S(=O)(=O)OCCc2ccc(Cl)cc2)cc1] | 3.53 [M + Na]+ | 0.881 | A |
| 2-1-3 | 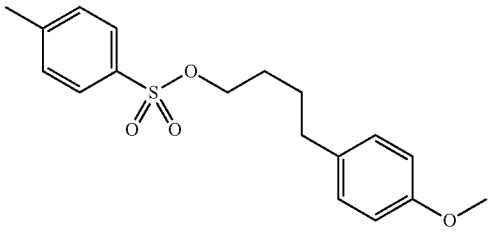 | 357 [M + Na]+ | 1.181 | B |
| 2-1-4 | 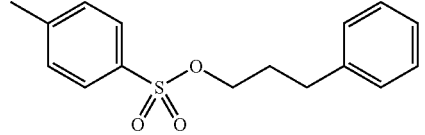 [SMILES: Cc1ccc(S(=O)(=O)OCCCc2ccccc2)cc1] | 313 [M + Na]+ | — | B |
| 2-1-5 | 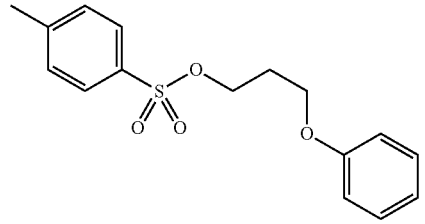 [SMILES: Cc1ccc(S(=O)(=O)OCCCOc2ccccc2)cc1] | 329 [M + Na]+ | 1.126 | B |
| 2-1-6 | 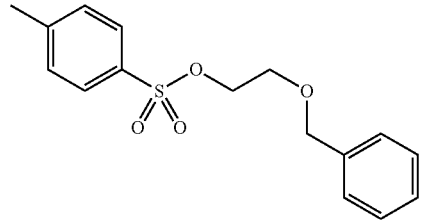 [SMILES: Cc1ccc(S(=O)(=O)OCCOCc2ccccc2)cc1] | 307 [M + H]+<br>329 [M + Na]+ | 1.082 | B |

The NMR data of Reference Example 2-1-4 is shown below. ¹H NMR (400 MHZ, CHLOROFORM-d) δ ppm 1.92-2.01 (m, 2H) 2.46 (s, 3H) 2.60-2.68 (m, 2H) 4.00-4.07 (m, 2H) 7.03-7.11 (m, 2H) 7.15-7.25 (m, 3H) 7.31-7.38 (m, 2H) 7.75-7.84 (m, 2H).

Reference Example 2-2-1

2-(2,3-Dihydro-1H-Inden-2-Yl)Ethyl 4-Methylbenzene-1-Sulfonate

[Chemical Formula 422]

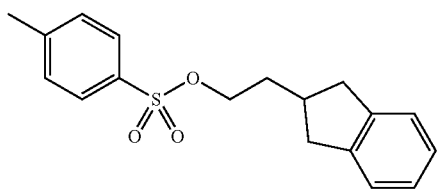

(1) A solution of (2,3-dihydro-1H-inden-2-yl) acetic acid (2.60 g) in tetrahydrofuran (20 mL) was ice-cooled, borane-tetrahydrofuran complex (1 mol/L tetrahydrofuran solution, 44.3 mL) was added thereto, and the reaction solution was stirred at room temperature for 3 days. Methanol was added to the reaction solution, which was then concentrated to afford 2-(2,3-dihydro-1H-inden-2-yl) ethan-1-ol (2.58 g) as a colorless oily substance.

(2) Using the compound (2.58 g) obtained in (1) above, the reaction was carried out in accordance with the method described in Reference Example 2-1-1, and the title compound (4.15 g) was obtained as a colorless solid.

MS ESI posi: 339 [M+Na]⁺.

Retention time: 1.276 min (method B)

Reference Example 2-3-1

3-(2-Fluorophenyl) Propyl 4-Methylbenzene-1-Sulfonate

[Chemical Formula 423]

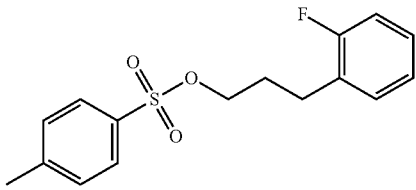

(1) To a solution of 1-fluoro-2-iodobenzene (150 mg) in acetonitrile (1.7 mL), triethylamine (0.471 mL), 2-propyn-1-ol (0.0468 mL), tris {tris[3,5-bis(trifluoromethyl)phenyl]phosphine}palladium (0) (SUPERSTABLE palladium (0) catalyst: FUJIFILM Wako Pure Chemical Corporation, 71.5 mg), and copper (I) iodide (12.9 mg) were added, and the reaction solution was stirred at room temperature for 30 minutes. The reaction solution was stirred at 60° C. for 5 hours and then stirred at room temperature overnight. The reaction solution was concentrated, and the obtained residue was purified by NH silica gel column chromatography (n-hexane:ethyl acetate=95:5 to 40:60) to afford 3-(2-fluorophenyl) prop-2-yn-1-ol as a light brown oily substance.

(2) To a solution of the compound obtained in (1) above in methanol (3.4 mL), palladium carbon (50 mg) was added, and the reaction solution was stirred at room temperature overnight under a hydrogen atmosphere. The reaction solution was filtered through Celite (registered trademark) and NH silica gel, and the filtrate was concentrated.

(3) Using the residue obtained in (2) above, the reaction was carried out in accordance with the method described in Reference Example 2-1-1, and the title compound (150 mg) was obtained as a colorless oily substance.

MS ESI posi: 331 [M+Na]⁺.

Retention time: 0.883 min (method A)

The following Reference Examples 2-3-2 to 2-3-5 were synthesized by the method described in Reference Example 2-3-1 or by a method equivalent thereto, using commercially available compounds or compounds obtained by synthesis according to methods described in literatures or methods equivalent thereto. The structures and LCMS data of the compounds are shown in Table 14-1.

TABLE 14-1

| Reference Example. No. | Structural Formula | MS posi m/z MS nega m/z | Retention time (min) | method |
|---|---|---|---|---|
| 2-3-2 | 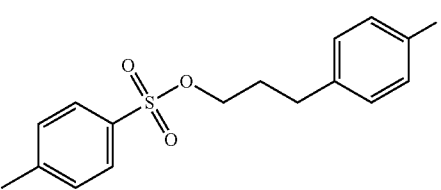 | 331 [M + Na]+ | 0.876 | A |

TABLE 14-1-continued

| Reference Example. No. | Structural Formula | MS posi m/z MS nega m/z | Retention time (min) | method |
|---|---|---|---|---|
| 2-3-3 | | 341 [M + Na]+ | 0.949 | A |
| 2-3-4 | | 341 [M + Na]+ | 0.958 | A |
| 2-3-5 | | 341 [M + Na]+ | 0.959 | A |

Reference Example 2-4-1

(3E)-4-Phenylpent-3-En-1-Yl 4-Methylbenzene-1-Sulfonate

[Chemical Formula 424]

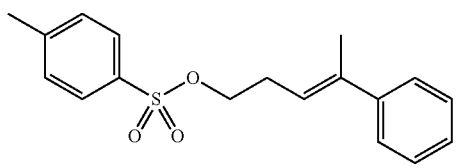

(1) A solution of triethyl phosphonoacetate (3.55 mL) in acetonitrile (50 mL) was ice-cooled, DBU (2.22 mL), lithium chloride (0.758 g), and 2-phenylpropionaldehyde (2 g) were added thereto, and the reaction solution was stirred at room temperature overnight. The reaction solution was ice-cooled, a saturated aqueous ammonium chloride solution was added thereto, and extraction with ethyl acetate was carried out. The organic layer was washed with a brine, and dried over magnesium sulfate. After filtering off the desiccating agent, the filtrate was concentrated, and the obtained residue was purified by silica gel column chromatography (n-hexane only to n-hexane:ethyl acetate=90:10) to afford ethyl(3E)-4-phenylpent-3-enoate (2.64 g) as a colorless oily substance and ethyl(3Z)-4-phenylpent-3-enoate (53 mg) as a colorless oily substance.

(2) A solution of ethyl(3E)-4-phenylpent-3-enoate (1.51 g) obtained in (1) above in tetrahydrofuran (12 mL) was ice-cooled, lithium borohydride (0.483 g) was added thereto, and the reaction solution was stirred at room temperature for 2 days. The reaction solution was ice-cooled, and a saturated aqueous ammonium chloride solution was slowly added thereto. The reaction solution was extracted with chloroform, filtered through Phase Separator, and concentrated to afford (3E)-4-phenylpent-3-en-1-ol (1.21 g) as a colorless oily substance.

(3) Using the compound (1.21 g) obtained in (2) above, the reaction was carried out in accordance with the method described in Reference Example 2-1-1, and the title compound (1.61 g) was obtained as a light yellow oily substance.
MS ESI posi: 339 [M+Na]+.
Retention time: 1.224 min (method B)

Reference Example 2-5-1

4,4-Difluoro-4-Phenylbutyl 4-Methylbenzene-1-Sulfonate

[Chemical Formula 425]

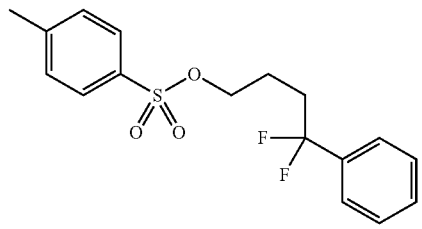

(1) A solution of methyl 3-benzoylpropionate (1.33 g) in tetrahydrofuran (11.5 mL) was ice-cooled, lithium borohydride (0.452 g) was added thereto, and the reaction solution was stirred at room temperature for 2 days. The reaction solution was ice-cooled, a saturated aqueous ammonium chloride solution was added thereto, and the reaction solution was stirred until no more bubbles were formed. The reaction solution was extracted with chloroform, filtered through Phase Separator, and concentrated to afford 1-phenylbutane-1,4-diol (1.06 g).

(2) To a mixed solution of the compound (1.06 g) obtained in (1) above in toluene-ethyl acetate (23 mL-8 mL), manganese (IV) oxide (6.02 g) was added, and the reaction solution was stirred at room temperature for 24 hours. The reaction solution was filtered through Celite (registered trademark), and the filtrate was concentrated. The obtained residue was purified by silica gel column chromatography (n-hexane only to ethyl acetate only) to afford 4-hydroxy-1-phenylbutan-1-one (502 mg) as a colorless oily substance.

(3) A solution of the compound (200 mg) obtained in (2) above in chloroform (3.0 mL) was ice-cooled, triethylamine (0.340 mL) and acetic anhydride (0.138 mL) were added thereto, and the reaction solution was stirred at room temperature for 40 hours. The reaction solution was ice-cooled, a saturated aqueous sodium bicarbonate solution was added thereto, and the reaction solution was extracted with chloroform, filtered through Phase Separator, and concentrated. The obtained residue was purified by silica gel column chromatography (n-hexane only to n-hexane:ethyl acetate=75:25) to afford 4-oxo-4-phenylbutyl acetate (190 mg) as a colorless oily substance.

(4) A solution of the compound (190 mg) obtained in (3) above in chloroform (3.0 mL) was ice-cooled, bis(2-methoxyethyl)aminosulfur trifluoride (0.674 mL) was added thereto, and the reaction solution was stirred at room temperature for 3 hours and with heating under reflux for 3 hours. Bis(2-methoxyethyl)aminosulfur trifluoride (1.12 mL) was further added thereto, and the reaction solution was stirred with heating under reflux for 24 hours. The reaction solution was ice-cooled, a saturated aqueous sodium bicarbonate solution was added thereto, and the reaction solution was extracted with chloroform, filtered through Phase Separator, and concentrated. The obtained residue was purified by silica gel column chromatography (n-hexane only to n-hexane:ethyl acetate=88:12) to afford 4,4-difluoro-4-phenylbutyl acetate (104 mg) as a colorless oily substance.

(5) To a solution of the compound (104 mg) obtained in (4) above in methanol (2 mL), an aqueous sodium hydroxide solution (1 mol/L, 0.5 mL) was added, and the reaction solution was stirred at room temperature for 1 hour. A saturated aqueous ammonium chloride solution was added thereto, the reaction solution was extracted with chloroform, filtered through Phase Separator, and concentrated. The obtained residue was purified by silica gel column chromatography (n-hexane only to n-hexane:ethyl acetate=60:40) to afford 4,4-difluoro-4-phenylbutan-1-ol (72.8 mg) as a colorless oily substance.

(6) Using the compound (72.8 mg) obtained in (5) above, the reaction was carried out in accordance with the method described in Reference Example 2-1-1, and the title compound (108 mg) was obtained as a pale yellow oily substance.

MS ESI posi: 363 [M+Na]$^+$.
Retention time: 1.155 min (method B)

Reference Example 2-6-1

3,3-Difluoro-4-Phenylbutyl 4-Methylbenzene-1-Sulfonate

[Chemical Formula 426]

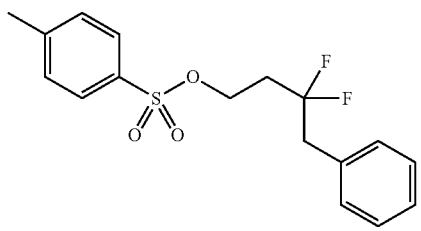

(1) A solution of methyl 3-oxo-4-phenylbutyrate (2 g) in tetrahydrofuran (10 mL) was ice-cooled, lithium borohydride (1.13 g) and ethanol (1.0 mL) were each slowly added thereto, and the reaction solution was stirred at room temperature for 17 hours. The reaction solution was ice-cooled, and 2 mol/L hydrochloric acid (8 mL) was added thereto to adjust the pH to 1. The reaction solution was stirred at 50° C. for 1 hour, and extracted with chloroform. The organic layer was filtered through Phase Separator and concentrated. The obtained residue was purified by silica gel column chromatography (chloroform only to chloroform:methanol=95:5) to afford 4-phenylbutane-1,3-diol (875 mg) as a colorless oily substance.

(2) Using the compound (200 mg) obtained in (1) above, the reaction was carried out in accordance with the method described in Reference Example 2-5-1 (3), and 3-hydroxy-4-phenylbutyl acetate (188 mg) was obtained as a colorless oily substance.

(3) A solution of the compound (188 mg) obtained in (2) above in chloroform (1.0 mL) was ice-cooled, the Dess-Martin reagent (0.536 g) was added thereto, and the reaction solution was gradually brought to room temperature and stirred at room temperature for 2 hours. The reaction solution was ice-cooled, and a mixed solution of saturated aqueous sodium thiosulfate solution-saturated aqueous sodium bicarbonate solution (1:1) was added thereto. The reaction solution was extracted with chloroform, then filtered through Phase Separator, and concentrated. The obtained residue was purified by silica gel column chromatography (n-hexane:ethyl acetate=75:25) to afford 3-oxo-4-phenylbutyl acetate (175 mg) as a colorless oily substance.

(4) Using the compound (175 mg) obtained in (3) above, the reaction was carried out in accordance with the method described in Reference Example 2-5-1 (4), and 3,3-difluoro-4-phenylbutyl acetate (159 mg) was obtained as a colorless oily substance.

(5) Using the compound (159 mg) obtained in (4) above, the reaction was carried out in accordance with the method described in Reference Example 2-5-1 (5), and 3,3-difluoro-4-phenylbutan-1-ol (124 mg) was obtained as a colorless oily substance.

(6) Using the compound (124 mg) obtained in (5) above, the reaction was carried out in accordance with the method described in Reference Example 2-1-1, and the title compound (209 mg) was obtained as a colorless oily substance.

MS ESI posi: 363 [M+Na]$^+$.
Retention time: 1.150 min (method B)

Reference Example 2-7-1

2-[(1S)-1-Phenylethoxy]Ethyl 4-Methylbenzene-1-Sulfonate

[Chemical Formula 427]

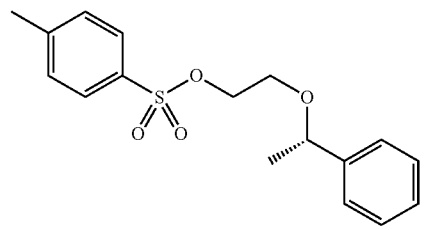 [SMILES: Cc1ccc(S(=O)(=O)OCCOC(C)(C)c2ccccc2)cc1]

(1) A suspension of sodium hydride (60% mineral oil dispersion, 1.96 g) in tetrahydrofuran (60 mL) was ice-cooled, a solution of (S)-(−)-1-phenylethyl alcohol (2 g) in tetrahydrofuran (15 mL) was slowly added thereto, and the reaction solution was stirred at room temperature for 1 hour. The reaction solution was ice-cooled, a solution of bromoacetic acid (2.50 g) in tetrahydrofuran (15 mL) was added thereto, and the reaction solution was stirred at room temperature for 2 days. Tetrahydrofuran (20 mL) was further added to the reaction solution, which was then ice-cooled, and water (60 mL) was slowly added thereto. Diethyl ether (40 mL) was added thereto, an aqueous sodium hydroxide solution was further added thereto to set the pH to 12 or higher, and extraction with water was carried out three times. The aqueous layers were combined, to which concentrated hydrochloric acid (4 mL) was then added to adjust the pH to 1 or less, and extracted with ethyl acetate twice. The organic layer was dried over magnesium sulfate, filtered through Phase Separator, and concentrated. A mixture (3.39 g) containing [(1S)-1-phenylethoxy]acetic acid was obtained as an orange oily substance.

(2) A solution of the mixture (3.39 g) obtained in (1) above in tetrahydrofuran (33 mL) was ice-cooled, borane-tetrahydrofuran complex (1 mol/L tetrahydrofuran solution, 49.1 mL) was added thereto, and the reaction solution was stirred at room temperature for 2 hours. The reaction solution was ice-cooled, and isopropyl alcohol (10 mL) was slowly added thereto. Methanol was added thereto at room temperature, and the reaction solution was stirred for 17 hours. After distilling off the solvent, ethyl acetate was added thereto, and the reaction solution was washed with a brine. The organic layer was concentrated to afford a mixture (2.92 g) containing 2-[(1S)-1-phenylethoxy]ethan-1-ol as a yellow oily substance.

(3) Using the mixture (2.92 g) obtained in (2) above, the reaction was carried out in accordance with the method described in Reference Example 2-1-1. However, instead of chloroform, tetrahydrofuran was used as the reaction solvent. By the above method, the title compound (4.20 g) was obtained as a yellow oily substance.

MS ESI posi: 343 [M+Na]$^+$.

Retention time: 1.141 min (method B)

The following Reference Examples 2-7-2 to 2-7-5 were synthesized by the method described in Reference Example 2-7-1 or by a method equivalent thereto, using commercially available compounds or compounds obtained by synthesis according to methods described in literatures or methods equivalent thereto. The structures and LCMS data of the compounds are shown in Tables 15-1 to 15-2.

TABLE 15-1

| Reference Example No. | Structural Formula | MS posi m/z MS nega m/z | Retention time (min) | method |
|---|---|---|---|---|
| 2-7-2 | | 343 [M + Na]+ | 1.143 | B |
| 2-7-3 | | 357 [M + Na]+ | 1.195 | B |

TABLE 15-2

| Reference Example No. | Structural Formula | MS posi m/z MS nega m/z | Retention time (min) | method |
|---|---|---|---|---|
| 2-7-4 | | 377 [M + Na]+ | 1.226 | B |

TABLE 15-2-continued

| Reference Example No. | Structural Formula | MS posi m/z MS nega m/z | Retention time (min) | method |
|---|---|---|---|---|
| 2-7-5 | | 377 [M + Na]+ | 1.231 | B |

Reference Example 2-8-1

[(1R)-1-(2-Chlorophenyl) Ethoxy]Acetic Acid

[Chemical Formula 428]

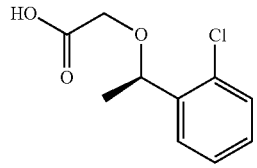

A suspension of sodium hydride (60% mineral oil dispersion, 192 mg) in tetrahydrofuran (4.8 mL) was ice-cooled, a solution of bromoacetic acid (266 mg) in tetrahydrofuran (1.2 mL) was slowly added thereto, and the reaction solution was stirred at room temperature for 10 minutes. The reaction solution was ice-cooled, a solution of (1R)-1-(2-chlorophenyl) ethan-1-ol (300 mg) in tetrahydrofuran (0.64 mL) was added thereto, and the reaction solution was stirred at room temperature for 7 hours. The reaction solution was ice-cooled, water (0.6 mL) was slowly added thereto, and the reaction solution was stirred at the same temperature for 30 minutes and concentrated. The obtained residue was purified by silica gel column chromatography (chloroform:methanol=99:1 to methanol only) to afford the title compound (340 mg) as a colorless solid.

MS ESI posi: 237 [M+Na]+.
MS ESI nega: 213 [M−H]−.
Retention time: 0.858 min (method B)

The following Reference Example 2-8-2 was synthesized by the method described in Reference Example 2-8-1 or by a method equivalent thereto, using a commercially available compound. The structure and LCMS data of the compound are shown in Table 15-3.

Reference Example 3-1-1

N-[(3,5-Dimethoxy-4-Methylphenyl)Methyl]-4-Phenylbutan-1-Amine

[Chemical Formula 429]

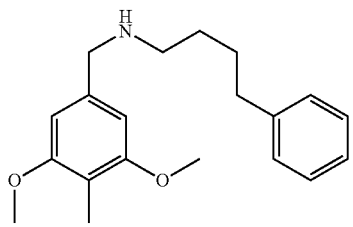 [SMILES: COc1cc(C(C)NCCCCc2ccccc2)cc(OC)c1C]

To a solution of the compound (1 g) obtained in Reference Example 1-4-3 in chloroform (11 mL), 4-phenylbutylamine (1.32 mL) and sodium triacetoxyborohydride (1.76 g) were added, and the reaction solution was stirred at room temperature overnight. A saturated aqueous ammonium chloride solution (5 mL) and a saturated aqueous sodium bicarbonate solution (5 mL) were added to the reaction solution, which was then extracted with chloroform (20 mL). The organic layer was washed with a saturated aqueous sodium bicarbonate solution (10 mL) twice, filtered through Phase Separator, and concentrated. The obtained residue was purified by NH silica gel column chromatography (n-hexane:ethyl acetate=95:5 to 50:50) to afford the title compound (1.65 g) as a colorless oily substance.

MS ESI posi: 314 [M+H]+.
Retention time: 0.706 min (method B)

The following Reference Examples 3-1-2 to 3-1-21 and Reference Examples 3-1-23 to 3-1-79 were synthesized by the method described in Reference Example 3-1-1 or by a

TABLE 15-3

| Reference Example No. | Structural Formula | MS posi m/z MS nega m/z | Retention time (min) | method |
|---|---|---|---|---|
| 2-8-2 | | 237 [M + Na]+ 213 [M + H]− | 0.850 | B | method equivalent thereto, using the compounds obtained in Reference Example 1-4-2, Reference Examples 1-5-1 to 1-5-29, Reference Examples 1-6-1 to 1-6-2, Reference Examples 1-7-1 to 1-7-5, Reference Examples 1-8-1 to 1-8-6, Reference Examples 1-9-2 to 1-9-3, Reference Examples 1-10-1 to 1-10-6, Reference Examples 1-11-1 to 1-11-2, Reference Example 1-12-2, Reference Examples 1-13-1 to 1-13-4, Reference Example 1-15-1, and Reference Example 1-15-4, commercially available compounds, or compounds obtained by synthesis according to methods described in literatures or methods equivalent thereto. The structures and LCMS data of the compounds are shown in Tables 16-1 to 16-15.

TABLE 16-1

| Reference Example No. | Structural Formula | MS posi m/z MS nega m/z | Retention time (min) | method |
|---|---|---|---|---|
| 3-1-2 | | 356 [M + H]+ | 0.631 | B |
| 3-1-3 | | 328 [M + H]+ | 0.761 | B |
| 3-1-4 | | 382 [M + H]+ | 0.327 | B |
| 3-1-5 | | 392 [M + H]+ | 0.816 | B |
| 3-1-6 | | 384 [M + H]+ | 0.743 | B |

TABLE 16-2

| Reference Example No. | Structural Formula | MS posi m/z MS nega m/z | Retention time (min) | method |
|---|---|---|---|---|
| 3-1-7 | | 400 [M + H]+ | 0.771 | B |
| 3-1-8 | | 400 [M + H]+ | 0.725 | B |
| 3-1-9 | | 386 [M + H]+ | 0.729 | B |
| 3-1-10 | | 400 [M + H]+ | 0.743 | B |
| 3-1-11 | | 367 [M + H]+ | 0.708 | B |

TABLE 16-3

| Reference Example No. | Structural Formula | MS posi m/z MS nega m/z | Retention time (min) | method |
|---|---|---|---|---|
| 3-1-12 | | 420 [M + H]+ | 0.767 | B |
| 3-1-13 | | 384 [M + H]+ | 0.969 | B |
| 3-1-14 | | 414 [M + H]+ | 0.801 | B |
| 3-1-15 | | 392 [M + H]+ | 0.823 | B |
| 3-1-16 | | 440 [M + H]+ | 0.911 | B |

TABLE 16-4

| Reference Example No. | Structural Formula | MS posi m/z MS nega m/z | Retention time (min) | method |
|---|---|---|---|---|
| 3-1-17 | | 382 [M + H]+ | 0.875 | B |
| 3-1-18 | | 386 [M + H]+ | 0.718 | B |
| 3-1-19 | | 404 [M + H]+ | 0.522 | B |
| 3-1-20 | | 420 [M + H]+ | 0.546 | B |
| 3-1-21 | | 438 [M + H]+ | 0.831 | B |

TABLE 16-5

| Reference Example No. | Structural Formula | MS posi m/z MS nega m/z | Retention time (min) | method |
|---|---|---|---|---|
| 2-1-23 | | 398 [M + H]+ | 0.519 | B |
| 2-1-24 | | 410 [M + H]+ | 0.630 | A |
| 2-1-25 | | 370 [M + H]+ | 0.635 | B |
| 2-1-26 | | 384 [M + H]+ | 0.719 | A |
| 2-1-27 | | 358 [M + H]+ | 0.662 | B |

TABLE 16-6

| Reference Example No. | Structural Formula | MS posi m/z MS nega m/z | Retention time (min) | method |
|---|---|---|---|---|
| 3-1-28 | | 360 [M + H]+ | 0.599 | B |
| 3-1-29 | | 340 [M + H]+ | 0.697 | B |
| 3-1-30 | | 370 [M + H]+ | 0.956 | B |
| 3-1-31 | | 342 [M + H]+ | 1.020 | B |
| 3-1-32 | | 242 [M + H]+ | 0.779 | B |

TABLE 16-7
| Reference Example No. | Structural Formula | MS posi m/z MS nega m/z | Retention time (min) | method |
|---|---|---|---|---|
| 3-1-33 | 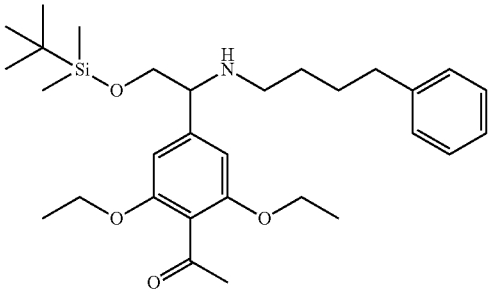 [SMILES: CCOc1cc(C(CO[Si](C)(C)C(C)(C)C)NCCCCc2ccccc2)cc(OCC)c1C(C)=O] | 514 [M + H]+ | 0.761 | A |
| 3-1-34 | 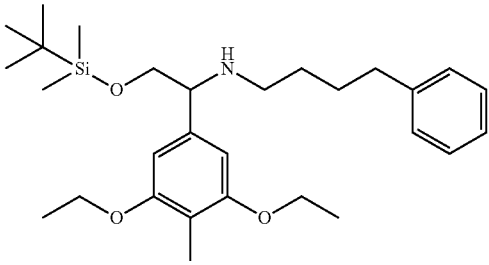 [SMILES: CCOc1cc(C(CO[Si](C)(C)C(C)(C)C)NCCCCc2ccccc2)cc(OCC)c1C] | 486 [M + H]+ | 0.838 | B |
| 3-1-35 | 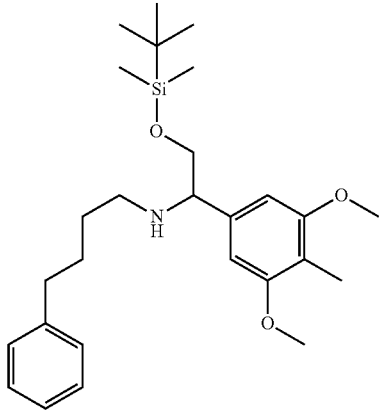 [SMILES: COc1cc(C(CO[Si](C)(C)C(C)(C)C)NCCCCc2ccccc2)cc(OC)c1C] | 458 [M + H]+ | 0.790 | B |
| 3-1-36 | 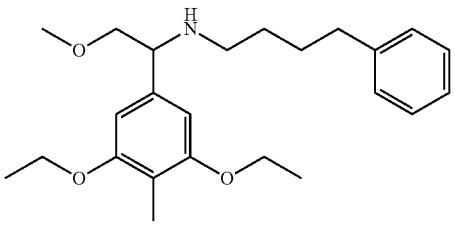 | 326 [M + H]+ | 0.685 | A |
| 3-1-37 | 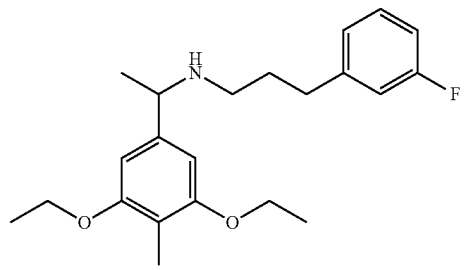 [SMILES: CCOc1cc(C(C)NCCCc2cccc(F)c2)cc(OCC)c1C] | 360 [M + H]+ | 0.786 | B |

TABLE 16-8

| Reference Example No. | Structural Formula | MS posi m/z MS nega m/z | Retention time (min) | method |
|---|---|---|---|---|
| 3-1-38 | | 392 [M + H]+ | 0.847 | B |
| 3-1-39 | | 356 [M + H]+ | 0.883 | B |
| 3-1-40 | | 356 [M + H]+ | 0.811 | B |
| 3-1-41 | | 376 [M + H]+ | 0.871 | B |
| 3-1-42 | | 342 [M + H]+ | 0.809 | B |

TABLE 16-9
| Reference Example No. | Structural Formula | MS posi m/z MS nega m/z | Retention time (min) | method |
|---|---|---|---|---|
| 3-1-43 | 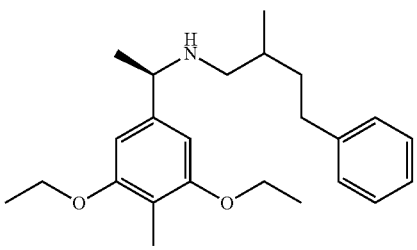 [SMILES: CCOc1cc([C@@H](C)NCC(C)CCc2ccccc2)cc(OCC)c1C] | 370 [M + H]+ | 0.886 | B |
| 3-1-44 | 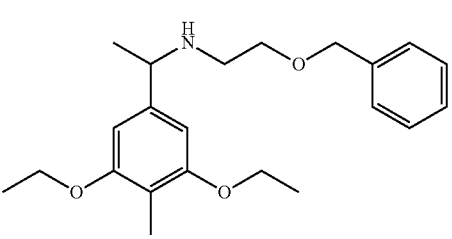 [SMILES: CCOc1cc(C(C)NCCOCc2ccccc2)cc(OCC)c1C] | 358 [M + H]+ | 0.896 | A |
| 3-1-45 | 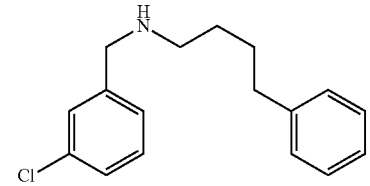 [SMILES: Clc1cccc(CNCCCCc2ccccc2)c1] | 274 [M + H]+ | 0.715 | B |
| 3-1-46 | 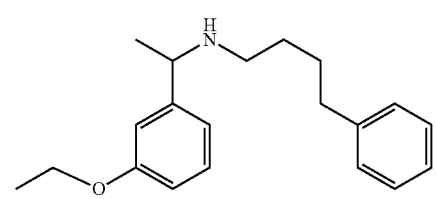 [SMILES: CCOc1cccc(C(C)NCCCCc2ccccc2)c1] | 298 [M + H]+<br>296 [M + H]− | 0.637 | B |
| 3-1-47 | 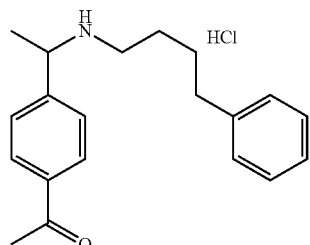 | 294 [M + H]+ | 0.868 | B |

TABLE 16-10

| Reference Example No. | Structural Formula | MS posi m/z MS nega m/z | Retention time (min) | method |
|---|---|---|---|---|
| 3-1-48 | | 279 [M + H]+ | 0.625 | B |
| 3-1-49 | | 272 [M + H]+ | 0.798 | B |
| 3-1-50 | | 268 [M + H]+ | 0.719 | B |
| 3-1-51 | | 349 [M + H]+ | 0.756 | B |
| 3-1-52 | | 342 [M + H]+ | 0.710 | B |

TABLE 16-11

| Reference Example No. | Structural Formula | MS posi m/z MS nega m/z | Retention time (min) | method |
|---|---|---|---|---|
| 3-1-53 | | 318 [M + H]+ | 0.665 | B |

TABLE 16-11-continued

| Reference Example No. | Structural Formula | MS posi m/z MS nega m/z | Retention time (min) | method |
|---|---|---|---|---|
| 3-1-54 | | 328 [M + H]+ | 0.672 | B |
| 3-1-55 | | 340 [M + H]+ | 0.598 | B |
| 3-1-56 | | 312 [M + H]+ | 0.720 | B |
| 3-1-57 | | 356 [M + H]+ | 0.822 | B |
| 3-1-58 | | 370 [M + H]+ | 0.868 | B |

TABLE 16-12

| Reference Example No. | Structural Formula | MS posi m/z MS nega m/z | Retention time (min) | method |
|---|---|---|---|---|
| 3-1-59 | | 341 [M + H]+ | 0.923 | B |

TABLE 16-12-continued

| Reference Example No. | Structural Formula | MS posi m/z MS nega m/z | Retention time (min) | method |
|---|---|---|---|---|
| 3-1-60 | | 323 [M + H ]+ | 0.560 | A |
| 3-1-61 | | 322 [M + H ]+ | 0.730 | B |
| 3-1-62 | | 362 [M + H ]+ | 0.687 | B |
| 3-1-63 | | 268 [M + H ]+ | 0.735 | B |

TABLE 16-13

| Reference Example No. | Structural Formula | MS posi m/z MS nega m/z | Retention time (min) | method |
|---|---|---|---|---|
| 3-1-64 | | 369 [M + H ]+ | 0.734 | B |
| 3-1-65 | | 355 [M + H ]+ | 0.860 | B |

TABLE 16-13-continued

| Reference Example No. | Structural Formula | MS posi m/z MS nega m/z | Retention time (min) | method |
|---|---|---|---|---|
| 3-1-66 | | 370 [M + H]+ | 0.818 | A |
| 3-1-67 | | 374 [M + H]+ | 0.626 | A |
| 3-1-68 | | 390 [M + H]+ | 0.650 | A |

TABLE 16-4

| Reference Example No. | Structural Formula | MS posi m/z MS nega m/z | Retention time (min) | method |
|---|---|---|---|---|
| 3-1-69 | | 316 [M + H]+ | 1.051 | B |
| 3-1-70 | | 315 [M + H]+ | 1.094 | B |
| 3-1-71 | | 299 [M + H]+ | 0.531 | B |

TABLE 16-4-continued

| Reference Example No. | Structural Formula | MS posi m/z MS nega m/z | Retention time (min) | method |
|---|---|---|---|---|
| 3-1-72 | | 310 [M + H]+ | 0.685 | B |
| 3-1-73 | | 312 [M + H]+ | 0.566 | B |

TABLE 16-15

| Reference Example No. | Structural Formula | MS posi m/z MS nega m/z | Retention time (min) | method |
|---|---|---|---|---|
| 3-1-74 | | 365 [M + H]+ | 0.782 | B |
| 3-1-75 | | 379 [M + H]+ | 0.801 | A |
| 3-1-76 | | 357 [M + H]+ | 0.804 | B |

TABLE 16-15-continued

| Reference Example No. | Structural Formula | MS posi m/z MS nega m/z | Retention time (min) | method |
|---|---|---|---|---|
| 3-1-77 | | 367 [M + H]+ | 0.452 | A |
| 3-1-78 | | 324 [M + H]+ | 0.692 | A |
| 3-1-79 | | 336 [M + H]+ | 0.837 | B |

Reference Example 3-1-80

N-{1-[3-Ethoxy-5-(Methoxymethyl)-4-Methylphenyl]Ethyl}-4-Phenylbutan-1-Amine

[Chemical Formula 430]

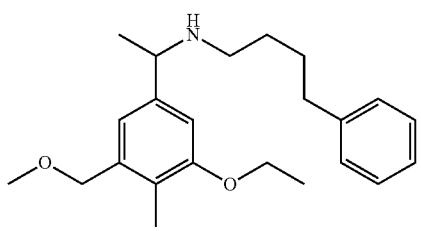

To a solution of the compound (30 mg) obtained in Reference Example 1-5-14 and 4-phenylbutylamine (23.5 µL) in ethanol (0.67 mL), acetic acid was added to adjust the pH to 5, and the reaction solution was stirred at 60° C. for 12 hours. p-Toluenesulfonic acid monohydrate (1 mg) was added to the reaction solution, which was then stirred with heating under reflux for 2 hours. Ethanol (1 mL) was added to the reaction solution, which was then ice-cooled, and sodium cyanoborohydride (25 mg) was added thereto. Acetic acid was added thereto to adjust the pH to 4 to 5, and the reaction solution was stirred at room temperature for 3 hours and left standing at the same temperature for 2 days. A saturated aqueous sodium bicarbonate solution was added to the reaction solution, which was then extracted with ethyl acetate. The organic layer was washed with a brine and dried over anhydrous magnesium sulfate. After filtering off the desiccating agent, the filtrate was concentrated to afford the title compound (58 mg) as a yellow oily substance.

MS ESI posi: 356 [M+H]$^+$.

Retention time: 0.914 min (method B)

Reference Example 3-2-1

3-Benzyl-N-[(1R)-1-(3,5-Diethoxy-4-Methylphenyl)Ethyl]Cyclobutan-1-Amine

[Chemical Formula 431]

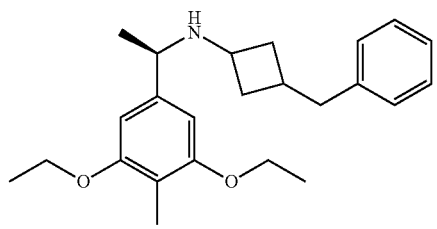

To a solution of the compound (50 mg) obtained in Reference Example 1-15-1 in chloroform (1.9 mL), triethylamine (80.5 µL) and 3-benzylcyclobutan-1-one (33.9 mg) were added, and the reaction solution was stirred at room temperature for 10 minutes. The reaction solution was ice-cooled, sodium triacetoxyborohydride (204 mg) was added thereto, and the reaction solution was stirred at the same temperature for 20 minutes and stirred at room temperature overnight. The reaction solution was ice-cooled, a saturated aqueous sodium bicarbonate solution was added thereto, and the reaction solution was stirred at room temperature for 1 hour and extracted with chloroform (4 mL) three times. The obtained residue was purified by silica gel column chromatography (chloroform:methanol=98:2 to 70:30) to afford the title compound (50 mg).

MS ESI posi: 368 [M+H]$^+$.

Retention time: 0.592 min (method A)

Reference Example 3-2-2

1-(2,6-Diethoxy-4-{(1R)-1-[(4-Phenylbutyl)Amino]Ethyl}Phenyl)Cyclopropan-1-Ol

[Chemical Formula 432]

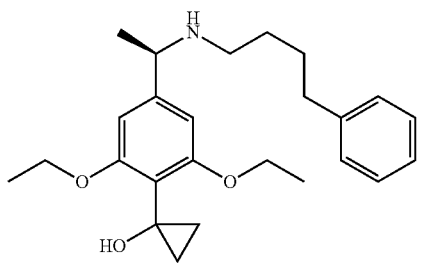

To a solution of the compound (30 mg) obtained in Reference Example 1-15-7 and 4-phenylbutanal (17 mg) in ethanol (0.57 mL), acetic acid was added to adjust the pH to 5 to 6, and the reaction solution was stirred at room temperature for 20 minutes. The reaction solution was ice-cooled, sodium cyanoborohydride (21 mg) was added thereto, and the reaction solution was stirred at room temperature for 1 hour. The reaction solution was ice-cooled, sodium cyanoborohydride (21 mg) was added thereto, and the reaction solution was stirred at room temperature for 15 hours. The reaction solution was ice-cooled, 4-phenylbutanal (13 mg) was added thereto, and the reaction solution was stirred at the same temperature for 4 hours. At the same temperature, 4-phenylbutanal (3 mg) was added thereto, and the reaction solution was stirred at the same temperature for 1 hour. A saturated aqueous sodium bicarbonate solution (2 mL) was added to the reaction solution, which was then extracted with ethyl acetate. The organic layer was washed with a brine, filtered through Phase Separator, and concentrated to afford the title compound (51 mg) as a colorless oily substance.

MS ESI posi: 398 [M+H]$^+$.

Retention time: 1.062 min (method C)

The following Reference Examples 3-2-3 to 3-2-4 were synthesized by the method described in Reference Example 3-2-2 or by a method equivalent thereto, using the compounds obtained in Reference Example 2-1-1, Reference Example 2-6-1, and Reference Examples 1-15-7 to 1-15-8, commercially available compounds, or compounds obtained by synthesis according to methods described in literatures or methods equivalent thereto. The structures and LCMS data of the compounds are shown in Table 17-1.

TABLE 17-1

| Reference Example No. | Structural Formula | MS posi m/z MS nega m/z | Retention time (min) | method |
|---|---|---|---|---|
| 3-2-3 | (structure) | 354 [M + H]+ | 1.022 | B |
| 3-2-4 | (structure) | 434 [M + H]+ | 1.055 | B |

Reference Example 3-3-1

1-(2,6-Diethoxy-4-{1-[(4-Phenylbutyl)Amino]Ethyl}Phenyl)Cyclopropan-1-Ol

[Chemical Formula 433]

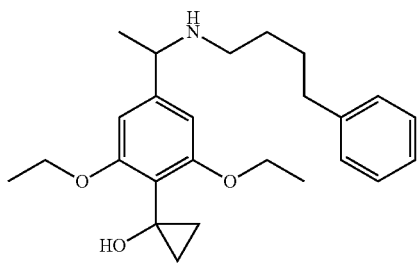

The present reaction was carried out with reference to the method described in the literature (Kanto Chemical Co., Inc.; THE CHEMICAL TIMES, vol. 228, p. 19, 2013). A solution of the compound (84 mg) obtained in Reference Example 1-9-1,4-phenylbutylamine (45.1 mg), formic acid (36.3 L), and chloro(pentamethylcyclopentadienyl) (8-quinolinolato) iridium (III) (8.07 mg) in ethyl acetate (1.6 mL) was stirred at 40° C. for 11 hours. After bringing the reaction solution back to room temperature, it was concentrated to afford the title compound as an orange oily substance.

MS ESI posi: 398 [M+H]$^+$.
Retention time: 0.713 min (method B)

The following Reference Examples 3-3-2 to 3-3-4 were synthesized by the method described in Reference Example 3-3-1 or by a method equivalent thereto, using the compounds obtained in Reference Example 1-7-7, Reference Example 1-7-9, and Reference Example 1-8-4, commercially available compounds, or compounds obtained by synthesis according to methods described in literatures or methods equivalent thereto. The structures and LCMS data of the compounds are shown in Table 18-1.

TABLE 18-1

| Reference Example No. | Structural Formula | NS posi n/z NS nega n/z | Retention time (min) | netbaod |
|---|---|---|---|---|
| 3-2-2 | | 370 [N + H]+ | 0.899 | E |
| 3-3-3 | | 380 [N + H]+ | 0.876 | B |
| 3-2-4 | | 368 [N + H]+ | 0.707 | C |

Reference Example 3-4-1

1-(2,6-Diethoxy-4-{(1R)-1-[(4-Phenylbutyl)Amino]Ethyl}Phenyl) Ethan-1-One Hydrochloride

[Chemical Formula 434]

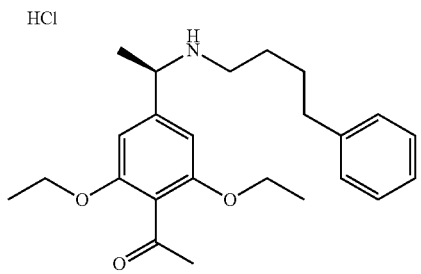

(1) To a solution of the compound (236 mg) obtained in Reference Example 1-16-3 in chloroform (2 mL), a saturated aqueous sodium bicarbonate solution was added, and the reaction solution was stirred at room temperature. The organic layer was filtered through Phase Separator and concentrated to afford 1-{4-[(1R)-1-aminoethyl]-2,6-diethoxyphenyl}ethan-1-one (217 mg).

(2) To a solution of the compound (5.25 g) obtained in (1) above in acetonitrile (105 mL), the compound (7.00 g) obtained in Reference Example 2-1-1 and N,N-diisopropylethylamine (10.9 mL) were added, and the reaction solution was stirred at 80° C. for 39 hours. The reaction solution was ice-cooled, a saturated aqueous sodium bicarbonate solution was added thereto, the reaction solution was extracted with chloroform twice, filtered through Phase Separator, and concentrated. The obtained residue was purified by NH silica gel column chromatography (n-hexane only to ethyl acetate only) and silica gel column chromatography (n-hexane only to n-hexane:ethyl acetate=50:50, and then chloroform only to chloroform:methanol=80:20) to afford 1-(2,6-diethoxy-4-{(1R)-1-[(4-phenylbutyl)amino]ethyl}phenyl) ethan-1-one (4.84 g) as a light yellow oily substance.

(3) A solution of the compound (1.87 g) obtained in (2) above in ethyl acetate (16 mL) was ice-cooled, a 4 mol/L hydrogen chloride-ethyl acetate solution (4.9 mL) was added thereto, and the reaction solution was stirred at room temperature for 50 minutes. The reaction solution was concentrated, a mixed solution of n-hexane-ethyl acetate (1:1, 20 mL) was added thereto, and the precipitated solid was filtered off to afford the title compound (2.05 g) as a colorless powder.

MS ESI posi: 384 [M+H]$^+$.
Retention time: 0.732 min (method B)

Reference Example 3-4-2

1-{3-Chloro-2,6-Diethoxy-4-[(1R)-1-({2-[(1S)-1-Phenylethoxy]Ethyl}Amino)Ethyl]Phenyl}Ethan-1-One

[Chemical Formula 435]

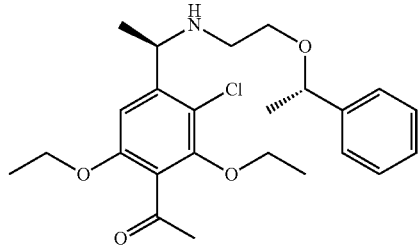

Using the compound (214 mg) obtained in Reference Example 1-16-1 and the compound (264 mg) obtained in Reference Example 2-7-1, the reaction was carried out in accordance with the method described in Reference Example 3-4-1 (2), and the title compound (96 mg) was obtained as a light yellow oily substance.

MS ESI posi: 434 [M+H]$^+$.
Retention time: 0.794 min (method B)

Reference Example 3-4-3

N-[(1R)-1-(4-Cyclopropyl-3,5-Diethoxyphenyl)Ethyl]-4-Phenylbutan-1-Amine

[Chemical Formula 436]

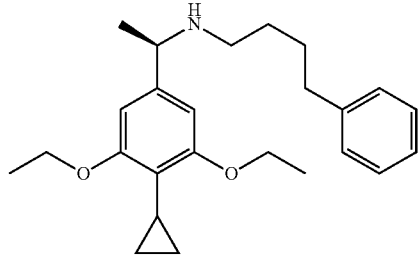

(1) To a solution of the compound (180 mg) obtained in Reference Example 1-17-1 in chloroform (5 mL), a saturated aqueous sodium bicarbonate solution (5 mL) was added, and the reaction solution was stirred at 50° C. for 10 minutes. The organic layer was separated, then dried over anhydrous magnesium sulfate, filtered through Phase Separator, and concentrated to afford (1R)-1-(4-cyclopropyl-3,5-diethoxyphenyl) ethan-1-amine (126 mg) as a colorless oily substance.

(2) Using the compound (63 mg) obtained in (1) above and the compound (84.6 mg) obtained in Reference Example 2-1-1, the reaction was carried out in accordance with the method described in Reference Example 3-4-1 (2), and the title compound (74.2 mg) was obtained as a brown oily substance.

MS ESI posi: 382 [M+H]$^+$.
Retention time: 0.862 min (method B)

The following Reference Examples 3-4-4 to 3-4-5 were synthesized by the method described in Reference Example 3-1-1, Reference Example 3-4-1, Reference Example 3-4-2, or Reference Example 3-4-3, or by a method equivalent thereto, using the compounds obtained in Reference Example 1-15-1, Reference Example 1-18-1, and Reference Example 2-1-1, commercially available compounds, or compounds obtained by synthesis according to methods described in literatures or methods equivalent thereto. The structures and LCMS data of the compounds are shown in Table 19-1.

TABLE 19-1

| Reference Example No. | Structural Formula | MS posi m/z MS nega m/z | Retention time (min) | method |
|---|---|---|---|---|
| 3-4-4 | | 366 [M + H]+ | 0.796 | B |
| 3-4-5 | | 354 [M + H]+ | 1.012 | B |

Reference Example 3-4-6

N-[(1R)-1-(3,5-Diethoxy-4-Ethylphenyl)Ethyl]-4-Phenylbutan-1-Amine

[Chemical Formula 437]

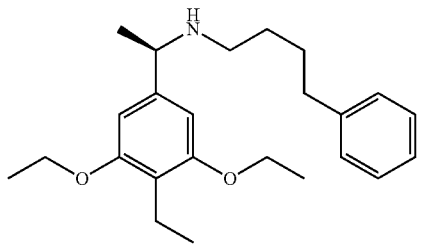

(1) Using the compound (2.96 g) obtained in Reference Example 1-15-6 and the compound (3.30 g) obtained in Reference Example 2-1-1, the reaction was carried out in accordance with the method described in Reference Example 3-4-3, and N-[(1R)-1-(4-bromo-3,5-diethoxyphenyl)ethyl]-4-phenylbutan-1-amine (3.78 g) was obtained as a colorless oily substance.

(2) A solution of the compound (3.78 g) obtained in (1) above in ethyl acetate (30 mL) was ice-cooled, a 4 mol/L hydrogen chloride-ethyl acetate solution (9.0 mL) was added thereto, and the reaction solution was stirred at room temperature for 30 minutes. Ethyl acetate (20 mL) was further added to the reaction solution. The reaction solution was concentrated, a mixed solution of n-hexane-ethyl acetate (1:1, 20 mL) was added thereto, and the precipitated solid was filtered off to afford N-[(1R)-1-(4-bromo-3,5-diethoxyphenyl)ethyl]-4-phenylbutan-1-amine hydrochloride (2.91 g) as a colorless solid.

(3) To a solution of the compound (1.0 g) obtained in (2) above in chloroform, a saturated aqueous sodium bicarbonate solution was added, and extraction with chloroform was carried out twice. The organic layer was filtered through Phase Separator and concentrated to afford a mixture containing N-[(1R)-1-(4-bromo-3,5-diethoxyphenyl)ethyl]-4-phenylbutan-1-amine.

(4) To a solution of the mixture obtained in (3) above in chloroform (11 mL), di-tert-butyl dicarbonate (0.53 g) was added, and the reaction solution was stirred at room temperature for 2 hours. Triethylamine (0.61 mL) was further added to the reaction solution, which was then stirred at room temperature overnight. 0.5 mol/L hydrochloric acid was added to the reaction solution, which was then extracted with chloroform. The organic layer was filtered through Phase Separator and concentrated. The obtained residue was purified by silica gel column chromatography (n-hexane only to n-hexane:ethyl acetate=80:20) to afford tert-butyl [(1R)-1-(4-bromo-3,5-diethoxyphenyl)ethyl](4-phenylbutyl) carbamate (1.30 g) as a colorless oily substance.

(5) The present reaction was carried out with reference to the method described in the literature (The Journal of Organic Chemistry, vol. 74, p. 3626, 2009). To a solution of the compound (200 mg) obtained in (4) above in toluene (3.8 mL), ethylboronic acid (42.6 mg), potassium carbonate (159 mg), palladium (II) acetate (17.3 mg), 2-dicyclohexylphosphino-2',6'-diisopropoxybiphenyl (71.7 mg), and water (384 μL) were added, and the reaction solution was stirred at 110° C. for 5 hours. The reaction solution was filtered through Celite (registered trademark), and the filtrate was concentrated. The obtained residue was purified by silica gel column chromatography (n-hexane only to n-hexane:ethyl acetate=80:20) to afford tert-butyl[(1R)-1-(3,5-diethoxy-4-ethylphenyl)ethyl](4-phenylbutyl) carbamate (133 mg) as a colorless oily substance.

(6) To a solution of the compound (133 mg) obtained in (5) above in ethyl acetate (2 mL), a 4 mol/L hydrogen chloride-ethyl acetate solution (2 mL) was added, and the reaction solution was stirred at room temperature for 1 hour. The reaction solution was concentrated, a saturated aqueous sodium bicarbonate solution was added thereto, and extraction with chloroform was carried out. The organic layer was filtered through Phase Separator and concentrated to afford the title compound (110 mg).

MS ESI posi: 370 [M+H]$^+$.

Retention time: 0.827 min (method A)

The following Reference Examples 3-4-7 to 3-4-51 were synthesized by the method described in Reference Example 3-4-1 to 3-4-3 or Reference Example 3-4-6, or by a method equivalent thereto, using the compounds obtained in Reference Example 1-15-1, Reference Example 1-15-3, Reference Example 1-15-5, Reference Example 1-15-7, Reference Examples 1-16-1 to 1-16-3, Reference Example 1-17-1, Reference Examples 1-18-1 to 1-18-2, Reference Examples 2-1-1 to 2-1-6, Reference Example 2-2-1, Reference Examples 2-3-1 to 2-3-5, Reference Example 2-4-1, Reference Example 2-5-1, Reference Example 2-6-1, and Reference Examples 2-7-1 to 2-7-5, commercially available compounds, or compounds obtained by synthesis according to methods described in literatures or methods equivalent thereto. The structures and LCMS data of the compounds are shown in Table 20-1 to Table 20-10.

TABLE 20-1

| Reference Example No. | Structural Formula | MS posi m/z MS nega m/z | Retention time (min) | method |
| --- | --- | --- | --- | --- |
| 3-4-7 | | 328 [M + H]+ | 0.692 | B |
| 3-4-8 | | 370 [M + H]+ | 1.694 | B |
| 3-4-9 | | 360 [M + H]+ | 0.650 | A |
| 3-4-10 | | F369 [M + H]+ | 0.641 | A |

TABLE 20-1-continued
| Reference Example No. | Structural Formula | MS posi m/z MS nega m/z | Retention time (min) | method |
|---|---|---|---|---|
| 3-4-11 | 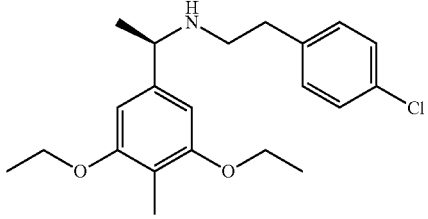 [SMILES: CCOc1cc([C@@H](C)NCCc2ccc(Cl)cc2)cc(OCC)c1C] | 362 [M + H]+ | 0.679 | A |
TABLE 20-2
| Reference Example No. | Structural Formula | MS posi m/z MS nega m/z | Retention time (min) | method |
|---|---|---|---|---|
| 3-4-12 | 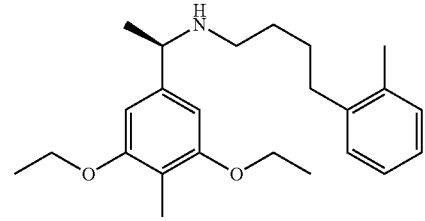 [SMILES: CCOc1cc([C@@H](C)NCCCCc2ccccc2C)cc(OCC)c1C] | 370 [M + H]+ | 0.616 | A |
| 3-4-13 | 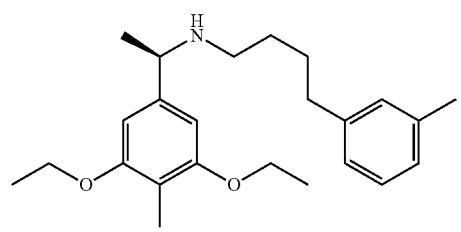 [SMILES: CCOc1cc([C@@H](C)NCCCCc2cccc(C)c2)cc(OCC)c1C] | 370 [M + H]+ | 0.619 | A |
| 3-4-14 | 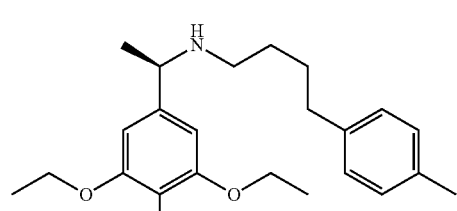 | 210 [M + H]+ | 0.621 | A |
| 3-4-15 | 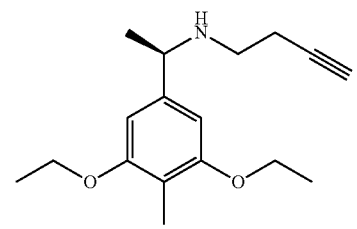 | 316 [M + H]+ | 0.604 | B |

TABLE 20-2-continued

| Reference Example No. | Structural Formula | MS posi m/z MS nega m/z | Retention time (min) | method |
|---|---|---|---|---|
| 3-4-16 | | 355 [M + H]+ | 0.644 | B |

TABLE 20-3

| Reference Example No. | Structural Formula | MS posi m/z MS nega m/z | Retention time (min) | method |
|---|---|---|---|---|
| 3-4-17 | | 396 [M + H]+ | 0.142 | B |
| 3-4-18 | | 410 [M + H]+ | 0.769 | B |
| 3-4-19 | | 370 [M + H]+ | 0.640 | B |
| 3-4-20 | | 368 [M + H]+ | 0.646 | A |

TABLE 20-3-continued
| Reference Example No. | Structural Formula | MS posi m/z MS nega m/z | Retention time (min) | method |
|---|---|---|---|---|
| 3-4-21 | 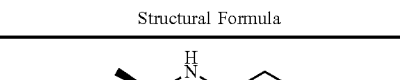 | 420 [M + H]+ | 0.765 | B |
TABLE 20-4
| Reference Example No. | Structural Formula | MS posi m/z MS nega m/z | Retention time (min) | method |
|---|---|---|---|---|
| 3-4-22 | | 418 [M + H]+ | 1.167 | F |
| 3-4-23 | | 390 [M + H]+ | 1.011 | F |
| 3-4-24 | | 392 [M + H]+ | 0.608 | A |
| 3-4-25 | | 120 [M + H]+ | 0.616 | B |

TABLE 20-4-continued

| Reference Example No. | Structural Formula | MS posi m/z MS nega m/z | Retention time (min) | method |
|---|---|---|---|---|
| 3-4-26 | | 118 [M + H]+ | 1.351 | F |

TABLE 20-5

| Reference Example No. | Structural Formula | MS posi m/z MS nega m/z | Retention time (min) | method |
|---|---|---|---|---|
| 3-4-27 | | 359 [M + H]+ | 1.133 | C |
| 3-4-28 | HCl | 402 [M + H]+ | 0.825 | B |
| 3-4-29 | | 385 [M + H]+ | 0.759 | B |
| 3-4-30 | | 380 [M + H]+ | 0.633 | B |

TABLE 20-5-continued

| Reference Example No. | Structural Formula | MS posi m/z MS nega m/z | Retention time (min) | method |
|---|---|---|---|---|
| 3-4-31 | | 338 [M + H]+ | 0.926 | F |

TABLE 20-6

| Reference Example No. | Structural Formula | MS posi m/z MS nega m/z | Retention time (min) | method |
|---|---|---|---|---|
| 3-4-32 | | 295 [M + H]+ | 0.869 | B |
| 3-4-33 | | 270 [M + H]+ | 0.982 | F |
| 3-4-34 | | 311 [M + H]+ | 1.041 | F |
| 3-4-35 | | 412 [M + H]+ | 0.927 | B |

TABLE 20-6-continued

| Reference Example No. | Structural Formula | MS posi m/z MS nega m/z | Retention time (min) | method |
|---|---|---|---|---|
| 3-4-36 | | 424 [M + H]+ | 0.801 | B |

TABLE 20-7

| Reference Example No. | Structural Formula | MS posi m/z MS nega m/z | Retention time (min) | method |
|---|---|---|---|---|
| 3-4-37 | | 420 [M + H]+ | 0.634 | B |
| 3-4-38 | | 454 [M + H]+ | 1.221 | C |
| 3-4-39 | | 418 [M + H]+ | 1.181 | C |
| 3-4-40 | | 414 [M + H]+ | 0.748 | B |

TABLE 20-7-continued

| Reference Example No. | Structural Formula | MS posi m/z MS nega m/z | Retention time (min) | method |
|---|---|---|---|---|
| 3-4-41 | | 409 [M + H]+ | 0.705 | B |

TABLE 20-8

| Reference Example No. | Structural Formula | MS posi m/z MS nega m/z | Retention time (min) | method |
|---|---|---|---|---|
| 3-4-42 | | 386 [M + H]+ | 0.628 | A |
| 3-4-43 | | 405 [M + H]+ | 0.343 | B |
| 3-4-44 | | 372 [M + H]+ | 0.800 | B |
| 3-4-45 | | 384 [M + H]+ | 0.811 | B |

TABLE 20-8-continued

| Reference Example No. | Structural Formula | MS posi m/z MS nega m/z | Retention time (min) | method |
|---|---|---|---|---|
| 3-4-46 | | 370 [M + H]+ | 0.881 | F |

TABLE 20-9

| Reference Example No. | Structural Formula | MS posi m/z MS nega m/z | Retention time (min) | method |
|---|---|---|---|---|
| 3-4-47 | | 400 [M + H]+ | 0.727 | B |
| 3-4-48 | | 398 [M + H]+ | 0.863 | B |

TABLE 20-10

| Reference Example No. | Structural Formula | MS posi m/z MS nega m/z | Retention time (min) | method |
|---|---|---|---|---|
| 3-4-49 | | 398 [M + H]+ | 0.807 | B |

TABLE 20-10-continued

| Reference Example No. | Structural Formula | MS posi m/z MS nega m/z | Retention time (min) | method |
|---|---|---|---|---|
| 3-4-50 | | 368 [M + H]+ | 0.401 | B |
| 3-4-51 | | 464 [M + H]+ | 0.793 | B |

Reference Example 3-5-1

N-Benzyl-N~2~-[(1R)-1-(3,5-Diethoxy-4-Methylphenyl)Ethyl]Glycinamide

[Chemical Formula 438]

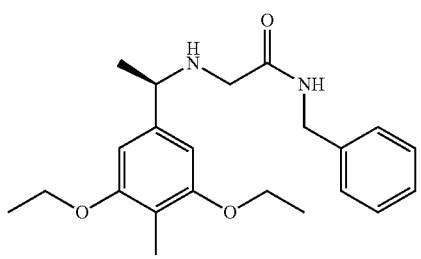

To a suspension of the compound (60 mg) obtained in Reference Example 1-15-1 and potassium carbonate (95.8 mg) in acetonitrile (1 mL), N-benzyl-2-chloroacetamide (50.9 mg) was added, and the reaction solution was stirred at 80° C. for 9 hours. Water was added to the reaction solution, which was then extracted with ethyl acetate. The organic layer was washed with a brine, and concentrated. The obtained residue was purified by silica gel column chromatography (n-hexane:ethyl acetate=90:10 to ethyl acetate only) to afford the title compound (78.8 mg) as a colorless solid.

MS ESI posi: 371 [M+H]+.

Retention time: 0.571 min (method A)

Reference Example 3-6-1

N-[(1R)-1-(3,5-Diethoxy-4-Methylphenyl)Ethyl]-5-Methylhexan-1-Amine

[Chemical Formula 439]

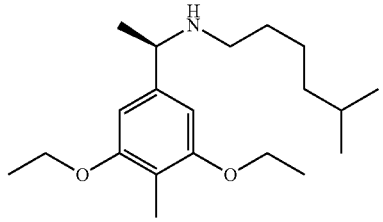

(1) To a solution of the compound (30 mg) obtained in Reference Example 1-15-1 in N,N-dimethylformamide (0.58 mL), N,N-diisopropylethylamine (80.5 L) and 5-methylhexanoic acid (16.4 µL) were added, and the reaction solution was stirred for 20 minutes under ice cooling. HATU (87.8 mg) was added to the reaction solution, which was then stirred at the same temperature for 30 minutes and stirred at room temperature overnight. Water was added to the reaction solution, which was then extracted with ethyl acetate. The organic layer was washed with a brine, filtered through Phase Separator, and concentrated. The obtained residue was purified by silica gel column chromatography (n-hexane:ethyl acetate=90:10 to 20:80) to afford N-[(1R)-1-(3,5-diethoxy-4-methylphenyl)ethyl]-5-methylhexanamide (38 mg) as a colorless powder.

(2) A solution of the compound (35 mg) obtained in (1) above in tetrahydrofuran (1.0 mL) was ice-cooled, and stirred for 10 minutes. At the same temperature, borane-tetrahydrofuran complex (0.9 mol/L tetrahydrofuran solution, 0.3 mL) was added thereto, and the reaction solution was stirred at the same temperature for 30 minutes and at room temperature overnight. The reaction solution was ice-cooled, methanol was added thereto, and the reaction solution was stirred at room temperature for 2 hours. The reaction solution was concentrated to afford the title compound.

MS ESI posi: 322 [M+H]$^+$.

Retention time: 0.603 min (method A)

The following Reference Examples 3-6-2 to 3-6-4 were synthesized by the method described in Reference Example 3-6-1 or by a method equivalent thereto, using the compound obtained in Reference Example 1-15-1, a commercially available compound, or a compound obtained by synthesis according to methods described in literatures or methods equivalent thereto. The structures and LCMS data of the compounds are shown in Table 21-1.

Reference Example 3-6-5

N-[(1R)-1-(3,5-Diethoxy-4-Methylphenyl)Ethyl] Butan-1-Amine

[Chemical Formula 440]

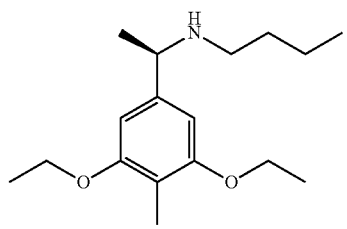

(1) Using the compound (88.5 mg) obtained in Reference Example 1-15-1 and butyric acid (30 mg), the reaction was carried out in accordance with the method described in

TABLE 21-1

| Reference Example No. | Structural Formula | MS posi m/z MS nega m/z | Retention time (min) | method |
|---|---|---|---|---|
| 3-6-2 | | 336 [M + H]+ | 0.628 | A |
| 3-6-3 | | 368 [M + H]+ | 0.624 | A |
| 3-6-4 | | 362 [M + H]+ | 1.162 | A |

Reference Example 3-6-1 (1), and N-[(1R)-1-(3,5-diethoxy-4-methylphenyl)ethyl]butanamide (87 mg) was obtained as a colorless oily substance.

(2) A solution of lithium aluminum hydride (104 mg) in tetrahydrofuran (1.7 mL) was ice-cooled, and stirred at the same temperature for 10 minutes. A solution of the compound (80 mg) obtained in (1) above in tetrahydrofuran (1 mL) was added thereto. The reaction solution was stirred at the same temperature for 10 minutes, with heating under reflux for 8 hours, at room temperature overnight, and with heating under reflux for 4 hours. The reaction solution was ice-cooled, and stirred for 10 minutes. Water was added thereto. The reaction solution was filtered through Celite (registered trademark), and the filtrate was concentrated. The obtained residue was purified by NH silica gel column chromatography (n-hexane:ethyl acetate=90:10 to 50:50) to afford the title compound (64 mg).

MS ESI posi: 280 [M+H]$^+$.

Retention time: 0.486 min (method A)

The following Reference Examples 3-6-6 to 3-6-13 were synthesized by the method described in Reference Example 3-6-5 or by a method equivalent thereto, using the compound obtained in Reference Example 1-15-1, a commercially available compound, or a compound obtained by synthesis according to methods described in literatures or methods equivalent thereto. The structures and LCMS data of the compounds are shown in Table 22-1 to Table 22-2.

TABLE 22-1

| Reference Example No. | Structural Formula | MS posi m/z MS nega m/z | Retention time (min) | method |
|---|---|---|---|---|
| 3-6-6 | | 356 [M + H]+ | 0.596 | A |
| 3-6-7 | | 313 [M + H]+ | 0.859 | C |
| 3-6-8 | | 357 [M + H]+ | 0.426 | B |
| 3-6-9 | | 367 [M + H]+ | 0.393 | B |

TABLE 22-1-continued

| Reference Example No. | Structural Formula | MS posi m/z MS nega m/z | Retention time (min) | method |
|---|---|---|---|---|
| 3-6-10 | | 342 [M + H]+ | 0.718 | C |

TABLE 22-2

| Reference Example No. | Structural Formula | MS posi m/z MS nega m/z | Retention time (min) | method |
|---|---|---|---|---|
| 3-6-11 | | 369 [M + H]+ | 0.577 | B |
| 3-6-12 | | 353 [M + H]+ | 0.548 | A |
| 3-6-13 | | 368 [M + H]+ | 0.512 | B |

Reference Example 3-6-14

1-{4-[(1R)-1-{[2-(Benzyloxy)Ethyl]Amino}Ethyl]-2,6-Dimethoxyphenyl}Ethan-1-One Hydrochloride

[Chemical Formula 441]

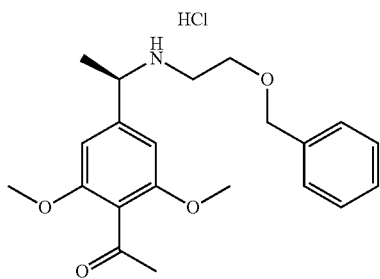

(1) Under a nitrogen atmosphere, to a solution of (benzyloxy) acetic acid (616 mg) in N,N-dimethylformamide (3.5 mL), the compound (1 g) obtained in Reference Example 1-15-9 and HOBt (620 mg) were added, and the reaction solution was water-cooled. EDC (776 mg) and N,N-diisopropylethylamine (1.47 mL) were added thereto, and the reaction solution was stirred at room temperature for 2 hours. Toluene (3 mL) was added to the reaction solution, which was then ice-cooled, and water (6 mL) was slowly added thereto. The reaction solution was stirred at room temperature for 10 minutes, and extracted with toluene. The organic layer was washed with a 5% aqueous potassium carbonate solution, a 5% aqueous sodium sulfate solution, and a brine sequentially, and dried over anhydrous magnesium sulfate. After filtering off the desiccating agent, the filtrate was concentrated. Methanol (20 mL) was added to the obtained residue, which was then dissolved at 65° C., and the reaction solution was stirred at room temperature for 14 hours. The precipitated solid was filtered off, and 2-(benzyloxy)-N-[(1R)-1-(4-bromo-3,5-dimethoxyphenyl)ethyl] acetamide (817 mg) was obtained as a colorless powder.

(2) Under a nitrogen atmosphere, borane-tetrahydrofuran complex (1 mol/L tetrahydrofuran solution, 6.00 mL) was ice-cooled, a suspension of the compound (817 mg) obtained in (1) above in tetrahydrofuran (1.8 mL) was added dropwise thereto, and the reaction solution was stirred at room temperature for 2 hours. The reaction solution was water-cooled, 2 mol/L hydrochloric acid (1.2 mL) was added dropwise thereto, and the reaction solution was stirred at 60° C. for 1.5 hours. Ethanol (5 mL) and water (10 mL) were added to the reaction solution and dissolved at 80° C., and the reaction solution was stirred at room temperature for 14 hours and for 30 minutes under ice cooling. The precipitated solid was filtered off, and (1R)—N-[2-(benzyloxy)ethyl]-1-(4-bromo-3,5-dimethoxyphenyl) ethan-1-amine hydrochloride (612 mg) was obtained as a colorless powder.

(3) Under a nitrogen atmosphere, to ethylene glycol monovinyl ether (255 L) and a solution of potassium carbonate (589 mg) in toluene (3.7 mL), the compound (612 mg) obtained in (2) above was added, and the reaction solution was degassed under reduced pressure. Palladium (II) acetate (6.38 mg) and 1,3-bis(diphenylphosphino) propane (23.4 mg) were added thereto, and the reaction solution was degassed under reduced pressure and stirred with heating under reflux for 18 hours. Water (1 mL) was added thereto at room temperature, and the reaction solution was stirred for 1 hour. The reaction solution was filtered through Celite (registered trademark), and a 2 mol/L hydrogen chloride-ethanol solution (1.42 mL) was added to the filtrate, which was then stirred at room temperature for 30 minutes. The reaction solution was washed with a 15% aqueous potassium carbonate solution, and the organic layer was dried over anhydrous sodium sulfate. After filtering off the desiccating agent, the filtrate was concentrated. The obtained residue was purified by silica gel column chromatography (n-hexane:ethyl acetate=78:22 to ethyl acetate only) to afford a mixture (479 mg) containing 1-{4-[(1R)-1-{[2-(benzyloxy)ethyl]amino}ethyl]-2,6-dimethoxyphenyl}ethan-1-one as a yellow oily substance.

(4) To a solution of the mixture (479 mg) obtained in (3) above in ethanol (1 mL), a 2 mol/L hydrogen chloride-ethanol solution (737 µL) was added, and the reaction solution was concentrated. Isopropyl ether (2 mL) and ethanol (0.8 mL) were added to the obtained residue, and the precipitated solid was filtered off to afford the title compound (412 mg) as a colorless powder.

MS ESI posi: 358 [M+H]$^+$.
Retention time: 0.556 min (method B)

Reference Example 3-6-15

1-{4-[(1R)-1-{[2-(Benzyloxy)Ethyl]Amino}Ethyl]-3-Chloro-2,6-Dimethoxyphenyl}Ethan-1-One

[Chemical Formula 442]

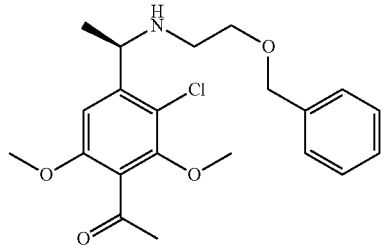 [SMILES: COc1cc([C@@H](C)NCCOCc2ccccc2)c(C)c(OC)c1C(C)=O]

Under a nitrogen atmosphere, a solution of the compound (301 mg) obtained in Reference Example 3-6-14 in chloroform (3.8 mL) was cooled with a mixture of sodium chloride-ice, sulfuryl chloride (64.8 µL) was added dropwise thereto, and the reaction solution was stirred at the same temperature for 1 hour. Water was slowly added thereto at the same temperature, and extraction with chloroform was carried out. The organic layer was washed with a saturated aqueous sodium bicarbonate solution, filtered through Phase Separator, and concentrated. The obtained residue was purified by silica gel column chromatography (n-hexane:ethyl acetate=88:12 to ethyl acetate only, and then chloroform:methanol=95:5 to 80:20) and preparative HPLC to afford the title compound (42 mg) as a colorless oily substance.

MS ESI posi: 392 [M+H]$^+$.
Retention time: 0.622 min (method B)

The following Reference Examples 3-6-16 to 3-6-18 were synthesized by the method described in Reference Example 3-6-14 to 3-6-15 or by a method equivalent thereto, using the compounds obtained in Reference Example 1-15-9 and Reference Example 1-15-11, commercially available compounds, or compounds obtained by synthesis according to methods described in literatures or methods equivalent thereto. The structures and LCMS data of the compounds are shown in Tables 22-3 to 22-4.

TABLE 22-3

| Reference Example No. | Structural Formula | MS posi m/z MS nega m/z | Retention time (min) | method |
|---|---|---|---|---|
| 3-6-16 | | 372 [M + H]+ | 0.596 | B |
| 3-6-17 | | 496 [M + H]+ | 0.676 | B |

TABLE 22-4

| Reference Example No. | Structural Formula | MS posi m/z MS nega m/z | Retention time (min) | method |
|---|---|---|---|---|
| 3-6-18 | | 470 [M + H]+ | 0.515 | B |

Reference Example 3-6-19

(1R)—N-[2-(Benzyloxy)Ethyl]-1-(4-Cyclopropyl-3,5-Dimethoxy-2-Methylphenyl) Ethan-1-Amine

[Chemical Formula 443]

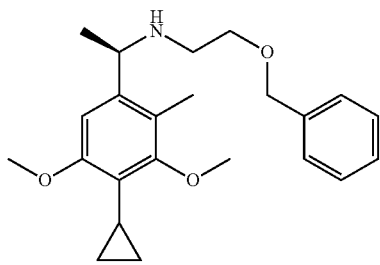

(1) To a solution of the compound (1 g) obtained in Reference Example 1-15-11 in N,N-dimethylformamide (13 mL), (benzyloxy) acetic acid (475 mg) and N,N-diisopropylethylamine (1.13 mL) were added, and the reaction solution was ice-cooled and stirred for 5 minutes. Then, HATU (1.18 g) was added thereto, and the reaction solution was stirred at room temperature overnight. By adding water (30 mL), ethyl acetate (30 mL), and n-hexane (1 mL) to the reaction solution, it was partitioned into two layers. By adding water (40 mL), ethyl acetate (10 mL), and n-hexane (1 mL) to the organic layer, the organic layer was partitioned into two layers. The organic layer was dried over anhydrous magnesium sulfate. After filtering off the desiccating agent, the filtrate was concentrated. The obtained residue was purified by silica gel column chromatography (n-hexane:ethyl acetate=50:50 to ethyl acetate only) to afford 2-(benzyloxy)-N-[(1R)-1-(4-bromo-3,5-dimethoxy-2-methylphenyl)ethyl]acetamide (960 mg) as a colorless powder.

(2) Using the compound (960 mg) obtained in (1) above, the reaction was carried out in accordance with the method described in Reference Example 3-6-26 (2), and (1R)-N-[2-(benzyloxy)ethyl]-1-(4-bromo-3,5-dimethoxy-2-methylphenyl) ethan-1-amine (854 mg) was obtained as a light yellow oily substance.

(3) To the compound (427 mg) obtained in (2) above, toluene (3.0 mL) and water (0.30 mL) were added, and the reaction solution was subjected to bubbling with nitrogen gas. Then, under a nitrogen atmosphere, cyclopropylboronic acid (118 mg), potassium carbonate (379 mg), palladium (II) acetate (20.5 mg), and 2-dicyclohexylphosphino-2',6'-diisopropoxybiphenyl(RuPhos, 85.3 mg) were added thereto, and the reaction solution was stirred at 120° C. for 2 hours under microwave irradiation. Water was added to the reaction solution, which was then filtered through Celite (registered trademark), and the filtrate was partitioned into two layers. The organic layer was washed with a brine and dried over anhydrous magnesium sulfate. After filtering off the desiccating agent, the filtrate was concentrated. The obtained residue was purified by silica gel column chromatography (n-hexane:ethyl acetate=82:18 to ethyl acetate only) to afford the title compound (199 mg) as a yellow oily substance.

MS ESI posi: 370 [M+H]$^+$.

Retention time: 0.789 min (method B)

The following Reference Examples 3-6-20 to 3-6-21 were synthesized by the method described in Reference Example 3-6-19 or by a method equivalent thereto, using the compounds obtained in Reference Example 1-15-9 and Reference Example 1-15-11, cyclopropylboronic acid, methylboronic acid, commercially available compounds, or compounds obtained by synthesis according to methods described in literatures or methods equivalent thereto. The structures and LCMS data of the compounds are shown in Table 22-5.

Reference Example 3-6-22

(1R)—N-[2-(Benzyloxy)Ethyl]-1-(4-Cyclopropyl-3,5-Dimethoxyphenyl) Ethan-1-Amine Hydrochloride

[Chemical Formula 444]

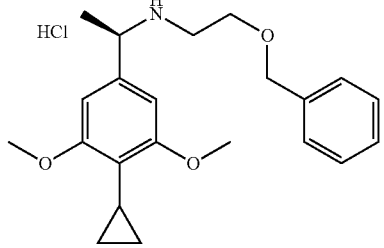

(1) To the compound (3.29 g) obtained in Reference Example 3-6-14 (2), chloroform and a saturated aqueous sodium bicarbonate solution were added, and the reaction solution was stirred and extracted with chloroform. The organic layer was filtered through Phase Separator and concentrated to afford (1R)—N-[2-(benzyloxy)ethyl]-1-(4-bromo-3,5-dimethoxyphenyl) ethan-1-amine (3.34 g) as a light yellow oily substance.

(2) A solution of the compound (3.34 g) obtained in (1) above in chloroform (26 mL) was ice-cooled, triethylamine (2.13 mL) and di-tert-butyl dicarbonate (1.83 g) were added thereto sequentially, and the reaction solution was stirred at room temperature for 1 hour. Triethylamine (639 μL) and di-tert-butyl dicarbonate (500 mg) were further added to the

TABLE 22-5

| Reference Example No. | Structural Formula | MS posi m/z MS nega m/z | Retention time (min) | method |
|---|---|---|---|---|
| 3-6-20 | | 384 [M + H]+ | 0.481 | A |
| 3-6-21 | | 380 [M + H]+ | 0.047 | B | reaction solution, which was then stirred at room temperature for 1 hour. 4-Dimethylaminopyridine (46.7 mg) was further added to the reaction solution, which was then stirred at room temperature for 30 minutes. 0.5 mol/L hydrochloric acid (20 mL) was added to the reaction solution, which was then extracted with chloroform. The organic layer was filtered through Phase Separator and concentrated. The obtained residue was purified by silica gel column chromatography (n-hexane only to n-hexane:ethyl acetate=80:20) to afford tert-butyl[2-(benzyloxy)ethyl][(1R)-1-(4-bromo-3,5-dimethoxyphenyl)ethyl]carbamate (3.58 g) as a colorless oily substance.

(3) Using the compound (3.50 g) obtained in (2) above and cyclopropylboronic acid (913 mg), the reaction was carried out in accordance with the method described in Reference Example 1-7-1, and tert-butyl[2-(benzyloxy)ethyl][(1R)-1-(4-cyclopropyl-3,5-dimethoxyphenyl)ethyl]carbamate (3.00 g) was obtained as a light brown oily substance.

(4) A solution of the compound (2.75 g) obtained in (3) above in a mixed solution of 1,4-dioxane-methanol (36 mL-12 mL) was ice-cooled, a 4 mol/L hydrogen chloride-1,4-dioxane solution (18 mL) was added thereto, and the reaction solution was stirred at room temperature for 15 hours. The reaction solution was concentrated to afford the title compound (2.13 g) as a light yellow powder.

MS ESI posi: 356 [M+H]$^+$.

Retention time: 0.582 min (method A)

The following Reference Examples 3-6-23 to 3-6-25 were synthesized by the method described in Reference Example 3-6-14 (1) to (2) or Reference Example 3-6-22 (2) to (4), or by a method equivalent thereto, using the compound obtained in Reference Example 1-15-13, cyclopropylboronic acid, methylboronic acid, commercially available compounds, or compounds obtained by synthesis according to methods described in literatures or methods equivalent thereto. The structures and LCMS data of the compounds are shown in Table 22-6.

TABLE 22-6

| Reference Example No. | Structural Formula | MS posi m/z MS mega m/z | Retention time (min) | method |
|---|---|---|---|---|
| 3-6-23 | | 368 [M + H]+ | 0.690 | A |
| 3-6-24 | | 263 [M + H]+ | 0.584 | A |
| 3-6-25 | | 242 [M + H]+ | 0.861 | A |

427

Reference Example 3-6-26

(1R)-1-(4-Cyclopropyl-3,5-Dimethoxyphenyl)-N-{2-[(1S)-1-Phenylethoxy]Ethyl}Ethan-1-Amine Hydrochloride

[Chemical Formula 445]

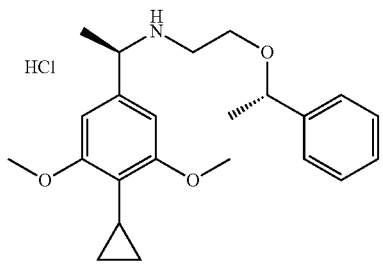

(1) To the compound (1.34 g) obtained in Reference Example 1-17-2, a solution of [(1S)-1-phenylethoxy]acetic acid (1.20 g) in N,N-dimethylformamide (30 mL), N,N-diisopropylethylamine (2.63 mL), and HATU (2.76 g) were added, and the reaction solution was stirred at room temperature for 5.5 hours. Water (30 mL) and a mixed solvent of n-hexane-ethyl acetate (1:1, 60 mL) were added to the reaction solution, which was then partitioned into two layers. The aqueous layer was extracted with a mixed solvent of n-hexane-ethyl acetate (1:1, 60 mL). The organic layers were combined, washed with 0.5 mol/L hydrochloric acid and a brine sequentially, and dried over anhydrous magnesium sulfate. After filtering off the desiccating agent, the filtrate was concentrated. The obtained residue was purified by silica gel column chromatography (n-hexane:ethyl acetate=90:10 to ethyl acetate only) to afford N-[(1R)-1-(4-cyclopropyl-3,5-dimethoxyphenyl)ethyl]-2-[(1S)-1-phenylethoxy]acetamide (2.28 g) as a light yellow solid.

(2) Under a nitrogen atmosphere, borane-tetrahydrofuran complex (1 mol/L tetrahydrofuran solution, 17.8 mL) was ice-cooled, and a solution of the compound (2.28 g) obtained in (1) above in tetrahydrofuran (20 mL) was added dropwise thereto. The reaction solution was stirred at room temperature for 2 hours. The reaction solution was water-cooled, 2 mol/L hydrochloric acid (3.6 mL) was slowly added dropwise thereto, and the reaction solution was stirred at 60 degrees for 5 hours. The reaction solution was ice-cooled, and a 1 mol/L aqueous sodium hydroxide solution (23.8 mL) was added thereto. The reaction solution was brought back to room temperature, and extracted with toluene. The organic layer was washed with a brine and dried over anhydrous magnesium sulfate. After filtering off the desiccating agent, the filtrate was concentrated. The obtained residue was purified by NH silica gel column chromatography (n-hexane only to n-hexane:ethyl acetate=15:85) to afford (1R)-1-(4-cyclopropyl-3,5-dimethoxyphenyl)-N-{2-[(1S)-1-phenylethoxy]ethyl}ethan-1-amine (1.95 g) as a colorless oil.

(3) A solution of the compound (1.95 g) obtained in (2) above in ethyl acetate (19.8 mL) was ice-cooled, a 4 mol/L hydrogen chloride-ethyl acetate solution (5.95 mL) was added thereto, and the reaction solution was stirred at room temperature for 30 minutes. The reaction solution was concentrated, suspended by adding tert-butyl methyl ether (10 mL) and ethyl acetate (5 mL), and concentrated. The obtained residue was suspended by adding tert-butyl methyl ether (10 mL), and the solid was filtered off to afford the title compound (1.61 g) as a colorless solid.

MS ESI posi: 370 [M+H]$^+$.

Retention time: 0.802 min (method B)

The following Reference Examples 3-6-27 to 3-6-33 were synthesized by the method described in Reference Example 3-6-26 or by a method equivalent thereto, using the compounds obtained in Reference Example 1-15-10, Reference Example 1-15-12, Reference Examples 1-17-3 to 1-17-4, and Reference Examples 2-8-1 to 2-8-2, commercially available compounds, or compounds obtained by synthesis according to methods described in literatures or methods equivalent thereto. The structures and LCMS data of the compounds are shown in Tables 22-7 to 22-8.

TABLE 22-7

| Reference Example No. | Structural Formula | MS posi m/z MS mega m/z | Retention time (min) | method |
|---|---|---|---|---|
| 3-6-27 | | 344 [M + H]+ | 0.717 | B |
| 3-6-28 | | 338 [M + H]+ | 0.770 | B |

TABLE 22-7-continued

| Reference Example No. | Structural Formula | MS posi m/z MS mega m/z | Retention time (min) | method |
|---|---|---|---|---|
| 3-6-29 | | 358 [M + H]+ | 0.849 | B |
| 3-6-30 | | 412 [M + H]+ | 0.839 | A |
| 3-6-31 | | 388 [M + H]+ | 0.523 | A |

TABLE 22-8

| Reference Example No. | Structural Formula | MS posi m/z MS mega m/z | Retention time (min) | method |
|---|---|---|---|---|
| 3-6-32 | | 402 [M + H]+ | 0.402 | A |
| 3-6-33 | | 402 [M + H]+ | 0.403 | A |

Reference Example 3-6-34

(1R)—N-[2-(Benzyloxy)Ethyl]-1-(2-Chloro-4-Cyclopropyl-3,5-Dimethoxyphenyl) Ethan-1-Amine

[Chemical Formula 446]

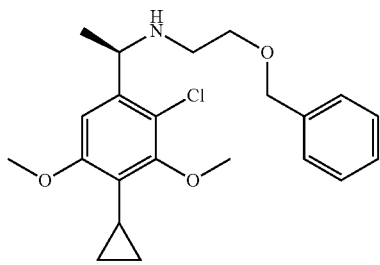 [SMILES: COc1cc([C@@H](C)NCCO[C@@H](C)c2ccccc2)c(Cl)c(OC)c1C1CC1]

A suspension of the compound (1.50 g) obtained in Reference Example 3-6-22 in toluene (23 mL) was ice-cooled, a solution of 1,3-dichloro-5,5-dimethylhydantoin (830 mg) in toluene (15 mL) was added dropwise thereto, and the reaction solution was stirred at the same temperature for 2 hours. A 20% aqueous sodium ascorbate solution (12 mL) was added to the reaction solution, which was then stirred overnight while raising the temperature to room temperature. A 5% aqueous sodium bicarbonate solution (15 mL) was added to the reaction solution, which was then stirred at room temperature for 15 minutes and partitioned into two layers. The organic layer was washed with a 5% aqueous sodium bicarbonate solution (15 ml) and water (15 mL) sequentially, and dried over anhydrous magnesium sulfate. After filtering off the desiccating agent, the filtrate was concentrated. The obtained residue was purified by silica gel column chromatography (n-hexane:ethyl acetate=84:16 to ethyl acetate only) to afford the title compound (1.30 g) as a yellow oily substance.

MS ESI posi: 390 [M+H]$^+$.

Retention time: 0.798 min (method B)

The following Reference Examples 3-6-35 to 3-6-37 were synthesized by the method described in Reference Example 3-6-15 or Reference Example 3-6-34, or by a method equivalent thereto, using the compounds obtained in Reference Example 3-4-32, Reference Example 3-4-45, and Reference Example 3-6-26. The structures and LCMS data of the compounds are shown in Table 22-9.

TABBLE 22-9

| Reference Example No. | Structural Formula | MS posi m/z MS mega m/z | Retention time (min) | method |
|---|---|---|---|---|
| 3-6-35 | | 404 [M + H]+ | 0.840 | B |
| 3-6-36 | | 418 [M + H]+ | 0.330 | B |

TABLE 22-9-continued

| Reference Example No. | Structural Formula | MS posi m/z MS mega m/z | Retention time (min) | method |
|---|---|---|---|---|
| 3-6-37 | | 432 [M + H]+ | 0.765 | A |

Reference Example 3-7-1

N-[1-(3,5-Diethoxyphenyl)Ethyl]-4-Phenylbutan-1-Amine

[Chemical Formula 447]

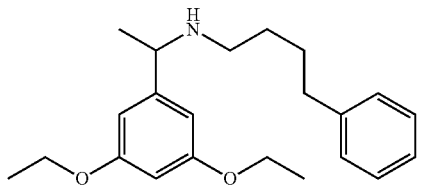 [SMILES: CCOc1cc(C(C)NCCCCc2ccccc2)cc(OCC)n1]

The compound (495 mg) obtained in Reference Example 1-14-5 and 4-phenylbutylamine (406 µL) were mixed, heated with a dryer, and stirred at room temperature for 30 minutes. Diethyl ether (6.4 mL) was added thereto, and the reaction solution was ice-cooled. Methyllithium (1 mol/L diethyl ether solution, 3.06 mL) was added thereto, and the reaction solution was stirred at the same temperature for 10 minutes and at room temperature for 20 minutes. The reaction solution was ice-cooled, water was added thereto, and the reaction solution was concentrated. The obtained residue was purified by preparative HPLC to afford the title compound (599 mg) as a colorless oily substance.

MS ESI/APCI Multi posi: 342 [M+H]$^+$.

Retention time: 0.751 min (method E)

The following Reference Examples 3-7-2 to 3-7-4 were synthesized by the method described in Reference Example 3-7-1 or by a method equivalent thereto, using the compounds obtained in Reference Examples 1-4-4 to 1-4-6, commercially available compounds, or compounds obtained by synthesis according to methods described in literatures or methods equivalent thereto. The structures and LCMS data of the compounds are shown in Table 23-1.

TABLE 23-1

| Reference Example No. | Structural Formula | MS posi m/z MS mega m/z | Retention time (min) | method |
|---|---|---|---|---|
| 3-7-2 | | 343 [M + H]+ | 0.719 | B |
| 3-7-3 | | 343 [M + H]+ | 0.703 | B |
| 3-7-4 | | 340 [M + H]+ | 0.605 | B |

Reference Example 3-8-1

N-[1-(4-Ethoxy-1-Ethyl-1H-Indazol-6-Yl)Ethyl]-4-Phenylbutan-1-Amine

[Chemical Formula 448]

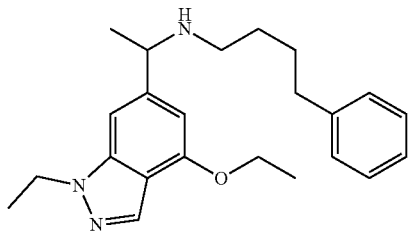

The compound (100 mg) obtained in Reference Example 1-7-6 and 4-phenylbutylamine (73.0 μL) were mixed, and stirred at room temperature for 3 hours while reducing the pressure. Diethyl ether (2.3 mL) was added to the reaction solution, which was then ice-cooled. Methyllithium (1 mol/L diethyl ether solution, 550 μL) was added thereto, and the reaction solution was stirred at the same temperature for 1 hour. Water was added to the reaction solution, which was then concentrated. The obtained residue was purified by silica gel column chromatography (chloroform:methanol=98:2 to 80:20) and silica gel column chromatography (n-hexane:ethyl acetate=70:30 to 50:50, and then chloroform only to chloroform:methanol=90:10) to afford the title compound (68 mg) as a light orange oily substance.

MS ESI posi: 366 [M+H]$^+$.

Retention time: 0.698 min (method B)

Reference Example 3-8-2

1-[2-Ethoxy-6-(Ethylamino)-4-{1-[(4-Phenylbutyl)Amino]Ethyl}Phenyl]Ethan-1-One

[Chemical Formula 449]

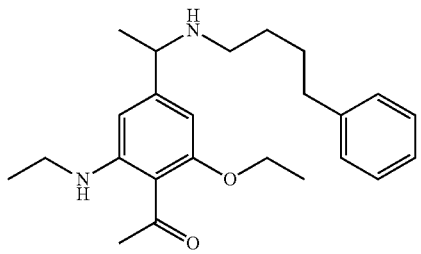

Reference Example 3-8-3

2-Ethoxy-6-(Ethylamino)-4-{1-[(4-Phenylbutyl)Amino]Ethyl}Benzonitrile

[Chemical Formula 450]

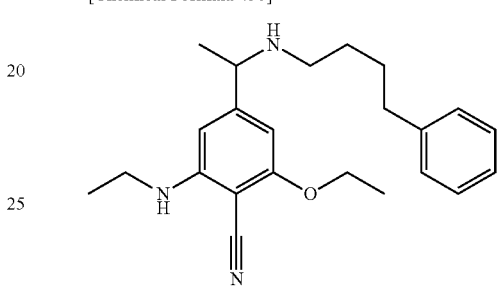

The compound (340 mg) obtained in Reference Example 1-7-6 and 4-phenylbutylamine (0.248 mL) were mixed, and stirred at room temperature for 1 hour while reducing the pressure. Diethyl ether (7.8 mL) was added thereto, and the reaction solution was ice-cooled. Methyllithium (1 mol/L diethyl ether solution, 3.74 mL) was added thereto, and the reaction solution was stirred at the same temperature for 2.5 hours. Water was added to the reaction solution, which was then concentrated. The obtained residue was purified by silica gel column chromatography (chloroform:methanol=98:2 to 80:20) and preparative HPLC to afford the title compounds, 1-[2-ethoxy-6-(ethylamino)-4-{1-[(4-phenylbutyl)amino]ethyl}phenyl]ethan-1-one (7 mg) (Reference Example 3-8-2) and 2-ethoxy-6-(ethylamino)-4-{1-[(4-phenylbutyl)amino]ethyl}benzonitrile (8 mg) (Reference Example 3-8-3), each as a light brown oily substance.

Reference Example 3-8-2

MS ESI posi: 383 [M+H]$^+$.

Retention time: 0.781 min (method B)

Reference Example 3-8-3

MS ESI posi: 366 [M+H]$^+$.

Retention time: 0.708 min (method B)

Reference Example 3-8-4

1-(2-Ethoxy-6-[Ethyl(Methyl)Amino]-4-{1-[(4-Phenylbutyl)Amino]Ethyl}Phenyl) Ethan-1-One Hydrochloride

[Chemical Formula 451]

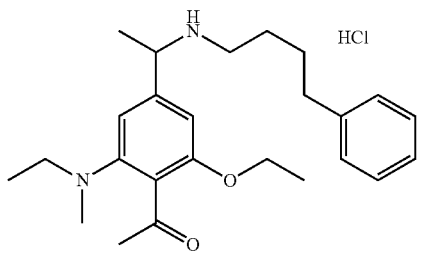 [SMILES: Cl ; CCOc1cc(C(C)NCCCCc2ccccc2)cc(N(CC)CC)c1C(C)=O]

(1) Using the compound (30 mg) obtained in Reference Example 3-8-2, the reaction was carried out in accordance with the method described in Reference Example 1-17-1 (1), and tert-butyl {1-[4-acetyl-3-ethoxy-5-(ethylamino)phenyl]ethyl}(4-phenylbutyl) carbamate (22 mg) was obtained as a colorless oily substance.

(2) To a solution of the compound (11 mg) obtained in (1) above in N,N-dimethylformamide (0.1 mL), potassium carbonate (6.93 mg) and iodomethane (8.51 μL) were added, and the reaction solution was stirred at 75° C. for 17 hours. Iodomethane (8.51 μL) was further added thereto, and the reaction solution was stirred at 75° C. for 1.5 hours. The reaction solution was brought back to room temperature and purified by preparative HPLC to afford tert-butyl(1-{4-acetyl-3-ethoxy-5-[ethyl(methyl)amino]phenyl}ethyl) (4-phenylbutyl) carbamate (8 mg) as a colorless oily substance.

(3) To a solution of the compound (8 mg) obtained in (2) above in ethyl acetate (0.5 mL), a 4 mol/L hydrogen chloride-ethyl acetate solution (0.2 mL) was added, and the reaction solution was stirred at room temperature for 20 hours. The reaction solution was concentrated to afford the title compound (8 mg) as a light yellow oily substance.

MS ESI posi: 397 [M+H]$^+$.

Retention time: 0.645 min (method B)

The following Reference Example 3-8-5 was synthesized by the method described in Reference Example 3-8-4 or by a method equivalent thereto, using the compound obtained in Reference Example 3-8-2, a commercially available compound, or a compound obtained by synthesis according to methods described in literatures or methods equivalent thereto. The structure and LCMS data of the compound are shown in Table 24-1.

TABLE 24-1

| Reference Example No. | Structural Formula | MS posi m/z MS mega m/z | Retention time (min) | method |
|---|---|---|---|---|
| 3-8-6 | 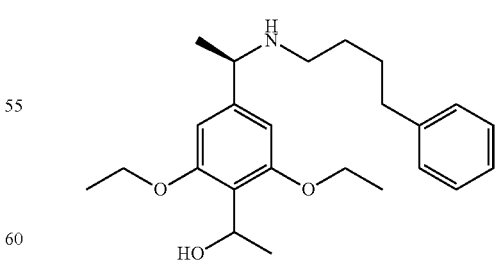 | 411 [M + H]+ | 0.607 | B |

Reference Example 3-9-1

1-(2,6-Diethoxy-4-{(1R)-1-[(4-Phenylbutyl)Amino]Ethyl}Phenyl) Ethan-1-Ol

[Chemical Formula 452]

Under a nitrogen atmosphere, a solution of lithium aluminum hydride (0.588 g) in tetrahydrofuran (50 mL) was ice-cooled, a solution of the compound (2.97 g) obtained in Reference Example 3-4-1 (2) in tetrahydrofuran (27 mL) was added dropwise thereto, and the reaction solution was stirred at the same temperature for 15 minutes. The reaction solution was ice-cooled, a mixed solvent of tetrahydrofuran-water (95:5, 60 mL) was added dropwise thereto, and the reaction solution was stirred at room temperature for 30 minutes. The reaction solution was filtered through Celite (registered trademark), and the filtrate was concentrated. The obtained residue was purified by NH silica gel column chromatography (n-hexane only to n-hexane:ethyl acetate=10:90) to afford the title compound (3.03 g) as a colorless oily substance.

MS ESI posi: 386 [M+H]$^+$.
Retention time: 0.719 min (method B)

The following Reference Examples 3-9-2 to 3-9-9 were synthesized by the method described in Reference Example 3-9-1 or by a method equivalent thereto, using the compounds obtained in Reference Example 3-1-51, Reference Example 3-4-2, Reference Example 3-4-21, Reference Example 3-4-25, Reference Example 3-4-30, Reference Example 3-4-28, and Reference Examples 3-4-37 to 3-4-38, commercially available compounds, or compounds obtained by synthesis according to methods described in literatures or methods equivalent thereto. The structures and LCMS data of the compounds are shown in Table 25-1 to Table 25-2.

TABLE 25-1

| Reference Example No. | Structural Formula | MS posi m/z MS mega m/z | Retention time (min) | method |
|---|---|---|---|---|
| 3-9-2 | 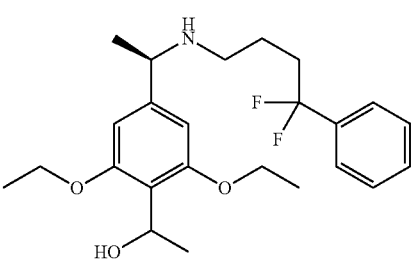 [SMILES: CCOc1cc([C@@H](C)NCCCC(F)(F)c2ccccc2)cc(OCC)c1C(C)O] | 422 [M + H]+ | 0.707 0.721 | B |
| 3-9-3 | 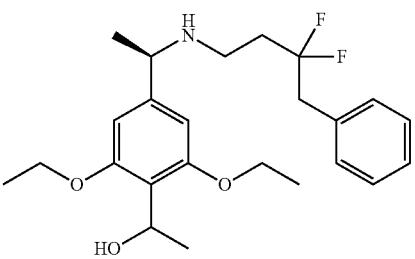 | 433 [M + H]+ | 0.705 0.723 | B |
| 3-9-4 | 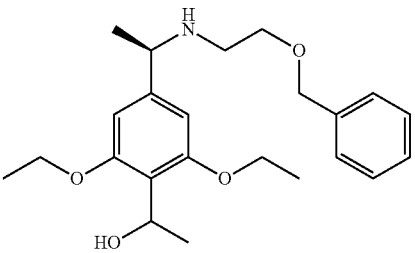 [SMILES: CCOc1cc([C@@H](C)NCCOCc2ccccc2)cc(OCC)c1C(C)O] | 388 [M + H]+ | 0.880 | B |
| 3-9-5 | 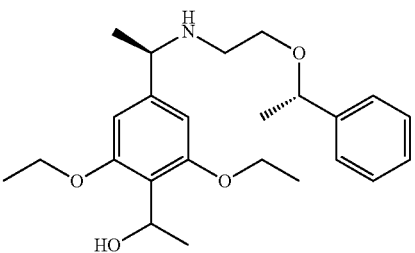 [SMILES: CCOc1cc([C@@H](C)NCCO[C@@H](C)c2ccccc2)cc(OCC)c1C(C)O] | 403 [M + H]+ | 0.711 | B |

TABLE 25-1-continued

| Reference Example No. | Structural Formula | MS posi m/z MS mega m/z | Retention time (min) | method |
|---|---|---|---|---|
| 3-9-6 | | 436 [M + H]+ | 0.736 0.746 | B |

TABLE 25-2

| Reference Example No. | Structural Formula | MS posi m/z MS mega m/z | Retention time (min) | method |
|---|---|---|---|---|
| 3-9-7 | | 342 [M + H]+ | 0.708 | B |
| 3-9-8 | | 450 [M + H]+ | 1.214 | C |
| 3-9-9 | | 422 [M + H]+ | 0.504 | A |

Reference Example 4-1-1

Ethyl 1-Amino-3-Methylcyclobutane-1-Carboxylate Trifluoroacetate

[Chemical Formula 453]

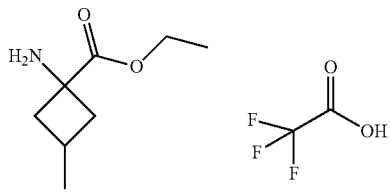

(1) Under a nitrogen atmosphere, methyltriphenylphosphonium bromide (0.444 g) was heated to dryness for 10 minutes while reducing the pressure, and tetrahydrofuran (1.6 mL) and potassium tert-butoxide (0.140 g) were added thereto. The reaction solution was ice-cooled, a solution of ethyl 1-[(tert-butoxycarbonyl)amino]-3-oxocyclobutane-1-carboxylate (200 mg) in tetrahydrofuran (1.6 mL) was added thereto, and the reaction solution was stirred at the same temperature for 1 hour and at room temperature overnight. The reaction solution was ice-cooled, a saturated aqueous sodium bicarbonate solution was added thereto, and extraction with ethyl acetate was carried out. The organic layer was washed with a brine, filtered through Phase Separator, and concentrated. The obtained residue was purified by silica gel column chromatography (n-hexane:ethyl acetate=90:10 to 40:60) to afford ethyl 1-[(tert-butoxycarbonyl)amino]-3-methylidenecyclobutane-1-carboxylate (50 mg) as a colorless oily substance.

(2) To a solution of the compound (50 mg) obtained in (1) above in methanol (3.9 mL), palladium carbon (100 mg) was added, and the reaction solution was stirred at room temperature overnight under a hydrogen atmosphere. The reaction solution was filtered through a mixed pad of Celite (registered trademark)-NH silica gel, and the filtrate was concentrated. The obtained residue was purified by silica gel column chromatography (n-hexane:ethyl acetate=95:5 to 60:40) to afford a mixture containing ethyl 1-[(tert-butoxycarbonyl)amino]-3-methylcyclobutane-1-carboxylate.

(3) To a solution of the mixture obtained in (2) above in chloroform (0.98 mL), trifluoroacetic acid (0.150 mL) was added, and the reaction solution was stirred at 60° C. for 10 hours and at room temperature overnight. The reaction solution was concentrated to afford the title compound (38 mg).

$^1$H NMR (400 MHZ, DMSO-$d_6$) δ ppm 0.89-1.47 (m, 6H) 1.90-2.10 (m, 1H) 2.15-2.81 (m, 4H) 4.18-4.31 (m, 2H) 8.10-8.94 (m, 3H).

Reference Example 4-2-1

Ethyl 1-Amino-3-[(Propan-2-Yl)Oxy]Cyclobutane-1-Carboxylate

[Chemical Formula 454]

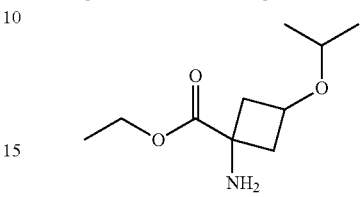

(1) A solution of ethyl 1-[(tert-butoxycarbonyl)amino]-3-oxocyclobutane-1-carboxylate (2 g) in ethanol (39 mL) was ice-cooled, and sodium borohydride (0.588 g) was added thereto. The reaction solution was stirred at the same temperature for 1 hour and at room temperature for 2 hours. The reaction solution was ice-cooled, and a saturated aqueous ammonium chloride solution (8 mL) and water (15 mL) were slowly added thereto. Ethanol in the reaction solution was distilled off under reduced pressure, and extraction with ethyl acetate was carried out. The organic layer was washed with a brine, dried over anhydrous sodium sulfate, filtered through Phase Separator, and concentrated. The obtained residue was purified by silica gel column chromatography (chloroform only to chloroform:methanol=88:12) to afford ethyl 1-[(tert-butoxycarbonyl)amino]-3-hydroxycyclobutane-1-carboxylate (1.94 g) as a colorless solid.

(2) To a solution of the compound (100 mg) obtained in (1) above in acetonitrile (7.7 mL), silver (I) oxide (1.79 g) and 2-iodopropane (385 μL) were added, and the reaction solution was stirred at 70° C. for 12 hours and at room temperature overnight. The reaction solution was filtered through Celite (registered trademark), and the filtrate was concentrated. The obtained residue was purified by NH silica gel column chromatography (n-hexane:ethyl acetate=96:4 to 60:40) to afford ethyl 1-[(tert-butoxycarbonyl)amino]-3-[(propan-2-yl)oxy]cyclobutane-1-carboxylate (39 mg) as a colorless oily substance.

(3) To a solution of the compound (35 mg) obtained in (2) above in chloroform (0.58 mL), trifluoroacetic acid (88.9 μL) was added, and the reaction solution was stirred at room temperature overnight. The reaction solution was concentrated, and the obtained residue was purified by NH silica gel column chromatography (chloroform only to chloroform:methanol=80:20) to afford the title compound (34 mg) as a colorless oily substance.

MS ESI/APCI Multi posi: 202 [M+H]$^+$.

Retention time: 0.213 min (method F)

The following Reference Examples 4-2-2 to 4-2-3 were synthesized by the method described in Reference Example 4-2-1 or by a method equivalent thereto, using commercially available compounds or compounds obtained by synthesis according to methods described in literatures or methods equivalent thereto. The structures and LCMS data of the compounds are shown in Table 26-1.

TABLE 26-1

| Reference Example No. | Structural Formula | MS posi m/z MS mega m/z | Retention time (min) | method |
|---|---|---|---|---|
| 4-2-2 | ![] | 188 [M + H]+ | 0.245-0.258 0.336-0.454 | F |
| 4-2-3 | ![] | 184 [M + H]+ | 0.246 | C |

Reference Example 4-2-4

Ethyl 3-(Acetoxy)-1-Aminocyclobutane-1-Carboxylate

[Chemical Formula 455]

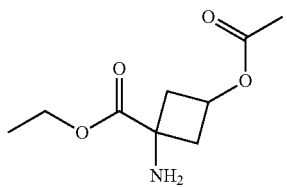

(1) To a solution of the compound (50 mg) obtained in Reference Example 4-2-1 (1) in chloroform (1.9 mL), N,N-diisopropylethylamine (0.101 mL) and 4-dimethylaminopyridine (2.36 mg) were added, and the reaction solution was ice-cooled. Acetic anhydride (36.5 µL) was added thereto, and the reaction solution was stirred for 3 hours and at room temperature overnight. Ice water was added thereto, and extraction with chloroform was carried out. The organic layer was washed with a saturated aqueous sodium bicarbonate solution twice, filtered through Phase Separator, and concentrated. The obtained residue was purified by silica gel column chromatography (n-hexane:ethyl acetate=95:5 to ethyl acetate only) to afford ethyl 3-(acetoxy)-1-[(tert-butoxycarbonyl)amino]cyclobutane-1-carboxylate (41 mg) as a colorless powder.

(2) Using the compound (40 mg) obtained in (1) above, the reaction was carried out in accordance with the method described in Reference Example 4-2-1 (3), and the title compound (60 mg) was obtained as a colorless oily substance.

MS ESI posi: 202 [M+H]+.

Retention time: 0.211 min (method B)

Reference Example 4-3-1

Ethyl Trans-1-Amino-3-Ethoxycyclobutane-1-Carboxylate Hydrochloride

[Chemical Formula 456]

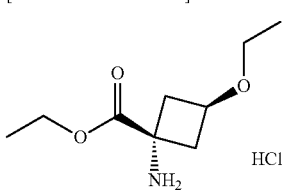

The present reaction was carried out with reference to the method described in the literature (Bioorganic & Medicinal Chemistry, vol. 17, p. 1982, 2009).

(1) To a solution of ethyl 1-[(tert-butoxycarbonyl)amino]-3-oxocyclobutane-1-carboxylate (15 g) in 1,4-dioxane (30 mL), a 4 mol/L hydrogen chloride-1,4-dioxane solution (120 mL) was added, and the reaction solution was stirred at room temperature for 14 hours. The precipitated solid was filtered off to afford ethyl 1-amino-3-oxocyclobutane-1-carboxylate hydrochloride (11.0 g) as a colorless solid.

(2) To a solution of the compound (200 mg) obtained in (1) above in toluene (5.2 mL), phthalic anhydride (306 mg) and triethylamine (288 µL) were added, and the reaction solution was stirred with heating under reflux for 4.5 hours. The reaction solution was brought back to room temperature, water and 1 mol/L hydrochloric acid were added thereto to adjust the pH to 2, and extraction with ethyl acetate was carried out twice. The organic layer was filtered through Phase Separator and concentrated. The obtained residue was purified by silica gel column chromatography (n-hexane only to n-hexane:ethyl acetate=50:50) to afford ethyl 1-(1,3-dioxo-1,3-dihydro-2H-isoindol-2-yl)-3-oxocyclobutane-1-carboxylate (404 mg) as a colorless solid.

(3) Under a nitrogen atmosphere, to a solution of the compound (200 mg) obtained in (2) above in tetrahydrofuran (2 mL), zinc chloride (0.5 mol/L tetrahydrofuran solution, 2.78 mL) was added, and the reaction solution was stirred at room temperature for 30 minutes. The reaction solution was cooled to −78° C., lithium tri-sec-butylborohydride (L-Selectride (registered trademark), 1 mol/L tetrahydrofuran solution, 1.04 mL) was slowly added dropwise thereto, and the reaction solution was stirred at the same temperature for 2 hours and at room temperature for 50 minutes. The reaction solution was ice-cooled, a saturated aqueous ammonium chloride solution (10 mL) was added thereto, and extraction with ethyl acetate was carried out twice. The organic layer was washed with a brine, filtered through Phase Separator, and concentrated. The obtained residue was purified by silica gel column chromatography (n-hexane only to n-hexane:ethyl acetate=50:50) to afford ethyl trans-1-(1,3-dioxo-1,3-dihydro-2H-isoindol-2-yl)-3-hydroxycyclobutane-1-carboxylate (179 mg) as a colorless oily substance.

(4) To a solution of the compound (2.0 g) obtained in (3) above in acetonitrile (35 mL), silver (I) oxide (16 g) and iodoethane (2.8 mL) were added, and the reaction solution was stirred at 80° C. for 24 hours, at room temperature for 2 days, at 80° C. for 12 hours, and at room temperature overnight. The reaction solution was filtered through Celite (registered trademark), and the filtrate was concentrated. The obtained residue was purified by column chromatography in which a NH silica gel column cartridge and a silica gel column cartridge were coupled (n-hexane:ethyl acetate=95:5 to 50:50, and then chloroform:methanol=90:10) to afford ethyl trans-1-(1,3-dioxo-1,3-dihydro-2H-isoindol-2-yl)-3-ethoxycyclobutane-1-carboxylate (1.38 g) as a light yellow solid.

$^1$H NMR (400 MHZ, CHLOROFORM-d) δ ppm 1.16-1.30 (m, 6H) 2.76-2.96 (m, 2H) 3.38-3.51 (m, 2H) 3.51-3.66 (m, 2H) 4.05-4.26 (m, 3H) 7.71-7.79 (m, 2H) 7.79-7.91 (m, 2H).

The obtained light yellow solid was recrystallized from ethanol to acquire a single crystal, which was confirmed to have the target structure below by X-ray structure analysis.

[Chemical Formula 457]

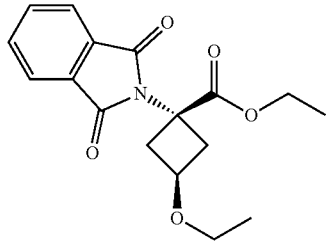

(5) To a solution of the compound (2.00 g) obtained in (4) above in ethanol (21 mL), hydrazine monohydrate (313 μL) was added, and the reaction solution was stirred at 40° C. for 1.2 hours. Hydrazine monohydrate (6.14 μL) was further added thereto, and the reaction solution was stirred at 40° C. for 0.8 hours, with heating under reflux for 6.5 hours, and at room temperature overnight. Insolubles were filtered off and the filtrate was concentrated. Ethanol was added to the obtained residue, insolubles were filtered off, and the filtrate was concentrated. Chloroform (15 mL) and 1 mol/L hydrochloric acid (12 mL) were added to the obtained residue, and the aqueous layer was washed with chloroform. The organic layers were combined, and extracted with 1 mol/L hydrochloric acid (10 mL). The aqueous layers were combined, to which a solution of sodium hydroxide (1.4 g) in water (3.5 mL) was then added to adjust the pH to 10, and extracted with chloroform. The organic layer was filtered through Phase Separator and concentrated to afford ethyl trans-1-amino-3-ethoxycyclobutane-1-carboxylate (475 mg) as a light brown oily substance.

(6) A solution of the compound (400 mg) obtained in (5) above in 2 mol/L hydrogen chloride-ethanol (3.20 mL) was stirred at room temperature for 1 hour. The reaction solution was concentrated, and toluene was added to the obtained residue. After concentration, the title compound (469 mg) was obtained as a colorless solid.

MS ESI posi: 188 [M+H]$^+$.

Retention time: 0.415 min (method C)

The following Reference Example 4-3-2 was synthesized by the method described in Reference Example 4-3-1 or by a method equivalent thereto, using a commercially available compound or a compound obtained by synthesis according to methods described in literatures or methods equivalent thereto. The structure and LCMS data of the compound are shown in Table 27-1.

TABLE 27-1

| Reference Example No. | Structural Formula | MS posi m/z MS mega m/z | Retention time (min) | method |
|---|---|---|---|---|
| 4-3-2 | 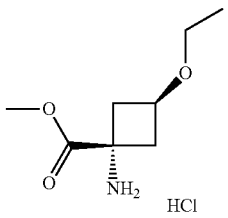 | 174 [M + H]+ | 0.352 | C |

Reference Example 4-3-3

Methyl Trans-1-Amino-3-Ethoxycyclobutane-1-Carboxylate Hydrochloride

[Chemical Formula 458]

(1) A suspension of the compound (100 mg) obtained in Reference Example 4-3-1 in ethyl acetate (4.5 mL) was ice-cooled, a solution of sodium bicarbonate (308 mg) in water (3.5 mL) was slowly added thereto, and benzyl chloroformate (89.0 μL) was added dropwise thereto. The reaction solution was stirred at room temperature for 14 hours. By adding ethyl acetate and water to the reaction solution, it was partitioned into two layers. The organic layer was washed with 1 mol/L hydrochloric acid, a saturated aqueous sodium bicarbonate solution, and a brine sequentially, and dried over anhydrous magnesium sulfate. After filtering off the desiccating agent, the filtrate was concentrated. The obtained residue was purified by silica gel column chromatography (n-hexane:ethyl acetate=88:12 to ethyl acetate only) to afford ethyl trans-1-{[(benzyloxy) carbonyl]amino}-3-ethoxycyclobutane-1-carboxylate (124 mg) as a colorless powder.

(2) To a solution of the compound (10.0 g) obtained in (1) above in methanol (39 mL), tetrahydrofuran (39 mL) and a 1 mol/L aqueous sodium hydroxide solution (31.1 mL) were added, and the reaction solution was stirred at room temperature for 3 hours. Methanol and tetrahydrofuran were distilled off under reduced pressure, the aqueous layer was washed with toluene (30 mL), and then 4 mol/L hydrochloric acid was added thereto. The aqueous layer was extracted with chloroform (30 mL) twice, and the organic layers were combined, filtered through Phase Separator, and concentrated. Toluene (50 mL) was added to the obtained residue, followed by concentration, thereby obtaining a mixture (8.35 g) containing trans-1-{[(benzyloxy) carbonyl]amino}-3-ethoxycyclobutane-1-carboxylic acid.

(3) To a solution of the mixture (2.00 g) obtained in (2) above in methanol (2.8 mL), toluene (17 mL) and p-toluenesulfonic acid monohydrate (131 mg) were added, and the reaction solution was stirred at 100° C. for 3 hours, at room temperature overnight, and at 100° C. for 2 hours. Toluene (10 mL) was added to the reaction solution, which was then sequentially washed with a saturated aqueous sodium bicarbonate solution (8 mL) twice and with a brine (8 mL). The organic layer was dried over anhydrous magnesium sulfate. After filtering off the desiccating agent, the filtrate was concentrated. The obtained residue was purified by silica gel column chromatography (n-hexane:ethyl acetate=90:10 to 20:80) to afford methyl trans-1-{[(benzyloxy) carbonyl] amino}-3-ethoxycyclobutane-1-carboxylate (1.65 g) as a pale brown solid.

(4) To a solution of the compound (1.00 g) obtained in (3) above in methanol (7.9 mL), palladium carbon (0.1 g) was added, and the reaction solution was stirred at room temperature for 2 hours under a hydrogen atmosphere. The reaction solution was filtered through KC FLOCK (registered trademark), and the filtrate was concentrated. The obtained residue was purified by NH silica gel column chromatography (n-hexane:ethyl acetate=70:30, and then chloroform only to chloroform:methanol=80:20) to afford a mixture containing methyl trans-1-amino-3-ethoxycyclobutane-1-carboxylate.

(5) To the mixture obtained in (4) above, a 2 mol/L hydrogen chloride-methanol solution (3.15 mL) was added, and the reaction solution was concentrated. Toluene (10 mL) was added to the obtained residue, and after concentration, the title compound (552 mg) was obtained as a colorless gum-like substance.

MS ESI posi: 174 [M+H]+.

Retention time: 0.239 min (method C)

Reference Example 4-3-4

Trans-1-{[(Benzyloxy) Carbonyl]Amino}-3-Hydroxycyclobutane-1-Carboxylic Acid

[Chemical Formula 459]

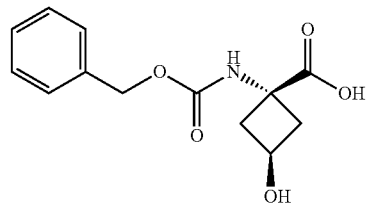

(1) To a solution of dipropan-2-yl 3,3-dimethoxycyclobutane-1,1-dicarboxylate (20.0 g) in isopropyl alcohol (52.9 g), a 35% aqueous tetraethylammonium hydroxide solution (30.7 g) was added, and the reaction solution was stirred at 60° C. for 6 hours and at room temperature for 38 hours. The reaction solution was concentrated, and toluene (60 mL) was added to the residue, which was thereby partitioned into two layers. A 50% aqueous citric acid solution (23.5 g) was added to the aqueous layer to adjust the pH to 4, and then extraction with ethyl acetate was carried out twice. The organic layer was washed with a 10% aqueous sodium sulfate solution and concentrated. Toluene was added to the obtained residue, and after concentration, 3,3-dimethoxy-1-{[(propan-2-yl)oxy]carbonyl}cyclobutane-1-carboxylic acid (13.9 g) was obtained as a light yellow oily substance.

(2) To a solution of the compound (4.58 g) obtained in (1) above in toluene (47.0 g), triethylamine (2.47 g) was added, a solution of diphenylphosphoryl azide (5.42 g) in toluene (17.0 g) was slowly added dropwise thereto at 90° C., and the reaction solution was stirred at 90° C. for 2 hours. Subsequently, benzyl alcohol (2.42 g) was added dropwise to the reaction solution, which was then stirred at the same temperature for 7 hours and at room temperature for 80 hours. A 10% aqueous potassium carbonate solution (16.6 g) was added to the reaction solution, which was then extracted. The organic layer was washed with a 10% aqueous citric acid solution and a 10% aqueous sodium sulfate solution sequentially, and then concentrated to afford a mixture (6.71 g) containing propan-2-yl 1-{[(benzyloxy) carbonyl]amino}-3,3-dimethoxycyclobutane-1-carboxylate as a yellow oily substance.

(3) To a solution of the mixture (5.94 g) obtained in (2) above in isopropyl alcohol (33.2 g), a mixed solution of concentrated hydrochloric acid (4.22 g) and water (4.22 g) was added dropwise at room temperature, and the reaction solution was stirred at 50° C. for 2 hours and at room temperature for 22.5 hours. A solution of potassium carbonate (3.50 g) in water (21.3 g) was added to the reaction solution, isopropyl alcohol was distilled off under reduced pressure, and isopropyl acetate (37.7 g) was added thereto for extraction. The organic layer was washed with a 10% aqueous sodium sulfate solution, and dried over anhydrous magnesium sulfate. After filtering off the desiccating agent, the filtrate was concentrated to afford the residue (4.60 g). The obtained residue (1.00 g) was recrystallized from a mixed solvent of isopropyl acetate-n-heptane, and precipitates were filtered off to afford propan-2-yl 1-{[(benzyloxy) carbonyl]amino}-3-oxocyclobutane-1-carboxylate (0.830 g) as a colorless solid.

(4) A solution of sodium borohydride (0.128 g) in ethanol (3.79 g) was ice-cooled, a solution of the compound (2.00 g) obtained in (3) above in ethanol (5.22 g) was added dropwise thereto, and the reaction solution was stirred at the same temperature for 2.5 hours. A solution of ammonium chloride (0.530 g) in water (3.61 g) was added to the reaction solution, and ethanol was distilled off under reduced pressure, followed by extraction with ethyl acetate. The organic layer was washed with a 10% aqueous sodium bicarbonate solution and a 10% aqueous sodium sulfate solution sequentially, and then concentrated to afford a mixture (1.94 g) containing propan-2-yl trans-1-{[(benzyloxy) carbonyl]amino}-3-hydroxycyclobutane-1-carboxylate as a colorless solid.

(5) To a solution of the compound (1.80 g) obtained in (4) above in methanol (5.79 g), a mixed solution of an 8 mol/L aqueous sodium hydroxide solution (1.46 mL) and water (1.46 mL) was added, and the reaction solution was stirred at room temperature for 17.5 hours. Concentrated hydrochloric acid (0.607 g) was added to the reaction solution to set the pH to 5.5, and methanol was distilled off under reduced pressure. To the obtained residue, water (4.00 g) and concentrated hydrochloric acid (0.60 g) were added to set the pH to 1.9. Then, water (3.00 g) was added thereto, and extraction with isopropyl acetate was carried out twice. The combined organic layers were washed with a 10% aqueous sodium sulfate solution, and dried over anhydrous magnesium sulfate. After filtering off the desiccating agent, the filtrate was concentrated to afford the residue (1.55 g). The obtained residue (1.13 g) was recrystallized from a mixed solvent of isopropyl acetate-n-heptane, and precipitates were filtered off to afford the title compound (0.710 g) as a colorless solid.

MS ESI posi: 266 [M+H]$^+$, 288 [M+Na]$^+$.
MS ESI nega: 264 [M–H]$^-$.
Retention time: 0.539 min (method B)

Reference Example 4-4-1

Ethyl Cis-1-Amino-3-Ethoxycyclobutane-1-Carboxylate Hydrochloride

[Chemical Formula 460]

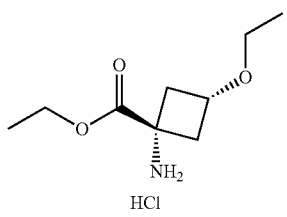

(1) Using dipropan-2-yl 3-oxocyclobutane-1,1-dicarboxylate (6.05 g), the reaction and post treatment were carried out in accordance with the method described in Reference Example 4-2-1 (1), and the obtained residue was purified by silica gel column chromatography (n-hexane: ethyl acetate=90:10 to 40:60) to afford dipropan-2-yl 3-hydroxycyclobutane-1,1-dicarboxylate (3.8 g) as a colorless oily substance.

(2) The present reaction was carried out with reference to the method described in the literature (The Journal of Organic Chemistry, vol. 82, p. 12863, 2017). To a solution of the compound (3.8 g) obtained in (1) above in isopropyl alcohol (78 mL), a 35% aqueous tetraethylammonium hydroxide solution (7.8 mL) was added, and the reaction solution was stirred at room temperature overnight. A 35% aqueous tetraethylammonium hydroxide solution (1.1 mL) was further added thereto, and the reaction solution was stirred at room temperature overnight. The reaction solution was concentrated, a 10% aqueous sodium bisulfate solution (70 mL) was added thereto to make the solution acidic, and the reaction solution was then extracted with ethyl acetate three times. The organic layer was washed with a 10% aqueous sodium bisulfate solution (70 mL) and a brine (70 mL) sequentially and dried over anhydrous magnesium sulfate, and the desiccating agent was filtered off. The filtrate was concentrated to afford 3-hydroxy-1-{[(propan-2-yl)oxy]carbonyl}cyclobutane-1-carboxylic acid (2.34 g) as a light yellow solid.

(3) To the compound (100 mg) obtained in (2) above and triethylamine (103 μL), tert-butyl alcohol (466 μL), toluene (9.9 mL), and diphenylphosphoryl azide (117 μL) were added, and the reaction solution was stirred at 100° C. for 5 hours and at room temperature overnight. A 10% aqueous sodium bisulfate solution was added to the reaction solution to make the solution acidic, and extraction with ethyl acetate was carried out three times. The organic layer was washed with a brine, filtered through Phase Separator, and concentrated. The obtained residue was purified by silica gel column chromatography (n-hexane:ethyl acetate=90:10 to 20:80) to afford propan-2-yl(1s,5s)-3-oxo-2-oxa-4-azabicyclo[3.1.1]heptane-5-carboxylate (86.3 mg) as a colorless powder.

$^1$H NMR (400 MHZ, CHLOROFORM-d) δ ppm 1.24-1.37 (m, 6H) 1.95-2.07 (m, 2H) 2.65-2.78 (m, 2H) 4.96-5.03 (m, 1H) 5.05-5.20 (m, 1H) 6.17 (br s, 1H).

The obtained colorless powder was recrystallized from ethanol to acquire a single crystal, which was confirmed to have the target structure below by X-ray structure analysis.

[Chemical Formula 461]

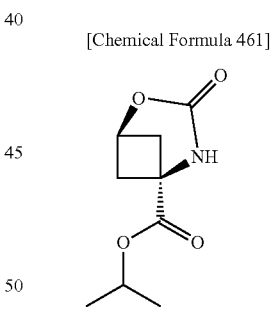

(4) To a mixed solution of the compound (970 mg) obtained in (3) above in water-ethanol (12 mL-6.1 mL), potassium hydroxide (1.37 g) was added, and the reaction solution was stirred at 80° C. for 10 hours. After bringing the reaction solution back to room temperature, ethanol was distilled off under reduced pressure. The aqueous layer was washed with diethyl ether twice, and then concentrated hydrochloric acid was added thereto little by little for neutralization. The aqueous layer was concentrated to afford a mixture containing cis-1-amino-3-hydroxycyclobutane-1-carboxylic acid.

(5) A solution of the mixture obtained in (4) above in ethanol (24 mL) was ice-cooled, thionyl chloride (1.07 mL) was added thereto, and the reaction solution was stirred at 70° C. for 2 hours and concentrated. The obtained residue was purified by NH silica gel column chromatography (n-hexane:ethyl acetate=60:40 to ethyl acetate only, and then chloroform:methanol=95:5 to 60:40) to afford ethyl cis-1-amino-3-hydroxycyclobutane-1-carboxylate (826 mg) as a colorless solid.

(6) A mixed solution of the compound (826 mg) obtained in (5) above in acetonitrile-water (10 mL-10 mL) was ice-cooled, triethylamine (3.59 mL) and di-tert-butyl dicarbonate (2.28 g) were added thereto, and the reaction solution was stirred at room temperature for 2 hours. A saturated aqueous sodium bicarbonate solution was added to the reaction solution, which was then extracted with ethyl acetate three times. The organic layer was washed with a saturated aqueous sodium bicarbonate solution, water, and a brine sequentially, filtered through Phase Separator, and concentrated. The obtained residue was purified by silica gel column chromatography (n-hexane:ethyl acetate=90:10 to ethyl acetate only) to afford ethyl cis-1-[(tert-butoxycarbonyl)amino]-3-hydroxycyclobutane-1-carboxylate (982 mg) as a colorless powder.

$^1$H NMR (400 MHZ, METHANOL-d$_4$) δ ppm 1.19-1.35 (m, 3H) 1.35-1.48 (m, 9H) 2.00-2.15 (m, 2H) 2.81-2.94 (m, 2H) 4.09-4.22 (m, 2H) 4.22-4.34 (m, 1H).

The obtained colorless powder was recrystallized from a mixed solvent of acetone-n-hexane to acquire a single crystal, which was confirmed to have the target structure below by X-ray structure analysis.

[Chemical Formula 462]

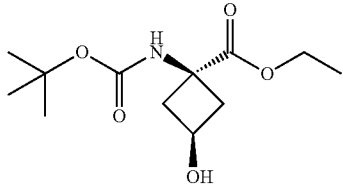

(7) Using the compound (500 mg) obtained in (6) above, the reaction was carried out in accordance with the method described in Reference Example 4-3-1 (4), and ethyl cis-1-[(tert-butoxycarbonyl)amino]-3-ethoxycyclobutane-1-carboxylate (487 mg) was obtained as a colorless oily substance.

(8) To the compound (470 mg) obtained in (7) above, 4 mol/L hydrogen chloride-ethyl acetate (2.0 mL) was added, and the reaction solution was stirred at room temperature for 30 minutes and concentrated. To this, a 4 mol/L hydrogen chloride-1,4-dioxane solution (2.0 mL) was added, and the reaction solution was stirred at room temperature for 30 minutes. The reaction solution was concentrated to afford the title compound (336 mg) as a light brown powder.

MS ESI/APCI Multi posi: 188 [M+H]$^+$.

Retention time: 0.375 min (method F)

The following Reference Examples 4-4-2 to 4-4-3 were synthesized by the method described in Reference Example 4-4-1 or by a method equivalent thereto, using commercially available compounds or compounds obtained by synthesis according to methods described in literatures or methods equivalent thereto. The structures and LCMS data of the compounds are shown in Table 28-1.

TABLE 28-1

| Reference Example No. | Structural Formula | MS posi m/z MS mega m/z | Retention time (min) | method |
|---|---|---|---|---|
| 4-4-2 | | 174 [M + H]+ | 0.334 | F |
| 4-4-3 | | 174 [M + H]+ | 0.327-0.376 | C |

Reference Example 4-5-1

Methyl Trans-3-Acetoxy-1-[(Tert-Butoxycarbonyl)Amino]-3-Methylcyclobutane-1-Carboxylate

[Chemical Formula 463]

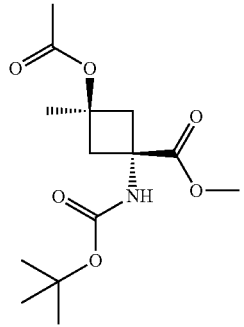

(1) To trans-1-amino-3-hydroxy-3-methylcyclobutane-1-carboxylic acid (200 mg), which was obtained by the method described in the literature (The Journal of Organic Chemistry, vol. 82, p. 12863, 2017), a 2 mol/L hydrogen chloride-methanol solution (0.276 mL) was added, and the reaction solution was stirred at 60° C. overnight and further stirred at room temperature overnight. The reaction solution was concentrated to afford a mixture containing methyl trans-1-amino-3-hydroxy-3-methylcyclobutane-1-carboxylate.

(2) To a solution of the mixture obtained in (1) above in acetonitrile (2.8 mL), triethylamine (96.0 L) and di-tert-butyl dicarbonate (90.2 mg) were added, and the reaction solution was stirred at room temperature for 4 hours. A saturated aqueous sodium bicarbonate solution was added to the reaction solution, which was then stirred at room temperature for 1 hour and extracted with chloroform. The organic layer was filtered through Phase Separator and concentrated to afford a mixture containing methyl trans-1-[(tert-butoxycarbonyl)amino]-3-hydroxy-3-methylcyclobutane-1-carboxylate.

(3) Using the mixture obtained in (2) above, the reaction was carried out in accordance with the method described in Reference Example 4-2-4 (1), and the title compound (5 mg) was obtained as a colorless oily substance.

¹H NMR (400 MHZ, CHLOROFORM-d) δ ppm 1.39-1.54 (m, 12H) 1.99 (s, 3H) 2.28-2.43 (m, 2H) 2.85-3.00 (m, 2H) 3.68 (s, 3H).

Reference Example 4-6-1

Methyl 1-Acetyl-3-Aminoazetidine-3-Carboxylate

[Chemical Formula 464]

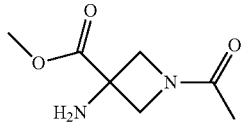

(1) Using methyl 3-[(tert-butoxycarbonyl)amino]azetidine-3-carboxylate hydrochloride (100 mg), the reaction was carried out in accordance with the method described in Reference Example 4-2-4 (1), and methyl 1-acetyl-3-[(tert-butoxycarbonyl)aminoJazetidine-3-carboxylate (79 mg) was obtained as a colorless powder.

(2) Using the compound (74 mg) obtained in (1) above, the reaction was carried out in accordance with the method described in Reference Example 4-2-1 (3), and the title compound (42 mg) was obtained as a yellow oily substance.

MS ESI posi: 173 [M+H]⁺.
Retention time: 0.209 min (method C)

The following Reference Examples 4-6-2 to 4-6-3 were synthesized by the method described in Reference Example 4-6-1 or by a method equivalent thereto, using commercially available compounds or compounds obtained by synthesis according to methods described in literatures or methods equivalent thereto. The structures and LCMS data of the compounds are shown in Table 29-1.

TABLE 29-1

| Reference Example No. | Structural Formula | MS posi m/z MS mega m/z | Retention time (min) | method |
|---|---|---|---|---|
| 4-6-2 | 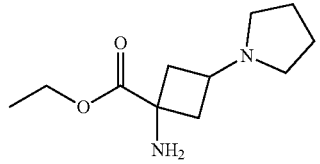 | 201 [M + H]+ 336 [M + Cl]+ | 0.178 | C |
| 4-6-3 | | 187 [M + H]+ | 0.233 | F |

Reference Example 4-7-1

Ethyl 1-Amino-3-(Pyrrolidin-1-Yl)Cyclobutane-1-Carboxylate

[Chemical Formula 465]

(1) To a solution of ethyl 1-[(tert-butoxycarbonyl)amino]-3-oxocyclobutane-1-carboxylate (100 mg) in chloroform (2.0 mL), pyrrolidine (48.7 μL) was added, and the reaction solution was stirred at room temperature for 1 hour. The reaction solution was ice-cooled, sodium triacetoxyborohydride (247 mg) was added thereto, and the reaction solution was stirred at room temperature overnight. A saturated aqueous sodium bicarbonate solution was added to the reaction solution, which was then extracted with chloroform, filtered through Phase Separator, and concentrated. The obtained residue was purified by NH silica gel column chromatography (n-hexane:ethyl acetate=95:5, and then chloroform only to chloroform:methanol=80:20) to afford ethyl 1-[(tert-butoxycarbonyl)amino]-3-(pyrrolidin-1-yl)cyclobutane-1-carboxylate (130 mg) as a colorless oily substance.

(2) To the compound (93.0 mg) obtained in (1) above, a 2 mol/L hydrogen chloride-ethanol solution (0.744 mL) was added, and the reaction solution was stirred at 60° C. for 29 hours and at room temperature overnight. The reaction solution was concentrated to afford the title compound (64 mg).

MS ESI posi: 213 [M+H]⁺.
Retention time: 0.329 min (method C)

The following Reference Examples 4-7-2 to 4-7-3 were synthesized by the method described in Reference Example 4-7-1 or by a method equivalent thereto, using commercially available compounds or compounds obtained by synthesis according to methods described in literatures or methods equivalent thereto. The structures and LCMS data of the compounds are shown in Table 30-1.

TABLE 30-1

| Reference Example No. | Structural Formula | MS posi m/z MS mega m/z | Retention time (min) | method |
|---|---|---|---|---|
| 4-7-2 | | 242 [M + H]+ | 0.152 | C |
| 4-7-3 | | 229 [M + H]+ | 0.217 | C |

Reference Example 4-8-1

Dibenzyl(1-Aminocyclopentyl)Phosphonate

[Chemical Formula 466]

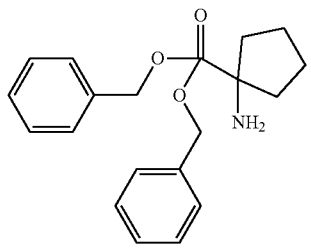

(1) To a solution of dibenzyl phosphite (500 mg), cyclopentanone (0.160 g), benzhydrylamine (0.349 g) in acetonitrile (9.5 mL), bismuth (III) chloride (60.1 mg) was added, and the reaction solution was stirred at 100° C. for 1 hour under microwave irradiation. The reaction solution was filtered through Celite (registered trademark), and the filtrate was concentrated. The obtained residue was purified by silica gel column chromatography (n-hexane only to n-hexane:ethyl acetate=70:30) to afford dibenzyl {1-[(diphenylmethyl)amino]cyclopentyl}phosphonate (301 mg) as a brown oily substance.

(2) The present reaction was carried out with reference to the method described in the literature (Organic Letters, vol. 1, p. 1395, 1999). To a solution of the compound (300 mg) obtained in (1) above in toluene (2 mL), molecular sieves 4 Å (300 mg) was added, and the reaction solution was stirred at room temperature for 20 minutes. To the reaction solution, 2,3-dichloro-5,6-dicyano-1,4-benzoquinone (0.146 g) was added, and the reaction solution was stirred at 60° C. for 3 hours with shielding from light. 2,3-Dichloro-5,6-dicyano-1,4-benzoquinone (66.6 mg) was further added thereto, and the reaction solution was stirred at 60° C. for 2 hours with shielding from light. The reaction solution was filtered through a NH silica gel pad, and the filtrate was concentrated.

(3) To a solution of the mixture obtained in (2) above in diethyl ether (2 mL), 0.5 mol/L hydrochloric acid (2 mL) was added, and the reaction solution was stirred at room temperature for 18 hours and at 40° C. for 2 hours. Diethyl ether was added to the reaction solution, which was then extracted with water. The aqueous layer was concentrated, a saturated aqueous sodium bicarbonate solution was added thereto, and extraction with chloroform was carried out. The organic layer was concentrated to afford dibenzyl(1-aminocyclopentyl)phosphonate (20.2 mg) as a pale yellow oily substance.

MS ESI/APCI Multi posi: 346 [M+H]$^+$.
Retention time: 0.934 min (method F)

Reference Example 4-9-1

1-[2-(Triphenylmethyl)-2H-Tetrazol-5-Yl]Cyclopropan-1-Amine

[Chemical Formula 467]

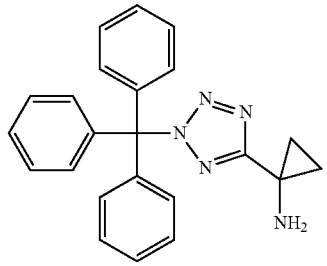

(1) To a mixed solution of 1-aminocyclopropanecarbonitrile hydrochloride (2.81 g) in 1,4-dioxane-water (59 mL-30 mL), potassium carbonate (9.83 g) was added, and the reaction solution was ice-cooled. Allyl chloroformate (2.76 mL) was added thereto, and the reaction solution was stirred at the same temperature for 2 hours. At the same temperature, 2 mol/L hydrochloric acid and water were added thereto to set the pH to 8, and extraction with ethyl acetate was carried out. The organic layer was dried over anhydrous magnesium sulfate. After filtering off the desiccating agent, the filtrate was concentrated. The obtained residue was purified by silica gel column chromatography (chloroform only to chloroform:methanol=90:10) to afford prop-2-en-1-yl(1-cyanocyclopropyl) carbamate (3.86 g) as a colorless solid.

(2) To a solution of the compound (3.86 g) obtained in (1) above in N,N-dimethylformamide (39 mL), ammonium chloride (1.74 g) and sodium azide (2.11 g) were added, and the reaction solution was stirred at 120° C. for 1 hour under microwave irradiation. The reaction solution was ice-cooled, 2 mol/L hydrochloric acid (17.4 mL) was added thereto to adjust the pH to 3, and extraction with ethyl acetate was carried out three times. The organic layer was washed with water and a brine sequentially, and concentrated to afford a mixture (10.3 g) containing prop-2-en-1-yl[1-(2H-tetrazol-5-yl)cyclopropyl]carbamate.

(3) A solution of the mixture (10.3 g) obtained in (2) above in tetrahydrofuran (116 mL) was ice-cooled, triethylamine (9.71 mL) and trityl chloride (7.12 g) were added thereto, and the reaction solution was stirred at room temperature for 18 hours. A saturated aqueous sodium bicarbonate solution was added to the reaction solution, which was then extracted with ethyl acetate. The organic layer was washed with a brine, filtered through Phase Separator, and concentrated. The obtained residue was purified by silica gel column chromatography (n-hexane only to n-hexane:ethyl acetate=60:40) to afford prop-2-en-1-yl {1-[2-(triphenylmethyl)-2H-tetrazol-5-yl]cyclopropyl}carbamate (5.45 g) as a colorless solid.

(4) To a solution of the compound (5.45 g) obtained in (3) above in tetrahydrofuran (121 mL), 1,3-dimethylbarbituric acid (2.07 g) was added, and the reaction solution was degassed under reduced pressure. Tetrakis(triphenylphosphine) palladium (0) (0.697 g) was added thereto, and the reaction solution was stirred at 60° C. for 1 hour under a nitrogen atmosphere. A saturated aqueous sodium bicarbonate solution was added to the reaction solution, which was then extracted with ethyl acetate three times. The organic layer was washed with a mixed solution of saturated saline solution-saturated aqueous sodium bicarbonate solution (2:1), and dried over anhydrous magnesium sulfate. After filtering off the desiccating agent, the filtrate was concentrated. The obtained residue was purified by silica gel column chromatography (chloroform:methanol=99:1 to 92:8) and NH silica gel column chromatography (n-hexane:ethyl acetate=95:5 to 60:40) to afford the title compound (2.32 g) as a colorless solid.

$^1$H NMR (400 MHZ, DMSO-$d_6$) δ ppm 1.00-1.13 (m, 4H) 6.96-7.08 (m, 6H) 7.34-7.44 (m, 9H).

The following Reference Examples 4-9-2 to 4-9-3 were synthesized by the method described in Reference Example 4-9-1 or by a method equivalent thereto, using the compound obtained in Reference Example 4-3-2, commercially available compounds, or compounds obtained by synthesis according to methods described in literatures or methods equivalent thereto. The structures and LCMS data of the compounds are shown in Table 31-1.

TABLE 31-1

| Reference Example No. | Structural Formula | MS posi m/z MS mega m/z | Retention time (min) | method |
|---|---|---|---|---|
| 4-9-2 | | 440 [M + Na]+ | — | M |
| 4-9-3 | | 431 [M + Na]+ | — | M |

The NMR data of Reference Examples 4-9-2 to 4-9-3 is shown below.

Reference Example 4-9-2

$^1$H NMR (400 MHZ, CHLOROFORM-d) δ ppm 2.75-2.89 (m, 2H) 3.21-3.38 (m, 2H) 7.05-7.12 (m, 6H) 7.28-7.42 (m, 9H).

Reference Example 4-9-3

$^1$H NMR (400 MHZ, CHLOROFORM-d) δ ppm 2.41-2.63 (m, 4H) 3.26 (s, 3H) 4.06-4.35 (m, 1H) 6.91-7.63 (m, 15H).

Reference Example 4-10-1

1-(1-Benzyl-1H-Tetrazol-5-Yl)-3,3-Difluorocyclobutan-1-Amine Hydrochloride

[Chemical Formula 468]

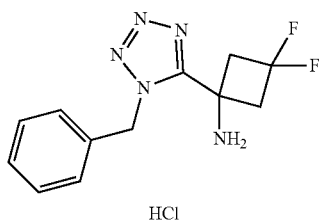

HCl (1) Using 1-amino-3,3-difluorocyclobutane-1-carboxylic acid (1.03 g), the reaction was carried out in accordance with the method described in Reference Example 4-5-1 (2), and 1-[(tert-butoxycarbonyl)amino]-3,3-difluorocyclobutane-1-carboxylic acid was obtained as a colorless solid.

(2) To a solution of the compound obtained in (1) above in chloroform (15 mL), N,N-diisopropylethylamine (3.55 mL) and ammonium chloride (0.509 g) were added, the reaction solution was ice-cooled, HATU (3.88 g) and N,N-dimethylformamide (4 mL) were added thereto, and the reaction solution was stirred at room temperature for 4 days. Extraction with ethyl acetate was carried out, and the organic layer was washed with water and concentrated. The obtained residue was suspended by adding ethyl acetate (7 mL) and n-hexane (10 mL) at 60° C., and chloroform (5 mL) and n-hexane (60 mL) were added thereto. The suspension was stirred at room temperature for 1 hour, and the solid was filtered off to afford tert-butyl(1-carbamoyl-3,3-difluorocyclobutyl) carbamate (905 mg) as a colorless powder.

(3) A suspension of the compound (300 mg) obtained in (2) above in chloroform (4.0 mL) was ice-cooled, pyridine (0.484 mL) and p-toluenesulfonyl chloride (0.457 g) were added thereto, and the reaction solution was stirred at room temperature for 18 hours. A saturated aqueous sodium bicarbonate solution was added to the reaction solution, which was then partitioned into two layers. The organic layer was filtered through Phase Separator and concentrated. The obtained residue was purified by silica gel column chromatography (n-hexane only to n-hexane:ethyl acetate=50:50) to afford tert-butyl(1-cyano-3,3-difluorocyclobutyl) carbamate (163 mg) as a colorless solid.

(4) Using the compound (490 mg) obtained in (3) above, the reaction and post treatment were carried out in accordance with the method described in Reference Example 4-9-1 (2), and the obtained residue was purified by silica gel column chromatography (chloroform only to chloroform:methanol=80:20) to afford tert-butyl[3,3-difluoro-1-(1H-tetrazol-5-yl)cyclobutyl]carbamate (1.02 g) as a colorless oily substance.

(5) A solution of the compound (1.02 g) obtained in (4) above in acetone (5.8 mL) was ice-cooled, potassium carbonate (0.478 g) and benzyl bromide (0.246 mL) were added thereto, and the reaction solution was stirred at room temperature for 18 hours. Insolubles in the reaction solution were filtered off, followed by concentration. The obtained residue was purified by silica gel column chromatography (n-hexane only to n-hexane:ethyl acetate=60:40) to afford a mixture (652 mg) of tert-butyl[1-(1-benzyl-1H-tetrazol-5-yl)-3,3-difluorocyclobutyl]carbamate and a regioisomer thereof as a colorless solid.

(6) To a solution of the compound (652 mg) obtained in (5) above in chloroform (3.6 mL), a 4 mol/L hydrogen chloride-1,4-dioxane solution (1.78 mL) was added, and the reaction solution was stirred at room temperature for 2 hours. The suspension was concentrated, chloroform was added thereto, and the precipitated solid was filtered off to afford the title compound (441 mg) as a colorless powder.

MS ESI posi: 266 [M+H]$^+$.

Retention time: 0.318 min (method B)

The following Reference Example 4-10-2 was synthesized by the method described in Reference Example 4-10-1 or by a method equivalent thereto, using a commercially available compound or a compound obtained by synthesis according to methods described in literatures or methods equivalent thereto. The structure and LCMS data of the compound are shown in Table 32-1.

TABLE 32-1

| Reference Example No. | Structural Formula | MS posi m/z MS mega m/z | Retention time (min) | method |
|---|---|---|---|---|
| 4-10-2 | 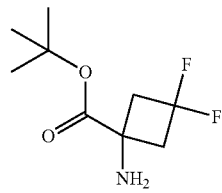 | 211 [M + H]+ | 0.223 | B |

Reference Example 4-11-1

Tert-Butyl 1-Amino-3,3-Difluorocyclobutane-1-Carboxylate

[Chemical Formula 469]

(1) A solution of 1-amino-3,3-difluorocyclobutane-1-carboxylic acid (1.00 g) and sodium carbonate (2.10 g) in water (22 mL) was ice-cooled, a solution of benzyl chloroformate (1.03 mL) in 1,4-dioxane (6.62 mL) was slowly added thereto, and the reaction solution was stirred for 12 hours while gradually raising the temperature to room temperature. The reaction solution was ice-cooled, benzyl chloroformate (0.47 mL) was added thereto, and the reaction solution was stirred at room temperature for 1 hour. By adding water and diethyl ether to the reaction solution, it was partitioned into two layers. The aqueous layer was ice-cooled, 1 mol/L hydrochloric acid was added thereto to set the pH to 1, and extraction with ethyl acetate was carried out. The organic layers were combined, and dried over anhydrous magnesium sulfate. After filtering off the desiccating agent, the filtrate was concentrated to afford a mixture (1.69 g) containing 1-{[(benzyloxy) carbonyl]amino}-3,3-difluorocyclobutane-1-carboxylic acid.

(2) The present reaction was carried out with reference to the method described in the literature (WO 2009/070485 A[1]). A solution of the mixture (1.69 g) obtained in (1) above, tert-butyl alcohol (675 µL), and 4-dimethylaminopyridine (362 mg) in chloroform (20 mL) was ice-cooled, EDC (1.25 g) was added thereto, and the reaction solution was stirred overnight while gradually raising the temperature to room temperature. Water was added to the reaction solution, which was then extracted with ethyl acetate. The organic layer was washed with a saturated aqueous sodium bicarbonate solution and a brine sequentially, and dried over anhydrous magnesium sulfate. After filtering off the desiccating agent, the filtrate was concentrated. The obtained residue was purified by silica gel column chromatography (n-hexane:ethyl acetate=95:5 to 60:40) to afford tert-butyl 1-{[(benzyloxy) carbonyl]amino}-3,3-difluorocyclobutane-1-carboxylate (708 mg) as a colorless powder.

(3) To a solution of the compound (200 mg) obtained in (2) above in methanol (1.5 mL), palladium carbon (20.0 mg) was added, and the reaction solution was stirred at room temperature for 1.5 hours under a hydrogen atmosphere. The reaction solution was filtered through KC FLOCK (registered trademark), and the filtrate was concentrated. Methanol was added to the obtained residue, insolubles were filtered off, and the filtrate was then concentrated to afford the title compound (92.0 mg) as a colorless oily substance. $^1$H NMR (600 MHZ, CHLOROFORM-d) δ ppm 1.50 (br s, 9H) 2.46-2.56 (m, 2H) 3.06-3.16 (m, 2H).

The following Reference Examples 4-11-2 to 4-11-3 were synthesized by the method described in Reference Example 4-11-1 or by a method equivalent thereto, using the compound obtained in Reference Example 4-3-3 (1), commercially available compounds, or compounds obtained by synthesis according to methods described in literatures or methods equivalent thereto. The structures, NMR data, and LCMS data of the compounds are shown in Table 32-2 to Table 32-3.

TABLE 32-2

| Reference Example No. | Structural Formula | Analytical data |
|---|---|---|
| 4-11-2 | | $^1$H NMR (400 MHz, DMSO-d) δ ppm 1.47-1.54 (m, 3H), 1.98 (s, 3H) 3.79 (s, 5 H) 4.28-4.36 (m, 1H) 6.82 (s, 2 H) 8.38 (br s, 3H) |

TABLE 32-3

| Reference Example No. | Structural Formula | MS posi m/z MS nega m/z | Retention time (min) | method |
|---|---|---|---|---|
| 4-11-3 | | 216 [M + H]+ | 0.623 | F |

Example 1-1

N-{[(1R)-1-(4-Acetyl-3,5-Diethoxyphenyl)Ethyl](4-Phenylbutyl) Carbamoyl}-2-Methylalanine

[Chemical Formula 470]

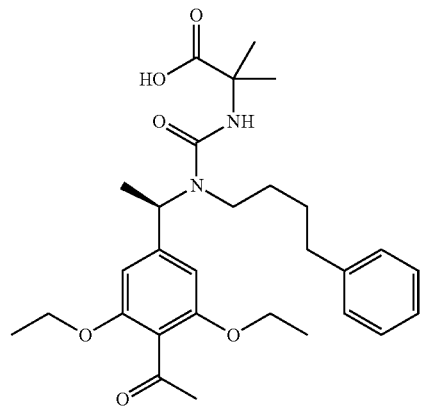

(1) To a solution of ethyl 2-methylalaninate hydrochloride (13.0 mg) in tetrahydrofuran (0.5 mL), N,N-diisopropylethylamine (72.6 µL) was added, and the reaction solution was stirred at room temperature for 5 minutes. The reaction solution was ice-cooled, a solution of 4-nitrophenyl chloroformate (15.6 mg) in tetrahydrofuran (0.5 mL) was added thereto, and the reaction solution was stirred at room temperature for 30 minutes. The compound (25 mg) obtained in Reference Example 3-4-1 was added thereto, and the reaction solution was stirred at 60° C. for 2 hours.

(2) A 1 mol/L aqueous sodium hydroxide solution (595 µL) and methanol (1 mL) were added to the reaction solution of (1) above, which was then stirred at 60° C. for 1 hour. The reaction solution was concentrated, and the obtained residue was purified by preparative HPLC and freeze-dried to afford the title compound (26.2 mg) as a colorless powder.

¹H NMR (400 MHZ, METHANOL-d₄) δ ppm 1.29-1.37 (m, 6H) 1.40-1.55 (m, 13H) 2.41 (s, 3H) 2.46-2.60 (m, 2H) 2.86-3.02 (m, 1H) 3.04-3.18 (m, 1H) 3.96-4.11 (m, 4H) 5.34-5.42 (m, 1H) 6.57 (s, 2H) 7.08-7.16 (m, 3H) 7.16-7.28 (m, 2H).

MS ESI/APCI Multi posi: 513 [M+H]⁺.

MS ESI/APCI Multi nega: 511 [M−H]⁻.

Retention time: 0.816 min (method D)

The following Examples 1-2 to 1-15 were synthesized by the method described in Example 1-1 or by a method equivalent thereto, using the compounds obtained in Reference Examples 3-1-1 to 3-1-2 and Reference Example 3-4-4, commercially available compounds, or compounds obtained by synthesis according to methods described in literatures or methods equivalent thereto. The structures and LCMS data of the compounds are shown in Table 33-1 to Table 33-3.

TABLE 33-1

| Example No. | Structural Formula | MS posi m/z MS nega m/z | Retention time (min) | method |
| --- | --- | --- | --- | --- |
| 1-2 |  | 441 [M + H]+ 463 [M + H]+ 411 [M + H]+ | 0.960 | A |
| 1-3 |  | 471 [M + H]+ 498 [M + H]+ 469 [M + H]+ | 1.066 | A |
| 1-4 |  | 513 [M + H]+ 511 [M + H]+ | 1.062 | D |

TABLE 33-1-continued
| Example No. | Structural Formula | MS posi m/z MS nega m/z | Retention time (min) | method |
|---|---|---|---|---|
| 1-5 | 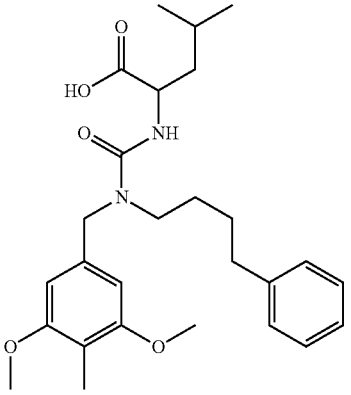 [SMILES: COc1cc(CN(CCCCc2ccccc2)C(=O)NC(CC(C)C)C(=O)O)cc(OC)c1C] | 471 [M + H]+ 493 [M + H]+ 469 [M + H]+ | 1.025 | A |
| 1-6 | 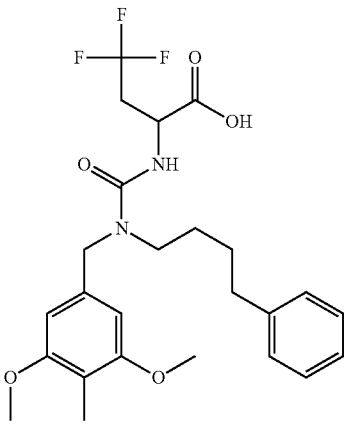 [SMILES: COc1cc(CN(CCCCc2ccccc2)C(=O)NC(CC(F)(F)F)C(=O)O)cc(OC)c1C] | 497 [M + H]+ 519 [M + H]+ 495 [M + H]+ | 1.011 | A |
TABLE 33-2
| Example No. | Structural Formula | MS posi m/z MS nega m/z | Retention time (min) | method |
|---|---|---|---|---|
| 1-7 | 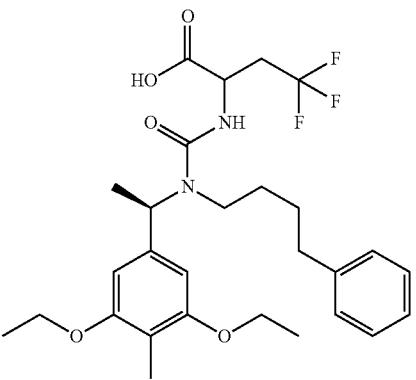 | 529 [M + H]+ 557 [M + H]+ | 1.013 | D |

TABLE 33-2-continued

| Example No. | Structural Formula | MS posi m/z MS nega m/z | Retention time (min) | method |
|---|---|---|---|---|
| 1-8 | | 547 [M + H]+ 546 [M + H]+ | 1.056 | D |
| 1-9 | | 561 [M + H]+ 579 [M + H]+ | 1.195 | D |
| 1-10 | | 548 [M + H]+ 516 [M + H]+ | 0.973 | D |

TABLE 33-2-continued

| Example No. | Structural Formula | MS posi m/z MS nega m/z | Retention time (min) | method |
|---|---|---|---|---|
| 1-11 | | 381 [M + H]+ 499 [M + H]+ | 0.877 | D |

TABLE 33-3

| Example No. | Structural Formula | MS posi m/z MS nega/m/z | Retention time (min) | method |
|---|---|---|---|---|
| 1-12 | | 515 [M + H]+ 513 [M + H]+ | 0.893 | D |
| 1-13 | | 485 [M + H]+ 483 [M + H]+ | 1.001 | D |

TABLE 33-3-continued

| Example No. | Structural Formula | MS posi m/z MS nega/m/z | Retention time (min) | method |
|---|---|---|---|---|
| 1-14 | | 471 [M + H]+ 469 [M + H]+ | 0.926 | D |
| 1-15 | | 484 [M + H]+ 483 [M + H]+ | 0.898 | D |

Example 1-16

1-({[(1R)-1-(4-Acetyl-3,5-Diethoxyphenyl)Ethyl](4-Phenylbutyl) Carbamoyl}Amino)Cyclopropane-1-Carboxylic Acid

[Chemical Formula 471]

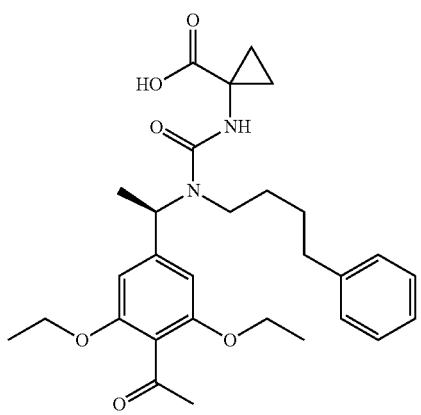

Using ethyl 1-aminocyclopropane-1-carboxylate hydrochloride (17.8 mg) and the compound (30 mg) obtained in Reference Example 3-4-1, the reaction was carried out in accordance with the method described in Example 1-1, and the title compound (32 mg) was obtained as a colorless powder.

$^1$H NMR (400 MHZ, METHANOL-$d_4$) δ ppm 1.01-1.10 (m, 2H) 1.26-1.39 (m, 6H) 1.39-1.57 (m, 9H) 2.41 (s, 3H) 2.47-2.56 (m, 2H) 2.83-2.92 (m, 1H) 3.03-3.14 (m, 1H) 3.99-4.10 (m, 4H) 5.43-5.50 (m, 1H) 6.60 (s, 2H) 7.08-7.16 (m, 3H) 7.17-7.26 (m, 2H).

MS ESI posi: 511 [M+H]$^+$, 533 [M+Na]$^+$.

MS ESI nega: 509 [M−H]$^−$.

Retention time: 0.841 min (method A)

The following Examples 1-17 to 1-20 were synthesized by the method described in Example 1-1 or by a method equivalent thereto, using the compounds obtained in Reference Examples 3-4-1 to 3-4-5, commercially available compounds, or compounds obtained by synthesis according to methods described in literatures or methods equivalent thereto. The structures and LCMS data of the compounds are shown in Table 34-1.

TABLE 34-1

| Example No. | Structural Formula | MS posi m/z MS nega m/z | Retention time (min) | method |
|---|---|---|---|---|
| 1-17 | | 483 [M + H]+<br>505 [M + H]+<br>481 [M + H]+ | 1.001 | A |
| 1-18 | | 509 [M + H]+<br>507 [M + H]+ | 1.249 | B |
| 1-19 | | 481 [M + H]+<br>479 [M + H]+ | 0.974 | B |

TABLE 34-1-continued

| Example No. | Structural Formula | MS posi m/z MS nega m/z | Retention time (min) | method |
|---|---|---|---|---|
| 1-20 | | 525 [M + H]+<br>547 [M + H]+<br>522 [M + H]+ | 0.888 | A |

Example 1-21

Example 1-22

1-{[{(1R)-1-[3,5-Diethoxy-4-(1-Hydroxyethyl)Phenyl]Ethyl}(4-Phenylbutyl) Carbamoyl]Amino}Cyclobutane-1-Carboxylic Acid

[Chemical Formula 472]

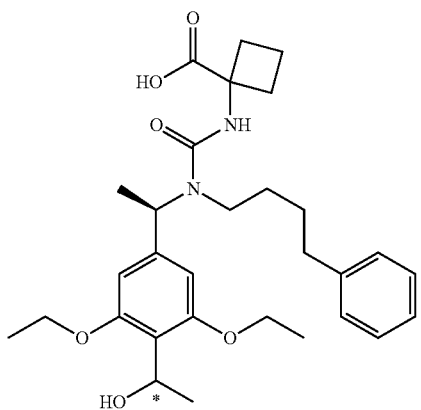

(1) To a solution of methyl 1-aminocyclobutane-1-carboxylate hydrochloride (32.9 mg) in tetrahydrofuran (0.5 mL), N,N-diisopropylethylamine (0.173 mL) was added, and the reaction solution was stirred at room temperature for 10 minutes. 4-Nitrophenyl chloroformate (40.1 mg) was added to the reaction solution, which was then stirred at room temperature for 1 hour. A solution of the compound (54.7 mg) obtained in Reference Example 3-9-1 in tetrahydrofuran (1.5 mL) was added to the reaction solution, which was then stirred at 60° C. for 2 hours and concentrated. The obtained residue was purified by NH silica gel column chromatography (n-hexane only to ethyl acetate only) to afford methyl 1-{[{(1R)-1-[3,5-diethoxy-4-(1-hydroxyethyl)phenyl]ethyl}(4-phenylbutyl) carbamoyl]amino}cyclobutane-1-carboxylate (72.1 mg) as a colorless oily substance.

(2) The compound (72.1 mg) obtained in (1) above was separated into optical isomers using preparative HPLC equipped with a chiral column. The isomer with a shorter retention time (Example 1-21 (2)) (35.5 mg) was obtained as a colorless oily substance, and the isomer with a longer retention time (Example 1-22 (2)) (39.7 mg) was obtained as a colorless oily substance.

(3) To a solution of Example 1-21 (2) (35.5 mg) obtained in (2) above in methanol (1 mL), a 1 mol/L aqueous sodium hydroxide solution (0.5 mL) was added, and the reaction solution was stirred at 60° C. for 2 hours. The reaction solution was purified by preparative HPLC and freeze-dried to afford one optical isomer of the title compound (Example 1-21) (19.3 mg) as a colorless amorphous.

$^1$H NMR (600 MHZ, METHANOL-$d_4$) δ ppm 1.32-1.56 (m, 16H) 1.88-2.06 (m, 2H) 2.18-2.28 (m, 2H) 2.45-2.54 (m, 2H) 2.55-2.66 (m, 2H) 2.84-2.94 (m, 1H) 3.07-3.16 (m, 1H) 4.01-4.12 (m, 4H) 4.57 (br s, 1H) 5.27-5.35 (m, 1H) 5.35-5.43 (m, 1H) 6.57 (s, 2H) 7.06-7.17 (m, 3H) 7.17-7.27 (m, 2H).

MS ESI posi: 509 [M−OH]+, 549 [M+Na]+.
MS ESI nega: 525 [M−H]−.
Retention time: 0.936 min (method A)

(4) Using Example 1-22 (2) (39.7 mg) obtained in (2) above, the reaction was carried out in accordance with the method described in (3) above, and the other optical isomer of the title compound (Example 1-22) (18.9 mg) was obtained as a colorless amorphous.

$^1$H NMR (600 MHZ, METHANOL-$d_4$) δ ppm 1.30-1.55 (m, 16H) 1.87-2.08 (m, 2H) 2.18-2.30 (m, 2H) 2.43-2.54 (m, 2H) 2.54-2.65 (m, 2H) 2.85-2.95 (m, 1H) 3.05-3.15 (m, 1H) 3.94-4.18 (m, 4H) 4.57 (br s, 1H) 5.27-5.35 (m, 1H) 5.35-5.42 (m, 1H) 6.57 (s, 2H) 7.07-7.15 (m, 3H) 7.18-7.26 (m, 2H).

MS ESI posi: 509 [M−OH]+, 549 [M+Na]+.
MS ESI nega: 525 [M−H]−.
Retention time: 0.931 min (method A)

The following Examples 1-23 to 1-29 were synthesized by the method described in Example 1-1 or by a method equivalent thereto, using the compounds obtained in Reference Examples 3-1-3 to 3-1-6 and Reference Examples 3-4-3 to 3-4-5, commercially available compounds, or compounds obtained by synthesis according to methods described in literatures or methods equivalent thereto. The structures and LCMS data of the compounds are shown in Table 35-1 to Table 35-2.

TABLE 35-1

| Example No. | Structural Formula | MS posi m/z MS nega m/z | Retention time (min) | method |
|---|---|---|---|---|
| 1-23 | | 469 [M + H]+ 467 [M + H]+ | 0.959 | D |
| 1-24 | | 497 [M + H]+ 493 [M + H]+ | 1.013 | D |
| 1-25 | | 559 [M + H]+ | 1.099 | A |
| 1-26 | | 528 [M + H]+ 531 [M + H]+ | 1.027 | E |

TABLE 35-1-continued

| Example No. | Structural Formula | MS posi m/z MS nega m/z | Retention time (min) | method |
|---|---|---|---|---|
| 1-27 | | 583 [M + H]+<br>581 [M + H]+ | 1.084 | B |

TABLE 35-2

| Example No. | Structural Formula | MS posi m/z MS nega m/z | Retention time (min) | method |
|---|---|---|---|---|
| 1-28 | | 455 [M + H]+<br>453 [M + H]+ | 1.071 | E |
| 1-29 | | 561 [M + H]+<br>587 [M + Na]+<br>559 [M + H]+ | 1.234 | B |

Example 1-30

1-({[(1R)-1-(4-Acetyl-3,5-Diethoxyphenyl)Ethyl](4-Phenylbutyl) Carbamoyl}Amino)-3,3-Difluorocyclobutane-1-Carboxylic Acid

[Chemical Formula 473]

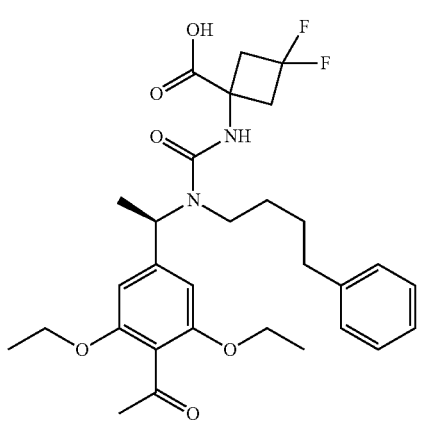

(1) Using methyl 1-amino-3,3-difluorocyclobutane-1-carboxylate hydrochloride (328 mg) and the compound (mixture containing 624 mg as the theoretical amount) obtained in Reference Example 3-1-6, the reaction was carried out in accordance with the method described in Example 1-21 (1), and methyl 1-({[1-(4-acetyl-3,5-diethoxyphenyl)ethyl](4-phenylbutyl) carbamoyl}amino)-3,3-difluorocyclobutane-1-carboxylate (443 mg) was obtained as a colorless amorphous.

(2) The compound (443 mg) obtained in (1) above was separated into optical isomers using preparative HPLC equipped with a chiral column. The isomer with a shorter retention time (Example 1-30 (2)-1) (180 mg) was obtained as a colorless amorphous, and the isomer with a longer retention time (Example 1-30 (2)-2) (181 mg) was obtained as a colorless amorphous.

(3) To a mixed solution of Example 1-30 (2)-1 (180 mg) obtained in (2) above in methanol-tetrahydrofuran (3 mL-3 mL), a 1 mol/L aqueous sodium hydroxide solution (3 mL) was added, and the reaction solution was stirred at room temperature for 2 hours. The reaction solution was concentrated, and the obtained residue was purified by silica gel column chromatography (n-hexane:ethyl acetate=50:50 to ethyl acetate only, and then chloroform only to chloroform:methanol=80:20) to afford the title compound (154 mg) as a colorless amorphous.

$^1$H NMR (400 MHz, DMSO-$d_6$) δ ppm 1.21-1.29 (m, 6H) 1.35-1.52 (m, 7H) 2.33 (s, 3H) 2.65-3.24 (m, 8H) 3.94-4.09 (m, 4H) 5.26-5.36 (m, 1H) 6.52 (s, 2H) 7.09-7.20 (m, 3H) 7.21-7.30 (m, 2H) 12.68 (br s, 1H).

MS ESI posi: 561 [M+H]$^+$, 583 [M+Na]$^+$.

MS ESI nega: 559 [M−H]$^-$.

Retention time: 1.233 min (method B)

Example 1-31

1-({[(1S)-1-(4-Acetyl-3,5-Diethoxyphenyl)Ethyl](4-Phenylbutyl) Carbamoyl}Amino)-3,3-Difluorocyclobutane-1-Carboxylic Acid

[Chemical Formula 474]

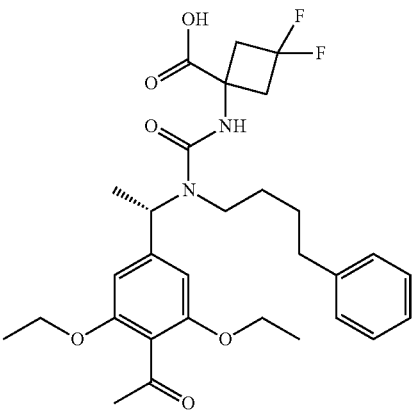

Using the compound (181 mg) obtained in Example 1-30 (2)-2, the reaction was carried out in accordance with the method described in Example 1-30 (3), and the title compound (154 mg) was obtained as a colorless amorphous.

$^1$H NMR (400 MHZ, DMSO-$d_6$) δ ppm 1.20-1.29 (m, 6H) 1.40-1.48 (m, 7H) 2.33 (s, 3H) 2.64-3.22 (m, 8H) 3.94-4.08 (m, 4H) 5.27-5.37 (m, 1H) 6.52 (s, 2H) 7.07-7.18 (m, 3H) 7.19-7.28 (m, 2H) 12.70 (br s, 1H).

MS ESI posi: 561 [M+H]$^+$, 583 [M+Na]$^+$.

MS ESI nega: 559 [M−H]$^-$.

Retention time: 1.228 min (method B)

The following Examples 1-32 to 1-39 were synthesized by the method described in Example 1-1 or Example 1-21, or by a method equivalent thereto, using the compounds obtained in Reference Examples 3-1-7 to 3-1-10, Reference Example 3-2-2, Reference Example 3-3-1, and Reference Example 3-9-1, commercially available compounds, or compounds obtained by synthesis according to methods described in literatures or methods equivalent thereto. The structures and LCMS data of the compounds are shown in Tables 36-1 to 36-2. Note that Example 1-35 (isomer with a shorter retention time) and Example 1-36 (isomer with a longer retention time) are optically active compounds.

TABLE 36-1

| Example No. | Structural Formula | MS posi m/z MS nega m/z | Retention time (min) | method |
|---|---|---|---|---|
| 1-32 | | 599 [M + Na]+ 559 [M + OH]+ 575 [M + H]+ | 0.921 | A |
| 1-33 | | 599 [M + Na]+ 559 [M + OH]+ 575 [M + H]+ | 0.923 | A |
| 1-34 | | 585 [M + Na]+ 545 [M + OH]+ 561 [M + H]+ | 0.946 | A |

TABLE 36-1-continued

| Example No. | Structural Formula | MS posi m/z MS nega m/z | Retention time (min) | method |
|---|---|---|---|---|
| 1-35 | | 585 [M + Na]+ 545 [M + OH]+ 561 [M + H]+ | 1.006 | A |
| 1-36 | | 585 [M + Na]+ 545 [M + OH]+ 561 [M + H]+ | 0.996 | A |

TABLE 36-2

| Example No. | Structural Formula | MS posi m/z MS nega m/z | Retention time (min) | method |
|---|---|---|---|---|
| 1-37 | | 597 [M + Na]+ 557 [M + OH]+ 575 [M + H]+ | 1.236 | B |

TABLE 36-2-continued

| Example No. | Structural Formula | MS posi m/z MS nega m/z | Retention time (min) | method |
|---|---|---|---|---|
| 1-38 | | 557 [M + OH]+<br>573 [M + H]+ | 1.125 | F |
| 1-39 | | 563 [M + H]+<br>585 [M + Na]+<br>561 [M + H]+ | | B |

Example 1-40

1-({[1-(4-Carbamoyl-3,5-Diethoxyphenyl)Ethyl](4-Phenylbutyl) Carbamoyl}Amino)-3,3-Difluorocyclobutane-1-Carboxylic Acid

[Chemical Formula 475]

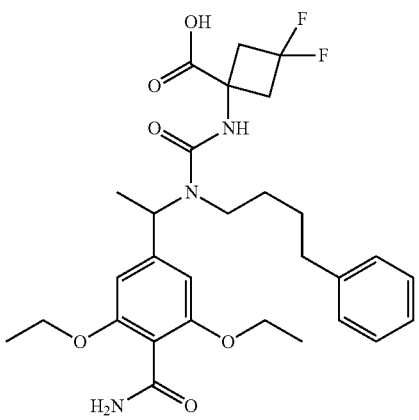

(1) To a solution of the compound (34.8 mg) obtained in Reference Example 1-12-1 in chloroform (1 mL), 4-phenylbutylamine (19.6 mg) and acetic acid (1.58 µL) were added, and the reaction solution was stirred at 60° C. for 2 hours. The reaction solution was ice-cooled, sodium triacetoxyborohydride (44.0 mg) was added thereto, and the reaction solution was stirred at 60° C. for 1 hour. The reaction solution was ice-cooled, a saturated aqueous sodium bicarbonate solution was added thereto, and extraction with chloroform was carried out. The organic layer was filtered through Phase Separator and concentrated to afford a mixture containing 2,6-diethoxy-4-{1-[(4-phenylbutyl)amino]ethyl}benzamide as a colorless oily substance.

(2) To a solution of methyl 1-amino-3,3-difluorocyclobutane-1-carboxylate hydrochloride (27.9 mg) in tetrahydrofuran (0.5 mL), N,N-diisopropylethylamine (121 µL) was added, and the reaction solution was stirred at room temperature for 10 minutes. The reaction solution was ice-cooled, 4-nitrophenyl chloroformate (27.9 mg) was added thereto, and the reaction solution was stirred at room temperature for 1 hour. The reaction solution was ice-cooled, a solution of the mixture obtained in (1) above in tetrahydrofuran (1.5 mL) was added thereto, and the reaction solution was stirred at 60° C. for 4 hours and at room temperature overnight.

(3) Methanol (1.4 mL) and a 1 mol/L aqueous sodium hydroxide solution (1.4 mL) were added to the reaction solution, which was then stirred at 60° C. for 2.5 hours. The reaction solution was concentrated, and the obtained residue was purified by preparative HPLC and freeze-dried to afford the title compound (17.1 mg) as a colorless amorphous.

¹H NMR (400 MHZ, DMSO-d₆) δ ppm 1.21-1.28 (m, 6H) 1.36-1.59 (m, 7H) 2.71-3.21 (m, 8H) 3.93-4.02 (m, 4H) 5.28-5.36 (m, 1H) 6.49 (s, 2H) 7.13-7.30 (m, 5H) 8.33 (s, 1H) 8.78 (s, 1H).
MS ESI posi: 562 [M+H]⁺, 584 [M+Na]⁺.
MS ESI nega: 560 [M−H]⁻.
Retention time: 0.976 min (method B)

The following Examples 1-41 to 1-45 were synthesized by the method described in Example 1-1 or Example 1-30, or by a method equivalent thereto, using the compounds obtained in Reference Example 3-1-2 and Reference Examples 3-1-11 to 3-1-12, commercially available compounds, or compounds obtained by synthesis according to methods described in literatures or methods equivalent thereto. The structures and LCMS data of the compounds are shown in Table 37-1. Note that Example 1-44 (isomer with a shorter retention time) and Example 1-45 (isomer with a longer retention time) are optically active compounds.

TABLE 37-1

| Example No. | Structural Formula | MS posi m/z MS nega m/z | Retention time (min) | method |
|---|---|---|---|---|
| 1-41 | | 544 [M + H]+ 542 [M + H]+ | 1.150 | E |
| 1-42 | | 597 [M + H]+ 595 [M + H]+ | 1.268 | E |
| 1-43 | | 574 [M + H]+ 581 [M + H]+ | 1.076 | D |

TABLE 37-1-continued

| Example No. | Structural Formula | MS posi m/z MS nega m/z | Retention time (min) | method |
|---|---|---|---|---|
| 1-44 | | 573 [M + H]+ 581 [M + H]+ | 1.057 | D |
| 1-45 | | 558 [M + H]+ 581 [M + H]+ | 1.057 | D |

Example 1-46

Sodium 1-({[(1R)-1-(4-Cyclopropyl-3,5-Diethoxyphenyl)Ethyl](4-Phenylbutyl) Carbamoyl}Amino)-3,3-Difluorocyclobutane-1-Carboxylate

[Chemical Formula 476]

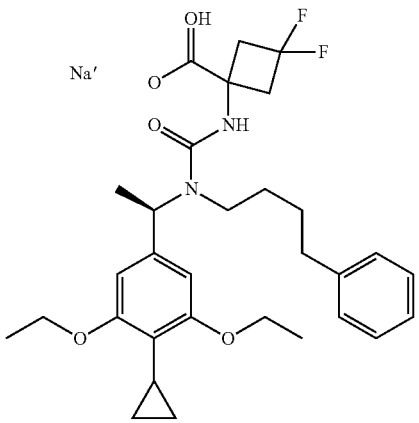 [SMILES: CCOc1cc(C(C)N(CCCCc2ccccc2)C(=O)NC2(C(=O)O)CC(F)(F)C2)cc(OCC)c1C1CC1]

(1) Using methyl 1-amino-3,3-difluorocyclobutane-1-carboxylate hydrochloride (72.0 mg) and the compound (mixture containing 136 mg as the theoretical amount) obtained in Reference Example 3-4-3, the reaction was carried out in accordance with the method described in Example 1-21 (1), and methyl 1-({[(1R)-1-(4-cyclopropyl-3,5-diethoxyphenyl)ethyl](4-phenylbutyl) carbamoyl}amino)-3,3-difluorocyclobutane-1-carboxylate (124 mg) was obtained as a colorless oily substance.

(2) To a mixed solution of the compound (124 mg) obtained in (1) above in methanol-tetrahydrofuran (2.2 mL-2.2 mL), a 1 mol/L aqueous sodium hydroxide solution (2.2 mL) was added, and the reaction solution was stirred at room temperature for 2 hours and concentrated. The obtained residue was purified by silica gel column chromatography (n-hexane:ethyl acetate=70:30 to ethyl acetate only, and then chloroform only to chloroform:methanol=80:20) and preparative HPLC to afford 1-({[(1R)-1-(4-cyclopropyl-3,5-diethoxyphenyl)ethyl](4-phenylbutyl) carbamoyl}amino)-3,3-difluorocyclobutane-1-carboxylic acid (74.9 mg) as a colorless amorphous.

(3) To a solution of the compound (74.9 mg) obtained in (2) above in tetrahydrofuran (536 μL), a 0.1 mol/L aqueous sodium hydroxide solution (1.34 mL) was added, and the reaction solution was stirred at room temperature for 30 minutes. The reaction solution was concentrated and freeze-dried to afford the title compound (77.4 mg) as a colorless amorphous.

$^1$H NMR (600 MHz, DMSO-$d_6$) δ ppm 0.65-0.73 (m, 2H) 0.97-1.06 (m, 2H) 1.26-1.31 (m, 6H) 1.34-1.46 (m, 7H) 1.84-1.93 (m, 1H) 2.44-2.49 (m, 2H) 2.77-3.19 (m, 6H) 3.88-3.98 (m, 4H) 5.25-5.37 (m, 1H) 6.43 (s, 2H) 6.90 (s, 1H) 7.09-7.16 (m, 3H) 7.20-7.28 (m, 2H).

MS ESI posi: 559 [M+H]$^+$, 581 [M+Na]$^+$.
MS ESI nega: 557 [M−H]$^−$.
Retention time: 1.087 min (method A)

The following Examples 1-47 to 1-49 were synthesized by the method described in Example 1-1 or Example 1-46, or by a method equivalent thereto, using the compounds obtained in Reference Example 3-1-13, Reference Example 3-3-2, and Reference Example 3-4-6, commercially available compounds, or compounds obtained by synthesis according to methods described in literatures or methods equivalent thereto. The structures and LCMS data of the compounds are shown in Table 38-1.

TABLE 38-1

| Example No. | Structural Formula | MS posi m/z MS nega m/z | Retention time (min) | method |
|---|---|---|---|---|
| 1-47 | 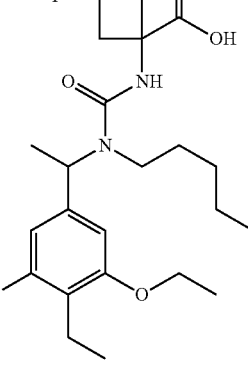 | 547 [M + H]+ 469 [M + Na]+ 545 [M + H]+ | 1.368 | B |
| 1-48 | 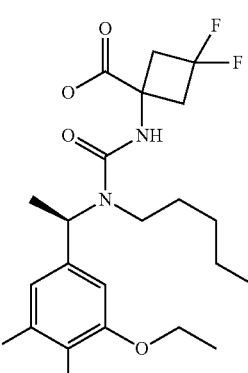 | 547 [M + H]+ 545 [M + H]+ | 1.080 | D |
| 1-49 | 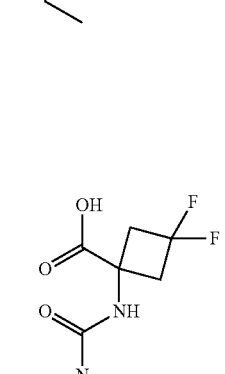 | 561 [M + H]+ 583 [M + Na]+ 559 [M + H]+ | 1.062 | A |

Example 1-50

1-{[{1-[3,5-Diethoxy-4-(Hydroxymethyl)Phenyl]Ethyl}(4-Phenylbutyl) Carbamoyl]Amino}-3,3-Difluorocyclobutane-1-Carboxylic Acid

[Chemical Formula 477]

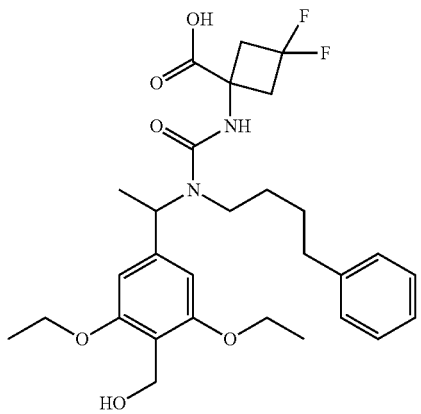 [SMILES: CCOc1cc(C(C)N(CCCCc2ccccc2)C(=O)NC2(C(=O)O)CC(F)(F)C2)cc(OCC)c1C(F)F]

(1) Using methyl 1-amino-3,3-difluorocyclobutane-1-carboxylate hydrochloride (28.7 mg) and the compound (mixture containing 45.3 mg as the theoretical amount) obtained in Reference Example 3-1-14, the reaction was carried out in accordance with the method described in Example 1-21 (1), and methyl 1-{[(1-{4-[(acetoxy)methyl]-3,5-diethoxyphenyl}ethyl) (4-phenylbutyl) carbamoyl]amino}-3,3-difluorocyclobutane-1-carboxylate (63.3 mg) was obtained as a colorless oily substance.

(2) To a solution of the compound (63.3 mg) obtained in (1) above in methanol-tetrahydrofuran (1 mL-1 mL), a 1 mol/L aqueous sodium hydroxide solution (1 mL) was added, and the reaction solution was stirred at room temperature for 1 hour. The reaction solution was ice-cooled, acetic acid (35.9 μL) was added thereto, and extraction with chloroform was carried out three times. The organic layer was filtered through Phase Separator and concentrated. The obtained residue was purified by preparative HPLC and freeze-dried to afford the title compound (17.3 mg) as a colorless amorphous.

$^1$H NMR (600 MHZ, METHANOL-$d_4$) δ ppm 1.34-1.43 (m, 6H) 1.43-1.52 (m, 7H) 2.44-2.53 (m, 2H) 2.78-2.93 (m, 3H) 3.05-3.26 (m, 3H) 4.00-4.10 (m, 4H) 4.67 (s, 2H) 5.35-5.46 (m, 1H) 6.55 (s, 2H) 7.04-7.16 (m, 3H) 7.16-7.26 (m, 2H).

MS ESI posi: 531 [M−OH]$^+$.

Retention time: 0.838 min (method A)

The following Examples 1-51 to 1-61 were synthesized by the method described in Example 1-1 or Example 1-40, or by a method equivalent thereto, using the compounds obtained in Reference Example 1-11-3, Reference Example 2-1-1, Reference Example 3-1-10, Reference Examples 3-1-15 to 3-1-23, and Reference Example 3-9-1, commercially available compounds, or compounds obtained by synthesis according to methods described in literatures or methods equivalent thereto. The structures and LCMS data of the compounds are shown in Tables 39-1 to 39-3.

TABLE 39-1

| Example No. | Structural Formula | MS posi m/z MS nega m/z | Retention time (min) | method |
|---|---|---|---|---|
| 1-51 | | 569 [M + H]+<br>591 [M + Na]+<br>567 [M + H]+ | 1.299 | B |

TABLE 39-1-continued
| Example No. | Structural Formula | MS posi m/z MS nega m/z | Retention time (min) | method |
|---|---|---|---|---|
| 1-52 | 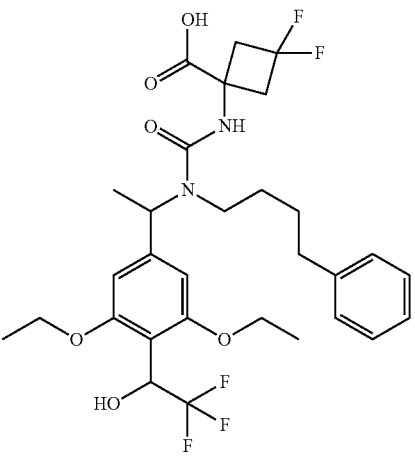 [SMILES: CCOc1cc(C(C)N(CCCCc2ccccc2)C(=O)NC2(C(=O)O)CC(F)(F)C2)cc(OCC)c1C(O)C(F)(F)F] | 617 [M + H]+<br>615 [M + H]+ | 0.937 | A |
| 1-53 | 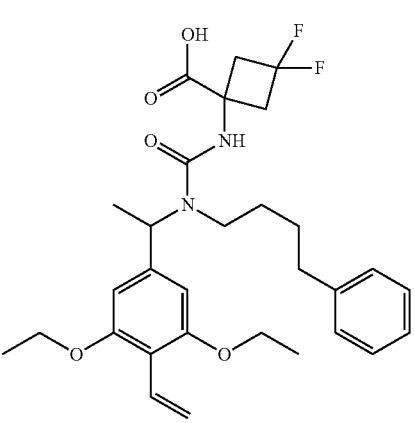 [SMILES: C=Cc1c(OCC)cc(C(C)N(CCCCc2ccccc2)C(=O)NC2(C(=O)O)CC(F)(F)C2)cc1OCC] | 545 [M + H]+<br>547 [M + Na]+<br>543 [M + H]+ | 1.065 | A |
| 1-54 | 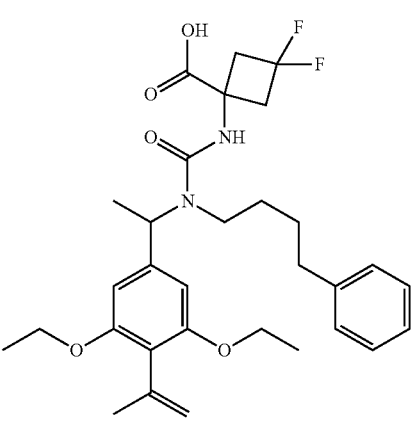 [SMILES: C=C(C)c1c(OCC)cc(C(C)N(CCCCc2ccccc2)C(=O)NC2(C(=O)O)CC(F)(F)C2)cc1OCC] | 559 [M + H]+<br>581 [M + Na]+<br>557 [M + H]+ | 1.012 | A |

TABLE 39-1-continued

| Example No. | Structural Formula | MS posi m/z MS nega m/z | Retention time (min) | method |
|---|---|---|---|---|
| 1-55 | | 568 [M + H]+<br>565 [M + Na]+<br>561 [M − H]+ | 1.281 | B |

TABLE 39-2

| Example No. | Structural Formula | MS posi m/z MS nega m/z | Retention time (min) | method |
|---|---|---|---|---|
| 1-56 | | 551 [M + H]+<br>570 [M + H]+ | 1.081 | B |
| 1-57 | | 597 [M + H]+<br>595 [M − H]+ | 1.039 | B |

TABLE 39-2-continued

| Example No. | Structural Formula | MS posi m/z MS nega m/z | Retention time (min) | method |
|---|---|---|---|---|
| 1-58 | | 576 [M + H]+<br>597 [M + Na]+<br>578 [M + H]+ | 0.922 | A |
| 1-59 | | 615 [M + H]+<br>612 [M + H]+ | 0.970 | A |
| 1-60 | | 577 [M + H]+<br>599 [M + Na]+<br>571 [M + H]+ | 1.182 | B |

TABLE 39-3

| Example No. | Structural Formula | MS posi m/z MS nega m/z | Retention time (min) | method |
|---|---|---|---|---|
| 1-61 | 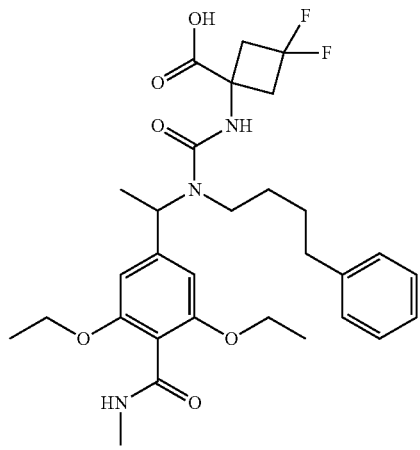 | 576 [M + H]+ 574 [M + H]+ | 1.012 | B |

Example 1-62

1-({[1-(4-Acetyl-3-Ethoxy-5-Hydroxyphenyl)Ethyl] (4-Phenylbutyl) Carbamoyl}Amino)-3,3-Difluorocyclobutane-1-Carboxylic Acid

[Chemical Formula 478]

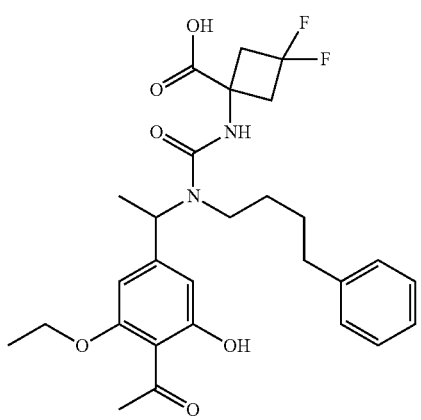 [SMILES: CCOc1cc(C(C)N(CCCCc2ccccc2)C(=O)NC2(C(=O)O)CC(F)(F)C2)cc(OCC)c1C(C)=O]

The present reaction was carried out with reference to the method described in the literature (US 2014-0148443). A solution of the compound (12.8 mg) obtained in Example 1-29 in chloroform (228 μL) was ice-cooled, boron tribromide (1 mol/L n-hexane solution, 114 μL) was added thereto, and the reaction solution was stirred at room temperature overnight. The reaction solution was ice-cooled, a saturated aqueous sodium bicarbonate solution (3 mL) was added thereto, and the reaction solution was stirred at the same temperature for 10 minutes. The reaction solution was concentrated, purified by preparative HPLC, and freeze-dried to afford the title compound (6.7 mg) as a colorless amorphous.

$^1$H NMR (600 MHz, DMSO-d$_6$) δ ppm 1.33-1.51 (m, 10H) 2.43-2.54 (m, 2H) 2.58 (s, 3H) 2.74-2.95 (m, 3H) 3.01-3.21 (m, 3H) 3.98-4.14 (m, 2H) 5.22-5.33 (m, 1H) 6.37 (s, 1H) 6.41 (s, 1H) 7.08-7.18 (m, 3H) 7.18-7.30 (m, 2H) 12.55 (s, 1H) 12.75 (br s, 1H).

MS ESI posi: 533 [M+H]$^+$, 555 [M+Na]$^+$.

MS ESI nega: 531 [M−H]$^-$.

Retention time: 1.201 min (method B)

The following Examples 1-63 to 1-76 were synthesized by the method described in Example 1-1 or Example 1-40, or by a method equivalent thereto, using the compounds obtained in Reference Example 1-5-16, Reference Example 1-5-30, Reference Example 2-1-1, Reference Example 3-1-3, Reference Example 3-1-5, Reference Examples 3-1-24 to 3-1-28, Reference Example 3-1-80, Reference Example 3-3-3, and Reference Example 3-4-5 to Reference Example 3-4-8, commercially available compounds, or compounds obtained by synthesis according to methods described in literatures or methods equivalent thereto. The structures and LCMS data of the compounds are shown in Tables 40-1 to 40-3.

TABLE 40-1

| Example No. | Structural Formula | MS posi m/z MS nega m/z | Retention time (min) | method |
|---|---|---|---|---|
| 1-63 | | 587 [M + H]+ 609 [M + Na]+ 565 [M + H]+ | 1.064 | A |
| 1-64 | | 525 [M + H]+ 523 [M + H]+ | 0.925 | A |
| 1-65 | | 569 [M + H]+ 567 [M + H]+ | 0.911 | D |

TABLE 40-1-continued

| Example No. | Structural Formula | MS posi m/z MS nega m/z | Retention time (min) | method |
|---|---|---|---|---|
| 1-66 | | 505 [M + H]+ 503 [M + H]+ | 0.950 | A |
| 1-67 | | 485 [M + H]+ 527 [M + Na]+ 508 [M + H]+ | 0.989 | A |

TABLE 40-2

| Example No. | Structural Formula | MS posi m/z MS nega m/z | Retention time (min) | method |
|---|---|---|---|---|
| 1-68 | | 539 [M + H]+ 541 [M + Na]+ 517 [M + H]+ | 1.020 | A |

TABLE 40-2-continued

| Example No. | Structural Formula | MS posi m/z MS nega m/z | Retention time (min) | method |
|---|---|---|---|---|
| 1-69 | | 547 [M + H]+ 569 [M + H]+ | 1.097 | A |
| 1-70 | | 581 [M + H]+ | 1.180 | A |
| 1-71 | | 525 [M + H]+ 557 [M + Na]+ 583 [M + H]+ | 0.875 | A |

TABLE 40-2-continued

| Example No. | Structural Formula | MS posi m/z<br>MS nega m/z | Retention time (min) | method |
|---|---|---|---|---|
| 1-72 | | 519 [M + OH]+<br>537 [M + H]+ | 0.842 | A |

TABLE 40-3

| Example No. | Structural Formula | MS posi m/z<br>MS nega m/z | Retention time (min) | method |
|---|---|---|---|---|
| 1-73 | | 557 [M + H]+<br>555 [M + H]+ | 1.085 | B |
| 1-74 | | 533 [M + H]+<br>555 [M + Na]+<br>531 [M + H]+ | 1.198 | A |

TABLE 40-3-continued

| Example No. | Structural Formula | MS posi m/z MS nega m/z | Retention time (min) | method |
|---|---|---|---|---|
| 1-75 | | 531 [M + H]+ 529 [M + H]+ | 1.075 | E |
| 1-76 | | 569 [M + H]+ 629 [M + OH]+ 545 [M + H]+ | 1.168 | D |

Example 1-77

1-{[{(1R)-1-[3-Ethoxy-4-(1-Hydroxyethyl)-2-Methylphenyl]Ethyl}(4-Phenylbutyl) Carbamoyl] Amino}-3,3-Difluorocyclobutane-1-Carboxylic Acid

[Chemical Formula 479]

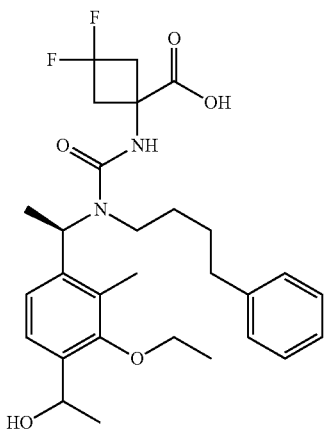

A solution of the compound (15 mg) obtained in Example 1-75 in methanol (0.3 mL) was ice-cooled, and sodium borohydride (9 mg) was added thereto. The reaction solution was stirred at the same temperature for 10 minutes, and sodium borohydride (5 mg) was further added thereto. Water was added to the reaction solution, which was then purified by preparative HPLC to afford the title compound (13 mg) as a colorless solid.

$^1$H NMR (400 MHZ, METHANOL-$d_4$) δ ppm 0.65-1.71 (m, 13H) 2.07-2.22 (m, 3H) 2.23-2.42 (m, 2H) 2.73-3.41 (m, 6H) 3.68-3.88 (m, 2H) 5.09-5.23 (m, 1H) 5.33-5.54 (m, 1H) 6.77-7.52 (m, 7H).

MS ESI posi: 515 [M−OH]$^+$, 555 [M+Na]$^+$.
MS ESI nega: 531 [M−H]$^-$.
Retention time: 1.102 to 1.113 min (method B)

Example 1-78

Example 1-79

1-{[{(1R)-1-[3-Ethoxy-4-(1-Hydroxyethyl)-2-Methylphenyl]Ethyl}(4-Phenylbutyl) Carbamoyl] Amino}-3,3-Difluorocyclobutane-1-Carboxylic Acid

[Chemical Formula 480]

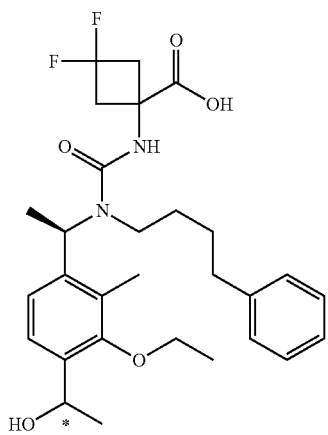 [SMILES: C=C(NC1(C(=O)O)CC(F)(F)C1)N(CCCCc1ccccc1)[C@H](C)c1ccc(C(C)(C)O)c(OCC)c1C]

The compound (9 mg) obtained in Example 1-77 was separated into optical isomers using preparative HPLC equipped with a chiral column. One optical isomer of the title compound with a shorter retention time (Example 1-78) (5.5 mg) was obtained as a colorless oily substance, and the other optical isomer of the title compound with a longer retention time (Example 1-79) (1.5 mg) was obtained as a colorless oily substance.

Example 1-78

$^1$H NMR (400 MHZ, METHANOL-$d_4$) δ ppm 0.66-1.55 (m, 13H) 2.18 (s, 3H) 2.23-2.33 (m, 2H) 2.81-3.03 (m, 4H) 3.08-3.43 (m, 2H) 3.69-3.87 (m, 2H) 5.13-5.21 (m, 1H) 5.42-5.52 (m, 1H) 6.98-7.04 (m, 2H) 7.07-7.13 (m, 1H) 7.15-7.27 (m, 3H) 7.35-7.40 (m, 1H).

MS ESI posi: 515 [M−OH]$^+$, 555 [M+Na]$^+$.

MS ESI nega: 531 [M−H]$^-$.

Retention time: 0.841 min (method A)

Example 1-79

$^1$H NMR (400 MHZ, METHANOL-$d_4$) δ ppm 0.92-1.54 (m, 13H) 2.17 (s, 3H) 2.31-2.42 (m, 2H) 2.78-3.37 (m, 6H) 3.69-3.80 (m, 2H) 5.11-5.20 (m, 1H) 5.35-5.49 (m, 1H) 7.01-7.07 (m, 2H) 7.07-7.14 (m, 1H) 7.16-7.25 (m, 3H) 7.36-7.43 (m, 1H).

MS ESI posi: 515 [M−OH]$^+$, 555 [M+Na]$^+$.

MS ESI nega: 531 [M−H]$^-$.

Retention time: 0.850 min (method A)

The following Examples 1-80 to 1-84 were synthesized by the method described in Example 1-1, Example 1-40, or Example 1-77, or by a method equivalent thereto, using the compounds obtained in Reference Example 3-1-29, Reference Example 3-2-3, Reference Example 3-4-1, and Reference Example 4-1-1, commercially available compounds, or compounds obtained by synthesis according to methods described in literatures or methods equivalent thereto. The structures and LCMS data of the compounds are shown in Table 41-1.

TABLE 41-1

| Example No. | Structural Formula | MS posi m/z MS nega m/z | Retention time (min) | method |
|---|---|---|---|---|
| 1-80 | | 517 [M + H]+ 515 [M + H]+ | 1.255 | E |

TABLE 41-1-continued
| Example No. | Structural Formula | MS posi m/z MS nega m/z | Retention time (min) | method |
|---|---|---|---|---|
| 1-81 | 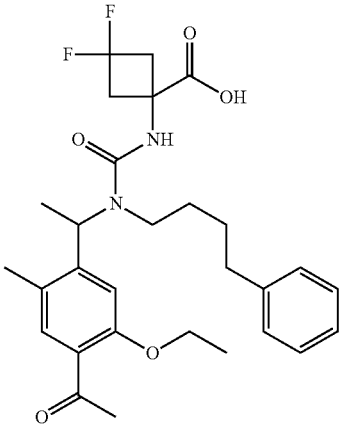 [SMILES: CCOc1cc(C(C)N(CCCCc2ccccc2)C(=O)NC2(C(=O)O)CC(F)(F)C2)c(C)cc1C(C)=O] | 531 [M + H]+ 529 [M + H]+ | 1.096 | E |
| 1-82 | 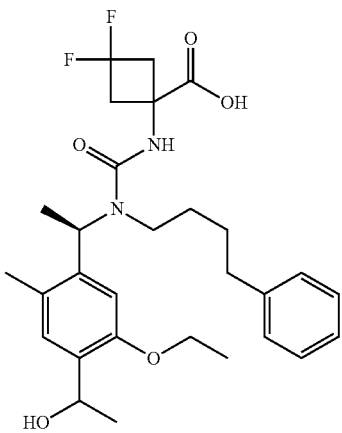 [SMILES: CCOc1cc([C@@H](C)N(CCCCc2ccccc2)C(=O)NC2(C(=O)O)CC(F)(F)C2)c(C)cc1C(C)O] | 515 [M + OH]+ 543 [M + Na]+ 551 [M + H]+ | 1.137- 1.152 | B |
| 1-83 | 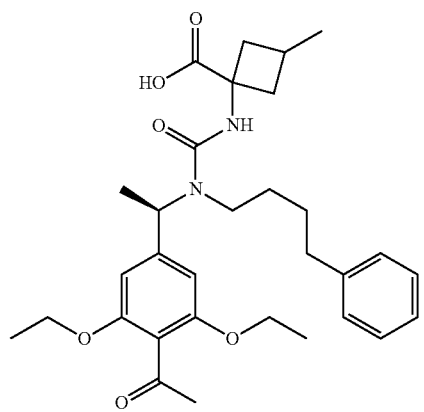 | 559 [M + H]+ 551 [M + Na]+ 527 [M + H]+ | 0.938 | A |

TABLE 41-1-continued

| Example No. | Structural Formula | MS posi m/z MS nega m/z | Retention time (min) | method |
|---|---|---|---|---|
| 1-84 | | 553 [M + H]+ 561 [M + H]+ | 0.959 | D |

Example 1-85

1-({[(1R)-1-(4-Acetyl-3,5-Diethoxyphenyl)Ethyl](4-Phenylbutyl) Carbamoyl}Amino)-3-Methoxycyclobutane-1-Carboxylic Acid

[Chemical Formula 481]

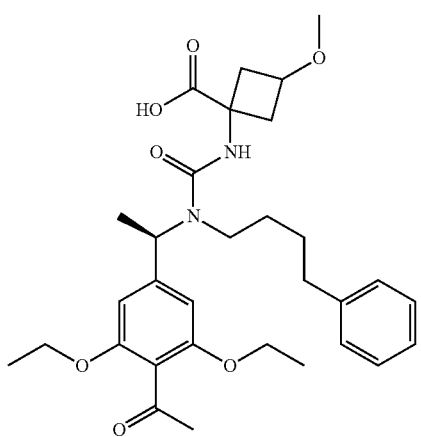

(1) Using the compound (64.9 mg) obtained in Reference Example 4-2-3 and the compound (100 mg) obtained in Reference Example 3-4-1, the reaction was carried out in accordance with the method described in Example 1-21 (1), and ethyl 1-({[(1R)-1-(4-acetyl-3,5-diethoxyphenyl)ethyl](4-phenylbutyl) carbamoyl}amino)-3-methoxycyclobutane-1-carboxylate (118 mg) was obtained as a colorless solid.

(2) Using the compound (mixture containing 27.8 mg as the theoretical amount) obtained in (1) above, the reaction was carried out in accordance with the method described in Example 1-30 (3), and the title compound (19.7 mg) was obtained as a colorless powder. $^1$H NMR (400 MHZ, METHANOL-$d_4$) δ ppm 1.28-1.55 (m, 13H) 2.14-3.66 (m, 14H) 3.84-3.97 (m, 1H) 3.97-4.12 (m, 4H) 5.37-5.45 (m, 1H) 6.58 (s, 2H) 7.08-7.17 (m, 3H) 7.17-7.28 (m, 2H).

MS ESI/APCI Multi posi: 555 [M+H]$^+$.
MS ESI/APCI Multi nega: 553 [M–H]$^-$.
Retention time: 0.812 min (method D)

Example 1-86

Trans-1-({[(1R)-1-(4-Acetyl-3,5-Diethoxyphenyl)Ethyl](4-Phenylbutyl) Carbamoyl}Amino)-3-Methoxycyclobutane-1-Carboxylic Acid

[Chemical Formula 482]

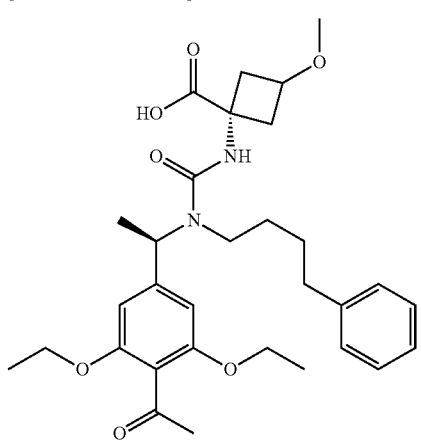 [SMILES: CCOc1cc([C@@H](C)N(CCCCc2ccccc2)C(=O)NC2(C(=O)O)CC(OCC)C2)cc(OCC)c1C(C)=O]

(1) The compound (170 mg) obtained in Example 1-85 (1) was separated into optical isomers using preparative HPLC equipped with a chiral column. The isomer with a shorter retention time (Example 1-86 (1)-1) (111 mg) was obtained as a colorless gum-like substance, and the isomer with a longer retention time (Example 1-86 (1)-2) (31 mg) was obtained as a light brown gum-like substance.

(2) To a solution of Example 1-86 (1)-1 (107 mg) obtained in (1) above in methanol (459 μL), tetrahydrofuran (459 μL) and a 4 mol/L aqueous sodium hydroxide solution (459 μL) were added, and the reaction solution was stirred at 60° C. for 1 hour. The reaction solution was concentrated, and the obtained residue was purified by silica gel column chromatography (chloroform:methanol=98:2 to 80:20) to afford the title compound (98 mg) as a colorless powder.

¹H NMR (400 MHZ, METHANOL-d₄) δ ppm 1.25-1.39 (m, 6H) 1.41-1.59 (m, 7H) 2.38-2.59 (m, 9H) 2.85-3.00 (m, 1H) 3.08-3.26 (m, 4H) 3.83-3.94 (m, 1H) 3.96-4.12 (m, 4H) 5.35-5.48 (m, 1H) 6.58 (s, 2H) 7.08-7.17 (m, 3H) 7.17-7.28 (m, 2H).

MS ESI posi: 555 [M+H]⁺.

MS ESI nega: 553 [M−H]⁻.

Retention time: 0.850 min (method A)

Example 1-87

Cis-1-({[(1R)-1-(4-Acetyl-3,5-Diethoxyphenyl)Ethyl](4-Phenylbutyl) Carbamoyl}Amino)-3-Methoxycyclobutane-1-Carboxylic Acid

[Chemical Formula 483]

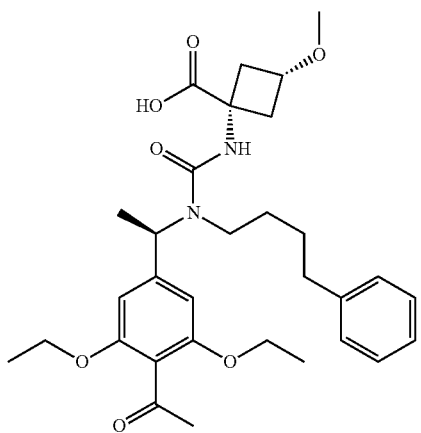

Using the compound (28 mg) obtained in Example 1-86 (1)-2, the reaction was carried out in accordance with the method described in Example 1-86 (2), and the title compound (26 mg) was obtained as a light brown powder.

¹H NMR (400 MHZ, METHANOL-d₄) δ ppm 1.26-1.38 (m, 6H) 1.42-1.56 (m, 7H) 2.12-2.28 (m, 2H) 2.41 (s, 3H) 2.46-2.58 (m, 2H) 2.81-3.01 (m, 3H) 3.04-3.17 (m, 1H) 3.25 (s, 3H) 3.96-4.11 (m, 5H) 5.34-5.45 (m, 1H) 6.58 (s, 2H) 7.08-7.16 (m, 3H) 7.17-7.26 (m, 2H).

MS ESI posi: 555 [M+H]⁺.

MS ESI nega: 553 [M−H]⁻.

Retention time: 0.842 min (method A)

The following Examples 1-88 to 1-122 were synthesized by the method described in Example 1-1, Example 1-21, Example 1-30, Example 1-40, Example 1-46, or Example 1-50, or by a method equivalent thereto, using the compounds obtained in Reference Examples 3-1-2 to 3-1-5, Reference Example 3-1-30, Reference Example 3-2-2, Reference Examples 3-4-1 to 3-4-8, Reference Example 3-9-1, Reference Examples 4-2-1 to 4-2-4, Reference Example 4-3-1 to Reference Example 4-3-2, Reference Examples 4-4-1 to 4-4-2, Reference Example 4-5-1, and Reference Examples 4-7-1 to 4-7-3, commercially available compounds, or compounds obtained by synthesis according to methods described in literatures or methods equivalent thereto. The structures and LCMS data of the compounds are shown in Tables 42-1 to 42-7. Note that Example 1-88 (isomer with a shorter retention time) and Example 1-89 (isomer with a longer retention time) are optically active compounds, and Example 1-98 (isomer with a shorter retention time) and Example 1-99 (isomer with a longer retention time) are optically active compounds. In addition, Example 1-117 is the optical isomer with a shorter retention time in preparative isolation by HPLC equipped with a chiral column.

TABLE 42-1

| Example No. | Structural Formula | MS posi m/z MS nega m/z | Retention time (min) | method |
|---|---|---|---|---|
| 1-88 | | 579 [M + Na]+ 529 [M + OH]+ 555 [M + H]+ | 0.893 | A |

TABLE 42-1-continued

| Example No. | Structural Formula | MS posi m/z MS nega m/z | Retention time (min) | method |
|---|---|---|---|---|
| 1-89 | | 579 [M + Na]+<br>529 [M + OH]+<br>555 [M + H]+ | 0.892 | A |
| 1-90 | | 551 [M + OH]+<br>567 [M + H]+ | 1.076 | E |
| 1-91 | | 527 [M + H]+<br>549 [M + Na]+<br>525 [M + H]+ | 0.980 | A |

TABLE 42-1-continued

| Example No. | Structural Formula | MS posi m/z MS nega m/z | Retention time (min) | method |
|---|---|---|---|---|
| 1-92 | | 552 [M + H]+ 551 [M + H]+ | 1.283 | E |

TABLE 42-2

| Example No. | Structural Formula | MS posi m/z MS nega m/z | Retention time (min) | method |
|---|---|---|---|---|
| 1-93 | | 525 [M + H]+ 547 [M + Na]+ 523 [M + H]+ | 0.866 | A |
| 1-94 | | 525 [M + H]+ 547 [M + Na]+ 523 [M + H]+ | 0.837 | A |

TABLE 42-2-continued

| Example No. | Structural Formula | MS posi m/z MS nega m/z | Retention time (min) | method |
|---|---|---|---|---|
| 1-95 | | 569 [M + H]+ 567 [M + H]+ | 0.838 | D |
| 1-96 | | 569 [M + H]+ 567 [M + H]+ | 0.880 | A |
| 1-97 | | 569 [M + H]+ 567 [M + H]+ | 0.874 | A |

TABLE 42-3

| Example No. | Structural Formula | MS posi m/z MS nega m/z | Retention time (min) | method |
|---|---|---|---|---|
| 1-98 | | 553 [M + OH]+ 569 [M + H]+ | 0.923 | A |
| 1-99 | | 593 [M + NA]+ 580 [M + OH]+ 569 [M + H]+ | 0.923 | A |
| 1-100 | | 541 [M + H]+ 589 [M + H]+ | 0.987 | A |

TABLE 42-3-continued

| Example No. | Structural Formula | MS posi m/z MS nega m/z | Retention time (min) | method |
|---|---|---|---|---|
| 1-101 | | 567 [M + H]+<br>585 [M + H]+ | 1.320 | E |
| 1-102 | | 539 [M + H]+<br>561 [M + Na]+<br>587 [M + H]+ | 0.987 | A |

TABLE 42-4

| Example No. | Structural Formula | MS posi m/z MS nega m/z | Retention time (min) | method |
|---|---|---|---|---|
| 1-103 | | 539 [M + H]+<br>527 [M + H]+ | 0.784 | D |

TABLE 42-4-continued

| Example No. | Structural Formula | MS posi m/z MS nega m/z | Retention time (min) | method |
|---|---|---|---|---|
| 1-104 | | 537 [M + OH]+ 552 [M + H]+ | 1.039 | E |
| 1-105 | | 558 [M + H]+ 552 [M + H]+ | 0.997 | D |
| 1-106 | | 512 [M + H]+ 511 [M + H]+ | 0.992 | A |

TABLE 42-4-continued

| Example No. | Structural Formula | MS posi m/z<br>MS nega m/z | Retention<br>time (min) | method |
|---|---|---|---|---|
| 1-107 | | 535 [M + H]+<br>538 [M + H]+ | 0.754 | D |

TABLE 42-5

| Example No. | Structural Formula | MS posi m/z<br>MS nega m/z | Retention<br>time (min) | method |
|---|---|---|---|---|
| 1-108 | | 566 [M + H]+<br>564 [M + H]+ | 0.841 | D |
| 1-109 | | 595 [M + H]+<br>593 [M + H]+ | 0.793 | B |

TABLE 42-5-continued

| Example No. | Structural Formula | MS posi m/z MS nega m/z | Retention time (min) | method |
|---|---|---|---|---|
| 1-110 | | 582 [M + H]+ 580 [M + H]+ | 0.890 | D |
| 1-111 | | 511 [M + H]+ 509 [M + H]+ | 0.972 | D |
| 1-112 | | 511 [M + H]+ | 1.423 | B |

TABLE 42-6

| Example No. | Structural Formula | MS posi m/z MS nega m/z | Retention time (min) | method |
|---|---|---|---|---|
| 1-113 | | 511 [M + H]+ | 1.474 | B |
| 1-114 | | 525 [M + H]+<br>523 [M + H]+ | 1.105 | B |
| 1-115 | | 547 [M + H]+ | 1.304 | B |
| 1-116 | | 483 [M + H]+ | 1.033 | B |

TABLE 42-6-continued

| Example No. | Structural Formula | MS posi m/z MS nega m/z | Retention time (min) | method |
|---|---|---|---|---|
| 1-117 | | 483 [M + H]+ | 1.017 | A |

TABLE 42-7

| Example No. | Structural Formula | MS posi m/z MS nega m/z | Retention time (min) | method |
|---|---|---|---|---|
| 1-118 | | 526 [M + H]+ 528 [M + H]+ | 1.069 | D |
| 1-119 | | 529 [M + H]+ 537 [M + H]+ | 1.108 | D |

TABLE 42-7-continued

| Example No. | Structural Formula | MS posi m/z MS nega m/z | Retention time (min) | method |
|---|---|---|---|---|
| 1-120 | | 569 [M + H]+ 567 [M + H]+ | 1.163 | B |
| 1-121 | | 537 [M + H]+ 535 [M + H]+ | 1.045 | D |
| 1-122 | | 559 [M + H]+ 557 [M + H]+ | 1.094 | D |

Example 1-123

2-({[(1R)-1-(3,5-Diethoxy-4-Methylphenyl)Ethyl](4-Phenylbutyl) Carbamoyl}Amino)-2,3-Dihydro-1H-Indene-2-Carboxylic Acid

[Chemical Formula 484]

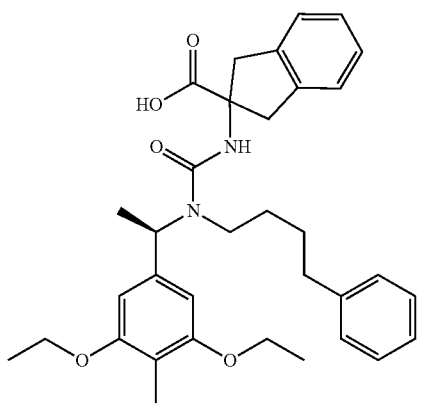

(1) Using methyl 2-amino-2,3-dihydro-1H-indene-2-carboxylate hydrochloride (80 mg) and the compound (150 mg) obtained in Reference Example 3-4-4, the reaction was carried out in accordance with the method described in Example 1-21 (1), and methyl 2-({[1-(3,5-diethoxy-4-methylphenyl)ethyl](4-phenylbutyl) carbamoyl}amino)-2,3-dihydro-1H-indene-2-carboxylate (128 mg) was obtained as a colorless gum-like substance.

(2) The compound (10 mg) obtained in (1) above was separated into optical isomers using preparative HPLC equipped with a chiral column. The isomer with a shorter retention time (Example 1-123 (2)-1) (4.0 mg) was obtained as a colorless oily substance, and the isomer with a longer retention time (Example 1-123 (2)-2) (4.2 mg) was obtained as a colorless oily substance.

(3) Using Example 1-123 (2)-1 (3.0 mg) obtained in (2) above, the reaction was carried out in accordance with the method described in Example 1-30 (3), and the title compound (1.8 mg) was obtained as a colorless gum-like substance. $^1$H NMR (400 MHZ, METHANOL-$d_4$) δ ppm 0.76-1.48 (m, 13H) 2.00 (s, 3H) 2.31-2.45 (m, 2H) 2.81-3.46 (m, 4H) 3.50-3.65 (m, 2H) 3.86-4.03 (m, 4H) 5.21-5.35 (m, 1H) 6.46 (s, 2H) 6.96-7.29 (m, 9H).

Example 1-124

2-({[(1S)-1-(3,5-Diethoxy-4-Methylphenyl)Ethyl](4-Phenylbutyl) Carbamoyl}Amino)-2,3-Dihydro-1H-Indene-2-Carboxylic Acid

[Chemical Formula 485]

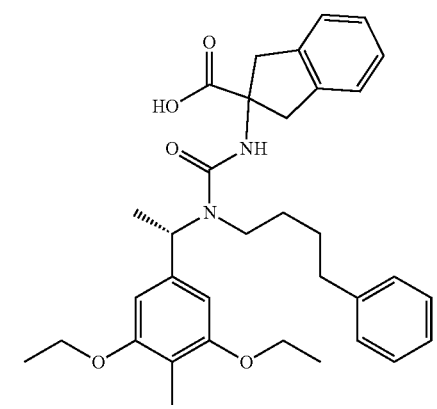

Using the compound obtained in Example 1-123 (2)-2 (4.2 mg), the reaction was carried out in accordance with the method described in Example 1-30 (3), and the title compound (3.5 mg) was obtained as a colorless gum-like substance.

$^1$H NMR (400 MHZ, METHANOL-$d_4$) δ ppm 1.08-1.50 (m, 13H) 1.99 (s, 3H) 2.29-2.44 (m, 2H) 2.82-3.43 (m, 4H) 3.51-3.67 (m, 2H) 3.85-4.03 (m, 4H) 5.21-5.38 (m, 1H) 6.44 (s, 2H) 6.96-7.30 (m, 9H).

The following Examples 1-125 to 1-148 were synthesized by the method described in Example 1-1, Example 1-21, Example 1-30, Example 1-40, Example 1-46, or Example 1-50, or by a method equivalent thereto, using the compounds obtained in Reference Example 3-1-2 and Reference Examples 3-4-1 to 3-4-5, commercially available compounds, or compounds obtained by synthesis according to methods described in literatures or methods equivalent thereto. The structures and LCMS data of the compounds are shown in Tables 43-1 to 43-5.

TABLE 43-1

| Example No. | Structural Formula | MS posi m/z MS nega m/z | Retention time (min) | method |
|---|---|---|---|---|
| 1-125 | | 526 [M + H]+ 547 [M + Na]+ | 0.879 | A |
| 1-126 | | 525 [M + H]+ 523 [M + H]+ | 0.863- 0.879 | A |
| 1-127 | | 494 [M + H]+ 498 [M + H]+ | 0.783 | D |

TABLE 43-1-continued

| Example No. | Structural Formula | MS posi m/z MS nega m/z | Retention time (min) | method |
|---|---|---|---|---|
| 1-128 | | 528 [M + H]+ 523 [M + H]+ | 0.817 | A |
| 1-129 | | 523 [M + H]+ | 0.820 | A |

TABLE 43-2

| Example No. | Structural Formula | MS posi m/z MS nega m/z | Retention time (min) | method |
|---|---|---|---|---|
| 1-130 | | 523 [M + H]+ 521 [M + H]+ | 1.203 | E |

TABLE 43-2-continued

| Example No. | Structural Formula | MS posi m/z MS nega m/z | Retention time (min) | method |
|---|---|---|---|---|
| 1-131 | | 526 [M + H]+ 537 [M + H]+ | 0.817 | D |
| 1-132 | | 535 [M + H]+ 537 [M + H]+ | 0.881 | D |
| 1-133 | | 535 [M + H]+ 537 [M + H]+ | 0.850 | D |

TABLE 43-2-continued
| Example No. | Structural Formula | MS posi m/z MS nega m/z | Retention time (min) | method |
|---|---|---|---|---|
| 1-134 | 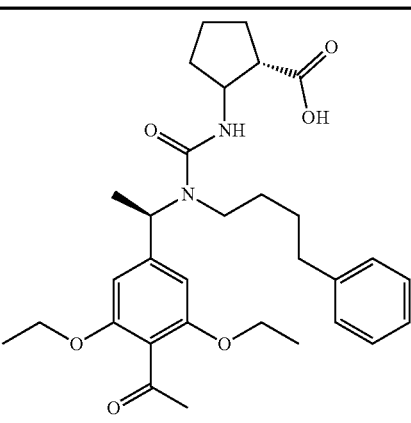 | 539 [M + H]+ 537 [M + H]+ | 0.854 | D |
TABLE 43-3
| Example No. | Structural Formula | MS posi m/z MS nega m/z | Retention time (min) | method |
|---|---|---|---|---|
| 1-135 | | 539 [M + H]+ 537 [M + H]+ | 0.811 | D |
| 1-136 | | 511 [M + H]+ 509 [M + H]+ | 1.080 | D |

TABLE 43-3-continued

| Example No. | Structural Formula | MS posi m/z MS nega m/z | Retention time (min) | method |
|---|---|---|---|---|
| 1-137 | | 511 [M + H]+ 509 [M + H]+ | 1.029 | D |
| 1-138 | | 529 [M + H]+ | 0.188 | D |
| 1-139 | | 529 [M + H]+ 562 [M + Na]+ 537 [M + H]+ | 0.891 | A |

TABLE 43-4

| Example No. | Structural Formula | MS posi m/z MS nega m/z | Retention time (min) | method |
|---|---|---|---|---|
| 1-140 | | 539 [M + H]+ 537 [M + H]+ | 0.807 | D |
| 1-141 | | 539 [M + H]+ 537 [M + H]+ | 0.789 | D |
| 1-142 | | 511 [M + H]+ 509 [M + H]+ | 0.963 | D |

TABLE 43-4-continued

| Example No. | Structural Formula | MS posi m/z MS nega m/z | Retention time (min) | method |
|---|---|---|---|---|
| 1-143 | | 525 [M + H]+ 523 [M + H]+ | 0.972 | D |
| 1-144 | | 525 [M + H]+ 523 [M + H]+ | 0.796 | D |

TABLE 43-5

| Example No. | Structural Formula | MS posi m/z MS nega m/z | Retention time (min) | method |
|---|---|---|---|---|
| 1-145 | | 525 [M + H]+ 523 [M + H]+ | 0.786 | D |

TABLE 43-5-continued

| Example No. | Structural Formula | MS posi m/z MS nega m/z | Retention time (min) | method |
|---|---|---|---|---|
| 1-146 | | 525 [M + H]+ 523 [M + H]+ | 1.082 | D |
| 1-147 | | 578 [M + H]+ 573 [M + H]+ | 1.102 | D |
| 1-148 | | 511 [M + H]+ 509 [M + H]+ | 0.555 | D |

Example 1-149

3-({[(1R)-1-(4-Acetyl-3,5-Diethoxyphenyl)Ethyl](4-Phenylbutyl) Carbamoyl}Amino) Oxetane-3-Carboxylic Acid

[Chemical Formula 486]

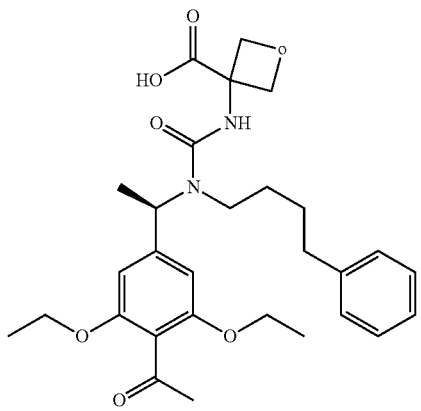

Using methyl 3-aminooxetane-3-carboxylate (8.12 mg) and the compound (20 mg) obtained in Reference Example 3-4-1, the reaction was carried out in accordance with the method described in Example 1-1, and the title compound (26.2 mg) was obtained as a colorless powder.

$^1$H NMR (400 MHZ, METHANOL-d$_4$) δ ppm 1.24-1.42 (m, 6H) 1.43-1.60 (m, 7H) 2.41 (s, 3H) 2.47-2.59 (m, 2H) 2.84-3.02 (m, 1H) 3.05-3.25 (m, 1H) 3.96-4.13 (m, 4H) 4.67-4.80 (m, 2H) 4.88-5.04 (m, 2H) 5.33-5.48 (m, 1H) 6.58 (s, 2H) 7.08-7.16 (m, 3H) 7.16-7.28 (m, 2H).

MS ESI posi: 527 [M+H]$^+$, 549 [M+Na]$^+$.

MS ESI nega: 525 [M−H]$^-$.

Retention time: 0.850 min (method A)

The following Examples 1-150 to 1-151 were synthesized by the method described in Example 1-1 or by a method equivalent thereto, using the compounds obtained in Reference Example 3-4-1 and Reference Example 3-4-4, commercially available compounds, or compounds obtained by synthesis according to methods described in literatures or methods equivalent thereto. The structures and LCMS data of the compounds are shown in Table 44-1.

TABLE 44-1

| Example No. | Structural Formula | MS posi m/z<br>MS nega m/z | Retention<br>time (min) | method |
|---|---|---|---|---|
| 1-150 | | 513 [M + H]+<br>511 [M + H]+ | 0.941 | D |
| 1-151 | | 555 [M + H]+<br>563 [M + H]+ | 0.783 | D |

Example 1-152

4-{[{(1R)-1-[3,5-Diethoxy-4-(1-Hydroxyethyl)Phenyl]Ethyl}(4-Phenylbutyl) Carbamoyl]Amino}Oxane-4-Carboxylic Acid

[Chemical Formula 487]

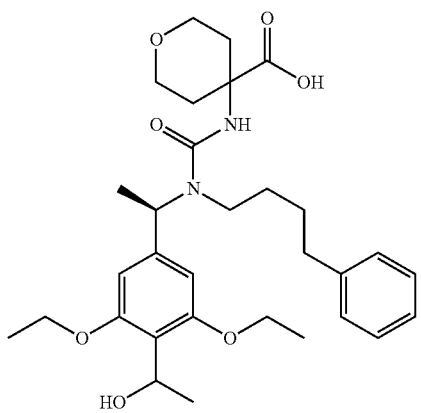

A mixed solution of the compound (72.6 mg) obtained in Example 1-151 in tetrahydrofuran-ethanol (3 mL-0.15 mL) was ice-cooled, lithium borohydride (17.1 mg) was added thereto, and the reaction solution was stirred at the same temperature for 3.5 hours. At the same temperature, a saturated aqueous ammonium chloride solution was added thereto, and extraction with chloroform was carried out. The organic layer was filtered through Phase Separator and concentrated. The obtained residue was purified by preparative HPLC and freeze-dried to afford the title compound (61.9 mg) as a colorless amorphous.

$^1$H NMR (600 MHZ, METHANOL-$d_4$) δ ppm 1.36-1.43 (m, 6H) 1.44-1.56 (m, 10H) 1.87-1.95 (m, 1H) 1.97-2.07 (m, 2H) 2.07-2.14 (m, 1H) 2.50-2.58 (m, 2H) 2.91-3.02 (m, 1H) 3.20-3.27 (m, 1H) 3.39-3.50 (m, 2H) 3.68-3.75 (m, 2H) 4.00-4.12 (m, 4H) 5.28-5.38 (m, 2H) 6.57 (s, 2H) 7.10-7.16 (m, 3H) 7.19-7.25 (m, 2H).

MS ESI posi: 539 [M−OH]$^+$.
MS ESI nega: 555 [M−H]$^−$.
Retention time: 0.822 min (method A)

The following Examples 1-153 to 1-157 were synthesized by the method described in Example 1-1 or by a method equivalent thereto, using the compounds obtained in Reference Examples 3-2-2 and Reference Examples 3-4-3 to 3-4-5, commercially available compounds, or compounds obtained by synthesis according to methods described in literatures or methods equivalent thereto. The structures and LCMS data of the compounds are shown in Table 45-1.

TABLE 45-1

| Example No. | Structural Formula | MS posi m/z MS nega m/z | Retention time (min) | method |
|---|---|---|---|---|
| 1-153 | | 551 [M + H]+ 567 [M + H]+ | 1.041 | E |
| 1-154 | | 527 [M + H]+ 525 [M + H]+ | 0.953 | D |

TABLE 45-1-continued

| Example No. | Structural Formula | MS posi m/z MS nega m/z | Retention time (min) | method |
|---|---|---|---|---|
| 1-155 | | 552 [M + H]+ 551 [M + H]+ | 1.264 | E |
| 1-156 | | 525 [M + H]+ 523 [M + H]+ | 0.972 | E |
| 1-157 | | 575 [M + H]+ 597 [M + Na]+ 573 [M + H]+ | 0.975 | A |

Example 1-158

3-({[(1R)-1-(3,5-Diethoxy-4-Methylphenyl)Ethyl](4-Phenylbutyl) Carbamoyl}Amino) Azetidine-3-Carboxylic Acid

[Chemical Formula 488]

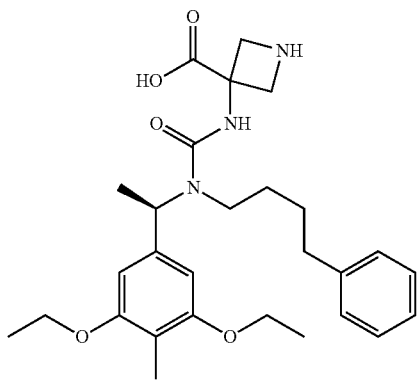

Example 1-159

1-Acetyl-3-({[(1R)-1-(3,5-Diethoxy-4-Methylphenyl)Ethyl](4-Phenylbutyl) Carbamoyl}Amino) Azetidine-3-Carboxylic Acid

[Chemical Formula 489]

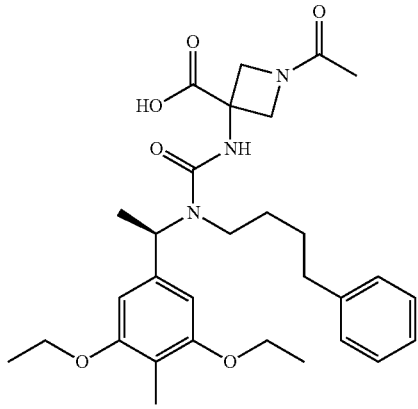

(1) Using the compound (19.7 mg) obtained in Reference Example 4-6-1 and the compound (32 mg) obtained in Reference Example 3-4-4, the reaction was carried out in accordance with the method described in Example 1-21 (1), and methyl 1-acetyl-3-({[(1R)-1-(3,5-diethoxy-4-methylphenyl)ethyl](4-phenylbutyl) carbamoyl}amino) azetidine-3-carboxylate (50 mg) was obtained as a colorless oily substance.

(2) To a solution of the compound (50 mg) obtained in (1) above in methanol (1 mL), tetrahydrofuran (1 mL), water (0.8 mL), and lithium hydroxide (39.1 mg) were added, and the reaction solution was stirred at room temperature overnight. The reaction solution was concentrated, and the obtained residue was purified by silica gel column chromatography (chloroform:methanol=95:5 to 60:40) and preparative HPLC to afford the title compounds, 3-({[(1R)-1-(3,5-diethoxy-4-methylphenyl)ethyl](4-phenylbutyl) carbamoyl}amino) azetidine-3-carboxylic acid (Example 1-158) (5 mg) as a colorless gum-like substance and 1-acetyl-3-({[(1R)-1-(3,5-diethoxy-4-methylphenyl)ethyl](4-phenylbutyl) carbamoyl}amino) azetidine-3-carboxylic acid (Example 1-159) (36 mg) as a colorless gum-like substance.

Example 1-158

$^1$H NMR (400 MHZ, METHANOL-$d_4$) δ ppm 1.28-1.54 (m, 13H) 2.03 (s, 3H) 2.43-2.54 (m, 2H) 3.02-3.19 (m, 2H) 3.91-4.07 (m, 4H) 4.28-4.37 (m, 2H) 4.56-4.68 (m, 2H) 5.36-5.52 (m, 1H) 6.52 (s, 2H) 7.05-7.15 (m, 3H) 7.15-7.27 (m, 2H) 8.47 (br s, 1H).

MS ESI posi: 498 [M+H]$^+$.

MS ESI nega: 496 [M−H]$^−$.

Retention time: 0.720 min (method A)

Example 1-159

$^1$H NMR (400 MHZ, METHANOL-$d_4$) δ ppm 1.30-1.54 (m, 13H) 1.90 (s, 3H) 2.04 (s, 3H) 2.36-2.57 (m, 2H) 2.82-3.01 (m, 1H) 3.02-3.17 (m, 1H) 3.90-4.12 (m, 5H) 4.16-4.37 (m, 2H) 4.56-4.70 (m, 1H) 5.26-5.49 (m, 1H) 6.41-6.62 (m, 2H) 7.00-7.15 (m, 3H) 7.15-7.26 (m, 2H).

MS ESI posi: 540 [M+H]$^+$.

MS ESI nega: 538 [M−H]$^−$.

Retention time: 0.941 min (method A)

The following Examples 1-160 to 1-167 were synthesized by the method described in Example 1-1 or Example 1-158, or by a method equivalent thereto, using the compounds obtained in Reference Examples 3-4-1 to 3-4-2, Reference Example 3-4-4, and Reference Examples 4-6-2 to 4-6-3, commercially available compounds, or compounds obtained by synthesis according to methods described in literatures or methods equivalent thereto. The structures and LCMS data of the compounds are shown in Tables 46-1 to 46-3.

TABLE 46-1

| Example No. | Structural Formula | MS posi m/z MS nega m/z | Retention time (min) | method |
|---|---|---|---|---|
| 1-160 | | 590 [M + Na]+ 555 [M + H]+ | 0.948 | A |
| 1-161 | | 541 [M + H]+ 535 [M + H]+ | 0.847 | D |
| 1-162 | | 541 [M + H]+ 539 [M + H]+ | 0.864 | D |

TABLE 46-1-continued
| Example No. | Structural Formula | MS posi m/z MS nega m/z | Retention time (min) | method |
|---|---|---|---|---|
| 1-163 | 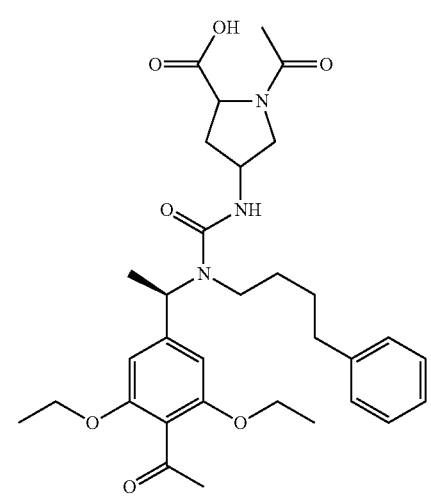 [SMILES: CCOc1cc([C@@H](C)N(CCCCc2ccccc2)C(=O)NC2CC(C(=O)O)N(C(C)=O)C2)cc(OCC)c1C(C)=O] | 582 [M + H]+<br>580 [M + H]+ | 0.725 | D |
| 1-164 | 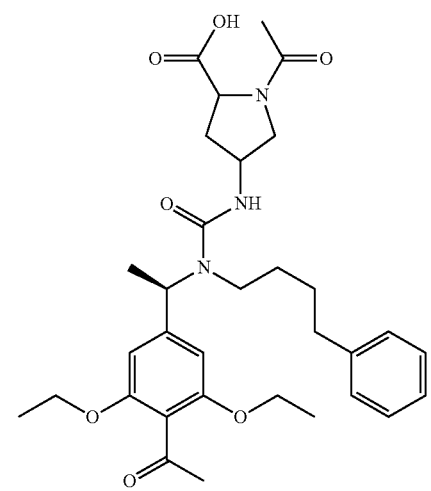 [SMILES: CCOc1cc([C@@H](C)N(CCCCc2ccccc2)C(=O)NC2CC(C(=O)O)N(C(C)=O)C2)cc(OCC)c1C(C)=O] | 582 [M + H]+<br>580 [M + H]+ | 0.708 | D |

TABLE 46-2

| Example No. | Structural Formula | MS posi m/z<br>MS nega m/z | Retention<br>time (min) | method |
|---|---|---|---|---|
| 1-165 | | 569 [M + H]+<br>567 [M + H]+ | 0.787 | D |
| 1-166 | | 564 [M + H]+<br>567 [M + H]+ | 0.771 | D |

TABLE 46-3

| Example No. | Structural Formula | MS posi m/z<br>MS nega m/z | Retention<br>time (min) | method |
|---|---|---|---|---|
| 1-167 | | 576 [M + H]+<br>574 [M + H]+ | 0.858 | D |

579
Example 2-1

1-[{[(1R)-1-(3,5-Diethoxy-4-Methylphenyl)Ethyl](4-Phenylbutyl) Carbamoyl}(Methyl)Amino]-3,3-Difluorocyclobutane-1-Carboxylic Acid

[Chemical Formula 490]

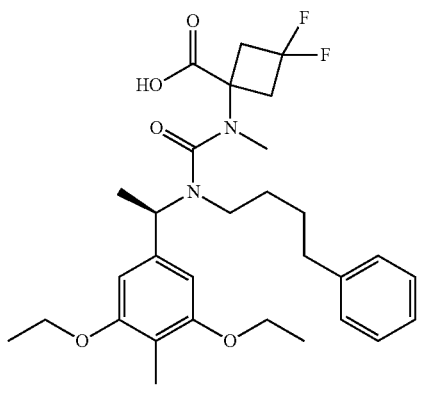

(1) Using methyl 1-amino-3,3-difluorocyclobutane-1-carboxylate hydrochloride (162 mg) and the compound (300 mg) obtained in Reference Example 3-4-4, the reaction was carried out in accordance with the method described in Example 1-21 (1), and methyl 1-({[(1R)-1-(3,5-diethoxy-4-methylphenyl)ethyl](4-phenylbutyl) carbamoyl}amino)-3,3-difluorocyclobutane-1-carboxylate (290 mg) was obtained as a colorless oily substance.

(2) A solution of the compound (10 mg) obtained in (1) above in N,N-dimethylformamide (0.37 mL) was ice-cooled, and sodium hydride (50% mineral oil dispersion, 1.76 mg) was added thereto under a nitrogen atmosphere. Iodomethane (2.28 μL) was added thereto, and the reaction solution was stirred at the same temperature for 10 minutes and at room temperature for 2 hours. The reaction solution was ice-cooled, water was added thereto, and extraction with ethyl acetate was carried out three times. The organic layer was washed with water and a brine sequentially. The organic layer was filtered through Phase Separator and concentrated to afford methyl 1-[{[(1R)-1-(3,5-diethoxy-4-methylphenyl)ethyl](4-phenylbutyl) carbamoyl}(methyl)amino]-3,3-difluorocyclobutane-1-carboxylate (7.4 mg) as a colorless gum-like substance.

(3) Using the compound (7.2 mg) obtained in (2) above, the reaction and post treatment were carried out in accordance with the method described in Example 1-21 (3), and the obtained residue was purified by silica gel column chromatography (chloroform:methanol=98:2 to 90:10) to afford the title compound (7.0 mg) as a colorless gum-like substance.

$^1$H NMR (400 MHZ, METHANOL-$d_4$) δ ppm 0.82-0.93 (m, 2H) 1.26-1.31 (m, 2H) 1.31-1.43 (m, 6H) 1.43-1.50 (m, 2H) 1.55 (d, J=7.0 Hz, 3H) 2.03 (s, 3H) 2.45-2.53 (m, 2H) 2.57-2.76 (m, 1H) 2.76-2.92 (m, 2H) 2.92-3.03 (m, 1H) 3.07 (s, 3H) 3.91-4.04 (m, 4H) 4.98 (q, J=7.0 Hz, 1H) 6.49 (s, 2H) 7.04-7.16 (m, 3H) 7.16-7.27 (m, 2H).

MS ESI/APCI Multi posi: 547 [M+H]$^+$.

MS ESI/APCI Multi nega: 545 [M−H]$^−$.

Retention time: 1.081 min (method D)

580
Example 3-1

1-({[(3,5-Dimethoxy-4-Methylphenyl)Methyl](4-Phenylbutyl) Carbamoyl}Amino)-3,3-Difluorocyclobutane-1-Carboxylic Acid

[Chemical Formula 491]

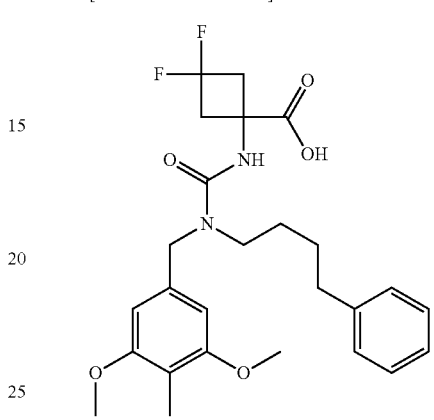

(1) To a solution of methyl 1-amino-3,3-difluorocyclobutane-1-carboxylate hydrochloride (30 mg) in tetrahydrofuran (0.5 mL), N,N-diisopropylethylamine (0.130 mL) was added, and the reaction solution was stirred at room temperature for 10 minutes. The reaction solution was ice-cooled, a solution of 4-nitrophenyl chloroformate (30.0 mg) in tetrahydrofuran (0.5 mL) was added thereto, and the reaction solution was stirred at room temperature for 1 hour. The compound (56.0 mg) obtained in Reference Example 3-1-1 was added to the reaction solution, which was then stirred at 60° C. for 4 hours.

(2) A 1 mol/L aqueous sodium hydroxide solution (1.5 mL) and methanol (1.5 mL) were added to the reaction solution of (1) above, which was then stirred at 60° C. for 2 hours. The reaction solution was concentrated, 1 mol/L hydrochloric acid was added thereto to make the solution acidic, and extraction with chloroform was carried out twice. The organic layer was concentrated. The obtained residue was purified by silica gel column chromatography (chloroform:methanol=98:2 to 90:10) to afford the title compound (21 mg) as a colorless powder.

$^1$H NMR (400 MHZ, METHANOL-$d_4$) δ ppm 1.50-1.63 (m, 4H) 2.00 (s, 3H) 2.53-2.61 (m, 2H) 2.78-2.91 (m, 2H) 3.16-3.28 (m, 4H) 3.77 (s, 6H) 4.44 (s, 2H) 6.48 (s, 2H) 7.09-7.16 (m, 3H) 7.16-7.27 (m, 2H).

MS ESI/APCI Multi posi: 491 [M+H]$^+$.

MS ESI/APCI Multi nega: 489 [M−H]$^−$.

Retention time: 0.929 min (method D)

The following Examples 3-2 to 3-3 were synthesized by the method described in Example 3-1 or by a method equivalent thereto, using the compounds obtained in Reference Examples 3-1-31 to 3-1-32, commercially available compounds, or compounds obtained by synthesis according to methods described in literatures or methods equivalent thereto. The structures and LCMS data of the compounds are shown in Table 47-1.

TABLE 47-1

| Example No. | Structural Formula | MS posi m/z MS nega m/z | Retention time (min) | method |
|---|---|---|---|---|
| 3-2 | | 467 [M + H]+ 519 [M + Na]+ | 1.081 | A |
| 3-3 | | 519 [M + H]+ 517 [M + H]+ | 1.060 | A |

Example 3-4

1-({[1-(4-Acetyl-3,5-Diethoxyphenyl)-2-Hydroxy-ethyl](4-Phenylbutyl) Carbamoyl}Amino)-3,3-Difluorocyclobutane-1-Carboxylic Acid

[Chemical Formula 492]

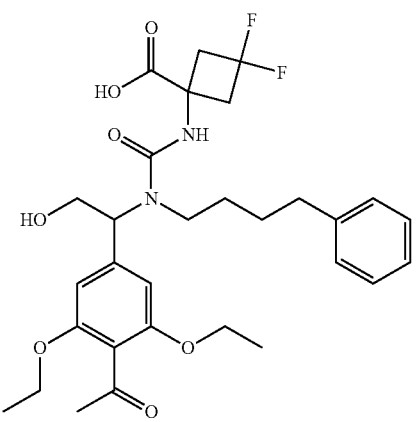

(1) A solution of 4-nitrophenyl chloroformate (38.3 mg) in chloroform (1 mL) was ice-cooled, methyl 1-amino-3,3-difluorocyclobutane-1-carboxylate hydrochloride (36.5 mg) and N,N-diisopropylethylamine (69.4 μL) were added thereto, and the reaction solution was stirred at room temperature for 1 hour and concentrated. To a solution of the obtained residue in N,N-dimethylformamide (2 mL), the compound (88 mg) obtained in Reference Example 3-1-33 and N,N-diisopropylethylamine (32.8 L) were added, and the reaction solution was stirred at 60° C. for 1 hour and at room temperature overnight. Water was added to the reaction solution, which was then extracted with ethyl acetate three times. The organic layer was washed with water and a brine, dried over anhydrous sodium sulfate, filtered through Phase Separator, and concentrated. The obtained residue was purified by preparative HPLC to afford methyl 1-({[1-(4-acetyl-3,5-diethoxyphenyl)-2-{[tert-butyl(dimethyl) silyl]oxy}ethyl](4-phenylbutyl) carbamoyl}amino)-3,3-difluoro-cyclobutane-1-carboxylate (30 mg) as a light yellow oily substance.

(2) A solution of the compound (30 mg) obtained in (1) above in tetrahydrofuran (0.5 mL) was ice-cooled, a 1 mol/L tetrabutylammonium fluoride-tetrahydrofuran solution (0.128 mL) was added thereto, and the reaction solution was stirred at the same temperature for 3 hours.

(3) Methanol (0.43 mL) and a 1 mol/L aqueous sodium hydroxide solution (0.43 mL) were added to the reaction solution obtained in (2) above, which was then stirred at 65° C. for 1 hour. The reaction solution was concentrated and purified by preparative HPLC to afford the title compound (16 mg) as a colorless amorphous.

$^1$H NMR (400 MHZ, CHLOROFORM-d) δ ppm 1.14-1.45 (m, 10H) 2.35-2.57 (m, 6H) 2.60-2.77 (m, 1H) 2.84-

3.05 (m, 1H) 3.05-3.29 (m, 2H) 3.33-3.54 (m, 1H) 3.75-4.14 (m, 6H) 5.24-5.51 (m, 1H) 6.23-6.41 (m, 2H) 6.96-7.09 (m, 2H) 7.09-7.23 (m, 3H).

MS ESI/APCI Multi posi: 577 [M+H]⁺.
MS ESI/APCI Multi nega: 575 [M−H]⁻.
Retention time: 0.794 min (method D)

The following Examples 3-5 to 3-10 were synthesized by the method described in Example 3-1 or Example 3-4, or by a method equivalent thereto, using the compounds obtained in Reference Examples 3-1-34 to 3-1-36, commercially available compounds, or compounds obtained by synthesis according to methods described in literatures or methods equivalent thereto. The structures and LCMS data of the compounds are shown in Tables 48-1 to 48-2.

TABLE 48-1

| Example No. | Structural Formula | MS posi m/z MS nega m/z | Retention time (min) | method |
|---|---|---|---|---|
| 3-5 | | 549 [M + H]+ 547 [M + H]+ | 0.938 | D |
| 3-6 | | 521 [M + H]+ 519 [M + H]+ | 0.854 | D |
| 3-7 | | 499 [M + H]+ 497 [M + H]+ | 0.882 | D |

TABLE 48-1-continued

| Example No. | Structural Formula | MS posi m/z MS nega m/z | Retention time (min) | method |
|---|---|---|---|---|
| 3-8 | | 575 [M + H]+ 573 [M + H]+ | 1.002 | D |
| 3-9 | | 547 [M + H]+ 545 [M + H]+ | 0.916 | D |

TABLE 48-2

| Example No. | Structural Formula | MS posi m/z MS nega m/z | Retention time (min) | method |
|---|---|---|---|---|
| 3-10 | | 563 [M + H]+ 583 [M + Na]+ 561 [M + H]+ | 0.977 | A |

Example 4-1

1-({Butyl[(1R)-1-(3,5-Diethoxy-4-Methylphenyl)Ethyl]Carbamoyl}Amino)-3,3-Difluorocyclobutane-1-Carboxylic Acid

[Chemical Formula 493]

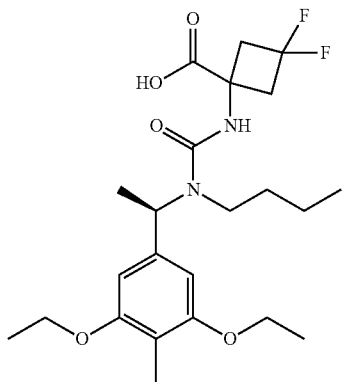

Using methyl 1-amino-3,3-difluorocyclobutane-1-carboxylate hydrochloride (44 mg) and the compound (64 mg) obtained in Reference Example 3-6-5, the reaction was carried out in accordance with the method described in Example 1-1, and the title compound (48 mg) was obtained as a colorless powder.

$^1$H NMR (400 MHZ, METHANOL-$d_4$) δ ppm 0.75-0.85 (m, 3H) 1.11-1.24 (m, 2H) 1.38 (t, J=6.9 Hz, 6H) 1.48-1.57 (m, 3H) 2.03 (s, 3H) 2.78-2.92 (m, 3H) 3.02-3.12 (m, 1H) 3.16-3.37 (m, 4H) 4.02 (q, J=6.9 Hz, 4H) 5.34-5.47 (m, 1H) 6.52 (s, 2H).

MS ESI posi: 457 [M+H]$^+$, 479 [M+Na]$^+$.

MS ESI nega: 455 [M−H].

Retention time: 0.929 min (method A)

The following Examples 4-2 to 4-3 were synthesized by the method described in Example 1-1 or by a method equivalent thereto, using the compounds obtained in Reference Examples 3-6-1 to 3-6-2, commercially available compounds, or compounds obtained by synthesis according to methods described in literatures or methods equivalent thereto. The structures and LCMS data of the compounds are shown in Table 49-1.

TABLE 49-1

| Example No. | Structural Formula | MS posi m/z MS nega m/z | Retention time (min) | method |
|---|---|---|---|---|
| 4-2 | | 459 [M + H]+ 521 [M + Na]+ 497 [M + H]+ | 1.031 | A |
| 4-3 | | 611 [M + H]+ | 1.072 | A |

Example 4-4

1-({[(1R)-1-(3,5-Diethoxy-4-Methylphenyl)Ethyl][3-(2-Fluorophenyl) Propyl]Carbamoyl}Amino)-3,3-Difluorocyclobutane-1-Carboxylic Acid

[Chemical Formula 494]

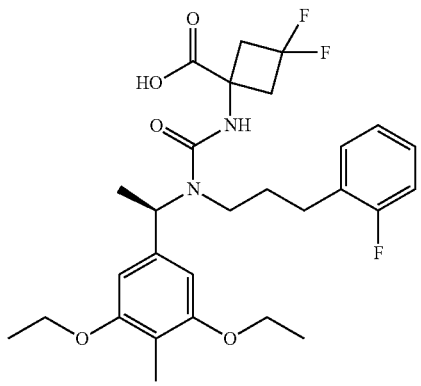

Using methyl 1-amino-3,3-difluorocyclobutane-1-carboxylate hydrochloride (27.9 mg) and the compound (mixture containing 41.5 mg as the theoretical amount) obtained in Reference Example 3-4-9, the reaction was carried out in accordance with the method described in Example 1-1, and the title compound (19 mg) was obtained as a colorless powder.

$^1$H NMR (400 MHZ, METHANOL-$d_4$) δ ppm 1.37 (t, J=6.9 Hz, 6H) 1.40-1.46 (m, 3H) 1.52-1.69 (m, 1H) 1.69-1.83 (m, 1H) 2.03 (s, 3H) 2.41-2.57 (m, 2H) 2.77-2.99 (m, 3H) 2.99-3.13 (m, 1H) 3.14-3.29 (m, 2H) 3.96 (q, J=6.9 Hz, 4H) 5.32-5.46 (m, 1H) 6.44 (s, 2H) 6.91-7.08 (m, 3H) 7.11-7.23 (m, 1H).

MS ESI posi: 537 [M+H]$^+$, 559 [M+Na]$^+$.
MS ESI nega: 535 [M−H]$^−$.
Retention time: 0.963 min (method A)

The following Examples 4-5 to 4-17 were synthesized by the method described in Example 1-1 or Example 1-40, or by a method equivalent thereto, using the compounds obtained in Reference Example 1-5-2, Reference Example 1-5-17, Reference Examples 3-1-37 to 3-1-41, and Reference Examples 3-4-10 to 3-4-14, commercially available compounds, or compounds obtained by synthesis according to methods described in literatures or methods equivalent thereto. The structures and LCMS data of the compounds are shown in Tables 50-1 to 50-3.

TABLE 50-1

| Example No. | Structural Formula | MS posi m/z MS nega m/z | Retention time (min) | method |
|---|---|---|---|---|
| 4-5 | | 531 [M + H]+ 559 [M + Na]+ 585 [M + H]+ | 0.957 | A |
| 4-6 | | 609 [M + H]+ | 0.934 | A |

TABLE 50-1-continued

| Example No. | Structural Formula | MS posi m/z<br>MS nega m/z | Retention<br>time (min) | method |
| --- | --- | --- | --- | --- |
| 4-7 | | 537 [M + H]+<br>559 [M + Na]+<br>573 [M + H]+ | 0.961 | A |
| 4-8 | | 551 [M + H]+<br>549 [M + H]+ | 1.076 | A |
| 4-9 | | 551 [M + H]+<br>549 [M + H]+ | 1.011 | A |

TABLE 50-2

| Example No. | Structural Formula | MS posi m/z MS nega m/z | Retention time (min) | method |
|---|---|---|---|---|
| 4-10 | | 569 [M + H]+ | 1.084 | A |
| 4-11 | | 529 [M + H]+<br>561 [M + Na]+<br>527 [M + H]+ | 0.995 | A |
| 4-12 | | 528 [M + H]+<br>555 [M + Na]+<br>521 [M + H]+ | 0.991 | A |
| 4-13 | | 528 [M + H]+<br>555 [M + Na]+<br>531 [M + H]+ | 1.000 | A |

TABLE 50-2-continued
| Example No. | Structural Formula | MS posi m/z MS nega m/z | Retention time (min) | method |
|---|---|---|---|---|
| 4-14 | 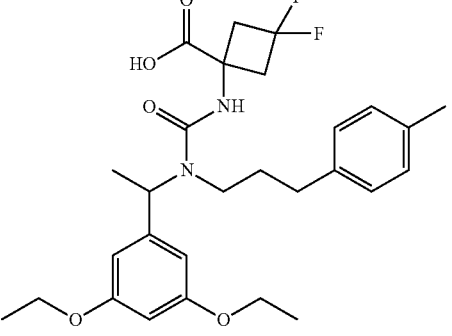 | 528 [M + H]+<br>555 [M + Na]+<br>531 [M + H]+ | 1.002 | A |
TABLE 50-3
| Example No. | Structural Formula | MS posi m/z MS nega m/z | Retention time (min) | method |
|---|---|---|---|---|
| 4-15 | 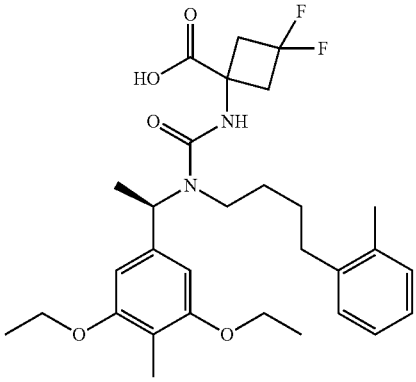 [SMILES: CCOc1cc([C@@H](C)N(CCCCc2ccccc2C)C(=O)NC2(C(=O)O)CC(F)(F)C2)cc(OCC)c1C] | 547 [M + H]+<br>569 [M + Na]+<br>515 [M + H]+ | 1.022 | A |
| 4-16 | 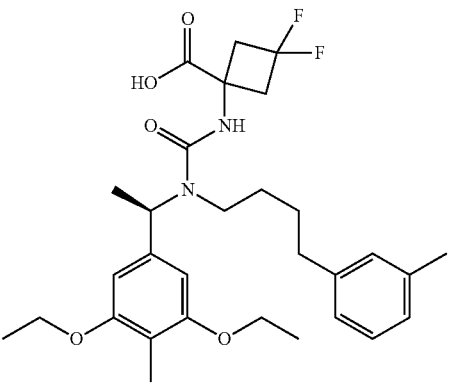 [SMILES: CCOc1cc([C@@H](C)N(CCCCc2cccc(C)c2)C(=O)NC2(C(=O)O)CC(F)(F)C2)cc(OCC)c1C] | 547 [M + H]+<br>569 [M + Na]+<br>545 [M + H]+ | 1.030 | A |

TABLE 50-3-continued

| Example No. | Structural Formula | MS posi m/z MS nega m/z | Retention time (min) | method |
|---|---|---|---|---|
| 4-17 | | 547 [M + H]+ 559 [M + Na]+ 545 [M + H]+ | 1.031 | A |

Example 4-18

1-({[(1R)-1-(3,5-Diethoxy-4-Methylphenyl)Ethyl][4-(3-Methoxyphenyl)Butyl]Carbamoyl}Amino)-3,3-Difluorocyclobutane-1-Carboxylic Acid

[Chemical Formula 495]

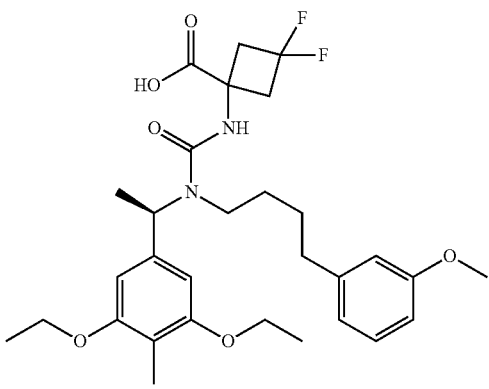 [SMILES: CCOc1cc([C@@H](C)N(CCCCc2ccc(OC)cc2)C(=O)NC2(C(=O)O)CC(F)(F)C2)cc(OCC)c1C]

(1) Using methyl 1-amino-3,3-difluorocyclobutane-1-carboxylate hydrochloride (119 mg) and the compound (148 mg) obtained in Reference Example 3-4-15, the reaction was carried out in accordance with the method described in Example 1-21 (1), and methyl 1-({{(but-3-yn-1-yl) [(1R)-1-(3,5-diethoxy-4-methylphenyl)ethyl]carbamoyl}amino)-3,3-difluorocyclobutane-1-carboxylate (214 mg) was obtained as a colorless amorphous.

(2) To a solution of the compound (30 mg) obtained in (1) above, 3-iodoanisole (18.1 mg), copper (I) iodide (1.23 mg), and bis(triphenylphosphine) palladium (II) dichloride (4.51 mg) in acetonitrile (1 mL), triethylamine (26.9 μL) was added, and the reaction solution was stirred at 80° C. for 2 hours. The reaction solution was concentrated, and the obtained residue was purified by silica gel column chromatography (n-hexane only to n-hexane:ethyl acetate=75:25) to afford methyl 1-({[(1R)-1-(3,5-diethoxy-4-methylphenyl)ethyl][4-(3-methoxyphenyl) but-3-yn-1-yl]carbamoyl}amino)-3,3-difluorocyclobutane-1-carboxylate (23.8 mg) as a brown oily substance.

(3) To a solution of the compound (23.8 mg) obtained in (2) above in methanol (2 mL), palladium carbon (5 mg) was added, and the reaction solution was stirred at room temperature for 3 days under a hydrogen atmosphere.

(4) A 1 mol/L aqueous sodium hydroxide solution (0.5 mL) was added to the reaction solution obtained in (3) above, which was then stirred at room temperature for 18 hours. For neutralization, 2 mol/L hydrochloric acid was added to the reaction solution, which was then filtered through Celite (registered trademark) and passed through Phase Separator, and the filtrate was concentrated. The obtained residue was purified by preparative HPLC and freeze-dried to afford the title compound (8.33 mg) as a colorless powder.

$^1$H NMR (400 MHZ, CHLOROFORM-d) δ ppm 1.41 (t, J=6.81 Hz, 6H) 1.49-1.71 (m, 7H) 2.09 (s, 3H) 2.32-2.54 (m, 2H) 2.54-2.67 (m, 2H) 2.99-3.47 (m, 4H) 3.79 (s, 3H) 3.97 (q, J=6.81 Hz, 4H) 4.68-5.29 (m, 2H) 6.41 (s, 2H) 6.66-6.77 (m, 3H) 7.15-7.23 (m, 1H).

MS ESI posi: 563 [M+H]+, 585 [M+Na]+.

MS ESI nega: 561 [M−H]−.

Retention time: 0.985 min (method A)

The following Examples 4-19 to 4-20 were synthesized by the method described in Example 1-1 or by a method equivalent thereto, using the compounds obtained in Reference Example 3-4-16 and Reference Example 3-6-3, commercially available compounds, or compounds obtained by synthesis according to methods described in literatures or methods equivalent thereto. The structures and LCMS data of the compounds are shown in Table 51-1.

TABLE 51-1

| Example No. | Structural Formula | MS posi m/z MS nega m/z | Retention time (min) | method |
|---|---|---|---|---|
| 4-19 | | 563 [M + H]+ 583 [M + Na]+ 561 [M + H]+ | 0.979 | A |
| 4-20 | | 536 [M + H]+ 557 [M + Na]+ 532 [M + H]+ | 0.934 | A |

Example 4-21

1-({[(1R)-1-(3,5-Diethoxy-4-Methylphenyl)Ethyl][2-(2,3-Dihydro-1H-Inden-2-Yl)Ethyl]Carbamoyl}Amino)-3,3-Difluorocyclobutane-1-Carboxylic Acid

[Chemical Formula 496]

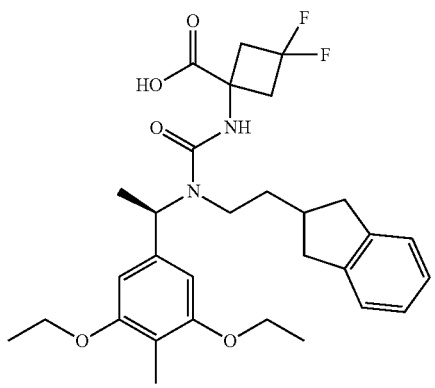

Using methyl 1-amino-3,3-difluorocyclobutane-1-carboxylate hydrochloride (22 mg) and the compound (35 mg) obtained in Reference Example 3-6-6, the reaction was carried out in accordance with the method described in Example 1-1, and the title compound (28 mg) was obtained as a colorless gum-like substance.

$^1$H NMR (400 MHZ, METHANOL-$d_4$) δ ppm 1.31-1.41 (m, 6H) 1.42-1.57 (m, 4H) 1.59-1.72 (m, 1H) 2.02 (s, 3H) 2.17-2.27 (m, 1H) 2.29-2.47 (m, 2H) 2.79-2.94 (m, 4H) 2.95-3.06 (m, 1H) 3.08-3.18 (m, 1H) 3.20-3.28 (m, 2H) 3.90-4.11 (m, 4H) 5.34-5.45 (m, 1H) 6.55 (s, 2H) 6.98-7.16 (m, 4H).

MS ESI posi: 545 [M+H]$^+$, 567 [M+Na]$^+$.

MS ESI nega: 543 [M−H]$^−$.

Retention time: 1.011 min (method A)

The following Examples 4-22 to 4-33 were synthesized by the method described in Example 1-1 or Example 1-40, or by a method equivalent thereto, using the compounds obtained in Reference Example 1-5-17, Reference Examples 3-4-17 to 3-4-18, Reference Example 3-6-4, Reference Examples 3-6-7 to 3-6-12, Reference Example 4-3-2, and Reference Example 4-4-2, commercially available compounds, or compounds obtained by synthesis according to methods described in literatures or methods equivalent thereto. The structures and LCMS data of the compounds are shown in Tables 52-1 to 52-3.

TABLE 52-1

| Example No. | Structural Formula | MS posi m/z MS nega m/z | Retention time (min) | method |
|---|---|---|---|---|
| 4-22 | | 567 [M + H]+ 589 [M + Na]+ 565 [M + H]+ | 0.910 | A |
| 4-23 | | 567 [M + H]+ 589 [M + Na]+ 565 [M + H]+ | 0.900 | A |
| 4-24 | | 581 [M + H]+ 603 [M + Na]+ 579 [M + H]+ | 0.925 | A |

TABLE 52-1-continued
| Example No. | Structural Formula | MS posi m/z MS nega m/z | Retention time (min) | method |
|---|---|---|---|---|
| 4-25 | 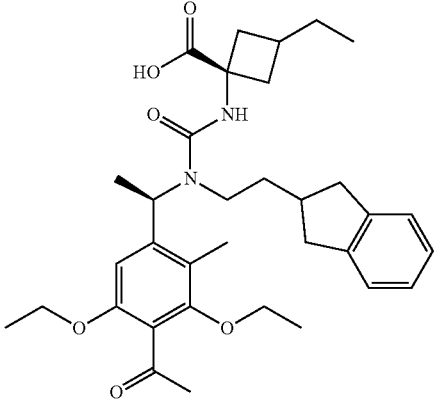 | 581 [M + H]+ 603 [M + Na]+ 579 [M − H]+ | 0.917 | A |
| 4-26 | 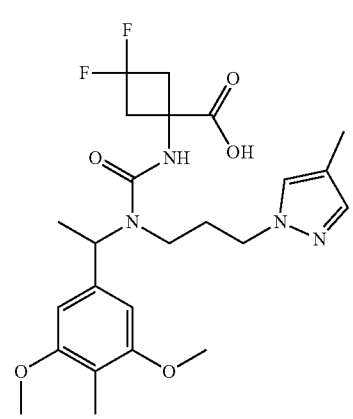 [SMILES: COc1cc(C(C)N(CCCn2cc(C)cn2)C(=O)NC2(C(=O)O)CC(F)(F)C2)cc(OC)c1C] | 495 [M + H]+ 493 [M − H]+ | 0.822 | A |
TABLE 52-2
| Example No. | Structural Formula | MS posi m/z MS nega m/z | Retention time (min) | method |
|---|---|---|---|---|
| 4-27 | 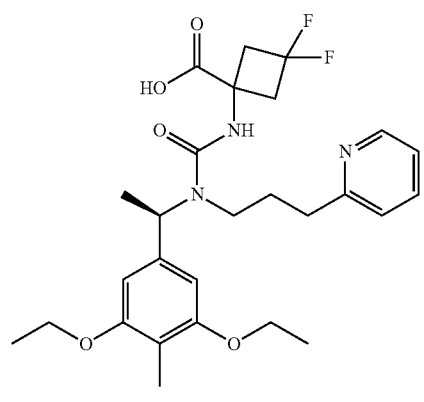 [SMILES: CCOc1cc([C@@H](C)N(CCCc2ccccn2)C(=O)NC2(C(=O)O)CC(F)(F)C2)cc(OCC)c1C] | 520 [M + H]+ 518 [M − H]+ | 0.763 | B |

TABLE 52-2-continued

| Example No. | Structural Formula | MS posi m/z MS nega m/z | Retention time (min) | method |
|---|---|---|---|---|
| 4-28 | | 534 [M + H]+ 532 [M + H]+ | 0.742 | B |
| 4-29 | | 534 [M + H]+ 532 [M + H]+ | 0.752 | B |
| 4-30 | | 520 [M + H]+ 518 [M + H]+ | 0.650 | B |
| 4-31 | | 546 [M + H]+ 544 [M + H]+ | 0.716 | B |

TABLE 52-3

| Example No. | Structural Formula | MS posi m/z MS nega m/z | Retention time (min) | method |
|---|---|---|---|---|
| 4-32 | | 530 [M + H]+ 552 [M + Na]+ 526 [M + H]+ | 0.951 | A |
| 4-32 | | 539 [M + H]+ 561 [M + Na]+ 537 [M + H]+ | 1.128 | A |

Example 4-34

1-({[(1R)-1-(3,5-Diethoxy-4-Methylphenyl)Ethyl] [4-(Piperidin-4-Yl)Butyl]Carbamoyl}Amino)-3,3-Difluorocyclobutane-1-Carboxylic Acid

[Chemical Formula 497]

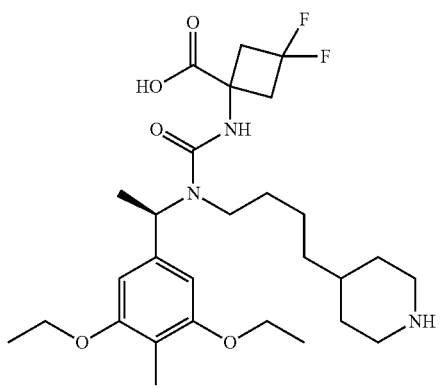

(1) To a solution of the compound (30 mg) obtained in Example 4-18 (1) and 4-iodopyridine (15.8 mg) in acetonitrile (0.3 mL), tris {tris[3,5-bis(trifluoromethyl)phenyl]phosphine}palladium (0) (SUPERSTABLE palladium (0) catalyst: manufactured by FUJIFILM Wako Pure Chemical Corporation, 6.81 mg), copper (I) iodide (1.23 mg), and triethylamine (44.8 μL) were added, and the reaction solution was stirred at 80° C. for 2 hours. The reaction solution was concentrated, and the obtained residue was purified by silica gel column chromatography (n-hexane only to n-hexane:ethyl acetate=40:60) to afford methyl 1-({[(1R)-1-(3,5-diethoxy-4-methylphenyl)ethyl][4-(pyridin-4-yl)but-3-yn-1-yl]carbamoyl}amino)-3,3-difluorocyclobutane-1-carboxylate (9.1 mg) as a yellow amorphous.

(2) To a solution of the compound (9.1 mg) obtained in (1) above in methanol, palladium carbon (10 mg) was added, and the reaction solution was stirred at room temperature for 6 hours under a hydrogen atmosphere.

(3) A 1 mol/L aqueous sodium hydroxide solution (0.5 mL) was added to the reaction solution obtained in (2) above, which was then stirred at room temperature for 18 hours. For neutralization, 2 mol/L hydrochloric acid was added to the reaction solution, which was then filtered through Celite (registered trademark) and passed through Phase Separator, and the filtrate was concentrated. The obtained residue was purified by preparative HPLC and freeze-dried to afford the title compound (4.70 mg) as a colorless solid.

$^1$H NMR (400 MHZ, CHLOROFORM-d) δ ppm 1.01-2.01 (m, 11H) 1.39 (br t, J=6.81 Hz, 4H) 1.50 (s, 3H) 2.06 (s, 3H) 2.62-3.22 (m, 11H) 3.26-3.38 (m, 2H) 3.99 (q, J=6.81 Hz, 4H) 5.23-5.51 (m, 1H) 5.82-6.03 (m, 1H) 6.46 (s, 2H).

MS ESI posi: 540 [M+H]$^+$.

MS ESI nega: 538 [M−H]$^−$.

Retention time: 0.691 min (method B)

Example 4-35

1-({[(1R)-1-(4-Acetyl-3,5-Diethoxyphenyl)Ethyl](3-Phenylpropyl) Carbamoyl}Amino)-3,3-Difluorocyclobutane-1-Carboxylic Acid

[Chemical Formula 498]

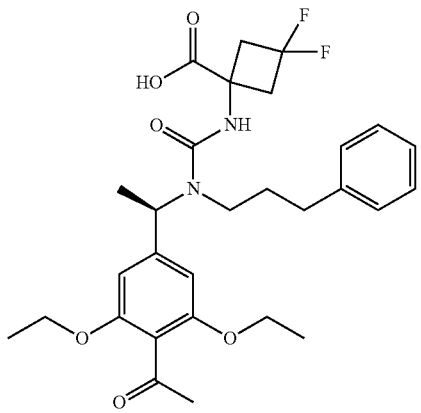

Using methyl 1-amino-3,3-difluorocyclobutane-1-carboxylate hydrochloride (27.5 mg) and the compound (45.8 mg) obtained in Reference Example 3-4-19, the reaction was carried out in accordance with the method described in Example 1-1, and the title compound (38.5 mg) was obtained as a colorless powder.

$^1$H NMR (400 MHZ, CHLOROFORM-d) δ ppm 1.36 (t, J=6.89 Hz, 6H) 1.48-1.54 (m, 3H) 1.62-1.94 (m, 2H) 2.25-2.43 (m, 2H) 2.44-2.65 (m, 2H) 2.48 (s, 3H) 2.86-3.08 (m, 2H) 3.13-3.32 (m, 2H) 3.99 (q, J=6.89 Hz, 4H) 4.41-4.56 (m, 1H) 5.26-5.62 (m, 1H) 6.40 (s, 2H) 7.11-7.17 (m, 2H) 7.22-7.27 (m, 1H) 7.29-7.35 (m, 2H).

MS ESI posi: 547 [M+H]$^+$, 569 [M+Na]$^+$.

MS ESI nega: 545 [M−H]$^−$.

Retention time: 1.123 min (method B)

The following Examples 4-36 to 4-39 were synthesized by the method described in Example 1-1 or Example 1-40, or by a method equivalent thereto, using the compounds obtained in Reference Example 1-5-2 and Reference Examples 3-1-42 to 3-1-43, commercially available compounds, or compounds obtained by synthesis according to methods described in literatures or methods equivalent thereto. The structures and LCMS data of the compounds are shown in Table 53-1.

TABLE 53-1

| Example No. | Structural Formula | MS posi m/z<br>MS nega m/z | Retention time (min) | method |
|---|---|---|---|---|
| 4-36 | | 519 [M + H]+<br>517 [M + H]+ | 1.206 | E |
| 4-37 | | 547 [M + H]+<br>545 [M + H]+ | 1.394 | E |

TABLE 53-1-continued

| Example No. | Structural Formula | MS posi m/z MS nega m/z | Retention time (min) | method |
|---|---|---|---|---|
| 4-38 | | 547 [M + H]+ 545 [M + H]+ | 1.388 | B |
| 4-39 | | 573 [M + H]+ 571 [M + H]+ | 1.122 | D |

Example 4-40

1-({[(1R)-1-(3,5-Diethoxy-4-Methylphenyl)Ethyl](4-Phenylpentyl) Carbamoyl}Amino)-3,3-Difluorocyclobutane-1-Carboxylic Acid

[Chemical Formula 499]

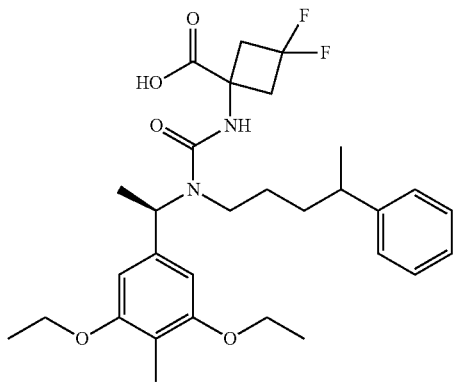 [SMILES: CCOc1cc([C@@H](C)N(CC/C=C(\C)c2ccccc2)C(=O)NC2(C(=O)O)CC(F)(F)C2)cc(OCC)c1C]

(1) Using methyl 1-amino-3,3-difluorocyclobutane-1-carboxylate hydrochloride (69.9 mg) and the compound (116 mg) obtained in Reference Example 3-4-20, the reaction was carried out in accordance with the method described in Example 1-21 (1), and methyl 1-({[(1R)-1-(3,5-diethoxy-4-methylphenyl)ethyl][(3E)-4-phenylpent-3-en-1-yl]carbamoyl}amino)-3,3-difluorocyclobutane-1-carboxylate (124 mg) was obtained as a colorless amorphous.

(2) To a solution of the compound (16 mg) obtained in (1) above in methanol (2 mL), palladium carbon (4 mg) was added, and the reaction solution was stirred at room temperature for 17 hours under a hydrogen atmosphere. Insolubles were filtered off, and the filtrate was then concentrated to afford a mixture containing methyl 1-({[(1R)-1-(3,5-diethoxy-4-methylphenyl)ethyl](4-phenylpentyl)carbamoyl}amino)-3,3-difluorocyclobutane-1-carboxylate.

(3) To a solution of the mixture obtained as described above in methanol (1 mL), a 1 mol/L aqueous sodium hydroxide solution (0.4 mL) was added, and the reaction solution was stirred at 60° C. for 1 hour. To the reaction solution, 2 mol/L hydrochloric acid was added to adjust the pH to 3, and extraction with chloroform was carried out. The organic layer was filtered through Phase Separator and concentrated. The obtained residue was purified by preparative HPLC and freeze-dried to afford the title compound (12.1 mg) as a colorless powder.

$^1$H NMR (400 MHZ, CHLOROFORM-d) δ ppm 1.00-1.79 (m, 13H) 1.18-1.28 (m, 3H) 2.08 (s, 3H) 2.22-2.54 (m, 2H) 2.55-2.73 (m, 1H) 2.92-3.14 (m, 1H) 3.14-3.44 (m, 3H) 3.84-4.06 (m, 4H) 4.61-4.79 (m, 1H) 4.79-5.33 (m, 1H) 6.37 (s, 2H) 7.02 (s, 5H).

MS ESI posi: 547 [M+H]$^+$.

Retention time: 1.080 min (method A)

The following Examples 4-41 to 4-43 were synthesized by the method described in Example 1-1 or by a method equivalent thereto, using the compounds obtained in Reference Example 3-2-1, Reference Example 3-4-20, and Reference Example 3-6-13, commercially available compounds, or compounds obtained by synthesis according to methods described in literatures or methods equivalent thereto. The structures and LCMS data of the compounds are shown in Table 54-1.

TABLE 54-1

| Example No. | Structural Formula | MS posi m/z MS nega m/z | Retention time (min) | method |
|---|---|---|---|---|
| 4-41 | | 545 [M + H]+<br>567 [M + Na]+<br>543 [M + H]+ | 1.092 | A |
| 4-42 | | 545 [M + H]+<br>567 [M + Na]+<br>513 [M + H]+ | 1.092 | A |
| 4-43 | | 545 [M + H]+<br>567 [M + Na]+<br>543 [M + H]+ | 1.024 | A |

Example 4-44

Trans-1-({[(1R)-1-(4-Acetyl-3,5-Diethoxyphenyl)Ethyl](4,4-Difluoro-4-Phenylbutyl)Carbamoyl}Amino)-3-Ethoxycyclobutane-1-Carboxylic Acid

[Chemical Formula 500]

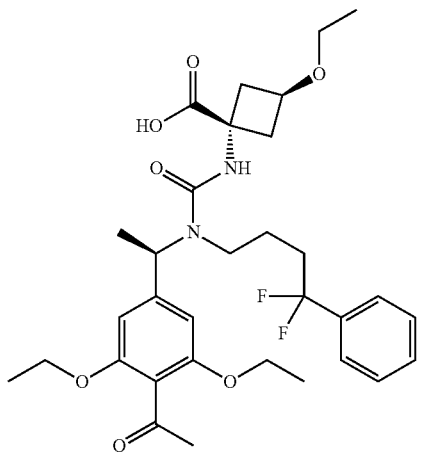

Using the compound (20.6 mg) obtained in Reference Example 4-3-1 and the compound (30 mg) obtained in Reference Example 3-4-21, the reaction was carried out in accordance with the method described in Example 1-1, and the title compound (32.1 mg) was obtained as a colorless amorphous.

$^1$H NMR (600 MHZ, METHANOL-$d_4$) δ ppm 1.18 (t, J=7.02 Hz, 3H) 1.30-1.36 (m, 6H) 1.46-1.58 (m, 5H) 2.00-2.11 (m, 2H) 2.41 (s, 3H) 2.46-2.50 (m, 1H) 2.50-2.57 (m, 3H) 2.94-3.02 (m, 1H) 3.12-3.20 (m, 1H) 3.41 (q, J=7.02 Hz, 2H) 3.94-3.99 (m, 1H) 3.99-4.08 (m, 4H) 5.36-5.44 (m, 1H) 6.57 (s, 2H) 7.40-7.44 (m, 5H).

MS ESI posi: 605 [M+H]$^+$.

MS ESI nega: 603 [M−H]$^−$.

Retention time: 0.891 min (method A)

The following Examples 4-45 to 4-96 were synthesized by the method described in Example 1-1 or Example 1-21, or by a method equivalent thereto, using the compounds obtained in Reference Example 3-2-4, Reference Examples 3-4-21 to 3-4-27, Reference Examples 3-9-2 to 3-9-3, Reference Examples 4-3-1 to 4-3-2, and Reference Examples 4-4-1 to 4-4-2, commercially available compounds, or compounds obtained by synthesis according to methods described in literatures or methods equivalent thereto. The structures and LCMS data of the compounds are shown in Tables 55-1 to 55-11. Note that the following pairs are optically active compounds:

Example 4-47 (isomer with a shorter retention time) and Example 4-48 (isomer with a longer retention time);

Example 4-52 (isomer with a shorter retention time) and Example 4-53 (isomer with a longer retention time);

Example 4-61 (isomer with a shorter retention time) and Example 4-62 (isomer with a longer retention time);

Example 4-76 (isomer with a shorter retention time) and Example 4-77 (isomer with a longer retention time); and Example 4-85 (isomer with a shorter retention time) and Example 4-86 (isomer with a longer retention time).

TABLE 55-1

| Example No. | Structural Formula | MS posi m/z MS nega m/z | Retention time (min) | method |
| --- | --- | --- | --- | --- |
| 4-45 | | 547 [M + H]+ 569 [M + Na]+ 545 [M + H]+ | 0.843 | A |

TABLE 55-1-continued

| Example No. | Structural Formula | MS posi m/z MS nega m/z | Retention time (min) | method |
|---|---|---|---|---|
| 4-46 | | 545 [M + H]+ 543 [M + H]+ | 1.195 | E |
| 4-47 | | 531 [M + OH]+ 547 [M + H]+ | 0.835 | A |
| 4-48 | | 531 [M + OH]+ 547 [M + H]+ | 0.834 | A |

TABLE 55-1-continued
| Example No. | Structural Formula | MS posi m/z MS nega m/z | Retention time (min) | method |
|---|---|---|---|---|
| 4-49 | 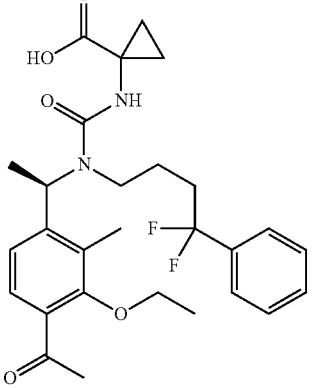 | 517 [M + H]+ 515 [M + H]+ | 0.934 | E |
TABLE 55-2
| Example No. | Structural Formula | MS posi m/z MS nega m/z | Retention time (min) | method |
|---|---|---|---|---|
| 4-50 | 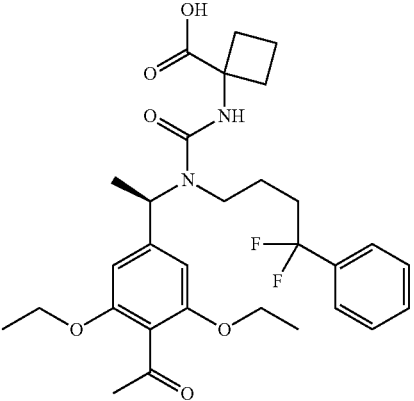 [SMILES: CCOc1cc([C@@H](C)N(CCCC(F)(F)c2ccccc2)C(=O)NC2(C(=O)O)CCC2)cc(OCC)c1C(C)=O] | 561 [M + H]+ 583 [M + Na]+ 559 [M + H]+ | 0.895 | A |
| 4-51 | 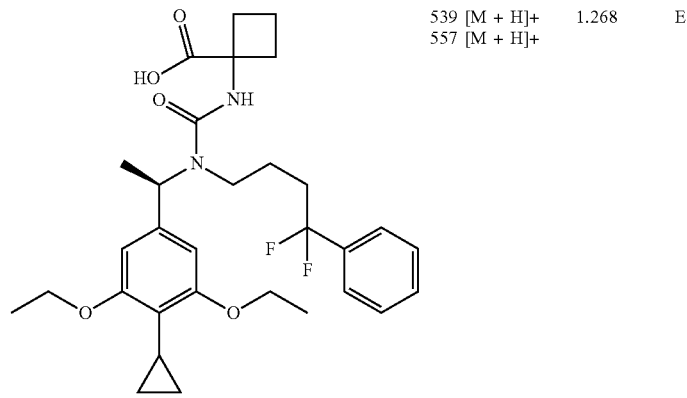 | 539 [M + H]+ 557 [M + H]+ | 1.268 | E |

TABLE 55-2-continued

| Example No. | Structural Formula | MS posi m/z MS nega m/z | Retention time (min) | method |
|---|---|---|---|---|
| 4-52 | | 545 [M + OH]+ 551 [M + H]+ | 0.891 | A |
| 4-53 | | 585 [M + Na]+ 545 [M + OH]+ 561 [M + H]+ | 0.892 | A |
| 4-54 | | 531 [M + H]+ 529 [M + H]+ | 1.023 | E |

TABLE 55-3

| Example No. | Structural Formula | MS posi m/z MS nega m/z | Retention time (min) | method |
|---|---|---|---|---|
| 4-55 | | 559 [M + H]+<br>557 [M + H]+ | 1.186 | E |
| 4-56 | | 597 [M + H]+<br>619 [M + Na]+<br>596 [M + H]+ | 0.800 | A |
| 4-57 | | 593 [M + OH]+<br>609 [M + H]+ | 1.078 | E |

TABLE 55-3-continued

| Example No. | Structural Formula | MS posi m/z<br>MS nega m/z | Retention<br>time (min) | method |
|---|---|---|---|---|
| 4-58 | | 565 [M + H]+<br>591 [M + Na]+<br>587 [M + H]+ | 1.035 | A |
| 4-59 | | 595 [M + H]+<br>593 [M + H]+ | 1.236 | E |

TABLE 55-4

| Example No. | Structural Formula | MS posi m/z<br>MA nega m/z | Retention<br>time (min) | method |
|---|---|---|---|---|
| 4-60 | | 567 [M + H]+<br>565 [M + H]+ | 1.117 | E |

TABLE 55-4-continued

| Example No. | Structural Formula | MS posi m/z MA nega m/z | Retention time (min) | method |
|---|---|---|---|---|
| 4-61 | | 575 [M + H]+ 591 [M + H]+ | 0.855 | A |
| 4-62 | | 575 [M + H]+ 591 [M + H]+ | 0.854 | A |
| 4-63 | | 561 [M + H]+ 559 [M + H]+ | 0.964 | E |

TABLE 55-4-continued
| Example No. | Structural Formula | MS posi m/z MA nega m/z | Retention time (min) | method |
|---|---|---|---|---|
| 4-64 | 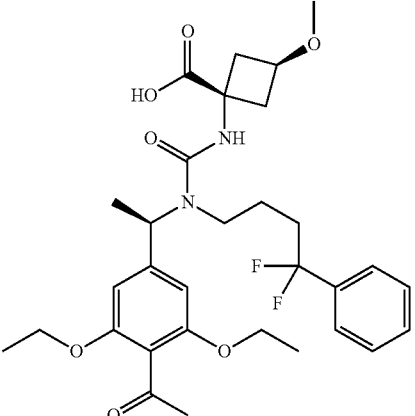 | 591 [M + H]+<br>613 [M + Na]+<br>589 [M + H]+ | 0.861 | A |
TABLE 55-5
| Example No. | Structural Formula | MS posi m/z MS nega m/z | Retention time (min) | method |
|---|---|---|---|---|
| 4-65 | 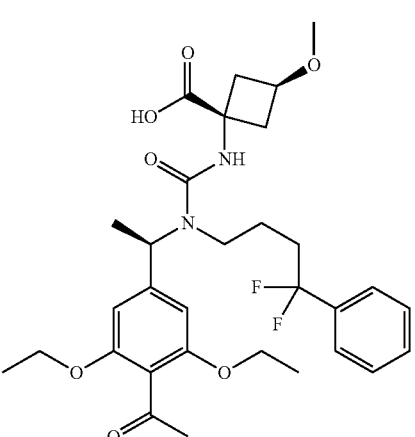 | 591 [M + H]+<br>589 [M + H]+ | 0.746 | D |
| 4-66 | 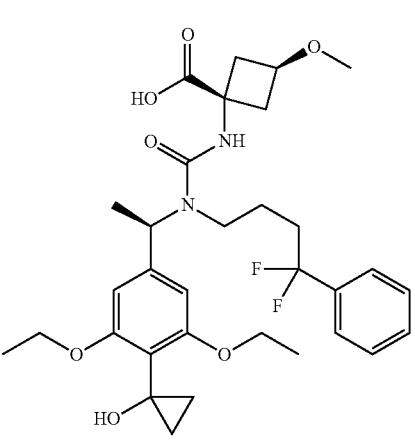 | 547 [M + H]+<br>469 [M + Na]+<br>545 [M + H]+ | 1.020 | E |

TABLE 55-5-continued
| Example No. | Structural Formula | MS posi m/z MS nega m/z | Retention time (min) | method |
|---|---|---|---|---|
| 4-67 | 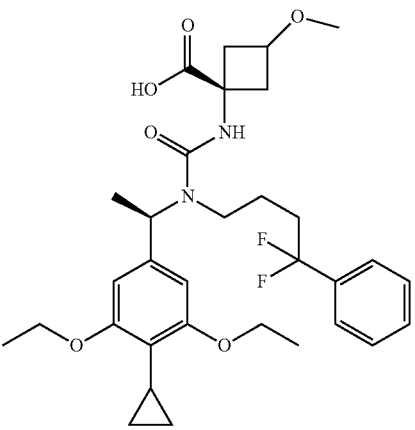 | 589 [M + H]+ 587 [M + H]+ | 1.227 | E |
| | 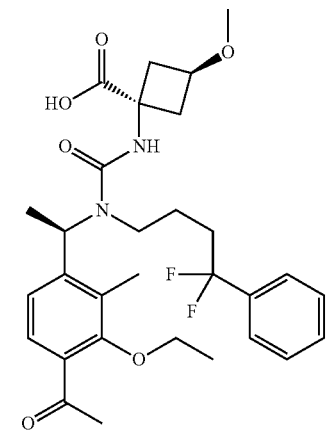 [SMILES: CCOc1c(C(C)=O)ccc([C@@H](C)N(CCCC(F)(F)c2ccccc2)C(=O)N[C@]2(C(=O)O)C[C@H](OC)C2)c1C] | 561 [M + H]+ 559 [M + H]+ | 0.711 | D |
| | 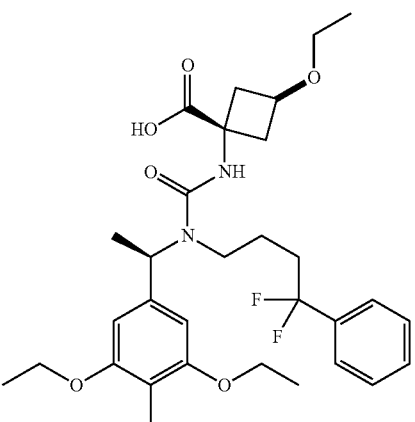 | 605 [M + H]+ 603 [M + H]+ | 0.777 | D |

TABLE 55-6

| Example No. | Structural Formula | MS posi m/z MS nega m/z | Retention time (min) | method |
|---|---|---|---|---|
| 4-70 | | 602 [M + H]+ 601 [M + H]+ | 1.264 | D |
| 4-71 | | 574 [M + H]+ 573 [M + H]+ | 0.748 | D |
| 4-72 | | 576 [M + H]+ 573 [M + H]+ | 1.013 | E |

TABLE 55-6-continued

| Example No. | Structural Formula | MS posi m/z MS nega m/z | Retention time (min) | method |
|---|---|---|---|---|
| 4-73 | | 591 [M + H]+ 613 [M + Na]+ 569 [M + H]+ | 0.839 | A |
| 4-74 | | 587 [M + H]+ 603 [M + H]+ | 0.991 | E |

40

TABLE 55-7

| Example No. | Structural Formula | MS posi m/z MS nega m/z | Retention time (min) | method |
|---|---|---|---|---|
| 4-75 | | 584 [M + H]+ 587 [M + H]+ | 1.200 | E |

TABLE 55-7-continued

| Example No. | Structural Formula | MS posi m/z MS nega m/z | Retention time (min) | method |
|---|---|---|---|---|
| 4-76 | | 575 [M + H]+ 591 [M + H]+ | 0.852 | A |
| 4-77 | | 575 [M + H]+ 591 [M + H]+ | 0.831 | A |
| 4-78 | | 561 [M + H]+ 559 [M + H]+ | 0.926 | D |

TABLE 55-7-continued

| Example No. | Structural Formula | MS posi m/z MS nega m/z | Retention time (min) | method |
|---|---|---|---|---|
| 4-79 | | 617 [M + H]+ 569 [M + Na]+ 545 [M + H]+ | 0.849 | |

TABLE 55-8

| Example No. | Structural Formula | MS posi m/z MS nega m/z | Retention time (min) | method |
|---|---|---|---|---|
| 4-80 | | 545 [M + H]+ 543 [M + H]+ | 1.207 | E |
| 4-81 | | 591 [M + H]+ 583 [M + Na]+ 569 [M + H]+ | 0.900 | A |

TABLE 55-8-continued

| Example No. | Structural Formula | MS posi m/z<br>MS nega m/z | Retention<br>time (min) | method |
|---|---|---|---|---|
| 4-82 | | 559 [M + H]+<br>557 [M + H]+ | 1.713 | E |
| 4-83 | | 559 [M + H]+<br>567 [M + H]+ | 1.158 | F |
| 4-84 | | 597 [M + H]+<br>619 [M + Na]+<br>595 [M + H]+ | 1.182 | B |

TABLE 55-9

| Example No. | Structural Formula | MS posi m/z MZ nega m/z | Retention time (min) | method |
|---|---|---|---|---|
| 4-85 | | 621 [M + Na]+<br>581 [M + OH]+<br>597 [M + H]+ | 0.900 | A |
| 4-86 | | 581 [M + OH]+<br>597 [M + H]+ | 0.895 | A |
| 4-87 | | 590 [M + H]+<br>593 [M + H]+ | 1.268 | E |

TABLE 55-9-continued
| Example No. | Structural Formula | MS posi m/z MZ nega m/z | Retention time (min) | method |
|---|---|---|---|---|
| 4-88 | 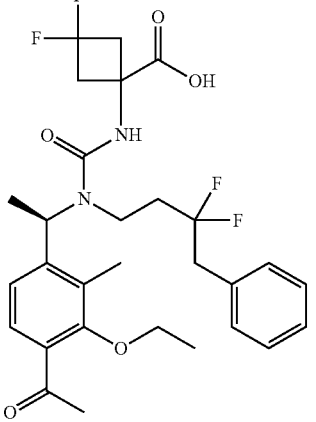 | 567 [M + H]+ 565 [M + H]+ | 1.373 | D |
| 4-89 | 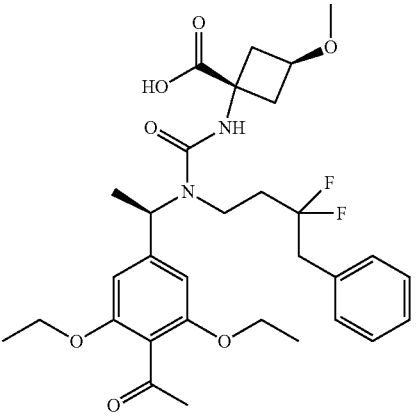 [SMILES: CCOc1cc([C@@H](C)N(CCC(F)(F)Cc2ccccc2)C(=O)N[C@]2(C(=O)O)C[C@@H](OC)C2)cc(OCC)c1C(C)=O] | 591 [M + H]+ 613 [M + Na]+ 559 [M + H]+ | 0.847 | A |
TABLE 55-10
| Example No. | Structural Formula | MS posi m/z MS nega m/z | Retention time (min) | method |
|---|---|---|---|---|
| 4-90 | 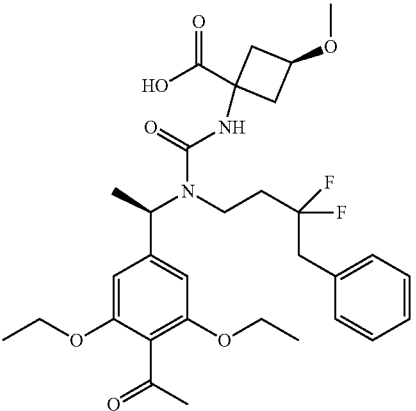 | 591 [M + H]+ 559 [M + H]+ | 0.750 | D |

TABLE 55-10-continued

| Example No. | Structural Formula | MS posi m/z MS nega m/z | Retention time (min) | method |
|---|---|---|---|---|
| 4-91 | | 589 [M + H]+ 587 [M + H]+ | 1.236 | E |
| 4-92 | | 605 [M + H]+ 627 [M + Na]+ 603 [M + H]+ | 0.897 | A |
| 4-93 | | 605 [M + H]+ 603 [M + H]+ | 0.782 | D |

TABLE 55-10-continued

| Example No. | Structural Formula | MS posi m/z MS nega m/z | Retention time (min) | method |
|---|---|---|---|---|
| 4-94 | | 603 [M + H]+ 601 [M + H]+ | 1.212 | D |

TABLE 55-11

| Example No. | Structural Formula | MS posi m/z MS nega m/z | Retention time (min) | method |
|---|---|---|---|---|
| 4-95 | | 601 [M + H]+ 613 [M + Na]+ 589 [M + H]+ | 1.059 | B |
| 4-96 | | 589 [M + H]+ 587 [M + H]+ | 1.211 | E |

Example 4-97

Trans-1-[([(1R)-1-(4-Acetyl-3,5-Diethoxyphenyl)Ethyl]{2-[(1S)-1-Phenylethoxy]Ethyl}Carbamoyl)Amino]-3-Ethoxycyclobutane-1-Carboxylic Acid

[Chemical Formula 501]

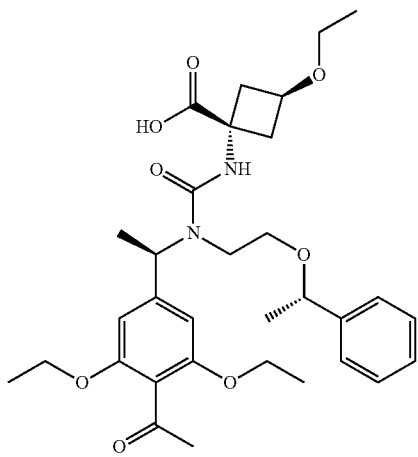

Using the compound (23.3 mg) obtained in Reference Example 4-3-1 and the compound (29.7 mg) obtained in Reference Example 3-4-28, the reaction was carried out in accordance with the method described in Example 1-1, and the title compound (30.4 mg) was obtained as a colorless amorphous.

$^1$H NMR (600 MHZ, METHANOL-$d_4$) δ ppm 1.13-1.20 (m, 3H) 1.27-1.51 (m, 12H) 2.34-2.60 (m, 7H) 3.12-3.37 (m, 4H) 3.37-3.46 (m, 3H) 3.91-4.14 (m, 5H) 5.47-5.56 (m, 1H) 6.51-6.62 (m, 2H) 7.22-7.38 (m, 5H).

MS ESI posi: 585 [M+H]$^+$, 607 [M+Na]$^+$.

MS ESI nega: 583 [M−H]$^-$.

Retention time: 0.924 min (method A)

Note that the title compound can also be obtained by the method shown below.

(1) To a solution of the compound (672 mg) obtained in Reference Example 4-3-1 in tetrahydrofuran (15 mL), N,N-diisopropylethylamine (2.18 mL) was added, and the reaction solution was stirred at room temperature for 5 minutes. The reaction solution was ice-cooled, a solution of 4-nitrophenyl chloroformate (605 mg) in tetrahydrofuran (5 mL) was slowly added thereto, and the reaction solution was stirred at room temperature for 1 hour. The reaction solution was ice-cooled, a solution of the compound (1.00 g) obtained in Reference Example 3-4-28 in tetrahydrofuran (5 mL) was added thereto, and the reaction solution was stirred at 60° C. for 30 minutes and overnight while bringing it back to room temperature. A saturated aqueous sodium bicarbonate solution was added to the reaction solution, which was then extracted with ethyl acetate. The organic layer was washed with a brine and dried over anhydrous magnesium sulfate. After filtering off the desiccating agent, the filtrate was concentrated. Ethyl acetate was added to the obtained residue, and the precipitated solid was filtered off to afford ethyl trans-1-[([(1R)-1-(4-acetyl-3,5-diethoxyphenyl)ethyl]{2-[(1S)-1-phenylethoxy]ethyl}carbamoyl)amino]-3-ethoxycyclobutane-1-carboxylate (648 mg) as a colorless powder.

(2) Ethanol (3.4 mL) was added to the compound (422 mg) obtained in (1) above, which was then dissolved at 60° C. A 3 mol/L aqueous potassium hydroxide solution (689 μL) was added thereto, and the reaction solution was stirred at room temperature for 3 days. The reaction solution was ice-cooled, and a 0.5 mol/L aqueous citric acid solution (3 mL) was added thereto (the pH was 3 to 4), followed by concentration. Water was added to the obtained residue, and the precipitated solid was filtered off to afford the title compound (371 mg) as a colorless powder. When the obtained powder was subjected to thermogravimetry-differential thermal analysis (TG/DTA), an endothermic peak was observed at 95.5° C.

The following Examples 4-98 to 4-163 were synthesized by the method described in Example 1-1, Example 1-21, Example 1-40, or Example 1-46, or by a method equivalent thereto, using the compounds obtained in Reference Example 1-5-2, Reference Example 3-1-44, Reference Examples 3-4-28 to 3-4-35, Reference Examples 3-4-46 to 3-4-48, Reference Example 3-5-1, Reference Examples 3-9-4 to 3-9-5, Reference Examples 4-3-1 to 4-3-2, and Reference Examples 4-4-1 to 4-4-2, commercially available compounds, or compounds obtained by synthesis according to methods described in literatures or methods equivalent thereto. The structures and LCMS data of the compounds are shown in Tables 56-1 to 56-14. Note that the following pairs are optically active compounds:

Example 4-103 (isomer with a shorter retention time) and Example 4-104 (isomer with a longer retention time);

Example 4-123 (isomer with a shorter retention time) and Example 4-124 (isomer with a longer retention time);

Example 4-125 (isomer with a shorter retention time) and Example 4-126 (isomer with a longer retention time);

Example 4-133 (isomer with a shorter retention time) and Example 4-134 (isomer with a longer retention time);

Example 4-135 (isomer with a shorter retention time) and Example 4-136 (isomer with a longer retention time); and Example 4-143 (isomer with a shorter retention time) and Example 4-144 (isomer with a longer retention time).

TABLE 56-1

| Example No. | Structural Formula | MS posi m/z MS nega m/z | Retention time (min) | method |
|---|---|---|---|---|
| 4-98 | | 555 [M + H]+<br>557 [M + Na]+<br>553 [M + H]+ | 0.963 | A |
| 4-99 | | 558 [M + H]+<br>563 [M + H]+ | 1.290 | E |
| 4-100 | | 513 [M + H]+<br>535 [M + Na]+<br>511 [M + H]+ | 0.881 | A |

TABLE 56-1-continued

| Example No. | Structural Formula | MS posi m/z MS nega m/z | Retention time (min) | method |
|---|---|---|---|---|
| 4-101 | | 527 [M + H]+ 615 [M + Na]+ 525 [M + H]+ | 0.891 | A |
| 4-102 | | 563 [M + H]+ 583 [M + Na]+ 561 [M + H]+ | 1.119 | B |

TABLE 56-2

| Example No. | Structural Formula | MS posi m/z MS nega m/z | Retention time (min) | method |
|---|---|---|---|---|
| 4-103 | | 587 [M + H]+ 547 [M + OH]+ 563 [M + H]+ | 0.885 | A |

TABLE 56-2-continued

| Example No. | Structural Formula | MS posi m/z MS nega m/z | Retention time (min) | method |
|---|---|---|---|---|
| 4-104 | | 587 [M + H]+ 547 [M + Na]+ 563 [M + H]+ | 0.885 | A |
| 4-105 | | 536 [M + H]+ 537 [M + Na]+ 543 [M + H]+ | 1.021 | A |
| 4-106 | | 533 [M + H]+ 555 [M + Na]+ 531 [M + H]+ | 1.174 | D |

TABLE 56-2-continued

| Example No. | Structural Formula | MS posi m/z<br>MS nega m/z | Retention<br>time (min) | method |
|---|---|---|---|---|
| 4-107 | | 557 [M + H]+<br>556 [M + H]+ | 0.796 | A |

TABLE 56-3

| Example No. | Structural Formula | MS posi m/z<br>MS nega m/z | Retention<br>time (min) | method |
|---|---|---|---|---|
| 4-108 | | 557 [M + H]+<br>579 [M + Na]+<br>555 [M + H]+ | 0.797 | A |
| 4-109 | | 571 [M + H]+<br>593 [M + Na]+<br>569 [M + H]+ | 0.891 | A |

TABLE 56-3-continued

| Example No. | Structural Formula | MS posi m/z MS nega m/z | Retention time (min) | method |
|---|---|---|---|---|
| 4-110 | | 557 [M + H]+<br>579 [M + Na]+<br>555 [M + H]+ | 0.832 | A |
| 4-111 | | 527 [M + H]+<br>549 [M + Na]+<br>525 [M + H]+ | 0.866 | A |
| 4-112 | | 525 [M + H]+<br>523 [M + H]+ | 1.216 | E |

TABLE 56-4

| Example No. | Structural Formula | MS posi m/z MS nega m/z | Retention time (min) | method |
|---|---|---|---|---|
| 4-113 | | 497 [M + H]+<br>495 [M + H]+ | 0.955 | E |
| 4-114 | | 541 [M + H]+<br>563 [M + Na]+<br>539 [M + H]+ | 0.931 | A |
| 4-115 | | 539 [M + H]+<br>537 [M + H]+ | 1.295 | E |

TABLE 56-4-continued

| Example No. | Structural Formula | MS posi m/z MS nega m/z | Retention time (min) | method |
|---|---|---|---|---|
| 4-116 | | 511 [M + H]+<br>509 [M + H]+ | 1.055 | E |
| 4-117 | | 577 [M + H]+<br>599 [M + Na]+<br>575 [M + H]+ | 0.933 | A |

40

TABLE 56-5

| Example No. | Structural Formula | MS posi m/z MS nega m/z | Retention time (min) | method |
|---|---|---|---|---|
| 4-118 | | 575 [M + H]+<br>597 [M + Na]+<br>573 [M + H]+ | 1.117 | A |

TABLE 56-5-continued

| Example No. | Structural Formula | MS posi m/z MS nega m/z | Retention time (min) | method |
|---|---|---|---|---|
| 4-119 | | 547 [M + H]+ 569 [M + Na]+ 545 [M + H]+ | 1.165 | B |
| 4-120 | | 555 [M + H]+ 553 [M + H]+ | 0.760 | D |
| 4-121 | | 571 [M + H]+ 593 [M + Na]+ 569 [M + H]+ | 0.887 | A |

TABLE 56-5-continued

| Example No. | Structural Formula | MS posi m/z MS nega m/z | Retention time (min) | method |
|---|---|---|---|---|
| 4-122 | | 571 [M + H]+ 569 [M + H]+ | 0.776 | D |

TABLE 56-6

| Example No. | Structural Formula | MS posi m/z MS nega m/z | Retention time (min) | method |
|---|---|---|---|---|
| 4-123 | | 595 [M + Na]+ 555 [M + OH]+ 571 [M + H]+ | 0.888 | A |
| 4-124 | | 555 [M + OH]+ 571 [M + H]+ | 0.887 | A |

TABLE 56-6-continued

| Example No. | Structural Formula | MS posi m/z MS nega m/z | Retention time (min) | method |
|---|---|---|---|---|
| 4-125 | | 555 [M + OH]+ 571 [M + H]+ | 0.884 | A |
| 4-126 | | 555 [M + OH]+ 571 [M + H]+ | 0.884 | A |
| 4-127 | | 567 [M + OH]+ 583 [M + H]+ | 1.044 | E |

TABLE 56-7

| Example No. | Structural Formula | MS posi m/z<br>MS nega m/z | Retention time (min) | method |
|---|---|---|---|---|
| 4-128 | | 569 [M + H]+<br>591 [M + Na]+<br>567 [M + H]+ | 1.009 | A |
| 4-129 | | 569 [M + H]+<br>567 [M + H]+ | 0.933 | D |
| 4-130 | | 541 [M + H]+<br>539 [M + H]+ | 0.990 | E |

TABLE 56-7-continued

| Example No. | Structural Formula | MS posi m/z MS nega m/z | Retention time (min) | method |
|---|---|---|---|---|
| 4-131 | | 541 [M + H]+ 539 [M + H]+ | 0.733 | D |
| 4-132 | | 585 [M + H]+ 583 [M + H]+ | 0.812 | D |

TABLE 56-8

| Example No. | Structural Formula | MS posi m/z MS nega m/z | Retention time (min) | method |
|---|---|---|---|---|
| 4-133 | | 609 [M + Na]+ 569 [M + OH]+ 585 [M + H]+ | 0.930 | A |

TABLE 56-8-continued

| Example No. | Structural Formula | MS posi m/z MS nega m/z | Retention time (min) | method |
|---|---|---|---|---|
| 4-134 | | 609 [M + Na]+ 569 [M + OH]+ 585 [M + H]+ | 0.929 | A |
| 4-135 | | 569 [M + H]+ 585 [M + H]+ | 0.921 | A |
| 4-136 | | 569 [M + OH]+ 585 [M + H]+ | 0.921 | A |

TABLE 56-8-continued

| Example No. | Structural Formula | MS posi m/z<br>MS nega m/z | Retention<br>time (min) | method |
|---|---|---|---|---|
| 4-137 | | 581 [M + H]+<br>597 [M + H]+ | 1.093 | E |

TABLE 56-9

| Example No. | Structural Formula | MS posi m/z<br>MS nega m/z | Retention<br>time (min) | method |
|---|---|---|---|---|
| 4-138 | | 583 [M + H]+<br>581 [M + H]+ | 1.287 | E |
| 4-139 | | 583 [M + H]+<br>581 [M + H]+ | 0.966 | D |

TABLE 56-9-continued

| Example No. | Structural Formula | MS posi m/z MS nega m/z | Retention time (min) | method |
|---|---|---|---|---|
| 4-140 | | 555 [M + H]+ 553 [M + H]+ | 1.044 | E |
| 4-141 | | 555 [M + H]+ 553 [M + H]+ | 0.776 | D |
| 4-142 | | 571 [M + H]+ 593 [M + Na]+ 569 [M + H]+ | 0.863 | A |

TABLE 56-10

| Example No. | Structural Formula | MS posi m/z MS nega m/z | Retention time (min) | method |
|---|---|---|---|---|
| 4-143 | | 595 [M +Na]+<br>555 [M + OH]+<br>591 [M + H]+ | 0.860 | A |
| 4-144 | | 563 [M + OH]+<br>571 [M + H]+ | 0.860 | A |
| 4-145 | | 583 [M + H]+<br>562 [M + H]+ | 1.222 | E |

TABLE 56-10-continued

| Example No. | Structural Formula | MS posi m/z MS nega m/z | Retention time (min) | method |
|---|---|---|---|---|
| 4-146 | | 511 [M + H]+ 509 [M + H]+ | 0.955 | E |
| 4-147 | | 497 [M + H]+ 495 [M + H]+ | 0.956 | E |

TABLE 56-11

| Example No. | Structural Formula | MS posi m/z MS nega m/z | Retention time (min) | method |
|---|---|---|---|---|
| 4-148 | | 511 [M + H]+ 509 [M + H]+ | 1.052 | E |

TABLE 56-11-continued

| Example No. | Structural Formula | MS posi m/z MS nega m/z | Retention time (min) | method |
|---|---|---|---|---|
| 4-149 | | 577 [M + H]+ 599 [M + Na]+ 575 [M + H]+ | 0.922 | A |
| 4-150 | | 576 [M + H]+ 597 [M + Na]+ 573 [M + H]+ | 1.038 | A |
| 4-151 | | 547 [M + H]+ 569 [M + Na]+ 545 [M + H]+ | 1.252 | B |

TABLE 56-11-continued

| Example No. | Structural Formula | MS posi m/z MS nega m/z | Retention time (min) | method |
|---|---|---|---|---|
| 4-152 | | 569 [M + H]+ 591 [M + Na]+ 567 [M + H]+ | 1.027 | A |

TABLE 56-12

| Example No. | Structural Formula | MS posi m/z MS nega m/z | Retention time (min) | method |
|---|---|---|---|---|
| 4-153 | | 571 [M + H]+ 593 [M + Na]+ 569 [M + H]+ | 0.582 | A |
| 4-154 | | 541 [M + H]+ 539 [M + H]+ | 0.984 | E |

TABLE 56-12-continued

| Example No. | Structural Formula | MS posi m/z MS nega m/z | Retention time (min) | method |
|---|---|---|---|---|
| 4-155 | | 541 [M + H]+<br>539 [M + H]+ | 0.739 | D |
| 4-156 | | 585 [M + H]+<br>607 [M + Na]+<br>583 [M + H]+ | 0.916 | A |
| 4-157 | | 555 [M + H]+<br>553 [M + H]+ | 1.040 | E |

TABLE 56-13

| Example No. | Structural Formula | MS posi m/z MS nega m/z | Retention time (min) | method |
|---|---|---|---|---|
| 4-158 | | 555 [M + H]+ 553 [M + H]+ | 0.773 | D |
| 4-159 | | 541 [M + H]+ 539 [M + H]+ | 0.946 | E |
| 4-160 | | 589 [M + H]+ 611 [M + Na]+ 587 [M + H]+ | 1.047 | A |

TABLE 56-13-continued

| Example No. | Structural Formula | MS posi m/z MS nega m/z | Retention time (min) | method |
|---|---|---|---|---|
| 4-161 | | 549 [M + H]+ | 1.317 | E |
| 4-162 | | 548 [M + H]+ 546 [M + H]+ | 0.892 | A |

TABLE 56-14

| Example No. | Structural Formula | MS posi m/z MS nega m/z | Retention time (min) | method |
|---|---|---|---|---|
| 4-163 | | 548 [M + H]+ 570 [M + Na]+ 546 [M + H]+ | 0.826 | A |

Note that the sodium salt of cis-1-[([(1R)-1-(4-cyclopropyl-3,5-diethoxyphenyl)ethyl]{2-[(1S)-1-phenylethoxy]ethyl}carbamoyl)amino]-3-methoxycyclobutane-1-carboxylic acid obtained in Example 4-129 can be obtained by the method shown below.

(1) To a solution of the compound (49.8 mg) obtained in Example 4-129 in acetonitrile (0.5 mL), a 1 mol/L aqueous sodium hydroxide solution (87.6 μL) and water (0.5 mL) were added, and the reaction solution was freeze-dried to afford a yellow amorphous (53.7 mg).

(2) n-Heptane (0.2 mL) and tetrahydrofuran (10 μL) were added to the compound (39 mg) obtained in (1) above, which was then dissolved at 45° C., and the reaction solution was stirred overnight while bringing it back to room temperature. n-Heptane (1 mL) was added to the solution, and the precipitated solid was filtered off to afford a colorless powder (23 mg). When the obtained powder was subjected to thermogravimetry-differential thermal analysis (TG/DTA), an endothermic peak was observed at 77.0° C.

In addition, trans-1-[([(1R)-1-(4-cyclopropyl-3,5-diethoxyphenyl)ethyl]{2-[(1S)-1-phenylethoxy]ethyl}carbamoyl)amino]-3-ethoxycyclobutane-1-carboxylic acid obtained in Example 4-138 can also be obtained by the method shown below.

(1) Using the compound (75.5 mg) obtained in Reference Example 4-3-1 and the compound (114 mg) obtained in Reference Example 3-4-32, the reaction was carried out in accordance with the method described in Example 4-97 (1), and ethyl trans-1-[([(1R)-1-(4-cyclopropyl-3,5-diethoxyphenyl)ethyl]{2-[(1S)-1-phenylethoxy]ethyl}carbamoyl)amino]-3-ethoxycyclobutane-1-carboxylate (145 mg) was obtained as a colorless powder.

(2) Ethanol (3.6 mL) was added to the compound (145 mg) obtained in (1) above, which was then dissolved at 60° C. A 3 mol/L aqueous potassium hydroxide solution (237 μL) was added thereto, and the reaction solution was stirred at room temperature for 18 hours, at 50° C. for 1 hour, and at 60° C. for 1 hour. The reaction solution was ice-cooled, and a 0.5 mol/L aqueous citric acid solution (1 mL) was added thereto. The reaction solution was concentrated, and water (10 mL) was added to the obtained residue (the pH was 4), which was then stirred at room temperature for 15 minutes. The precipitated solid was filtered off to afford a colorless powder (121 mg). When the obtained powder was subjected to thermogravimetry-differential thermal analysis (TG/DTA), an endothermic peak was observed at 86.9° C.

Furthermore, the potassium salt of cis-1-[([(1R)-1-(4-cyclopropyl-3,5-diethoxyphenyl)ethyl]{2-[(1S)-1-phenylethoxy]ethyl}carbamoyl)amino]-3-ethoxycyclobutane-1-carboxylic acid obtained in Example 4-139 can be obtained by the method shown below.

(1) To a solution of the compound (32.1 mg) obtained in Example 4-139 in acetonitrile (0.5 mL), a 3 mol/L aqueous potassium hydroxide solution (18.4 μL) and water (0.5 mL) were added, and the reaction solution was freeze-dried to afford a colorless amorphous (36.4 mg).

(2) Tetrahydrofuran (10 μL) and n-heptane (200 μL) were added to the compound (27 mg) obtained in (1) above, and the reaction solution was stirred at room temperature. Tetrahydrofuran (50 μL) and n-heptane (1 mL) were added to the solution and dissolved at 60° C. The reaction solution was stirred at room temperature for 16.5 hours. The precipitated solid was filtered off to afford a colorless powder (22 mg). When the obtained powder was subjected to thermogravimetry-differential thermal analysis (TG/DTA), an endothermic peak was observed at 81.1° C.

The following Examples 4-164 to 4-181 were synthesized by the method described in Example 1-1 or by a method equivalent thereto, using the compounds obtained in Reference Examples 3-4-50 to 3-4-51, Reference Example 3-6-21, Reference Examples 3-6-23 to 3-6-25, Reference Examples 3-6-31 to 3-6-33, and Reference Example 4-3-1, commercially available compounds, or compounds obtained by synthesis according to methods described in literatures or methods equivalent thereto. The structures and LCMS data of the compounds are shown in Tables 56-15 to 56-18.

TABLE 56-15

| Example No. | Structural Formula | MS posi m/z MS nega m/z | Retention time (min) | method |
|---|---|---|---|---|
| 4-164 | 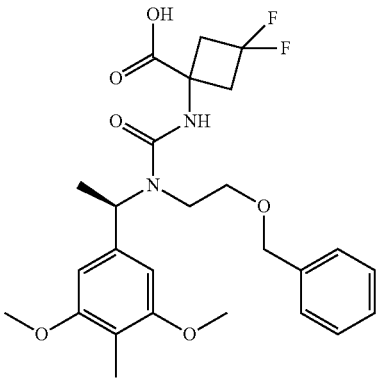 [SMILES: COc1cc([C@@H](C)N(CCOCc2ccccc2)C(=O)NC2(C(=O)O)CC(F)(F)C2)cc(OC)c1C] | 507 [M + H]+<br>529 [M + Na]+<br>505 [M + H]+ | 0.884 | A |

TABLE 56-15-continued

| Example No. | Structural Formula | MS posi m/z MS nega m/z | Retention time (min) | method |
|---|---|---|---|---|
| 4-165 | | 514 [M + H]+ 537 [M + Na]+ 512 [M + H]+ | 0.874 | A |
| 4-166 | | 509 [M + H]+ 507 [M + H]+ | 0.937 | A |
| 4-167 | | 545 [M + H]+ 543 [M + H]+ | 0.930 | D |

TABLE 56-15-continued

| Example No. | Structural Formula | MS posi m/z MS nega m/z | Retention time (min) | method |
|---|---|---|---|---|
| 4-168 | | 519 [M + H]+ 517 [M + H]+ | 0.886 | D |

TABLE 56-16

| Example No. | Structural Formula | MS posi m/z MS nega m/z | Retention time (min) | method |
|---|---|---|---|---|
| 4-169 | | 575 [M + H]+ 571 [M + H]+ | 0.912 | D |
| 4-170 | | 563 [M + H]+ 561 [M + H]+ | 0.938 | D |

TABLE 56-16-continued

| Example No. | Structural Formula | MS posi m/z MS nega m/z | Retention time (min) | method |
| --- | --- | --- | --- | --- |
| 4-171 | | 509 [M + H]+<br>507 [M + H]+ | 0.961 | D |
| 4-172 | | 545 [M + H]+<br>543 [M + H]+ | 0.943 | D |
| 4-173 | | 553 [M + H]+<br>551 [M + H]+ | 0.952 | D |

TABLE 56-17

| Example No | Structural Formula | MS posi m/z MS nega m/z | Retention time (min) | method |
|---|---|---|---|---|
| 4-174 | | 609 [M + H]+ 631 [M + Na]+ 607 [M + H]+ | 0.947 | A |
| 4-175 | | 645 [M + H]+ 667 [M + Na]+ 642 [M + H]+ | 0.832 | A |
| 4-176 | | 609 [M + H]+ 631 [M + Na]+ 607 [M + H]+ | 0.963 | A |

TABLE 56-17-continued

| Example No | Structural Formula | MS posi m/z MS nega m/z | Retention time (min) | method |
|---|---|---|---|---|
| 4-177 | | 645 [M + H]+<br>667 [M + Na]+<br>643 [M + H]+ | 0.939 | A |
| 4-178 | | 583 [M + H]+<br>565 [M + Na]+<br>581 [M + H]+ | 1.037 | A |

TABLE 56-18

| Example No. | Structural Formula | MS posi m/z MS nega m/z | Retention time (min) | method |
|---|---|---|---|---|
| 4-179 | | 569 [M + H]+<br>571 [M + H]+ | 1.037 | A |

TABLE 56-18-continued

| Example No. | Structural Formula | MS posi m/z MS nega m/z | Retention time (min) | method |
|---|---|---|---|---|
| 4-180 | | 543 [M + H]+ 565 [M + Na]+ 541 [M + H]+ | 1.034 | A |
| 4-181 | | 579 [M + H]+ 601 [M + Na]+ 577 [M + H]+ | 1.016 | A |

Example 5-1

1-({[1-(3,5-Diethoxyphenyl)Ethyl](4-Phenylbutyl) Carbamoyl}Amino)-3,3-Difluorocyclobutane-1-Carboxylic Acid

[Chemical Formula 502]

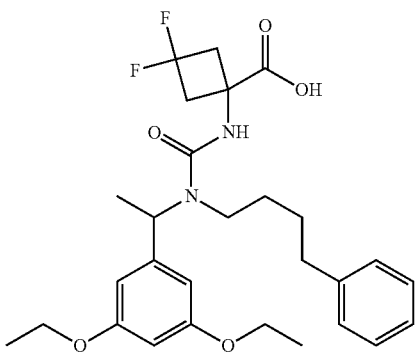

(1) Using methyl 1-amino-3,3-difluorocyclobutane-1-carboxylate hydrochloride (101 mg) and the compound (132 mg) obtained in Reference Example 3-7-1, the reaction and post treatment were carried out in accordance with the method described in Example 1-21 (1), and purification by preparative HPLC was carried out to afford methyl 1-({[1-(3,5-diethoxyphenyl)ethyl](4-phenylbutyl) carbamoyl}amino)-3,3-difluorocyclobutane-1-carboxylate (110 mg) as a colorless oily substance.

(2) Using the compound (15 mg) obtained in (1) above, the reaction was carried out in accordance with the method described in Example 1-21 (3), and the title compound (13 mg) was obtained as a colorless oily substance.

$^1$H NMR (600 MHz, CHLOROFORM-d) δ ppm 1.41 (t, J=7.02 Hz, 6H) 1.49-1.56 (m, 3H) 1.56-1.65 (m, 4H) 2.39-2.55 (m, 2H) 2.56-2.65 (m, 2H) 3.03-3.18 (m, 1H) 3.21-3.36 (m, 3H) 3.98 (q, J=7.02 Hz, 4H) 4.74-5.33 (m, 1H) 4.81-4.89 (m, 1H) 6.37-6.39 (m, 1H) 6.39-6.41 (m, 2H) 7.14 (d, J=7.20 Hz, 2H) 7.19 (t, J=7.20 Hz, 1H) 7.28 (t, J=7.20 Hz, 2H).

MS ESI/APCI Multi posi: 519 [M+H]$^+$.
MS ESI/APCI Multi nega: 517 [M−H]$^-$.
Retention time: 1.260 min (method E)

The following Examples 5-2 to 5-25 were synthesized by the method described in Example 1-1 or Example 1-40, or by a method equivalent thereto, using the compounds obtained in Reference Examples 3-1-45 to 3-1-65 and Reference Example 3-9-7, commercially available compounds, or compounds obtained by synthesis according to methods described in literatures or methods equivalent thereto. The structures and LCMS data of the compounds are shown in Tables 57-1 to 57-5.

TABLE 57-1

| Example No. | Structural Formula | MS posi m/z MS nega m/z | Retention time (min) | method |
|---|---|---|---|---|
| 5-2 | | 429 [M + H]+ 451 [M + Na]+ 427 [M + H]+ | 1.343 | B |
| 5-3 | | 475 [M + H]+ 473 [M + H]+ | 1.185 | E |
| 5-4 | | 473 [M + H]+ 495 [M + Na]+ 471 [M + H]+ | 1.124 | B |
| 5-5 | | 456 [M + H]+ 454 [M + H]+ | 0.812 | D |

TABLE 57-1-continued
| Example No. | Structural Formula | MS posi m/z MS nega m/z | Retention time (min) | method |
|---|---|---|---|---|
| 5-6 | 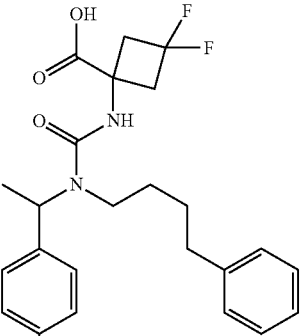 | 449 [M + H]+<br>471 [M +Na]+<br>447 [M + H]+ | 1.220 | B |
TABLE 57-2
| Example No. | Structural Formula | MS posi m/z MS nega m/z | Retention time (min) | method |
|---|---|---|---|---|
| 5-7 | 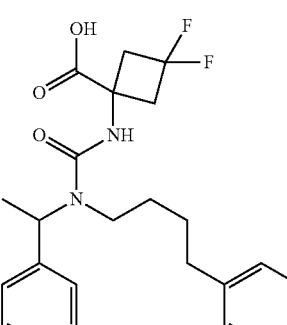 | 445 [M + H]+<br>461 [M + Na]+<br>443 [M + H]+ | 1.029 | A |
| 5-8 | | 517 [M + H]+<br>515 [M + H]+ | 1.020 | A |

TABLE 57-2-continued
| Example No. | Structural Formula | MS posi m/z MS nega m/z | Retention time (min) | method |
|---|---|---|---|---|
| 5-9 | 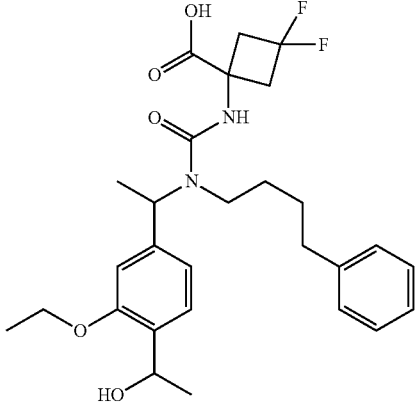 [SMILES: CCOc1cc(C(C)N(CCCCc2ccccc2)C(=O)NC2(C(=O)O)CC(F)(F)C2)ccc1C(C)O] | 601 [M + Na]+ 541 [M + OH]+ 617 [M + H]+ | 0.968 | A |
| 5-10 | 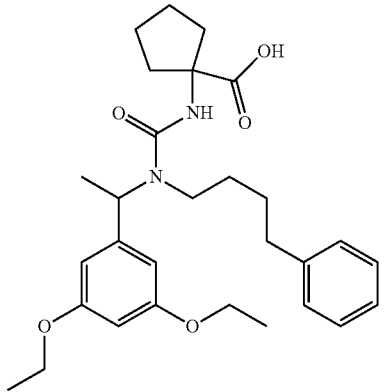 [SMILES: CCOc1cc(OCC)cc(C(C)N(CCCCc2ccccc2)C(=O)NC2(C(=O)O)CCCC2)c1] | 497 [M + H]+ | 1.328 | B |
| 5-11 | 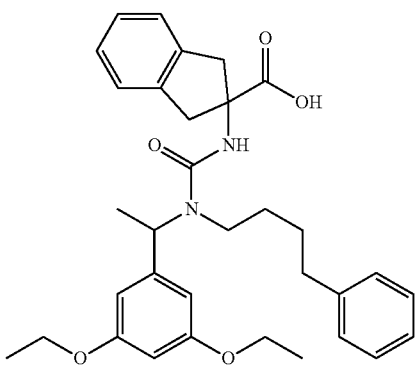 [SMILES: CCOc1cc(OCC)cc(C(C)N(CCCCc2ccccc2)C(=O)NC2(C(=O)O)Cc3ccccc3C2)c1] | 545 [M + H]+ 543 [M + H]+ | 1.339 | B |

TABLE 57-3

| Example No. | Structural Formula | MS posi m/z MS nega m/z | Retention time (min) | method |
|---|---|---|---|---|
| 5-12 | | 645 [M + H]+ 543 [M + H]+ | 1.313 | E |
| 5-13 | | 489 [M + H]+ | 1.192 | B |
| 5-14 | | 505 [M + H]+ 527 [M + Na]+ 503 [M + H]+ | 0.971 | A |
| 5-15 | | 517 [M + H]+ 539 [M +Na ]+ 515 [M + H]+ | 1.009 | A |

TABLE 57-3-continued

| Example No. | Structural Formula | MS posi m/z MS nega m/z | Retention time (min) | method |
|---|---|---|---|---|
| 5-16 | | 519 [M + H]+ 517 [M + H]+ | | E |

TABLE 57-4

| Example No. | Structural Formula | MS posi m/z MS nega m/z | Retention time (min) | method |
|---|---|---|---|---|
| 5-17 | | 533 [M + H]+ 555 [M + Na]+ 531 [M + H]+ | 1.345 | B |
| 5-18 | | 547 [M + H]+ 545 [M + H]+ | 1.342 | E |

TABLE 57-4-continued
| Example No. | Structural Formula | MS posi m/z MS nega m/z | Retention time (min) | method |
|---|---|---|---|---|
| 5-19 | 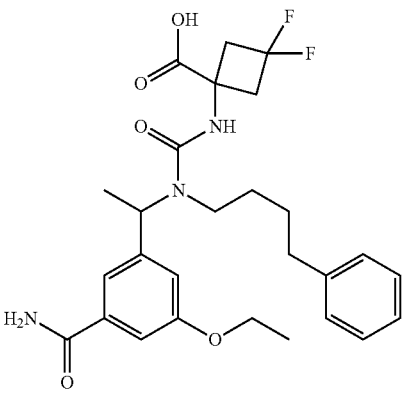 | 618 [M + H]+<br>549 [M + Na]+<br>515 [M + H]+ | 0.990 | E |
| 5-20 | 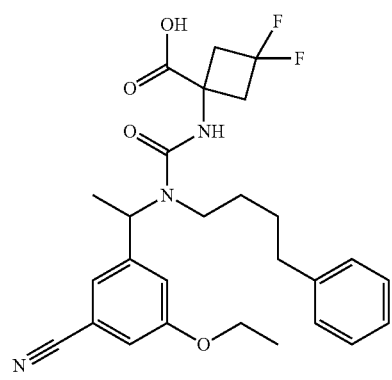 [SMILES: CCOc1cc(C#N)cc(C(C)N(CCCCc2ccccc2)C(=O)NC2(C(=O)O)CC(F)(F)C2)c1] | 500 [M + H]+<br>522 [M + Na]+<br>498 [M + H]+ | 0.995 | D |
| 5-21 | 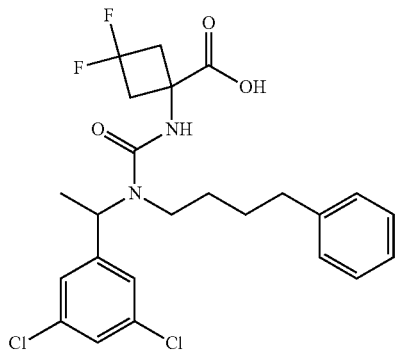 [SMILES: CC(c1cc(Cl)cc(Cl)c1)N(CCCCc1ccccc1)C(=O)NC1(C(=O)O)CC(F)(F)C1] | 499 [M + H]+<br>497 [M + H]+ | 1.273 | E |

TABLE 57-5

| Example No. | Structural Formula | MS posi m/z MS nega m/z | Retention time (min) | method |
|---|---|---|---|---|
| 5-22 | | 539 [M + H]+<br>537 [M + H]+ | 1.224 | E |
| 5-23 | | 423 [M + H]+<br>415 [M + Na]+<br>421 [M + H]+ | 1.113 | B |
| 5-24 | | 567 [M + H]+<br>565 [M + H]+ | 0.563 | D |
| 5-25 | | 532 [M + H]+<br>654 [M + Na]+<br>530 [M + H]+ | 1.244 | F |

Example 5-26

Trans-1-[([(1R)-1-(4-Acetyl-2-Chloro-3,5-Diethoxyphenyl)Ethyl]{2-[(1S)-1-Phenylethoxy]Ethyl}Carbamoyl)Amino]-3-Ethoxycyclobutane-1-Carboxylic Acid

[Chemical Formula 503]

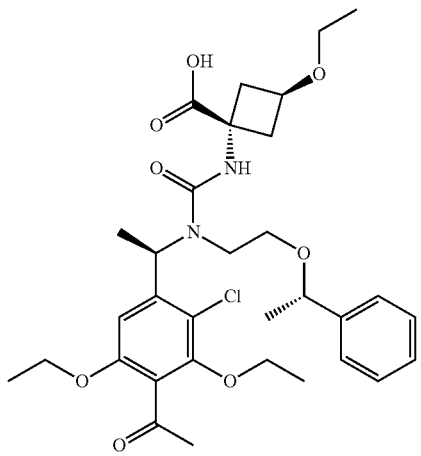

Using the compound (24.7 mg) obtained in Reference Example 4-3-1 and the compound (40 mg) obtained in Reference Example 3-4-2, the reaction was carried out in accordance with the method described in Example 1-1, and the title compound (31.2 mg) was obtained as a colorless powder.

$^1$H NMR (400 MHZ, METHANOL-$d_4$) δ ppm 1.14-1.20 (m, 3H) 1.30-1.37 (m, 6H) 1.38-1.42 (m, 3H) 1.44-1.48 (m, 3H) 2.32-2.50 (m, 6H) 2.54-2.63 (m, 1H) 2.64-2.76 (m, 1H) 3.03-3.16 (m, 1H) 3.23-3.47 (m, 4H) 3.94-4.03 (m, 2H) 4.03-4.13 (m, 3H) 4.27-4.37 (m, 1H) 5.55-5.63 (m, 1H) 6.86 (s, 1H) 7.20-7.34 (m, 5H).
MS ESI posi: 619 [M+H]$^+$, 641 [M+Na]$^+$.
MS ESI nega: 617 [M−H]$^−$.
Retention time: 0.947 min (method A)

Note that the hydrate of the N-methyl-D-glucamine salt of the title compound can be obtained by the method shown below.

(1) To the title compound (500 mg) and N-methyl-D-glucamine (158 mg), acetonitrile (2 mL) and water (2 mL) were added, and the resulting solution was freeze-dried to afford a colorless powder (654 mg).

(2) A mixed solvent of tert-butyl methyl ether-water (100:1, 500 µL) and n-heptane (50 µL) were added to the compound (50 mg) obtained in (1) above, which was then dissolved at 40° C., and the reaction solution was stirred at room temperature overnight. The precipitated solid was filtered off to afford a colorless solid (46 mg). When the obtained solid was subjected to thermogravimetry-differential thermal analysis (TG/DTA), endothermic peaks were observed at 50.1° C. and 76.3° C.

Note that the above-described solid of the title compound was identified as a hydrate by X-ray structure analysis.

The following Examples 5-27 to 5-51 were synthesized by the method described in Example 1-1 or by a method equivalent thereto, using the compounds obtained in Reference Example 3-4-2, Reference Examples 3-4-36 to 3-4-39, Reference Example 4-2-3, Reference Example 4-3-2, and Reference Examples 4-4-1 to 4-4-2, commercially available compounds, or compounds obtained by synthesis according to methods described in literatures or methods equivalent thereto. The structures and LCMS data of the compounds are shown in Tables 58-1 to 58-5.

TABLE 58-1

| Example No. | Structural Formula | MS posi m/z MS nega m/z | Retention time (min) | method |
|---|---|---|---|---|
| 5-27 | | 619 [M + H]+ 617 [M + H]+ | 0.841 | D |

TABLE 58-1-continued

| Example No. | Structural Formula | MS posi m/z MS nega m/z | Retention time (min) | method |
|---|---|---|---|---|
| 5-28 | | 605 [M + H]+ 627 [M + Na]+ 603 [M + H]+ | 0.921 | A |
| 5-29 | | 605 [M + H]+ 603 [M + H]+ | 0.805 | D |
| 5-30 | | 575 [M + H]+ 597 [M + Na]+ 573 [M + H]+ | 0.957 | A |

TABLE 58-1-continued

| Example No. | Structural Formula | MS posi m/z MS nega m/z | Retention time (min) | method |
|---|---|---|---|---|
| 5-31 | | 561 [M + H]+ 583 [M + Na]+ 559 [M + H]+ | 0.889 | A |

TABLE 58-2

| Example No. | Structural Formula | MS posi m/z MS nega m/z | Retention time (min) | method |
|---|---|---|---|---|
| 5-32 | | 611 [M + H]+ 633 [M + Na]+ 609 [M + H]+ | 0.950 | A |
| 5-33 | | 605 [M + H]+ 627 [M + Na]+ 603 [M + H]+ | 0.892 | A |

TABLE 58-2-continued

| Example No. | Structural Formula | MS posi m/z MS nega m/z | Retention time (min) | method |
|---|---|---|---|---|
| 5-34 | | 605 [M + H]+<br>627 [M + Na]+<br>603 [M + H]+ | 0.882 | A |
| 5-35 | | 605 [M + H]+<br>627 [M + Na]+<br>603 [M + H]+ | 0.910 | A |
| 5-36 | | 591 [M + H]+<br>613 [M + Na]+<br>589 [M + H]+ | 0.888 | A |

TABLE 58-3

| Example No. | Structural Formula | MS posi m/z MS nega m/z | Retention time (min) | method |
|---|---|---|---|---|
| 5-37 | | 561 [M + H]+<br>583 [M + Na]+<br>559 [M − H]+ | 0.882 | A |
| 5-38 | | 597 [M + H]+ | 0.874 | A |
| 5-39 | | 591 [M + H]+ | 0.804 | A |

TABLE 58-3-continued
| Example No. | Structural Formula | MS posi m/z MS nega m/z | Retention time (min) | method |
|---|---|---|---|---|
| 5-40 | 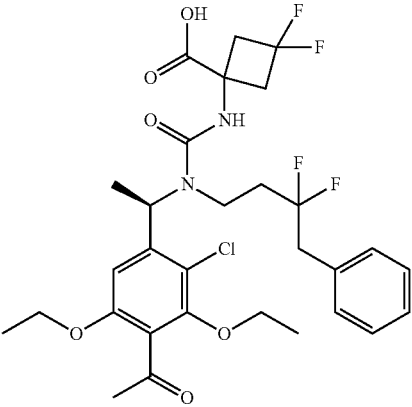 [SMILES: CCOc1cc([C@@H](C)N(CCC(F)(F)Cc2ccccc2)C(=O)NC2(C(=O)O)CC(F)(F)C2)c(Cl)c(OCC)c1C(C)=O] | 631 [M + H]+<br>653 [M + Na]+<br>629 [M + H]+ | 0.936 | A |
| 5-41 | 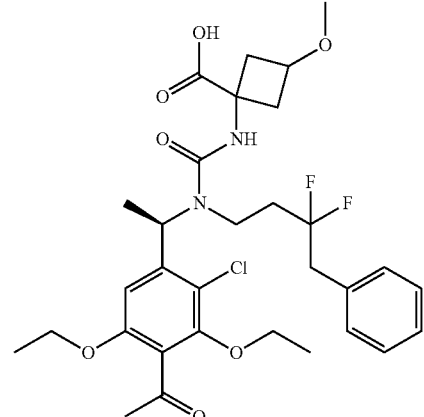 | 625 [M + H]+<br>547 [M + Na]+<br>623 [M + H]+ | 0.897 | A |
TABLE 58-4
| Example No. | Structural Formula | MS posi m/z MS nega m/z | Retention time (min) | method |
|---|---|---|---|---|
| 5-42 | 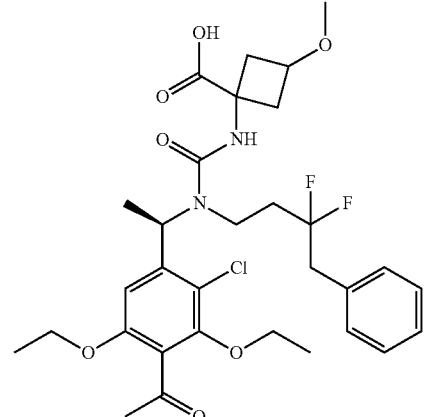 | 625 [M + H]+<br>647 [M + Na]+<br>623 [M + H]+ | 0.903 | A |

TABLE 58-4-continued
| Example No. | Structural Formula | MS posi m/z MS nega m/z | Retention time (min) | method |
|---|---|---|---|---|
| 5-43 | 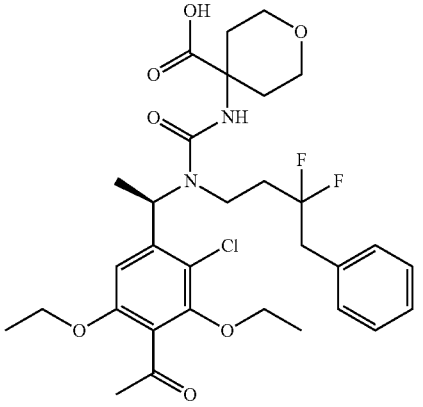 [SMILES: CCOc1cc([C@@H](C)N(CCC(F)(F)Cc2ccccc2)C(=O)NC2(C(=O)O)CCOCC2)c(Cl)c(OCC)c1C(C)=O] | 625 [M + H]+ 647 [M + Na]+ 623 [M + H]+ | 0.884 | A |
| 5-44 | 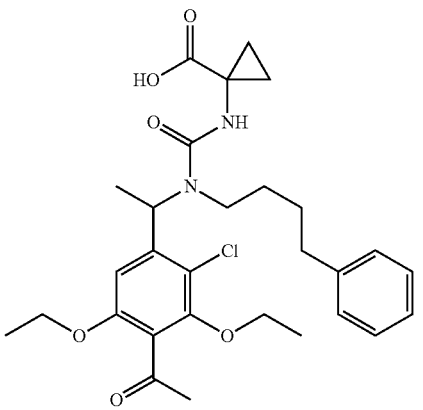 [SMILES: CCOc1cc(C(C)N(CCCCc2ccccc2)C(=O)NC2(C(=O)O)CC2)c(Cl)c(OCC)c1C(C)=O] | 545 [M + H]+ 567 [M + Na]+ 643 [M + H]+ | 0.006 | A |
| 5-45 | 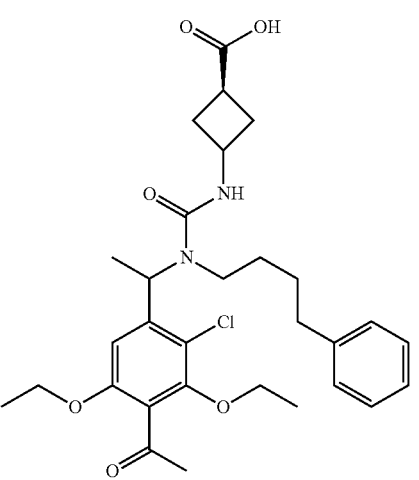 | 559 [M + H]+ 581 [M + Na]+ 557 [M + H]+ | 0.930 | A |

TABLE 58-4-continued

| Example No. | Structural Formula | MS posi m/z MS nega m/z | Retention time (min) | method |
|---|---|---|---|---|
| 5-46 | | 595 [M + H]+ 617 [M + Na]+ 593 [M + H]+ | 0.912 | A |

TABLE 58-5

| Example No. | Structural Formula | MS posi m/z MS nega m/z | Retention time (min) | method |
|---|---|---|---|---|
| 5-47 | | 589 [M + H]+ 611 [M + Na]+ 587 [M + H]+ | 0.878 | A |
| 5-48 | | 589 [M + H]+ 611 [M + Na]+ 587 [M + H]+ | 0.940 | A |

TABLE 58-5-continued

| Example No. | Structural Formula | MS posi m/z MS nega m/z | Retention time (min) | method |
|---|---|---|---|---|
| 5-49 | | 689 [M + H]+<br>587 [M + H]+ | 0.814 | D |
| 5-50 | | 603 [M + H]+<br>601 [M + H]+ | 0.847 | D |
| 5-51 | | 589 [M + H]+<br>611 [M + Na]+<br>587 [M + H]+ | 0.912 | A |

Note that the potassium salt of 1-[([(1R)-1-(4-acetyl-2-chloro-3,5-diethoxyphenyl)ethyl]{2-[(1S)-1-phenylethoxy]ethyl}carbamoyl)amino]cyclopropane-1-carboxylic acid obtained in Example 5-31 can be obtained by the method shown below.

(1) To a mixed solution of the compound (603 mg) obtained in Example 5-31 in tetrahydrofuran-water (11 mL-2.7 mL), a 3 mol/L aqueous potassium hydroxide solution (358 μL) was added, and the reaction solution was stirred at room temperature for 1 hour and concentrated. A mixed solvent of acetonitrile-water (3 mL-3 mL) was added to the obtained residue, which was then freeze-dried to afford a colorless amorphous (648 mg).

(2) Acetonitrile (0.5 mL), tert-butyl methyl ether (10 mL), and ethyl acetate (1 mL) were added to the compound (648 mg) obtained in (1) above, and the reaction solution was stirred at room temperature overnight. The precipitated solid was filtered off to afford a colorless solid (315 mg). When the obtained solid was subjected to thermogravimetry-differential thermal analysis (TG/DTA), an endothermic peak was observed at 95.9° C.

Example 5-52

Example 5-53

1-{[{(1R)-1-[2-Chloro-3,5-Diethoxy-4-(1-Hydroxyethyl)Phenyl]Ethyl}(4-Phenylbutyl) Carbamoyl]Amino}-3,3-Difluorocyclobutane-1-Carboxylic Acid

[Chemical Formula 504]

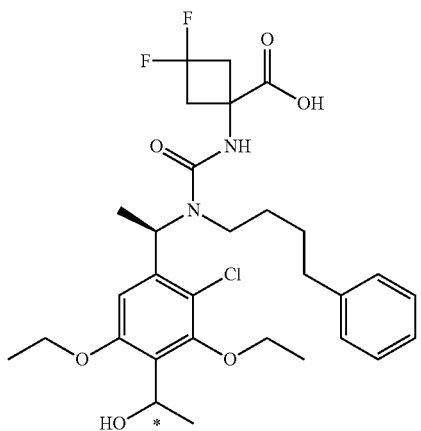

A mixed solution of the compound (9 mg) obtained in Example 5-46 in tetrahydrofuran-ethanol (0.3 mL-15 μL) was ice-cooled, lithium borohydride (0.988 mg) was added thereto, and the reaction solution was stirred at the same temperature for 2 hours. At the same temperature, lithium borohydride (0.988 mg) was further added thereto, and the reaction solution was stirred at the same temperature for 2 hours. At the same temperature, a saturated aqueous ammonium chloride solution was added to the reaction solution, which was then extracted with a mixed solvent of chloroform-methanol (4:1). The organic layer was filtered through Phase Separator and concentrated. The obtained residue was purified by preparative HPLC, and one optical isomer of the title compound with a shorter retention time (Example 5-52) (3.40 mg) was obtained as a colorless amorphous, and the other optical isomer of the title compound with a longer retention time (Example 5-53) (4.11 mg) was obtained as a colorless amorphous.

Example 5-52

$^1$H NMR (400 MHZ, METHANOL-$d_4$) δ ppm 0.90-1.62 (m, 16H) 2.28-2.45 (m, 2H) 2.76-2.94 (m, 2H) 2.95-3.10 (m, 2H) 3.11-3.27 (m, 2H) 3.87-4.01 (m, 2H) 4.07-4.23 (m, 2H) 5.22-5.33 (m, 1H) 5.44-5.59 (m, 1H) 6.89 (s, 1H) 7.01-7.16 (m, 3H) 7.16-7.29 (m, 2H).

MS ESI posi: 579 [M–OH]$^+$, 619 [M+Na]$^+$.

MS ESI nega: 595 [M–H]$^-$.

Retention time: 0.864 min (method A)

Example 5-53

$^1$H NMR (400 MHZ, METHANOL-$d_4$) δ ppm 0.99-1.60 (m, 16H) 2.32-2.48 (m, 2H) 2.76-2.94 (m, 2H) 2.95-3.10 (m, 2H) 3.10-3.28 (m, 2H) 3.88-4.03 (m, 2H) 4.07-4.23 (m, 2H) 5.21-5.32 (m, 1H) 5.43-5.55 (m, 1H) 6.88 (s, 1H) 6.99-7.15 (m, 3H) 7.15-7.29 (m, 2H).

MS ESI posi: 579 [M–OH]$^+$, 619 [M+Na]$^+$.

MS ESI nega: 595 [M–H]$^-$.

Retention time: 0.895 min (method A)

The following Examples 5-54 to 5-66 were synthesized by the method described in Example 1-1, Example 1-21, Example 1-152, or Example 5-52, or by a method equivalent thereto, using the compounds obtained in Reference Examples 3-4-37 to 3-4-59, Reference Example 3-9-6, Reference Example 3-9-9, Reference Examples 4-3-1 to 4-3-2, and Reference Examples 4-4-1 to 4-4-2, commercially available compounds, or compounds obtained by synthesis according to methods described in literatures or methods equivalent thereto. The structures and LCMS data of the compounds are shown in Tables 59-1 to 59-3. Note that the following pairs are optically active compounds:

Example 5-55 (isomer with a shorter retention time) and Example 5-56 (isomer with a longer retention time);

Example 5-57 (isomer with a shorter retention time) and Example 5-58 (isomer with a longer retention time);

Example 5-59 (isomer with a shorter retention time) and Example 5-60 (isomer with a longer retention time);

Example 5-61 (isomer with a shorter retention time) and Example 5-62 (isomer with a longer retention time);

Example 5-63 (isomer with a shorter retention time) and Example 5-64 (isomer with a longer retention time); and Example 5-65 (isomer with a shorter retention time) and Example 5-66 (isomer with a longer retention time).

TABLE 59-1

| Example No. | Structural Formula | MS posi m/z MS nega m/z | Retention time (min) | method |
|---|---|---|---|---|
| 5-54 | | 599 [M + H]+<br>621 [M + Na]+<br>581 [M + OH]+<br>597 587 [M + H]+ | 0.828<br>0.839 | A |
| 5-55 | | 599 [M + H]+<br>621 [M + Na]+<br>581 [M + OH]+<br>597 [M + H]+ | 0.840 | A |
| 5-56 | | 581 [M + OH]+<br>597 [M + H]+ | 0.787 | D |

TABLE 59-1-continued

| Example No. | Structural Formula | MS posi m/z MS nega m/z | Retention time (min) | method |
|---|---|---|---|---|
| 5-57 | | 629 [M + Na]+ 589 [M + OH]+ 605 [M + H]+ | 0.883 | A |
| 5-58 | | 629 [M + Na]+ 589 [M + OH]+ 605 [M + H]+ | 0.867 | A |

TABLE 59-2

| Example No. | Structural Formula | MS posi m/z MS nega m/z | Retention time (min) | method |
|---|---|---|---|---|
| 5-59 | | 607 [M + H]+ 629 [M + Na]+ 605 [M + H]+ | 0.890 | A |

TABLE 59-2-continued

| Example No. | Structural Formula | MS posi m/z MS nega m/z | Retention time (min) | method |
| --- | --- | --- | --- | --- |
| 5-60 | | 607 [M + H]+<br>629 [M + Na]+<br>605 [M + H]+ | 0.873 | A |
| 5-61 | | 643 [M + Na]+<br>603 [M + OH]+ | 0.920 | A |
| 5-62 | | 643 [M + Na]+<br>603 [M + OH]+ | 0.907 | A |

TABLE 59-2-continued

| Example No. | Structural Formula | MS posi m/z MS nega m/z | Retention time (min) | method |
|---|---|---|---|---|
| 5-63 | | 621 [M + H]+ 619 [M + H]+ | 0.967 | A |

TABLE 59-3

| Example No. | Structural Formula | MS posi m/z MS nega m/z | Retention time (min) | method |
|---|---|---|---|---|
| 5-64 | | 621 [M + H]+ 619 [M + H]+ | 0.953 | A |
| 5-65 | | 589 [M + H]+ | 0.806 | A |

TABLE 59-3-continued

| Example No. | Structural Formula | MS posi m/z MS nega m/z | Retention time (min) | method |
|---|---|---|---|---|
| 5-66 | (structure shown) | 613 [M + Na]+<br>573 [M + OH]+<br>589 [M + H]+ | 0.836 | A |

Example 5-67

Example 5-68

4-{[{(1R)-1-[2-Chloro-3,5-Diethoxy-4-(1-Hydroxy-ethyl)Phenyl]Ethyl}(3,3-Difluoro-4-Phenylbutyl) Carbamoyl]Amino}Oxane-4-Carboxylic Acid

[Chemical Formula 505]

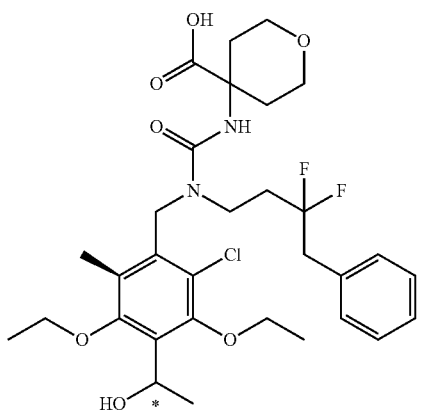

(1) Using methyl 4-aminoxane-4-carboxylate hydrochloride (26 mg) and the compound (50 mg) obtained in Reference Example 3-9-8, the reaction and post treatment were carried out in accordance with the method described in Example 1-21 (1), and purification by preparative HPLC was carried out to afford the isomer with a shorter retention time (Example 5-67 (1)) (18 mg) as a colorless amorphous and the isomer with a longer retention time (Example 5-68 (1)) (22 mg) as a colorless amorphous.

(2) Using Example 5-67 (1) (18 mg) obtained in (1) above, the reaction was carried out in accordance with the method described in Example 1-21 (3), and one isomer of the title compound (Example 5-67) (12 mg) was obtained as a colorless powder.

$^1$H NMR (400 MHZ, CHLOROFORM-d) δ ppm 1.43-1.57 (m, 12H) 1.78-1.87 (m, 2H) 2.18-2.32 (m, 2H) 2.98-3.12 (m, 2H) 3.32-3.50 (m, 4H) 3.59-3.67 (m, 1H) 3.69-3.81 (m, 2H) 3.89-3.99 (m, 1H) 3.99-4.15 (m, 3H) 4.54 (s, 1H) 5.13-5.26 (m, 1H) 5.35-5.50 (m, 1H) 6.63 (s, 1H) 7.12-7.19 (m, 2H) 7.28-7.34 (m, 3H).

MS ESI posi: 609 [M–OH]+, 649 [M+Na]+.

MS ESI nega: 625 [M–H]−.

Retention time: 0.832 min (method A)

(3) Using Example 5-68 (1) (22 mg) obtained in (1) above, the reaction was carried out in accordance with the method described in Example 1-21 (3), and the other isomer of the title compound (Example 5-68) (13 mg) was obtained as a colorless powder.

MS ESI posi: 609 [M–OH]+, 649 [M+Na]+.

MS ESI nega: 625 [M–H]−.

Retention time: 0.858 min (method A)

The following Examples 5-69 to 5-84 were synthesized by the method described in Example 1-1 or Example 5-52, or by a method equivalent thereto, using the compounds obtained in Reference Examples 3-1-67 to 3-1-68, Reference Examples 3-4-37 to 3-4-44, Reference Examples 4-3-1 to 4-3-2, and Reference Example 4-4-2, commercially available compounds, or compounds obtained by synthesis according to methods described in literatures or methods equivalent thereto. The structures and LCMS data of the compounds are shown in Tables 60-1 to 60-4. Note that Example 5-69 (isomer with a shorter retention time) and Example 5-70 (isomer with a longer retention time) are optically active compounds.

TABLE 60-1

| Example No. | Structural Formula | MS posi m/z  MS nega m/z | Retention time (min) | method |
| --- | --- | --- | --- | --- |
| 5-69 | | 593 [M + H]+  615 [M + Na]+  591 [M + H]+ | 0.755-0.767 | A |
| 5-70 | | 593 [M + H]+  615 [M + Na]+ | 0.771 | A |
| 5-71 | | 585 [M + H]+  607 [M + Na]+  583 [M + H]+ | 0.912 | A |

TABLE 60-1-continued
| Example No. | Structural Formula | MS posi m/z MS nega m/z | Retention time (min) | method |
|---|---|---|---|---|
| 5-72 | 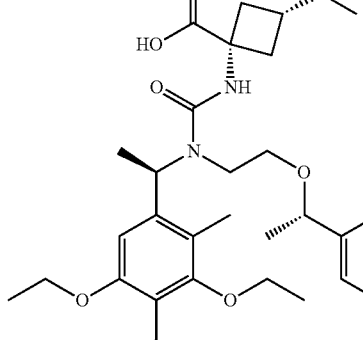 | 585 [M + H]+<br>607 [M + Na]+<br>583 [M + H]+ | 0.908 | A |
| 5-73 | 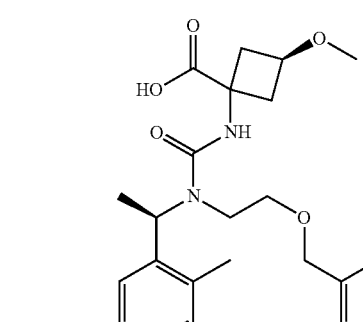 | 571 [M + H]+<br>593 [M + Na]+<br>569 [M + H]+ | 0.875 | A |
TABLE 60-2
| Example No. | Structural Formula | MS posi m/z MS nega m/z | Retention time (min) | method |
|---|---|---|---|---|
| 5-74 | | 571 [M + H]+<br>593 [M + Na]+<br>669 [M + H]+ | 0.871 | A |

TABLE 60-2-continued

| Example No. | Structural Formula | MS posi m/z MS nega m/z | Retention time (min) | method |
|---|---|---|---|---|
| 5-75 | | 513 [M + H]+<br>535 [M + Na]+<br>611 [M + H]+ | 0.980 | A |
| 5-76 | | 647 [M + H]+ | 1.050 | A |
| 5-77 | | 677 [M + H]+<br>599 [M + Na]+<br>576 [M + H]+ | 0.980 | A |
| 5-78 | | 543 [M + H]+<br>565 [M + Na]+ | 0.977 | A |

TABLE 60-3

| Example No. | Structural Formula | MS posi m/z MS nega m/z | Retention time (min) | method |
|---|---|---|---|---|
| 5-79 | | 557 [M + H]+ 579 [M + Na]+ | 1.012 | A |
| 5-80 | | 591 [M + H]+ | 1.010 | A |
| 5-81 | | 557 [M + H]+ 579 [M + Na]+ | 1.010 | A |

TABLE 60-3-continued

| Example No. | Structural Formula | MS posi m/z MS nega m/z | Retention time (min) | method |
|---|---|---|---|---|
| 5-82 | | 571 [M + H]+<br>593 [M + Na]+ | 1.043 | A |
| 5-83 | | 551 [M + H]+<br>549 [M + H]+ | 1.039 | A |

TABLE 60-4

| Example No. | Structural Formula | MS posi m/z MS nega m/z | Retention time (min) | method |
|---|---|---|---|---|
| 5-84 | | 567 [M + H]+<br>589 [M + Na]+<br>565 [M + H]+ | 0.992 | A |

Note that the potassium salt of trans-1-[([(1R)-1-(3,5-diethoxy-2,4-dimethylphenyl)ethyl]{2-[(1S)-1-phenylethoxy]ethyl}carbamoyl)amino]-3-ethoxycyclobutane-1-carboxylic acid obtained in Example 5-82 can be obtained by the method shown below.

(1) To a solution of the compound (101 mg) obtained in Example 5-82 in acetonitrile (0.5 mL), a 3 mol/L aqueous potassium hydroxide solution (59 μL) and water (0.5 mL) were added and dissolved, and the reaction solution was freeze-dried to afford a colorless amorphous (110 mg).

(2) tert-Butyl methyl ether and water were mixed and then partitioned into two layers.

(3) To the compound (80 mg) obtained in (1) above, the organic layer (240 μL) obtained in (2) above and n-heptane (1.2 mL) were added, and the reaction solution was stirred at room temperature for 14 hours. n-Heptane (2 mL) was added to the solution, and the precipitated solid was filtered off to afford a colorless powder (71 mg). When the obtained powder was subjected to thermogravimetry-differential thermal analysis (TG/DTA), an endothermic peak was observed at 76.2° C.

Example 5-85

1-({[1-(4,6-Diethoxypyridin-2-Yl)Ethyl](4-Phenylbutyl)Carbamoyl}Amino)-3,3-Difluorocyclobutane-1-Carboxylic Acid

[Chemical Formula 506]

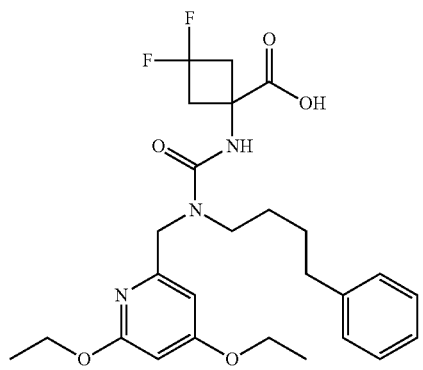 [SMILES: CCOc1cc(C(C)N(CCCCc2ccccc2)C(=O)NC2(C(=O)O)CC(F)(F)C2)cc(OCC)n1]

Using methyl 1-amino-3,3-difluorocyclobutane-1-carboxylate hydrochloride (36 mg) and the compound (41 mg) obtained in Reference Example 3-7-2, the reaction was carried out in accordance with the method described in Example 1-1, and the title compound (48 mg) was obtained as a colorless gum-like substance.

$^1$H NMR (400 MHZ, CHLOROFORM-d) δ ppm 1.36 (t, J=7.03 Hz, 3H) 1.42 (t, J=7.03 Hz, 3H) 1.48-1.57 (m, 4H) 1.58-1.66 (m, 3H) 2.50-2.63 (m, 2H) 2.63-2.84 (m, 2H) 3.16-3.27 (m, 1H) 3.27-3.48 (m, 3H) 4.03 (q, J=6.97 Hz, 4H) 4.45-4.77 (m, 1H) 6.10 (d, J=1.71 Hz, 1H) 6.36 (d, J=1.71 Hz, 1H) 7.08-7.33 (m, 5H) 8.51-9.38 (m, 1H).

MS ESI/APCI Multi posi: 520 [M+H]$^+$.

MS ESI/APCI Multi nega: 518 [M−H]$^−$.

Retention time: 1.225 min (method E)

The following Examples 5-86 to 5-98 were synthesized by the method described in Example 1-1 or Example 1-40, or by a method equivalent thereto, using the compounds obtained in Reference Example 1-7-8, Reference Examples 3-1-69 to 3-1-77, Reference Example 3-3-4, and Reference Examples 3-7-3 to 3-7-4, commercially available compounds, or compounds obtained by synthesis according to methods described in literatures or methods equivalent thereto. The structures and LCMS data of the compounds are shown in Tables 61-1 to 61-3.

TABLE 61-1

| Example No. | Structural Formula | MS posi m/z MS nega m/z | Retention time (min) | method |
|---|---|---|---|---|
| 5-86 | | 620 [M + H]+ 518 [M + H]+ | 1.259 | E |
| 5-87 | | 493 [M + H]+ 401 [M + H]+ | 1.226 | B |

TABLE 61-1-continued
| Example No. | Structural Formula | MS posi m/z MS nega m/z | Retention time (min) | method |
|---|---|---|---|---|
| 5-88 | 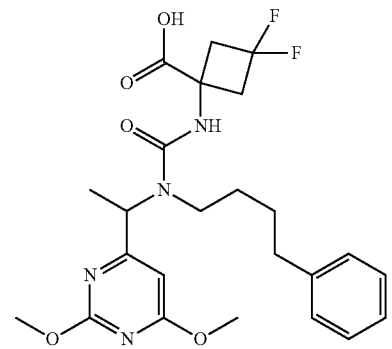 [SMILES: COc1cc(C(C)N(CCCCc2ccccc2)C(=O)NC2(C(=O)O)CC(F)(F)C2)nc(OC)n1] | 493 [M + H]+<br>401 [M + H]+ | 1.161 | B |
| 5-89 | 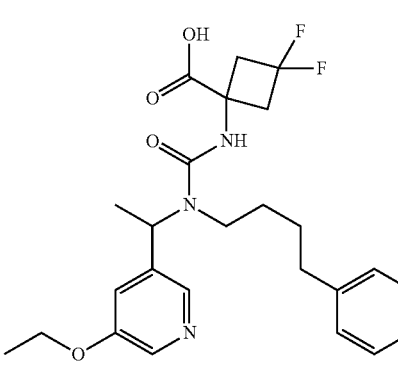 | 476 [M + H]+<br>474 [M + H]+ | 0.903 | B |
| 5-90 | 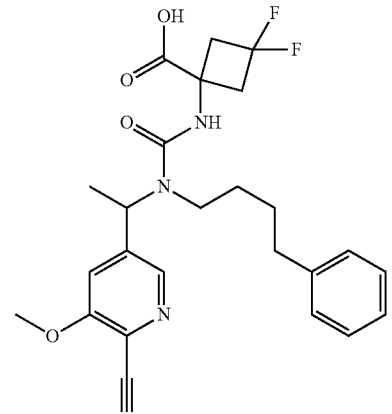 | 487 [M + H]+<br>503 [M + Na]+<br>486 [M + H]+ | 1.092 | B |

TABLE 61-2

| Example No. | Structural Formula | MS posi m/z MS nega m/z | Retention time (min) | method |
|---|---|---|---|---|
| 5-91 | | 489 [M + H]+ 487 [M + H]+ | 1.101 | E |
| 5-92 | | 617 [M + H]+ 539 [M + Na]+ 515 [M + H]+ | 1.152 | B |
| 5-93 | | 520 [M + H]+ 542 [M + Na]+ 618 [M + H]+ | 0.979 | B |

TABLE 61-2-continued

| Example No. | Structural Formula | MS posi m/z MS nega m/z | Retention time (min) | method |
|---|---|---|---|---|
| 5-94 | | 543 [M + H]+<br>541 [M + H]+ | 0.718 | B |
| 5-95 | | 542 [M + H]+<br>564 [M + Na]+<br>540 [M + H]+ | 0.979 | A |

TABLE 61-3

| Example No. | Structural Formula | MS posi m/z MS nega m/z | Retention time (min) | method |
|---|---|---|---|---|
| 5-96 | | 335 [M + H]+ | 1.019 | A |

TABLE 61-3-continued

| Example No. | Structural Formula | MS posi m/z MS nega m/z | Retention time (min) | method |
|---|---|---|---|---|
| 5-97 | | 544 [M + H]+ 542 [M + H]+ | 0.970 | A |
| 5-98 | | 544 [M + H]+ 542 [M + H]+ | 0.986 | A |

Example 5-99

1-({[1-(4-Ethoxy-1-Ethyl-1H-Indazol-6-Yl)Ethyl](4-Phenylbutyl) Carbamoyl}Amino)-3,3-Difluorocyclobutane-1-Carboxylic Acid

[Chemical Formula 507]

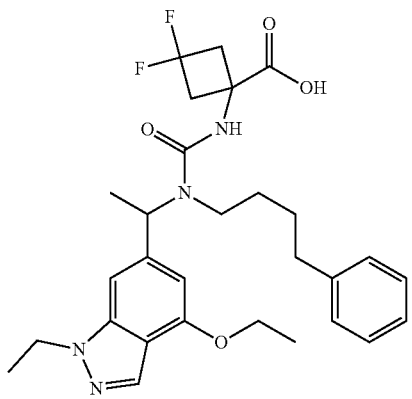

Using methyl 1-amino-3,3-difluorocyclobutane-1-carboxylate hydrochloride (6.6 mg) and the compound (8 mg) obtained in Reference Example 3-8-1, the reaction was carried out in accordance with the method described in Example 1-1, and the title compound (2.5 mg) was obtained as a colorless oily substance.

$^1$H NMR (400 MHZ, CHLOROFORM-d) δ ppm 1.22-1.53 (m, 10H) 1.60-1.70 (m, 3H) 2.37-2.62 (m, 4H) 2.89-3.16 (m, 1H) 3.16-3.37 (m, 3H) 4.04-4.22 (m, 2H) 4.33-4.43 (m, 2H) 4.83-4.94 (m, 1H) 5.13-5.53 (m, 1H) 6.33 (s, 1H) 6.86 (s, 1H) 7.05-7.12 (m, 2H) 7.15-7.25 (m, 3H) 8.04 (s, 1H).

MS ESI/APCI Multi posi: 543 [M+H]$^+$.

MS ESI/APCI Multi nega: 541 [M−H]$^−$.

Retention time: 1.140 min (method E)

The following Examples 5-100 to 5-115 were synthesized by the method described in Example 1-1, Example 1-30, Example 1-40, or Example 1-62, or by a method equivalent thereto, using the compounds obtained in Reference Examples 3-8-1 to 3-8-5, commercially available compounds, or compounds obtained by synthesis according to methods described in literatures or methods equivalent thereto. The structures and LCMS data of the compounds are shown in Tables 62-1 to 62-4. Note that the following pairs are optically active compounds:

Example 5-108 (isomer with a shorter retention time) and Example 5-109 (isomer with a longer retention time); and Example 5-110 (isomer with a shorter retention time) and Example 5-111 (isomer with a longer retention time).

In addition, Example 5-115 is the optical isomer with a shorter retention time in preparative isolation by HPLC equipped with a chiral column.

TABLE 62-1

| Example No. | Structural Formula | MS posi m/z MS nega m/z | Retention time (min) | method |
|---|---|---|---|---|
| 5-100 | | 589 [M + H]+ | 1.288 | B |
| 5-101 | | 586 [M + H]+ 683 [M + H]+ | 0.965 | B |
| 5-102 | | 560 [M + H]+ 558 [M + H]+ | 1.267 | B |

TABLE 62-1-continued

| Example No. | Structural Formula | MS posi m/z MS nega m/z | Retention time (min) | method |
|---|---|---|---|---|
| 5-103 | | 624 [M + H]+ 522 [M + H]+ | 1.263 | B |
| 5-104 | | 686 [M + H]+ 586 [M + H]+ | 1.382 | B |

TABLE 62-2

| Example No. | Structural Formula | MS posi m/z MS nega m/z | Retention time (min) | method |
|---|---|---|---|---|
| 5-105 | | 602 [M + H]+ 600 [M + H]+ | 1.140 | B |

TABLE 62-2-continued
| Example No. | Structural Formula | MS posi m/z MS nega m/z | Retention time (min) | method |
| --- | --- | --- | --- | --- |
| 5-106 | 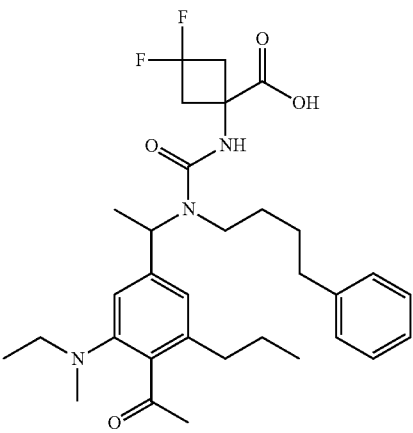 [SMILES: CCCc1cc(C(C)N(CCCCc2ccccc2)C(=O)NC2(C(=O)O)CC(F)(F)C2)cc(N(C)CC)c1C(C)=O] | 574 [M + H]+ 572 [M + H]+ | 0.941 | B |
| 5-107 | 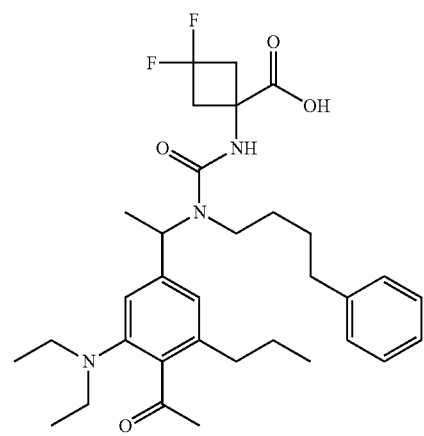 [SMILES: CCCc1cc(C(C)N(CCCCc2ccccc2)C(=O)NC2(C(=O)O)CC(F)(F)C2)cc(N(CC)CC)c1C(C)=O] | 588 [M + H]+ 586 [M + H]+ | 0.832 | B |
| 5-108 | 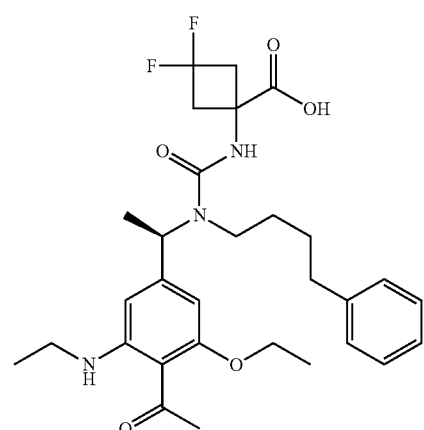 | 560 [M + H]+ 568 [M + H]+ | 1.257 | B |

TABLE 62-2-continued

| Example No. | Structural Formula | MS posi m/z MS nega m/z | Retention time (min) | method |
|---|---|---|---|---|
| 5-109 | | 560 [M + H]+ 558 [M + H]+ | 1.259 | B |

TABLE 62-3

| Example No. | Structural Formula | MS posi m/z MS nega m/z | Retention time (min) | method |
|---|---|---|---|---|
| 5-110 | | 521 [M + H]+ 522 [M + H]+ | 1.261 | B |
| 5-111 | | 521 [M + H]+ 522 [M + H]+ | 1.264 | B |

TABLE 62-3-continued

| Example No. | Structural Formula | MS posi m/z MS nega m/z | Retention time (min) | method |
|---|---|---|---|---|
| 5-112 | | 632 [M + H]+ 530 [M + H]+ | 1.116 | B |
| 5-113 | | 507 [M + H]+ 503 [M + H]+ | 1.164 | B |
| 5-114 | | 543 [M + H]+ 541 [M + H]+ | 1.160 | E |

TABLE 62-4

| Example No. | Structural Formula | MS posi m/z MS nega m/z | Retention time (min) | method |
|---|---|---|---|---|
| 5-115 | | 543 [M + H]+ 541 [M + H]+ | 1.165 | B |

Example 5-116

1-{[(4,6-Dichloro-2,3-Dihydro-1H-Inden-1-Yl)(4-Phenylbutyl) Carbamoyl]Amino}-3,3-Difluorocyclobutane-1-Carboxylic Acid

[Chemical Formula 508]

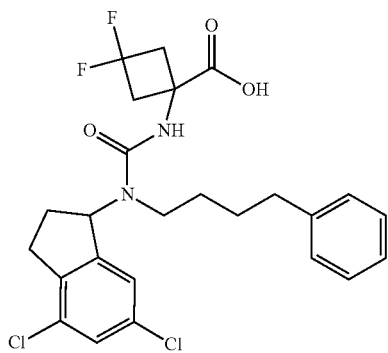

Using methyl 1-amino-3,3-difluorocyclobutane-1-carboxylate hydrochloride (12 mg) and the compound (20 mg) obtained in Reference Example 3-1-78, the reaction and post treatment were carried out in accordance with the method described in Example 1-1. The obtained residue was purified by silica gel column chromatography (n-hexane:ethyl acetate=10:90 to ethyl acetate only, and then chloroform only to chloroform:methanol=80:20) to afford the title compound (3 mg) as a colorless amorphous.

MS ESI posi: 511 [M+H]$^+$.

MS ESI nega: 509 [M−H]$^−$.

Retention time: 1.054 min (method A)

The following Example 5-117 was synthesized by the method described in Example 1-1 or by a method equivalent thereto, using the compound obtained in Reference Example 3-1-79, a commercially available compound, or a compound obtained by synthesis according to methods described in literatures or methods equivalent thereto. The structure and LCMS data of the compound are shown in Table 63-1.

TABLE 63-1

| Example No. | Structural Formula | MS posi m/z MS nega m/z | Retention time (min) | method |
|---|---|---|---|---|
| 5-117 | | 513 [M + H]+ 511 [M + H]+ | 0.991 | A |

Example 5-118

Trans-1-[[[(1R)-1-(4-Acetyl-3,5-Diethoxy-2-Methylphenyl)Ethyl]{2-[(1S)-1-Phenylethoxy]Ethyl}Carbamoyl)Amino]-3-Ethoxycyclobutane-1-Carboxylic Acid

[Chemical Formula 509]

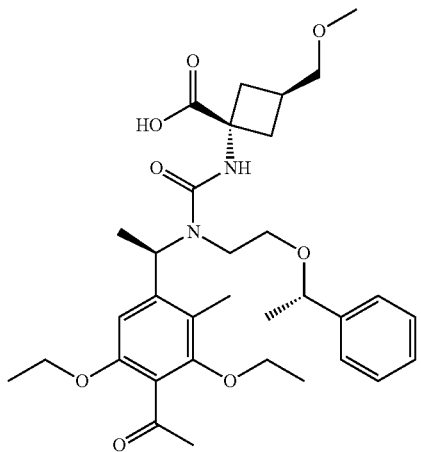 [SMILES: CCOc1cc([C@@H](C)N(CCO[C@@H](C)c2ccccc2)C(=O)NC2(C(=O)O)CC(OCC)C2)c(C)c(OCC)c1C(C)=O]

(1) A solution of the compound (272 mg) obtained in Reference Example 4-3-1 and 4-nitrophenyl chloroformate (292 mg) in tetrahydrofuran (12 mL) was cooled with a mixture of sodium chloride-ice and stirred for 5 minutes. Then, N,N-diisopropylethylamine (1.05 mL) was added dropwise thereto, and the reaction solution was stirred at the same temperature for 3 hours. A solution of the compound (500 mg) obtained in Reference Example 3-4-40 in tetrahydrofuran (1 mL) was added to the reaction solution, which was then stirred at room temperature for 22 hours. A saturated aqueous sodium bicarbonate solution was added to the reaction solution, which was then extracted with toluene. The organic layer was washed with a brine and dried over anhydrous magnesium sulfate. After filtering off the desiccating agent, the filtrate was concentrated. The obtained residue was purified by column chromatography in which a NH silica gel column cartridge and a silica gel column cartridge were coupled (n-hexane:ethyl acetate=50:50) to afford ethyl trans-1-[[[(1R)-1-(4-acetyl-3,5-diethoxy-2-methylphenyl)ethyl]{2-[(1S)-1-phenylethoxy]ethyl}carbamoyl)amino]-3-ethoxycyclobutane-1-carboxylate (617 mg) as a colorless powder.

(2) To a solution of the compound (617 mg) obtained in (1) above in ethanol (4.9 mL), a 3 mol/L aqueous potassium hydroxide solution (984 µL) was added, and the reaction solution was stirred at room temperature for 3 days. The reaction solution was ice-cooled, and a 0.5 mol/L aqueous citric acid solution (3 mL) was added thereto, followed by concentration. Chloroform and water were added to the obtained residue, which was then extracted with chloroform. The organic layer was filtered through Phase Separator and concentrated. The obtained residue was purified by preparative HPLC and freeze-dried to afford the title compound (513 mg) as a colorless amorphous.

$^1$H NMR (600 MHz, METHANOL-$d_4$) δ ppm 1.10-1.24 (m, 3H) 1.24-1.53 (m, 12H) 2.18 (s, 3H) 2.28-2.40 (m, 2H) 2.40-2.50 (m, 5H) 2.64-2.69 (m, 1H) 2.99-3.04 (m, 1H) 3.18-3.24 (m, 1H) 3.28-3.48 (m, 3H) 3.79-3.87 (m, 2H) 3.97-4.15 (m, 3H) 4.19-4.24 (m, 1H) 5.55-5.60 (m, 1H) 6.79 (s, 1H) 7.14-7.36 (m, 5H).

MS ESI/APCI Multi posi: 599 [M+H]$^+$.
MS ESI/APCI Multi nega: 597 [M−H]$^-$.
Retention time: 0.830 min (method D)

The following Example 5-119 was synthesized by the method described in Example 5-118 or by a method equivalent thereto, using the compounds obtained in Reference Example 3-4-40 and Reference Example 4-4-3, commercially available compounds, or compounds obtained by synthesis according to methods described in literatures or methods equivalent thereto. The structure and LCMS data of the compound are shown in Table 64-1.

TABLE 64-1

| Example No. | Structural Formula | MS posi m/z MS nega m/z | Retention time (min) | method |
|---|---|---|---|---|
| 5-119 | ![structure] | 599 [M + H]+ 597 [M + H]+ | 0.828 | D |

Example 5-120

Trans-1-[([(1R)-1-(4-Acetyl-2,6-Dichloro-3,5-Diethoxyphenyl)Ethyl]{2-[(1S)-1-Phenylethoxy]Ethyl}Carbamoyl)Amino]-3-Ethoxycyclobutane-1-Carboxylic Acid

[Chemical Formula 510]

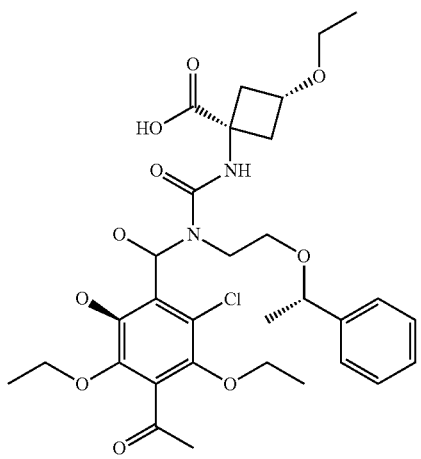

(1) Using the compound (18.5 mg) obtained in Reference Example 4-3-1 and the compound (30 mg) obtained in Reference Example 3-4-28, the reaction and post treatment were carried out in accordance with the method described in Example 5-118 (1). The obtained residue was purified by preparative HPLC and freeze-dried to afford ethyl trans-1-[([(1R)-1-(4-acetyl-3,5-diethoxyphenyl)ethyl]{2-[(1S)-1-phenylethoxy]ethyl}carbamoyl)amino]-3-ethoxycyclobutane-1-carboxylate (20 mg) as a colorless powder.

(2) Under a nitrogen atmosphere, a solution of the compound (100 mg) obtained in (1) above in chloroform (0.8 mL) was ice-cooled, a solution of sulfuryl chloride (14.4 μL) in chloroform (0.8 mL) was added dropwise thereto, and the reaction solution was stirred at the same temperature for 30 minutes. The reaction solution was cooled with a mixture of sodium chloride-ice, a saturated aqueous sodium bicarbonate solution was added thereto, and extraction with chloroform was carried out. The organic layer was filtered through Phase Separator and concentrated. The obtained residue was purified by silica gel column chromatography (n-hexane only to n-hexane:ethyl acetate=50:50) to afford ethyl trans-1-[([(1R)-1-(4-acetyl-2,6-dichloro-3,5-diethoxyphenyl)ethyl]{2-[(1S)-1-phenylethoxy]ethyl}carbamoyl)amino]-3-ethoxycyclobutane-1-carboxylate (46 mg) as a colorless amorphous.

(3) To a solution of the compound (17 mg) obtained in (2) above in ethanol (0.5 mL), a 3 mol/L aqueous potassium hydroxide solution (24.9 μL) was added, and the reaction solution was stirred at room temperature for 16 hours. A 3 mol/L aqueous potassium hydroxide solution (12.5 μL) was further added to the reaction solution, which was then stirred at room temperature for 55 hours. The reaction solution was ice-cooled, and a solution of citric acid (10.5 mg) in water (0.5 mL) was added thereto. The reaction solution was concentrated and extracted with toluene. The organic layer was washed with water, filtered through Phase Separator, concentrated, and freeze-dried to afford the title compound (12 mg) as a colorless amorphous.

$^1$H NMR (600 MHz, CHLOROFORM-d) δ ppm 1.14-1.20 (m, 3H) 1.31-1.44 (m, 9H) 1.51-1.62 (m, 3H) 2.22-2.32 (m, 1H) 2.45-2.61 (m, 6H) 3.05-3.15 (m, 1H) 3.29-3.43 (m, 3H) 3.55-3.69 (m, 2H) 3.90-4.03 (m, 5H) 4.27-4.35 (m, 1H) 5.71-5.81 (m, 1H) 7.14-7.22 (m, 2H) 7.27-7.32 (m, 1H) 7.32-7.39 (m, 2H).

MS ESI posi: 653, 655 [M+H]$^+$.
MS ESI nega: 651, 653 [M−H]$^−$.
Retention time: 1.024 min (method A)

The following Examples 5-121 to 5-128 were synthesized by the method described in Example 1-1 or Example 5-118, or by a method equivalent thereto, using the compounds obtained in Reference Examples 3-6-14 to 3-6-17 and Reference Examples 4-3-1 to 4-3-2, commercially available compounds, or compounds obtained by synthesis according to methods described in literatures or methods equivalent thereto. The structures and LCMS data of the compounds are shown in Tables 65-1 to 65-2.

TABLE 65-1

| Example No. | Structural Formula | MS posi m/z<br>MS nega m/z | Retention time (min) | method |
|---|---|---|---|---|
| 5-121 | | 529 [M + H]+<br>527 [M + H]+ | 0.736 | A |

TABLE 65-1-continued

| Example No. | Structural Formula | MS posi m/z MS nega m/z | Retention time (min) | method |
|---|---|---|---|---|
| 5-122 | | 543 [M + H]+ 565 [M + Na]+ 541 [M + H]+ | 0.779 | A |
| 5-123 | | 563 [M + H]+ 561 [M + H]+ | 0.767 | A |
| 5-124 | | 577 [M + H]+ 599 [M + Na]+ 575 [M + H]+ | 0.809 | A |

TABLE 65-1-continued

| Example No. | Structural Formula | MS posi m/z MS nega m/z | Retention time (min) | method |
|---|---|---|---|---|
| 5-125 | | 543 [M + H]+ 541 [M + H]+ | 0.178 | A |

TABLE 65-2

| Example No. | Structural Formula | MS post m z MS mega m/z | Retention time (min) | method |
|---|---|---|---|---|
| 5-126 | | 557 [M + H]+ 579 [M + Na]+ 555 [M + H]+ | 0.823 | A |
| 5-127 | | 577 [M + H]+ 575 [M + H]+ | 0.807 | A |

TABLE 65-2-continued

| Example No. | Structural Formula | MS post m/z<br>MS mega m/z | Retention time<br>(min) | method |
|---|---|---|---|---|
| 5-128 | | 591 [M + H]+<br>613 [M + Na]+<br>589 [M + H]+ | 0.848 | A |

The following Examples 5-129 to 5-228 were synthesized by the method described in Example 1-1 or by a method equivalent thereto, using the compounds obtained in Reference Examples 3-4-36 to 3-4-37, Reference Example 3-4-39, Reference Examples 3-4-41 to 3-4-42, Reference Examples 3-4-44 to 3-4-45, Reference Example 3-4-49, Reference Examples 3-6-14 to 3-6-15, Reference Examples 3-6-18 to 3-6-20, Reference Example 3-6-22, Reference Examples 3-6-26 to 3-6-30, Reference Examples 3-6-34 to 3-6-37, Reference Examples 4-3-1 to 4-3-2, and Reference Examples 4-4-1 to 4-4-2, commercially available compounds, or compounds obtained by synthesis according to methods described in literatures or methods equivalent thereto. The structures and LCMS data of the compounds are shown in Tables 66-1 to 66-20.

TABLE 66-1

| Example No. | Structural Formula | MS post m/z<br>MS mega m/z | Retention time (min) | method |
|---|---|---|---|---|
| 5-129 | | 517 [M + H]+<br>513 [M + H]+ | 0.308 | A |

TABLE 66-1-continued
| Example No. | Structural Formula | MS post m/z MS mega m/z | Retention time (min) | method |
|---|---|---|---|---|
| 5-130 | 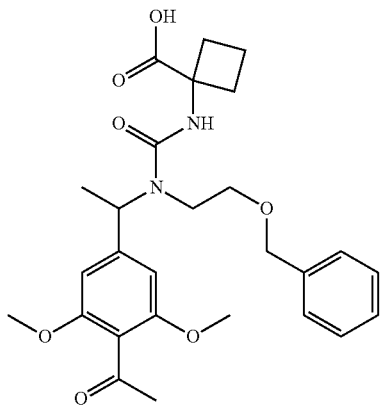 [SMILES: COc1cc(C(C)N(CCOCc2ccccc2)C(=O)NC2(C(=O)O)CCC2)cc(OC)c1C(C)=O] | 499 [M + H]+<br>621 [M + Na]+<br>492 [M + H]+ | 0.778 | A |
| 5-131 | 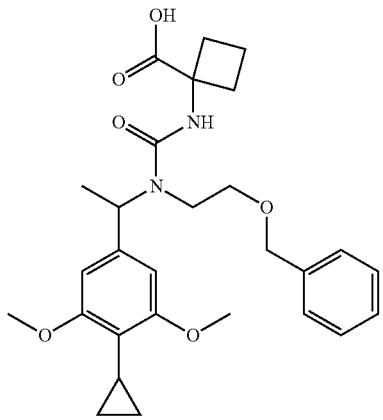 [SMILES: COc1cc(C(C)N(CCOCc2ccccc2)C(=O)NC2(C(=O)O)CCC2)cc(OC)c1C1CC1] | 487 [M + H]+<br>519 [M + Na]+<br>485 [M + H]+ | 0.939 | A |
| 5-132 | 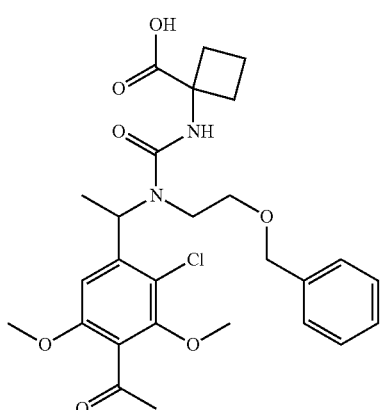 | 533 [M + H]+<br>665 [M + Na]+<br>531 [M + H]+ | 0.853 | A |

TABLE 66-1-continued

| Example No. | Structural Formula | MS post m/z MS mega m/z | Retention time (min) | method |
|---|---|---|---|---|
| 5-133 | | 631 [M + H]+ 663 [M + Na]+ 630 [M + H]+ | 0.942 | A |

TABLE 66-2

| Example No. | Structural Formula | MS post m/z MS mega m/z | Retention time (min) | method |
|---|---|---|---|---|
| 5-134 | | 513 [M + H]+ 633 [M + Na]+ 611 [M + H]+ | 0.847 | A |
| 5-135 | | 511 [M + H]+ 633 [M + Na]+ 509 [M + H]+ | 0.993 | A |

TABLE 66-2-continued
| Example No. | Structural Formula | MS post m/z MS mega m/z | Retention time (min) | method |
|---|---|---|---|---|
| 5-136 | 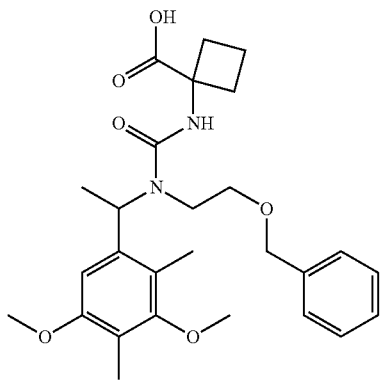 [SMILES: COc1cc(C(C)N(CCOCc2ccccc2)C(=O)NC2(C(=O)O)CCC2)c(C)c(OC)c1C] | 485 [M + H]+ 601 [M + Na]+ 483 [M + H]+ | 1.219 | B |
| 5-137 | 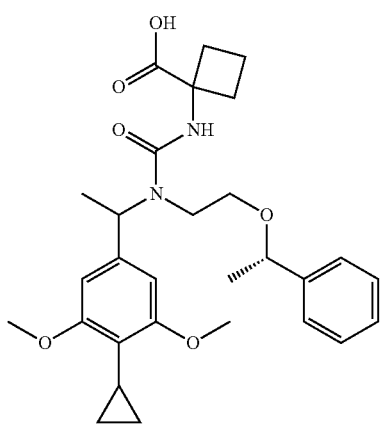 [SMILES: COc1cc(C(C)N(CCO[C@@H](C)c2ccccc2)C(=O)NC2(C(=O)O)CCC2)cc(OC)c1C1CC1] | 511 [M + H]+ 533 [M + Na]+ 509 [M + H]+ | 0.976 | A |
| 5-138 | 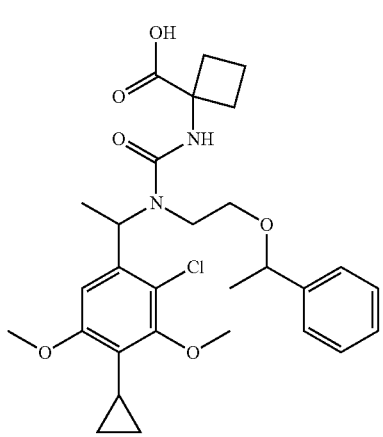 | 645 [M + H]+ 557 [M + Na]+ 643 [M + H]+ | 0.979 | A |

TABLE 66-3

| Example No. | Structural Formula | MS post m/z MS mega m/z | Retention time (min) | method |
|---|---|---|---|---|
| 5-139 | | 636 [M + H]+<br>647 [M + Na]+<br>523 [M + H]+ | 0.082 | A |
| 5-140 | | 489 [M + H]+<br>521 [M + Na]+<br>497 [M + H]+ | 1.267 | B |
| 5-141 | | 535 [M + H]+<br>567 [M + Na]+<br>538 [M + H]+ | 0.789 | A |

TABLE 66-3-continued
| Example No. | Structural Formula | MS post m/z MS mega m/z | Retention time (min) | method |
|---|---|---|---|---|
| 5-142 | | 633 [M + H]+<br>605 [M + Na]+<br>631 [M + H]+ | 0.526 | A |
| 5-143 | | 569 [M + H]+<br>591 [M + Na]+<br>567 [M + H]+ | 0.859 | A |
TABLE 66-4
| Example No. | Structural Formula | MS post m/z MS mega m/z | Retention time (min) | method |
|---|---|---|---|---|
| 5-144 | | 567 [M + H]+<br>589 [M + Na]+<br>565 [M + H]+ | 0.933 | A |
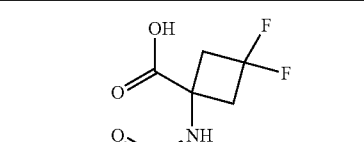

TABLE 66-4-continued

| Example No. | Structural Formula | MS post m/z<br>MS mega m/z | Retention time (min) | method |
|---|---|---|---|---|
| 5-145 | | 549 [M + H]+<br>571 [M + Na]+<br>647 [M + H]+ | 0.853 | A |
| 5-146 | | 547 [M + H]+<br>569 [M + Na]+<br>545 [M + H]+ | 0.986 | A |
| 5-147 | | 621 [M + H]+<br>543 [M + Na]+<br>619 [M + H]+ | 1.214 | B |

TABLE 66-4-continued
| Example No. | Structural Formula | MS post m/z<br>MS mega m/z | Retention time<br>(min) | method |
|---|---|---|---|---|
| 5-148 | 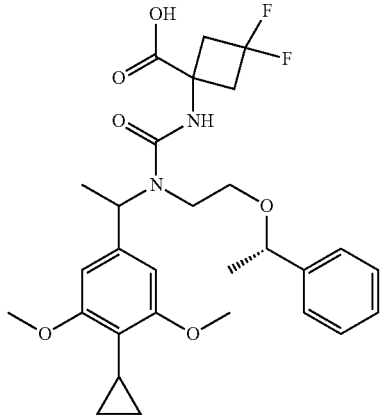 [SMILES: COc1cc(C(C)N(CCO[C@@H](C)c2ccccc2)C(=O)NC2(C(=O)O)CC(F)(F)C2)cc(OC)c1C1CC1] | 547 [M + H]+<br>569 [M + Na]+<br>545 [M − H]+ | 0.959 | A |
TABLE 66-5
| Example No. | Structural Formula | MS post m/z<br>MS mega m/z | Retention time<br>(min) | method |
|---|---|---|---|---|
| 5-149 | 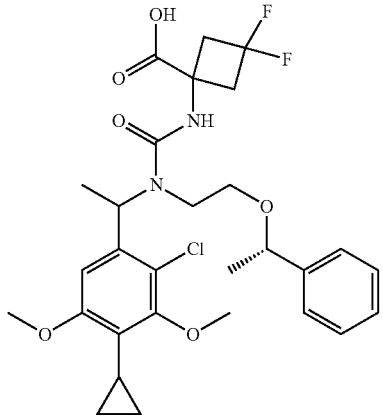 [SMILES: COc1cc(C(C)N(CCO[C@@H](C)c2ccccc2)C(=O)NC2(C(=O)O)CC(F)(F)C2)c(Cl)c(OC)c1C1CC1] | 581 [M + H]+<br>603 [M + Na]+<br>579 [M − H]+ | 0.963 | A |
| 5-150 | 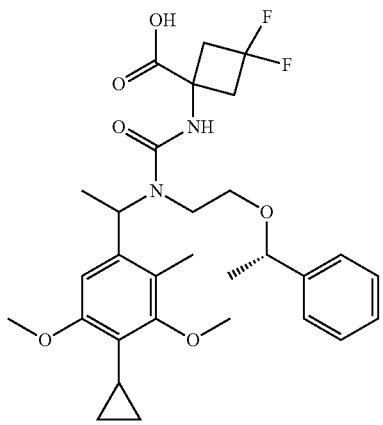 [SMILES: COc1cc(C(C)N(CCO[C@@H](C)c2ccccc2)C(=O)NC2(C(=O)O)CC(F)(F)C2)c(C)c(OC)c1C1CC1] | 561 [M + H]+<br>583 [M + Na]+<br>559 [M − H]+ | 0.967 | A |

TABLE 66-5-continued

| Example No. | Structural Formula | MS post m/z MS mega m/z | Retention time (min) | method |
|---|---|---|---|---|
| 5-151 | | 535 [M + H]+ 557 [M + Na]+ 533 [M + H]+ | 1.265 | B |
| 5-152 | | 627 [M + H]+ 549 [M + Na]+ 525 [M + H]+ | 0.885 | A |
| 5-153 | | 561 [M + H]+ 583 [M + Na]+ 559 [M + H]+ | 0.899 | A |

TABLE 66-6

| Example No. | Structural Formula | MS post m/z MS mega m/z | Retention time (min) | method |
|---|---|---|---|---|
| 5-154 | | 548 [M + H]+<br>565 [M + Na]+<br>543 [M + H]+ | 0.796 | A |
| 5-155 | | 541 [M + H]+<br>583 [M + Na]+<br>539 [M + H]+ | 0.948 | A |
| 5-156 | | 616 [M + H]+<br>637 [M + Na]+<br>613 [M + H]+ | 1.157 | B |

TABLE 66-6-continued

| Example No. | Structural Formula | MS post m/z MS mega m/z | Retention time (min) | method |
|---|---|---|---|---|
| 5-157 | | 541 [M + H]+ 563 [M + Na]+ 533 [M + H]+ | 0.974 | A |
| 5-158 | | 675 [M + H]+ 567 [M + Na]+ 673 [M + H]+ | 0.931 | A |

TABLE 66-7

| Example No. | Structural Formula | MS post m/z MS mega m/z | Retention time (min) | method |
|---|---|---|---|---|
| 5-159 | | 640 [M + H]+ 677 [M + Na]+ 638 [M + H]+ | 0.932 | A |

TABLE 66-7-continued

| Example No. | Structural Formula | MS post m/z MS mega m/z | Retention time (min) | method |
|---|---|---|---|---|
| 5-160 | | 529 [M + H]+ 551 [M + Na]+ 527 [M + H]+ | 1.207 | B |
| 5-161 | | 561 [M + H]+ 583 [M + Na]+ 559 [M + H]+ | 0.801 | A |
| 5-162 | | 541 [M + H]+ 563 [M + Na]+ 539 [M + H]+ | 0.421 | A |

TABLE 66-7-continued

| Example No. | Structural Formula | MS post m/z MS mega m/z | Retention time (min) | method |
|---|---|---|---|---|
| 5-163 | | 675 [M + H]+ 673 [M + H]+ | 0.930 | A |

TABLE 66-8

| Example No. | Structural Formula | MS post m/z MS mega m/z | Retention time (min) | method |
|---|---|---|---|---|
| 5-164 | | 557 [M + H]+ 574 [M + Na]+ 558 [M + H]+ | 0.813 | A |
| 5-165 | | 555 [M + H]+ 577 [M + Na]+ 554 [M + H]+ | 0.980 | A |

TABLE 66-8-continued

| Example No. | Structural Formula | MS post m/z MS mega m/z | Retention time (min) | method |
|---|---|---|---|---|
| 5-166 | | 629 [M + H]+<br>651 [M + Na]+<br>627 [M + H]+ | 1.295 | B |
| 5-167 | | 555 [M + H]+<br>577 [M + Na]+<br>553 [M + H]+ | 0.960 | A |
| 5-168 | | 651 [M + H]+<br>621 [M + Na]+<br>687 [M + H]+ | 0.966 | A |

TABLE 66-9
| Example No. | Structural Formula | MS post m/z MS mega m/z | Retention time (min) | method |
|---|---|---|---|---|
| 5-169 | 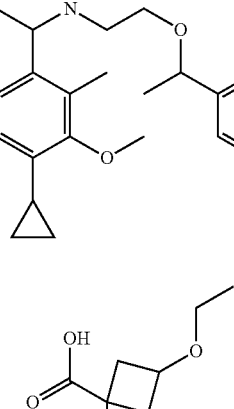 | 589 [M + H]+ 591 [M + Na]+ 557 [M + H]+ | 0.963 | A |
| 5-170 |  | 643 [M + H]+ 685 [M + Na]+ 641 [M + H]+ | 1.253 | B |
| 5-171 | 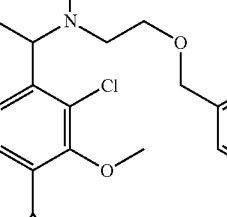 | 675 [M + H]+ 673 [M + H]+ | 0.939 | A |

TABLE 66-9-continued

| Example No. | Structural Formula | MS post m/z MS mega m/z | Retention time (min) | method |
|---|---|---|---|---|
| 5-172 | | 529 [M + H]+ 651 [M + Na]+ 527 [M + H]+ | 0.706 | A |
| 5-173 | | 527 [M + H]+ 649 [M + Na]+ 625 [M + H]+ | 0.365 | A |

TABLE 66-10

| Example No. | Structural Formula | MS post m/z MS mega m/z | Retention time (min) | method |
|---|---|---|---|---|
| 5-174 | | 653 [M + H]+ 631 [M + Na]+ 661 [M + H]+ | 0.785 | A |

TABLE 66-10-continued

| Example No. | Structural Formula | MS post m/z MS mega m/z | Retention time (min) | method |
|---|---|---|---|---|
| 5-175 | | 561 [M + H]+<br>659 [M + H]+ | 0.875 | A |
| 5-176 | | 513 [M + H]+<br>563 [M + Na]+<br>641 [M + H]+ | 0.988 | A |
| 5-177 | | 541 [M + H]+<br>563 [M + Na]+<br>539 [M + H]+ | 0.932 | A |

TABLE 66-10-continued

| Example No. | Structural Formula | MS post m/z MS mega m/z | Retention time (min) | method |
|---|---|---|---|---|
| 5-178 | | 616 [M + H]+ 637 [M + Na]+ 613 [M + H]+ | 1.131 | B |

TABLE 66-11

| Example No. | Structural Formula | MS post m/z MS mega m/z | Retention time (min) | method |
|---|---|---|---|---|
| 5-179 | | 641 [M + H]+ 633 [M + H]+ | 0.993 | A |
| 5-180 | | 575 [M + H]+ 573 [M + H]+ | 0.903 | A |

TABLE 66-11-continued

| Example No. | Structural Formula | MS post m/z MS mega m/z | Retention time (min) | method |
|---|---|---|---|---|
| 5-181 | | 656 [M + H]+ 653 [M + H]+ | 0.908 | A |
| 5-182 | | 629 [M + H]+ 627 [M + H]+ | 0.860 | A |
| 5-183 | | 611 [M + H]+ 633 [M + Na]+ 639 [M + H]+ | 0.957 | A |

TABLE 66-12

| Example No. | Structural Formula | MS post m/z MS mega m/z | Retention time (min) | method |
|---|---|---|---|---|
| 5-184 | | 547 [M + H]+ 669 [M + Na]+ 546 [M + H]+ | 0.830 | A |
| 5-185 | | 545 [M + H]+ 567 [M + Na]+ 543 [M + H]+ | 0.365 | A |
| 5-186 | | 527 [M + H]+ 525 [M + H]+ | 0.728 | D |

TABLE 66-12-continued

| Example No. | Structural Formula | MS post m/z MS mega m/z | Retention time (min) | method |
|---|---|---|---|---|
| 5-187 | | 661 [M + H]+ 583 [M + Na]+ 559 [M + H]+ | 0.897 | A |
| 5-188 | | 625 [M + H]+ 637 [M + Na]+ 623 [M + H]+ | 1.419 | A |

TABLE 66-13

| Example No. | Structural Formula | MS post m/z MS mega m/z | Retention time (min) | method |
|---|---|---|---|---|
| 5-189 | | 561 [M + H]+ 583 [M + Na]+ 559 [M + H]+ | 0.892 | A |

TABLE 66-13-continued

| Example No. | Structural Formula | MS post m/z MS mega m/z | Retention time (min) | method |
|---|---|---|---|---|
| 5-190 | | 559 [M + H]+ 581 [M + Na]+ 537 [M + H]+ | 1.029 | A |
| 5-191 | | 541 [M + H]+ 539 [M + H]+ | 0.799 | D |
| 5-192 | | 539 [M + H]+ 561 [M + Na]+ 537 [M + H]+ | 1.035 | A |

TABLE 66-13-continued

| Example No. | Structural Formula | MS post m/z MS mega m/z | Retention time (min) | method |
|---|---|---|---|---|
| 5-193 | | 513 [M + H]+ 535 [M + Na]+ 511 [M + H]+ | 0.991 | A |

TABLE 66-14

| Example No. | Structural Formula | MS post m/z MS mega m/z | Retention time (min) | method |
|---|---|---|---|---|
| 5-194 | | 527 [M + H]+ 549 [M + Na]+ 525 [M + H]+ | 1.022 | A |
| 5-195 | | 575 [M + H]+ 597 [M + Na]+ 573 [M + H]+ | 0.964 | A |

TABLE 66-14-continued

| Example No. | Structural Formula | MS post m/z MS mega m/z | Retention time (min) | method |
|---|---|---|---|---|
| 5-196 | | 561 [M + H]+ 583 [M + Na]+ 559 [M + H]+ | 1.010 | A |
| 5-197 | | 595 [M + H]+ 617 [M + Na]+ 593 [M + H]+ | 1.016 | A |
| 5-198 | | 569 [M + H]+ 591 [M + Na]+ 567 [M + H]+ | 0.884 | A |

TABLE 66-15

| Example No. | Structural Formula | MS posi m/z MS nega m/z | Retention time (min) | method |
|---|---|---|---|---|
| 5-199 | | 555 [M + H]+<br>577 [M + Na]+<br>553 [M + H]+ | 0.981 | A |
| 5-200 | | 589 [M + H]+<br>611 [M + Na]+<br>587 [M + H]+ | 0.990 | A |
| 5-201 | | 569 [M + H]+<br>591 [M + Na]+<br>667 [M + H]+ | 0.998 | A |

TABLE 66-15-continued

| Example No. | Structural Formula | MS posi m/z MS nega m/z | Retention time (min) | method |
|---|---|---|---|---|
| 5-202 | | 603 [M + H]+ 625 [M + Na]+ 601 [M + H]+ | 1.079 | A |
| 5-203 | | 683 [M + H]+ 605 [M + Na]+ 581 [M + H]+ | 1.029 | A |

TABLE 66-16

| Example No. | Structural Formula | MS posi m/z MS nega m/z | Retention time (min) | method |
|---|---|---|---|---|
| 5-204 | | 554 [M + H]+ 577 [M + Na]+ 552 [M + H]+ | 0.983 | A |

TABLE 66-16-continued

| Example No. | Structural Formula | MS posi m/z MS nega m/z | Retention time (min) | method |
|---|---|---|---|---|
| 5-205 | | 589 [M + H]+ 613 [M + Na]+ 583 [M + H]+ | 0.846 | A |
| 5-206 | | 689 [M + H]+ 611 [M + Na]+ 587 [M + H]+ | 0.987 | A |
| 5-207 | | 603 [M + H]+ 625 [M + Na]+ 601 [M + H]+ | 1.075 | A |

TABLE 66-16-continued
| Example No. | Structural Formula | MS posi m/z MS nega m/z | Retention time (min) | method |
|---|---|---|---|---|
| 5-208 | 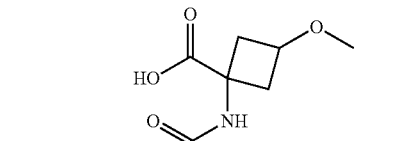 | 605 [M + H]+<br>627 [M + Na]+<br>603 [M + H]+ | 0.918 | A |
TABLE 66-17
| Example No. | Structural Formula | MS posi m/z MS nega m/z | Retention time (min) | method |
|---|---|---|---|---|
| 5-209 | 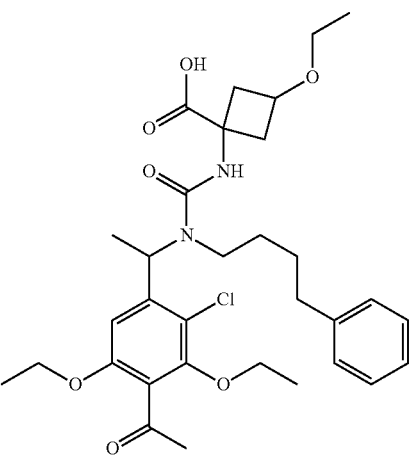 [SMILES: CCOc1cc(C(C)N(CCCCc2ccccc2)C(=O)NC2(C(=O)O)CC(OCC)C2)c(Cl)c(OCC)c1C(C)=O] | 603 [M + H]+<br>623 [M + Na]+<br>601 [M + H]+ | 0.949 | A |
| 5-210 | 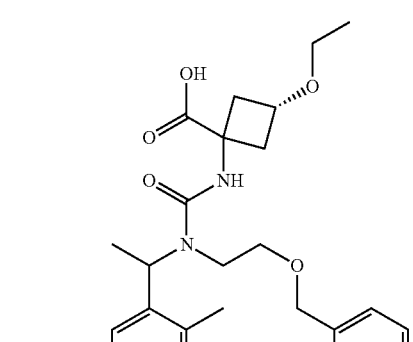 | 583 [M + H]+<br>605 [M + Na]+<br>581 [M + H]+ | 0.918 | A |

TABLE 66-17-continued

| Example No. | Structural Formula | MS posi m/z MS nega m/z | Retention time (min) | method |
|---|---|---|---|---|
| 5-211 | | 569 [M + H]+ 531 [M + H]+ | 1.016 | A |
| 5-212 | | 605 [M + H]+ 627 [M + Na]+ 603 [M + H]+ | 0.883 | A |
| 5-213 | | 603 [M + H]+ 601 [M + H]+ | 1.021 | A |

TABLE 66-18

| Example No. | Structural Formula | MS posi m/z<br>MS nega m/z | Retention time (min) | method |
|---|---|---|---|---|
| 5-214 | | 585 [M + H]+<br>583 [M + H]+ | 0.790 | D |
| 5-215 | | 583 [M + H]+<br>605 [M + Na]+<br>681 [M + H]+ | 1.022 | A |
| 5 216 | | 617 [M + H]+<br>639 [M + Na]+<br>615 [M + H]+ | 1.117 | A |

TABLE 66-18-continued

| Example No. | Structural Formula | MS posi m/z<br>MS nega m/z | Retention time (min) | method |
|---|---|---|---|---|
| 5-217 | | 597 [M + H]+<br>595 [M + H]+ | 1.055 | A |
| 5-218 | | 619 [M + H]+<br>641 [M + Na]+<br>617 [M + H]+ | 1 345 | B |

TABLE 66-19

| Example No. | Structural Formula | MS posi m/z<br>MS nega m/z | Retention time (min) | method |
|---|---|---|---|---|
| 5-219 | | 569 [M + H]+<br>591 [M + Na]+<br>567 [M + H]+ | 1.013 | A |

TABLE 66-19-continued
| Example No. | Structural Formula | MS posi m/z MS nega m/z | Retention time (min) | method |
|---|---|---|---|---|
| 5-220 | 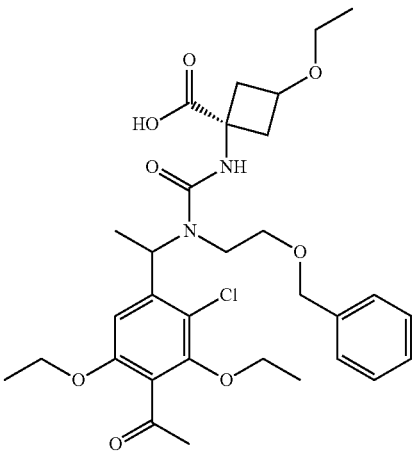 | 605 [M + H]+<br>627 [M + Na]+<br>603 [M + H]+ | 0.583 | A |
| 5-221 | 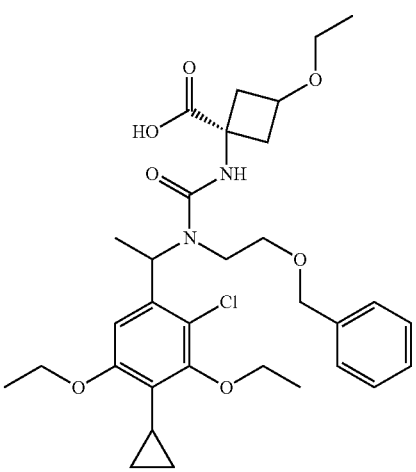 | 603 [M + H]+<br>625 [M + Na]+<br>601 [M + H]+ | 1.021 | A |
| 5-222 | 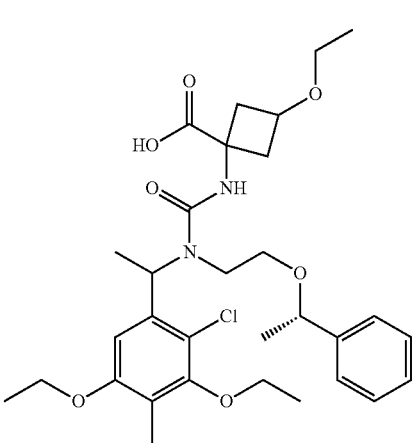 | 617 [M + H]+<br>639 [M + Na]+<br>615 [M + H]+ | 1.110 | A |

TABLE 66-19-continued

| Example No. | Structural Formula | MS posi m/z MS nega m/z | Retention time (min) | method |
|---|---|---|---|---|
| 5-223 | | 619 [M + H]+ 641 [M + Na]+ 617 [N + H]+ | 0.960 | A |

TABLE 66-20

| Example No. | Structural Formula | MS posi m/z MS nega m/z | Retention time (min) | method |
|---|---|---|---|---|
| 5-224 | | 555 [M + H]+ 577 [M + Na]+ 553 [M + H]+ | 0.963 | A |
| 5-225 | | 589 [M + H]+ 611 [M + Na]+ 587 [M + H]+ | 0.971 | A |

TABLE 66-20-continued

| Example No. | Structural Formula | MS posi m/z MS nega m/z | Retention time (min) | method |
|---|---|---|---|---|
| 5-226 | | 671 [M + H]+ 569 [M + H]+ | 0.726 | D |
| 5-227 | | 569 [M + H]+ 567 [M + H]+ | 0.979 | A |
| 5-228 | | 613 [M + H]+ 611 [N + H]+ | 0.921 | A |

Example 6-1

1-({[1-(3,5-Diethoxy-4-Methylphenyl)Ethyl](4-Phenylbutyl) Carbamoyl}Amino)Cyclopentane-1-Carboxamide

[Chemical Formula 511]

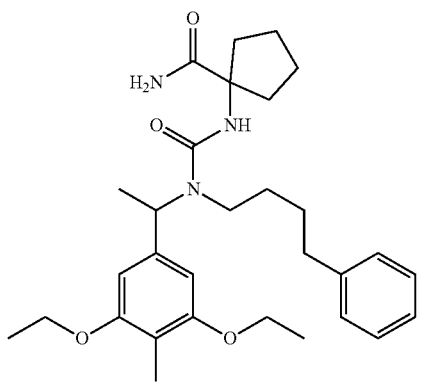

To a solution of the compound (50 mg) obtained in Example 1-112 in N,N-dimethylformamide (1 mL), ammonium chloride (26.2 mg) and N,N-diisopropylethylamine (75.9 mg) were added, and the reaction solution was stirred at room temperature for 30 minutes. EDC (37.5 mg) and HOBt (30.0 mg) were further added to the reaction solution, which was then stirred at room temperature for 7 hours. Water was added to the reaction solution, which was then extracted with chloroform. The organic layer was concentrated, and the obtained residue was purified by silica gel column chromatography (chloroform only to chloroform:methanol=95:5) to afford the title compound (30.7 mg) as a colorless solid.

$^1$H NMR (600 MHZ, CHLOROFORM-d) δ ppm 1.24-1.81 (m, 20H) 2.03-2.14 (m, 3H) 2.14-2.27 (m, 2H) 2.54-2.66 (m, 2H) 3.01-3.19 (m, 1H) 3.25-3.38 (m, 1H) 3.92-4.03 (m, 4H) 4.36-4.51 (m, 1H) 4.96-5.11 (m, 1H) 5.11-5.27 (m, 1H) 6.41-6.48 (m, 2H) 7.07-7.32 (m, 5H).

MS ESI/APCI Multi posi: 510 [M+H]$^+$, 532 [M+Na]$^+$.

Retention time: 0.968 min (method D)

Example 6-2

Methyl 1-({[1-(3,5-Diethoxyphenyl)Ethyl](4-Phenylbutyl) Carbamoyl}Amino)Cyclopentane-1-Carboxylate

[Chemical Formula 512]

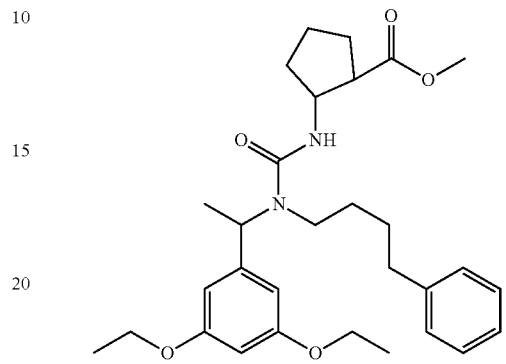

Using methyl 1-aminocyclopentanecarboxylate hydrochloride (139 mg) and the compound (189 mg) obtained in Reference Example 3-7-1, the reaction and post treatment were carried out in accordance with the method described in Example 1-21 (1), and purification by preparative HPLC was carried out to afford the title compound (115 mg) as a colorless oily substance.

$^1$H NMR (600 MHz, CHLOROFORM-d) δ ppm 1.39 (t, J=7.02 Hz, 6H) 1.47-1.57 (m, 5H) 1.58-1.60 (m, 2H) 1.61-1.78 (m, 5H) 1.80-1.97 (m, 1H) 2.11-2.25 (m, 2H) 2.53-2.61 (m, 2H) 2.92-3.06 (m, 1H) 3.11-3.24 (m, 1H) 3.68 (s, 3H) 3.99 (q, J=7.02 Hz, 4H) 4.54-4.59 (m, 1H) 5.19-5.35 (m, 1H) 6.34 (t, J=2.27 Hz, 1H) 6.45 (d, J=2.27 Hz, 2H) 7.11-7.18 (m, 3H) 7.24-7.29 (m, 2H).

MS ESI/APCI Multi posi: 511 [M+H]$^+$.

Retention time: 1.374 min (method E)

Example 6-3

Methyl 1-[([(1R)-1-(4-Acetyl-2-Chloro-3,5-Diethoxyphenyl)Ethyl]{2-[(1S)-1-Phenylethoxy]Ethyl}Carbamoyl)Amino]Cyclopropane-1-Carboxylate

[Chemical Formula 513]

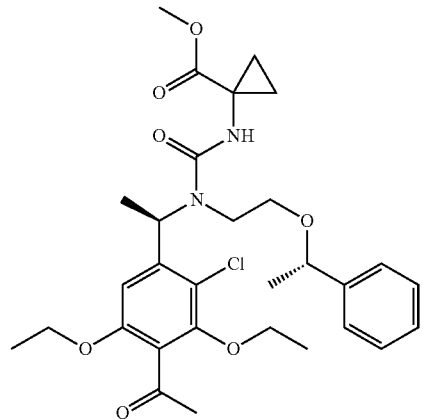 [SMILES: CCOc1cc(C(C)N(CCO[C@@H](C)c2ccccc2)C(=O)NC2(C(=O)OC)CC(F)(F)C2)c(Cl)c(OCC)c1C(C)=O]

A solution of methyl 1-aminocyclopropane-1-carboxylate hydrochloride (27.1 mg) and 4-nitrophenyl chloroformate (36.0 mg) in tetrahydrofuran (1.5 mL) was ice-cooled and stirred for 10 minutes, N,N-diisopropylethylamine (130 μL) was then added thereto, and the reaction solution was stirred at the same temperature for 2 hours. The compound (70 mg) obtained in Reference Example 3-4-2 was added to the reaction solution, which was then stirred at room temperature for 18 hours. The reaction solution was concentrated, purified by preparative HPLC, and freeze-dried to afford the title compound (64.3 mg) as a colorless amorphous.

$^1$H NMR (600 MHz, CHLOROFORM-d) δ ppm 1.03-1.13 (m, 2H) 1.31-1.64 (m, 14H) 2.47 (s, 3H) 2.70-2.78 (m, 1H) 3.04-3.17 (m, 2H) 3.28-3.37 (m, 1H) 3.71 (s, 3H) 3.97-4.05 (m, 4H) 4.29-4.37 (m, 1H) 5.63-5.72 (m, 1H) 6.69 (s, 1H) 7.11-7.36 (m, 6H).

MS ESI posi: 575 [M+H]$^+$, 597 [M+Na]$^+$.

Retention time: 0.936 min (method A)

The following Examples 6-4 to 6-17 were synthesized by the method described in Example 6-2 or by a method equivalent thereto, using the compounds obtained in Reference Example 3-4-2, Reference Example 3-4-28, Reference Examples 4-3-1 to 4-3-3, and Reference Examples 4-11-1 to 4-11-3, commercially available compounds, or compounds obtained by synthesis according to methods described in literatures or methods equivalent thereto. The structures and LCMS data of the compounds are shown in Tables 67-1 to 67-3.

TABLE 67-1

| Example No. | Structural Formula | MS posi m/z<br>MS nega m/z | Retention<br>time (min) | method |
|---|---|---|---|---|
| 6-4 | | 599 [M + H]+<br>621 [M + Na]+ | 0.962 | A |
| 6-5 | | 633 [M + H]+<br>655 [M + Na]+ | 0.934 | A |

TABLE 67-1-continued

| Example No. | Structural Formula | MS posi m/z MS nega m/z | Retention time (min) | method |
|---|---|---|---|---|
| 6-6 | | 591 [M + H]+ 613 [M + Na]+ | 0.961 | A |
| 6-7 | | 625 [M + H]+ 647 [M + Na]+ | 0.981 | A |

TABLE 67-2

| Example No. | Structural Formula | MS posi m/z MS nega m/z | Retention time (min) | method |
|---|---|---|---|---|
| 6-8 | | 589 [M + H]+ 611 [M + Na]+ | 0.965 | A |

TABLE 67-2-continued

| Example No. | Structural Formula | MS posi m/z MS nega m/z | Retention time (min) | method |
|---|---|---|---|---|
| 6-9 | | 613 [M + H]+ 635 [M + Na]+ | 0.993 | A |
| 6-10 | | 647 [M + H]+ 669 [M + Na]+ | 1.067 | A |
| 6-11 | | 606 [M + H]+ 527 [M + Na]+ | 0.990 | A |

TABLE 67-2-continued

| Example No. | Structural Formula | MS posi m/z<br>MS nega m/z | Retention<br>time (min) | method |
|---|---|---|---|---|
| 6-12 | | 639 [M + H]+<br>661 [M + Na]+ | 1.008 | A |

TABLE 67-3

| Example No. | Structural Formula | MS posi m/z<br>MS nega m/z | Retention<br>time (min) | method |
|---|---|---|---|---|
| 6-13 | | 617 [M + H]+<br>639 [M + Na]+ | 1.038 | A |
| 6-14 | | 641 [M + H]+<br>643 [M + Na]+ | 1.053 | A |

TABLE 67-3-continued

| Example No. | Structural Formula | MS posi m/z<br>MS nega m/z | Retention<br>time (min) | method |
|---|---|---|---|---|
| 6-15 | | 674 [M + H]+<br>697 [M + Na]+ | 1.079 | A |
| 6-16 | | 633 [M + H]+<br>656 [M + Na]+ | 1.048 | A |
| 6-17 | | 657 [M − H]+<br>689 [M + Na]+ | 1.067 | A |

Example 7-1

1-({[(1R)-1-(4-Acetyl-3,5-Diethoxyphenyl)Ethyl](4-Phenylbutyl) Carbamoyl}Amino)-3,3-Difluoro-N-(Methanesulfonyl)Cyclobutane-1-Carboxamide

[Chemical Formula 514]

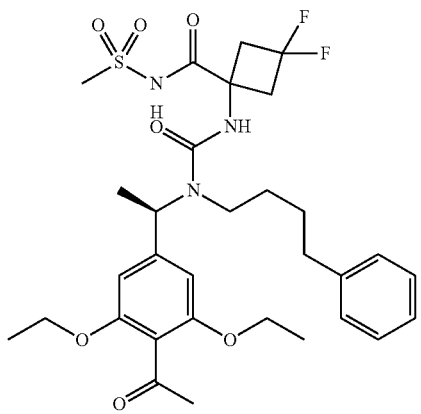 [SMILES: CCOc1cc(C(C)N(CCCCc2ccccc2)C(=O)NC2(C(=O)NS(C)(=O)=O)CC(F)(F)C2)cc(OCC)c1C(C)O]

A solution of the compound (31 mg) obtained in Example 1-30 in tetrahydrofuran (0.8 mL) was ice-cooled, N,N-diisopropylethylamine (77.1 µL) and CDI (17.9 mg) were added thereto, and the reaction solution was stirred at 50° C. for 1 hour. A solution of methanesulfonamide (21.0 mg) in tetrahydrofuran (0.4 mL) was added to the reaction solution, which was then stirred at 60° C. for 5 hours. N,N-Diisopropylethylamine (77.1 µL) and CDI (17.9 mg) were further added thereto, and the reaction solution was stirred at 60° C. for 1 hour. Then, methanesulfonamide (21.0 mg) was further added thereto, and the reaction solution was stirred at 60° C. for 2 hours. To the reaction solution, 2 mol/L hydrochloric acid was added to adjust the pH to 3, and purification by preparative thin layer chromatography (chloroform:methanol=85:15, Rf=0.55) and preparative HPLC was carried out to afford the title compound (15.5 mg) as a colorless solid.

$^1$H NMR (600 MHZ, CHLOROFORM-d) δ ppm 1.24-1.39 (m, 6H) 1.48-1.68 (m, 7H) 2.44-2.62 (m, 7H) 2.97-3.05 (m, 1H) 3.07-3.20 (m, 1H) 3.20-3.35 (m, 5H) 3.95-4.03 (m, 4H) 4.81-4.93 (m, 1H) 5.04-5.50 (m, 1H) 6.40 (s, 2H) 7.12-7.16 (m, 2H) 7.18-7.32 (m, 3H) 11.21 (br s, 1H).

MS ESI posi: 638 [M+H]$^+$, 660 [M+Na]$^+$.
MS ESI nega: 636 [M–H]$^-$.
Retention time: 0.951 min (method A)

The following Examples 7-2 to 7-3 were synthesized by the method described in Example 1-1 or Example 7-1, or by a method equivalent thereto, using the compounds obtained in Reference Example 3-9-1 and Example 1-112, commercially available compounds, or compounds obtained by synthesis according to methods described in literatures or methods equivalent thereto. The structures and LCMS data of the compounds are shown in Table 68-1.

TABLE 68-1

| Example No. | Structural Formula | MS posi m/z MS nega m/z | Retention time (min) | method |
|---|---|---|---|---|
| 7-2 | | 662 [M + Na]+ | 0.952 | A |
| 7-3 | | 588 [M + H]+ 568 [M + H]+ | 1.057 | D |

Example 7-4

1-({[(1R)-1-(4-Acetyl-3,5-Diethoxyphenyl)Ethyl](4-Phenylbutyl) Carbamoyl}Amino)-3,3-Difluoro-N-Sulfamoylcyclobutane-1-Carboxamide

[Chemical Formula 515]

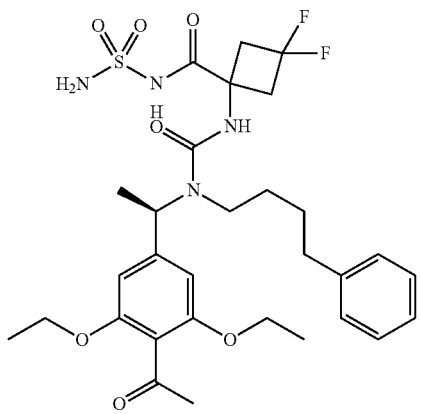

Using the compound (31 mg) obtained in Example 1-30 and sulfamide (42.5 mg), the reaction was carried out in accordance with the method described in Example 7-1,2 mol/L hydrochloric acid was added thereto to adjust the pH to 1, and extraction with chloroform was carried out. The organic layer was filtered through Phase Separator and concentrated. The obtained residue was purified by preparative HPLC and preparative thin layer chromatography (chloroform:methanol=85:15, Rf=0.55) and freeze-dried to afford the title compound (5.63 mg) as a colorless powder.

$^1$H NMR (600 MHz, CHLOROFORM-d) δ ppm 1.32-1.40 (m, 6H) 1.49-1.54 (m, 3H) 1.54-1.69 (m, 4H) 2.42-2.57 (m, 5H) 2.59-2.63 (m, 2H) 2.92-3.09 (m, 1H) 3.10-3.19 (m, 1H) 3.19-3.36 (m, 3H) 3.95-4.05 (m, 4H) 4.84 (br s, 1H) 5.17-5.35 (m, 2H) 6.41 (s, 2H) 7.13-7.16 (m, 2H) 7.17-7.25 (m, 1H) 7.27-7.33 (m, 2H) 11.03 (br s, 1H).

MS ESI posi: 639 [M+H]$^+$, 661 [M+Na]$^+$.

MS ESI nega: 637 [M−H]$^−$.

Retention time: 0.919 min (method A)

Example 7-5

1-({[1-(3,5-Diethoxy-4-Methylphenyl)Ethyl](4-Phenylbutyl) Carbamoyl}Amino)-N-(Dimethylsulfamoyl)Cyclopentane-1-Carboxamide

[Chemical Formula 516]

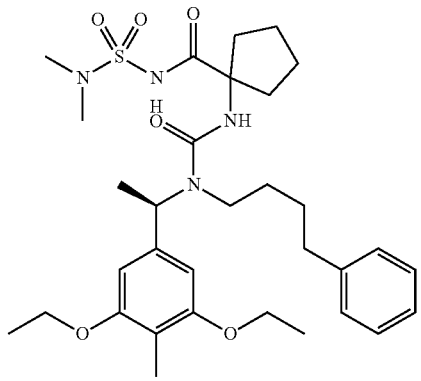

A solution of the compound (80 mg) obtained in Example 1-112 and N,N-dimethylsulfamide (38.9 mg) in N,N-dimethylformamide (1 mL) was ice-cooled, EDC (90.1 mg) and 4-dimethylaminopyridine (57.4 mg) were added thereto, and the reaction solution was stirred at 60° C. for 14 hours. Water was added to the reaction solution, which was then extracted with diethyl ether. The organic layer was washed with a brine and dried over anhydrous magnesium sulfate. After filtering off the desiccating agent, the filtrate was concentrated. The obtained residue was purified by preparative HPLC and freeze-dried to afford the title compound (11.1 mg) as a colorless solid.

$^1$H NMR (400 MHZ, CHLOROFORM-d) δ ppm 1.38-1.44 (m, 6H) 1.49-1.65 (m, 13H) 2.08 (s, 3H) 2.13-2.27 (m, 2H) 2.55-2.65 (m, 2H) 2.93 (s, 6H) 3.01-3.15 (m, 1H) 3.24-3.41 (m, 1H) 3.92-4.02 (m, 4H) 4.38-4.44 (m, 1H) 4.94-5.13 (m, 1H) 6.41 (s, 2H) 7.11-7.24 (m, 3H) 7.27-7.33 (m, 2H) 10.52 (br s, 1H).

MS ESI/APCI Multi posi: 617 [M+H]$^+$, 639 [M+Na]$^+$.

MS ESI/APCI Multi nega: 615 [M−H]$^−$.

Retention time: 1.061 min (method D)

Example 8-1

[1-({[1-(3,5-Diethoxy-4-Methylphenyl)Ethyl](4-Phenylbutyl) Carbamoyl}Amino)Cyclopentyl]Phosphonic Acid

[Chemical Formula 517]

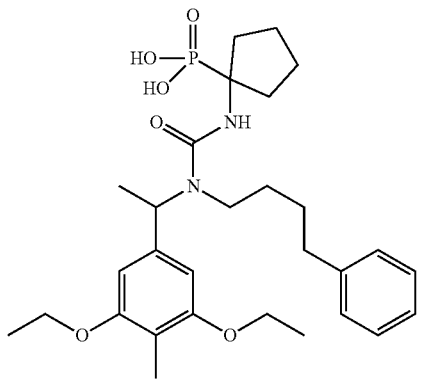

(1) To a solution of the compound (20 mg) obtained in Reference Example 4-8-1 in tetrahydrofuran (1 mL), N,N-diisopropylethylamine (50.4 μL), 4-nitrophenyl chloroformate (11.7 mg), and a solution of the compound (22.6 mg) obtained in Reference Example 3-1-2 in tetrahydrofuran (0.5 mL) were added, and the reaction solution was stirred at room temperature for 3 hours. Water was added to the reaction solution, which was then extracted with chloroform, and the organic layer was concentrated. The obtained residue was purified by NH silica gel column chromatography (n-hexane only to n-hexane:ethyl acetate=60:40) to afford dibenzyl[1-({[1-(3,5-diethoxy-4-methylphenyl)ethyl](4-phenylbutyl) carbamoyl}amino)cyclopentyl]phosphonate (7.9 mg) as a colorless gum-like substance.

(2) To a solution of the compound (7.9 mg) obtained in (1) above in methanol (2 mL), palladium carbon (4 mg) was added, and the reaction solution was stirred at room temperature for 2 hours under a hydrogen atmosphere. The reaction solution was filtered through Celite (registered trademark), and the filtrate was concentrated. The obtained residue was purified by preparative thin layer chromatography (chloroform:methanol=70:30, Rf=0.15) and preparative HPLC to afford the title compound (3.08 mg) as a colorless solid.

$^1$H NMR (400 MHZ, CHLOROFORM-d) δ ppm 1.06-1.32 (m, 3H) 1.37 (t, J=6.60 Hz, 6H) 1.47 (br s, 8H) 1.74-1.96 (m, 2H) 1.99-2.18 (m, 5H) 2.43-2.59 (m, 2H) 2.89-3.07 (m, 1H) 3.07-3.25 (m, 1H) 3.95 (q, J=6.60 Hz, 4H) 4.40-4.68 (m, 1H) 5.03-5.29 (m, 1H) 6.40 (s, 2H) 7.05-7.24 (m, 5H).

MS ESI/APCI Multi posi: 547 [M+H]$^+$.
MS ESI/APCI Multi nega: 545 [M−H]$^-$.
Retention time: 1.020 min (method D)

The following Example 8-2 was synthesized by the method described in Example 8-1 or by a method equivalent thereto, using the compounds obtained in Reference Example 3-4-4 and Reference Example 4-8-1, commercially available compounds, or compounds obtained by synthesis according to methods described in literatures or methods equivalent thereto. The structure and LCMS data of the compound are shown in Table 69-1.

TABLE 69-1

| Example No. | Structural Formula | MS posi m/z MS nega m/z | Retention time (min) | method |
|---|---|---|---|---|
| 8-2 | | 547 [M + H]+<br>589 [M + Na]+<br>545 [M + H]+ | 1.039 | D |

881

Example 9-1

N-[1-(3,5-Diethoxy-4-Methylphenyl)Ethyl]-N'-[1-(5-Oxo-2,5-Dihydro-1,2,4-Oxadiazol-3-Yl)Cyclopentyl]-N-(4-Phenylbutyl) Urea

[Chemical Formula 518]

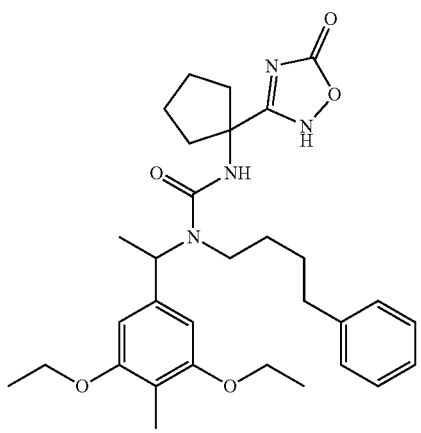

(1) Using 1-aminocyclopentane-1-carbonitrile hydrochloride (193 mg) and the compound (400 mg) obtained in Reference Example 3-1-2, the reaction was carried out in accordance with the method described in Example 1-21 (1), and N'-(1-cyanocyclopentyl)-N-[1-(3,5-diethoxy-4-methylphenyl)ethyl]-N-(4-phenylbutyl) urea (278 mg) was obtained as a colorless oily substance.

(2) To a solution of the compound (96.0 mg) obtained in (1) above in ethanol (976 μL), water (244 μL), hydroxylamine hydrochloride (40.7 mg), and sodium carbonate (62.1 mg) were added, and the reaction solution was stirred at 80° C. for 1 hour. The reaction solution was concentrated, and the obtained residue was purified by silica gel column chromatography (n-hexane only to n-hexane:ethyl acetate=30:70) to afford 1-({[1-(3,5-diethoxy-4-methylphenyl)ethyl](4-phenylbutyl) carbamoyl}amino)-N'-hydroxycyclopentane-1-carboximidamide (22.4 mg) as a colorless oily substance.

(3) To a solution of the compound (22.4 mg) obtained in (2) above in tetrahydrofuran (427 μL), CDI (8.31 mg) and DBU (7.01 μL) were added, and the reaction solution was stirred at room temperature for 17 hours. The reaction solution was concentrated, and the obtained residue was purified by preparative HPLC to afford the title compound (11.4 mg) as a colorless solid.

$^1$H NMR (400 MHz, CHLOROFORM-d) δ ppm 1.20-1.64 (m, 16H) 1.65-1.78 (m, 2H) 1.81-1.99 (m, 2H) 2.08 (s, 3H) 2.11-2.31 (m, 2H) 2.52-2.69 (m, 2H) 2.95-3.20 (m, 1H) 3.20-3.45 (m, 1H) 3.87-4.04 (m, 4H) 4.39-4.54 (m, 1H) 4.87-5.14 (m, 1H) 6.40 (s, 2H) 7.08-7.23 (m, 3H) 7.23-7.31 (m, 2H).

MS ESI/APCI Multi posi: 551 [M+H]$^+$.

MS ESI/APCI Multi nega: 549 [M−H]$^−$.

Retention time: 1.051 min (method D)

882

Example 10-1

N-[(1R)-1-(4-Acetyl-3,5-Diethoxyphenyl)Ethyl]-N-{2-[(1S)-1-Phenylethoxy]Ethyl}-N'-[1-(2H-Tetrazol-5-Yl)Cyclopropyl]Urea

[Chemical Formula 519]

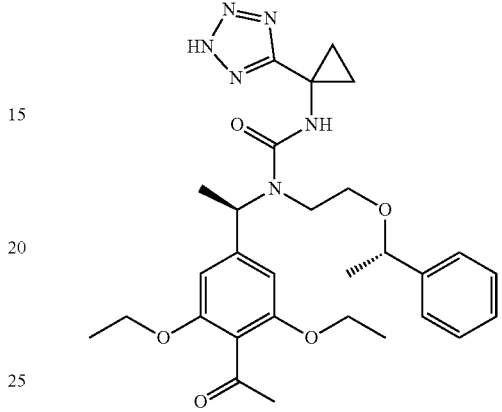

(1) A solution of the compound (25.3 mg) obtained in Reference Example 4-9-1 in tetrahydrofuran (1 mL) was ice-cooled, N,N-diisopropylethylamine (59.9 μL) and 4-nitrophenyl chloroformate (13.9 mg) were added thereto, and the reaction solution was stirred at room temperature for 1.5 hours. The compound (25 mg) obtained in Reference Example 3-4-28 was added to the reaction solution, which was then stirred at 60° C. for 1.5 hours. The reaction solution was ice-cooled, a saturated aqueous sodium bicarbonate solution was added thereto, and extraction with ethyl acetate was carried out. The organic layer was washed with each of a saturated sodium bicarbonate solution and a brine, then filtered through Phase Separator, and concentrated to afford a mixture containing N-[(1R)-1-(4-acetyl-3,5-diethoxyphenyl)ethyl]-N-{2-[(1S)-1-phenylethoxy]ethyl}-N'-{1-[2-(triphenylmethyl)-2H-tetrazol-5-yl]cyclopropyl}urea.

(2) A solution of the mixture (11.4 mg) obtained in (1) above in isopropyl alcohol (0.5 mL) was ice-cooled, a 2 mol/L hydrogen chloride-isopropyl alcohol solution (0.2 mL) was added thereto, and the reaction solution was stirred for 1 hour while gradually bringing it back to room temperature. The reaction solution was ice-cooled and neutralized with a saturated aqueous sodium bicarbonate solution (the pH was 7 or more), 2 mol/L hydrochloric acid was added thereto (the pH was 5 to 3), and extraction with chloroform was carried out. The organic layer was filtered through Phase Separator and concentrated. The obtained residue was purified by preparative HPLC and freeze-dried to afford the title compound (6.7 mg) as a colorless powder.

$^1$H NMR (600 MHz, CHLOROFORM-d) δ ppm 1.13-1.19 (m, 1H) 1.22-1.27 (m, 1H) 1.30-1.38 (m, 12H) 1.50-1.63 (m, 2H) 2.46 (s, 3H) 3.00-3.07 (m, 1H) 3.09-3.19 (m, 2H) 3.19-3.25 (m, 1H) 3.90-4.05 (m, 4H) 4.20-4.30 (m, 1H) 5.65-5.75 (m, 1H) 6.43 (s, 2H) 7.01-7.11 (m, 2H) 7.22-7.36 (m, 3H) 7.70 (br s, 1H) 13.84-14.30 (m, 1H).

MS ESI posi: 551 [M+H]$^+$, 573 [M+Na]$^+$.

MS ESI nega: 549 [M−H]$^−$.

Retention time: 0.802 min (method A)

The following Examples 10-2 to 10-6 were synthesized by the method described in Example 10-1 or by a method equivalent thereto, using the compounds obtained in Reference Example 3-4-1, Reference Example 3-4-21, Reference Example 3-4-30, and Reference Example 4-9-1, commercially available compounds, or compounds obtained by synthesis according to methods described in literatures or methods equivalent thereto. The structures and LCMS data of the compounds are shown in Table 70-1.

TABLE 70-1

| Example No. | Structural Formula | MS posi m/z MS nega m/z | Retention time (min) | method |
|---|---|---|---|---|
| 10-2 | | 537 [M + H]+<br>535 [M + H]+ | 0.839 | A |
| 10-3 | | 536 [M + H]+<br>535 [M + H]+ | 0.816 | A |
| 10-4 | | 571 [M + H]+<br>569 [M + H]+ | 0.788 | A |

TABLE 70-1-continued

| Example No. | Structural Formula | MS posi m/z MS nega m/z | Retention time (min) | method |
|---|---|---|---|---|
| 10-5 | | 537 [M + H]+ 536 [M + H]+ | 0.703 | A |
| 10-6 | | 549 [M + H]+ 581 [M + Na]+ 547 [M + H]+ | 1.049 | A |

Example 10-7

N-[(1R)-1-(4-Acetyl-3,5-Diethoxyphenyl)Ethyl]-N'-[3,3-Difluoro-1-(1H-Tetrazol-5-Yl)Cyclobutyl]-N-(4-Phenylbutyl) Urea

[Chemical Formula 520]

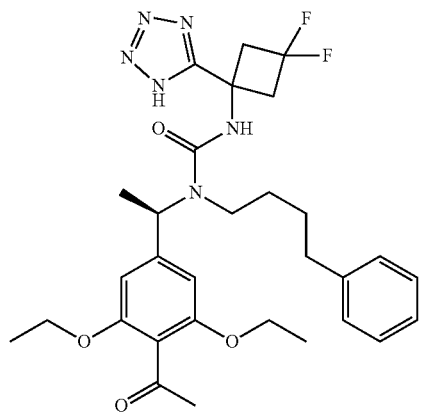

(1) Using the compound (40 mg) obtained in Reference Example 4-10-1 and the compound (50 mg) obtained in Reference Example 3-4-1, the reaction was carried out in accordance with the method described in Example 10-1 (1), and N-[(1R)-1-(4-acetyl-3,5-diethoxyphenyl)ethyl]-N'-[1-(2-benzyl-2H-tetrazol-5-yl)-3,3-difluorocyclobutyl]-N-(4-phenylbutyl) urea (64 mg) was obtained as a colorless oily substance.

(2) To a solution of the compound (64 mg) obtained in (1) above in methanol (4 mL), palladium carbon (32 mg) was added, and the reaction solution was stirred at room temperature for 20 hours under a hydrogen atmosphere. The reaction solution was filtered through Celite (registered trademark), and the filtrate was concentrated. The obtained residue was purified by preparative HPLC and freeze-dried to afford the title compound (23 mg) as a colorless powder.

$^1$H NMR (400 MHz, CHLOROFORM-d) δ ppm 1.30-1.40 (m, 6H) 1.45-1.66 (m, 7H) 2.46 (s, 3H) 2.56-2.65 (m, 2H) 2.81-3.07 (m, 3H) 3.07-3.23 (m, 1H) 3.41-3.61 (m, 2H) 3.84-4.04 (m, 4H) 4.91-5.05 (m, 1H) 5.10-5.35 (m, 1H) 6.36 (s, 2H) 7.26 (s, 5H).

MS ESI posi: 585 [M+H]$^+$.

Retention time: 0.873 min (method A)

The following Example 10-8 was synthesized by the method described in Example 10-7 or by a method equivalent thereto, using the compounds obtained in Reference Example 3-4-39 and Reference Example 4-10-1, commercially available compounds, or compounds obtained by synthesis according to methods described in literatures or methods equivalent thereto. The structures and LCMS data of the compounds are shown in Table 71-1.

TABLE 71-1

| Example No. | Structural Formula | MS posi m/z MS nega m/z | Retention time (min) | method |
|---|---|---|---|---|
| 10-8 | 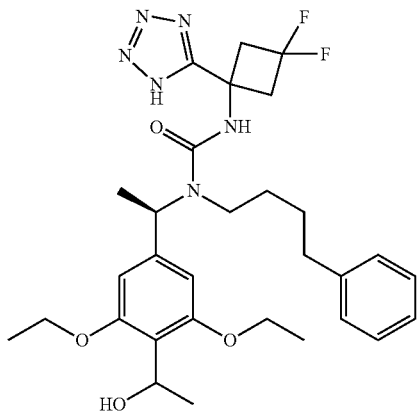 | 619 [M + H]+ 641 [M + Na]+ 617 [M + H]+ | 0.896 | A |

Example 10-9

N-{(1R)-1-[3,5-Diethoxy-4-(1-Hydroxyethyl)Phenyl]Ethyl}-N'-[3,3-Difluoro-1-(1H-Tetrazol-5-Yl)Cyclobutyl]-N-(4-Phenylbutyl) Urea

[Chemical Formula 521]

A solution of the compound (10 mg) obtained in Example 10-7 in tetrahydrofuran (2 mL) was ice-cooled, lithium borohydride (7.45 mg) was added thereto, and the reaction solution was stirred at room temperature for 2 hours. The reaction solution was ice-cooled, methanol, water, and acetic acid were added thereto, and the reaction solution was stirred for a while and concentrated. The obtained residue was purified by preparative HPLC and freeze-dried to afford the title compound (6.69 mg) as a colorless powder.

$^1$H NMR (400 MHZ, CHLOROFORM-d) δ ppm 1.15-1.57 (m, 16H) 2.56-2.64 (m, 2H) 2.77-2.91 (m, 2H) 2.95-3.08 (m, 2H) 3.15-3.21 (m, 1H) 3.42-3.57 (m, 2H) 3.80-3.89 (m, 1H) 3.89-4.06 (m, 4H) 4.88-4.97 (m, 1H) 5.24-5.36 (m, 1H) 6.38 (s, 2H) 7.08-7.15 (m, 2H) 7.17-7.32 (m, 3H).

MS ESI posi: 569 [M−OH]+, 609 [M+Na]+.

MS ESI nega: 585 [M−H]−.

Retention time: 0.869 min (method A)

Example 10-10

Example 10-11

N-{(1R)-1-[3,5-Diethoxy-4-(1-Hydroxyethyl)Phenyl]Ethyl}-N'-[3,3-Difluoro-1-(1H-Tetrazol-5-Yl)Cyclobutyl]-N-(4-Phenylbutyl) Urea

[Chemical Formula 522]

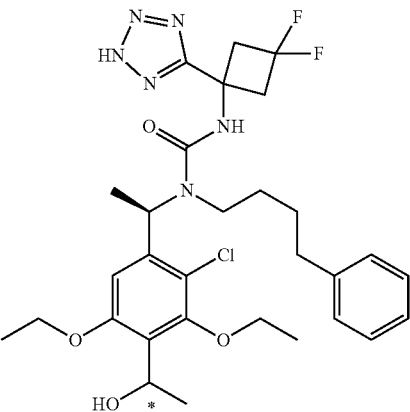

Using the compound (8.5 mg) obtained in Example 10-8, the reaction was carried out in accordance with the method described in Example 10-9. Purification by preparative HPLC and freeze-drying were carried out to afford one optical isomer of the title compound with a shorter retention time (Example 10-10) (2.67 mg) as a colorless powder and the other optical isomer of the title compound with a longer retention time (Example 10-11) (3.59 mg) as a colorless powder.

Example 10-10

¹H NMR (400 MHZ, CHLOROFORM-d) δ ppm 1.20-1.59 (m, 16H) 2.45-2.57 (m, 2H) 2.81-2.99 (m, 2H) 3.03-3.17 (m, 2H) 3.35-3.51 (m, 1H) 3.53-3.69 (m, 1H) 3.88-4.15 (m, 5H) 4.90-5.00 (m, 1H) 5.14-5.24 (m, 1H) 5.35-5.48 (m, 1H) 6.62 (s, 1H) 7.08-7.14 (m, 2H) 7.16-7.30 (m, 3H).
MS ESI posi: 603 [M−OH]⁺, 643 [M+Na]⁺.
MS ESI nega: 619 [M−H]⁻.
Retention time: 0.848 min (method A)

Example 10-11

¹H NMR (400 MHZ, CHLOROFORM-d) δ ppm 1.17-1.60 (m, 16H) 2.45-2.57 (m, 2H) 2.81-3.11 (m, 5H) 3.37-3.54 (m, 1H) 3.54-3.72 (m, 1H) 3.89-3.99 (m, 2H) 4.02-4.16 (m, 2H) 4.96-5.04 (m, 1H) 5.10-5.30 (m, 1H) 5.40-5.53 (m, 1H) 6.64 (s, 1H) 7.06-7.13 (m, 2H) 7.16-7.30 (m, 3H).
MS ESI posi: 603 [M−OH]⁺, 643 [M+Na]⁺.
MS ESI nega: 619 [M−H].
Retention time: 0.868 min (method A)

The following Examples 10-12 to 10-18 were synthesized by the method described in Example 1-152, Example 10-1, Example 10-7, or Example 10-9, or by a method equivalent thereto, using the compounds obtained in Reference Example 3-1-2, Reference Example 3-4-1, Reference Example 3-4-28, Reference Example 3-4-32, Reference Example 3-4-38, Reference Example 3-4-45, Reference Examples 4-9-2 to 4-9-3, and Reference Examples 4-10-1 to 4-10-2, commercially available compounds, or compounds obtained by synthesis according to methods described in literatures or methods equivalent thereto. The structures and LCMS data of the compounds are shown in Tables 72-1 to 72-2.

TABLE 72-1

| Example No. | Structural Formula | MS posi m/z<br>MS nega m/z | Retention<br>time (min) | method |
|---|---|---|---|---|
| 10-12 | | 655 [M + H]+<br>663 [M + H]+ | 0.924 | A |
| 10-13 | | 585 [M + H]+<br>607 [M + Na]+<br>583 [M + H]+ | 0.996 | A |

TABLE 72-1-continued

| Example No. | Structural Formula | MS posi m/z MS nega m/z | Retention time (min) | method |
|---|---|---|---|---|
| 10-14 | | 579 [M + H]+ 601 [M + Na]+ 577 [M + H]+ | 0.831 | A |
| 10-15 | | 593 [M + H]+ 615 [M + Na]+ 591 [M + H]+ | 1.020 | A |
| 10-16 | | 585 [M + H]+ 617 [M + Na]+ 693 [M − H]− | 0.868 | A |

TABLE 72-2

| Example No. | Structural Formula | MS posi m/z<br>MS nega m/z | Retention time (min) | method |
|---|---|---|---|---|
| 10-17 | | 615 [M + Na]+<br>579 [M + OH]+<br>595 [M + H]+ | 0.826 | A |
| 10-18 | | 535 [M + H]+<br>545 [M + H]+ | 1.080 | D |

The LPA1 receptor antagonistic activity of the inventive compounds of the present application was evaluated by the method shown in Test Example 1 below.

Test Example 1

(1) Preparation of RH7777 cells stably expressing human LPAR1

The human LPAR1 expression vector was transfected into RH7777 cells to acquire human LPAR1 expressing cells.

(2) Test of antagonism against response of LPA-induced increase in intracellular $Ca^{2+}$ concentration Cells stably expressing human LPAR1 were used for a test of antagonism against response of LPA-induced increase in intracellular $Ca^{2+}$ concentration.

The cells were seeded onto the Poly-D-Lysine 96 well black plate and incubated overnight. After incubation in the medium without FBS for 2 hours or longer, the medium was removed by suction, and 100 μL of the Loading Buffer (1×HBSS, 20 mM HEPES, 2.5 mM Probenecid, 0.05% BSA, 0.25 mg/mL Amaranth, 0.05% Pluronic F-127, 2 M Fluo-4, pH 7.4) was added, and incubation was carried out for 60 minutes. 50 μL of the Basal Buffer (1×HBSS, 20 mM HEPES, 2.5 mM Probenecid, 0.05% BSA, 0.25 mg/mL Amaranth, pH 7.4) containing the test compound was added thereto, followed by incubation at 37° C. for 30 minutes. In FDSS6000 (Hamamatsu Photonics K.K.), LPAs were added, and the change in intracellular $Ca^{2+}$ concentration was detected using the fluorescence value of a wavelength of 540 nm by an excitation wavelength of 480 nm as an indicator. The ratio (Rmax) between the basal fluorescence value and the maximum fluorescence value was determined, and the concentration producing 50% antagonism against response of LPA-induced increase in intracellular $Ca^{2+}$ concentration ($IC_{50}$ value) was calculated. The Rmax under Basal Buffer stimulation without the test compound was used as the control value. The Rmax under Basal Buffer stimulation with no LPAs or test compounds was used as the basal value.

The percentage (%) of increase in intracellular $Ca^{2+}$ concentration was calculated by dividing the value obtained by subtracting the basal value from Rmax in the presence of LPAs and each concentration of the test compound by the value obtained by subtracting the basal value from the control value. The concentration of each test compound was plotted on the X axis and the percentage (%) of increase in intracellular $Ca^{2+}$ concentration was plotted on the Y axis, and the $IC_{50}$ value was calculated by nonlinear regression using XLfit. The test results are shown in Table 73-1 to Table 73-6.

TABLE 73-1

| Example No. | $IC_{50}$ value (nM) |
|---|---|
| 1-1 | 3.17 |
| 1-2 | 7360 |
| 1-3 | 1800 |
| 1-4 | 25.5 |
| 1-5 | 4680 |

TABLE 73-1-continued

| Example No. | IC$_{50}$ value (nM) |
|---|---|
| 1-6 | 1580 |
| 1-7 | 11.6 |
| 1-8 | 125 |
| 1-9 | 129 |
| 1-10 | 88.5 |
| 1-11 | 352 |
| 1-12 | 3600 |
| 1-13 | 20.4 |
| 1-14 | 5690 |
| 1-15 | 280 |
| 1-16 | 2.23 |
| 1-17 | 23.7 |
| 1-18 | 1.09 |
| 1-19 | 4.10 |
| 1-20 | 0.621 |
| 1-21 | 3.38 |
| 1-22 | 1.47 |
| 1-23 | 13.0 |
| 1-24 | 3.54 |
| 1-25 | 2.71 |
| 1-26 | 0.998 |
| 1-27 | 2.30 |
| 1-28 | 2.82 |
| 1-29 | 3.12 |
| 1-30 | 1.75 |
| 1-31 | 177 |
| 1-32 | 8.93 |
| 1-33 | 7.13 |
| 1-34 | 1.99 |
| 1-35 | 1.81 |
| 1-36 | 1.04 |
| 1-37 | 3.45 |
| 1-38 | 5.40 |
| 1-39 | 5640 |
| 1-40 | 103 |
| 1-41 | 6.15 |
| 1-42 | 4.02 |
| 1-43 | 5.72 |
| 1-44 | 1.99 |
| 1-45 | 139 |
| 1-46 | 1.00 |
| 1-47 | 2.71 |
| 1-48 | 2.47 |
| 1-49 | 5.21 |
| 1-50 | 3.68 |
| 1-51 | 3.52 |
| 1-52 | 7.96 |
| 1-53 | 3.00 |
| 1-54 | 3.25 |
| 1-55 | 7.44 |
| 1-56 | 33.0 |
| 1-57 | 26.6 |
| 1-58 | 4.24 |
| 1-59 | 14.9 |
| 1-60 | 5.46 |
| 1-61 | 103 |
| 1-62 | 6.76 |
| 1-63 | 10.9 |
| 1-64 | 3.18 |
| 1-65 | 2.42 |
| 1-66 | 3.96 |
| 1-67 | 1.60 |
| 1-68 | 3.78 |
| 1-69 | 5.04 |
| 1-70 | 8.22 |
| 1-71 | 3.48 |
| 1-72 | 4.22 |
| 1-73 | 7.43 |
| 1-74 | 7.15 |
| 1-75 | 1.24 |
| 1-76 | 3.05 |
| 1-77 | 3.12 |
| 1-78 | 5.87 |
| 1-79 | 7.86 |
| 1-80 | 13.1 |
| 1-81 | 0.944 |
| 1-82 | 0.961 |
| 1-83 | 2.44 |

TABLE 73-1-continued

| Example No. | IC$_{50}$ value (nM) |
|---|---|
| 1-84 | 3.12 |
| 1-85 | 2.53 |
| 1-86 | 2.33 |
| 1-87 | 1.37 |
| 1-88 | 3.35 |
| 1-89 | 2.21 |
| 1-90 | 9.18 |
| 1-91 | 1.99 |
| 1-92 | 0.991 |
| 1-93 | 4.00 |
| 1-94 | 11.8 |
| 1-95 | 3.09 |
| 1-96 | 2.11 |
| 1-97 | 3.94 |
| 1-98 | 4.33 |
| 1-99 | 2.58 |
| 1-100 | 3.13 |
| 1-101 | 1.44 |
| 1-102 | 2.03 |
| 1-103 | 4.57 |
| 1-104 | 10.3 |
| 1-105 | 4.92 |
| 1-106 | 8.72 |
| 1-107 | 3.34 |
| 1-108 | 512 |
| 1-109 | 312 |
| 1-110 | 20.2 |
| 1-111 | 2.31 |
| 1-112 | 18.7 |
| 1-113 | 4.09 |
| 1-114 | 128 |
| 1-115 | 12.4 |
| 1-116 | 57.4 |
| 1-117 | 16.8 |
| 1-118 | 42.8 |
| 1-119 | 53.6 |
| 1-120 | 1670 |

TABLE 73-2

| Example No. | IC$_{50}$ value (nM) |
|---|---|
| 1-121 | 9.23 |
| 1-122 | 12.7 |
| 1-123 | 12.7 |
| 1-124 | 237 |
| 1-125 | 3.09 |
| 1-126 | 3.13 |
| 1-127 | 33.7 |
| 1-128 | 6.38 |
| 1-129 | 9.98 |
| 1-130 | 6.48 |
| 1-131 | 6.56 |
| 1-132 | 7.10 |
| 1-133 | 1.21 |
| 1-134 | 14.5 |
| 1-135 | 2.17 |
| 1-136 | 18.2 |
| 1-137 | 102 |
| 1-138 | 11.8 |
| 1-139 | 3.09 |
| 1-140 | 65.9 |
| 1-141 | 42.9 |
| 1-142 | 49.2 |
| 1-143 | 200 |
| 1-144 | 28.7 |
| 1-145 | 1.72 |
| 1-146 | 24.3 |
| 1-147 | 40.6 |
| 1-148 | 25.5 |
| 1-149 | 2.24 |
| 1-150 | 8.00 |
| 1-151 | 3.57 |
| 1-152 | 5.17 |
| 1-153 | 173 |

TABLE 73-2-continued

| Example No. | IC$_{50}$ value (nM) |
|---|---|
| 1-154 | 11.3 |
| 1-155 | 0.997 |
| 1-156 | 3.68 |
| 1-157 | 3.24 |
| 1-158 | 294 |
| 1-159 | 2.56 |
| 1-160 | 11.9 |
| 1-161 | 9.64 |
| 1-162 | 3.92 |
| 1-163 | 20.5 |
| 1-164 | 38.4 |
| 1-165 | 64.8 |
| 1-166 | 11.0 |
| 1-167 | 16.7 |
| 2-1 | 608 |
| 3-1 | 110 |
| 3-2 | 85.8 |
| 3-3 | 30.1 |
| 3-4 | 4.03 |
| 3-5 | 4.88 |
| 3-6 | 7.07 |
| 3-7 | 74.5 |
| 3-8 | 33.5 |
| 3-9 | 62.7 |
| 3-10 | 114 |
| 4-1 | 2500 |
| 4-2 | 8.34 |
| 4-3 | 31.5 |
| 4-4 | 9.64 |
| 4-5 | 6.91 |
| 4-6 | 42.0 |
| 4-7 | 25.2 |
| 4-8 | 8.87 |
| 4-9 | 11.6 |
| 4-10 | 26.4 |
| 4-11 | 126 |
| 4-12 | 192 |
| 4-13 | 59.8 |
| 4-14 | 19.7 |
| 4-15 | 32.7 |
| 4-16 | 4.05 |
| 4-17 | 9.68 |
| 4-18 | 18.1 |
| 4-19 | 60.8 |
| 4-20 | 148 |
| 4-21 | 2.74 |
| 4-22 | 7.62 |
| 4-23 | 7.17 |
| 4-24 | 5.57 |
| 4-25 | 10.4 |
| 4-26 | 1830 |
| 4-27 | 220 |
| 4-28 | 27.1 |
| 4-29 | 17.6 |
| 4-30 | 178 |
| 4-31 | 28.4 |
| 4-32 | 733 |
| 4-33 | 30.7 |
| 4-34 | 7630 |
| 4-35 | 2.26 |
| 4-36 | 5.70 |
| 4-37 | 30.6 |
| 4-38 | 10.5 |
| 4-39 | 46.4 |
| 4-40 | 3.15 |
| 4-41 | 4.16 |
| 4-42 | 25.2 |
| 4-43 | 37.2 |
| 4-44 | 3.34 |
| 4-45 | 1.59 |
| 4-46 | 1.21 |
| 4-47 | 10.5 |
| 4-48 | 2.55 |
| 4-49 | 4.94 |
| 4-50 | 1.21 |
| 4-51 | 1.11 |
| 4-52 | 2.68 |
| 4-53 | 1.72 |
| 4-54 | 3.75 |
| 4-55 | 3.17 |
| 4-56 | 1.33 |
| 4-57 | 4.47 |
| 4-58 | 1.15 |
| 4-59 | 1.62 |
| 4-60 | 2.90 |
| 4-61 | 3.99 |
| 4-62 | 5.15 |

TABLE 73-3

| Example No. | IC$_{50}$ value (nM) |
|---|---|
| 4-63 | 3.94 |
| 4-64 | 2.69 |
| 4-65 | 5.30 |
| 4-66 | 10.6 |
| 4-67 | 1.27 |
| 4-68 | 8.85 |
| 4-69 | 4.90 |
| 4-70 | 1.27 |
| 4-71 | 8.06 |
| 4-72 | 3.34 |
| 4-73 | 3.68 |
| 4-74 | 50.5 |
| 4-75 | 0.992 |
| 4-76 | 10.7 |
| 4-77 | 5.87 |
| 4-78 | 8.44 |
| 4-79 | 34.6 |
| 4-80 | 23.6 |
| 4-81 | 7.89 |
| 4-82 | 4.10 |
| 4-83 | 80.8 |
| 4-84 | 2.88 |
| 4-85 | 16.1 |
| 4-86 | 2.75 |
| 4-87 | 2.53 |
| 4-88 | 15.4 |
| 4-89 | 7.59 |
| 4-90 | 10.1 |
| 4-91 | 1.97 |
| 4-92 | 7.79 |
| 4-93 | 10.1 |
| 4-94 | 3.61 |
| 4-95 | 37.4 |
| 4-96 | 8.25 |
| 4-97 | 3.63 |
| 4-98 | 5.48 |
| 4-99 | 36.0 |
| 4-100 | 2.29 |
| 4-101 | 1.25 |
| 4-102 | 0.815 |
| 4-103 | 1.98 |
| 4-104 | 1.31 |
| 4-105 | 6.42 |
| 4-106 | 1.04 |
| 4-107 | 4.08 |
| 4-108 | 3.60 |
| 4-109 | 1.59 |
| 4-110 | 4.31 |
| 4-111 | 3.07 |
| 4-112 | 1.49 |
| 4-113 | 8.95 |
| 4-114 | 2.54 |
| 4-115 | 1.23 |
| 4-116 | 3.91 |
| 4-117 | 2.52 |
| 4-118 | 0.948 |
| 4-119 | 3.13 |
| 4-120 | 15.2 |
| 4-121 | 3.35 |
| 4-122 | 4.53 |
| 4-123 | 7.82 |

TABLE 73-3-continued

| Example No. | IC$_{50}$ value (nM) |
|---|---|
| 4-124 | 5.44 |
| 4-125 | 7.11 |
| 4-126 | 3.91 |
| 4-127 | 21.3 |
| 4-128 | 1.08 |
| 4-129 | 1.03 |
| 4-130 | 6.66 |
| 4-131 | 10.3 |
| 4-132 | 5.62 |
| 4-133 | 5.70 |
| 4-134 | 3.92 |
| 4-135 | 5.33 |
| 4-136 | 3.43 |
| 4-137 | 21.9 |
| 4-138 | 2.91 |
| 4-139 | 1.32 |
| 4-140 | 5.67 |
| 4-141 | 7.62 |
| 4-142 | 5.90 |
| 4-143 | 47.4 |
| 4-144 | 8.19 |
| 4-145 | 1.37 |
| 4-146 | 10.9 |
| 4-147 | 11.6 |
| 4-148 | 3.22 |
| 4-149 | 3.40 |
| 4-150 | 1.55 |
| 4-151 | 2.62 |
| 4-152 | 1.34 |
| 4-153 | 4.07 |
| 4-154 | 3.68 |
| 4-155 | 8.59 |
| 4-156 | 5.16 |
| 4-157 | 3.71 |
| 4-158 | 4.39 |
| 4-159 | 6.22 |
| 4-160 | 10.4 |
| 4-161 | 3.81 |
| 4-162 | 13.2 |
| 4-163 | 384 |
| 4-164 | 3.26 |
| 4-165 | 4.85 |
| 4-166 | 2.02 |
| 4-167 | 2.50 |
| 4-168 | 6.29 |
| 4-169 | 2.17 |
| 4-170 | 3.33 |
| 4-171 | 3.38 |
| 4-172 | 2.43 |
| 4-173 | 3.51 |
| 4-174 | 3.40 |
| 4-175 | 3.47 |
| 4-176 | 15.3 |
| 4-177 | 4.02 |
| 4-178 | 24.0 |
| 4-179 | 10.4 |
| 4-180 | 6.22 |
| 4-181 | 3.27 |
| 5-1 | 99.6 |

TABLE 73-4

| Example No. | IC$_{50}$ value (nM) |
|---|---|
| 5-2 | 4520 |
| 5-3 | 45.5 |
| 5-4 | 128 |
| 5-5 | 39.7 |
| 5-6 | 164 |
| 5-7 | 132 |
| 5-8 | 3.62 |
| 5-9 | 2.82 |
| 5-10 | 35.4 |
| 5-11 | 79.7 |
| 5-12 | 45.4 |

TABLE 73-4-continued

| Example No. | IC$_{50}$ value (nM) |
|---|---|
| 5-13 | 4.32 |
| 5-14 | 19.1 |
| 5-15 | 6.10 |
| 5-16 | 8.97 |
| 5-17 | 8.86 |
| 5-18 | 11.0 |
| 5-19 | 104 |
| 5-20 | 3.92 |
| 5-21 | 17.1 |
| 5-22 | 7.13 |
| 5-23 | 3930 |
| 5-24 | 75.8 |
| 5-25 | 43.2 |
| 5-26 | 1.46 |
| 5-27 | 3.84 |
| 5-28 | 2.31 |
| 5-29 | 4.63 |
| 5-30 | 2.15 |
| 5-31 | 2.59 |
| 5-32 | 2.04 |
| 5-33 | 2.77 |
| 5-34 | 4.18 |
| 5-35 | 3.97 |
| 5-36 | 1.62 |
| 5-37 | 292 |
| 5-38 | 0.468 |
| 5-39 | 0.516 |
| 5-40 | 4.63 |
| 5-41 | 10.3 |
| 5-42 | 7.45 |
| 5-43 | 22.1 |
| 5-44 | 3.38 |
| 5-45 | 32.9 |
| 5-46 | 1.36 |
| 5-47 | 2.10 |
| 5-48 | 3.77 |
| 5-49 | 3.88 |
| 5-50 | 3.10 |
| 5-51 | 2.56 |
| 5-52 | 1.95 |
| 5-53 | 2.54 |
| 5-54 | 1.00 |
| 5-55 | 1.09 |
| 5-56 | 1.04 |
| 5-57 | 4.08 |
| 5-58 | 3.82 |
| 5-59 | 8.01 |
| 5-60 | 9.05 |
| 5-61 | 3.17 |
| 5-62 | 1.56 |
| 5-63 | 8.05 |
| 5-64 | 4.21 |
| 5-65 | 3.62 |
| 5-66 | 3.84 |
| 5-67 | 43.4 |
| 5-68 | 31.0 |
| 5-69 | 3.30 |
| 5-70 | 4.29 |
| 5-71 | 2.51 |
| 5-72 | 3.62 |
| 5-73 | 1.42 |
| 5-74 | 1.93 |
| 5-75 | 4.74 |
| 5-76 | 2.47 |
| 5-77 | 14.0 |
| 5-78 | 1.05 |
| 5-79 | 1.21 |
| 5-80 | 43.5 |
| 5-81 | 1.07 |
| 5-82 | 1.75 |
| 5-83 | 3.36 |
| 5-84 | 3.36 |
| 5-85 | 5.12 |
| 5-86 | 11.0 |
| 5-87 | 195 |
| 5-88 | 43.1 |
| 5-89 | 55.3 |
| 5-90 | 143 |

TABLE 73-4-continued

| Example No. | IC$_{50}$ value (nM) |
|---|---|
| 5-91 | 711 |
| 5-92 | 23.1 |
| 5-93 | 1530 |
| 5-94 | 190 |
| 5-95 | 7.22 |
| 5-96 | 143 |
| 5-97 | 10.1 |
| 5-98 | 38.3 |
| 5-99 | 5.60 |
| 5-100 | 36.2 |
| 5-101 | 2120 |
| 5-102 | 7.35 |
| 5-103 | 1.71 |
| 5-104 | 20.7 |
| 5-105 | 12.2 |
| 5-106 | 5.05 |
| 5-107 | 90.9 |
| 5-108 | 1.51 |
| 5-109 | 191 |
| 5-110 | 1.78 |
| 5-111 | 128 |
| 5-112 | 15.1 |
| 5-113 | 3.58 |
| 5-114 | 4.19 |
| 5-115 | 2.34 |
| 5-116 | 22.2 |
| 5-117 | 5.59 |
| 5-118 | 1.86 |
| 5-119 | 2.91 |
| 5-120 | 11.1 |
| 5-121 | 12.1 |

TABLE 73-5

| Example No. | IC$_{50}$ value (nM) |
|---|---|
| 5-122 | 30.3 |
| 5-123 | 4.33 |
| 5-124 | 10.8 |
| 5-125 | 10.9 |
| 5-126 | 26.1 |
| 5-127 | 3.94 |
| 5-128 | 10.3 |
| 5-129 | 38.4 |
| 5-130 | 7.90 |
| 5-131 | 10.8 |
| 5-132 | 4.97 |
| 5-133 | 3.50 |
| 5-134 | 4.55 |
| 5-135 | 1.88 |
| 5-136 | 30.7 |
| 5-137 | 8.18 |
| 5-138 | 3.21 |
| 5-139 | 2.95 |
| 5-140 | 10.8 |
| 5-141 | 3.49 |
| 5-142 | 1.74 |
| 5-143 | 3.11 |
| 5-144 | 1.11 |
| 5-145 | 2.43 |
| 5-146 | 1.02 |
| 5-147 | 3.62 |
| 5-148 | 3.40 |
| 5-149 | 2.58 |
| 5-150 | 3.37 |
| 5-151 | 4.46 |
| 5-152 | 2.36 |
| 5-153 | 0.961 |
| 5-154 | 4.30 |
| 5-155 | 1.10 |
| 5-156 | 7.52 |
| 5-157 | 3.54 |
| 5-158 | 3.51 |
| 5-159 | 4.59 |
| 5-160 | 4.55 |

TABLE 73-5-continued

| Example No. | IC$_{50}$ value (nM) |
|---|---|
| 5-161 | 1.46 |
| 5-162 | 3.66 |
| 5-163 | 1.84 |
| 5-164 | 4.84 |
| 5-165 | 2.05 |
| 5-166 | 5.99 |
| 5-167 | 5.26 |
| 5-168 | 5.97 |
| 5-169 | 7.97 |
| 5-170 | 6.25 |
| 5-171 | 1.63 |
| 5-172 | 54.2 |
| 5-173 | 34.7 |
| 5-174 | 30.0 |
| 5-175 | 4.93 |
| 5-176 | 20.9 |
| 5-177 | 2.77 |
| 5-178 | 55.7 |
| 5-179 | 32.5 |
| 5-180 | 6.40 |
| 5-181 | 3.51 |
| 5-182 | 30.0 |
| 5-183 | 1.68 |
| 5-184 | 2.53 |
| 5-185 | 0.919 |
| 5-186 | 2.63 |
| 5-187 | 4.16 |
| 5-188 | 0.855 |
| 5-189 | 1.46 |
| 5-190 | 0.817 |
| 5-191 | 1.45 |
| 5-192 | 0.470 |
| 5-193 | 2.00 |
| 5-194 | 2.15 |
| 5-195 | 2.07 |
| 5-196 | 1.41 |
| 5-197 | 1.04 |
| 5-198 | 2.90 |
| 5-199 | 0.761 |
| 5-200 | 0.548 |
| 5-201 | 0.712 |
| 5-202 | 1.62 |
| 5-203 | 1.33 |
| 5-204 | 0.882 |
| 5-205 | 2.74 |
| 5-206 | 0.853 |
| 5-207 | 1.36 |
| 5-208 | 3.50 |
| 5-209 | 2.75 |
| 5-210 | 2.44 |
| 5-211 | 1.10 |
| 5-212 | 1.98 |
| 5-213 | 0.847 |
| 5-214 | 1.92 |
| 5-215 | 1.01 |
| 5-216 | 2.56 |
| 5-217 | 1.65 |
| 5-218 | 1.99 |
| 5-219 | 0.813 |
| 5-220 | 2.13 |
| 5-221 | 0.695 |
| 5-222 | 1.79 |
| 5-223 | 2.08 |
| 5-224 | 0.949 |
| 5-225 | 0.809 |
| 5-226 | 4.00 |
| 5-227 | 0.851 |
| 5-228 | 3.17 |
| 6-1 | 1890 |
| 6-2 | 3760 |
| 6-3 | 672 |
| 6-4 | 344 |
| 6-5 | 272 |
| 6-6 | 435 |
| 6-7 | 443 |
| 6-8 | 2840 |
| 6-9 | 1010 |
| 6-10 | 1040 |

TABLE 73-5-continued

| Example No. | IC$_{50}$ value (nM) |
| --- | --- |
| 6-11 | 1360 |
| 6-12 | 1270 |
| 6-13 | 3040 |

TABLE 73-6

| Example No. | IC$_{50}$ value (nM) |
| --- | --- |
| 6-14 | 3530 |
| 6-15 | 3340 |
| 6-16 | 13000 |
| 6-17 | 10200 |
| 7-1 | 2.75 |
| 7-2 | 9.55 |
| 7-3 | 88.3 |
| 7-4 | 3.42 |
| 7-5 | 272 |
| 8-1 | 52.1 |
| 8-2 | 20.0 |
| 9-1 | 506 |
| 10-1 | 3.22 |
| 10-2 | 2.48 |
| 10-3 | 1.90 |
| 10-4 | 2.63 |
| 10-5 | 2.85 |
| 10-6 | 1.88 |
| 10-7 | 2.97 |
| 10-8 | 9.30 |
| 10-9 | 4.69 |
| 10-10 | 7.08 |
| 10-11 | 8.10 |
| 10-12 | 21.5 |
| 10-13 | 3.17 |
| 10-14 | 5.08 |
| 10-15 | 2.38 |
| 10-16 | 4.86 |
| 10-17 | 16.7 |
| 10-18 | 38.4 |

In addition, the LPA3 receptor antagonistic activity of the inventive compounds of the present application can also be evaluated by the method shown in Test Example 2 below.

Test Example 2

(1) Test of antagonism against response of LPA-induced increase in intracellular Ca$^{2+}$ concentration Cells stably expressing human LPAR3 are used for a test of antagonism against response of LPA-induced increase in intracellular Ca$^{2+}$ concentration.

The cells are seeded onto the Poly-D-Lysine 96 well black plate and incubated overnight. After washing with PBS, 100 µL of the Loading Buffer (1×HBSS, 20 mM HEPES, 2.5 mM Probenecid, 0.05% BSA, 0.25 mg/mL Amaranth, 0.05% Pluronic F-127, 200 nM Fluo-8, pH 7.4) is added, and incubation is carried out for 60 minutes. 50 µL of the Basal Buffer (1×HBSS, 20 mM HEPES, 2.5 mM Probenecid, 0.05% BSA, 0.25 mg/mL Amaranth, pH 7.4) containing the test compound is added thereto, followed by incubation at 37° C. for 30 minutes. In FDSS7000 (Hamamatsu Photonics K.K.), LPAs are added, and the change in intracellular Ca$^{2+}$ concentration is detected using the fluorescence value of a wavelength of 540 nm by an excitation wavelength of 480 nm as an indicator. The ratio (Rmax) between the basal fluorescence value and the maximum fluorescence value is determined, and the concentration producing 50% antagonism against response of LPA-induced increase in intracellular Ca$^{2+}$ concentration (IC$_{50}$ value) is calculated. The Rmax under Basal Buffer stimulation without the test compound is used as the control value. The Rmax under Basal Buffer stimulation with no LPAs or test compounds is used as the basal value.

The percentage (%) of increase in intracellular Ca$^{2+}$ concentration is calculated by dividing the value obtained by subtracting the basal value from Rmax in the presence of LPAs and each concentration of the test compound by the value obtained by subtracting the basal value from the control value. The concentration of each test compound is plotted on the X axis and the percentage (%) of increase in intracellular Ca$^{2+}$ concentration is plotted on the Y axis, and the IC$_{50}$ value is calculated by nonlinear regression using XLfit.

INDUSTRIAL APPLICABILITY

The compound of the present invention has an excellent LPA1 receptor antagonistic activity, and it is expected that the present invention makes it possible to provide a medical product that is effective in the prevention or treatment of diseases associated with fibrosis and the like, such as systemic scleroderma, thereby reducing the burden on patients and contributing to the progress in the pharmaceutical industry.

The invention claimed is:

1. A compound represented by formula [I]:

[Chemical Formula 1]

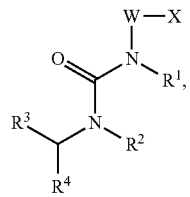

[I]

or a pharmaceutically acceptable salt thereof, or a hydrate thereof, wherein

X represents carboxy, C$_{1-4}$ alkoxycarbonyl, carbamoyl, tetrazolyl, or a group selected from formula group [II]:

[Chemical Formula 2]
[II]

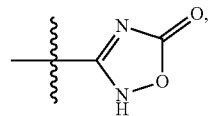

[II-1]

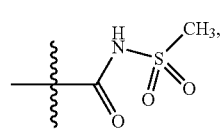

[II-2]

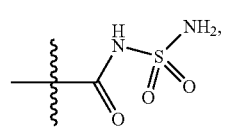

[II-3]

-continued

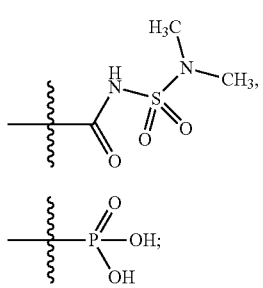
[II-4]

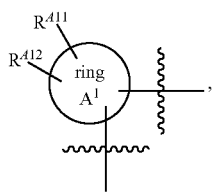
[II-5]

W represents a structure selected from formula group [III]:

[Chemical Formula 3]
[III]

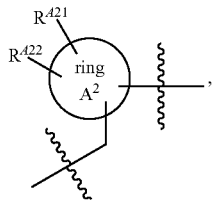
[III-1]

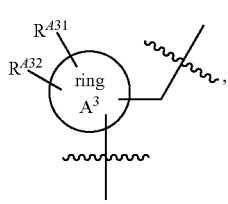
[III-2]

[III-3]

where
ring $A^1$, ring $A^2$, and ring $A^3$ each represent $C_{3-8}$ cycloalkane, a partially saturated 9- to 10-membered fused hydrocarbon aromatic ring, an oxygen atom-containing 4- to 8-membered saturated heterocycle, a sulfur atom-containing 4- to 8-membered saturated heterocycle, or a nitrogen atom-containing 4- to 8-membered saturated heterocycle, where
the sulfur atom in the sulfur atom-containing 4- to 8-membered saturated heterocycle is optionally substituted with one to two oxo,
the nitrogen atom in the nitrogen atom-containing 4- to 8-membered saturated heterocycle is optionally substituted with one group selected from the group consisting of $C_{1-4}$ alkylcarbonyl and $C_{1-4}$ alkoxycarbonyl, and
$R^{A11}$, $R^{A21}$, and $R^{A31}$ each independently represent a hydrogen atom, hydroxy, carboxy, a halogen atom, $C_{1-6}$ alkyl, $C_{1-6}$ alkoxy, $C_{1-6}$ alkylcarbonyl, or nitrogen atom-containing 4- to 6-membered saturated heterocyclyl(the nitrogen atom-containing 4- to 6-membered saturated heterocyclyl is optionally substituted with one $C_{1-3}$ alkyl), and $R^{A12}$, $R^{A22}$, and $R^{A32}$ each independently represent a hydrogen atom, a halogen atom, or methyl, or
$R^{A11}$ and $R^{A12}$, $R^{A21}$ and $R^{A22}$, and $R^{A31}$ and $R^{A32}$ each optionally together form oxo, or
$R^{A11}$ and $R^{A12}$, $R^{A21}$ and $R^{A22}$, and $R^{A31}$ and $R^{A32}$ each optionally form $C_{3-6}$ cycloalkane together with the carbon atom(s) in the adjacent ring;
$R^1$ represents a hydrogen atom or methyl;
$R^2$ represents $C_{6-10}$ alkyl, $C_{6-10}$ alkenyl, $C_{6-10}$ alkynyl, or a group represented by formula [IV-1] or [IV-2]:

[Chemical Formula 4]

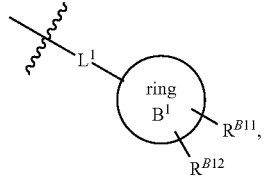
[IV-1]

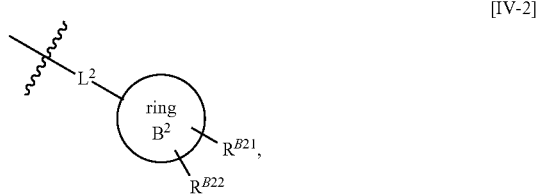
[IV-2]

where
ring $B^1$ represents $C_{3-8}$ cycloalkyl, nitrogen atom-containing 4- to 8-membered saturated heterocyclyl, phenyl, or nitrogen atom-containing 5- to 6-membered heteroaryl,
$R^{B11}$ and $R^{B12}$ each independently represent a hydrogen atom, a halogen atom, $C_{1-6}$ alkyl, or $C_{1-6}$ alkoxy,
$L^1$ represents $C_{3-8}$ alkanediyl(the $C_{3-8}$ alkanediyl is optionally substituted with 1 to 5 fluorine atoms), a structure represented by formula [V-6]: —$CH_2CH_2CH=C(CH_3)$—, or a structure represented by formula [V-1]:

[Chemical Formula 5]

[V-1]

where
n11 represents an integer of 0 to 3,
n12 represents an integer of 0 to 5,
n13 represents an integer of 0 to 3, and
one carbon atom in the $C_{3-8}$ alkanediyl, that is two or more atoms away from the nitrogen atom to which $R^2$ is bonded, is optionally replaced with formula —O—, formula —S—, or formula —N ($R^{L11}$)—, and furthermore,
two consecutive carbon atoms in the $C_{3-8}$ alkanediyl, that are one or more atoms away from the nitrogen atom to which $R^2$ is bonded, are optionally replaced with formula —C(=O)N($R^{L12}$)—,
$R^{L11}$ represents a hydrogen atom or $C_{1-3}$ alkyl, and
$R^{L12}$ represents a hydrogen atom or $C_{1-3}$ alkyl, ring B² represents partially saturated 9- to 10-membered fused aryl or nitrogen atom-containing 9- to 10-membered fused heteroaryl, $R^{B21}$ and $R^{B22}$ each independently represent a hydrogen atom, a halogen atom, $C_{1-6}$ alkyl, or $C_{1-6}$ alkoxy, L² represents $C_{1-2}$ alkanediyl(the $C_{1-2}$ alkanediyl is optionally substituted with 1 to 4 fluorine atoms), $C_{3-6}$ alkanediyl(the $C_{3-6}$ alkanediyl is optionally substituted with 1 to 5 fluorine atoms), or a structure represented by formula [V-2]:

[Chemical Formula 6]

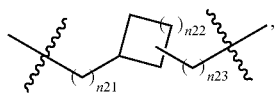

[V-2]

where n21 represents an integer of 0 to 3, n22 represents an integer of 0 to 5, n23 represents an integer of 0 to 3, and one carbon atom in the $C_{3-6}$ alkanediyl, that is two or more atoms away from the nitrogen atom to which R² is bonded, is optionally replaced with formula —O—, formula —S—, or formula —N ($R^{L21}$)—, and furthermore, two consecutive carbon atoms in the $C_{3-6}$ alkanediyl, that are one or more atoms away from the nitrogen atom to which R² is bonded, are optionally replaced with formula —C(=O)N($R^{L22}$)—, $R^{L21}$ represents a hydrogen atom or $C_{1-3}$ alkyl, and $R^{L22}$ represents a hydrogen atom or $C_{1-3}$ alkyl;

R³ represents a hydrogen atom or $C_{1-3}$ alkyl(the $C_{1-3}$ alkyl is optionally substituted with one group selected from the group consisting of hydroxy and methoxy); and R⁴ represents a group represented by formula [VI]:

[Chemical Formula 7]

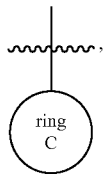

[VI]

where ring C represents phenyl, nitrogen atom-containing 6-membered heteroaryl, or 9- to 10-membered fused heteroaryl, the phenyl is substituted with one group selected from the group consisting of a halogen atom, $C_{1-6}$ alkyl, $C_{1-6}$ alkoxy, and $C_{1-6}$ alkylcarbonyl, and furthermore, the phenyl is optionally substituted with one to four groups that are the same or different, selected from the group consisting of hydroxy, carboxy, carbamoyl, cyano, a halogen atom, $C_{1-6}$ alkyl(the $C_{1-6}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one hydroxy), $C_{2-6}$ alkenyl, $C_{2-6}$ alkynyl, $C_{3-8}$ cycloalkyl(the $C_{3-8}$ cycloalkyl is optionally substituted with one hydroxy), $C_{1-6}$ alkoxy, halo-$C_{1-6}$ alkoxy, $C_{3-8}$ cycloalkoxy, $C_{1-6}$ alkylsulfanyl, $C_{1-6}$ alkylsulfinyl, $C_{1-6}$ alkylsulfonyl, mono-$C_{1-6}$ alkylamino, di-$C_{1-6}$ alkylamino, $C_{1-6}$ alkylcarbonyl, halo-$C_{1-6}$ alkylcarbonyl, $C_{1-6}$ alkoxycarbonyl, mono-$C_{1-6}$ alkylaminocarbonyl, and di-$C_{1-6}$ alkylaminocarbonyl, the nitrogen atom-containing 6-membered heteroaryl is substituted with one $C_{1-6}$ alkoxy, and furthermore, the nitrogen atom-containing 6-membered heteroaryl is optionally substituted with one to two groups that are the same or different, selected from the group consisting of cyano, $C_{1-6}$ alkyl, $C_{1-6}$ alkoxy, and oxo, and the 9- to 10-membered fused heteroaryl is optionally substituted with one to four groups that are the same or different, selected from the group consisting of $C_{1-6}$ alkyl, $C_{1-6}$ alkoxy, and oxo; or R³ and R⁴, together with their adjacent carbon atom, optionally form a partially saturated 9- to 10-membered fused hydrocarbon aromatic ring or a partially saturated oxygen atom-containing 9- to 10-membered fused heteroaromatic ring, where the partially saturated 9- to 10-membered fused hydrocarbon aromatic ring is optionally substituted with one to two halogen atoms, and the partially saturated oxygen atom-containing 9- to 10-membered fused heteroaromatic ring is optionally substituted with one to two halogen atoms.

2. The compound according to claim 1, or a pharmaceutically acceptable salt thereof, or a hydrate thereof wherein, in formula group [III] for W, $R^{411}$, $R^{421}$, and $R^{431}$ each independently represent a hydrogen atom, hydroxy, carboxy, a halogen atom, $C_{1-6}$ alkyl, $C_{1-6}$ alkoxy, or nitrogen atom-containing 4- to 6-membered saturated heterocyclyl(the nitrogen atom-containing 4- to 6-membered saturated heterocyclyl is optionally substituted with one $C_{1-3}$ alkyl), and $R^{412}$, $R^{422}$, and $R^{432}$ each independently represent a hydrogen atom, a halogen atom, or methyl, or $R^{411}$ and $R^{412}$, $R^{421}$ and $R^{422}$, and $R^{431}$ and $R^{432}$ each optionally together form oxo, or $R^{411}$ and $R^{412}$, $R^{421}$ and $R^{422}$, and $R^{431}$ and $R^{432}$ each optionally form $C_{3-6}$ cycloalkane together with the carbon atom(s) in the adjacent ring, and wherein, in formula [IV-1] for R², L¹ represents $C_{3-8}$ alkanediyl(the $C_{3-8}$ alkanediyl is optionally substituted with 1 to 5 fluorine atoms) or a structure represented by formula [V-1], where one carbon atom in the $C_{3-8}$ alkanediyl, that is two or more atoms away from the nitrogen atom to which R² is bonded, is optionally replaced with formula —O—, formula —S—, or formula —N ($R^{L11}$)—, and furthermore, two consecutive carbon atoms in the $C_{3-8}$ alkanediyl, that are one or more atoms away from the nitrogen atom to which R² is bonded, are optionally replaced with formula —C(=O)N($R^{L12}$)—, $R^{L11}$ represents a hydrogen atom or $C_{1-3}$ alkyl, and $R^{L12}$ represents a hydrogen atom or $C_{1-3}$ alkyl.

3. The compound according to claim 1, or a pharmaceutically acceptable salt thereof, or a hydrate thereof,
wherein, in the above formula [I],
W is a structure selected from formula group [III]:

[Chemical Formula 8]
[III]

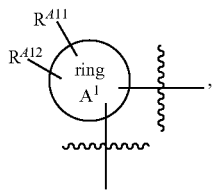
[III-1]

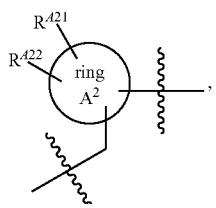
[III-2]

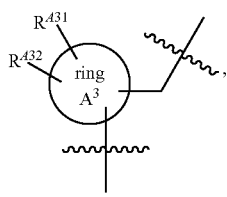
[III-3]

where
ring $A^1$ is $C_{3-8}$ cycloalkane, dihydroindene, oxetane, tetrahydrofuran, tetrahydropyran, tetrahydrothiopyran, azetidine, pyrrolidine, or piperidine, ring $A^2$ is $C_{3-8}$ cycloalkane or tetrahydropyran, and ring $A^3$ is $C_{3-8}$ cycloalkane, dihydroindene, or tetrahydropyran, where
the sulfur atom in the tetrahydrothiopyran is optionally substituted with one to two oxo, and the nitrogen atom in each of the azetidine, pyrrolidine, and piperidine is optionally substituted with one $C_{1-4}$ alkylcarbonyl, and $R^{A11}$ is a hydrogen atom, hydroxy, carboxy, a halogen atom, $C_{1-6}$ alkyl, $C_{1-6}$ alkoxy, $C_{1-6}$ alkylcarbonyl, or nitrogen atom-containing 4- to 6-membered saturated heterocyclyl(the nitrogen atom-containing 4- to 6-membered saturated heterocyclyl is optionally substituted with one $C_{1-3}$ alkyl), and $R^{A12}$ represents a hydrogen atom, a halogen atom, or methyl, or $R^{A11}$ and $R^{A12}$ optionally together form oxo, $R^{A21}$ and $R^{A22}$ are both hydrogen atoms, $R^{A31}$ and $R^{A32}$ are both hydrogen atoms, or $R^{A11}$ and $R^{A12}$ optionally form $C_{3-6}$ cycloalkane together with the carbon atom(s) in the adjacent ring;

$R^2$ is $C_{6-10}$ alkyl or a group represented by formula [IV-1] or [IV-2]:

[Chemical Formula 9]

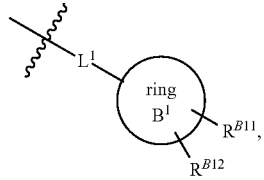
[IV-1]

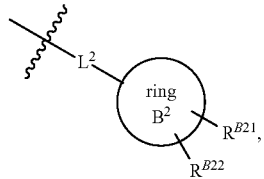
[IV-2]

where
ring $B^1$ is $C_{3-8}$ cycloalkyl, piperidinyl, phenyl, pyrazolyl, or pyridyl, $R^{B11}$ and $R^{B12}$ are each independently a hydrogen atom, a halogen atom, $C_{1-6}$ alkyl, or $C_{1-6}$ alkoxy, and $L^1$ is any of structures represented by formulas [V-3] to [V-12] and [V-14] to [V-19]:

[Chemical Formula 10]

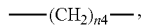
[V-3]
—$(CH_2)_{n4}$—,

[V-4]
—$CH_2CH(CH_3)CH_2CH_2$—,

[V-5]
—$CH_2CH_2CH_2CH(CH_3)$—,

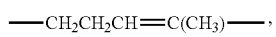
[V-6]
—$CH_2CH_2CH=C(CH_3)$—,

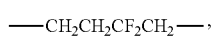
[V-7]
—$CH_2CH_2CF_2CH_2$—,

[V-8]
—$CH_2CH_2CH_2CF_2$—,

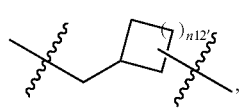
[V-9]

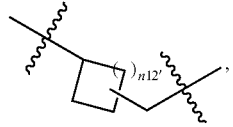
[V-10]

[V-11]
—$CH_2CH_2CH_2$—O—,

-continued

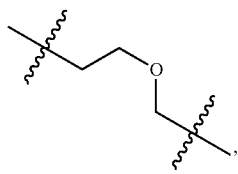
[V-12]

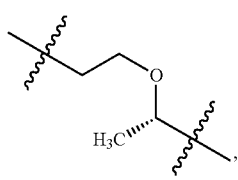
[V-14]

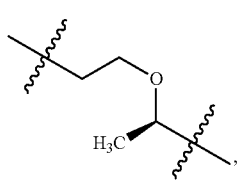
[V-15]

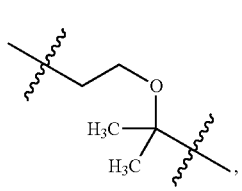
[V-16]

—CH₂CH₂CH₂—S— , [V-17]

—CH₂CH₂CH₂—N(CH₃)— , [V-18]

—CH₂—C(=O)NH—CH₂— , [V-19]

where
n4 represents an integer of 3 to 5,
n12' represents an integer of 0 to 3,
n12" represents an integer of 0 to 3, and
ring B² is dihydroindenyl, indolyl, or isoindolinyl,
$R^{B21}$ and $R^{B22}$ are both hydrogen atoms, and
L² is a structure represented by formula [V-20]:
[Chemical Formula 11]

—(CH₂)$_{n5}$— [V-20]

where
n5 represents an integer of 1 to 2; and
$R^4$ is a group represented by formula [VI]:

[Chemical Formula 12]

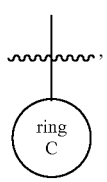
[VI]

where
ring C is phenyl, pyridyl, pyrimidinyl, dihydropyridinyl, dihydrobenzofuranyl, benzodioxanyl, indolyl, indazolyl, benzimidazolyl, pyrazolopyridinyl, indolinyl, or dihydroquinazolinyl, the phenyl is substituted with one group selected from the group consisting of a halogen atom, $C_{1-6}$ alkyl, $C_{1-6}$ alkoxy, and $C_{1-6}$ alkylcarbonyl, and furthermore, the phenyl is optionally substituted with one to four groups that are the same or different, selected from the group consisting of hydroxy, carboxy, carbamoyl, cyano, a halogen atom, $C_{1-6}$ alkyl(the $C_{1-6}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one hydroxy), $C_{2-6}$ alkenyl, $C_{3-8}$ cycloalkyl(the $C_{3-8}$ cycloalkyl is optionally substituted with one hydroxy), $C_{1-6}$ alkoxy, halo-$C_{1-6}$ alkoxy, $C_{3-8}$ cycloalkoxy, $C_{1-6}$ alkylsulfinyl, $C_{1-6}$ alkylsulfonyl, mono-$C_{1-6}$ alkylamino, di-$C_{1-6}$ alkylamino, $C_{1-6}$ alkylcarbonyl, halo-$C_{1-6}$ alkylcarbonyl, $C_{1-6}$ alkoxycarbonyl, and mono-$C_{1-6}$ alkylaminocarbonyl, the pyridyl is substituted with one $C_{1-6}$ alkoxy, and furthermore, the pyridyl is optionally substituted with one group selected from the group consisting of cyano and $C_{1-6}$ alkoxy, the pyrimidinyl is substituted with one $C_{1-6}$ alkoxy, and furthermore, the pyrimidinyl is optionally substituted with one $C_{1-6}$ alkoxy, the dihydropyridinyl is substituted with one $C_{1-6}$ alkoxy, and furthermore, the dihydropyridinyl is optionally substituted with one to two groups that are the same or different, selected from the group consisting of $C_{1-6}$ alkyl and oxo, the dihydrobenzofuranyl and benzodioxanyl are optionally substituted with one $C_{1-6}$ alkoxy, the indolyl, indazolyl, benzimidazolyl, pyrazolopyridinyl, and indolinyl are optionally substituted with one to two groups that are the same or different, selected from the group consisting of $C_{1-6}$ alkyl and $C_{1-6}$ alkoxy, and the dihydroquinazolinyl is optionally substituted with one to four groups that are the same or different, selected from the group consisting of $C_{1-6}$ alkyl, $C_{1-6}$ alkoxy, and oxo; and the fused ring formed by $R^3$ and $R^4$ together with their adjacent carbon atom is dihydroindene or dihydrobenzofuran, and the dihydroindene and dihydrobenzofuran are optionally substituted with one to two halogen atoms.

4. The compound according to claim 1, or a pharmaceutically acceptable salt thereof, or a hydrate thereof
wherein, in the above formula [I],
X is carboxy, $C_{1-4}$ alkoxycarbonyl, or tetrazolyl;
$R^1$ is a hydrogen atom; and
$R^2$ is a group represented by the above formula [IV-1] or [IV-2]:

[Chemical Formula 13]

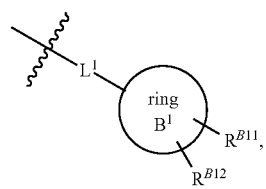
[IV-1]

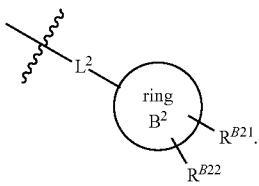

[IV-2]

5. The compound according to claim 1, or a pharmaceutically acceptable salt thereof, or a hydrate thereof,
wherein, in the above formula [I],
W is a structure represented by formula [III-1]:

[Chemical Formula 14]

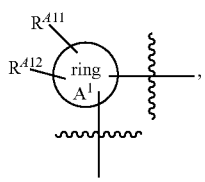

[III-1]

wherein, in the structure represented by formula [III-1],
ring $A^1$ is $C_{3-8}$ cycloalkane, a partially saturated 9- to 10-membered fused hydrocarbon aromatic ring, an oxygen atom-containing 4- to 8-membered saturated heterocycle, a sulfur atom-containing 4- to 8-membered saturated heterocycle, or a nitrogen atom-containing 4- to 8-membered saturated heterocycle,
where
the sulfur atom in the sulfur atom-containing 4- to 8-membered saturated heterocycle is optionally substituted with one to two oxo, and
the nitrogen atom in the nitrogen atom-containing 4- to 8-membered saturated heterocycle is optionally substituted with one group selected from the group consisting of $C_{1-4}$ alkylcarbonyl and $C_{1-4}$ alkoxycarbonyl, and
$R^{A11}$ is a hydrogen atom, hydroxy, carboxy, a halogen atom, $C_{1-6}$ alkyl, $C_{1-6}$ alkoxy, or nitrogen atom-containing 4- to 6-membered saturated heterocyclyl(the nitrogen atom-containing 4- to 6-membered saturated heterocyclyl is optionally substituted with one $C_{1-3}$ alkyl), and
$R^{A12}$ is a hydrogen atom, a halogen atom, or methyl, or
$R^{A11}$ and $R^{A12}$ optionally together form oxo, or
$R^{A11}$ and $R^{A12}$ optionally form $C_{3-6}$ cycloalkane together with the carbon atom(s) in the adjacent ring.

6. The compound according to claim 1, or a pharmaceutically acceptable salt thereof, or a hydrate thereof
wherein, in the above formula [I],
$R^4$ is a group represented by formula [VI]:

[Chemical Formula 15]

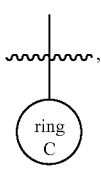

[VI]

where
ring C is phenyl,
the phenyl is substituted with one group selected from the group consisting of a halogen atom, $C_{1-6}$ alkyl, $C_{1-6}$ alkoxy, and $C_{1-6}$ alkylcarbonyl, and furthermore,
the phenyl is optionally substituted with one to four groups that are the same or different, selected from the group consisting of hydroxy, carboxy, carbamoyl, cyano, a halogen atom, $C_{1-6}$ alkyl(the $C_{1-6}$ alkyl is optionally substituted with one group selected from the group consisting of hydroxy and $C_{1-6}$ alkoxy), halo-$C_{1-6}$ alkyl(the halo-$C_{1-6}$ alkyl is optionally substituted with one hydroxy), $C_{2-6}$ alkenyl, $C_{2-6}$ alkynyl, $C_{3-8}$ cycloalkyl(the $C_{3-8}$ cycloalkyl is optionally substituted with one hydroxy), $C_{1-6}$ alkoxy, halo-$C_{1-6}$ alkoxy, $C_{3-8}$ cycloalkoxy, $C_{1-6}$ alkylsulfanyl, $C_{1-6}$ alkylsulfinyl, $C_{1-6}$ alkylsulfonyl, mono-$C_{1-6}$ alkylamino, di-$C_{1-6}$ alkylamino, $C_{1-6}$ alkylcarbonyl, halo-$C_{1-6}$ alkylcarbonyl, $C_{1-6}$ alkoxycarbonyl, mono-$C_{1-6}$ alkylaminocarbonyl, and di-$C_{1-6}$ alkylaminocarbonyl.

7. The compound according to claim 1, or a pharmaceutically acceptable salt thereof, or a hydrate thereof,
wherein, in the above formula [I],
$R^2$ is a group represented by formula [IV-1] or [IV-2]:

[Chemical Formula 16]

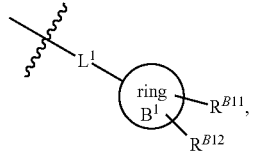

[IV-1]

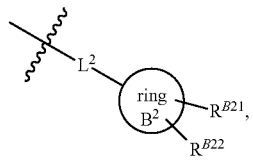

[IV-2]

where
ring $B^1$ is phenyl,
$R^{B11}$ and $R^{B12}$ are each independently a hydrogen atom, a halogen atom, $C_{1-6}$ alkyl, or $C_{1-6}$ alkoxy, and
$L^1$ is any of structures represented by formulas [V-3] to [V-5], [V-7] to [V-8], [V-11] to [V-12], and [V-14] to [V-16]:

[Chemical Formula 17]

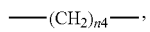

—(CH$_2$)$_{n4}$—,

[V-3]

[V-4]

—CH$_2$CH(CH$_3$)CH$_2$CH$_2$—,

[V-5]

—CH$_2$CH$_2$CH$_2$CH(CH$_3$)—,

[V-7]

—CH$_2$CH$_2$CF$_2$CH$_2$—,

[V-8]

—CH$_2$CH$_2$CH$_2$CF$_2$—,

[V-11]

—CH$_2$CH$_2$CH$_2$—O—,

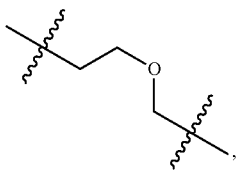 [V-12]

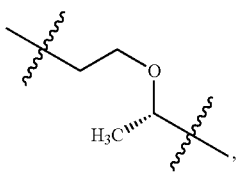 [V-14]

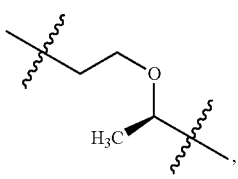 [V-15]

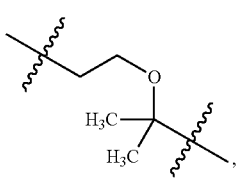 [V-16]

where
n4 represents an integer of 3 to 5, and
ring $B^2$ is dihydroindenyl, indolyl, or isoindolinyl, $R^{B21}$ and $R^{B22}$ are both hydrogen atoms, and
$L^2$ is a structure represented by formula [V-20]:
[Chemical Formula 18]

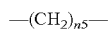 [V-20]

where
n5 is an integer of 1 to 2.

8. The compound according to claim 4, or a pharmaceutically acceptable salt thereof, or a hydrate thereof,
wherein, in the above formula [I],
X is carboxy;
W is any of structures represented by formulas [III-5] to [III-17]:

[Chemical Formula 19]

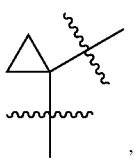 [III-5]

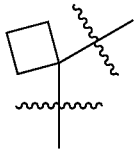 [III-6]

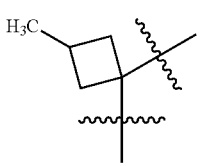 [III-7]

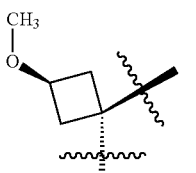 [III-8]

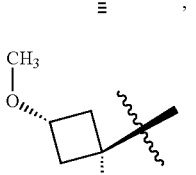 [III-9]

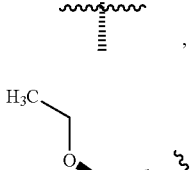 [III-10]

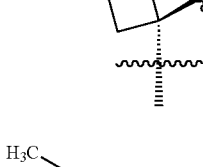 [III-11]

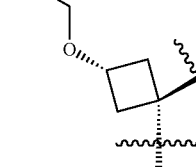 [III-12]

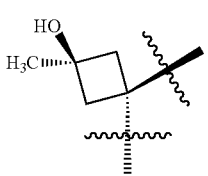 [III-13]

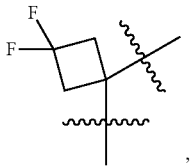 [III-14]

-continued

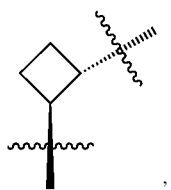
[III-15]

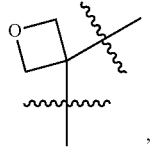
[III-16]

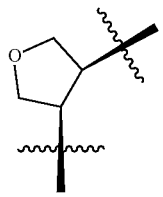
[III-17]

$R^2$ is a group represented by formula [IV-1] or [IV-2]:

[Chemical Formula 20]

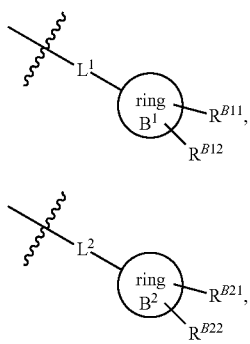

[IV-1]

[IV-2]

where
ring $B^1$ is phenyl,
$R^{B11}$ and $R^{B12}$ are both hydrogen atoms, and
$L^1$ is a structure represented by formula [V-3], [V-8], [V-12], [V-14], or [V-15]:

[Chemical Formula 21]

[V-3]

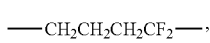
[V-8]

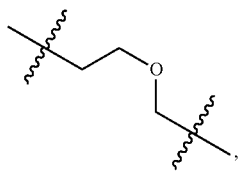
[V-12]

-continued

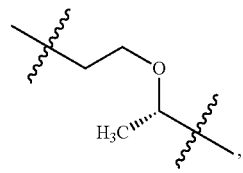
[V-14]

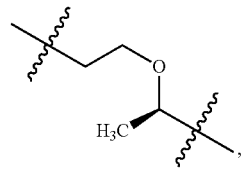
[V-15]

where
n4 is an integer of 3 to 4, and
ring $B^2$ is dihydroindenyl,
$R^{B21}$ and $R^{B22}$ are both hydrogen atoms, and
$L^2$ is a structure represented by formula [V-20]:

[Chemical Formula 22]

$$-(CH_2)_{n5}- \quad [V-20],$$

where
n5 is 2;
$R^3$ is methyl having a steric configuration represented by formula [VII]:

[Chemical Formula 23]

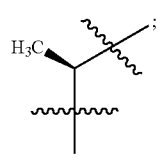
[VII]

and
$R^4$ is a group represented by any of formulas [VI-1] to [VI-21]:

[Chemical Formula 24]

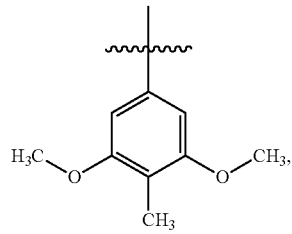
[VI-1]

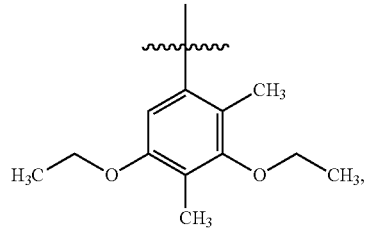
[VI-2]

-continued

[VI-3]

[VI-4]

[VI-5]

[VI-6]

[VI-7]

[Chemical Formula 25]

[VI-8]

-continued

[VI-9]

[VI-10]

[VI-11]

[VI-12]

[VI-13]

[Chemical Formula 26]

[VI-14]

[VI-15]
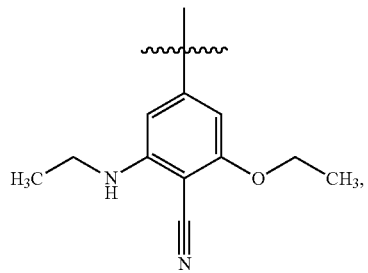
[VI-16]
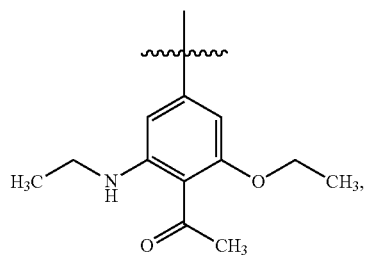
[VI-17]
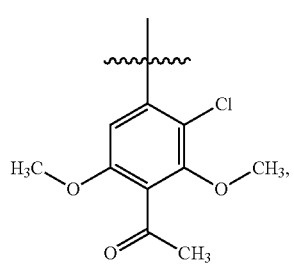
[VI-18]
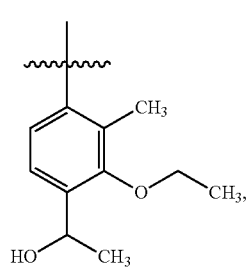
[VI-19]
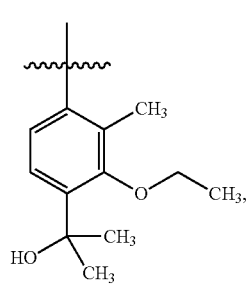
[VI-20]
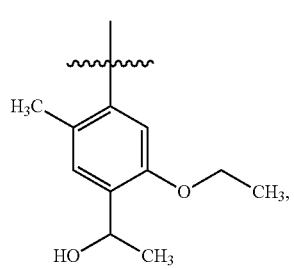
[VI-21]
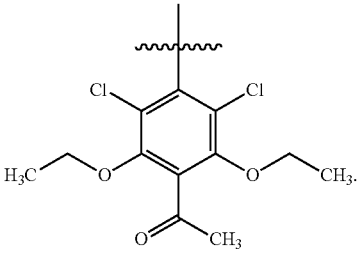
9. The compound according to claim 4, or a pharmaceutically acceptable salt thereof, or a hydrate thereof,
wherein, in the above formula [I],
X is carboxy;
W is a structure represented by any of formulas [III-5] to [III-14], [III-18] to [III-19], and [III-18] to [III-19]:
[Chemical Formula 27]
[III-5]
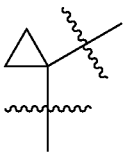
[III-6]
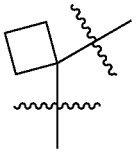
[III-7]
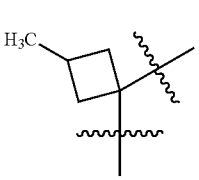
[III-8]
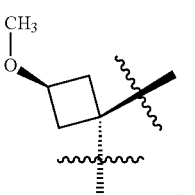
[III-9]
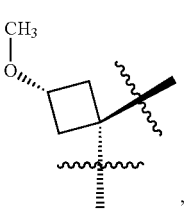

[III-10]

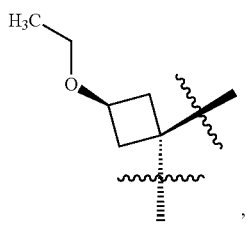

,

[III-11]

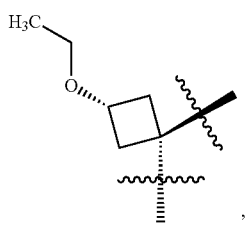

,

[III-13]

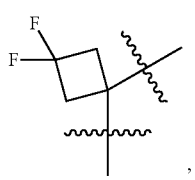

,

[III-14]

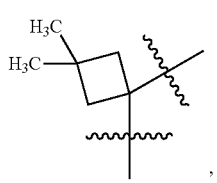

,

[III-18]

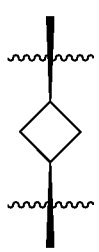

,

[III-19]

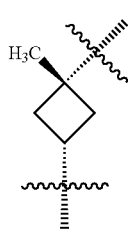

;

$R^2$ is a group represented by formula [IV-1] or [IV-2]:

[Chemical Formula 28]

[IV-1]

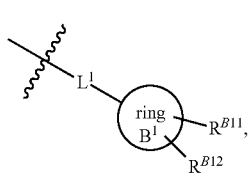

,

[IV-2]

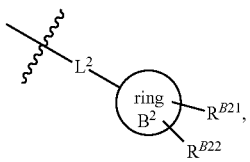

, where ring $B^1$ is phenyl, $R^{B11}$ and $R^{B12}$ are both hydrogen atoms, and $L^1$ is a structure represented by formula [V-3], [V-8], or [V-14]:

[Chemical Formula 29]

—(CH$_2$)$_{n4}$— , [V-3]

—CH$_2$CH$_2$CH$_2$CF$_2$— , [V-8]

[V-14]

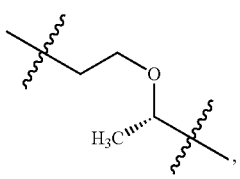

, where n4 is 4, and ring $B^2$ is dihydroindenyl, $R^{B21}$ and $R^{B22}$ are both hydrogen atoms, and $L^2$ is a structure represented by formula [V-20]:

[Chemical Formula 30]

—(CH$_2$)$_{n5}$— [V-20]

where n5 is 2;

$R^3$ is methyl having a steric configuration represented by formula [VII]:

[Chemical Formula 31]

[VII]

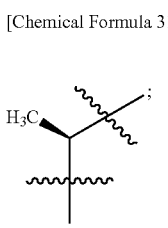

and $R^4$ is a group represented by formula [VI-2], [VI-3], [VI-8], [VI-10] to [VI-12], [VI-16], [VI-19], or [VI-21]:

[Chemical Formula 32]

[VI-2]
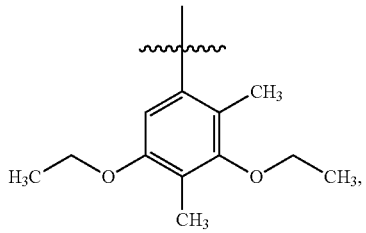

[VI-3]
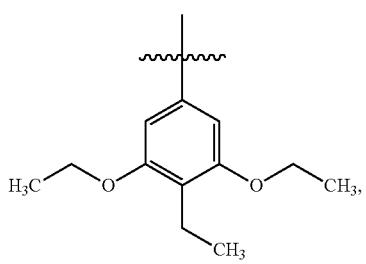

[VI-8]
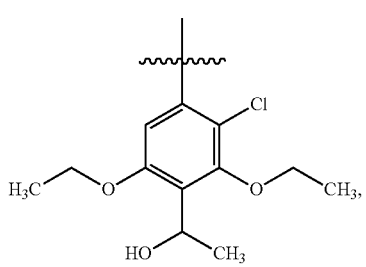

[VI-10]
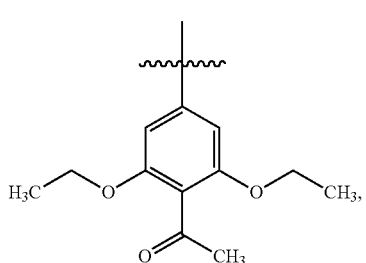

[VI-11]
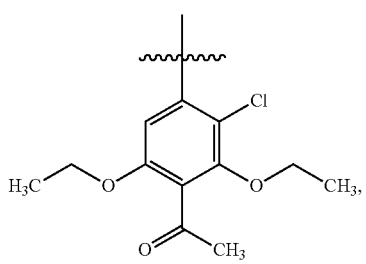

-continued

[Chemical Formula 33]

[VI-12]
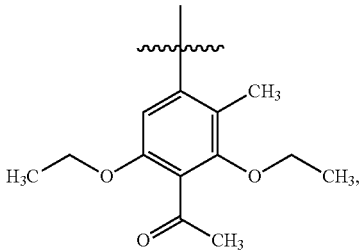

[VI-16]
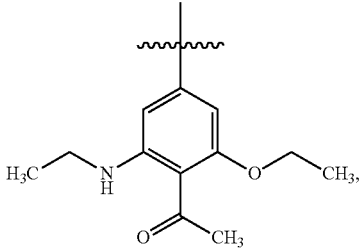

[VI-19]
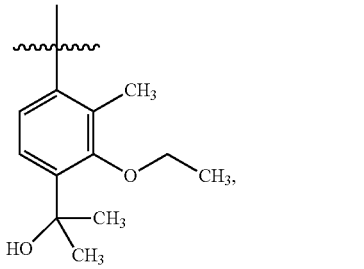

[VI-21]
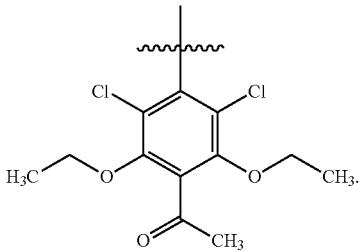

10. The compound according to claim 4, or a pharmaceutically acceptable salt thereof, or a hydrate thereof, wherein, in the above formula [I], X is carboxy or tetrazolyl;

W is a structure represented by formula [III-5], [III-8] to [III-11], or [III-13]:

[Chemical Formula 34]

[III-5]
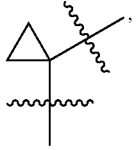

-continued

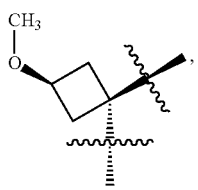 [III-8]

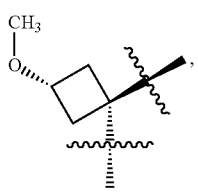 [III-9]

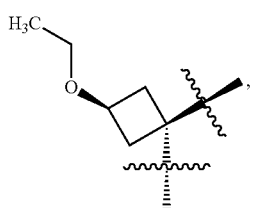 [III-10]

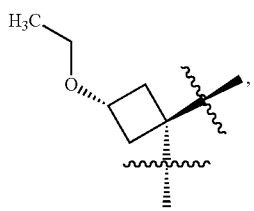 [III-11]

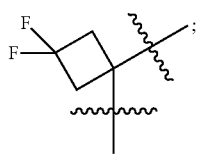 [III-13]

R² is a group represented by formula [IV-1] or [IV-2]:

[Chemical Formula 35]

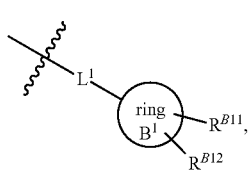 [IV-1]

-continued

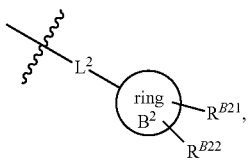 [IV-2]

where ring B¹ is phenyl, $R^{B11}$ and $R^{B12}$ are both hydrogen atoms, and

L¹ is a structure represented by formula [V-3], [V-12], or [V-14]:

[Chemical Formula 36]

 [V-3]

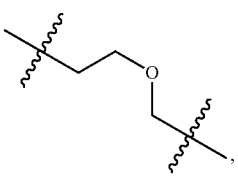 [V-12]

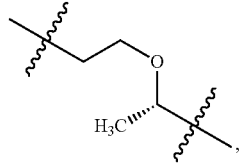 [V-14]

where n4 is an integer of 4, and ring B² is dihydroindenyl, $R^{B21}$ and $R^{B22}$ are both hydrogen atoms, and L² is a structure represented by formula [V-20]:

[Chemical Formula 37]

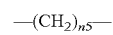 [V-20]

where n5 is 2;

R³ is methyl having a steric configuration represented by formula [VII]:

[Chemical Formula 38]

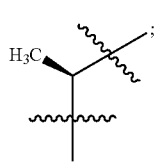 [VII]

and
$R^4$ is a group represented by formula [VI-2], [VI-7], [VI-8], [VI-10], [VI-11], or [VI-12]:
[Chemical Formula 39]
[VI-2]
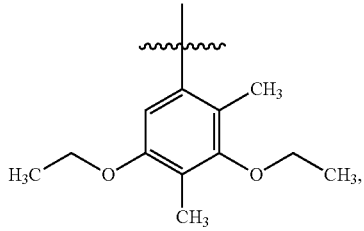
[VI-7]
[VI-8]
[VI-10]
[VI-11]
[VI-12]
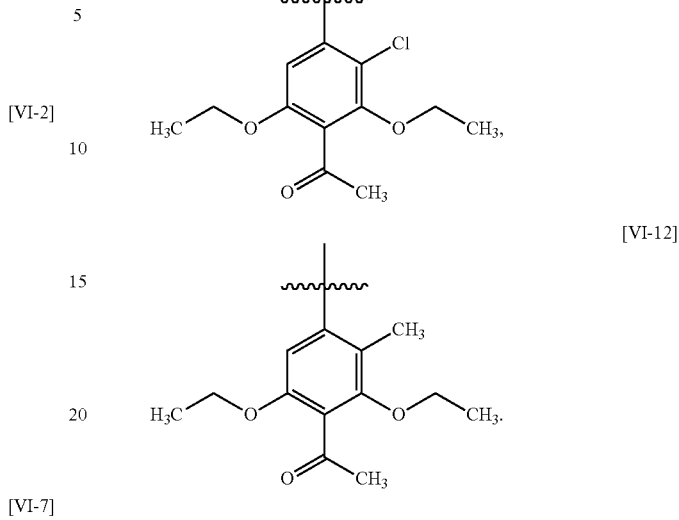
11. The compound according to claim 1, which is any of the following:
[Chemical Formula 40]
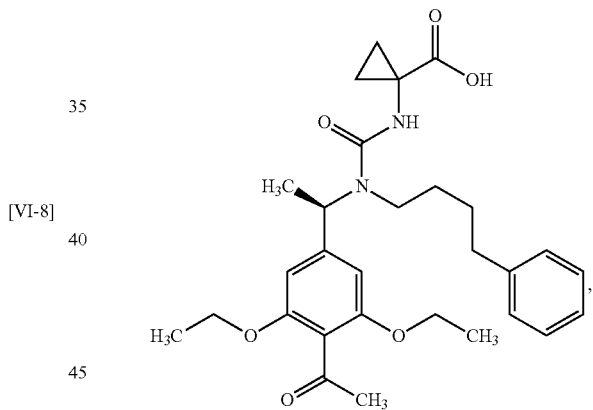
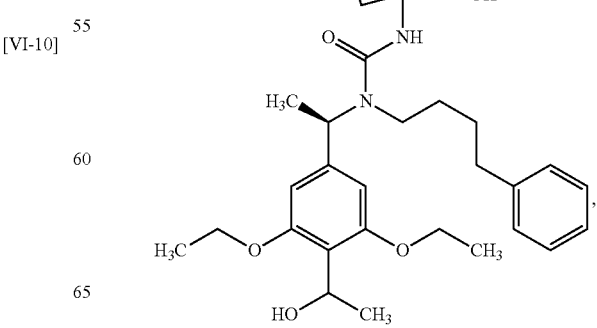

931
-continued
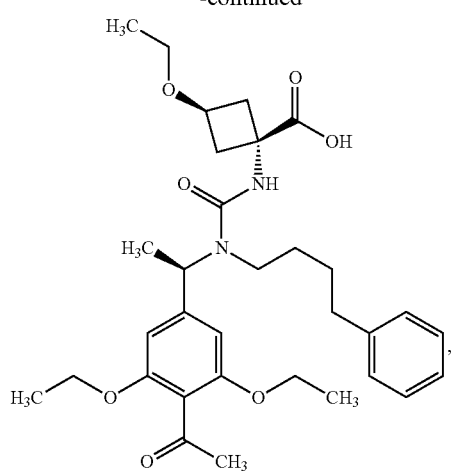
932
-continued
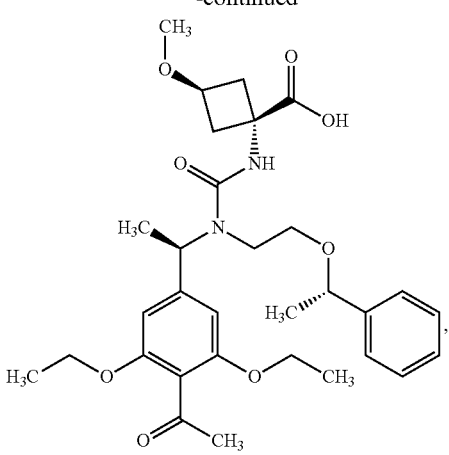
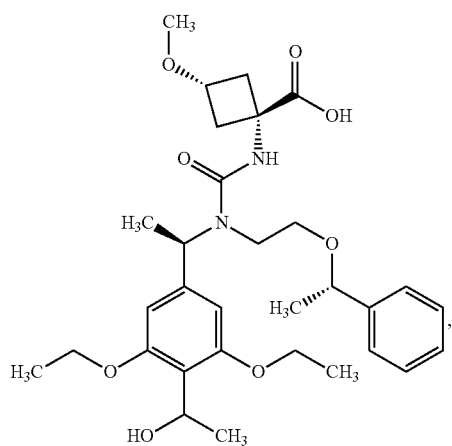
[Chemical Formula 41]
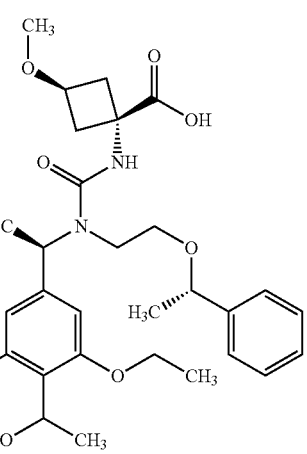
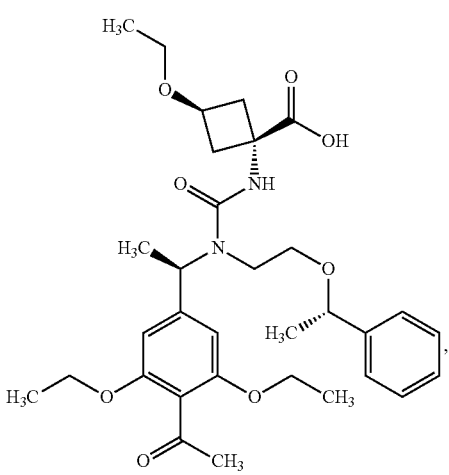

| 933 -continued | 934 -continued |
|---|---|
| 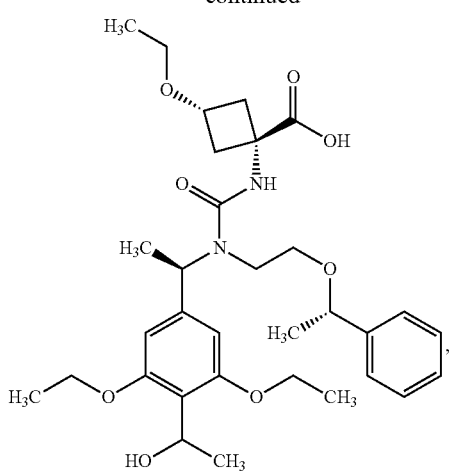 | 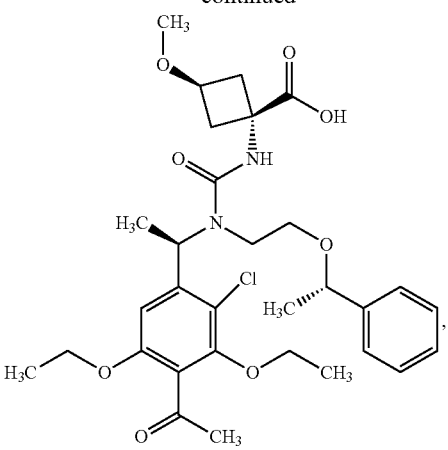 |
| 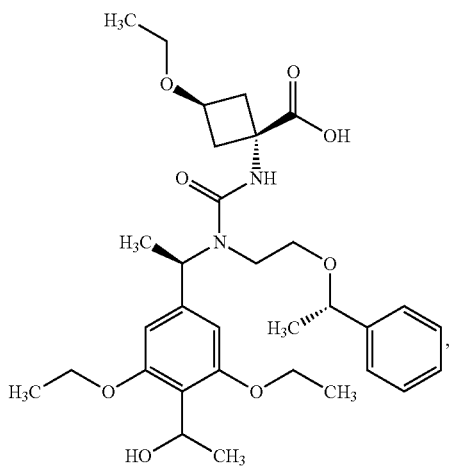 | [Chemical Formula 42]<br/>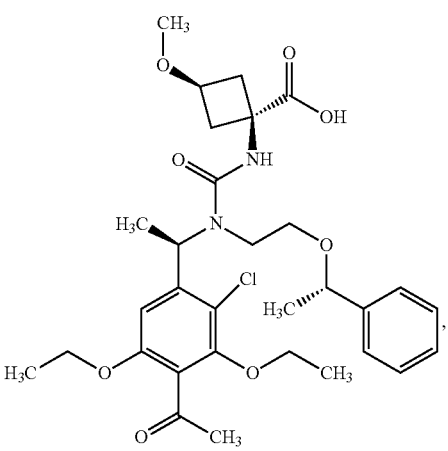 |
| 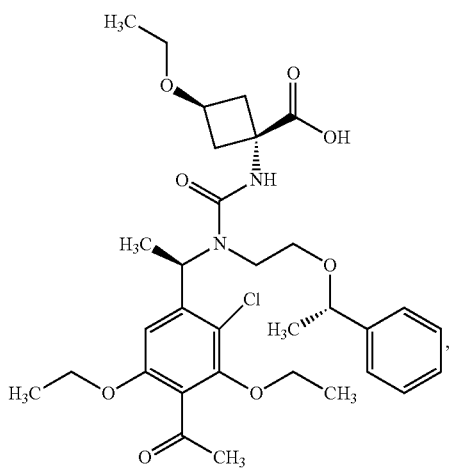 | 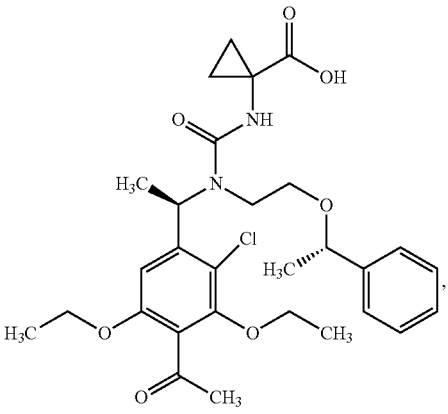 |

935
-continued
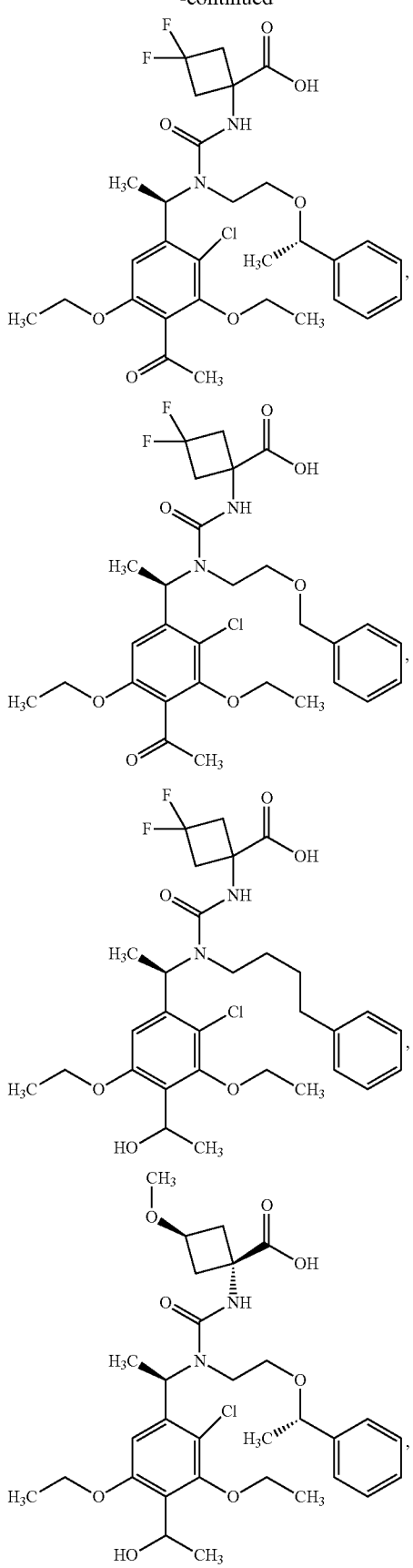
936
-continued
[Chemical Formula 43]
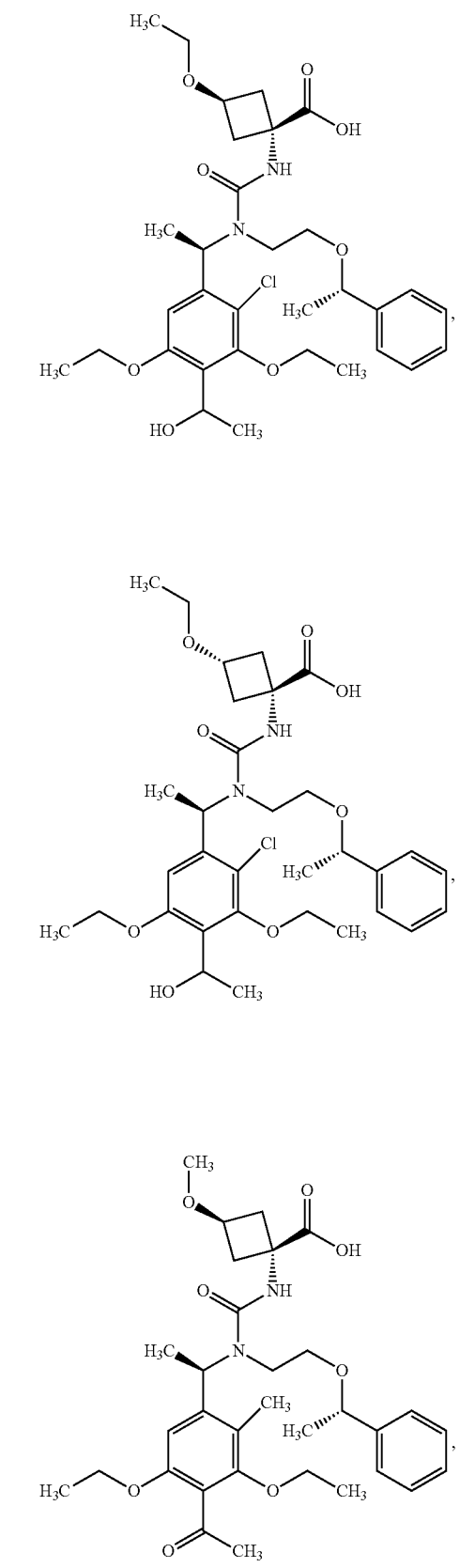

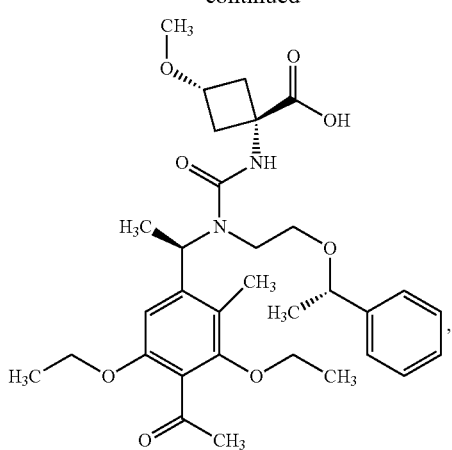
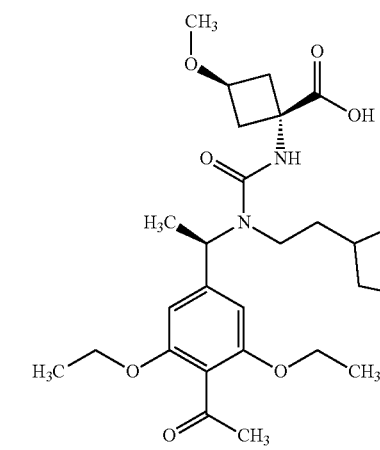
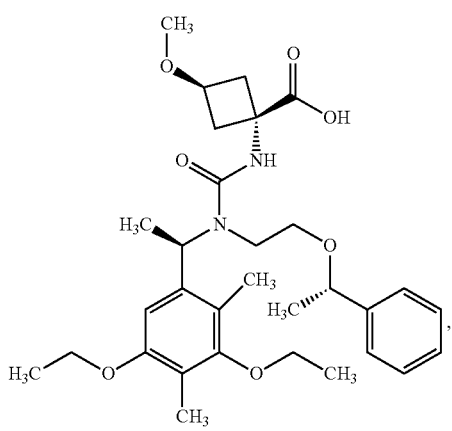
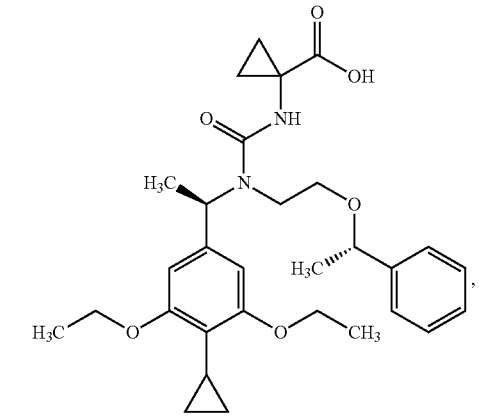
or a pharmaceutically acceptable salt thereof, or a hydrate thereof.
12. The compound according to claim 1, which is any of the following:
[Chemical Formula 45]
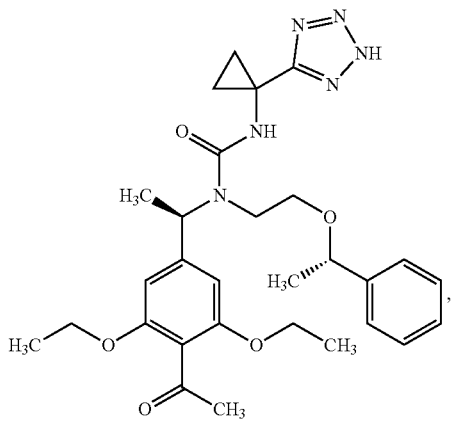
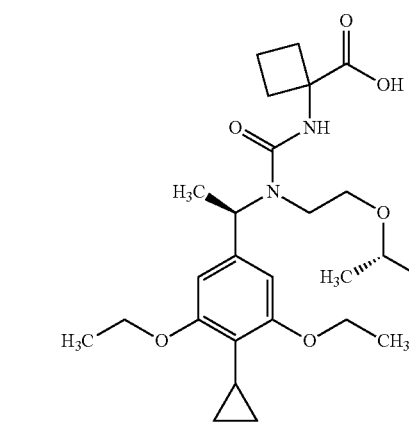

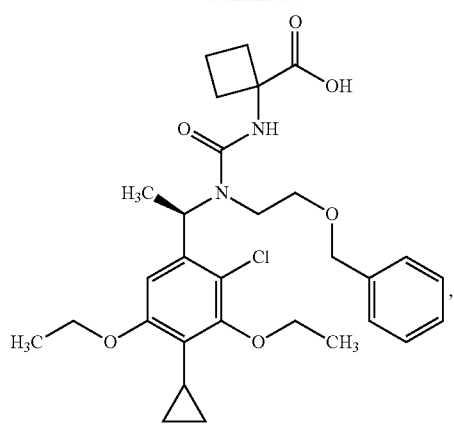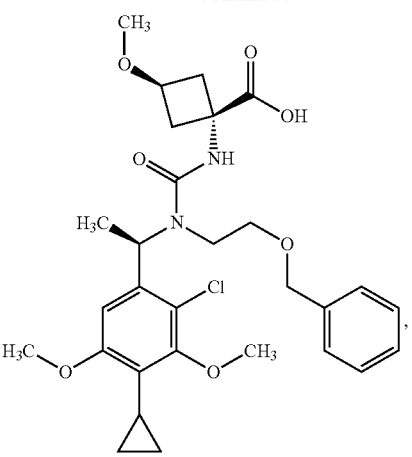

941
-continued
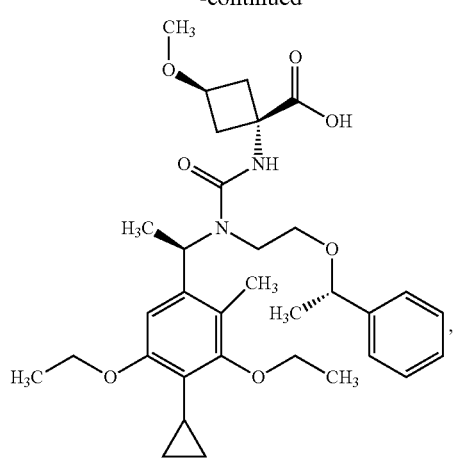
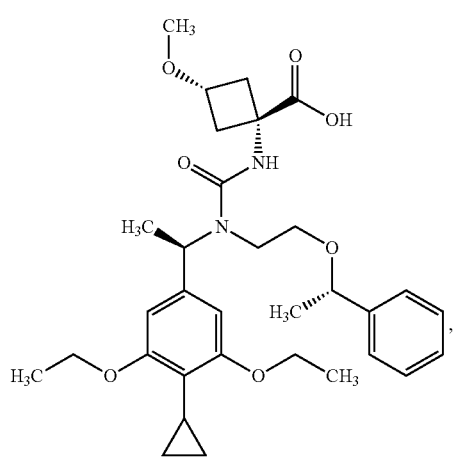
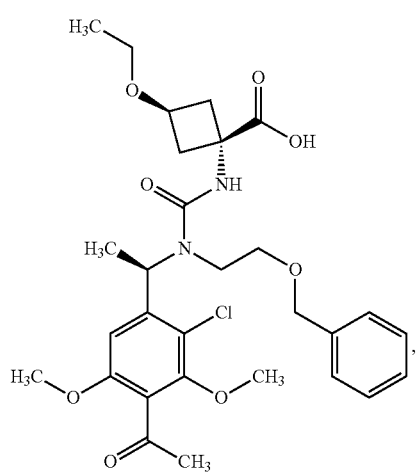
942
-continued
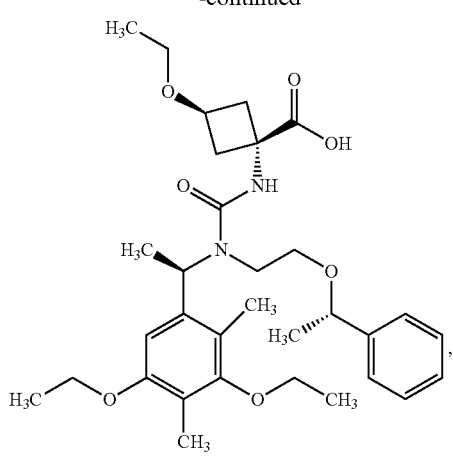
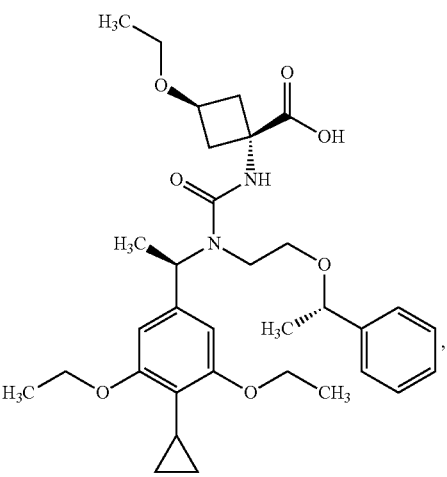
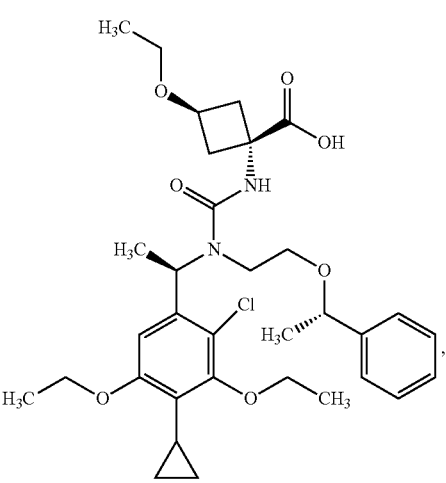

943

-continued

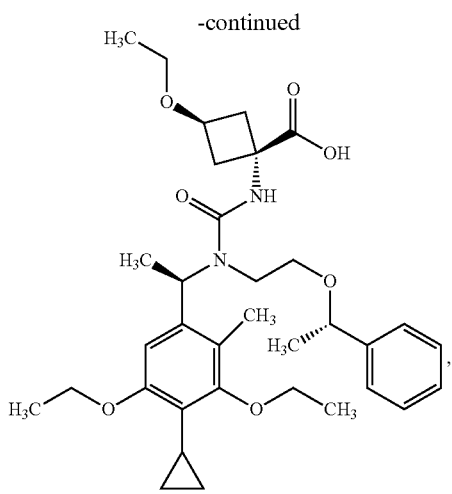

[Chemical Formula 47]

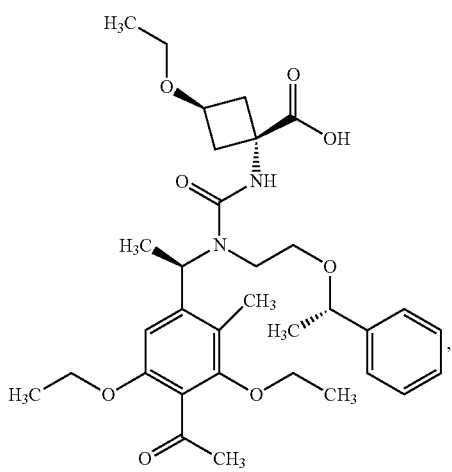

944

-continued

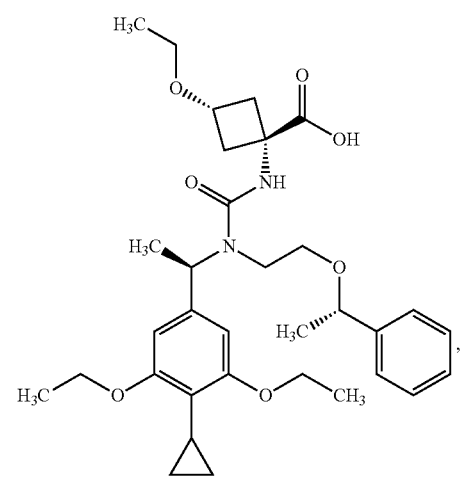

or a pharmaceutically acceptable salt thereof, or a hydrate thereof.

13. A medicament comprising the compound according to claim 1 or a pharmaceutically acceptable salt thereof.

14. A method of antagonizing an LPA1 receptor in a patient in need thereof, the method comprising administering to the patient an effective amount of the compound according to claim 1 or a pharmaceutically acceptable salt thereof, or a hydrate thereof.

15. A method of preventing or treating systemic scleroderma in a patient in need thereof, the method comprising administering to the patient an effective amount of the compound according to claim 1 or a pharmaceutically acceptable salt thereof, or a hydrate thereof.

* * * * *